(12) United States Patent
Tojo et al.

(10) Patent No.: US 6,884,868 B1
(45) Date of Patent: Apr. 26, 2005

(54) CYCLIC HEXAPEPTIDES HAVING ANTIBIOTIC ACTIVITY

(75) Inventors: Takashi Tojo, Osaka (JP); Hidenori Ohki, Takarazuka (JP); Nobuyuki Shiraishi, Nishinomiya (JP); Takahiro Matsuya, Ikeda (JP); Hiroshi Matsuda, Kyoto (JP); Kenji Murano, Osaka (JP); David Barrett, Nara (JP); Takashi Ogino, Yamatokooriyama (JP); Keiji Matsuda, Takatsuki (JP); Masaharu Ichihara, Mino (JP); Norio Hashimoto, Ibaraki (JP); Atsushi Kanda, Nishinomiya (JP); Atsushi Ohigashi, Nishinomiya (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/926,385

(22) PCT Filed: Apr. 25, 2000

(86) PCT No.: PCT/JP00/02710

§ 371 (c)(1),
(2), (4) Date: Oct. 24, 2001

(87) PCT Pub. No.: WO00/64927

PCT Pub. Date: Nov. 2, 2000

(30) Foreign Application Priority Data

Apr. 27, 1999 (AU) .............................................. PP9997

(51) Int. Cl.$^7$ ................................................. C07K 7/50
(52) U.S. Cl. ........................ 530/317; 530/329; 514/11; 514/17
(58) Field of Search ................................ 530/317, 329; 514/11, 17

(56) References Cited

U.S. PATENT DOCUMENTS

| 5,376,634 A | 12/1994 | Iwamoto et al. ................ 514/9 |
| 5,569,646 A | 10/1996 | Ohki et al. .................... 514/11 |
| 5,693,750 A | 12/1997 | Ohki et al. .................. 530/317 |
| 6,107,458 A | 8/2000 | Ohki et al. .................. 530/317 |
| 6,232,290 B1 | 5/2001 | Ohki et al. .................... 514/11 |
| 6,265,536 B1 | 7/2001 | Ohki et al. .................. 530/317 |
| 6,331,521 B1 | 12/2001 | Hori et al. ...................... 514/9 |
| 6,399,567 B1 | 6/2002 | Kanasaki et al. ............. 514/11 |

FOREIGN PATENT DOCUMENTS

| EP | 0 535 959 | 4/1993 |
| EP | 0 644 199 | 3/1995 |
| WO | WO 96/11210 | 4/1996 |

OTHER PUBLICATIONS

R. A. Zambias, et al., Biooraganic & Medicinal Chemistry Letters, vol. 5, No. 20, pps. 2357–2362, "Antifungal Lipopeptides: Structure–Activity Relationships of 3–Hydroxyglutamine–Modified Pneumocandin BO Derivatives", Oct. 19, 1995.

*Primary Examiner*—Jon Weber
*Assistant Examiner*—David Lukton
(74) *Attorney, Agent, or Firm*—Oblon, Spivak, McClelland, Maier & Neustadt, P.C.

(57) ABSTRACT

This invention relates to new polypeptide compound represented by general formula (I), wherein $R^1$, $R^2$, $R^3$, $R^4$, $R^5$ and $R^6$ are as defined in the description or a salt thereof which has antimicrobial activities (especially, antifungal activities), inhibitory activity on β-1,3-glucan synthase, to process for preparation thereof, to a pharmaceutical composition comprising the same, and to a method for prophylactic and/or therapeutic treatment of infectious diseases including *Pneumocystis carinii* infection (e.g. *Pneumocystis carinii* pneumonia) in a human being or an animal.

8 Claims, No Drawings

CYCLIC HEXAPEPTIDES HAVING ANTIBIOTIC ACTIVITY

This application is a 371 of PCT/JP00/02710, filed Apr. 25, 2000, which claims priority to Australian PP 9997, filed Apr. 27, 1999.

TECHNICAL FIELD

The present invention relates to new polypeptide compounds and salts thereof which are useful as a medicament.

BACKGROUND ART

In U.S. Pat. Nos. 5,376,634, 5,569,646, WO 96/11210 and WO 99/40108, there are disclosed the polypeptide compound and a pharmaceutically acceptable salt thereof, which have antimicrobial activities (especially antifungal activity).

DISCLOSURE OF INVENTION

The present invention relates to new polypeptide compound and a salt thereof.

More particularly, it relates to new polypeptide compound and a salt thereof, which have antimicrobial activities [especially, antifungal activities, in which the fungi may include *Aspergillus, Cryptococcus, Candida, Mucor, Actinomyces, Histoplasma, Dermatphyte, Malassezia, Fusarium* and the like.], inhibitory activity on β-1,3-glucan synthase, and further which are expected to be useful for the prophylactic and/or therapeutic treatment of *Pneumocystis carinii* infection (e.g. *Pneumocystis carinii* pneumonia) in a human being or an animal, to a process for preparation thereof, to a pharmaceutical composition comprising the same, and to a methods for the prophylactic and/or therapeutic treatment of infectious disease including *Pneumocystis carinii* infection (e.g. *Pneumocystis carinii* pneumonia) in a human being or an animal.

The object polypeptide compounds of the present invention are new and can be represented by the following general formula (I):

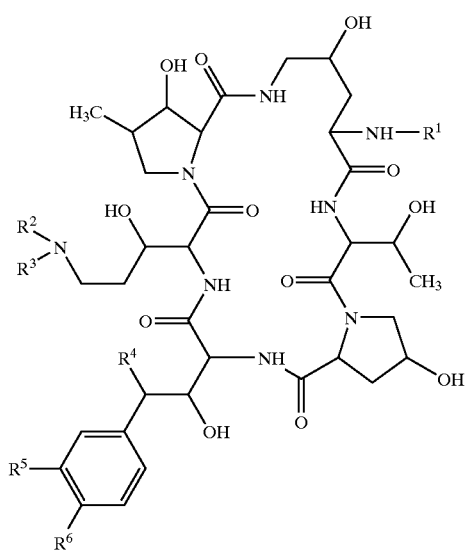

(I)

wherein
$R^1$ is hydrogen or acyl group,
$R^2$ and $R^3$ are independently hydrogen, lower alkyl which may have one or more suitable substituent(s), acyl group, heterocyclic group which may have one or more suitable substituent(s), lower alkylidenyl which may have one or more suitable substituent(s), higher alkyl which may have one or more suitable substituent(s) or cyano,
$R^4$ is hydrogen or hydroxy,
$R^5$ is hydrogen, hydroxy, lower alkoxy or hydroxysulfonyloxy, and
$R^6$ is hydroxy or acyloxy, or a salt thereof.

The new polypeptide compound (I) or a salt thereof can be prepared by the process as illustrated in the following reaction schemes.

Process 1

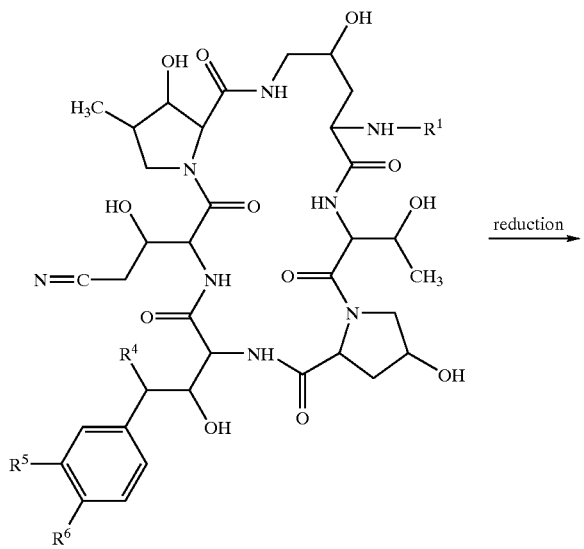

(II)
or a salt thereof reduction →

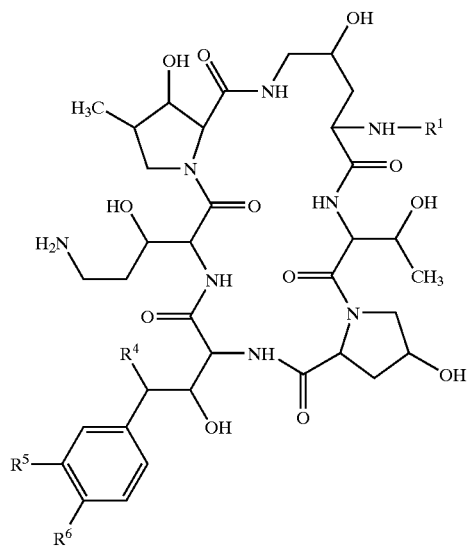

(Ia)
or a salt thereof

Process 2
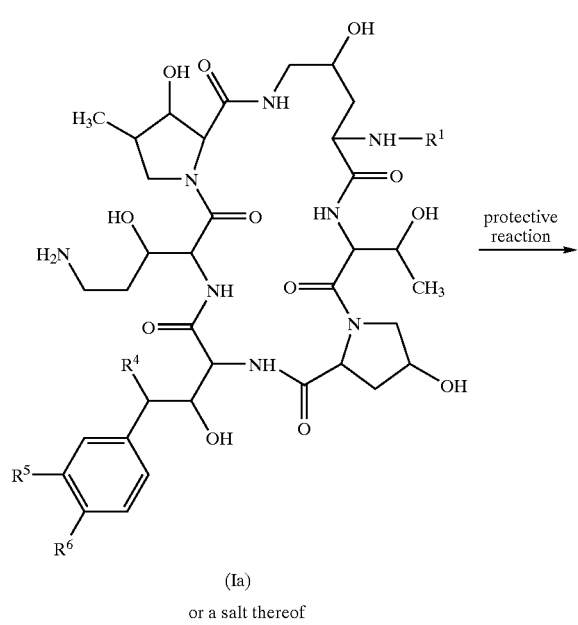
(Ia)
or a salt thereof
Process 3
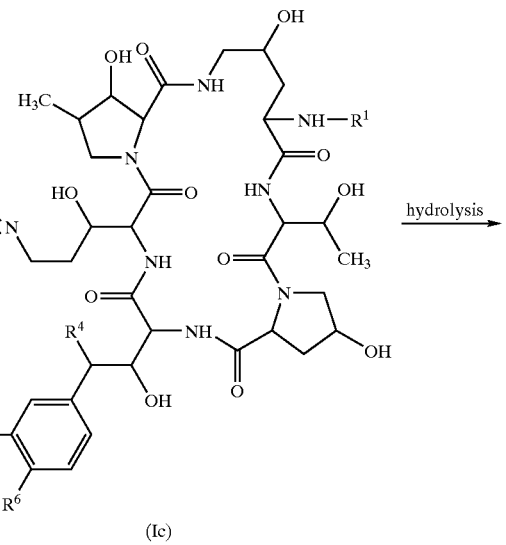
(Ic)
or its reactive derivative
at the sulfonic acid group
or a salt thereof
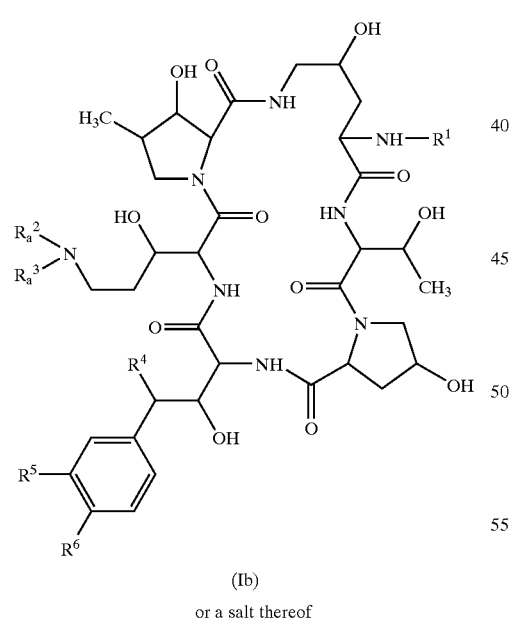
(Ib)
or a salt thereof
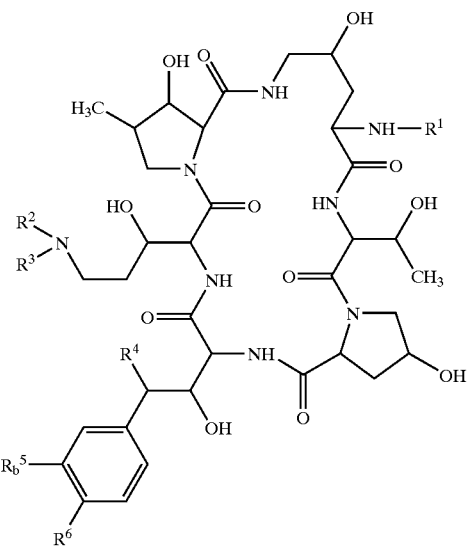
(Id)
or a salt thereof Process 4
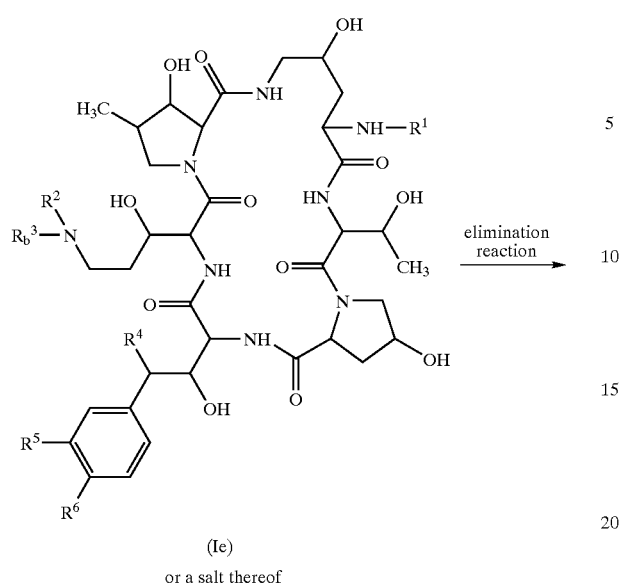
(Ie) or a salt thereof
→ elimination reaction
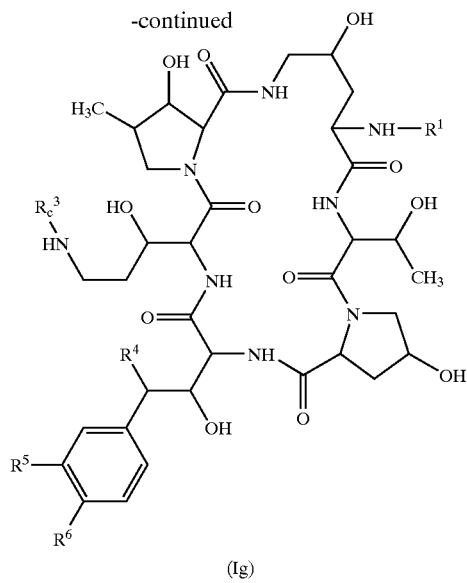
(Ig) or a salt thereof
Process 6
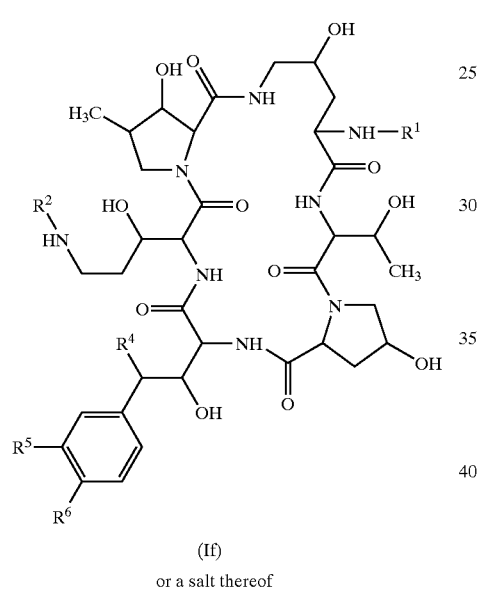
(If) or a salt thereof
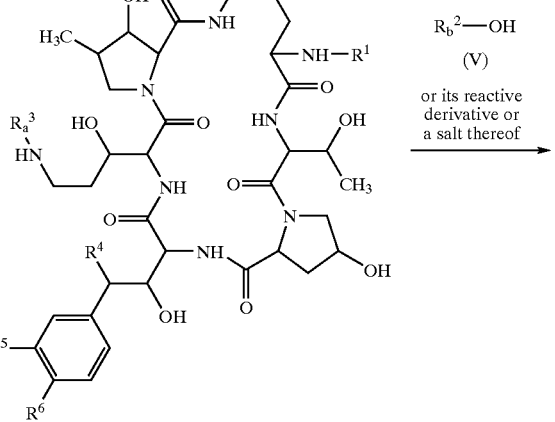
(Ih) or a salt thereof
$R_b^2$—OH
(V)
or its reactive derivative or a salt thereof
→
Process 5
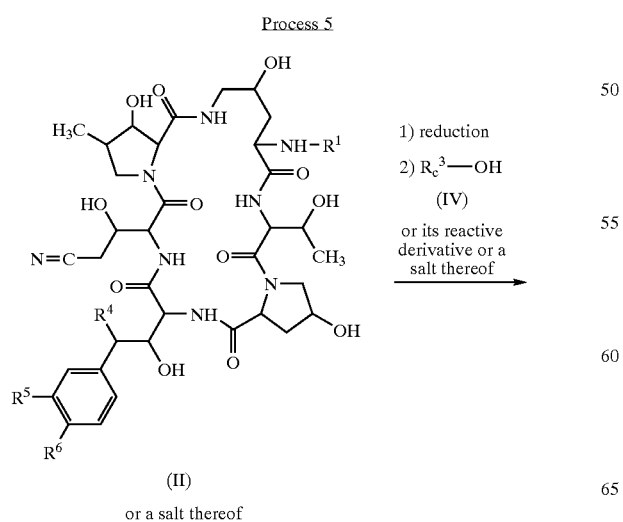
(II) or a salt thereof
1) reduction
2) $R_c^3$—OH
(IV)
or its reactive derivative or a salt thereof
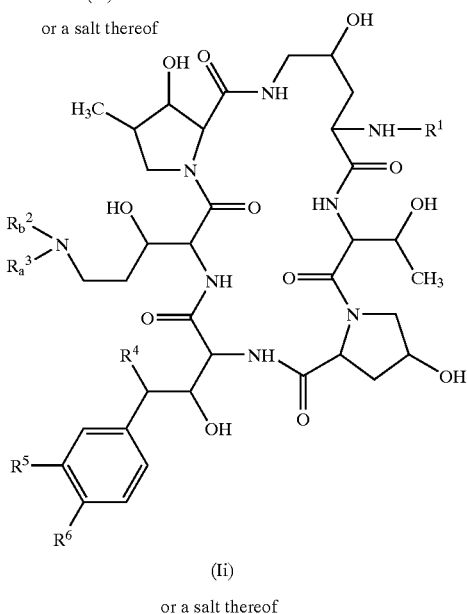
(Ii) or a salt thereof Process 7

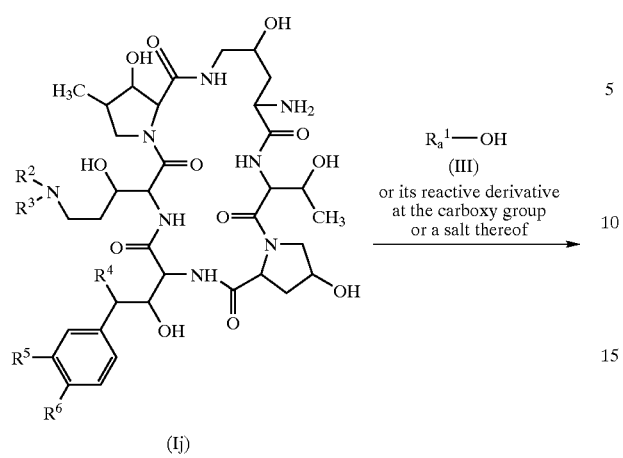

(Ij)

or its reactive derivative at the amino group or a salt thereof

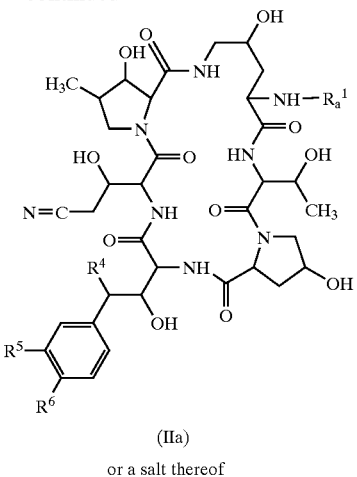

(IIa)

or a salt thereof wherein

R$^1$, R$^2$, R$^3$, R$^4$, R$^5$ and R$^6$ are defined above,

R$_a^1$ is acyl group,

R$_a^2$ is hydrogen, lower alkyl which may have one or more suitable substituent(s), acyl group, heterocyclic group which may have one or more suitable substituent(s), lower alkylidenyl which may have one or more suitable substituent(s), higher alkyl which may have one or more suitable substituent(s) or cyano, R$_b^2$ is acyl group, R$_a^3$ is lower alkyl which may have one or more suitable substituent(s), acyl group, heterocyclic group which may have one or more suitable substituent(s), lower alkylidenyl which may have one or more suitable substituent(s), higher alkyl which may have one or more suitable substituent(s) or cyano, R$_b^3$ is amino protective group, R$_c^3$ is acyl group, R$_a^5$ is hydroxysulfonyloxy, and R$_b^5$ is hydroxy.

(Ik)

or a salt thereof

The Starting compound (II) or a salt thereof can be prepared by the process as illustrated in the following reaction scheme.

Process A

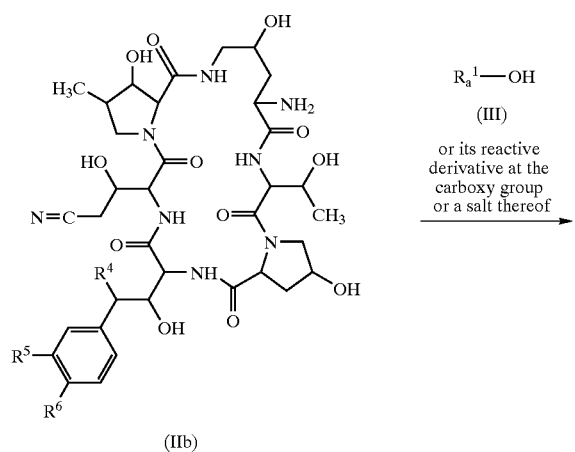

(IIb)

or its reactive derivative at the amino group or a salt thereof

Suitable salt of the new polypeptide compound (I) is a pharmaceutically acceptable and conventional non-toxic salt, and may include a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt;

a salt with an organic base, for example, an organic amine salt (e.g., triethylamine salt, diisopropylethylamine salt, pyridine salt, picoline salt, ethanolamine salt, triethanolamine salt, dicyclohexylamine salt, N,N'-dibenzylethylenediamine salt, 4-dimethylaminopyridine salt, etc.);

an inorganic acid addition salt (e.g., hydrochloride hydrobromide, sulfate, phosphate, etc.);

an organic carboxylic sulfonic acid addition salt (e.g., formate, acetate, trifluoroacetate, maleate, tartrate, fumarate, methanesulfonate, benzenesulfonate, toluenesulfonate, etc.);

a salt with a basic or acidic amino acid (e.g., arginine, aspartic acid, glutamic acid, etc.).

Suitable examples and illustration of the various definitions in the above and subsequent descriptions of the present specification, which the present invention intends to include within the scope thereof, are explained in detail as follows:

The term "lower" is used to intend a group having 1 to 6 carbon atom(s), unless otherwise provided.

Suitable example of "one or more" may be the number of 1 to 6, in which the preferred one may be the number of 1 to 3.

Suitable example of "halogen" may be fluorine, chlorine, bromine, iodine and the like.

Suitable example of "lower alkoxy" may include straight or branched one such as methoxy, ethoxy, propoxy, isopropoxy, butoxy, isobutoxy, tert-butoxy, pentyloxy, tert-pentyloxy, neo-pentyloxy, hexyloxy, isohexyloxy and the like.

Suitable example of "higher alkoxy" may include straight or branched one such as heptyloxy, octyloxy, 3,5-dimethyloctyloxy, 3,7-dimethyloctyloxy, nonyloxy, decyloxy, undecyloxy, dodecyloxy, tridecyloxy, tetradecyloxy, hexadecyloxy, heptadecyloxy, octadecyloxy, nonadecyloxy, icosyloxy, and the like.

Suitable example of "lower alkyl" may include straight or branched one having 1 to 6 carbon atom(s), such as methyl, ethyl, propyl, isopropyl, butyl, isobutyl, sec-butyl, tert-butyl, pentyl, tert-pentyl, neo-pentyl, hexyl, isohexyl and the like.

Suitable example of "higher alkyl" may include straight or branched one such as heptyl, octyl, 3,5-dimethyloctyl, 3,7-dimethyloctyl, nonyl, decyl, undecyl, dodecyl, tridecyl, tetradecyl, hexadecyl, heptadecyl, octadecyl, nionadecyl, icosyl, and the like.

Suitable example of "aryl" and "ar" moiety may include phenyl which may have lower alkyl (e.g., phenyl, mesityl, xylyl, tolyl, etc.), naphthyl, anthryl, indanyl, fluorenyl, and the like, and this aryl and "ar" moiety may have one or more halogen.

Suitable example of "aroyl" may include benzoyl, toluoyl, naphthoyl, anthrylcarbonyl, and the like.

Suitable example of "heterocyclic" group may include unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, azetidinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 or 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 or 2 oxygen atom(s) and 1 to 3 nitrogen atom(s), for example, morpholinyl, sydnonyl, morpholino, etc.;

unsaturated condensed heterocyclic group containing 1 or 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 or 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 or 2 sulfur atom(s) and 1 to 3 nitrogen atom(s), for example thiazolidinyl, thiomorpholinyl, thiomorpholino, etc.;

unsaturated 3 to 8-membered (more preferably 5 or 6-membered) heteromonocyclic group containing 1 or 2 sulfur atom(s), for example, thienyl, dihydrodithiinyl, dihydrodithionyl, etc.;

unsaturated condensed heterocyclic group containing 1 or 2 sulfur atom(s) and 1 to 3 nitrogen atom(s), for example, benziothiazolyl, benzothiadiazolyl, imidazothiadiazolyl, etc.;

unsaturated 3 to 8-membered (more preferably 5 or 6-membered) heteromonocyclic group containing an oxygen atom, for example, furyl etc.;

saturated 3 to 8-membered (more preferably 5 or 6-membered) heteromonocyclic group containing 1 or 2 oxygen atom(s), for example, tetrahydrofuran, tetrahydropyran, dioxacyclopentane, dioxacyclohexane, etc.;

unsaturated 3 to 8-membered (more preferably 5 or 6-membered) heteromonocyclic group containing an oxygen atom and 1 or 2 sulfur atom(s), for example, dihydrooxathiinyl, etc.;

unsaturated condensed heterocyclic group containing 1 or 2 sulfur atom(s), for example benzothienyl, benzodithiinyl, etc.;

unsaturated condensed heterocyclic group containing an oxygen atom and 1 or 2 sulfur atom(s), for example, benzoxathiinyl, etc.; and the like, and this "heterocyclic group" may have one or more suitable substituent(s) selected from the group consisting of lower alkyl, oxo, cyclo(lower)alkyl, hydroxy(lower)alkyl, carboxy (lower)alkanoyl which may have amino and heterocycliccarbonyl.

Suitable example of "cyclo(lower)alkyl" may include cyclopropyl, cyclobutyl, cyclopentyl, cyclohexyl, and the like, and this "cyclo(lower)alkyl" may have one or more lower alkyl.

Suitable example of "cyclo(lower)alkyloxy" may include cyclopropyloxy, cyclobutyloxy, cyclopentyloxy, cyclohexyloxy, and the like.

Suitable example of "acyl group" may include aliphatic acyl, aromatic acyl, arylaliphatic acyl and heterocyclic-aliphatic acyl derived from carboxylic acid, carbonic acid, carbamic acid, sulfonic acid, and the like.

Suitable example of said "acyl group" may be illustrated as follows.

Carboxy; carbamoyl; mono or di(lower)alkylcarbamoyl (e.g., methylcarbamoyl, dimethylcarbamoyl, ethylcarbamoyl, diethylcarbamoyl, etc.)

Aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.);

lower or higher alkoxycarbonyl (e.g., methoxycarbonyl, ethoxycarbonyl, t-butoxycarbonyl, t-pentyloxycarbonyl, heptyloxycarbonyl, etc.); lower alkenyloxycarbonyl (e.g., vinyloxycarbonyl, propenyloxycarbonyl, allyloxycarbonyl, butenyloxycarbonyl, butedienyloxycarbonyl, pentenyloxycarbonyl, hexenyloxycarbonyl, etc.);

lower or higher alkylsulfonyl (e.g., methylsulfonyl, ethylsulfonyl, etc.);

lower or higher alkoxysulfonyl (e.g., methoxysulfonyl, ethoxysulfonyl, etc.); or the like;

Aromatic acyl such as aroyl (e.g., benzoyl, toluoyl, naphthoyl, etc.);

ar(lower)alkanoyl [e.g., phenyl($C_1$–$C_6$)alkanoyl (e.g., phenylacetyl, phenylpropanoyl, phenylbutanoyl, phenylisobutanoyl, phenylpentanoyl, phenylhexanoyl, etc.), naphthyl($C_1$–$C_6$)alkanoyl (e.g., naphthylacetyl, naphthylpropanoyl, naphthylbutanoyl, etc.), etc.];

ar(lower)alkenoyl [e.g., phenyl($C_3$–$C_6$)alkenoyl (e.g., phenylpropenoyl, phenylbutenoyl, phenylmethacryloyl, phenylpentanoyl, phenylhexenoyl, etc.), naphthyl($C_3$–$C_6$)alkenoyl (e.g., naphthylpropenoyl, naphthylbutenoyl, etc.), etc.];

ar(lower)alkoxycarbonyl [e.g., phenyl($C_1$–$C_6$) alkoxycarbonyl (e.g., benzyloxycarbonyl, etc.), fluorenyl ($C_1$–$C_6$)alkoxycarbonyl (e.g., fluorenylmethyloxycarbonyl, etc.), etc.];

aryloxycarbonyl (e.g., phenoxycarbonyl, naphthyloxycarbonyl, etc.);

aryloxy(lower)alkanoyl (e.g., phenoxyacetyl, phenoxypropionyl, etc.);

arylcarbamoyl (e.g., phenylcarbamoyl, etc.);

arylthiocarbamoyl (e.g., phenylthiocarbamoyl, etc.);

arylglyoxyloyl (e.g., phenylglyoxyloyl, naphthylglyoxyloyl, etc.);

arylsulfonyl which may have 1 to 4 lower alkyl (e.g., phenylsulfonyl, p-tolylsulfonyl, etc.); or the like;

Heterocyclic acyl such as heterocycliccarbonyl;

heterocyclic(lower)alkanoyl (e.g., heterocyclicacetyl, heterocyclicpropanoyl, heterocyclicbutanoyl, heterocyclicpentanoyl, heterocyclichexanoyl, etc.);

heterocyclic(lower)alkenoyl (e.g., heterocyclicpropenoyl, heterocyclicbutenoyl, heterocyclicpentenoyl, heterocyclichexenoyl, etc.);

heterocyclicglyoxyloyl; or the like;

in which suitable "heterocyclic" moiety in the terms "heterocycliccarbonyl", "heterocyclic(lower)alkanoyl", "heterocyclic(lower)alkenoyl" and "heterocyclicglyoxyloyl" can be referred to aforementioned "heterocyclic" moiety, and this "acyl group" may have one or more suitable substituent(s) selected from the group consisting of lower alkyl, oxo, amino and hydroxy.

Suitable example of "acyl group" of $R^1$ can be referred to aforementioned "acyl group", in which the preferred one may be aroyl which may have one or more suitable substituent(s), lower alkoxycarbonyl, higher alkanoyl and heterocycliccarbonyl which may have one or more suitable substituent(s).

Suitable example of "suitable substituent(s)" in the term of "aroyl substituted with one or more suitable substituent(s)" and "heterocycliccarbonyl which may have one or more suitable substituent(s)" may be heterocyclic group substituted with aryl having lower alkoxy, heterocyclic group substituted with aryl having lower alkoxy(lower)alkoxy, heterocyclic group substituted with aryl having lower alkoxy(higher)alkoxy, heterocyclic group substituted with aryl having cyclo(lower)alkyloxy, heterocyclic group substituted with aryl having heterocyclic group, heterocyclic group substituted with cyclo(lower)alkyl having cyclo(lower)alkyl, heterocyclic group substituted with aryl having aryl substituted with lower alkoxy(lower)alkoxy, heterocyclic group substituted with aryl having heterocyclic group substituted with cyclo(lower)alkyl, heterocyclic group substituted with aryl having aryl substituted with heterocyclic group, heterocyclic group substituted with aryl having aryl substituted with lower alkoxy(lower)alkyl, heterocyclic group substituted with aryl having heterocyclic group substituted with aryl(lower)alkoxy, heterocyclic group substituted with aryl having heterocyclic group substituted with lower alkoxy and aryl having halogen, heterocyclic group substituted with aryl having aryl substituted with lower alkoxy, heterocyclic group substituted with aryl having cyclo(lower)alkyl, heterocyclic group substituted with aryl having heterocyclic group substituted with aryl, heterocyclic group substituted with aryl having heterocyclic group substituted with aryloxy, heterocyclic group substituted with aryl having heterocyclic group substituted with lower alkoxy(lower)alkoxy, heterocyclic group substituted with aryl is having heterocyclic group substituted with lower alkoxy(lower)alkylthio, heterocyclic group substituted with aryl having heterocyclic higher alkoxy, heterocyclic group substituted with aryl having heterocyclic group substituted with cyclo(lower)alkyloxy, heterocyclic group substituted with aryl having heterocyclic group substituted with aryl having lower alkoxy(lower)alkoxy, heterocyclic group substituted with aryl having aryloxy(lower)alkoxy, heterocyclic group substituted with aryl having heterocyclic group substituted with lower alkylthio, heterocyclic group substituted with aryl having heterocyclic group substituted with lower alkoxy and aryl, aryl substituted with heterocyclic group having aryl substituted with heterocyclic group, aryl substituted with lower alkoxy having cyclo(lower)alkyl and amino, aryl substituted with heterocyclic group having cyclo(lower)alkyl, aryl substituted with lower alkoxy having cyclo(lower)alkyl and protected amino, aryl substituted with heterocyclic group having lower alkyl, aryl substituted with aryl having lower alkoxy, heterocyclic group substituted with cyclo(lower)alkyl having lower alkyl, heterocyclic group substituted with cyclo(lower)alkyl having lower alkoxy and cyclo(lower)alkyl, heterocyclic group substituted with cyclo(lower)alkyl having cyclo(lower)alkyl substituted with lower alkoxy, heterocyclic group substituted with aryl having lower alkoxy(lower)alkylsulfonyl, heterocyclic group substituted with aryl having lower alkoxy (higher)alkylsulfonyl, higher alkoxy, aryl substituted with lower alkoxy(higher)alkoxy, heterocyclic group substituted with aryl having higher alkoxy, heterocyclic group substituted with higher alkyl, in which the preferred one may be unsaturated condensed heterocyclic group containing 1 or 2 sulfur atom(s) and 1 to 3 nitrogen atom(s) substituted with phenyl having ($C_4$–$C_6$)alkoxy, unsaturated 3 to 8-membered heteromonocyclic group containing 1 or 2 sulfur atom(s) and 1 to 3 nitrogen atom(s) substituted with phenyl having ($C_1$–$C_4$)alkoxy($C_4$–$C_6$)alkoxy, unsaturated 3 to 8-membered heteromonocyclic group containing 1 or 2 sulfur atom(s) and 1 to 3 nitrogen atom(s) substituted with phenyl having ($C_1$–$C_4$)alkoxy($C_7$–$C_{14}$)alkoxy, saturated 3 to 8-membered heteromonocyclic group containing 1 to 4 nitrogen atom(s) substituted with phenyl having ($C_1$–$C_4$)alkoxy($C_7$–$C_{14)}$ alkoxy, unsaturated condensed heterocyclic group containing 1 or 2 sulfur atom(s) and 1 to 3 nitrogen atom(s) substituted with phenyl having cyclo($C_4$–$C_6$)alkyloxy, unsaturated condensed heterocyclic group containing 1 or 2 sulfur atom(s) and 1 to 3 nitrogen atom(s) substituted with phenyl having saturated 3 to 8-membered heteromonocyclic group containing 1 or 2 oxygen atom(s) and 1 to 3 nitrogen atom(s), saturated 3 to 8-membered heteromonocyclic group containing 1 to 4 nitrogen atom(s) substituted with cyclo $(C_4-C_6)$alkyl having cyclo$(C_4-C_6)$alkyl, unsaturated 3 to 8-membered heteromonocyclic group containing 1 or 2 sulfur atom(s) and 1 to 3 nitrogen atom(s) substituted with phenyl having phenyl substituted with $(C_1-C_4)$alkoxy $(C_1-C_4)$alkoxy, unsaturated 3 to 8-membered heteromonocyclic group containing 1 or 2 sulfur atom(s) and 1 to 3 nitrogen atom(s) substituted with phenyl having saturated 3 to 8-membered heteromonocyclic group containing 1 to 4 nitrogen atom(s) substituted with cyclo$(C_4-C_6)$alkyl, unsaturated condensed heterocyclic group containing 1 or 2 sulfur atom(s) and 1 to 3 nitrogen atom(s) substituted with phenyl having saturated 3 to 8-membered heteromonocyclic group containing 1 to 4 nitrogen atom(s) having cyclo$(C_4-C_6)$alkyl,

- unsaturated 3 to 8-membered heteromonocyclic group containing 1 or 2 sulfur atom(s) and 1 to 3 nitrogen atom(s) substituted with phenyl having $(C_4-C_6)$alkoxy,
- unsaturated 3 to 8-membered heteromonocyclic group containing 1 or 2 sulfur atom(s) and 1 to 3 nitrogen atom(s) substituted with phenyl having cyclo$(C_4-C_6)$alkyl,
- unsaturated 3 to 9-membered heteromonocyclic group containing 1 or 2 sulfur atom(s) and 1 to 3 nitrogen atom(s) substituted with phenyl having phenyl substituted with $(C_1-C_4)$alkoxy,
- unsaturated 3 to 8-membered heteromonocyclic group containing 1 or 2 sulfur atom(s) and 1 to 3 nitrogen atom(s) substituted with phenyl having phenyl substituted with $(C_1-C_4)$alkoxy$(C_1-C_4)$alkyl,
- unsaturated 3 to 8-membered heteromonocyclic group containing 1 or 2 sulfur atom(s) and 1 to 3 nitrogen atom(s) substituted with phenyl having phenyl substituted with saturated 3 to 8-membered heteromonocyclic group containing 1 or 2 oxygen atom(s) and 1 to 3 nitrogen atom(s) having di$(C_1-C_4)$alkyl,
- unsaturated 3 to 8-membered heteromonocyclic group containing 1 or 2 sulfur atom(s) and 1 to 3 nitrogen atom(s) substituted with phenyl having saturated 3 to 8-membered heteromonocyclic group containing 1 to 4 nitrogen atom(s) substituted with cyclo$(C_4-C_6)$alkyl, having $(C_1-C_4)$alkyl,
- unsaturated 3 to 8-membered heteromonocyclic group containing 1 or 2 sulfur atom(s) and 1 to 3 nitrogen atom(s) substituted with phenyl having saturated 3 to 8-membered heteromonocyclic group containing 1 to 4 nitrogen atom(s) substituted with phenyl,
- unsaturated 3 to 8-membered heteromonocyclic group containing 1 or 2 sulfur atom(s) and 1 to 3 nitrogen atom(s) substituted with phenyl having saturated 3 to 8-membered heteromonocyclic group containing 1 to 4 nitrogen atom(s) substituted with phenoxy,
- unsaturated 3 to 8-membered heteromonocyclic group containing 1 or 2 sulfur atom(s) and 1 to 3 nitrogen atom(s) substituted with phenyl having saturated 3 to 8-membered heteromonocyclic group containing 1 to 4 nitrogen atom(s) substituted with phenyl$(C_1-C_4)$alkoxy,
- unsaturated 3 to 8-membered heteromonocyclic group containing 1 or 2 sulfur atom(s) and 1 to 3 nitrogen atom(s) substituted with phenyl having saturated 3 to 8-membered heteromonocyclic group containing 1 to 4 nitrogen atom(s) substituted with $(C_1-C_4)$alkoxy and chlorophenyl,
- unsaturated 3 to 8-membered heteromonocyclic group containing 1 or 2 sulfur atom(s) and 1 to 3 nitrogen atom(s) substituted with phenyl having saturated 3 to 8-membered heteromonocyclic group containing 1 or 2 oxygen atom(s) and 1 to 3 nitrogen atom(s) substituted with di$(C_1-C_4)$alkyl,
- unsaturated 3 to 8-membered heteromonocyclic group containing 1 to 4 nitrogen atom(s) substituted with phenyl having $(C_7-C_{14})$alkoxy,
- unsaturated 3 to 8-membered heteromonocyclic group containing 1 or 2 oxygen atom(s) and 1 to 3 nitrogen atom(s) substituted with phenyl having $(C_4-C_6)$alkoxy,
- unsaturated 3 to 8-membered heteromonocyclic group containing 1 or 2 oxygen atom(s) and 1 to 3 nitrogen atom(s) substituted with phenyl having $(C_1-C_4)$alkoxy $(C_4-C_6)$alkoxy,
- unsaturated 3 to 8-membered heteromonocyclic group containing 1 or 2 oxygen atom(s) and 1 to 3 nitrogen atom(s) substituted with phenyl having $(C_1-C_4)$alkoxy $(C_7-C_{14})$alkoxy,
- unsaturated 3 to 8-membered heteromonocyclic group containing 1 or 2 oxygen atom(s) and 1 to 3 nitrogen atom(s) substituted with phenyl having $(C_7-C_{14})$alkoxy substituted with saturated 3 to 8-membered heteromonocyclic group containing 1 or 2 oxygen atom(s) and 1 to 3 nitrogen atom(s) having di$(C_1-C_4)$alkyl,
- unsaturated 3 to 8-membered heteromonocyclic group containing 1 or 2 oxygen atom(s) and 1 to 3 nitrogen atom(s) substituted with phenyl having saturated 3 to 8-membered heteromonocyclic group containing 1 or 2 oxygen atom(s) and 1 to 3 nitrogen atom(s) substituted with di$(C_1-C_4)$alkyl,
- unsaturated 3 to 8-membered heteromonocyclic group containing 1 or 2 oxygen atom(s) and 1 to 4 nitrogen atom(s) substituted with phenyl having $(C_1-C_4)$alkoxy $(C_7-C_{14})$alkylsulfonyl,
- saturated 3 to 8-membered heteromonocyclic group containing 1 to 4 nitrogen atom(s) substituted with phenyl having $(C_1-C_4)$alkoxy$(C_4-C_6)$alkoxy,
- saturated 3 to 8-membered heteromonocyclic group containing 1 to 4 nitrogen atom(s) substituted with phenyl having $(C_1-C_4)$alkoxy substituted with phenoxy,
- saturated 3 to 8-membered heteromonocyclic group containing 1 to 4 nitrogen atom(s) substituted with phenyl having cyclo$(C_4-C_6)$alkyl,
- saturated 3 to 8-membered heteromonocyclic group containing 1 to 4 nitrogen atom(s) substituted with phenyl having phenyl substituted with $(C_1-C_4)$alkoxy$(C_4-C_6)$ alkoxy,
- saturated 3 to 8-membered heteromonocyclic group containing 1 to 4 nitrogen atom(s) substituted with phenyl having phenyl substituted with saturated 3 to 8-membered heteromonocyclic group containing 1 or 2 oxygen atom(s) and 1 to 3 nitrogen atom(s) substituted with di$(C_1-C_4)$alkyl,
- saturated 3 to 8-membered heteromonocyclic group containing 1 to 4 nitrogen atom(s) substituted with phenyl having saturated 3 to 8-membered heteromonocyclic group containing 1 to 4 nitrogen atom(s) substituted with cyclo$(C_4-C_6)$alkyloxy,
- saturated 3 to 8-membered heteromonocyclic group containing 1 to 4 nitrogen atom(s) substituted with phenyl having saturated 3 to 8-membered heteromonocyclic group containing 1 to 4 nitrogen atom(s) substituted with phenyl,
saturated 3 to 8-membered heteromonocyclic group containing 1 to 4 nitrogen atom(s) substituted with phenyl having saturated 3 to 8-membered heteromonocyclic group containing 1 to 4 nitrogen atom(s) substituted with phenyl having $(C_1-C_4)$alkoxy$(C_4-C_6)$alkoxy,
saturated 3 to 8-membered heteromonocyclic group containing 1 to 4 nitrogen atom(s) substituted with phenyl having saturated 3 to 8-membered heteromonocyclic group containing 1 to 4 nitrogen atom(s) substituted with $(C_1-C_4)$alkylthio,
saturated 3 to 8-membered heteromonocyclic group containing 1 to 4 nitrogen atom(s) substituted with phenyl having saturated 3 to 8-membered heteromonocyclic group containing 1 to 4 nitrogen atom(s) substituted with $(C_1-C_4)$alkoxy$(C_4-C_6)$alkylthio,
saturated 3 to 8-membered heteromonocyclic group containing 1 to 4 nitrogen atom(s) substituted with phenyl having saturated 3 to 8-membered heteromonocyclic group containing 1 to 4 nitrogen atom(s) substituted with cyclo$(C_4-C_6)$alkyl,
saturated 3 to 8-membered heteromonocyclic group containing 1 to 4 nitrogen atom(s) substituted with phenyl having saturated 3 to 8-membered heteromonocyclic group containing 1 to 4 nitrogen atom(s) substituted with saturated 3 to 8-membered heteromonocyclic group containing 1 or 2 oxygen atom(s),
saturated 3 to 8-membered heteromonocyclic group containing 1 to 4 nitrogen atom(s) substituted with phenyl having saturated 3 to 8-membered heteromonocyclic group containing 1 to 4 nitrogen atom(s) substituted with $(C_1-C_4)$alkoxy and phenyl,
saturated 3 to 8-membered heteromonocyclic group containing 1 to 4 nitrogen atom(s) substituted with phenyl having saturated 3 to 8-membered heteromonocyclic group containing 1 to 4 nitrogen atom(s) substituted with $(C_1-C_4)$alkoxy and chlorophenyl,
saturated 3 to 8-membered heteromonocyclic group containing 1 to 4 nitrogen atom(s) substituted with phenyl having saturated 3 to 8-membered heteromonocyclic group containing 1 or 2 oxygen atom(s) and 1 to 4 nitrogen atom(s) substituted with di$(C_1-C_4)$alkyl,
saturated 3 to 8-membered heteromonocyclic group containing 1 to 4 nitrogen atom(s) substituted with cyclo$(C_4-C_6)$alkyl having $(C_4-C_6)$alkyl,
saturated 3 to 8-membered heteromonocyclic group containing 1 to 4 nitrogen atom(s) substituted with cyclo$(C_4-C_6)$alkyl having cyclo$(C_4-C_6)$alkyl and $(C_1-C_4)$alkoxy,
saturated 3 to 8-membered heteromonocyclic group containing 1 to 4 nitrogen atom(s) substituted with cyclo$(C_4-C_6)$alkyl having cyclo$(C_4-C_6)$alkyl substituted with $(C_1-C_4)$alkoxy,
unsaturated condensed heterocyclic group containing 1 or 2 sulfur atom(s) and 1 to 3 nitrogen atom(s) substituted with phenyl having $(C_1-C_4)$alkoxy$(C_4-C_6)$alkoxy,
unsaturated condensed heterocyclic group containing 1 or 2 sulfur atom(s) and 1 to 3 nitrogen atom(s) substituted with phenyl having saturated 3 to 8-membered heteromonocyclic group 1 to 4 nitrogen atom(s) substituted with $(C_1-C_4)$alkoxy$(C_1-C_6)$alkoxy,
unsaturated condensed heterocyclic group containing 1 or 2 sulfur atom(s) and 1 to 3 nitrogen atom(s) substituted with phenyl having saturated 3 to 8-membered heteromonocyclic group 1 to 4 nitrogen atom(s) substituted with $(C_1-C_4)$alkoxy$(C_4-C_6)$alkylthio,
unsaturated condensed heterocyclic group containing 1 or 2 sulfur atom(s) and 1 to 3 nitrogen atom(s) substituted with phenyl having saturated 3 to 8-membered heteromonocyclic group 1 or 2 oxygen atom(s) and 1 to 3 nitrogen atom(s) substituted with di$(C_1-C_4)$alkyl,
phenyl substituted with $(C_1-C_4)$alkoxy having cyclo$(C_4-C_6)$alkyl and protected amino,
phenyl substituted with $(C_1-C_4)$alkoxy having cyclo$(C_4-C_6)$alkyl and amino,
phenyl substituted with phenyl having $(C_4-C_6)$alkoxy,
phenyl substituted with unsaturated 3 to 8-membered heteromonocyclic group containing 1 or 2 sulfur atom(s) and 1 to 3 nitrogen atom(s) having $(C_4-C_6)$alkyl,
phenyl substituted with saturated 3 to 8-membered heteromonocyclic group containing 1 to 4 nitrogen atom(s) substituted with cyclo$(C_4-C_6)$alkyl,
phenyl substituted with saturated 3 to 8-membered heteromonocyclic group containing 1 to 4 nitrogen atom(s) having phenyl substituted with saturated 3 to 8-membered heteromonocyclic group containing 1 or 2 oxygen atom(s) and 1 to 3 nitrogen atom(s) having di$(C_1-C_4)$alkyl,
phenyl substituted with condensed heterocyclic group containing 1 or 2 oxygen atom(s) and 1 to 3 nitrogen atom(s) having $(C_4-C_6)$alkyl, $(C_7-C_{14})$alkoxy,
unsaturated 3 to 8-membered heteromonocyclic group containing 1 to 4 nitrogen atom(s) substituted with $(C_7-C_{14})$alkyl,
unsaturated 3 to 8-membered heteromonocyclic group containing 1 to 4 nitrogen atom(s) substituted with phenyl having $(C_4-C_6)$alkoxy,
unsaturated 3 to 8-membered heteromonocyclic group containing 1 to 4 nitrogen atom(s) substituted with phenyl having saturated 3 to 8-membered heteromonocyclic group containing 1 to 4 nitrogen atom(s),
xylyl substituted with $(C_1-C_4)$alkoxy$(C_7-C_{14})$alkoxy, and the most preferred one may be imidazothiadiazolyl substituted with phenyl having pentyloxy, thiadiazolyl substituted with phenyl having methoxyhexyloxy, thiadiazolyl substituted with phenyl having methoxyoctyloxy, thiadiazolyl substituted with phenyl having methoxyheptyloxy, imidazothiadiazolyl substituted with phenyl having cyclohexyloxy, imidazothiadiazolyl substituted with phenyl having dimethylmorpholino, piperazinyl substituted with phenyl having methoxyheptyloxy, piperazinyl substituted with phenyl having methoxyoctyloxy, piperazinyl substituted with cyclohexyl having cyclohexyl, thiadiazolyl substituted with phenyl having phenyl substituted with methoxyethoxy, thiadiazolyl substituted with phenyl having phenyl substituted with methoxybutoxy, thiadiazolyl substituted with phenyl having phenyl substituted with ethoxypropoxy, imidazothiadiazolyl substituted with phenyl having piperazinyl substituted with cyclohexyl, imidazothiadiazolyl substituted with phenyl having piperazinyl substituted with cyclohexyl,
thiazolyl substituted with phenyl having pentyloxy,
thiadiazolyl substituted with phenyl having methoxyheptyloxy,
thiadiazolyl substituted with phenyl having cyclohexyl,
thiadiazolyl substituted with phenyl having cyclohexyloxy, thiadiazolyl substituted with phenyl having phenyl substituted with propoxy,
thiadiazolyl substituted with phenyl having phenyl substituted with ethoxymethyl,
thiadiazolyl substituted with phenyl having phenyl substituted with methoxypropoxy,
thiadiazolyl substituted with phenyl having piperazinyl substituted with cyclohexyl,
thiadiazolyl substituted with phenyl having phenyl substituted with dimethylmorpholino,
thiadiazolyl substituted with phenyl having piperazinyl substituted with methylcyclohexyl,
thiadiazolyl substituted with phenyl having piperidyl,
thiadiazolyl substituted with phenyl having piperidyl substituted with phenyl,
thiadiazolyl substituted with phenyl having piperidyl substituted with phenoxy,
thiadiazolyl substituted with phenyl having piperidyl substituted with benzyloxy,
thiadiazolyl substituted with phenyl having piperidyl substituted with methoxy and chlorophenyl,
thiadiazolyl substituted with phenyl having dimethylmorpholino,
pyrimidinyl substituted with phenyl having octyloxy,
isoxazolyl substituted with phenyl having pentyloxy,
isoxazolyl substituted with phenyl having methoxyhexyloxy,
isosxazolyl substituted with phenyl having methoxyheptyloxy,
isoxazolyl substituted with phenyl having heptyloxy substituted with dimethylmorpholino,
isoxazolyl substituted with phenyl having octyloxy substituted with dimethylmorpholino,
isoxazolyl substituted with phenyl having dimethylmorpholino,
oxadiazolyl substituted with phenyl having pentyloxy,
oxadiazolyl substituted with phenyl having methoxyheptyloxy,
oxadiazolyl substituted with phenyl having methoxynonyloxy,
oxadiazolyl substituted with phenyl having methoxyheptylsulfonyl,
oxadiazolyl substituted with phenyl having methoxynonylsulfonyl,
piperazinyl substituted with phenyl having methoxyhexyloxy,
piperazinyl substituted with phenyl having methoxyheptyloxy,
piperazinyl substituted with phenyl having phenoxypropoxy,
piperazinyl substituted with phenyl having cyclohexyl,
piperazinyl substituted with phenyl having phenyl substituted with methoxypentyloxyphenyl,
piperazinyl substituted with phenyl having phenyl substituted with dimethylmorpholino,
piperazinyl substituted with phenyl having piperidyl substituted with cyclohexyloxy,
piperazinyl substituted with phenyl having piperidyl substituted with phenyl,
piperazinyl substituted with phenyl having piperidyl substituted with methoxybutoxyphenyl,
piperazinyl substituted with phenyl having piperidyl substituted with propylthio,
piperazinyl substituted with phenyl having piperidyl substituted with methoxyhexylthio,
piperazinyl substituted with phenyl having piperidyl substituted with cyclobutanespiro,
piperazinyl substituted with phenyl having piperidyl substituted with dioxacyclobutanespiro,
piperazinyl substituted with phenyl having piperidyl substituted with methoxy and phenyl,
piperazinyl substituted with phenyl having piperidyl substituted with methoxy and chlorophenyl,
piperazinyl substituted with phenyl having dimethylmorpholino,
piperazinyl substituted with cyclohexyl having tert-butyl,
piperazinyl substituted with cyclohexyl having cyclohexyl and methoxy,
piperazinyl substituted with cyclohexyl having cyclohexyl substituted with propoxy,
imidazothiadiazolyl substituted with phenyl having methoxybutoxy,
imidazolthiadiazolyl substituted with phenyl having cyclohexyloxy,
imidazothiadiazolyl substituted with phenyl having piperazinyl substituted with cyclohexyl,
imidazolthiadiazolyl substituted with phenyl having piperidyl substituted with methoxypropoxy,
imidazothiadiazolyl substituted with phenyl having piperidyl substituted with methoxybutoxy,
imidazothiadiazolyl substituted with phenyl having piperidyl substituted with methoxypentyloxy,
imidazothiadiazolyl substituted with phenyl having piperidyl substituted with methoxyhexyloxy,
imidazothiadiazolyl substituted with phenyl having piperidyl substituted with methoxyhexylthio,
imidazothiadiazolyl substituted with phenyl having dimethylmorpholino,
phenyl substituted with propoxy having cyclohexyl and tert-butoxycarbonylamino,
phenyl substituted with propoxy having cyclohexyl and amino,
phenyl substituted with phenyl having pentyloxy,
phenyl substituted with thiazolyl having pentyl,
phenyl substituted with piperazinyl having cyclohexyl,
phenyl substituted with piperazinyl having phenyl substituted with dimethylmorpholino,
phenyl substituted with bezoxazolyl having pentyl, octyloxy,
pyrazolyl substituted with decyl,
pyrazolyl substituted with phenyl having hexyloxy,
pyrazolyl substituted with phenyl having piperidyl,
xylyl substituted with methoxyheptyloxy.

The more suitable example of "acyl group" may be benzoyl which has imidazolthiadiazolyl substituted with phenyl having pentyloxy, benzoyl which has thiadiazolyl substituted with phenyl having methoxyhexyloxy, benzoyl which has thiadiazolyl substituted with phenyl having methoxyoctyloxy, benzoyl which has thiadiazolyl substituted with phenyl having methoxyheptyloxy, benzoyl which has imidazothiadiazolyl substituted with phenyl having cyclohexyloxy, benzoyl which has imidazothiadiazolyl substituted with phenyl having dimethylmorpholino, benzoyl which has piperazinyl substituted with phenyl having methoxyheptyloxy, benzoyl which has piperazinyl substituted with phenyl having methoxyoctyloxy, benzoyl which has piperazinyl substituted with cyclohexyl having cyclohexyl, benzoyl which has thiadiazolyl substituted with phenyl having phenyl substituted with methoxyethoxy, benzoyl which has thiadiazolyl substituted with phenyl having phenyl substituted with methoxybutoxy, benzoyl which has thiadiazolyl substituted with phenyl having phenyl substituted with ethoxypropoxy, benzoyl which has imidazothiadiazolyl substituted with phenyl having piperazinyl substituted with cyclohexyl, benzoyl which has imidazothiadiazolyl substituted with phenyl having piperazinyl substituted with cyclohexyl,

- benzoyl which has thiazolyl substituted with phenyl having pentyloxy,
- benzoyl which has thiadiazolyl substituted with phenyl having methoxyheptyloxy,
- benzoyl which has thiadiazolyl substituted with phenyl having cyclohexyl,
- benzoyl which has thiadiazolyl substituted with phenyl having cyclohexyloxy,
- benzoyl which has thiadiazolyl substituted with phenyl having phenyl substituted with propoxy,
- benzoyl which has thiadiazolyl substituted with phenyl having phenyl substituted with ethoxymethyl,
- benzoyl which has thiadiazolyl substituted with phenyl having phenyl substituted with methoxypropoxy,
- benzoyl which has thiadiazolyl substituted with phenyl having phenyl substituted with dimethylmorpholino,
- benzoyl which has thiadiazolyl substituted with phenyl having piperazinyl substituted with cyclohexyl,
- benzoyl which has thiadiazolyl substituted with phenyl having piperazinyl substituted with methylcyclohexyl,
- benzoyl which has thiadiazolyl substituted with phenyl having piperidyl,
- benzoyl which has thiadiazolyl substituted with phenyl having piperidyl substituted with phenyl,
- benzoyl which has thiadiazolyl substituted with phenyl having piperidyl substituted with phenoxy,
- benzoyl which has thiadiazolyl substituted with phenyl having piperidyl substituted with benzyloxy,
- benzoyl which has thiadiazolyl substituted with phenyl having piperidyl substituted with methoxy and chlorophenyl,
- benzoyl which has thiadiazolyl substituted with phenyl having dimethylmorpholino,
- benzoyl which has pyrimidinyl substituted with phenyl having octyloxy,
- benzoyl which has isoxazolyl substituted with phenyl having pentyloxy,
- benzoyl which has isoxazolyl substituted with pentyl having methoxyhexyloxy,
- benzoyl which has isoxazolyl substituted with phenyl having methoxyheptyloxy,
- benzoyl which has isoxazolyl substituted with phenyl having heptyloxy substituted with dimethylmorpholino,
- benzoyl which has isoxazolyl substituted with phenyl having octyloxy substituted with dimethylmorpholino,
- benzoyl which has isoxazolyl substituted with phenyl having dimethylmorpholino,
- benzoyl which has oxadiazolyl substituted with phenyl having pentyloxy,
- benzoyl which has oxadiazolyl substituted with phenyl having methoxyheptyloxy,
- benzoyl which has oxadiazolyl substituted with phenyl having methoxynonyloxy,
- benzoyl which has oxadiazolyl substituted with phenyl having methoxyheptylsulfonyl,
- benzoyl which has oxadiazolyl substituted with phenyl having methoxynonylsulfonyl,
- benzoyl which has piperazinyl substituted with phenyl having methoxyhexyloxy,
- benzoyl which has piperazinyl substituted with phenyl having methoxyheptyloxy,
- benzoyl which has piperazinyl substituted with phenyl having phenoxypropoxy,
- benzoyl which has piperazinyl substituted with phenyl having cyclohexyl,
- benzoyl which has piperazinyl substituted with phenyl having phenyl substituted with methoxypentyloxyphenyl,
- benzoyl which has piperazinyl substituted with phenyl having phenyl substituted with dimethylmorpholino,
- benzoyl which has piperazinyl substituted with phenyl having piperidyl substituted with cyclohexyloxy,
- benzoyl which has piperazinyl substituted with phenyl having piperidyl substituted with phenyl,
- benzoyl which has piperazinyl substituted with phenyl having piperidyl substituted with methoxybutoxyphenyl,
- benzoyl which has piperazinyl substituted with phenyl having piperidyl substituted with propylthio,
- benzoyl which has piperazinyl substituted with phenyl having piperidyl substituted with methoxyhexylthio,
- benzoyl which has piperazinyl substituted with phenyl having piperidyl substituted with cyclobutanespiro,
- benzoyl which has piperazinyl substituted with phenyl having piperidyl substituted with dioxacyclobutanespiro,
- benzoyl which has piperazinyl substituted with phenyl having piperidyl substituted with methoxy and phenyl,
- benzoyl which has piperazinyl substituted with phenyl having piperidyl substituted with methoxy and chlorophenyl,
- benzoyl which has piperazinyl substituted with phenyl having dimethylmorpholino,
- benzoyl which has piperazinyl substituted with cyclohexyl having tert-butyl,
- benzoyl which has piperazinyl substituted with cyclohexyl having cyclohexyl and methoxy,
- benzoyl which has piperazinyl substituted with cyclohexyl having cyclohexyl substituted with propoxy,
- benzoyl which has imidazothiadiazolyl substituted with phenyl having methoxybutoxy,
- benzoyl which has imidazothiadiazolyl substituted with phenyl having cyclohexyloxy,
- benzoyl which has imidazothiadiazolyl substituted with phenyl having piperazinyl substituted with cyclohexyl,
- benzoyl which has imidazothiadiazolyl substituted with phenyl having piperidyl substituted with methoxypropoxy,
- benzoyl which has imidazothiadiazolyl substituted with phenyl having piperidyl substituted with methoxybutoxy, benzoyl which has imidazothiadiazolyl substituted with phenyl having piperidyl substituted with methoxypentyloxy, benzoyl which has imidazothiadiazolyl substituted with phenyl having piperidyl substituted with methoxyhexyloxy, benzoyl which has imidazothiadiazolyl substituted with phenyl having piperidyl substituted with methoxyhexylthio, benzoyl which has imidazothiadiazolyl substituted with phenyl having dimethylmorpholino, benzoyl which has phenyl substituted with propoxy having cyclohexyl and tert-butoxycarbonylamino, benzoyl which has phenyl substituted with propoxy having cyclohexyl and amino, benzoyl which has phenyl substituted with phenyl having pentyloxy, benzoyl which has phenyl substituted with thiazolyl having pentyl, benzoyl which has phenyl substituted with piperazinyl having cyclohexyl, benzoyl which has phenyl substituted with piperazinyl having phenyl substituted with dimethylmorpholino, benzoyl which has phenyl substituted with benzoxazolyl having pentyl, benzoyl which has octyloxy, thiadiazolylcarbonyl which has pyrazolyl substituted with decyl, thiadiazolylcarbonyl which has pyrazolyl substituted with phenyl having hexyloxy, thiadiazolylcarbonyl which has pyrazolyl substituted with phenyl having piperidyl, piperazinylcarbonyl which has xylyl substituted with methoxyheptyloxy, palmitoyl.

Suitable example of "lower alkyl" in the term of "lower alkyl which may have one or more suitable substituent(s)" can be referred to aforementioned "lower alkyl".

Suitable example of "suitable substituent(s)" in the term of "lower alkyl which may have one or more suitable substituent(s)" may be imino, amino, carbamoyl, lower alkoxy, heterocyclic group which may have one or more lower alkyl, carboxy, cyano(lower)alkylidene, lower alkylthio, sulfonic acid group, hydroxysulfonyloxy, and the like, in which the preferred one may be imino, amino, carbamoyl, lower alkoxy, pyrazolyl which may have lower alkyl, carboxy, hydroxy(lower)alkylamino which may have hydroxy(lower)alkyl, cyano(lower)alkylidene, lower alkylthio, sulfonic acid group or hydroxysulfonyloxy, and the more preferred one may be imino, amino, carbamoyl, methoxy, pyrazolyl which may have methyl, carboxy, hydroxyethylamino which may have hydroxymethyl, cyanomethylidene, sulfonic acid group or hydroxysulfonyloxy.

Suitable example of "lower alkyl which may have one or more suitable substituent(s)" may be iminomethyl, 1-iminoethyl, amidino, 1-imino-2-carbamoylethyl, 1-imino-3-methoxypropyl, carboxymethyl, 3-aminopropyl, 1-methylpyrazol-4-ylmethyl, methyl, pyrazolylmethyl having methyl, aminopropyl, aminobutyl, aminopentyl, carboxypentyl, carboxymethyl, cyanomethylidenemethylthiomethyl, 2-cyano-1-methylthiovinyl, 2-cyano-1-aminovinyl, sulfopropyl, sulfobutyl, hydroxysulfonyloxypropyl and carboxyethyl.

Suitable example of "acyl group" of $R^2$ and $R^3$ can be referred to aforementioned "acyl group", in which the preferred one may be lower alkanoyl, ar(lower)alkoxycarbonyl, lower alkenyloxycarbonyl, lower alkoxycarbonyl which may have lower alkanoyloxy, heterocyclic(lower)alkoxycarbonyl which may have oxo and lower alkyl, amino(lower)alkanoyl which may have amino or hydroxy, heterocyclic(lower)alkanoyl which may have amino, sulfonic acid group, heterocycliccarbonyl, mono or di lower alkylcarbamoyl, and the most preferred one may be acetyl, sulfo, 2,5-diaminopentanoyl, fluorenylmethoxycarbonyl, allyloxycarbonyl, tert-butoxycarbonyl, 1,3-dioxy-2-oxo-4-methyl-4-cyclopenten-5-ylmethoxycarbonyl, acetyloxymethoxycarbonyl, aminopropionyl, aminopentanoyl, aminohexanoyl, 5-amino-2-hydroxybutanoyl, 2,6-diaminohexanoyl, 2-amino-3-(pyrazol-4-yl)propionyl, morpholinocarbonyl, dimethylcarbamoyl, diethylcarbamoyl or pyrrolidin-1-ylcarbonyl.

Suitable example of "suitable substituent(s)" in the term of "heterocyclic group which may have one or more suitable substituent(s)" of $R^2$ and $R^3$ may be lower alkyl, hydroxy(lower)alkyl, carboxy(lower)alknonoyl which may have amino and heterocycliccarbonyl, cyclo(lower)alkyl, oxo, and the like.

Suitable example of "heterocyclic group which may have one or more suitable substituent(s)" of $R^2$ and $R^3$ may be piperidyl which may have one or more suitable substituent(s) selected from the group consisting of lower alkyl, hydroxy(lower)alkyl, carboxy(lower)alkanoyl which may have amino and heterocycliccarbonyl; 1,3-dioxacyclohexyl which may have one or more suitable substituent(s) selected from the group consisting of lower alkyl and cyclo(lower)alkyl; thiopyranyl which may have one or more oxo; in which the most preferred one may be N,N-dimethylpiperidyl, N-hydroxyethyl-N-methylpiperidyl, carboxypropanoylpiperidyl, 4-amino-4-carboxybutanoylpiperidyl, azetidinylcarbonylpiperidyl, dimethyl-1,3-dioxacyclohexyl, cyclohexyl-1,3-dioxacyclohexyl, dioxopyranyl.

Suitable example of "lower alkylidene which may have one or more suitable substituent(s)" of $R^2$ and $R^3$ may be lower alkylidene which may have one or more lower alkylamino, in which the preferred one may be dimethylaminomethylidene.

Suitable example of "higher alkyl which may have one or more suitable substituent(s)" of $R^2$ and $R^3$ may be higher alkyl which may have one or more carboxy, in which the preferred one may be carboxyoctyl.

Suitable example of "acyl" moiety of "acyloxy" can be referred to aforementioned "acyl group", in which the preferred one may be lower alkenyloxycarbonyl, and the most preferred one may be allyloxycarbonyl.

Suitable example of "acyloxy" may be lower alkenyloxycarbonyloxy, and the more preferred one may be allyloxycarbonyloxy.

Suitable example of "amino protective group" may be included in aforementioned "acyl group", a conventional protective group such as ar(lower)alkoxycarbonyl and lower alkoxycarbonyl, in which the preferred one may be phenyl$(C_1-C_4)$alkoxycarbonyl and fluorenyl$(C_1-C_4)$ alkoxycarbonyl and $(C_1-C_4)$alkoxycarbonyl, and the most preferred one may be benzyloxycarbonyl, fluorenylmethoxycarbonyl and tert-butoxycarbonyl.

Suitable example of "protected amino" may be amino substituted with aforementioned "acyl group", a conventional protected amino such as ar(lower)alkoxycarbonylamino and lower alkoxycarbonylamino, in which the preferred one may be phenyl$(C_1-C_4)$ alkoxycarbonylamino and fluorenyl($C_1$–$C_4$) alkoxycarbonylamino and ($C_1$–$C_4$)alkoxycarbonylamino, and the most preferred one may be benzyloxycarbonylamino, fluorenylmethoxycarbonylamino and tert-butoxycarbonylamino.

Particularly, the preferred examples of the compound (I) in the present invention are as follows: the compound (I), wherein $R^1$ is hydrogen; lower alkoxycarbonyl;
  aroyl which has heterocyclic group substituted with aryl having a suitable substituent selected from the group consisting of lower alkoxy, lower alkoxy(lower)alkoxy, lower alkoxy(higher)alkoxy, aryl substituted with lower alkoxy(lower)alkoxy, cyclo(lower)alkyl, cyclo(lower)alkyloxy, aryl substituted with lower alkoxy, aryl substituted with lower alkoxy(lower)alkyl, aryl substituted with heterocyclic group, heterocyclic group substituted with cyclo(lower)alkyl, heterocyclic group, heterocyclic group substituted with aryl, heterocyclic group substituted with aryloxy, heterocyclic group substituted with ar(lower)alkoxy, heterocyclic group substituted with lower alkoxy and aryl, higher alkoxy, heterocyclic (higher)alkoxy, lower alkoxy(higher)alkylsulfonyl, aryloxy(lower)alkoxy, heterocyclic group substituted with cyclo(lower)alkyloxy, heterocyclic group substituted with aryl having lower alkoxy(lower)alkyl, heterocyclic group substituted with lower alkylthio, heterocyclic group substituted with lower alkoxy(lower)alkylthio, and heterocyclic group substituted with lower alkoxy(lower)alkoxy;
  aroyl which has aryl substituted with a suitable substituent selected from the group consisting of lower alkoxy having cyclo(lower)alkyl and amino, lower alkoxy having cyclo(lower)alkyl and protected amino, aryl having lower alkoxy, heterocyclic group having lower alkyl, heterocyclic group having cyclo(lower)alkyl, and heterocyclic group having aryl substituted with heterocyclic group;
  aroyl which has heterocyclic group substituted with cyclo(lower)alkyl having one or more suitable substituent(s) selected from the group consisting of lower alkyl, lower alkoxy, cyclo(lower)alkyl, and cyclo(lower)alkyl substituted with lower alkoxy;
  higher alkanoyl;
  aroyl which has higher alkoxy; or
  heterocycliccarbonyl which has a suitable substituent(s) selected from the group consisting of heterocyclic group substituted with higher alkyl, heterocyclic group substituted with aryl having lower alkoxy, heterocyclic group substituted with aryl having heterocyclic group, and aryl substituted with lower alkoxy(higher)alkoxy, $R^2$ and $R^3$ are independently hydrogen;
  lower alkyl which may have one or more suitable substituent(s) selected from the group consisting of amino, carboxy, sulfinic acid group, sulfonic acid group, hydroxy(lower)alkylamino which may have hydroxy(lower)alkyl, hydroxysulfonyloxy, imino, lower alkoxy, oxo, lower alkylthio, cyano(lower)alkylidene, and heterocyclic group which may have one or more lower alkyl;
  lower alkoxycarbonyl which may have one or more suitable substituent(s) selected from the group consisting of lower alkanoyloxy and heterocyclic group;
  lower alkenyloxycarbonyl;
  ar(lower)alkoxycarbonyl;
  lower alkanoyl which may have one or more suitable substituent(s) selected from the group consisting of amino, hydroxy and heterocyclic group;
  heterocycliccarbonyl;
  mono or di(lower)alkylcarbamoyl;
  sulfonic acid group;
  heterocyclic group which may have one or more suitable substituent(s) selected from the group consisting of lower alkyl, hydroxy(lower)alkyl, carboxy(lower)alkanoyl which may have amino, heterocycliccarbonyl, cyclo(lower)alkyl, and oxo;
  lower alkylidene which may have mono or di lower alkylamino;
  carboxy(higher)alkyl or
  cyano;

$R^4$ is hydrogen or hydroxy;
$R^5$ is hydrogen, hydroxy, lower alkoxy or hydroxysulfonyloxy; and
$R^6$ is hydroxy or lower alkenyloxycarbonyloxy, the more preferred one is the compound (I), wherein $R^1$ is hydrogen; ($C_1$–$C_4$)alkoxycarbonyl;
  benzoyl which has thiazolyl substituted with phenyl having ($C_4$–$C_6$)alkoxy;
  benzoyl which has thiadiazolyl substituted with phenyl having a suitable substituent selected from the group consisting of ($C_1$–$C_4$)alkoxy($C_4$–$C_6$)alkoxy, phenyl substituted with ($C_1$–$C_4$)alkoxy($C_1$–$C_4$)alkoxy, ($C_1$–$C_4$)alkoxy($C_7$–$C_{14}$)alkoxy, cyclo($C_4$–$C_6$)alkyl, cyclo($C_4$–$C_6$)alkyloxy, phenyl substituted with ($C_1$–$C_4$)alkoxy, phenyl substituted with ($C_1$–$C_4$)alkoxy($C_1$–$C_4$)alkyl, phenyl substituted with di($C_1$–$C_4$)alkylmorpholino, piperazinyl substituted with cyclo($C_4$–$C_6$)alkyl, piperazinyl substituted with cyclo($C_4$–$C_6$)alkyl having ($C_1$–$C_4$)alkyl; piperidyl, piperidyl substituted with phenyl, piperidyl substituted with phenoxy, piperidyl substituted with benzyloxy, piperidyl substituted with ($C_1$–$C_4$)alkoxy and chlorophenyl, and phenyl having di($C_1$–$C_4$)alkylmorpholino;
  benzoyl which has pyrimidinyl substituted with phenyl having ($C_7$–$C_{14}$)alkoxy;
  benzoyl which has isoxazolyl substituted with phenyl having a suitable substituent selected from the group consisting of ($C_4$–$C_6$)alkoxy, ($C_1$–$C_4$)alkoxy($C_4$–$C_6$)alkoxy, ($C_1$–$C_4$)alkoxy($C_7$–$C_{14}$)alkoxy, ($C_7$–$C_{14}$)alkoxy substituted with di($C_1$–$C_4$)alkylmorpholino, and di($C_1$–$C_4$)alkylmorpholino;
  benzoyl which has oxadiazolyl substituted with phenyl having a suitable substituent selected from the group consisting of ($C_4$–$C_6$)alkoxy, ($C_1$–$C_4$)alkoxy($C_7$–$C_{14}$)alkoxy, ($C_1$–$C_4$)alkoxy($C_7$–$C_{14}$)alkoxy, and ($C_1$–$C_4$)alkoxy($C_7$–$C_{14}$)alkylsulfonyl;
  benzoyl which has piperazinyl substituted with phenyl having a suitable substituent selected from the group consisting of ($C_1$–$C_4$)alkoxy($C_4$–$C_6$)alkoxy, ($C_1$–$C_4$)alkoxy($C_7$–$C_{14}$)alkoxy, phenoxy($C_1$–$C_4$)alkoxy, cyclo($C_4$–$C_6$)alkyl, phenyl substituted with ($C_1$–$C_4$)alkoxy($C_4$–$C_6$)alkoxyphenyl, phenyl substituted with di($C_1$–$C_4$)alkylmorpholino, piperidyl substituted with cyclo($C_4$–$C_6$)alkyloxy, piperidyl substituted with phenyl, piperidyl substituted with ($C_1$–$C_4$)alkoxy($C_1$–$C_4$)alkoxyphenyl, piperidyl substituted with ($C_1$–$C_4$)alkylthio, piperidyl substituted with ($C_1$–$C_4$)alkoxy($C_4$–$C_6$)alkylthio, piperidyl substituted with cyclo($C_4$–$C_6$)alkanespiro, piperidyl substituted with dioxacyclo($C_4$–$C_6$)alkanespiro, piperidyl substituted with ($C_1$–$C_4$)alkoxy and phenyl, piperidyl substituted with $(C_1-C_4)$alkoxy and chlorophenyl, and di$(C_1-C_4)$alkylmorpholino;

benzoyl which has piperazinyl substituted with cyclo$(C_4-C_6)$alkyl having a suitable substituent selected from the group consisting of cyclo$(C_4-C_6)$alkyl, $(C_4-C_6)$alkyl, cyclo$(C_4-C_6)$alkyl and $(C_1-C_4)$ alkoxy, and cyclo$(C_4-C_6)$alkyl substituted with $(C_1-C_4)$alkoxy;

benzoyl which has imidazolthiadiazolyl substituted with phenyl having a suitable substituent selected from the group consisting of $(C_4-C_6)$alkoxy, $(C_1-C_4)$alkoxy$(C_4-C_6)$alkoxy, cyclo$(C_4-C_6)$ alkyloxy, piperazinyl substituted with cyclo$(C_4-C_6)$ alkyl, piperidyl substituted with $(C_1-C_4)$alkoxy $(C_1-C_4)$alkoxy, piperidyl substituted with $(C_1-C_4)$ alkoxy$(C_4-C_6)$alkoxy, piperidyl substituted with $(C_1-C_4)$alkoxy$(C_4-C_6)$alkylthio, and di$(C_1-C_4)$ alkylmorpholino;

benzoyl which has phenyl substituted with a suitable substituent selected from the group consisting of $(C_1-C_4)$alkoxy having cyclo$(C_4-C_6)$alkyl and $(C_1-C_4)$alkoxycarbonylamino, $(C_1-C_4)$alkoxy having cyclo$(C_4-C_6)$alkyl and amino, phenyl having $(C_4-C_6)$alkoxy, thiazolyl having $(C_4-C_6)$alkyl, piperazinyl having cyclo$(C_4-C_6)$alkyl, piperazinyl having phenyl substituted with di$(C_1-C_4)$ alkylmorpholino, and benzoxazolyl having $(C_4-C_6)$ alkyl;

benzoyl which has $(C_7-C_{14})$alkoxy;

thiadiazolylcarbonyl which has pyrazolyl substituted with a suitable substituent selected from the group consisting of $(C_7-C_{14})$alkyl, phenyl having $(C_4-C_6)$ alkoxy, and phenyl having piperidyl;

piperazinylcarbonyl which has xylyl substituted with $(C_1-C_4)$alkoxy$(C_7-C_{14})$alkoxy; or $(C_7-C_{14})$ alkanoyl;

$R^2$ and $R^3$ are independently hydrogen;

$(C_1-C_6)$alkyl which may have 1 or 2 suitable substituent(s) selected from the group consisting of amino, carboxy, sulfinic acid group, sulfonic acid group, hydroxy$(C_1-C_4)$alkylamino which may have hydroxy$(C_1-C_4)$alkyl, hydroxysulfonyloxy, imino, $(C_1-C_4)$alkoxy, oxo, cyano$(C_2-C_4)$alkylidene, $(C_1-C_4)$alkylthio, and pyrazolyl which may have $(C_1-C_4)$alkyl;

$(C_1-C_4)$alkoxycarbonyl which may have $(C_1-C_4)$ alkanoyloxy, dioxacyclo$(C_4-C_6)$alkenyl which may have oxo, and $(C_1-C_4)$alkyl;

fluorenyl$(C_1-C_4)$alkoxycarbonyl;

$(C_2-C_4)$alkenyloxycarbonyl;

$(C_1-C_6)$alkanoyl which may have 1 or 2 suitable substituent(s) selected from the group consisting of amino, hydroxy and pyrazolyl;

pyrrolidinylcarbonyl;

morpholinocarbonyl;

mono or di$(C_1-C_4)$alkylcarbamoyl;

sulfonic acid group;

piperidyl which may have 1 or 2 suitable substituent(s) selected from the group consisting of $(C_1-C_4)$alkyl, hydroxy$(C_1-C_4)$alkyl, carboxy$(C_1-C_4)$alkanoyl which may have amino, and azetidinylcarbonyl;

dioxacyclo$(C_4-C_6)$alkyl which may have 1 or 2 suitable substituent(s) selected from the group consisting of $(C_1-C_4)$alkyl, and cyclo$(C_4-C_6)$alkyl;

thiopyranyl which may have 1 or 2 oxo;

$(C_2-C_4)$alkylidene which may have mono or di$(C_1-C_4)$ alkylamino;

carboxy$(C_7-C_{14})$alkyl or cyano, $R^4$ is hydrogen or hydroxy, $R^5$ is hydrogen, hydroxy, $(C_1-C_4)$alkoxy or hydroxysulfonyloxy, and $R^6$ is hydroxy or $(C_2-C_4)$alkenyloxycarbonyloxy.

Process 1

The object compound (Ia) or a salt thereof can be prepared by reducing a compound (II) or a salt thereof.

Suitable salts of the compounds (Ia) and (II) may be the same as those exemplified for the compound (I).

The reaction can be carried out in a conventional manner namely, chemical reduction or catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, hydride transfer reagent such as aluminum hydride compound (e.g. lithium aluminum hydride, lithium hydridotri-t-butoxyaluminate, etc.), borohydride compound (e.g. sodium borohydride, sodium cyanoborohydride, etc.) or the like etc.].

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g., spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reaction of this process is usually carried out in a solvent such as water, alcohol [e.g. methanol, ethanol, propanol, etc.], acetic acid, diethyl ether, dioxane, tetrahydrofuran, methylene chloride, etc. or a mixture thereof.

The reaction is preferably carried out under somewhat milder conditions such as under cooling to warming.

It is included within the scope of the present invention that "hydroxy" in $R^4$ may be reduced to "hydrogen" during the reaction.

Process 2

The object compound (Ib) or a salt thereof can be prepared by subjecting the compound (Ia) or a salt thereof to protective reaction of amino.

This protective reaction may include acylation or alkylation reaction of amino and the like, and can be carried out according to a conventional manner such as the one described in Examples or the similar manners thereto.

Process 3

The object compound (Id) or a salt thereof can be prepared by subjecting the compound (Ic) or its reactive derivative at the sulfonic acid group or a salt thereof to hydrolysis reaction of the sulfonic acid group.

The hydrolysis is preferably carried out in the presence of a base or an acid including Lewis acid.

Suitable base may include an inorganic base and an organic base such as an alkali metal [e.g., sodium potassium, etc.], an alkaline earth metal [e.g., magnesium, calcium, etc.], the hydroxide or carbonate or hydrogencarbonate thereof, trialkylamine [e.g. trimethylamine, triethylamine, etc.], picoline, 1,5-diazabicyclo[4.3.0]non-5-ene, or the like.

Suitable acid may include an organic acid [e.g., formic acid, acetic acid, propionic acid, trichloroacetic acid, trifluoroacetic acid, etc.], and an inorganic acid [e.g., hydrochloric acid, hydrobromic acid, sulfuric acid, hydrogen chloride, hydrogen bromide, etc.].

The elimination using Lewis acid such as trihaloacetic acid [e.g., trichloroacetic acid, trifluoroacetic acid, etc.], or the like preferably carried out in the presence of cation trapping agent [e.g., anisole, phenol, etc.].

The reaction is usually carried out in a conventional solvent such as water, alcohol [e.g. methanol, ethanol, isopropyl alcohol, etc.], tetrahydrofuran, dioxane, toluene, methylene chloride, ethylene dichloride, chloroform, N,N-dimethylformamide, N,N-dimethylacetamide or any other organic solvent which do not adversely affect the reaction, or the mixture thereof.

The reaction temperature is not critical and the reaction is usually carried out under cooling to warming.

Process 4

The object compound (If) or a salt thereof can be prepared by subjecting a compound (Ie) or a salt thereof to elimination reaction of amino protective group.

This reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium, sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman. copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

Process 5

The compound (Ig) or a salt thereof can be prepared by reducing the compound (II) or a salt thereof, and then reacting with the compound (IV) of the formula:

$$R_c^3\text{—OH} \qquad (IV)$$

(wherein $R_c^3$ is acyl group) or its reactive derivative, or a salt thereof.

Suitable reactive derivative of the compound (IV) may include an acid halide, an acid anhydride, an activated ester, and the like. The suitable example may be an acid chloride; acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.); aromatic carboxylic acid (e.g., benzoic acid, etc.); a symmetrical acid anydride; an activated amide with imidazole, 4-substitutd imidazole, dimethylpyrazole, triazole or tetrazole; an activated ester (e.g., cyanomethyl, ester methoxymethyl ester, dimethyliminomethyl [$(CH_3)_2N^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthioester, p-nitrophenyl thioester, p-cresyl thioester, carboxymethyl thioester, pyranyl ester, pyridyl ester, piperidyl ester, 8-quinolyl thioester, etc.); an ester with a N-hydroxy compound (e.g., N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.); and the like. These reactive derivatives can optionally be selected from them according to the kind of the compound (IV) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which do not adversely affect the reaction, or the mixture thereof.

When the compound (IV) is used in free acid form or its salt form in the reaction, the reaction is preferably carried out in the presence of a conventional condensing agent such as N,N'-dicyclohexylcarbodiimide; N-cyclohexyl-N'-morphoinoethylcarbodiimide); N-cyclohexyl-N'-(4-diethylaminocyclohexyl)carbodiimide; N,N'-diisopropylcarboxiimide; N-ethyl-N'-(3-dimethylaminopropyl)carbodiimide; N,N-carbonyl-bis(2-methylimidazole); pentamethyleneketene-N-cyclohexylimine; diphenylketene-N-cyclohexylimine, ethoxyacetylene; 1-alkoxy-1-chloroethylene; trialkyl phosphite; isopropyl polyphosphate; phosphorous oxychloride (phosphoryl chloride); phosphorous trichloride; thionyl chloride; oxalyl chloride; triphenylphosphite; 2-ethyl-7-hydroxybenzisoxazolium salt; 2-ethyl-5-(m-sulfophenyl) isoxazolium hydroxide intra-molecular salt; 1-(p-chlorobenzenesulfonyloxy)-6-chloro-1H-benzotriazole: so-called Vilsmeier reagent prepared by the reaction of N,N-dimethylformamide with thionyl chloride, phosgene, phosphorous oxychloride, etc.; or the like.

The reaction may also be carried out in the presence of an organic or inorganic base such as an alkali metal bicarbonate, tri(lower)alkylamine (e.g., triethylamine, diisopropylethylamine, etc.), pyridine, di(lower) alkylaminopyridine (e.g., 4-dimethylaminopyridine, etc.) N-(lower)alkylmorphorine, N,N-di(lower) alkylbenzylamine, or the like.

The reaction temperature is not critical, and the reaction is usually carried out under cooling to heating.

Process 6

The object compound (Ii) or a salt thereof can be prepared by reacting the compound (Ih) or a salt thereof with the compound (V) of the formula:

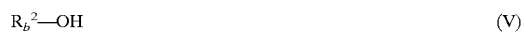

$$R_b^2\text{—OH} \qquad (V)$$

(wherein $R_b^2$ is acyl group)
or its reactive derivative, or a salt thereof.

This reaction can be carried out according to a conventional manner such as the one described in Process 5, Examples or the similar manner thereto.

Process 7

The object compound (Ik) or a salt thereof can be prepared by reacting the compound (Ij) or its reactive derivative at the amino group or a salt thereof with the compound (III) or its reactive derivative at the carboxy group or a salt thereof.

Suitable reactive derivative at the carboxy group of the compound (III) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g., dialkylphosphoric acid, phenylphosphoric acid, diphenylphosphoric acid, dibenzylphosphoric acid, halogenated phosphoric acid, etc.], dialkylphosphorous acid, sulfurous acid, thiosuluric acid, sulfuric acid, sulfonic acid [e.g., methanesulfonic acid, etc.], aliphatic carboxylic acid [e.g., acetic acid, propionic acid, butyric acid, isobutyric acid, pivaric acid, pentanoic acid, isopentanoic acid, 2-ethylbutyric acid, trichloroacetic acid, etc.]; or aromatic carboxylic acid [e.g., benzoic acid, etc.]; a symmetrical acid anhydride; an activated amide with imidazole, 4-substituted imidazole, dimethylpyrazole, triazole, tetrazole or 1-hydroxy-1H-benzotriazole; or an activated ester [e.g., cyanomethyl ester, methoxymethyl ester, dimethyliminomethyl [(CH$_3$)$_2$N$^+$=CH—] ester, vinyl ester, propargyl ester, p-nitrophenyl ester, 2,4-dinitrophenyl ester, trichlorophenyl ester, pentachloropentyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)pyridone, N-hydroxysuccinimide, N-hydroxyphthalimide, 1-hydroxy-1H-benzotriazole, etc.], and the like. These reactive derivatives can optionally be selected from them according to the kind of the compound (III) to be used.

Suitable salts of the compound (III) and its reactive derivative can be referred to the ones as exemplified for the object compound (I).

The reaction is usually carried out in a conventional solvent such as water, alcohol [e.g., methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may also be used in a mixture with water.

In this reaction, when the compound (III) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine, ethoxyacetylene; 1-alkoxy-2-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g., ethyl chloroformate, isopropyl chloroformate, etc.]; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorous oxychloride, methanesulfonyl chloride, etc.; or the like.

The reaction may also be carried out in the presence of an inorganic or organic base such as an alkali metal carbonate alkali metal bicarbonate, tri(lower)alkylamine (e.g., triethylamine, diisopropylethylamine, etc.), pyridine, di(lower)alkylaminopyridine (e.g., 4-dimethylaminopyridine, etc.) N-(lower)alkylmorpholine, N,N-di(lower)alkylbenzylamine, or the like.

The reaction temperature is not critical, and the reaction is usually carried out under cooling to warming.

Process A

The object compound (IIa) or a salt thereof can be prepared by reacting the compound (IIb) or its reactive derivative at the amino group or a salt thereof with the compound (III) or its reactive derivative at the carboxy group or a salt thereof.

Suitable reactive derivative at the carboxy group of the compound (III) may include an acid halide, an acid anhydride, an activated amide, an activated ester, and the like.

Suitable examples of the reactive derivatives may be an acid chloride; an acid azide; a mixed acid anhydride with an acid such as substituted phosphoric acid [e.g., dialkylphosphoric acid, phenylphosphoric acid, diphenylphosphoric acid, dibenzylphosphoric acid, halogenated phosphoric acid, etc.], dialkylphosphorous acid, sulfurous acid, thiosulturic acid, sulfuric acid, sulfonic acid [e.g., methanesulfonic acid, etc.], aliphatic carboxylic acid [e.g., acetic acid, propionic acid, butyric acid, isobutyric acid, pivaric acid, pentanoic acid, isopentanoic acid, 2-ethylbutyric acid trichloroacetic acid, etc.]; or aromatic carboxylic acid [e.g., benzoic acid, etc.]; a symmetrical acid, anhydride; an activated amide with imidazole, 4-substituted imidazole, dimethylpyrazole, triazole, tetrazole or 1-hydroxy-1H-benzotriazole; or an activated ester [e.g., cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachloropentyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (III) to be used.

Suitable salts of the compound (III) and its reactive derivative can be referred to the ones as exemplified for the object compound (I).

The reaction is usually carried out in a conventional solvent such as water, alcohol [e.g., methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (III) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine, ethoxyacetylene; 1-alkoxy-2-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g., ethyl chloroformate, isopropyl chloroformate, etc.]; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorous oxychloride, methanesulfonyl chloride, etc.; or the like.

The reaction may also be carried out in the presence of an inorganic or organic base such as an alkali metal carbonate, alkali metal bicarbonate, tri(lower)alkylamine (e.g., triethylamine, diisopropylethylamine, etc.), pyridine, di(lower)alkylaminopyridine (e.g., 4-dimethylaminopyridine, etc.), N-(lower)alkylmorpholine, N,N-di(lower)alkylbenzylamine, or the like.

The reaction temperature is not critical, and the reaction is usually carried out under cooling to warming.

The compounds obtained by the above Processes 1 to 7 and Process A can be isolated and purified by a conventional method such as pulverization, recrystallization, column-chromatography, high-performance liquid chromatography (HPLC), reprecipitation, desalting resin column chromatography, or the like.

The compounds obtained by the above Processes 1 to 2 and Process A may be obtained as its solvate, such as hydrate, and its solvate, such as hydrate is included within the scope of the present invention.

It is to be noted that each of the object compound (I) may include one or more stereoisomer such as optical isomer(s) and geometrical isomer(s) due to asymmetric carbon atom(s) and double bond(s) and all such isomers and the mixture thereof are included within the scope of the present invention.

The object compound (I) or a salt thereof may include solvated compound [e.g., enclosure compound (e.g., hydrate, etc.)].

The object compound (I) or a salt thereof may include both its crystal form and non-crystal form.

It should be understood that the compounds in the present invention may include the prodrug form.

The patent applications and publications cited herein are incorporated by reference.

Biological Property of the Polypeptide Compound (I) of the Present Invention

In order to show the usefulness of the polypeptide compound (I) of the present invention, the biological data of the representative compound is explained in the following.

Test (Antimicrobial Activity):

In vitro antimicrobial activity of the object compound of Example 5 disclosed later was determined by $MIC_S$ in mouse serum as described below.

Test Method:

The $MIC_S$ in mouse serum were determined by the microdilution method using ICR mouse serum buffered with 20 mM HEPES buffer (pH 7.3) as a test medium. Inoculum suspension of $10^6$ cells/ml were prepared by a hemocytometric procedure and diluted to obtain an inoculum size of approximately $1.0\times10^3$ cells/ml. Microplates were incubated at 37° C. for 24 hours in 5% $CO_2$. The $MIC_S$ were defined as the lowest concentrations at which no visible growth was observed.

Test Result:

| | MIC ($\mu$g/ml) |
|---|---|
| Test organism | Test compound The object compound of Example 5 |
| *Candida albicans* FP-633 | <0.3 |

From the test result, it is realized that the object compound (I) of the present invention has an, antimicrobial activity (especially, antifungal activity).

In more details, the object compound (I) of the present invention have an antifungal activity, particularly against the following fungi.

Acremonium;
Absidia (e.g., *Absidia corymbifera*, etc);
Aspergillus (e.g., *Aspergillus clavatus, Aspergillus flavus, Aspergillus fumigatus, Aspergillus nidulans, Aspergillus niger, Aspergillus terreus, Aspergillus versicolor*, etc);
Blastomyces (e.g., *Blastomyces dermatitidis*, etc);
Candida (e.g., *Candida albicans, Candida glabrata, Candida guilliermondii, Candida kefyr, Candida krusei, Candida parapsilosis, Candida stellatoidea, Candida tropicalis, candida utilis*, etc.);
Cladosporium (e.g., *Cladosporium trichloides*, etc);
Coccidioides (e.g., *Coccidioides immitis*, etc);
Cryptococcus (e.g., *Cryptococcus neoformans*, etc);
Cunninghamella (e.g., *Cunninghamella elegans*, etc);
Dermatophyte;
Exophiala (e.g., *Exophiala dermatitidis, Exophiala spinifera*, etc);
Epidermophyton (e.g., *Epidermophyton floccosum*, etc);
Fonsecaea (e.g., *Fonsecaea pedrosoi*, etc);
Fusarium (e.g., *Fusarium solani*, etc);
Geotrichum (e.g., *Geotrichum candiddum*, etc);
Bistoplasma (e.g., *Histoplasma capsulatum* var. *capsulatum*, etc).
Malassezia (e.g., *Malassezia furfur*, etc);
Hicrosporum (e.g., *Microsporum canis, Microsporum gypseum*, etc);
Mucor;
Paracoccidioides (e.g., *Paracoccidioides brasiliensis*, etc);
Penicillium (e.g., *Penicillium marneffei*, etc);
Phialophora;
Pneumocystis (e.g., *Pneumocystis carinii*, etc);
Pseudallescheria (e.g., *Pseudallescheria boydii*, etc);
Rhizopus (e.g., *Rhizopus microsporus* var. *rhizopodiformis, Rhizopus oryzae*, etc);
Saccharomyces (e.g., *Saccharomyces cerevisiae*, etc);
Scopulariopsis;
Sporothrix (e.g., *Sporothrix schenckii*, etc);
Trichophyton (e.g., *Trichophyton mentagrophytes, Trichophyton rubrum*, etc)
Trichosporon (e.g., *Trichosporon asahii, Trichosporon cutaneum*, etc).

The above fungi are well-known to cause various infection diseases in skin, hair, nail, oral mucosa, gastrointestinal tract, bronchus, lung, endocardium, brain, meninges, urinary organ, vaginal protion, oral cavity, ophthalmus, systemic, kidney, bronchus, heart, external auditory canal, bone, nasal cavity, paranasal cavity, spleen, liver, hypodermal tissue, lymph doct, gastrointestine, articulation, muscle, tendon, interstitial plasma cell in lung, and so on.

Therefore, the object compound (I) of the present invention are useful for preventing and treating various infectious diseases, such as dermatophytosis (e.g., trichophytosis, etc), pityriasis versicolor, candidiasis, cryptococcosis, geotrichosis, trichosporosis, aspergillosis, penicilliosis, fusariosis, zygomycosis, sporotrichosis, chromomycosis, coccidioidomycosis, histoplasmosis, blastomycosis, paracoccidioidomycosis, pseudallescheriosis, mycetoma, mycotic keratitis, otomycosis, pneumocystosis, and so on.

The pharmaceutical composition of the present invention can be used in the form of a pharmaceutical preparation, for example, in solid, semisolid or liquid form, which contains the object compound (I) or a pharmaceutically acceptable salt thereof, as an active ingredient in admixture with an organic or inorganic carrier or excipient which is suitable for rectal; pulmonary (nasal or buccal inhalation); ocular; external (topical); oral administration; parenteral (including subcutaneous, intravenous and intramuscular) administrations; insufflation (including aerosols from metered dose inhalator); nebulizer; or dry powder inhalator.

The active ingredient may be compounded, for example, with the usual non-toxic, pharmaceutically acceptable carriers in a solid form such as granules, tablets, dragees, pellets, troches, capsules, or suppositories; creams; ointments; aerosols; powders for insufflation; in a liquid form such as solutions, emulsions, or suspensions for injection; ingestion; eye drops; and any other form suitable for use. And, if necessary, there may be included in the above preparation auxiliary substance such as stabilizing, thickening, wetting, emulsifying and coloring agents; perfumes or buffer; or any other commonly may be used as additives.

The object compound (I) or a pharmaceutically acceptable salt thereof is/are included in the pharmaceutical composition in an amount sufficient to produce the desired antimicrobial effect upon the process or condition of diseases.

For applying the composition to humans, it is preferable to apply it by intravenous, intramuscular, pulmonary, oral administration, eye drop administration or insufflation. While the dosage of therapeutically effective amount of the object compound (I) varies from and also depends upon the age and condition of each individual patient to be treated, in the case of intravenous administration, a daily dose of 0.01–20 mg of the object compound (I) per kg weight of human being in the case of intramuscular administration, a daily dose of 0.1–20 mg of the object compound (I) per kg weight of human being, in case of oral administration, a daily dose of 0.5–50 mg of the object compound (I) per kg weight of human being is generally given for treating or preventing infectious diseases.

Especially in case of the treatment of prevention of *Pneumocystis carinii* infection, the followings are to be noted.

For administration by inhalation, the compounds of the present invetion are conveniently delivered in the form of an aerosol spray presentation form pressurized as powders which may be formulated and the powder compositions may be inhaled with the aid of an insufflation powder inhaler device. The preferred delivery system for inhalation is a metered dose inhalation aerosol, which may be formulated as a suspension or solution of compound in suitable propellants such as fluorocarbons or hydrocarbons.

Because of desirability to directly treat lung and bronchi, aerosol administration is a preferred method of administration. Insufflation is also a desirable method, especially where infection may have spread to ears and other body cavities.

Alternatively, parenteral administration may be employed using drip intravenous administration.

The following Preparations and Examples are given for the purpose of illustrating the present invention in more detail.

The Starting Compounds used and the Object Compounds obtained in the following Preparations 1 to 23 are given in the table as below, in which the formulas of the starting compounds are in the upper column and the formulas of the object compounds are in the lower column, respectively.

| Preparation No. | Formula |
|---|---|
| 1 | 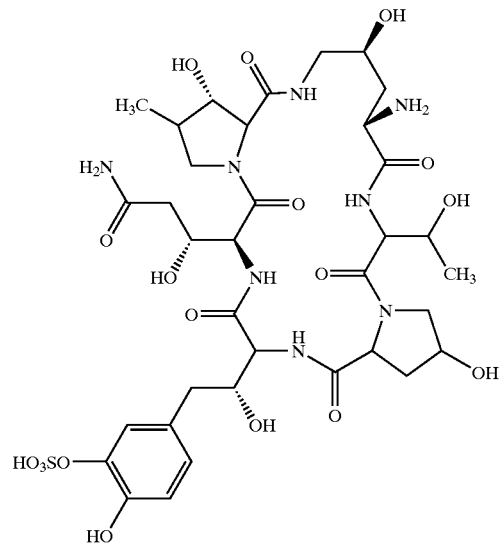 |
| | 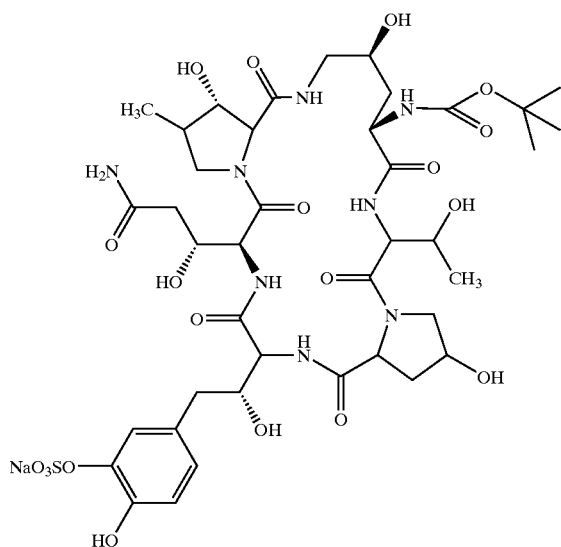 |

| Preparation No. | Formula |
|---|---|
| 2 | |

-continued
| Preparation No. | Formula |
|---|---|
| 3 | 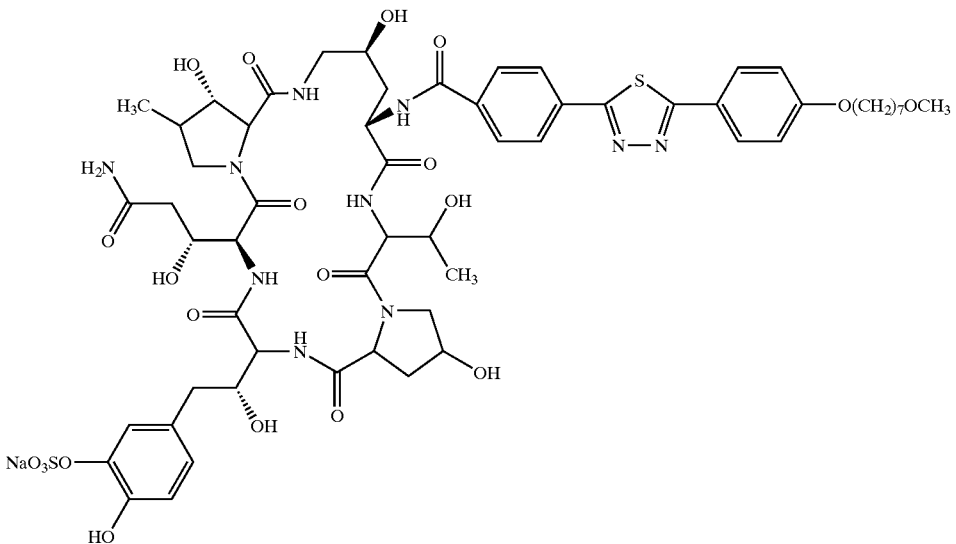 |
| | 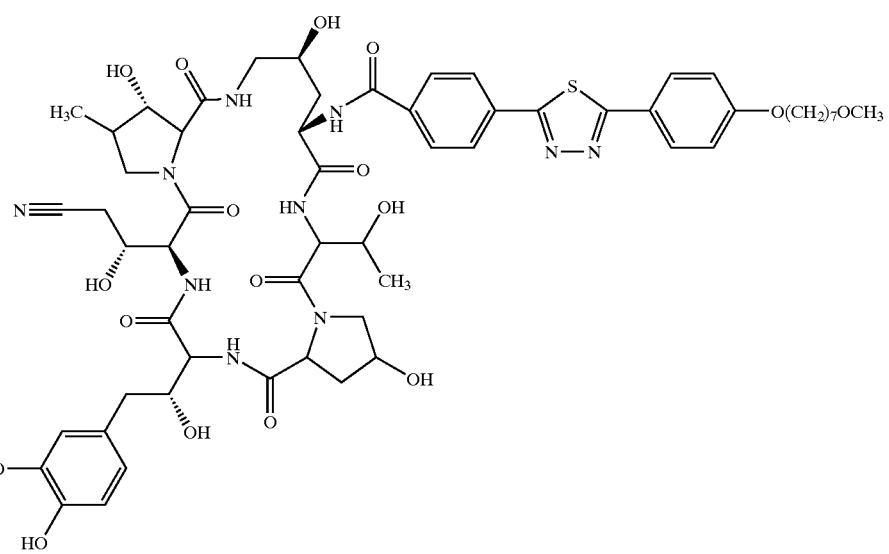 |

| Preparation No. | Formula |
|---|---|
| 4 | 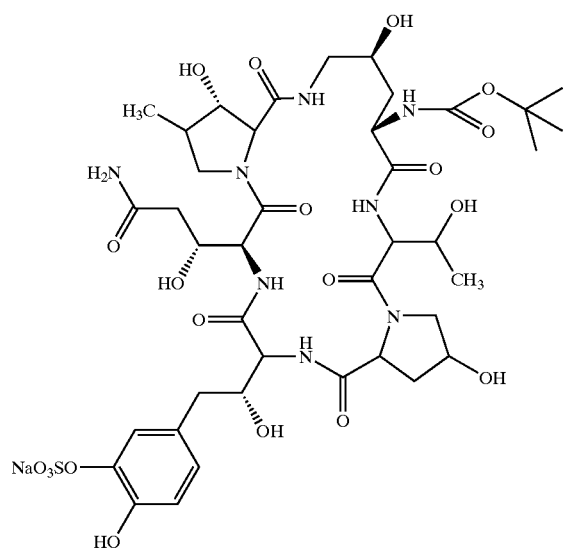 |
| | 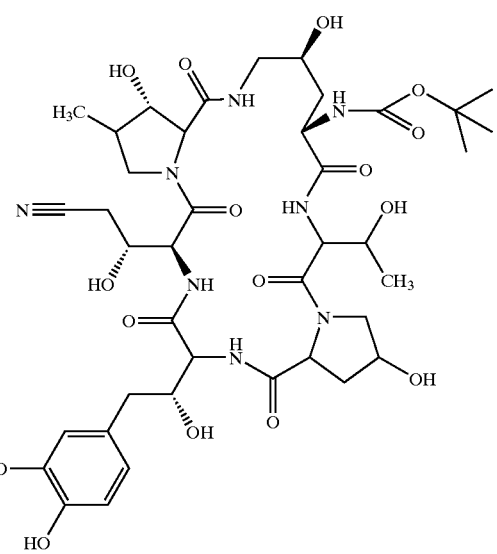 |

-continued
| Preparation No. | Formula |
|---|---|
| 5 | 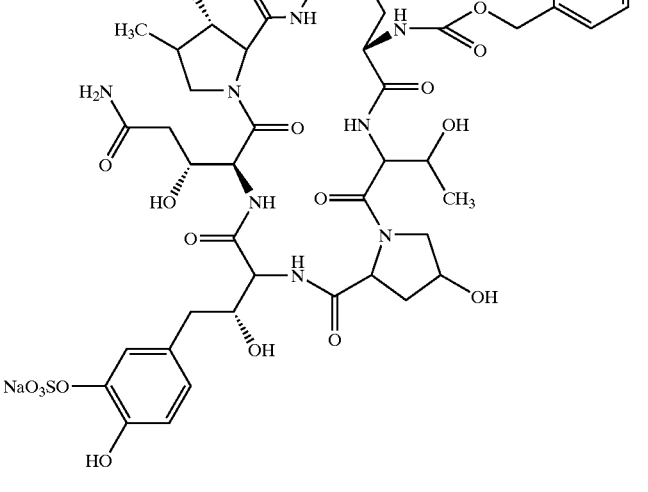 |
| | 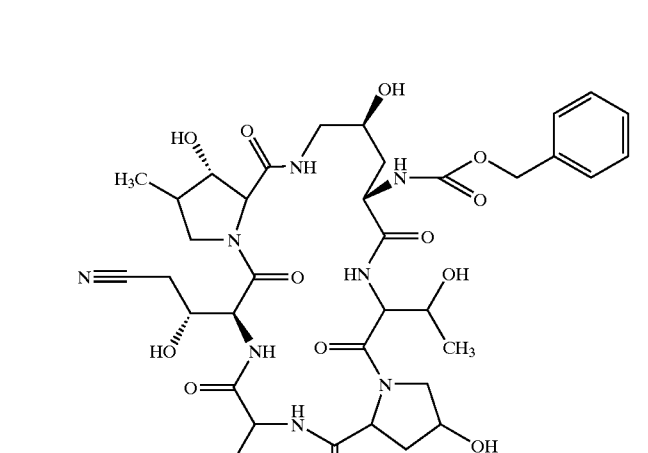 |

-continued
| Preparation No. | Formula |
|---|---|
| 6 | 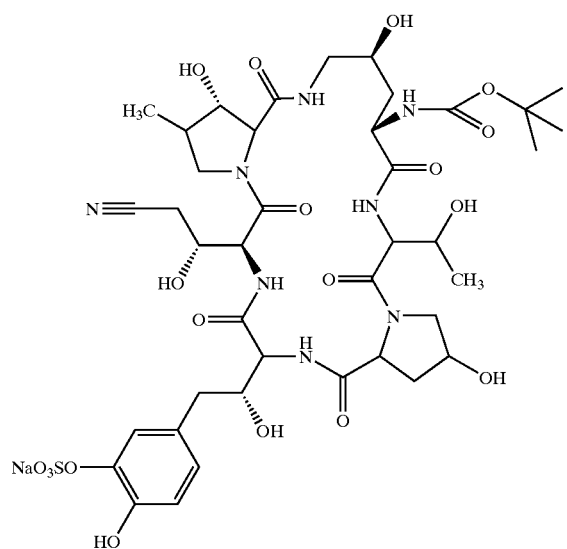 |
| | 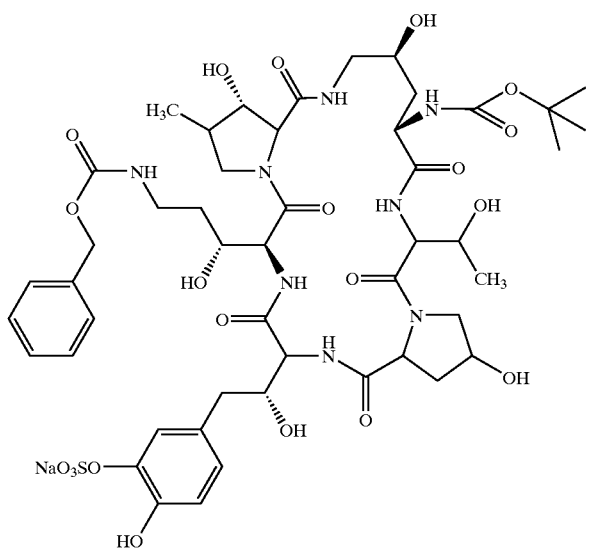 |

| Preparation No. | Formula |
|---|---|
| 7 | 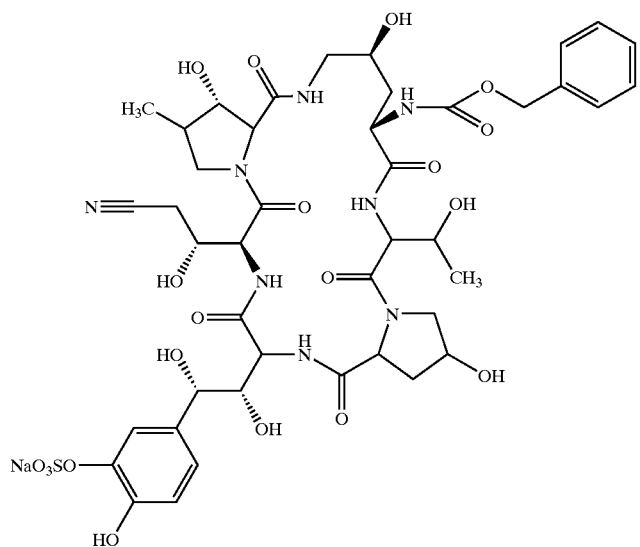 |
| | 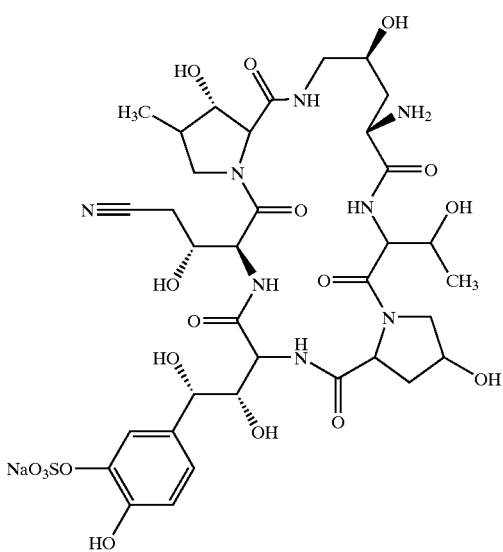 |

-continued
| Preparation No. | Formula |
|---|---|
| 8 | 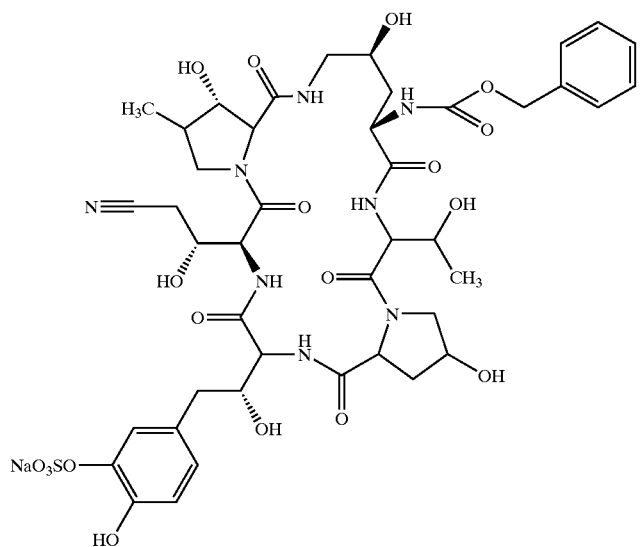 |
| | 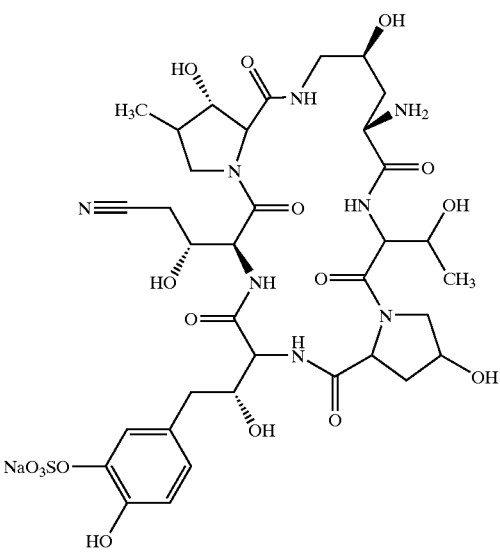 |

-continued
| Preparation No. | Formula |
|---|---|
| 9 | 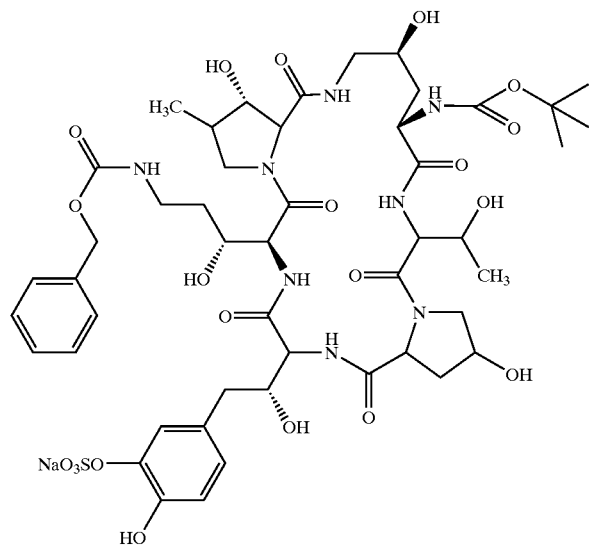 |
| | 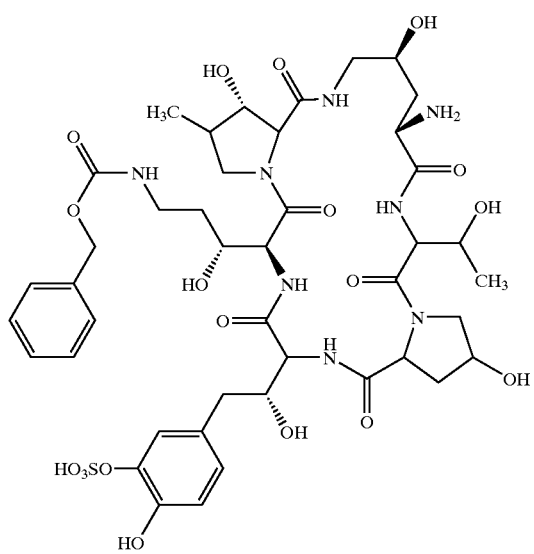 |

-continued
| Preparation No. | Formula |
|---|---|
| 10 | 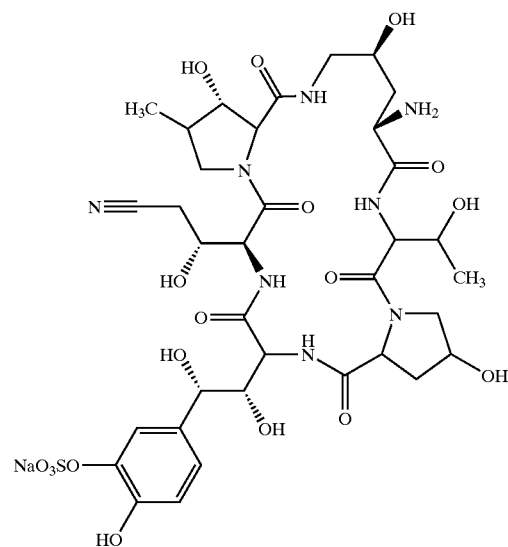 |
| | 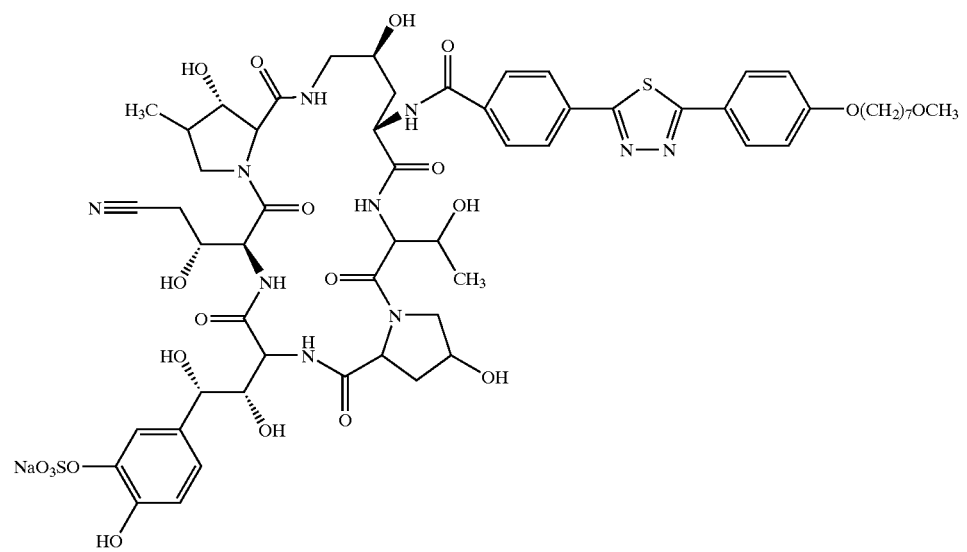 |

-continued
| Preparation No. | Formula |
|---|---|
| 11~21 | 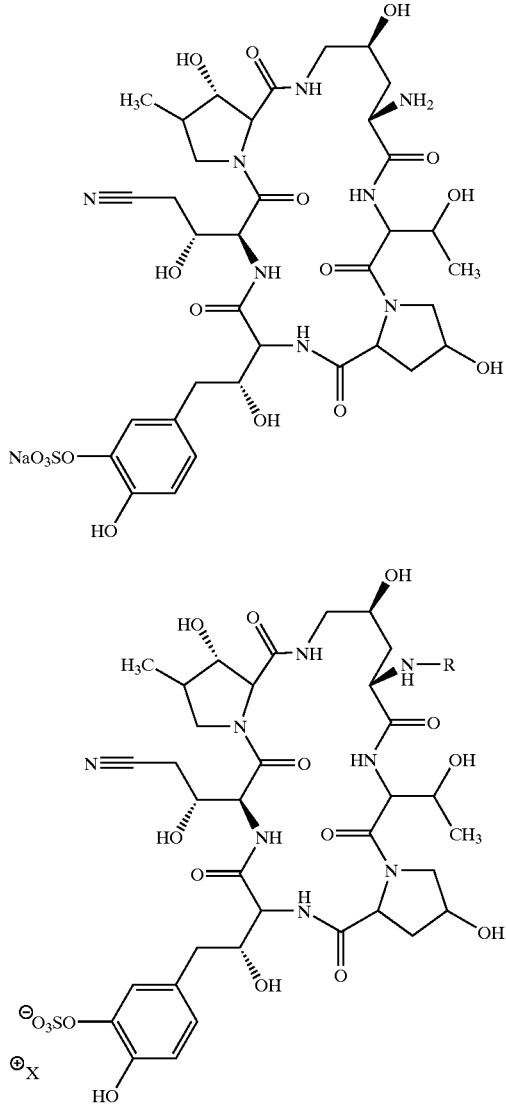 |
| Preparation No. | R | X |
|---|---|---|
| 11 | 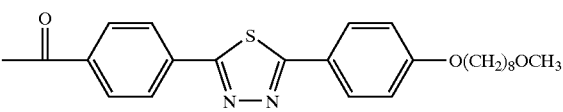 | Na |
| 12 | 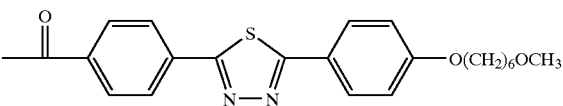 | Na |
| 13 | 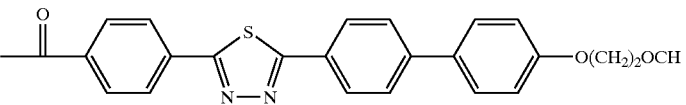 | Na |

-continued
| Preparation No. | R | X |
|---|---|---|
| 14 | 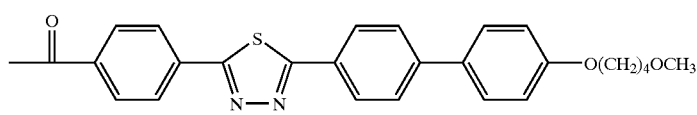 | Na |
| 15 | 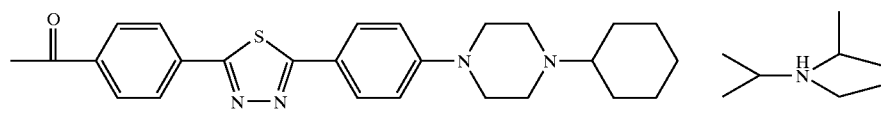 | 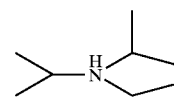 |
| 16 | 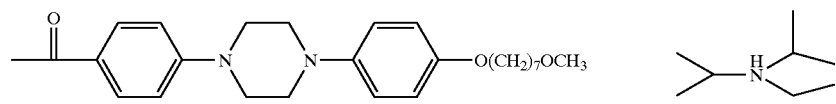 | 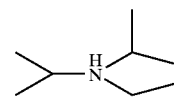 |
| 17 | 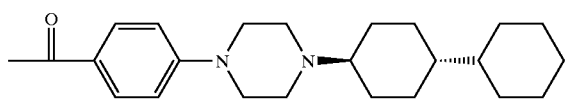 | Na |
| 18 | 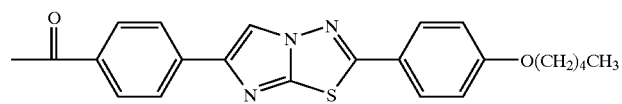 | 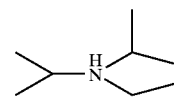 |
| 19 | 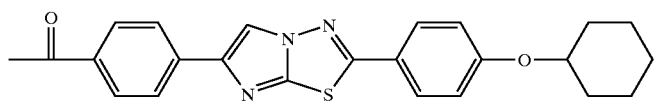 | Na |
| 20 | 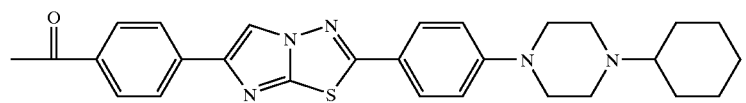 | Na |
| 21 | 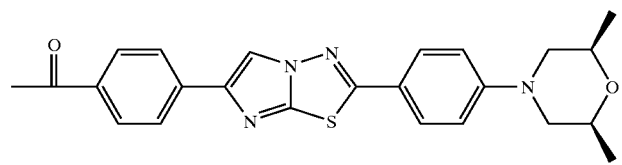 | Na |

| Preparation No. | Formula |
|---|---|
| 22 | 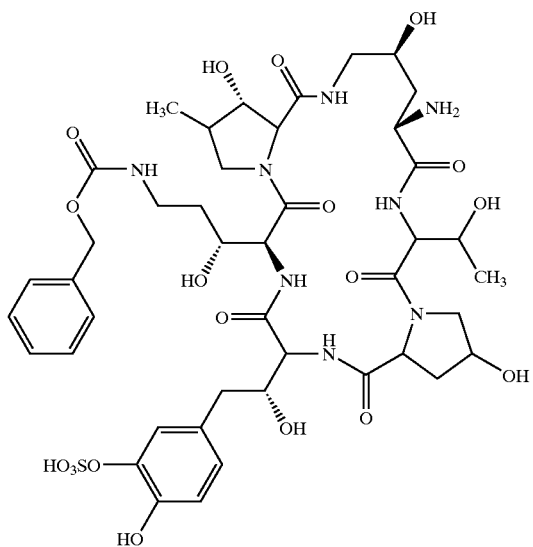 |
| | 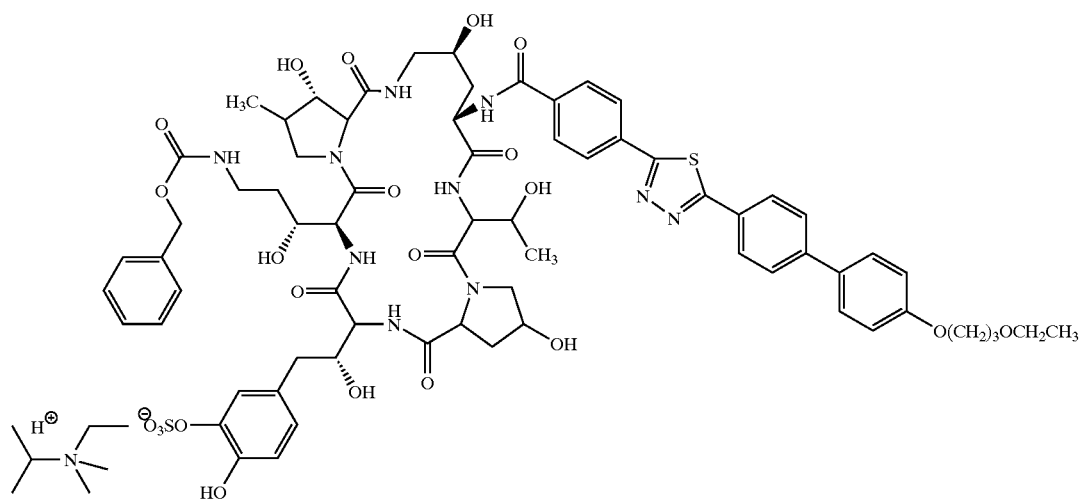 |

| Preparation No. | Formula |
|---|---|
| 23 | 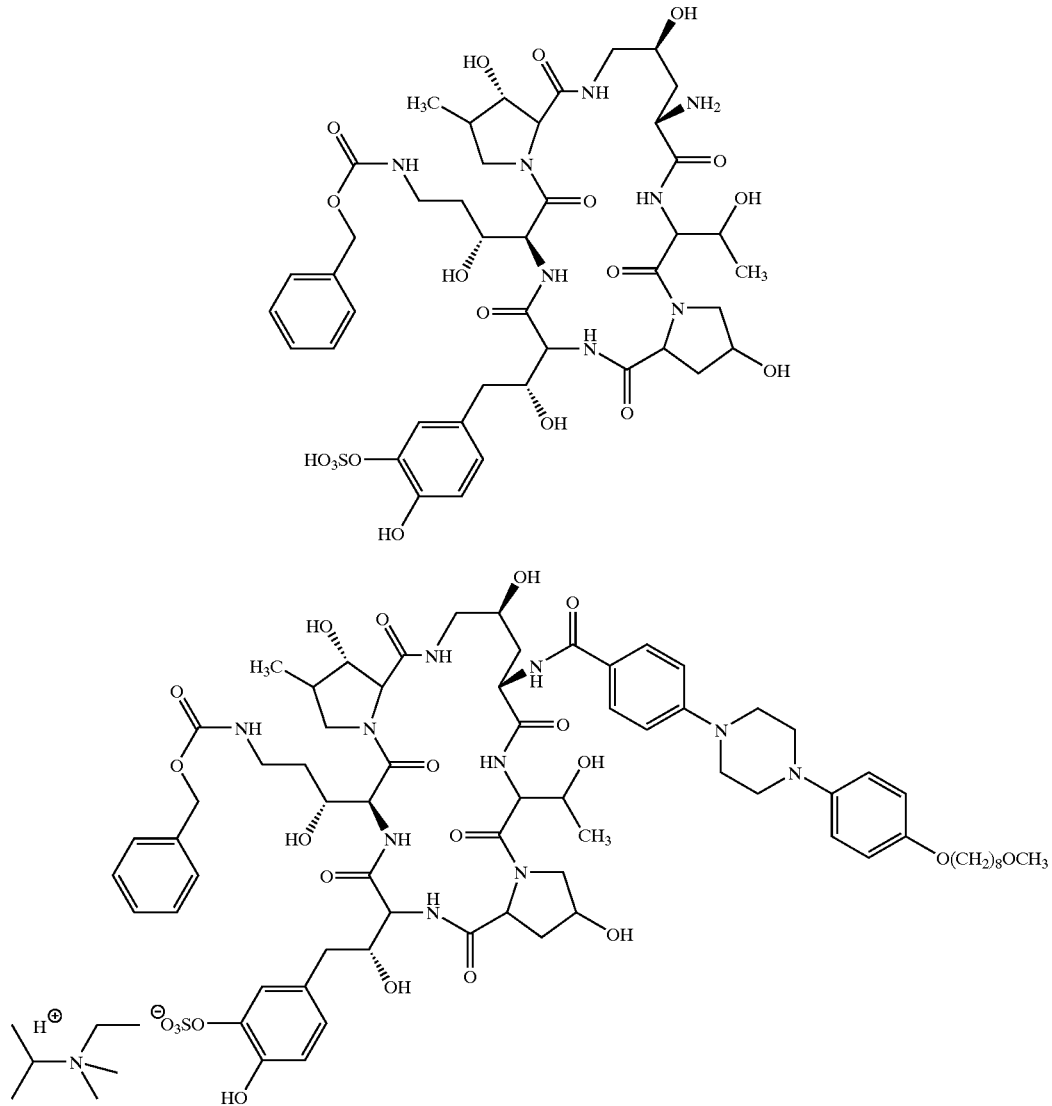 |

PREPARATION 1

A solution of starting compound (20 g) in 1,4-dioxane (100 ml) was treated with a solution of 1N-sodium hydroxide (44.2 ml) diluted to 100 ml with water, and to the stirred mixture was added a solution of di-tert-butyldicarbonate (9.2 g) in 1,4-dioxane (50 ml) and then stirred for 2 hours at room temperature. 500 ml of pH 6.86 phosphate buffer and 100 ml ethyl acetate were added and the mixture was stirred and the organic layer discarded. The aqueous layer was adjusted to pH 7.0 with 1N-hydrochloric acid then evaporated to remove organic solvent, filtered, and purified by ODS column chromatography eluting with aqueous methanol (5–15%). Object compound containing fractions were pooled, evaporated, and lyophilized to give object compound (19.61 g) as an amorphous white powder.

NMR (DMSO-$d_6$, δ): 0.95 (3H, d, J=6.8 Hz), 1.07 (3H, d, J=5.5 Hz), 1.34 (9H, s), 1.40–2.50 (9H, m), 2.80–3.0 (1H, m), 3.4–4.5 (15H, m), 4.70–5.40 (8H, m), 6.60–7.05 (6H, m), 7.25–8.00 (5H, m), 8.71 (1H, s).

MASS (m/z): 1003.3 ($M^+$−1).

PREPARATION 2

A mixture of starting compound (500 mg), N,N-dimethylformamide (5 ml) and synthetic A-4 zeolite (500 mg, Wako Chemical) was treated with diisopropyl ethylamine (66 mg), followed by methanesulfonyl chloride (58.5 mg) dropwise. After 1 hour at room temperature, further diisopropyl ethylamine (66 mg) and methanesulfonyl chloride (58.5 mg) were added. After 1.5 hours, additional diisopropylamine (66 mg) and methanesulfonyl chloride (58.5 mg) were added. After 1.5 hours, the mixture was filtered and the filtrate was poured into ethyl acetate. The precipitate was collected, washed with ethyl acetate and dried. The powder was dissolved in saturated sodium hydrogen carbonate solution then purified by ODS column chromatography (Daisogel SP-120 ODS Daiso) eluting with aqueous methanol (5–12.5%). Object compound-containing fractions were pooled, evaporated to remove methanol, and lyophilized to give object compound (210 mg) as an amorphous white powder.

IR (KBr): 2258.2, 1664.3, 1629.6, 1529.3, 1517.7, 1446.4, 1268.9 cm$^{-1}$.

NMR (DMSO-d$_6$, δ): 0.94 (3H, d, J=6.7 Hz), 1.07 (3H, d, J=5 Hz), 1.40–3.00 (9H, m), 3.10–4.50 (15H, m), 4.50–5.30 (10H, m), 5.66–5.69 (1H, m), 6.73 (1H, d, J=8.2 Hz), 6.82 (1H, d, J=8 Hz), 7.05 (1H, d, J=1.7 Hz), 7.33 (5H, s), 7.20–7.50 (3H, m), 7.6–7.7 (1H, m), 8.27 (1H, d, J=8.3 Hz), 8.84 (1H, s).

MASS (m/z): 1081.3 (M$^+$+Na).

Elemental Analysis Calcd. for $C_{43}H_{55}N_8O_{20}SNa \cdot 6H_2O$: C, 44.25, H, 5.79, N, 9.60. Found: C, 44.30, H, 5.79, N, 9.48.

The following compounds [Preparations 3 to 5] were obtained according to a similar manner to that of Preparation 2.

PREPARATION 3

IR (KBr): 2256.3, 1631.5, 1538.9, 1513.8, 1442.5, 1257.4 cm$^{-1}$.

NMR (DMSO-d$_6$, δ): 0.97 (3H, d, J=6.7 Hz), 1.12 (3H, d, J=5.5 Hz), 1.20–1.60 (8H, m), 1.65–3.05 (13H, m), 3.21 (3H, s), 3.30 (2H, t, J=6.4 Hz), 3.45–4.57 (16H, m), 4.70–5.30 (7H, m), 5.87 (1H, d, J=6.1 Hz), 6.72 (1H, d, J=8.2 Hz), 6.76–6.81 (1H, m), 6.98 (1H, d, J=1.3 Hz), 7.13 (2H, d, J=8.8 Hz), 7.40–7.53 (2H, m), 7.79 (1H, br s), 7.98 (2H, d, J=8.7 Hz), 8.10 (4H, s), 8.34 (1H, d, J=7.9 Hz), 8.72 (1H, d, J=5.7 Hz), 8.73 (1H, s).

MASS (m/z): 1293.4 (M$^+$–Na).

Elemental Analysis Calcd. for $C_{58}H_{73}N_{10}O_{20}SNa \cdot 6H_2O$: C, 48.87, H, 6.01, N, 9.83. Found: C, 48.69, H, 6.09, N, 9.70.

PREPARATION 4

IR (KBr): 2256.3, 1666.2, 1631.5, 1535.1, 1515.8, 1448.3, 1442.5, 1272.8, 1251.6, 1166.7, 1083.8, 1047.2 cm$^{-1}$.

NMR (DMSO-d$_6$, δ): 0.95 (3H, d, J=6.7 Hz), 1.09 (3H, d, J=5.1 Hz), 1.35 (9H, s), 1.50–3.00 (9H, m), 3.10–4.50 (17H, m), 4.65–5.00 (5H, m), 5.15–5.17 (2H, m), 5.70–5.90 (1H, m), 6.68–6.78 (2H, m), 6.86–6.96 (2H, m), 7.32 (1H, d, J=8 Hz), 7.40–7.50 (1H, m), 7.70–7.80 (1H, m), 8.30–8.40 (1H, m), 8.72 (1H, s).

MASS (m/z): 985.3 (M$^+$–Na).

Elemental Analysis Calcd. for $C_{40}H_{58}N_8O_{19}SNa \cdot 9H_2O$: C, 41.02, H, 6.45, N, 9.57. Found: C, 41.35, H, 6.42, N, 9.61.

PREPARATION 5

IR (KBr): 2256.3, 1668.1, 1648.8, 1631.5, 1538.9, 1513.8, 1454.1, 1267.0 cm$^{-1}$.

NMR (DMSO-d$_6$, δ): 0.95 (3H, d, J=6.8 Hz), 1.07 (3H, d, J=5.2 Hz), 1.5–2.9 (10H, m), 3.2–4.5 (15H, m), 4.7–5.2 (9H, m), 5.7–5.8 (1H, m), 6.60–6.78 (2H, m), 6.96 (1H, br s), 7.33 (5H, s), 7.2–7.5 (3H, m), 7.7–7.8 (1H, m), 8.3 (1H, d, J=7.5 Hz), 8.73 (1H, br s).

MASS (m/z): 1065.2 (M$^+$+Na).

Elemental Analysis Calcd. for $C_{43}H_{55}N_8O_{19}SNa \cdot 7H_2O$: C, 44.18, H, 5.95, N, 9.58. Found: C, 44.21, H, 5.82, N, 9.54.

PREPARATION 6

A solution of starting compound (2.0 g) in methanol (100 ml)-water (20 ml) was treated with cobalt(II) chloride hexahydrate (1.89 g) and then stirred to give a pink solution. Sodium borohydride (1.5 g) was then added portion wise and then stirred for 1 hour at room temperature. The reaction mixture was filtered through a bed of celite, washing with methanol (100 ml)-water (30 ml) solution. The ice-cooled filtrate was then treated dropwise with a solution of benzyloxy carbonyl chloride (Z-chloride) (0.34 ml) in tetrahydrofuran (5 ml) and stirred for 1 hour at the same temperature. Ethyl acetate (50 ml) was added followed by water (200 ml) and after stirring-5 minutes, the separated organic layer was discarded. The aqueous layer was adjusted to pH 8.8 and evaporated to remove organic solvent and then purified by ODS column chromatography, eluting with aqueous acetonitrile (10–30%). Object compound containing fractions were pooled, evaporated, and lyophilized to give object compound (1.61 g) as an amorphous white powder.

IR (KBr): 1666.2, 1631.5, 1517.7, 1444.4, 1267.0 cm$^{-1}$.

NMR (DMSO-d$_6$, δ): 0.94 (3H, d, J=6.7 Hz), 1.00–1.15 (3H, m), 1.33 (9H, s), 1.35–2.10 (6H, m), 2.10–2.50 (4H, m), 2.80–3.30 (4H, m), 3.60–4.55 (12H, m), 4.60–4.90 (2H, m), 4.99 (2H, s), 4.50–5.30 (4H, m), 6.60–7.10 (4H, m), 7.33 (5H, s), 7.35–7.90 (3H, m), 8.72 (1H, br s).

MASS (m/z): 1123.3 (M$^+$–Na).

Elemental Analysis Calcd. for $C_{48}H_{67}N_8O_{21}SNa \cdot 6H_2O$: C, 45.93, H, 6.34, N, 8.93. Found: C, 45.68, H, 6.33, N, 8.82.

PREPARATION 7

A solution of starting compound (2.0 g) in methanol (30 ml) was treated with wet 10% palladium on carbon (1.5 g) and exposed to one atmosphere of hydrogen gas via balloon. After 5.5 hours, water (4 ml) was added and hydrogenation continued for a further 30 minutes. Methanol (100 ml) was added and the catalyst removed by filtration. The solution was concentrated in vacuo to remove methanol and the aqueous residue lyophilized to give object compound (1.69 g) as a pink colored amorphous powder.

IR (KBr): 2256.3, 1648.8, 1631.5, 1538.9, 1515.8, 1440.6, 1083.8, 1047.2 cm$^{-1}$.

NMR (DMSO-d$_6$, δ): 0.94 (3H, d, J=6.7 Hz), 1.09 (3H, d, J=5.9 Hz), 1.7–2.8 (10H, m), 3.0–4.5 (19H, m), 4.6–5.3 (6H, m), 5.85–6.0 (1H, m), 6.72 (1H, d, J=8.2 Hz), 6.82 (1H, dd, J=1.8 and 8.4 Hz), 7.06 (1H, d, J=1.7 Hz), 7.32 (1H, d, J=8.9 Hz), 7.44 (1H, d, J=9.1 Hz), 7.6–7.8 (2H, m), 7.8–8.0 (1H, br s).

MASS (m/z): 901.2 (M$^+$–Na).

Elemental Analysis Calcd. for $C_{35}H_{49}N_8O_{18}SNa \cdot 6H_2O$: C, 40.70, H, 5.95, N, 10.85. Found: C, 40.60, H, 5.94, N, 10.71.

The following compound was obtained according to a similar manner to that of Preparation 7.

PREPARATION 8

IR (KBr): 2256.3, 1648.8, 1631.5, 1538.9, 1513.8, 1267.0, 1083.8, 1047.2 cm$^{-1}$.

NMR (DMSO-d$_6$, δ): 0.96 (3H, d, J=6.7 Hz), 1.08 (3H, d, J=5.9 Hz), 1.7–2.1 (5H, m), 2.1–2.9 (7H, m), 3.1–4.6 (16H, m), 4.7–5.4 (6H, m), 6.1 (1H, br s), 6.70 (1H, d, J=8.2 Hz), 6.75 (1H, d, J=8.2 Hz), 6.96 (1H, br s), 7.2–7.55 (2H, m), 7.6–7.9 (2H, m).

MASS (m/z): 885.3 (M$^+$–Na).

Elemental Analysis Calcd. for $C_{35}H_{49}N_8O_{17}SNa \cdot 6H_2O$: C, 41.34, H, 6.05, N, 11.02. Found: C, 41.58, H, 5.99, N, 10.94.

PREPARATION 9

A suspension of starting compound (1.6 g) in dichloromethane (41 ml) was stirred with cooling at 5° C. and treated with triethylsilane (1.1 ml), followed by trifluoroacetic acid (5.3 ml) dropwise over 30 minutes. After warming to room temperature, the clear solution was stirred for 2 hours, then poured into 450 ml of pH 6.86 phosphate buffer and adjusted to pH 8.5 with 4N-sodium hydroxide solution. Organic solvent was removed by evaporation and the remaining aqueous solution purified by ODS column chromatography, eluting with aqueous acetonitrile (5–20%). Object compound-containing fractions were pooled, evaporated, and lyophilized to give object compound (1.25 g) as an amorphous white powder.

IR (KBr): 1633.4, 1537.0, 1517.7, 1440.6, 1267.0 cm$^{-1}$.

NMR (DMSO-d$_6$, δ): 0.95 (3H, d, J=6.7 Hz), 1.12 (3H, d, J=5.8 Hz), 1.27 (2H, d, J=6.6 Hz), 1.28–1.70 (2H, m), 1.75–2.45 (4H, m), 2.65–3.30 (5H, m), 3.50–4.50 (11H, m), 4.60–4.90 (2H, m), 5.00 (2H, s), 5.05–5.40 (5H, m), 6.70 (2H, d, J=8.2 Hz), 6.76 (2H, d, J=8.2 Hz), 6.96 (1H, s), 7.00–7.15 (1H, m), 7.34 (5H, s), 7.40–7.95 (3H, m), 8.60–8.90 (1H, m).

MASS (m/z): 1023.3 (M$^+$−1).

Elemental Analysis Calcd. for C$_{43}$H$_{60}$N$_8$O$_{19}$S.6H$_2$O: C, 45.58, H, 6.40, N, 9.89. Found: C, 45.49, H, 6.24, N, 9.70.

PREPARATION 10

A solution of starting compound (3 g) in N,N-dimethylformamide (60 ml) was treated with 4-[5-[4-(7-methoxy-n-heptyloxy)phenyl]-1,3,4-thiadiazol-2-yl]benzoic acid benzotriazol-1-yl ester (2.65 g) and diisopropylethylamine (0.564 ml) and stirred for 4 hours 20 minutes at room temperature. Ethyl acetate (1 l) was added and the resulting precipitate collected, washed with isopropyl ether, and dried to give object compound (5.62 g) as a crude powder, which was used directly in the next step without purification.

The following compounds [Preparations 11 to 17] were obtained according to a similar manner to that of Preparation 10.

PREPARATION 11

The object compound was used directly in the next reaction without purification.

PREPARATION 12

The object compound was used directly in the next reaction without purification.

PREPARATION 13

MASS (m/z): 1299.3 (M$^+$−Na).

PREPARATION 14

The object compound was used directly in the next reaction without purification.

PREPARATION 15

The object compound was used directly in the next reaction without purification.

PREPARATION 16

The object compound was used directly in the next reaction without purification.

PREPARATION 17

MASS (m/z): 1237.3 (M$^+$−Na).

PREPARATION 18

A mixture of 4-[2-(4-pentyloxyphenyl)imidazo[2,1-b][1,3,4]thiadiazol-6-yl]benzoic acid (1.44 g), 1-hydroxybenzotriazole (714 mg), diisopropyl ethylamine (0.58 ml) and 1-ethyl-3-(3'-dimethylaminopropyl)carbodiimide hydrochloride (810 mg) in N,N-dimethylformamide (50 ml) was stirred 6 hours at room temperature, then treated with starting compound (2 g) and stirred overnight. Additional N,N-dimethylformamide (20 ml) was added and stirring continued for a further 5.5 hours. The clear solution was poured into ethyl acetate (1 l) and the precipitate collected and washed with isopropyl ether and dried to give crude object compound (3.58 g), which was used directly in the next step without purification.

The following compounds [Preparations 19 and 20] were obtained according to a similar manner to that of Preparation 18.

PREPARATION 19

MASS (m/z): 1286.3 (M$^+$−Na).

PREPARATION 20

MASS (m/z): 1354.4 (M$^+$−Na).

The following compound was obtained according to a similar manner to that of Preparation 18.

PREPARATION 21

IR (KBr): 1648.8, 1631.5, 1537.0, 1513.8, 1456.0 cm$^{-1}$.

NMR (DMSO-d$_6$, δ): 0.96 (3H, d, J=7 Hz), 1.10 (3H, d, J=5.6 Hz), 1.18 (6H, d, J=6 Hz), 1.4–5.3 (38H, m), 5.88 (1H, d, J=6 Hz), 6.71 (1H, d, J=8 Hz), 6.75–6.80 (1H, m), 6.97 (1H, br s), 7.12 (2H, d, J=9 Hz), 7.42 (1H, d, J=7.6 Hz), 7.50 (1H, d, J=9 Hz), 7.78 (2H, d, J=8.8 Hz), 7.7–8.0 (1H, br s), 7.96 (4H, s), 8.32 (1H, d, J=8 Hz), 8.50 (1H, d, J=7.1 Hz), 8.72 (1H, s), 8.79 (1H, s).

MASS (m/z): 1301.4 (M$^+$−Na).

The following compounds [Preparations 22 to 23] were obtained according to a similar manner to that of Preparation 10.

PREPARATION 22

NMR (DMSO-d$_6$, δ): 0.95 (3H, d, J=6.6 Hz), 6.67 (1H, d, J=6.9 Hz), 6.73–6.75 (1H, m), 6.96 (1H, br s), 7.07 (2H, d, J=8.8 Hz), 7.32 (5H, s), 7.73 (2H, d, J=8.7 Hz), 7.87 (2H, d, J=8.5 Hz), 8.06–8.14 (6H, m), 8.72 (1H, s), 8.80 (1H, d, J=7.1 Hz).

MASS (m/z): 1465.5 (M$^+$−Na).

PREPARATION 23

The object compound was used directly in the next reaction without purification.

PREPARATION 24

To a solution of 1-(tert-butoxycarbonyl)-4-hydroxypiperidine (6 g) in N,N-dimethylformamide (30 ml) was portion wise added sodium hydride (60%, 1.6 g) at 5° C. with stirring. The mixture was stirred at room temperature for 0.5 hour and at 60° C. for an hour. To the reaction mixture was added dropwise 1,4-dibromobutane (19 g) at 5° C. with stirring. The mixture was stirred at room temperature for 4 hours and at 50° C. for 2 hours. The reaction mixture was poured into ice-water and extracted with a mixture of ethyl acetate and tetrahydrofuran (1:1). The organic layer was washed with saturated sodium chloride aqueous solution and dried over magnesium sulfate. The magnesium sulfate was filtered under reduced pressure, and the filtrate was concentrated under reduced pressure to give oil. The oil was subjected to column chromatography on silica gel (silica gel 60 F254, Merck) and eluted with a mixture of ethyl acetate and n-hexane (1:10–1:3). The fractions containing the objective compound were combined and concentrated under reduced pressure to give 1-(tert-butoxycarbonyl)-4-[(4-bromo)butoxy]piperidine (1.5 g).

NMR (CDCl$_3$, δ): 1.41 (9H, s), 1.43–1.60 (2H, m), 1.65–1.80 (4H, m), 1.85–2.3 (2H, m), 3.02–3.20 (2H, m), 3.38–3.51 (4H, m), 3.68–3.80 (2H, m).

MASS (m/z): 238 (M$^+$–Boc–2).

PREPARATION 25

The mixture of 1-(tert-butoxycarbonyl)-4-[4-(bromobutoxy)]piperidine (3 g) and 28% sodium methoxide in methanol solution (20 ml) in methanol (50 ml) was refluxed for 8.5 hours with stirring. The reaction mixture was concentrated under reduced pressure, added water to the residue and adjusted to pH 4 using the hydrochloric acid. The mixture was extracted with a mixture of ethyl acetate and tetrahydrofuran (1:1), washed with saturated sodium chloride aqueous solution and dried over magnesium sulfate. The magnesium sulfate was filtered by suction, and the filtrate was concentrated under reduced pressure to give an oil. The oil was subjected to column chromatography on silica gel (silica gel 60 F254, Merck) and eluted with a mixture of ethyl acetate and n-hexane (1:5–1:3). The fractions containing the objective compound were combined and concentrated under reduced pressure to give 1-(tert-butoxycarbonyl)-4-(4-methoxybutoxy)piperidine (2.2 g).

NMR (CDCl$_3$, δ): 1.40 (9H, s), 1.43–1.60 (2H, m), 1.6–1.70.(4H, m), 1.76–1.85 (2H, m), 3.01–3.15 (2H, m), 3.33 (3H, s), 3.36–3.50 (5H, m), 3.69–3.80 (2H, m).

MASS (m/z): 188 (M$^+$–Boc+1).

PREPARATION 26

To a mixture of 1-(tert-butoxycarbonyl)-4-[4-methoxybutoxy]piperidine (2.2 g) and anisole (5 ml) in dichloromethane (10 ml) was added dropwise trifluoroacetic acid (10 ml) at 5° C. with stirring. The mixture was stirred at room temperature for 3 hours and evaporated to dryness in vacuo at 70° C. to give an oil (2.5 g). The mixture of the above oil (2.5 g), 4-fluorobenzonitrile (1.5 g) and potassium carbonate (3 g) in dimethylsulfoxide (25 ml) was heated at 160° C. for 3 hours with stirring. The reaction mixture was poured into ice-water and extracted with a mixture of ethyl acetate and tetrahydrofuran (1:1). The organic layer was separated, washed with saturated sodium chloride aqueous solution and dried over magnesium sulfate. The magnesium sulfate was filtered by suction and the filtrate was concentrated under reduced pressure to give solid. The solid was subjected to column chromatography on silica gel (silica gel 60 F$_{254}$, Merck) and eluted first a mixture of ethyl acetate and n-hexane (1:5), second a mixture of dichloromethane and methanol (10:1). The fractions containing the objective compound were combined and concentrated under reduced pressure to give 4-[4-(4-methoxybutoxy)piperidin-1-yl]benzonitrile (2.0 g).

NMR (CDCl$_3$, δ): 1.58–1.76 (6H, m), 1.89–2.00 (2H, m), 3.08–3.21 (2H, m), 3.33 (3H, s), 3.37–3.68 (7H, m), 6.85 (2H, d, J=9 Hz), 7.46 (2H, d, J=9 Hz).

MASS (m/z) (API-ES-Positive): 312 (M$^+$+Na+1).

PREPARATION 27

The mixture of 4-[4-(4-methoxybutoxy)piperidin-1-yl] benzonitrile (2 g), thiosemicarbazide (1 g) and trifluoroacetic acid (10 ml) in toluene (20 ml) was stirred at 60–65° C. for 9 hours. The reaction mixture was poured into ice-water and adjusted to pH 9 using sodium hydroxide aqueous solution. The mixture was extracted with a mixture of ethyl acetate and tetrahydrofuran (1:1), washed with saturated sodium chloride aqueous solution and dried over magnesium sulfate. The magnesium sulfate was filtered by suction, the filtrate was concentrated under reduced pressure and the residue was triturated with isopropyl ether. The precipitates were collected by filtration, washed with isopropyl ether and dried in vacuo to give 2-amino-5-[4-(4-methoxybutoxy) piperidin-1-yl)phenyl][1,3,4]thiadiazole (2.0 g).

NMR (DMSO-d$_6$, δ): 1.40–1.60 (6H, m), 1.80–2.00 (2H, m), 2.86–3.15 (2H, m), 3.23 (3H, s), 3.30–3.50 (5H, m), 3.50–3.61 (2H, m), 6.98 (2H, d, J=8.9 Hz), 7.19 (2H, s), 7.54 (2H, d, J=8.9 Hz).

MASS (m/z): 363 (M$^+$+1).

PREPARATION 28

A mixture of 2-amino-5-[4-(4-methoxybutoxy)piperidin-1-yl]phenyl[1,3,4]thiadiazole (2 g) and 4-(ethoxycarbonyl) phenacylbromide (2.3 g) in ethanol (25 ml) was refluxed for 6 hours with stirring. After cooling, the reaction mixture was poured into isopropyl ether. The precipitates were collected by filtration, washed with isopropyl ether and dried in vacuo to give solid. The mixture of this solid and trifluoroacetic acid (10 ml) in xylene (60 ml) was heated at 130° C. for 6 hours with stirring. The reaction mixture was concentrated under reduced pressure and the residue was triturated with isopropyl ether. The precipitates were collected by filtration, washed with isopropyl ether and dried in vacuo to give ethyl-4-[2-[4-(4-methoxybutoxypiperidin-1-yl)phenyl] imidazo[2,1-b][1,3,4]thiadiazol-6-yl]benzoate (2.4 g).

IR (KBr): 2939, 2854, 1708, 1604, 1469 cm$^{-1}$.

NMR (DMSO-d$_6$, δ): 1.34 (3H, t, J=7.2 Hz), 1.40–1.65 (6H, m), 1.75–1.95 (4H, m), 3.00–3.20 (2H, m), 3.22 (3H, s), 3.25–3.40 (2H, m), 3.40–3.90 (3H, m), 4.33 (2H, q, J=7.5 Hz), 7.02 (2H, d, J=8.8 Hz), 7.57 (2H, d, J=8.8 Hz), 7.75 (2H, d, J=8.8 Hz), 8.00 (1H, s), 8.14 (2H, d, J=9.0 Hz).

MASS (m/z): 535 (M$^+$+1).

PREPARATION 29

A solution of ethyl-4-[2-4-[4-methoxybutoxypiperidin-1-yl)phenyl]imidazo[2,1-b][1,3,4]thiadiazol-6-yl]benzoate (2.4 g) and 10% sodium hydroxide aqueous solution (15 ml) in methanol (50 ml) and tetrahydrofuran (25 ml) was refluxed for 6 hours with stirring. The reaction mixture was concentrated under reduced pressure, ice-water was added to the residue and adjusted to pH 3 using hydrochloric acid. The mixture was shaked with a mixture of ethyl acetate and tetrahydrofuran (1:1). The precipitates were collected by filtration, washed with water and dried in vacuo to give 4-[2-[4-(4-methoxybutoxy)piperidin-1-yl-phenyl]imidazo [2,1-b][1,3,4]thiadiazol-6-yl]benzoic acid (2 g).

IR (KBr): 2854, 2650, 2550, 1691, 1678, 1608, 1599, 1476 cm$^{-1}$.

NMR (DMSO-d$_6$, δ): 1.20–1.60 (6H, m), 1.60–2.05 (2H, m), 3.00–3.30 (2H, m), 3.22 (3H, m), 3.00–4.00 (7H, m), 7.10 (2H, d, J=8.8 Hz), 7.75 (2H, d, J=8.7 Hz), 7.99 (4H, m), 8.81 (1H, s), 12.90 (1H, br s).

MASS (m/z): 507 (M$^+$+1).

PREPARATION 30

To a solution of 4-[2-[4-(4-methoxybutoxypiperidin-1-yl)phenyl]imidazo[2,1-b][1,3,4]thiadiazol-6-yl]benzoic acid (2.4 g) in dichloromethane (150 ml) was added triethylamine (1.3 g), 3-(3-dimethylaminopropyl)-1-ethylcarbodiimide hydrochloride (2 g) and 1-hydroxybenzotriazole (1 g). The mixture was stirred overnight at room temperature. The reaction mixture was concentrated under reduced pressure and the residue was triturated with water. The precipitates were collected by filtration, washed with water and isopropyl ether and dried in vacuo to give 4-[2-[4-(4-methoxybutoxy)piperidin-1-yl-phenyl]imidazo[2,1-b][1,3,4]thiadiazol-6-yl]benzoic acid benzotriazol-1-yl ester (2.5 g).

IR (KBr): 3427, 2937, 2856, 1774, 1602, 1471 cm$^{-1}$.

NMR (DMSO-d$_6$, δ): 1.30–1.65 (6H, m), 1.70–2.10 (2H, m), 3.21 (3H, m), 2.80–3.60 (7H, m), 3.60–3.80 (2H, m), 7.05–8.00 (10H, m), 8.00 (1H, s), 8.21 (1H, d, J=8.6 Hz), 8.33 (1H, d, J=8.6 Hz).

MASS (m/z): 624 (M$^+$+1).

The following compound was obtained according to a similar manner to that of Preparation 26.

PREPARATION 31

4-(3-Methoxypropoxypiperidin-1-yl)benzonitrile

IR (KBr): 2931, 2866, 2215, 1678, 1604, 1516 cm$^{-1}$.

NMR (DMSO-d$_6$, δ): 1.35–1.60 (2H, m), 1.60–1.80 (2H, m), 1.80–2.00 (2H, m), 2.86–3.25 (2H, m), 3.21 (3H, s), 3.30–3.60 (5H, m), 3.60–3.80 (2H, m), 7.01 (2H, d, J=9 Hz), 7.55 (2H, d, J=8.9 Hz).

MASS (m/z): 275 (M$^+$+1).

The following compound was obtained according to a similar manner to that of Preparation 27.

PREPARATION 32

2-Amino-5-[4-(3-methoxypropoxypiperidin-1-yl)phenyl][1,3,4]thiadiazole

NMR (DMSO-d$_6$, δ): 1.30–1.60 (2H, m), 1.65–1.80 (2H, m), 1.80–2.00 (2H, m), 2.80–3.20 (2H, m), 3.21 (3H, s), 3.30–3.70 (7H, m), 6.98 (2H, d, J=8.9 Hz), 7.19 (2H, br s), 7.54 (2H, d, J=8.8 Hz).

MASS (m/z): 349 (M$^+$+1).

The following compound was obtained according to a similar manner to that of Preparation 28.

PREPARATION 33

Ethyl-4-[2-[4-(3-methoxypropoxypiperidin-1-yl)phenyl]imidazo[2,1-b][1,3,4]thiadiazol-6-yl]benzoate IR (KBr): 3411, 3211, 3132, 2943, 2862, 1709, 1604 cm$^{-1}$.

NMR (DMSO-d$_6$, δ): 1.30–1.60 (5H, m), 1.65–1.80 (2H, m), 1.80–2.00 (2H, m), 2.80–3.10 (2H, m), 3.22 (3H, s), 3.30–3.80 (6H, m), 4.20–4.50 (3H, m), 6.98 (2H, d, J=9 Hz), 7.40 (1H, 8), 7.54 (2H, d, J=8.8 Hz), 7.80–8.40 (4H, m).

MASS (m/z): 521 (M$^+$+1).

The following compound was obtained according to a similar manner to that of Preparation 29.

PREPARATION 34

4-[2-[4-(3-Methoxypropoxypiperidin-1-yl)phenyl]imidazo[2,1-b][1,3,4]thiadiazol-6-yl]benzoic acid IR (KBr): 3423, 2935, 2858, 2650, 2550, 1682, 1603, 1468 cm$^{-1}$.

NMR (DMSO-d$_6$, δ): 1.40–1.60 (2H, m), 1.60–1.80 (2H, m), 1.80–2.00 (2H, m), 2.80–3.20 (2H, m), 3.22 (3H, s), 3.30–3.80 (7H, m), 6.98 (2H, d, J=8.7 Hz), 7.19 (1H, s), 7.54 (2H, d, J=8.7 Hz), 7.80–8.20 (4H, m).

MASS (m/z): 493 (M$^+$+1).

The following compound was obtained according to a similar manner to that of Preparation 30.

PREPARATION 35

4-[2-[4-(3-Methoxypropoxypiperidin-1-yl)phenyl]imidazo[2,1-b][1,3,4]thiadiazol-6-yl]benzoic acid benzotriazol-1-yl ester IR (KBr): 3464, 3429, 3425, 3402, 2932, 2931, 1774, 1605, 1469 cm$^{-1}$.

NMR (DMSO-d$_6$, δ): 1.30–1.60 (2H, m), 1.60–1.80 (2H, m), 1.80–2.00 (2H, m), 2.80–3.30 (2H, m), 3.22 (3H, s), 3.35–3.80 (7H, m), 7.08 (2H, d, J=9.1 Hz), 7.20–8.00 (8H, m), 8.00 (1H, s), 8.14 (1H, d, J=8.6 Hz), 8.33 (1H, d, J=8.5 Hz).

MASS (m/z): 610 (M$^+$+1).

PREPARATION 36

A mixture of methyl 4-methylsulfinylbenzoate (6.0 g), sodium acetate (11 g) and acetic anhydride (60 ml) was stirred for 7.5 hours at 180° C. The reaction mixture was cooled and filtered by suction. The filtrate was concentrated under reduced pressure and the residue was triturated with water. The precipitates were collected by filtration, washed with aqueous sodium carbonate and water. The solid was subjected to column chromatography on silica gel (silica gel 60 F254, Merck: 200 g) and eluted with a mixture of ethyl acetate and toluene (1:5). The fractions containing the objective compound were combined and concentrated under reduced pressure to give methyl 4-acetoxymethylthiobenzoate (5.5 g).

IR (KBr): 1746, 1704, 1593 cm$^{-1}$.

NMR (CDCl$_3$, δ): 2.12 (3H, s), 3.92 (3H, s), 5.50 (2H, s), 7.63 (2H, d, J=8.3 Hz), 7.98 (2H, d, J=8,3 Hz).

MASS (m/z) (API-ES-Positive): 263 (M$^+$+23).

PREPARATION 37

To a solution of methyl 4-acetoxymethylthiobenzoate (15.5 g) in a mixture of methanol (20 ml) and dichloromethane (60 ml) was portionwise added magnesium monoperoxyphthalate hexahydrate (24 g) at 5° C., with stirring. The mixture was stirred at room temperature for 2 hours. The reaction mixture was washed with ice-water, aqueous sodium carbonate and brine, then dried over magnesium sulfate. The organic solvent was concentrated under reduced pressure to give acetoxymethyl-(4-methoxycarbonylphenyl)sulfone (5.9 g).

IR (KBr): 1759, 1724, 1434 cm$^{-1}$.

NMR (CDCl$_3$, δ): 2.09 (3H, s), 3.98 (3H, s), 5.18 (2H, s), 8.01 (2H, d, J=8.5 Hz), 8.26 (2H, d, J=8.5 Hz).

MASS (m/z): 273 (M$^+$+1).

PREPARATION 38

To a solution of methyl 4-acetoxymethylsulfonylbenzoate (5.5 g) in a mixture of tetrahydrofuran (50 ml) and methanol (25 ml) was added dropwise 10% aqueous sodium hydroxide at 5° C. with stirring. The mixture was stirred at room temperature for 3 hours. The reaction mixture was concentrated under reduced pressure and to the residue was added water. The solution was washed with toluene and the aqueous layer was concentrated under reduced pressure and dried in vacuo at 50° C. to give sodium methoxycarbonylbenzenesulfinate (4.5 g).

IR (KBr): 3424, 3300, 1718, 1594 cm$^{-1}$.

NMR (DMSO-d$_6$, δ): 3.84 (3H, s), 7.60 (2H, d, J=8.0 Hz), 7.92 (2H, d, J=8.0 Hz).

MASS (m/z) (API-ES-Positive): 245 (M$^+$+23).

PREPARATION 39

A mixture of sodium-4-(1-methoxycarbonyl)benzene sulfinate (2.2 g) and 1,7-dibromoheptane (2.6 g) in N,N-dimethylformamide (50 ml) was stirred at 100° C. for 5 hours. The reaction mixture was concentrated under reduced pressure and the residue was triturated with water. The mixture was extracted with a mixture of ethyl acetate and tetrahydrofuran (1:1), washed with brine and dried over magnesium sulfate. After removing the magnesium sulfate, the filtrate was concentrated under reduced pressure to give a yellow oil. The oily product was subjected to column chromatography on silica gel (silica gel 60 F254, Merck: 250 g) and eluted with a mixture of ethyl acetate and toluene (1:10). The fractions containing the objective compound were combined and concentrated under reduced pressure to give 7-bromoheptyl-[4-(methoxycarbonyl)phenyl]sulfone (1.4 g).

IR (Neat): 3423, 2927, 2852, 1725, 1280 cm$^{-1}$.

NMR (CDCl$_3$, δ): 1.20–1.43 (6H, m), 1.60–1.85 (4H, m), 3.11 (2H, m), 3.38 (2H, t, J=6.7 Hz), 3.98 (3H, s), 8.00 (2H, d, J=8.4 Hz), 8.23 (2H, d, J=8.4 Hz).

MASS (m/z): 379 (M$^+$).

PREPARATION 40

A mixture of 7-bromoheptyl-[(4-methoxycarbonyl)phenyl]sulfone (1.4 g) and sodium methoxide in methanol solution (28%) (2 ml) in methanol (20ml) was refluxed for 10 hours with stirring. The reaction mixture was concentrated under reduced pressure and subjected to column chromatography on silica gel (silica gel 60 F254, Merck) and eluted with a mixture of ethyl acetate and toluene (1:5–1:3). The fractions containing the objective compound were combined and concentrated under reduced pressure to give 7-methoxyheptyl[4-(methoxycarbonyl)phenyl]sulfone (0.85 g).

IR (Neat): 2929, 2857, 1723, 1280 cm$^{-1}$.

NMR (CDCl$_3$, δ): 3.15–3.40 (8H, m), 3.40–3.80 (4H, m), 3.98 (3H, s), 8.00 (2H, d, J=8.5 Hz), 8.23 (2H, d, J=8.5 Hz).

MASS (m/z): 328 (M$^+$+1).

PREPARATION 41

A mixture of 7-methoxyheptyl-[4-(methoxycarbonyl)phenyl]sulfone (0.85 g) and 1N-aqueous sodium hydroxide (5 ml) in a mixture of ethanol (20 ml) and tetrahydrofuran (10 ml) was stirred at 80° C. for 5 hours. The reaction mixture was concentrated under reduced pressure and the residue was triturated with water. The solution was adjusted to pH 1.0 using diluted hydrochloric acid. The precipitates were collected by filtration, washed with water and dried in vacuo to give 7-methoxyheptyl-(4-carboxyphenyl)sulfone (0.8 g) white solid.

IR (KBr): 2674, 2555, 1698, 1425, 1285 cm$^{-1}$.

NMR (DMSO-d$_6$, δ): 1.1–1.4 (6H, m), 1.40–1.60 (4H, m), 3.21 (3H, s), 3.18–3.40 (4H, m), 8.00 (2H, d, J=8.5 Hz), 8.18 (2H, d, J=8.5 Hz).

MASS (m/z): 315 (M$^+$+1).

PREPARATION 42

A mixture of 7-methoxyheptyl-4-carboxyphenylsulfone (0.8 g) and thionyl chloride (10 ml) was refluxed for 2 hours with stirring. The reaction mixture was concentrated under reduced pressure and the residue was dissolved in tetrahydrofuran (10 ml). To a mixture of 4-(methoxycarbonyl) benzamide oxime (0.49 g) in pyridine (25 ml) was added dropwise the above acid chloride solution at 5° C. with stirring. The mixture was stirred at 5° C. for 0.5 hour and continued at room temperature for an hour. The reaction mixture was concentrated under reduced pressure and the residue was triturated with water. The precipitates were collected by filtration, washed with water and dried to give 4-(methoxycarbonyl)-O-4'-[(7-methoxyheptylsulfonyl)benzoyl]benzamide oxime (1.0 g).

IR (KBr): 3492, 3369, 2933, 2857, 1724, 1616, 1276 cm$^{-1}$.

NMR (DMSO-d$_6$, δ): 1.15–1.54 (12H, m), 3.23 (3H, s), 3.22–3.40 (2H, m), 3.90 (3H, s), 7.25 (2H, br s), 7.95 (2H, d, J=8.3 Hz), 8.00–8.17 (4H, m), 8.47 (2H, d, J=8.3 Hz).

MASS (m/z): 491 (M$^+$+1).

PREPARATION 43

A solution of 4-methoxycarbonyl-O-[4'-(7-methoxyheptylsulfonyl)benzoyl]benzamide oxime (1.0 g) in N,N-dimethylformamide (10 ml) was stirred at 100° C. for 6 hours. The reaction mixture was poured into ice-water and adjusted to pH 1 using diluted hydrochloric acid. The precipitates were collected by filtration, washed with water and dried to give methyl-4-[5-[4-(7-methoxyheptylsulfonyl)phenyl]-1,2,4-oxadiazol-3-yl]benzoate (0.82 g).

IR (KBr): 2931, 2857, 1724, 1280 cm$^{-1}$.

NMR (DMSO-d$_6$, δ): 1.20–1.60 (1H, m), 3.17 (3H, s), 3.22–3.43 (4H, m), 3.92 (3H, s), 8.17–8.30 (6H, m), 8.47 (2H, d, J=8.3 Hz).

MASS (m/z): 473 (M$^+$+1).

PREPARATION 44

A mixture of methyl 4-[5-[4-(7-methoxyheptylsulfonyl)phenyl]-1,2,4-oxazol-3-yl]benzoate (0.8 g) and 10% sodium hydroxide aqueous solution (2 ml) in a mixture of ethanol (25 ml) and tetrahydrofuran (10 ml) was refluxed for 3.5 hours with stirring. The reaction mixture was concentrated under reduced pressure and to the residue was added water and adjusted to pH 1 using diluted hydrochloric acid. The precipitates were collected by filtration, washed with water and dried to give 4-[5-[4-(7-methoxyheptylsulfonyl)phenyl]-1,2,4-oxadiazol-3-yl]benzoic acid (0.8 g).

IR (KBr): 2931, 2857, 2750, 2650, 1693, 1415 cm$^{-1}$.

NMR (DMSO-d$_6$, δ): 1.15–1.60 (10H, m), 3.18 (3H, s), 3.20–3.50 (4H, m), 8.16–8.30 (6H, m), 8.47 (2H, d, J=8.4 Hz).

MASS (m/z): 459 (M$^+$+1).

PREPARATION 45

To a solution of 4-[5-[4-(7-methoxyheptylsulfonyl)phenyl]-1,2,4-oxadiazol-3-yl]benzoic acid (0.8 g) and triethylamine (0.4 g) in dichloromethane (30 ml) was added 3-(3-dimethylaminopropyl)-1-ethylcarbodimide (0.7 g) and 1-hydroxybenzotriazole (0.36 g). The mixture was stirred at room temperature for 8 hours. The reaction mixture was washed with water, saturated sodium chloride aqueous solution and dried over magnesium sulfate. After magnesium sulfate was filtered off, the filtrate was concentrated under reduced pressure and the residue was triturated with isopropyl ether. The precipitates were collected by filtration, washed with isopropyl ether and dried in vacuo to give 4-[5-[4-(7-methoxyheptylsulfonyl)phenyl]-1,2,4-oxadiazol-3-yl]benzoic acid benzotriazol-1-yl ester (0.89 g).

IR (KBr): 2931, 2857, 1787, 1616, 1409, 1282 cm$^{-1}$.

NMR (DMSO-d$_6$, δ): 1.10–1.50 (10H, m), 3.18 (3H, s), 3.22–3.40 (4H, m), 7.25–7.60 (2H, m), 7.70 (1H, d, J=8.5 Hz), 7.96 (1H, d, J=8.5 Hz), 8.19–8.24 (6H, m), 8.47 (2H, d, J=8.3 Hz).

MASS (m/z): 576 (M$^+$+1).

The following compound was obtained according to a similar manner to that of Preparation 39.

PREPARATION 46

1-[4-(Methoxycarbonyl)phenylsulfonyl]-9-bromoheptane

IR (KBr): 2925, 2850, 1724, 1461, 1280 cm$^{-1}$.

NMR (DMSO-d$_6$, δ): 1.10–1.35 (10H, m), 1.40–1.55 (2H, m), 1.60–1.80 (2H, m), 3.33–3.41 (2H, m), 3.50 (2H, t, J=6.7 Hz), 3.91 (3H, s), 8.05 (2H, d, J=8.4 Hz), 8.20 (2H, d, J=8.4 Hz).

MASS (m/z): 405 (M$^+$).

The following compound was obtained according to a similar manner to that of Preparation 40.

PREPARATION 47

1-[4-(Methoxycarbonyl)phenyl]sulfonyl-9-methoxyheptane

IR (KBr): 2927, 2854, 1699, 1425, 1286 cm$^{-1}$.

NMR (DMSO-d$_6$, δ): 1.10–1.30 (10H, m), 1.30–1.48 (6H, m), 3.19 (3H, s), 3.23–3.39 (4H, m), 3.90 (3H, s), 8.01 (2H, d, J=8.3 Hz), 8.17 (2H, d, J=8.3 Hz).

MASS (m/z): 357 (M$^+$+1).

The following compound was obtained according to a similar manner to that of Preparation 41.

PREPARATION 48

1-[4-Carboxyphenylsulfonyl)-9-methoxyheptane

IR (KBr): 2937, 2852, 2672, 2550, 1698, 1425, 1320, 1286 cm$^{-1}$.

NMR (DMSO-d$_6$, δ): 1.10–1.30 (10H, m), 1.40–1.47 (4H, m), 3.19 (3H, s), 3.23–3.39 (3H, m), 8.01 (2H, d, J=8.3 Hz), 8.17 (2H, d, J=8.3 Hz).

MASS (m/z): 343 (M$^+$+1).

The following compound was obtained according to a similar manner to that of Preparations 42 and 43.

PREPARATION 49

Methyl 4-[5-[4-(9-methoxy-n-nonylsulfonyl)phenyl]-1,2,4-oxadiazol-3-yl]benzoate

IR (KBr): 2925, 2854, 1724, 1612, 1409, 1278 cm$^{-1}$.

NMR (DMSO-d$_6$, δ): 1.19–1.57 (14H, m), 3.17 (3H, s), 3.12–3.43 (4H, m), 3.92 (3H, s), 8.17–8.30 (6H, m), 8.47 (2H, d, J=8.4 Hz).

MASS (m/z): 501 (M$^+$+1).

The following compound was obtained according to a similar manner to that of Preparation 44.

PREPARATION 50

4-[5-[4'-(9-Methoxy-n-nonylsulfonyl)phenyl]-1,2,4-oxadiazol-3-yl]benzoic acid

IR (KBr): 2927, 2854, 2667, 2550, 1691, 1614, 1415, 1282 cm$^{-1}$.

NMR (DMSO-d$_6$, δ): 1.10–1.30 (10H, m), 1.30–1.60 (4H, m), 3.17 (3H, s), 3.19–3.46 (4H, m), 8.00–8.27 (6H, m), 8.47 (2H, d, J=8.3 Hz), 13.34 (1H, br s).

MASS (m/z): 487 (M$^+$+1).

The following compound was obtained according to a similar manner to that of Preparation 45.

PREPARATION 51

4-[5-[4-(9-Methoxy-n-nonylsulfonyl)phenyl]-1,2,4-oxadiazol-3-yl]benzoic acid benzotriazol-1-yl ester IR (KBr): 2927, 2854, 1785, 1614, 1411, 1282 cm$^{-1}$.

NMR (DMSO-d$_6$, δ): 1.10–1.30 (10H, m), 1.30–1.60 (4H, m), 3.17 (3H, s), 3.03–3.43 (4H, m), 7.36–7.58 (2H, m), 7.72 (1H, d, J=8.3 Hz), 7.98 (1H, d, J=8.3 Hz), 8.17–8.27 (6H, m), 8.47 (2H, d, J=8.4 Hz).

MASS (m/z): 604 (M$^+$+1).

PREPARATION 52

To a mixture of methyl 4-hydroxybenzoate (1.52 g) and potassium carbonate (0.76 g) in acetone (30 ml) was added dropwise a solution of 1,7-dibromoheptane (3.1 g) in acetone (10 ml) at room temperature with stirring. The mixture was stirred at room temperature for 2.5 hours, and then refluxed for overnight with stirring. The reaction mixture was filtered under reduced pressure and the filtrate was concentrated under reduced pressure to give an oily solid. The oily solid was subjected to column chromatography on silica gel (silica gel 60 F254, Merck: 200 g) and eluted with a mixture of ethyl acetate and n-hexane (1:3). The fractions containing the objective compound were combined and concentrated under reduced pressure to give methyl 4-(7-bromo-n-heptyloxy]benzoate (2.3 g).

NMR (CDCl$_3$, δ): 1.43–1.60 (6H, m), 1.74–1.90 (4H, m), 3.42 (2H, t, J=6.8 Hz), 3.88 (3H, s), 4.00 (2H, t, J=6.8 Hz), 6.89 (2H, d, J=8.9 Hz), 7.98 (2H, d, J=8.9 Hz).

MASS (m/z) (API-ES-Positive): 329 (M$^+$).

PREPARATION 53

A solution of methyl 4-[7-bromo-n-heptyloxy)benzoate (2.3 g) in methanol (50 ml) and a solution of 28% sodium methoxide in methanol (3.5 ml) was refluxed for 12 hours with stirring. The reaction mixture was concentrated under reduced pressure and water was added to the residue and adjusted to pH 1 using hydrochloric acid. The precipitates were collected by filtration, washed with water and dried in vacuo to give an oil. The oil was subjected to column chromatography on silica gel (silica gel 60 F254, Merck: 100 g) and eluted with a mixture of ethyl acetate and n-hexane (1:5). The fractions containing the objective compound were combined and concentrated under reduced pressure to give methyl 4-(7-methoxyheptyloxy)benzoate (1.6 g) as an oil.

IR (Neat): 2937, 2867, 1718, 1607, 1469, 1442 cm$^{-1}$.

NMR (CDCl$_3$, δ): 1.15–1.60 (8H, m), 1.60–1.84 (2H, m), 3.33 (3H, s), 3.30–3.40 (2H, t, J=6.4 Hz), 3.88 (3H, 9), 4.00 (2H, t, J=6.4 Hz), 6.92 (2H, d, J=8.8 Hz), 8.00 (2H, d, J=8.8 Hz).

MASS (m/z): 281 (M$^+$+1).

PREPARATION 54

A mixture of methyl 4-(7-methoxy-n-heptyloxy)benzoate (1.5 g) and 1N-sodium hydroxide aqueous solution in ethanol (10 ml) and tetrahydrofuran (10 ml) was heated at 40–60° C. for 5 hours with stirring. The reaction mixture was concentrated under reduced pressure and water added to the residue and adjusted to pH 1 using hydrochloric acid. The precipitates were collected by filtration, washed with water and dried in vacuo to give 4-[7-methoxy-n-heptyloxy)benzoic acid (1.4 g) as a white solid.

IR (KBr): 2937, 2857, 2665, 2561, 1691, 1666, 1606, 1428 cm$^{-1}$.

NMR (DMSO-d$_6$, δ): 1.20–1.55 (8H, m), 1.60–1.80 (2H, m), 3.20 (3H, s), 3.29 (2H, d, J=6.4 Hz), 4.03 (2H, d, J=6.4 Hz), 7.00 (2H, d, J=8.7 Hz), 7.87 (2H, d, J=8.7 Hz).

MASS (m/z) (API-ES-Positive): 289 (M$^+$+23), 249.

PREPARATION 55

A mixture of 4-(7-methoxy-n-heptyloxy)benzoic acid (4 g) and thionyl chloride (40 ml) was refluxed for 2 hours with stirring. The reaction mixture was concentrated under reduced pressure and the residue was dissolved in tetrahydrofuran (40 ml). To a mixture of 4-(methoxycarbonyl)benzamide oxime (2.8 g) in pyridine (30 ml) was added dropwise the above acid chloride solution at 5° C. with stirring. The mixture was stirred at 5° C. for 0.5 hour and continued at room temperature for 0.5 hour. The reaction mixture was poured into water. The precipitates were collected by filtration, washed with water and dried in vacuo to give 4-(methoxycarbonyl)-O-[4-(7-methoxy-n-heptyloxy)benzoyl]benzamide oxime (6.0 g).

IR (KBr): 3478, 3372, 2931, 2854, 1714, 1605 cm$^{-1}$.

NMR (DMSO-d$_6$, δ): 1.20–1.55 (8H, m), 1.60–1.80 (2H, m), 3.21 (3H, s), 3.30 (3H, t, J=6.4 Hz), 3.89 (3H, s), 4.07 (2H, t, J=6.4 Hz), 7.03 (2H, d, J=8.4 Hz), 7.08 (2H, br s), 7.92 (2H, d, J=8.4 Hz), 8.05 (2H, d, J=8.4 Hz), 8.14 (2H, d, J=8.8 Hz).

MASS (m/z): 443 (M$^+$+1).

PREPARATION 56

A solution of 4-(methoxycarbonyl)-O-[4-(7-methoxy-n-heptyloxy)benzoyl]benzamide oxime (6.0 g) in N,N-dimethylformamide (60 ml) was stirred at 100° C. for 24 hours. The reaction mixture was concentrated under reduced pressure and water added to the residue and adjusted to pH 1 using hydrochloric acid. The precipitates were collected by filtration, washed with water and dried in vacuo to give a solid. The solid was subjected to column chromatography on silica gel (silica gel 60 P254, Merck: 300 g) and eluted with a mixture of ethyl acetate and toluene (1:10–1:5). The fractions containing the objective compound were combined and concentrated under reduced pressure to give methyl 4-[5-[4-(7-methoxy-n-heptyloxy)phenyl]-1,2,4-oxadiazol-3-yl]benzoate (5.4 g).

IR (KBr): 2939, 2863, 1722, 1612, 1471, 1417, 1270 cm$^{-1}$.

NMR (DMSO-d$_6$, δ): 1.15–1.60 (8H, m), 1.60–1.80 (2H, m), 2.10–2.20 (2H, m), 3.21 (3H, s), 3.90 (3H, s), 4.10 (2H, t, J=6.3 Hz), 7.20 (2H, d, J=8.5 Hz), 8.12–8.27 (6H, m).

MASS (m/z): 425 (M$^+$+1).

PREPARATION 57

A mixture of methyl 4-[5-[4-(7-methoxy-n-heptyloxy)phenyl]-1,2,4-oxadiazol-3-yl]benzoate (5.4 g) and 10% sodium hydroxide aqueous solution (15 ml) in ethanol (60 ml) and tetrahydrofuran (30 ml) was stirred at 60–70° C. for 2 hours. The reaction mixture was concentrated under reduced pressure and water added to the residue and adjusted to pH 1 using hydrochloric acid. The precipitates were collected by filtration, washed with water and dried in vacuo to give 4-[5-[4-(7-methoxy-n-heptyloxy)phenyl]-1,2,4-oxadiazol-3-yl]benzoic acid (4.4 g).

IR (KBr): 2931, 2857, 2667, 2560, 1693, 1614, 1419 cm$^{-1}$.

NMR (DMSO-d$_6$, δ): 1.10–1.50 (8H, m), 1.60–1.80 (2H, m), 3.21 (3H, s), 4.10 (2H, t, J=6.3 Hz), 7.18 (2H, d, J=9.1 Hz), 7.90–8.10 (4H, m), 8.13 (2H, d, J=8.9 Hz).

MASS (m/z): 411 (M$^+$+1).

PREPARATION 58

To a mixture of 4-[5-[4-(7-methoxy-n-heptyloxy)phenyl]-1,2,4-oxadiazol-3-yl]benzoic acid (2.0 g) and triethylamine (1.1 g) in dichloromethane (60 ml) was added 3-(3-dimethylaminopropyl)-1-ethylcarbodiimide hydrochloride (1.4 g) and 1-hydroxybenzotriazole (0.8 g). The mixture was stirred at room temperature overnight. The reaction mixture was washed with water, brine and dried over magnesium sulfate. The magnesium sulfate was filtered off, and the filtrate was concentrated under reduced pressure, and the residue was triturated with isopropyl ether. The precipitates were collected by filtration, washed with isopropyl ether and dried to give 4-[5-(4-(7-methoxy-n-heptyloxy)phenyl]-1,2,4-oxadiazol-3-yl]benzoic acid benzotriazol-1-yl ester (2.1 g).

IR (KBr): 2933, 2859, 1781, 1612 cm$^{-1}$.

NMR (CDCl$_3$, δ): 1.30–1.70 (8H, m), 1.65–1.90 (2H, m), 3.24 (3H, s), 3.39 (2H, t, J=6.4 Hz), 4.06 (2H, t, J=6.4 Hz), 7.05 (2H, d, J=8.9 Hz), 7.40–7.65 (3H, m), 8.10–8.25 (3H, m), 8.42 (4H, s).

MASS (m/z): 528 (M$^+$+1).

The following compound was obtained according to a similar manner to that of Preparation 52.

PREPARATION 59

Methyl 4-(9-bromo-n-nonyloxy)benzoate

IR (KBr): 2940, 2923, 2856, 1711, 1604, 1511 cm$^{-1}$.

NMR (CDCl$_3$, δ): 1.20–1.50 (10H, m), 1.60–1.90 (4H, m), 3.41 (2H, t, J=6.8 Hz), 3.88 (3H, s), 4.00 (2H, t, J=6.8 Hz), 6.91 (2H, d, J=8.8 Hz), 7.98 (2H, d, J=8.7 Hz).

MASS (m/z): 357 (M$^+$).

The following compound was obtained according to a similar manner to that of Preparation 53.

PREPARATION 60

Methyl 4-(9-methoxy-n-nonyloxy)benzoate

IR (KBr): 2929, 2852, 1724, 1606 cm$^{-1}$.

NMR (CDCl$_3$, δ): 1.20–1.40 (10H, m), 1.45–1.60 (2H, m), 1.65–1.83 (2H, m), 3.33 (3H, s), 3.37 (2H, t, J=6.5 Hz), 3.88 (3H, s), 4.01 (2H, t, J=6.5 Hz), 6.90 (2H, d, J=8.9 Hz), 8.00 (2H, d, J=8.9 Hz).

MASS (m/z): 308 (M$^+$+1).

The following compound was obtained according to a similar manner to that of Preparation 54.

PREPARATION 61

4-(9-Methoxy-n-nonyloxy)benzoic acid

IR (KBr): 2929, 2856, 2650, 2560, 1695, 1664, 1610 cm$^{-1}$.

NMR (DMSO-d$_6$, δ): 1.20–1.35 (10H, m), 1.40–1.60 (2H, m), 1.60–1.80 (2H, m), 3.20 (3H, s), 3.28 (2H, t, J=6.4 Hz), 4.02 (2H, t, J=6.4 Hz), 7.00 (2H, d, J=8.7 Hz), 7.87 (2H, d, J=8.7 Hz).

The following compound was obtained according to a similar manner to that of Preparation 55.

PREPARATION 62

4-(Methoxycarbonyl)-O-4'-(9-methoxy-n-nonyloxy) benzoylbenzamide oxime

IR (KBr): 3488, 3367, 2929, 2856, 1719, 1615, 1589 cm$^{-1}$.

NMR (DMSO-d$_6$, δ): 1.20–1.40 (10H, m), 1.40–1.60 (2H, m), 1.60–1.80 (2H, m), 3.20 (3H, s), 3.28 (2H, t, J=6.5 Hz), 3.89 (3H, s), 4.00 (2H, t, J=6.4 Hz), 7.03 (2H, d, J=8.9 Hz), 7.07 (2H, br s), 7.92 (2H, d, J=8.4 Hz), 8.05 (2H, d, J=8.4 Hz), 8.14 (2H, d, J=8.9 Hz).

MASS (m/z): 471 (M$^+$+1).

The following compound was obtained according to a similar manner to that of Preparation 56.

PREPARATION 63

Methyl 4-[5-[4-(9-methoxy-n-nonyloxy)phenyl]-1,2,4-oxadiazol-3-yl]benzoate

IR (KBr): 2933, 2856, 1722, 1616, 1276 cm$^{-1}$.

NMR (DMSO-d$_6$, δ): 1.20–1.40 (10H, m), 1.40–1.60 (2H, m), 1.60–1.80 (2H, m), 3.27–3.33 (2H, m), 3.20 (3H, s), 4.00 (3H, s), 4.05–4.11 (2H, m), 7.19 (2H, d, J=9 Hz), 7.90 (2H, d, J=9 Hz), 8.12–8.25 (4H, m).

MASS (m/z): 453 (M$^+$+1).

The following compound was obtained according to a similar manner to that of Preparation 57.

PREPARATION 64

4-[5-[4-(9-Methoxy-n-nonyloxy)phenyl]-1,2,4-oxadiazol-3-yl]benzoic acid

IR (KBr): 2931, 2857, 2667, 2560, 1693, 1614, 1419 cm$^{-1}$.

NMR (DMSO-d$_6$, δ): 1.15–1.40 (10H, m), 1.40–1.50 (2H, m), 1.60–1.80 (2H, m), 3.21 (3H, s), 3.27 (2H, t, J=6.5 Hz), 4.10 (2H, t, J=6.5 Hz), 7.18 (2H, d, J=8.8 Hz), 8.10–8.25 (6H, m).

MASS (m/z): 439 (M$^+$+1).

The following compound was obtained according to a similar manner to that of Preparation 58.

PREPARATION 65

4-[5-[4-(9-Methoxy-n-nonyloxy)phenyl]-1,2,4-oxadiazol-3-yl]benzoic acid benzotriazol-1-yl ester IR (KBr): 2931, 2856, 1781, 1612 cm$^{-1}$.

NMR (CDCl$_3$, δ): 1.20–1.40 (10H, m), 1.40–1.60 (2H, m), 1.60–1.80 (2H, m), 3.33 (3H, s), 3.37 (2H, t, J=6.5 Hz), 4.06 (2H, t, J=6.5 Hz), 7.05 (2H, d, J=8.8 Hz), 7.40–7.60 (3H, m), 8.10–8.20 (3H, m), 8.42 (4H, br s).

MASS (m/z): 556 (M$^+$+1).

PREPARATION 66

A mixture of 4-bromophenol (10 g), 1,6-dibromohexane (49.4 g) and potassium carbonate (9.59 g) in N,N-dimethylformamide (50 ml) was stirred for 4 hours at 60° C. (bath temp.), and then cooled to ambient temperature. To the reaction mixture was added ethyl acetate (200 ml), and the mixture was washed with water (200 ml×2) and brine. The organic layer was dried over magnesium sulfate. Magnesium sulfate was filtered off, and the filtrate was evaporated under reduced pressure to give a crude product. The crude product was purified by silica gel chromatography (1:0–1:1 hexane-ethyl acetate) to give 1-bromo-4-(6-bromohexyloxy)benzene (15.61 g).

IR (KBr): 2940.9, 2910.1, 2861.8, 1490.7, 1467.6, 1292.1, 1245.8 cm$^{-1}$.

NMR (DMSO-d$_6$, δ): 1.3–1.5 (4H, m), 1.6–2.0 (4H, m), 3.54 (2H, t, J=6.6 Hz), 3.94 (2H, t, J=6.4 Hz), 6.90 (2H, d, J=4.5 Hz), 7.43 (2H, d, J=4.5 Hz).

PREPARATION 67

A mixture of 1-bromo-4-(6-bromohexyloxy)benzene (6.0 g) and sodium methylate (28% in methanol) (10.3 ml) in methanol (30 ml) was stirred for 2 hours at 70° C. (bath temp.), and then the solvent was evaporated. The residue was neutralized by 1N-hydrochloric acid and extracted with ethyl acetate (100 ml), and washed with water and brine. The organic layer was dried over magnesium sulfate. Magnesium sulfate was filtered off, and the filtrate was evaporated under reduced pressure to give a crude product. The crude product was purified by silica gel chromatography (20:1–10:1 hexane-ethyl acetate) to give 1-bromo-4-(6-methoxyhexyloxy)benzene (15.61 g) as a colorless oil.

IR (KBr): 2937.1, 2861.8, 1591.0, 1488.8, 1473.3, 1286.3, 1243.9, 823.5 cm$^{-1}$.

NMR (DMSO-d$_6$, δ): 1.2–1.6 (6H, m), 1.6–1.8 (2H, m), 3.21 (3H, s), 3.30 (2H, t, J=6.4 Hz), 3.93 (2H, t, J=6.4 Hz), 6.90 (2H, d, J=6.8 Hz), 7.42 (2H, d, J=6.8 Hz).

PREPARATION 68

Under a nitrogen atmosphere, to a mixture of 1-bromo-4-(6-methoxyhexyloxy)benzene (3.68 g), 2-methyl-3-butyn-2-ol (1.86 ml) and triethylamine (18 ml) in pyridine (7.4 ml) was added triphenylphosphine (67.2 mg), copper(I) iodide (24.4 mg) and dichlorobis(triphenylphosphine)palladium(II) (18.0 mg), and refluxed overnight. After cooling, insoluble material was filtered off and washed with isopropyl ether. The filtrate was evaporated under reduced pressure. To the residue was added isopropyl ether and the mixture was washed with 0.1N-hydrochloric acid, water and brine. The organic layer was dried over magnesium sulfate. Magnesium sulfate was filtered off, and the filtrate was evaporated under reduced pressure to give a crude yellow oil. The crude yellow oil was purified by silica gel chromatography (10:1–2:1 hexane-ethyl acetate) to give 4-[4-(6-methoxyhexyloxy)phenyl]-2-methyl-3-butyn-2-ol (3.17 g) as a yellow powder.

IR (KBr): 3426.9, 3415.3, 2979.5, 2937.1, 2858.0, 2219.7, 1606.4, 1510.0, 1243.9, 1168.7, 1105.0 cm$^{-1}$.

NMR (DMSO-d$_6$, δ): 1.2–1.6 (12H, m), 1.6–1.8 (2H, m), 3.20 (3H, s), 3.30 (2H, t, J=6.4 Hz), 3.95 (2H, t, J=6.4 Hz), 5.39 (1H, s), 6.89 (2H, d, J=8.7 Hz), 7.29 (2H, d, J=8.7 Hz).

PREPARATION 69

Under a nitrogen atmosphere, to a solution of 4-[4-(6-methoxyhexyloxy)phenyl]-2-methyl-3-butyn-2-ol (3.0 g) in toluene (18 ml) was added sodium hydride (abt. 60% in oil suspension), and the mixture was refluxed for 2 hours. After cooling, to the reaction mixture was added isopropyl ether (100 ml) and water (100 ml), and neutralized by 1N-hydrochloric acid. The organic layer was separated, washed with water and brine, dried over magnesium sulfate. Magnesium sulfate was filtered off, and the filtrate was evaporated under reduced pressure to give a crude red oil. The crude red oil was purified by silica gel chromatography (10:1 hexane-ethyl acetate) to give 1-ethynyl-4-(6-methoxyhexyloxy)benzene (2.39 g) as an orange powder.

IR (KBr): 3263.0, 2929.3, 2861.8, 2100.1, 1604.5, 1510.0, 1249.6, 1116.6, 840.8 cm$^{-1}$.

NMR (DMSO-d$_6$, δ): 1.2–1.6 (6H, m), 1.6–1.8 (2H, m), 3.21 (3H, s), 3.30 (2H, t, J=6.4 Hz), 3.97 (2H, t, J=6.4 Hz), 4.00 (1H, s), 6.91 (2H, d, J=8.7 Hz), 7.39 (2H, d, J=8.7 Hz).

MASS (m/z): 233.3 (M$^+$+1).

PREPARATION 70

To a solution of 4-methoxycarbonylphenylhydroxyiminomethyl chloride (975 mg) and 1-ethynyl-4-(6-methoxyhexyloxy)benzene (1.06 g) in tetrahydrofuran (10 ml) was added triethylamine (0.83 ml) in tetrahydrofuran (10 ml) over a period of 30 minutes at 40° C., and the mixture was stirred at 40° C. for 3 hours and 30 minutes. The mixture was diluted with dichloromethane and washed with water and brine. The separated organic layer was dried over magnesium sulfate and evaporated under reduced pressure. The residue was triturated with acetonitrile. The precipitate was collected by filtration and dried to give 4-[5-[4-(6-methoxyhexyloxy)phenyl]isoxazol-3-yl]benzoic acid methyl ester (1.37 g).

IR (KBr): 2937.1, 2859.9, 1716.3, 1278.6, 1116.6 cm$^{-1}$.

NMR (CDCl$_3$, δ): 1.3–1.7 (6H, m), 1.7–2.0 (2H, m), 3.34 (3H, s), 3.39 (2H, t, J=6.3 Hz), 3.95 (3H, s), 4.02 (2H, t, J=6.4 Hz), 4.00 (1H, s), 6.74 (1H, s), 6.98 (2H, d, J=8.8 Hz), 7.77 (2H, d, J=8.8 Hz), 7.94 (2H, d, J=8.4 Hz), 8.14 (2H, d, J=8.4 Hz).

MASS (m/z): 410 (M$^+$+1).

PREPARATION 71

To a solution of 4-[5-[4-(6-methoxyhexyloxy)phenyl]isoxazol-3-yl]benzoic acid methyl ester (1.0 g) in a mixture of ethanol (10 ml) and tetrahydrofuran (20 ml) was added 10% sodium hydroxide aqueous solution (4.4 ml) and refluxed for 1 hour. The reaction mixture was adjusted to pH 1–2 with 1N-hydrochloric acid, and the resulting precipitate was collected by filtration to give 4-[5-[4-(6-methoxyhexyloxy)phenyl]isoxazol-3-yl]benzoic acid (964.2 mg).

IR (KBr): 2939.0, 2863.8, 2669.0, 2545.6, 1685.5, 1616.1, 1284.4, 1253.5 cm$^{-1}$.

NMR (DMSO-d$_6$, δ): 1.2–1.6 (6H, m), 1.6–1.9 (2H, m), 3.21 (3H, s), 3.31 (2H, t, J=6.2 Hz), 4.04 (2H, t, J=6.4 Hz), 6.11 (2H, d, J=8.8 Hz), 7.54 (1H, s), 7.85 (2H, d, J=8.7 Hz), 8.07 (2H, d, J=8.4 Hz), 8.15 (2H, d, J=8.4 Hz).

MASS (m/z): 396 (M$^+$+1).

PREPARATION 72

A mixture of 1-bromo-4-fluorobenzene (10 g), cis-2,6-dimethylmorpholine (7.74 ml) and potassium carbonate (15.8 g) in dimethylsulfoxide (50 ml) was stirred for 25 hours at 150° C. The reaction mixture was cooled and poured into water (500 ml), and stirred for 10 minutes. The reaction mixture was extracted with ethyl acetate (100 ml×2), washed with brine, dried over magnesium sulfate and evaporated under reduced pressure to give a crude yellow oil (680 mg). The crude oil was purified by silica gel chromatography (1:0–10:1 hexane-ethyl acetate) to give 4-(4-bromophenyl)-cis-2,6-dimethylmorpholine (360 mg).

IR (KBr): 2971.8, 2871.5, 1821.3, 1494.6, 1452.1, 1241.9, 1176.4, 1145.5, 1085.7 cm$^{-1}$.

NMR (CDCl$_3$, δ): 1.25 (6H, d, J=6.3 Hz), 2.39 (2H, t, J=11.2 Hz), 3.39 (2H, d, J=10.4 Hz), 3.7–3.9 (2H, m), 6.77 (2H, d, J=9.0 Hz), 7.34 (2H, d, J=9.0 Hz).

MASS (m/z): 270 (M$^+$).

The following compound was obtained according to a similar manner to that of Preparation 68.

PREPARATION 73

4-[4-(cis-2,6-Dimethylmorpholin-4-yl)phenyl]-2-methyl-3-butyn-2-ol

IR (KBr): 3326.6, 2979.5, 2931.3, 2873.4, 2832.9, 2223.5, 1606.4, 1511.9, 1454.1, 1376.9, 1334.5, 1238.1, 1174.4, 1151.3, 1081.9 cm$^{-1}$.

NMR (DMSO-d$_6$, δ): 1.14 (6H, d, J=6.1 Hz), 1.44 (6H, s), 2.25 (2H, dd, J=11.0 and 12.3 Hz), 3.5–3.8 (4H, m), 5.34 (1H, s), 6.90 (2H, d, J=8.9 Hz), 7.21 (2H, d, J=8.8 Hz).

MASS (m/z): 274 (M$^+$+1).

The following compound was obtained according to a similar manner to that of Preparation 69.

PREPARATION 74

4-(4-Ethynylphenyl)-cis-2,6-dimethylmorpholine

IR (KBr): 3313.1, 2933.2, 2869.6, 2852.2, 2102.0, 1602.6, 1243.9, 1145.5, 1078.0 cm$^{-1}$.

NMR (DMSO-d$_6$, δ): 1.15 (6H, d, J=6.1 Hz), 2.27 (2H, t, J=11.7 Hz), 3.6–3.8 (4H, m), 3.93 (1H, s), 6.91 (2H, d, J=8.9 Hz), 7.30 (2H, d, J=8.8 Hz).

MASS (m/z): 344 (M$^+$+1).

The following compound was obtained according to a similar manner to that of Preparation 70.

PREPARATION 75

4-[5-[4-(cis-2,6-Dimethylmorpholin-4-yl)phenyl]isoxazol-3-yl]benzoic acid methylester IR (KBr): 2973.7, 2873.4, 1718.3, 1614.1, 1510.0, 1450.2, 1278.6, 1241.9, 1178.3, 1106.9, 1089.6 cm$^{-1}$.

NMR (CDCl$_3$, δ): 1.18 (6H, d, J=6.1 Hz), 2.36 (2H, t, J=11.0 Hz), 3.6–3.9 (4H, m), 3.90 (3H, s), 7.11 (2H, d, J=8.9 Hz), 7.48 (1H, s), 7.76 (2H, d, J=8.8 Hz), 8.06 (2H, d, J=8.3 Hz), 8.11 (2H, d, J=8.6 Hz).

MASS (m/z): 393 (M$^+$+1).

The following compound was obtained according to a similar manner to that of Preparation 71.

PREPARATION 76

4-[5-[4-(cis-2,6-Dimethylmorpholin-4-yl)phenyl]isoxazol-3-yl]benzoic acid

IR (KBr): 3430, 2975, 2857, 2652, 2530, 1689, 1614, 1508, 1450, 1240, 1176 cm$^{-1}$.

NMR (DMSO-d$_6$, δ): 1.18 (6H, d, J=6.0 Hz), 2.36 (2H, t, J=11.1 Hz), 3.4–4.0 (5H, m), 7.11 (2H, d, J=8.9 Hz), 7.46 (1H, s), 7.76 (2H, d, J=8.7 Hz), 8.03 (2H, d, J=8.4 Hz), 8.09 (2H, d, J=8.4 Hz).

MASS (m/z): 379 (M$^+$+1).

The following compound was obtained according to a similar manner to that of Preparation 66.

PREPARATION 77

1-Bromo-4-(8-bromooctyloxy)benzene

IR (KBr): 1937.1, 2856.1, 1490.7, 1471.4, 1290.1, 1247.7, 1014.4 cm$^{-1}$.

NMR (DMSO-d$_6$, δ): 1.2–1.6 (8H, m), 1.6–2.0 (4H, m), 3.52 (2H, t, J=6.7 Hz), 3.94 (2H, t, J=6.4 Hz), 6.89 (2H, d, J=8.9 Hz), 7.42 (2H, d, J=8.9 Hz).

The following compound was obtained according to a similar manner to that of Preparation 67.

PREPARATION 78

4-[8-(4-Bromophenoxy)octyl]-cis-2,6-dimethylmorpholine

IR (KBr): 2933.2, 2867.6, 2850.3, 1490.7, 1471.4, 1238.1, 1145.5, 1076.1 cm$^{-1}$.

NMR (DMSO-d$_6$, δ): 1.02 (6H, d, J=6.3 Hz), 1.2–1.8 (14H, m), 2.1–2.3 (2H, m), 2.69 (2H, d, J=10.4 Hz), 3.4–3.6 (2H, m), 3.93 (2H, t, J=6.4 Hz), 6.89 (2H, d, J=8.9 Hz), 7.42 (2H, d, J=8.9 Hz).

MASS (m/z): 398 (M$^+$).

The following compound was obtained according to a similar manner to that of Preparation 68.

PREPARATION 79

4-[4-[8-(cis-2,6-Dimethylmorpholin-4-yl)octyloxy]phenyl]-2-methyl-3-butyn-2-ol

IR (KBr): 3187.8, 2973.7, 2933.2, 2858.0, 1602.6, 1506.1, 1469.5, 1241.9, 1164.8, 1139.7, 1081.9 cm$^{-1}$.

NMR (DMSO-d$_6$, δ): 1.02 (6H, d, J=6.3 Hz), 1.2–1.8 (20H, m), 2.1–2.3 (2H, m), 2.69 (2H, d, J=10.4 Hz), 3.4–3.7 (2H, m), 3.95 (2H, t, J=6.4 Hz), 5.38 (1H, s), 6.89 (2H, d, J=8.8 Hz), 7.29 (2H, d, J=8.7 Hz).

MASS (m/z): 402 (M$^+$+1).

The following compound was obtained according to a similar manner to that of Preparation 69.

PREPARATION 80

4-[8-(4-Ethynylphenoxy)octyl]-cis-2,6-dimethylmorpholine

IR (KBr): 3313.1, 2933.2, 2869.6, 2852.2, 2102.0, 1602.6, 1243.9, 1145.5, 1078.0 cm$^{-1}$.

NMR (DMSO-d$_6$, δ): 1.02 (6H, d, J=6.3 Hz), 1.2–1.8 (14H, m), 2.1–2.3 (2H, m), 2.69 (2H, d, J=10.4 Hz), 3.4–3.7 (2H, m), 3.97 (2H, t, J=6.5 Hz), 4.00 (1H, s), 6.91 (2H, d, J=8.7 Hz), 7.38 (2H, d, J=8.7 Hz).

MASS (m/z): 344 (M$^+$+1).

The following compound was obtained according to a similar manner to that of Preparation 70.

PREPARATION 81

4-[5-[4-[8-(cis-2,6-Dimethylmorpholin-4-yl)octyloxy]phenyl]isoxazol-3-yl]benzoic acid methyl ester IR (KBr): 2931.3, 2871.5, 2850.3, 1714.4, 1618.0, 1508.1, 1272.8 cm$^{-1}$.

NMR (CDCl$_3$, δ): 1.16 (6H, d, J=6.3 Hz), 1.2–2.0 (14H, m), 2.2–2.4 (2H, m), 2.75 (2H, d, J=10.5 Hz), 3.6–3.8 (2H, m), 3.96 (3H, s), 4.02 (2H, t, J=6.5 Hz), 6.74 (1H, s), 6.99 (2H, d, J=8.8 Hz), 7.77 (2H, d, J=8.8 Hz), 7.94 (2H, d, J=8.3 Hz), 8.15 (2H, d, J=8.3 Hz).

MASS (m/z): 521 (M$^+$+1).

The following compound was obtained according to a similar manner to that of Preparation 71.

PREPARATION 82

4-[5-[4-[8-(cis-2,6-Dimethylmorpholin-4-yl)octyloxy]phenyl]isoxazol-3-yl]benzoic acid IR (KBr): 3444.2, 2942.8, 2634.3, 2520.5, 1697.1, 1618.0 1452.1, 1278.6, 1259.3, 1180.2 cm$^{-1}$.

NMR (CDCl$_3$, δ): 1.12 (6H, d, J=6.3 Hz), 1.2–1.9 (14H, m), 2.3–2.7 (2H, m), 2.8–3.2 (2H, m), 3.7–4.0 (2H, m), 4.0–4.2 (2H, m), 7.12 (2H, d, J=8.8 Hz), 7.56 (1H, s), 7.86 (2H, d, J=8.7 Hz), 8.04 (2H, d, J=8.5 Hz), 8.10 (2H, d, J=8.5 Hz).

MASS (m/z): 493 (M$^+$+1).

The following compound was obtained according to a similar manner to that of Preparation 67.

PREPARATION 83

1-Bromo-4-(7-methoxyheptyloxy)benzene

NMR (DMSO-d$_6$, δ): 1.2–1.6 (8H, m), 1.6–1.8 (2H, m), 3.20 (3H, s), 3.29 (2H, t, J=6.4 Hz), 3.96 (2H, t, J=6.4 Hz), 5.39 (1H, s), 6.89 (2H, d, J=8.8 Hz), 7.29 (2H, d, J=8.8 Hz).

MASS (m/z): 301 (M$^+$).

The following compound was obtained according to a similar manner to that of Preparation 68.

PREPARATION 84

4-[4-(7-Methoxyheptyloxy)phenyl]-2-methyl-3-butyn-2-ol

IR (KBr): 3394.1, 3309.2, 2979.5, 2939.0, 2871.5, 2852.2, 1606.4, 1510.0, 1469.5, 1247.7, 1160.9 cm$^{-1}$.

NMR (DMSO-d$_6$, δ): 1.2–1.6 (14H, m), 1.6–1.8 (2H, m), 3.20 (3H, s), 3.29 (2H, t, J=6.4 Hz), 3.93 (2H, t, J=6.5 Hz), 6.89 (2H, d, J=9.0 Hz), 7.42 (2H, d, J=9.0 Hz).

MASS (m/z): 305.2 (M$^+$+1).

The following compound was obtained according to a similar manner to that of Preparation 69.

PREPARATION 85

1-Ethynyl-4-(7-methoxyheptyloxy)benzene

IR (KBr): 3313.1, 3290.0, 2935.1, 2859.9, 2105.9, 1606.4, 1506.1, 1247.7, 1114.7 cm$^{-1}$.

NMR (DMSO-d$_6$, δ): 1.2–1.6 (8H, m), 1.6–1.8 (2H, m), 3.20 (3H, s), 3.29 (2H, t, J=6.4 Hz), 3.97 (2H, t, J=6.5 Hz), 6.92 (2H, d, J=8.9 Hz), 7.39 (2H, d, J=8.8 Hz).

MASS (m/z): 247.2 (M$^+$+1).

The following compound was obtained according to a similar manner to that of Preparation 70.

PREPARATION 86

4-[5-[4-(7-Methoxyheptyloxy)phenyl]isoxazol-3-yl]benzoic acid methyl ester

IR (KBr): 2935.1, 2861.8, 1720.2, 1618.0, 1436.7, 1276.6, 1112.7 cm$^{-1}$.

NMR (CDCl$_6$, δ): 1.2–1.7 (8H, m), 1.7–2.0 (2H, m), 3.34 (3H, s), 3.38 (2H, t, J=6.5 Hz), 3.96 (3H, s), 4.02 (2H, t, J=6.4 Hz), 6.75 (1H, s), 6.99 (2H, d, J=8.9 Hz), 7.77 (2H, d, J=8.8 Hz), 7.94 (2H, d, J=8.5 Hz), 8.15 (2H, d, J=8.4 Hz).

MASS (m/z): 424 (M$^+$+1).

The following compound was obtained according to a similar manner to that of Preparation 71.

PREPARATION 87

4-[5-[4-(7-Methoxyheptyloxy)phenyl]isoxazol-3-yl]benzoic acid

IR (KBr): 2933.2, 2856.1, 2669.0, 2549.1, 1683.6, 1614.1, 1506.1, 1454.1, 1427.1, 1284.4, 1257.4, 1120.4 cm$^{-1}$.

NMR (DMSO-d$_6$, δ): 1.2–1.6 (5H, m), 1.7–1.9 (2H, m), 3.21 (3H, s), 3.2–3.5 (2H, m), 4.0–4.2 (2H, m), 7.0–7.2 (2H, m), 7.5 (1H, s), 7.8–8.0 (2H, m), 8.0–8.2 (4H, m).

MASS (m/z): 410 (M$^+$+1).

The following compound was obtained according to a similar manner to that of Preparation 66.

PREPARATION 88

1-Bromo-4-(7-bromoheptyloxy)benzene

IR (KBr): 2939.0, 2910.1, 2856.1, 1591.0, 1488.8, 1467.6, 1288.2, 1245.8 cm$^{-1}$.

NMR (DMSO-d$_6$, δ): 1.2–1.5 (6H, m), 1.6–1.9 (4H, m), 3.53 (2H, t, J=6.7 Hz), 3.94 (2H, t, J=6.5 Hz), 6.90 (2H, d, J=9.0 Hz), 7.42 (2H, d, J=9.0 Hz).

MASS (m/z): 350 (M$^+$).

PREPARATION 89

A mixture of 1-bromo-4-(7-bromoheptyloxy)benzene (4.405 g), cis-2,6-dimethylmorpholine (1.55 ml) and potassium carbonate (2.09 g) in N,N-dimethylformamide (22 ml) was stirred for 1 hour at 70° C. To the reaction mixture was added cis-2,6-dimethylmorpholine (7.75 ml) and stirred for 1 hour at 70° C. Ethyl acetate (100 ml) was added, and the mixture washed with water (50 ml×2) and brine. The separated organic layer was dried over magnesium sulfate and evaporated under reduced pressure to give a crude pale yellow oil (5.30 g). The crude oil was purified by silica gel chromatography (20:1–1:2 hexane-ethyl acetate) to give 4-[7-(4-bromophenoxy)heptyl]-cis-2,6-dimethylmorpholine (4.43 g) as a pale yellow oil.

IR (KBr): 2971.8, 2935.1, 2859.9, 2811.7, 2773.1, 1488.8, 1469.5, 1243.9, 1145.5, 1078 cm$^{-1}$.

NMR (DMSO-d$_6$, δ): 1.02 (6H, d, J=6.3 Hz), 1.2–1.8 (12H, m), 2.1–2.3 (2H, m), 2.69 (2H, d, J=10.5 Hz), 3.4–3.6 (2H, m), 3.94 (2H, t, J=6.4 Hz), 6.89 (2H, d, J=8.9 Hz), 7.42 (2H, d, J=8.9 Hz).

MASS (m/z): 386 (M$^+$+2).

The following compound was obtained according to a similar manner to that of Preparation 68.

PREPARATION 90

4-[4-[7-(cis-2,6-Dimethylmorpholin-4-yl)heptyloxy]phenyl]-2-methyl-3-butyn-2-ol

IR (KBr): 3151.1, 2973.7, 2935.1, 2859.9, 2825.2, 1604.5, 1506.1, 1243.9, 1160.9, 1139.7 cm$^{-1}$.

NMR (DMSO-d$_6$, δ): 1.02 (6H, d, J=6.3 Hz), 1.2–1.8 (18H, m), 2.1–2.3 (2H, m), 2.69 (2H, d, J=10.2 Hz), 3.4–3.7 (2H, m), 3.95 (2H, t, J=6.4 Hz), 5.39 (1H, s), 6.89 (2H, d, J=8.7 Hz), 7.28 (2H, d, J=8.6 Hz).

MASS (m/z): 388 (M$^+$+1).

The following compound was obtained according to a similar manner to that of Preparation 69.

PREPARATION 91

4-[7-(4-Ethynylphenoxy)heptyl]-cis-2,6-dimethylmorpholine

IR (KBr): 3290.0, 2971.8, 2935.1 2859.9, 2811.7, 2775.1, 2105.9, 1606.4, 1506.1, 1469.5, 1288.2, 1247.7, 1170.6, 1145.5, 1079.9, 833.1 cm$^{-1}$.

NMR (DMSO-d$_6$, δ): 1.02 (6H, d, J=6.3 Hz), 1.2–1.8 (12H, m), 2.1–2.3 (2H, m), 2.69 (2H, d, J=10.3 Hz), 3.4–3.6 (2H, m), 3.95 (2H, t, J=6.5 Hz), 4.00 (1H, s), 6.92 (2H, d, J=8.8 Hz), 7.39 (2H, d, J=8.7 Hz).

MASS (m/z): 330 (M$^+$+1).

The following compound was obtained according to a similar manner to that of Preparation 70.

PREPARATION 92

4-[5-[4-[7-(cis-2,6-Dimethylmorpholin-4-yl)heptyloxy]phenyl]isoxazol-3-yl]benzoic acid methyl ester IR (KBr): 2946.7, 2931.3, 2869.6, 2815.6, 2767.3, 1720.2, 1616.1, 1506.1, 1450.2, 1434.8, 1307.5, 1270.9, 1178.3, 1143.6, 1105.0 1078.0 cm$^{-1}$.

NMR (CDCl$_3$, δ): 1.16 (6H, d, J=6.3 Hz), 1.2–2.0 (12H, m), 2.2–2.4 (2H, m), 2.75 (2H, d, J=10.4 Hz), 3.5–3.9 (2H, m), 3.96 (3H, s), 4.02 (2H, t, J=6.5 Hz), 6.75 (1H, s), 6.99 (2H, d, J=8.8 Hz), 7.77 (2H, d, J=8.8 Hz), 7.94 (2H, d, J=8.5 Hz), 8.15 (2H, d, J=8.4 Hz).

MASS (m/z): 507 (M$^+$+1).

The following compound was obtained according to a similar manner to that of Preparation 71.

PREPARATION 93

4-[5-[4-[7-(cis-2,6-Dimethylmorpholin-4-yl)heptyloxy]phenyl]isoxazol-3-yl]benzoic acid IR (KBr): 3446.2, 2939.0, 2636.2, 2520.5, 1693.2, 1618.0, 1508.1, 1452.1, 1265.1 cm$^{-1}$.

NMR (DMSO-d$_6$, δ): 1.12 (6H, d, J=6.2 Hz), 1.2–1.9 (12H, m), 2.3–2.7 (2H, m), 2.8–3.2 (2H, m), 3.7–4.0 (2H, m), 4.07 (2H, t, J=6.3 Hz), 7.13 (2H, d, J=8.8 Hz), 7.55 (1H, s), 7.86 (2H, d, J=8.5 Hz), 8.04 (2H, d, J=8.5 Hz), 8.10 (2H, d, J=8.4 Hz).

MASS (m/z): 507 (M$^+$+1).

PREPARATION 94

To a solution of 4-hydroxypiperidine (15 g) in a mixture of tetrahydrofuran (THF) (150 ml) and water (100 ml) was added dropwise a solution of di-tert-butyl dicarbonate (48.5 g) in THF (100 ml) keeping pH 9 with 1N-sodium hydroxide under ice-cooling. The mixture was stirred at ambient temperature for 1 hour. The reaction mixture was successively washed with water and saturated sodium chloride, dried over anhydrous magnesium sulfate. Magnesium sulfate was filtered off, and the filtrate was evaporated under reduced pressure to give crystals. The crystals were washed with n-hexane (300 ml), collected by filtration and dried in vacuo to give 1-N-t-butyloxycarbonyl-4-hydroxypiperidine (24.66 g).

PREPARATION 95

To a solution of 1-N-t-butyloxycarbonyl-4-hydroxypiperidine (5.0 g) in dimethylformamide (DMF) (25 ml) was portionwise added sodium hydride (60% in oil) (1.29 g) with stirring under ice-cooling. The mixture was successively stirred at ambient temperature for 30 minutes, stirred at 60° C. for 1 hour and cooled with an ice bath. To the reaction mixture was added 1,5-dibromopentane (6.72 ml), and the mixture was stirred at ambient temperature for 3 hours. The reaction solution was poured into water (100 ml) and extracted twice with a mixture of ethyl acetate (80 ml) and n-hexane (30 ml). The extract was washed with saturated aqueous sodium chloride, dried over magnesium sulfate and evaporated in vacuo. The resulting residue was chromatographed on silica gel (200 ml) eluting with a mixture of n-hexane and ethyl acetate (5:1 v/v). The fractions containing the desired compound were collected and evaporated under reduced pressure to give 4-(5-bromopentyloxy)-1-N-t-butyloxycarbonylpiperidine (2.44 g).

NMR (CDCl$_3$, δ): 1.46 (9H, s), 1.50–1.70 (6H, m), 1.70–1.96 (4H, m), 3.00–3.15 (2H, m), 3.35–3.50 (5H, m), 3.70–3.90 (2H, m).

APCI MASS (m/z): 250 (M$^+$–101).

PREPARATION 96

To a solution of 4-(5-bromopentyloxy)-1-N-t-butyloxycarbonylpiperidine (2.44 g) in methanol (13 ml) was added 28% sodium methoxide methanol solution (14.2 ml), and the mixture was stirred under reflux for 4 hours. The reaction mixture was evaporated in vacuo. The resulting residue was chromatographed on silica gel (250 ml) eluting with a mixture of n-hexane and ethyl acetate (5:1 v/v). The fractions containing the object compound were collected and evaporated under reduced pressure to give 4-(5-methoxypentyloxy)-1-N-t-butyloxycarbonylpiperidine (1.97 g).

NMR (CDCl$_3$, δ): 1.45 (9H, s), 1.45–1.95 (10H, m), 3.03 (1H, dd, J=3.47 and 9.20 Hz), 3.10 (1H, dd, J=3.47 and 9.20 Hz), 3.44 (3H, s), 3.34–3.50 (5H, m), 3.70–3.85 (2H, m).

APCI MASS (m/z): 202 (M$^+$–101).

PREPARATION 97

To a solution of 4-(5-methoxypentyloxy)-1-N-t-butyloxycarbonylpiperidine (1.97 g) in ethyl acetate (20 ml) was added 4N-hydrogen chloride ethyl acetate solution (16.3 ml), and the mixture was stirred at ambient temperature for 2 hours. The reaction mixture was evaporated in vacuo. The resulting residue was dissolved in a mixture of dichloromethane and methanol (10:1; 50 ml:5 ml). To this solution was added 1N-sodium hydroxide (5 ml) with stirring. The organic layer was separated and evaporated under reduced pressure to give 4-(5-methoxypentyloxy)piperidine (0.62 g).

NMR (CDCl$_3$, δ): 1.25–1.50 (2H, s), 1.50–1.75 (6H, m), 1.90–2.10 (2H, m), 2.70–2.90 (2H, m), 2.95–3.20 (2H, m), 3.33 (3H, s), 3.35–3.50 (5H, m).

APCI MASS (m/z): 202 (M$^+$).

PREPARATION 98

A solution of 4-fluorobenzonitrile (0.38 g), 4-(5-methoxypentyloxy)piperidine (0.62 g) and potassium carbonate (0.87 g) in DMF (8 ml) was stirred at 90–95° C. for 6 hours. The reaction mixture was poured into water (50 ml) and extracted twice with a mixture of ethyl acetate and n-hexane (50 ml:20 ml). The extracts were combined, washed with saturated aqueous sodium chloride, dried over magnesium sulfate and evaporated in vacuo. The resulting residue was chromatographed on silica gel (100 ml) eluting with a mixture of n-hexane and ethyl acetate (5:1 v/v–2:1 v/v). The fractions containing the desired compound were collected and evaporated under reduced pressure to give 4-(5-methoxypentyloxy)-N-(4-cyanophenyl)piperidine (294 mg).

NMR (CDCl$_3$, δ): 1.35–1.55 (2H, s), 1.55–1.75 (5H, m), 1.85–2.05 (2H, m), 3.13 (1H, dd, J=3.47 and 9.20 Hz), 3.17 (1H, dd, J=3.47 and 9.20 Hz), 3.33 (3H, s), 3.35–3.75 (8H, m), 6.85 (2H, d, J=9.0 Hz), 7.47 (2H, d, J=8.96 Hz).

APCI MASS (m/z): 303 (M$^+$).

PREPARATION 99

A solution of 4-(5-methoxypentyloxy)-N-(4-cyanophenyl)piperidine (294 mg) and thiosemicarbazide (0.68 g) in toluene (20 ml) and trifluoroacetic acid (10 ml) was stirred at 60–65° C. for 7 hours. After cooling, the reaction mixture was poured into a mixture of water (100 ml) and ethyl acetate (200 ml) and adjusted to pH 10 with 1N-sodium hydroxide. The mixture was dissolved in a mixture of THF (50 ml) and methanol (10 ml). The organic layer was separated, washed with saturated aqueous sodium chloride, dried over anhydrous magnesium sulfate and evaporated in vacuo. The resulting precipitate was washed with isopropyl ether and dried in vacuo to give 2-amino-5-[4-[4-(5-methoxypentyloxy)piperidin-1-yl]phenyl]-1,3,4-thiadiazole (1.29 g).

NMR (CDCl$_3$+CD$_3$OD, δ): 1.30–1.50 (2H, m), 1.50–1.80 (6H, m), 1.90–2.10 (2H, m), 2.90–3.10 (2H, m), 3.34 (3H, s), 3.35–3.70 (7H, m), 6.93 (2H, d, J=8.91 Hz), 7.63 (2H, d, J=8.83 Hz).

APCI MASS (m/z): 377 (M$^+$).

PREPARATION 100

To a suspension of 2-amino-5-[4-[4-(5-methoxypentyloxy)piperidin-1-yl]phenyl]-1,3,4-thiadiazole (1.29 g) in ethanol (20 ml) was added ethyl 4-bromoacetylbenzoate (1.39 g) and stirred at reflux for 5 hours. The reaction mixture was cooled and poured into diisopropyl ether (IPE) (60 ml). The resulting precipitate was collected by filtration and dried. To a suspension of the precipitate in xylene (40 ml) was added trifluoroacetic acid (4 ml), and the mixture was stirred at reflux (130° C.) for 5 hours. The reaction mixture was cooled and poured into IPE (300 ml). The resulting precipitate was filtered and dried to give 4-[2-[4-[4-(5-methoxypentyloxy)piperidin-1-yl]phenyl]imidazo[2,1-b][1,3,4]thiadiazol-6-yl]benzoic acid ethyl ester trifluroacetic acid salt (2.01 g).

NMR (CDCl$_3$, δ): 1.42 (3H, t, J=7.12 Hz), 1.45–1.75 (6H, m), 1.85–2.10 (2H, m), 2.30–2.50 (2H, m), 3.36 (3H, s), 3.35–3.55 (5H, m), 3.60–3.80 (2H, m), 4.40 (2H, q, J=7.14 Hz), 7.57 (2H, d, J=8.78 Hz), 7.84 (2H, d, J=8.40 Hz), 7.91 (2H, d, J=8.79 Hz), 8.13 (1H, s).

ESI MASS (m/z): 549 (M$^+$+1).

PREPARATION 101

To a solution of 4-[2-[4-[4-(5-methoxypentyloxy)piperidin-1-yl]phenyl]imidazo[2,1-b][1,3,4]thiadiazol-6-yl]benzoic acid ethyl ester trifluroacetic acid salt (2.01 g) in a mixture of methanol (40 ml) and tetrahydrofuran (20 ml) was added 4N-NaOR (20 ml), and the mixture was refluxed for 6 hours. The reaction mixture was cooled, poured into water (200 ml) and adjusted to pH 2 with conc. HCl. The resulting precipitate was collected by filtration, washed in turn with water, isopropyl alcohol (30 ml) and IPE (50 ml) to give 4-[2-[4-[4-(5-methoxypentyloxy)piperidin-1-yl]phenyl]imidazo[2,1-b][1,3,4]thiadiazol-6-yl]benzoic acid (1.28 g).

ESI MASS (m/z) (Negative): 519.2 ($M^+$+1).

PREPARATION 102

To a solution of 4-[2-[4-[4-(5-methoxypentyloxy)piperidin-1-yl]phenyl]imidazo[2,1-b][1,3,4]thiadiazol-6-yl]benzoic acid (1.28 g) and 1-hydroxybenzotriazole (465 mg) in dichloromethane (50 ml) was added 1-ethyl-3-(3'-dimethylaminopropyl)carbodiimide hydrochloride (WSCD.HCl) (943 mg), and the mixture was stirred overnight at ambient temperature. The reaction mixture was evaporated in vacuo. To the resulting precipitate was added water (50 ml), and the solid was washed with water and IPE (50 ml) and dried under reduced pressure for 3 hours to give 4-[2-[4-[4-(5-methoxypentyloxy)piperidin-1-yl]phenyl]imdazo[2,1-b][1,3,4]thiadiazol-6-yl]benzoic acid benzotriazol-1-yl ester (1.26 g).

IR (KBr): 1774.2, 1708.6, 1604.5, 1471.4 1365.4, 1230.4 $cm^{-1}$.

NMR (CDCl$_3$, δ): 1.30–1.80 (8H, m), 1.85–2.10 (2H, m), 3.05–3.30 (2H, m), 3.33 (3H, s), 3.35–3.55 (4H, m), 3.55–3.75 (2H, m), 6.94 (2H, d, J=8.94 Hz), 7.30–7.60 (3H, m), 7.73 (2H, d, J=8.79 Hz), 8.00–8.20 (4H, m), 8.30 (2H, d, J=8.46 Hz).

ESI MASS (m/z) (Positive): 660.1 ($M^+$+Na).

PREPARATION 103

To a solution of 4-hydroxy-N-(benzyloxycarbonyl)piperidine (5.0 g) in THF (50 ml) were added 3-bromocyclohexene (3.67 ml) and silver oxide (7.4 g). The mixture was stirred at ambient temperature overnight. To the solution were added 3-bromocyclohexene (4.0 ml) and silver oxide (5.0 g), and the mixture was stirred at 40° C. for 6 hours. The reaction mixture was filtered, and the filtrate was evaporated in vacuo. The resulting residue was chromatographed on silica gel (300 ml) eluting with a mixture of n-hexane and ethyl acetate (5:1 v/v). The fractions containing the desired compound were collected and evaporated under reduced pressure to give 4-(2-cyclohexenyloxy)-N-(benzyloxycarbonyl)piperidine (3.83 g).

NMR (CDCl$_3$, δ): 1.40–2.20 (12H, m), 3.10–3.30 (2H, m), 3.50–3.70 (1H, m), 3.80–4.10 (3H, m), 5.12 (2H, s), 5.40–5.90 (2H, m), 7.35 (5H, m).

ESI MASS (m/z) (Positive): 338.3 ($M^+$+Na).

PREPARATION 104

A solution of 4-(2-cyclohexenyloxy)-N-(benzyloxycarbonyl)piperidine (3.80 g), and 10% palladium on carbon (50% wet) (1.0 g) in methanol (40 ml) was hydrogenated under an atmospheric pressure of hydrogen at ambient temperature for 6 hours. The catalyst was filtered off, and the filtrate was evaporated in vacua and dried in vacuo to give 4-(cyclohexyloxy)piperidine (2.42 g).

NMR (CDCl$_3$, δ): 1.10–1.40 (4H, m), 1.40–2.00 (10H, m), 2.60–2.90 (2H, m), 3.05–3.20 (2H, m), 3.30–3.50 (1H, m), 3.50–3.75 (1H, m).

APCI MASS (m/z): 184.4 ($M^+$+1).

PREPARATION 105

A solution of 4-fluorobenzonitrile (1.50 g), 4-(cyclohexyloxy)piperidine (2.40 g) and potassium carbonate (3.3 g) in DMF (30 ml) was stirred at 90–95° C. for 6 hours. The reaction mixture was poured into water (100 ml) and extracted twice with a mixture of ethyl acetate and n-hexane (80 ml:30 ml). The extracts were combined, washed with saturated aqueous sodium chloride, dried over magnesium sulfate and evaporated in vacuo. The resulting residue was chromatographed on silica gel (200 ml) eluting with a mixture of n-hexane and ethyl acetate (6:1 v/v–5:1 v/v). The fractions containing the desired compound were collected and evaporated under reduced pressure to give 4-[4-cyclohexyloxypiperidin-1-yl)benzonitrile (1.90 g).

NMR (CDCl$_3$, δ): 1.10–1.40 (5H, m), 1.40–2.00 (9H, m), 3.00–3.20 (2H, m), 3.20–3.45 (1H, m), 3.55–3.80 (3H, m), 6.85 (2H, d, J=8.99 Hz), 7.46 (2H, d, J=8.95 Hz).

APCI MASS (m/z): 285 ($M^+$).

PREPARATION 106

A solution of 4-(4-cyclohexyloxypiperidin-1-yl)benzonitrile (1.90 g), thiosemicarbazide (0.91 g) in toluene (20 ml) and trifluroacetic acid (10 ml) was stirred at 60–65° C. with stirring for 7 hours. After cooling, the reaction mixture was poured into a mixture of water (100 ml) and ethyl acetate (100 ml) and adjusted to pH 10 with 1N-sodium hydroxide. The mixture was dissolved in a mixture of THF (50 ml) and ethyl acetate (100 ml). The organic layer was separated, washed with saturated aqueous sodium chloride, dried over anhydrous magnesium sulfate and evaporated in vacuo. The resulting precipitate was washed diisopropyl ether and dried in vacuo to give 2-amino-5-[4-[4-(cyclohexyloxy)piperidin-1-yl]phenyl]-1,3,4-thiadiazole (1.72 g).

NMR (DMSO-d$_6$, δ): 1.10–1.45 (4H, m), 1.45–1.95 (10H, m), 2.85–3.10 (2H, m), 3.25–3.45 (1H, m), 3.50–3.80 (3H, m), 6.97 (2H, d, J=8.92 Hz), 7.54 (2H, d, J=8.80 Hz).

APCI MASS (m/z): 360 ($M^+$+1).

PREPARATION 107

To a suspension of 2-amino-5-[4-[4-(cyclohexyloxy)piperidin-1-yl]phenyl]-1,3,4-thiadiazole (1.72 g) in ethanol (30 ml) was added ethyl 4-bromoacetylbenzoate (1.95 g) and the mixture was stirred at reflux for 5 hours. The reaction mixture was cooled and poured into IPE (60 ml). The resulting precipitate was collected by filtration and dried. To a suspension of the precipitate in xylene (40 ml) was added trifluoroacetic acid (4 ml), and the mixture was stirred at reflux (130° C.) for 5 hours. The reaction mixture was cooled and poured into IPE (300 ml). The resulting precipitate was filtered and dried to give 4-[2-[4-[4-(cyclohexyloxy)piperidin-1-yl]phenyl]imidazo[2,1-b][1,3,4]-thiadiazol-6-yl]benzoic acid ethyl ester trifluoroacetic acid salt (2.01 g). This compound was immediately used as the starting compound for the next step.

The following compound was obtained according to a similar manner to that of Preparation 101.

PREPARATION 108

4-[2-[4-[4-(Cyclohexyloxy)piperidin-1-yl]phenyl]imidazo[2,1-b][1,3,4]thiadiazol-6-yl]benzoic acid NMR (CDCl$_3$+CD$_3$OD, δ): 1.10–2.10 (14H, m), 2.90–3.20 (2H, m), 4.20–4.60 (1H, m), 6.96 (2H, d, J=8.24 Hz), 7.50–8.20 (7H, m).

ESI MASS (m/z): 525.3 ($M^+$+Na).

The following compound was obtained according to a similar manner to that of Preparation 102.

PREPARATION 109

4-[2-[4-[4-(Cyclohexyloxy)piperidin-1-yl]phenyl]
imidazo[2,1-b][1,3,4]thiadiazol-6-yl]benzoic acid
benzotriazol-1-yl ester IR (KBr): 1772, 1703, 1606, 1470, 1369 cm$^{-1}$.

PREPARATION 110

To a solution of 4-(4-methanesulfonyloxypiperidin-1-yl) benzonitrile (4.90 g) in N,N-dimethylformamide (DMF) (50 ml) were added potassium carbonate (4.83 g) and 2,6-dimethylmorpholine (3.02 g), and the mixture was stirred at 90–95° C. for 6 hours. After cooling, the reaction mixture was poured into water (300 ml) and extracted twice with a mixture of ethyl acetate and n-hexane (100 ml:30 ml). The extracts were combined and washed in turn with water and saturated aqueous sodium chloride, dried over anhydrous magnesium sulfate and evaporated in vacuo. The resulting precipitates were washed with IPE (100 ml), collected by filtration and dried in vacuo to give 4-[4-(2,6-dimethylmorpholin-4-yl)piperidin-1-yl]benzonitrile (2.29 g).

NMR (CDCl$_3$, δ): 1.18 (6H, d, J=6.03 Hz), 1.60–1.90 (2H, m), 1.90–2.15 (2H, m), 2.35–2.60 (2H, m), 3.10–3.30 (2H, m), 3.40–4.10 (6H, m), 4.80–5.05 (1H, m), 6.87 (2H, d, J=8.97 Hz), 7.48 (2H, d, J=8.96 Hz).

APCI MASS (m/z): 300 (M$^+$).

The following compound was obtained according to a similar manner to that of Preparation 99.

PREPARATION 111

2-Amino-5-[4-[4-(2,6-dimethylmorpholin-4-yl)
piperidin-1-yl]phenyl]-1,3,4-thiadiazole NMR (CDCl$_3$, δ): 1.19 (6H, d, J=6.22 Hz), 1.70–2.15 (4H, m), 3.10–3.25 (2H, m), 3.40–3.70 (4H, m), 3.70–4.10 (2H, m), 4.80–5.00 (1H, m), 6.94 (2H, d, J=8.88 Hz), 7.65 (2H, d, J=8.82 Hz).

APCI MASS (m/z): 374 (M$^+$).

The following compound was obtained according to a similar manner to that of Preparation 100.

PREPARATION 112

4-[2-[4-[4-(2,6-Dimethylmorpholin-4-yl)piperidin-1-
yl]phenyl]imidazo[2,1-b][1,3,4]thiadiazol-6-yl]
benzoic acid ethyl ester trifluoroacetic acid salt NMR (CDCl$_3$, δ): 1.19 (6H, d, J=6.20 Hz), 1.41 (3H, t, J=7.11 Hz), 1.70–1.90 (2H, m), 1.90–2.20 (2H, m), 2.40–2.65 (2H, m), 3.20–3.40 (2H, m), 3.40–4.30 (8H, m), 4.39 (2H, q, J=7.07 Hz), 4.85–5.10 (1H, m), 7.02 (2H, d, J=8.93 Hz), 7.76 (2H, d, J=8.81 Hz), 7.87 (2H, d, J=8.34 Hz), 8.08 (1H, s), 8.11 (2H, d, J=9.71 Hz).

The following compound was obtained according to a similar manner to that of Preparation 101.

PREPARATION 113

4-[2-[4-[4-(2,6-Dimethylmorpholin-4-yl)piperidin-1-
yl)phenyl]imidazo[2,1-b][1,3,4]thiadiazol-6-yl]
benzoic acid APCI MASS (m/z): 519 (M$^+$+1).

The following compound was obtained according to a similar manner to that of Preparation 102.

PREPARATION 114

4-12-[4-[4-(2,6-Dimethylmorpholin-4-yl)piperidin-
1-yl]phenyl]imidazo[2,1-b][1,3,4]thiadiazol-6-yl]
benzoic acid benzotriazol-1-yl ester IR (KBr): 1774, 1691, 1605, 1466, 1429, 1232 cm$^{-1}$.

PREPARATION 115

A solution of 4-[4-(methanesulfonyloxy)piperidin-1-yl] nitrobenzene (2.0 g), and potassium thioacetate (1.14 g) in dimethylsulfoxide (DMSO) (20 ml) was stirred at 100–110° C. for 3 hours. The reaction mixture was poured into water (100 ml) and extracted twice with ethyl acetate (100 ml). The extracts were collected, washed with saturated aqueous sodium chloride, dried over anhydrous magnesium sulfate and evaporated in vacuo. The resulting precipitates were washed with IPE (50 ml), collected by filtration and dried in vacuo to give 4-(4-acetylthiopiperidin-1-yl)nitrobenzene (1.15 g).

NMR (CDCl$_3$, δ): 1.60–1.85 (2H, m), 2.00–2.20 (2H, m), 2.34 (3H, s), 3.15–3.35 (2H, m), 3.65–3.90 (3H, m), 6.81 (2H, d, J=9.47 Hz), 8.12 (2H, d, J=9.43 Hz).

APCI MASS (m/z): 281 (M$^+$).

PREPARATION 116

To a solution of 4-(4-acetylthiopiperidin-1-yl) nitrobenzene (3.34 g) in a mixture of THF (30 ml) and methanol (30 ml) was added 28% sodium methoxide methanol solution (2.67 ml) at 0–5° C. and stirred at the same temperature for 30 minutes. To the mixture was added iodopropane (1.51 ml) at the same temperature and stirred at ambient temperature for 2 hours. The reaction mixture was evaporated in vacuo and dissolved in ethyl acetate (100 ml). The solution was washed three times with saturated aqueous sodium chloride, dried over anhydrous magnesium sulfate and evaporated in vacuo. A solution of the resulting residue, ammonium chloride (1.0 g) and iron powder (4.0 g) in a mixture of ethanol (60 ml) and water (30 ml) was refluxed for 2 hours. The reaction mixture was evaporated in vacuo. The resulting residue was chromatographed on silica gel (300 ml) eluting with ethyl acetate. The fractions containing the desired compound were collected and evaporated under reduced pressure to give 4-(4-propylthiopiperidin-1-yl) aniline (2.47 g).

NMR (CDCl$_3$, δ): 1.00 (3H, t, J=7.16 Hz), 1.50–1.90 (4H, m), 1.95–2.15 (2H, m), 2.55 (2H, t, J=7.56 Hz), 2.60–2.80 (3H, m), 3.35–3.55 (4H, m), 6.63 (2H, d, J=8.81 Hz), 6.81 (2H, d, J=8.80 Hz).

APCI MASS (m/z): 251 (M$^+$).

PREPARATION 117

A solution of 4-(4-propylthiopiperidin-1-yl)aniline (2.44 g), 1-[2-(p-toluenesulfonyloxy)ethyl]-2-oxazolidone (3.08 g) and potassium carbonate (3.28 g) in a mixture of acetonitrile (25 ml) and DMF (13 ml) was stirred at 120° C. for 5 hours. The reaction mixture was poured into water (100 ml) and extracted twice with ethyl acetate (60 ml). The extracts were collected, washed twice with saturated aqueous sodium chloride, dried over anhydrous magnesium sulfate and evaporated in vacuo. The resulting residue was chromatographed on silica gel (200 ml) eluting with ethyl acetate. The fractions containing the desired compound were collected and evaporated under reduced pressure to give 1-[(2-oxazolidon-3-yl)ethylaminol-4-[4-(propylthio) piperidin-1-yl]benzene (1.98 g).

NMR (CDCl$_3$, δ): 1.00 (3H, t, J=7.34 Hz), 1.50–1.90 (5H, m), 2.00–2.20 (2H, m), 2.55 (2H, t, J=7.5 Hz), 2.55–2.90 (3H, m), 3.10–3.65 (8H, m), 4.29 (2H, dd, J=6.56 and 8.29 Hz), 6.40–6.70 (2H, m), 6.70–6.95 (2H, m).

APCI MASS (m/z): 364 (M$^+$).

PREPARATION 118

A solution of 1-[(2-oxazolidon-3-yl)ethylamino]-4-(4-propylthiopiperidin-1-yl)benzene (1.96 g) in 30% HBr in acetic acid solution (15 ml) was stirred at ambient temperature overnight. IPE (100 ml) was added to the reaction mixture, and the resulting precipitates were collected by filtration, washed with IPE (40 ml) and dried under reduced pressure. The precipitates were dissolved in a mixture of ethanol (20 ml) and n-butylalcohol (40 ml), and the solution was refluxed for 6 hours. After cooling, to the reaction mixture was added IPE (100 ml), and the resulting precipitates were collected by filtration, washed with IPE (20 ml) and dried in vacuo to give 1-[4-(4-propylthiopiperidin-1-yl)phenyl-1-yl]piperazine (2.51 g).

NMR (CDCl$_3$+CD$_3$OD, δ): 1.03 (3H, t, J=6.98 Hz), 1.50–1.90 (2H, m), 2.10–2.40 (3H, m), 2.50–2.90 (5H, m), 6.80–7.00 (2H, m), 7.55–7.70 (2H, m).

APCI MASS (m/z): 320 (M$^+$).

PREPARATION 119

A solution of 1-[4-(4-propylthiopiperidin-1-yl)benzen-1-yl]piperazine (2.45 g) and potassium carbonate (2.81 g) in N,N-dimethylsulfoxide (30 ml) was stirred at 100° C. for 30 minutes and then at 150° C. for 5 hours. The reaction mixture was poured into water (100 ml) and extracted twice with ethyl acetate (100 ml). The extracts were collected, washed twice with saturated aqueous sodium chloride, dried over anhydrous magnesium sulfate and evaporated in vacuo. The resulting residue was chromatographed on silica gel (200 ml) eluting with a mixture of dichloromethane and methanol (9:1 v/v). The fractions containing the desired compound were collected and evaporated under reduced pressure and washed with IPE. The precipitates were collected by filtration and dried in vacuo to give 4-[1-[4-(4-propylthiopiperidin-1-yl)phenyl]piperazin-4-yl]benzoic acid ethyl ester (1.22 g).

NMR (CDCl$_3$, δ): 1.01 (3H, t, J=7.36 Hz), 1.37 (3H, t, J=7.79 Hz), 1.50–1.90 (4H, m), 2.00–2.20 (2H, m), 2.56 (2H, t, J=7.53 Hz), 2.65–2.90 (3H, m), 3.15–3.30 (4H, m), 3.40–3.60 (6H, m), 4.33 (2H, q, J=7.11 Hz), 6.91 (2H, d, J=9.10 Hz), 6.92 (4H, s), 7.95 (2H, d, J=8.97 Hz).

APCI MASS (m/z): 468 (M$^+$).

PREPARATION 120

To a solution of 4-[1-[4-(4-propylthiopiperidin-1-yl)phenyl]piperazin-4-yl]benzoic acid ethyl ester (1.22 g) in a mixture of ethanol (10 ml) and tetrahydrofuran (40 ml) was added 10% aqueous NaOH (2.1 ml) and 1N-NaOR (10 ml), and the mixture was refluxed for 6 hours. The reaction mixture was cooled and adjusted to pH 2.5–3.0 with 1N-HCl. The resulting precipitates were collected by filtration, washed in turn with water (30 ml) and IPE (50 ml) and dried in vacuo to give 4-[1-[4-(4-propylthiopiperidin-1-yl)phenyl]piperazin-4-yl]benzoic acid (0.99 g).

NMR (DMSO-d$_6$, δ): 0.94 (3H, t, J=7.38 Hz), 1.40–1.70 (5H, m), 1.85–2.15 (2H, m), 2.60–2.90 (4H, m), 3.00–3.20 (5H, m), 3.30–3.55 (6H, m), 6.88 (4H, s), 7.01 (2H, d, J=9.00 Hz), 7.78 (2H, d, J=8.89 Hz).

APCI MASS (m/z): 440 (M$^+$).

PREPARATION 121

To a solution of 4-[1-[4-(4-propylthiopiperidin-1-yl)phenyl]piperazin-4-yl]benzoic acid (0.98 g), 1-hydroxybenzotriazole (0.39 g) in dichloromethane (20 ml) was added 1-ethyl-3-(3'-dimethylaminopropyl)carbodiimide hydrochloride (WSCD.HCl) (0.85 g), and the mixture was stirred for 15 minutes. To the solution was added triethylamine (0.31 ml), and the mixture was stirred overnight at ambient temperature. The reaction mixture was poured into a mixture of 0.1N-hydrochloric acid (25 ml) and dichloromethane (60 ml). The organic layer was washed with water and saturated aqueous sodium chloride, dried over anhydrous magnesium sulfate and evaporated in vacuo. To the resulting precipitates were washed with water and IPE (50 ml), collected by filtration and dried under reduced pressure to give 4-[1-[4-(4-propylthiopiperidin-1-yl)phenyl)piperazin-4-yl]benzoic acid benzotriazol-1-yl ester (1.04 g).

NMR (CDCl$_3$, δ): 1.01 (3H, t, J=7.36 Hz), 1.50–1.90 (5H, m), 2.00–2.20 (2H, m), 2.56 (2H, t, J=7.56 Hz), 2.65–2.90 (3H, m), 3.20–3.30 (4H, m), 3.45–3.70 (6H, m), 6.94 (4H, s), 7.00 (2H, d, J=9.19 Hz), 7.35–7.60 (3H, m), 8.05–8.20 (3H, m).

APCI MASS (m/z): 557 (M$^+$).

PREPARATION 122

To a solution of N-t-butyloxycarbonyl-4-acetylthiopiperidine (5.5 g) in a mixture of THF (50 ml) and methanol (50 ml) was added 28% sodium methoxide methanol solution (4.76 ml) with stirring under ice-cooling and stirred at the same temperature for 30 minutes. To the solution was added 1,6-dibromohexane (17.1 g) under ice-cooling, and the mixture was successively stirred at ambient temperature for 30 minutes and then stirred at 45° C. for 2 hours. The reaction mixture was concentrated in vacuo. The resulting residue was chromatographed on silica gel (500 ml) eluting with a mixture of n-hexane and ethyl acetate (6:1 v/v). The fractions containing the desired compound were collected and evaporated under reduced pressure to give 4-(6-bromohexylthio)-N-t-butyloxycarbonylpiperidine (4.95 g).

NMR (CDCl$_3$, δ): 1.45 (9H, s), 1.45–1.70 (8H, m), 1.80–2.00 (4H, m), 2.55 (1H, t, J=7.34 Hz), 2.65–3.05 (3H, m), 3.30–3.50 (2H, m), 3.85–4.10 (2H, m).

APCI MASS (m/z): 250 (M$^+$–101).

PREPARATION 123

To a solution of 4-(6-bromohexylthio)-N-t-butyloxycarbonylpiperidine (4.95 g) in methanol (20 ml) was added 28% sodium methoxide methanol solution (26.6 ml), and the mixture was stirred under reflux for 4 hours. After cooling, the reaction mixture was evaporated in vacuo. The resulting residue was chromatographed on silica gel (400 ml) eluting with a mixture of n-hexane and ethyl acetate (5:1 v/v). The fractions containing the object compound were collected and evaporated under reduced pressure to give 4-(6-methoxyhexylthio)-N-t-butyloxycarbonylpiperidine (3.32 g).

NMR (CDCl$_3$, δ): 1.25–1.45 (6H, m), 1.45 (9H, s), 1.45–1.60 (4H, m), 1.80–2.00 (2H, m), 2.54 (2H, t, J=7.47 Hz), 2.60–3.00 (3H, m), 3.30 (3H, s), 3.37 (2H, t, J=6.34 Hz), 3.96 (2H, m).

PREPARATION 124

To a solution of 4-(6-methoxyhexylthio)-N-t-butoxycarbonylpiperidine (3.32 g) in dichloromethane (40 ml) were added triethylsilane (8.0 ml) and trifluoroacetic acid (15.4 ml) with stirring in an ice bath. The mixture was stirred at ambient temperature for 2 hours. The reaction mixture was evaporated in vacuo. The resulting residue was chromatographed on silica gel (400 ml) eluting with a mixture of dichloromethane and methanol (4:1 v/v). The fractions containing the object compound were collected and evaporated under reduced pressure to give 4-(6-methoxyhexylthio)piperidine (4.77 g). This compound was immediately used as the starting compound for the next step.

NMR ($CD_3OD$, δ): 1.30–1.90 (10H, m), 2.10–2.30 (2H, m), 2.60 (2H, t, J=7.30 Hz), 3.31 (3H, s), 3.42 (2H, t, J=4.28 Hz).

APCI MASS (m/z): 232.4 ($M^+$+1).

The following compound was obtained according to a similar manner to that of Preparation 98.

PREPARATION 125

4-(6-Methoxyhexylthiopiperidin-1-yl)benzonitrile

NMR ($CDCl_3$, δ): 1.30–1.50 (4H, m), 1.50–1.80 (6H, m), 1.95–2.15 (2H, m), 2.57 (2H, t, J=7.50 Hz), 2.75–3.10 (3H, m), 3.33 (3H, s), 3.37 (2H, t, J=6.32 Hz), 3.65–3.90 (2H, m), 6.84 (2H, d, J=9.08 Hz), 7.47 (2H, d, J=9.08 Hz).

APCI MASS (m/z): 347 ($M^+$).

The following compound was obtained according to a similar manner to that of Preparation 99.

PREPARATION 126

2-Amino-5-[4-[4-(6-methoxyhexylthio)piperidin-1-yl]phenyl]-1,3,4-thiadiazole

NMR (DMSO-$d_6$, δ): 1.20–1.60 (10H, m), 1.85–2.05 (2H, m), 2.45–2.60 (2H, m), 2.80–3.00 (3H, m), 3.21 (3H, s), 3.29 (2H, t, J=6.42 Hz), 3.60–3.80 (2H, m), 6.97 (2H, d, J=8.94 Hz), 7.20 (2H, s), 7.55 (2H, d, J=8.80 Hz).

APCI MASS (m/z): 421 ($M^+$).

The following compound was obtained according to a similar manner to that of Preparation 100.

PREPARATION 127

4-[2-[4-[4-(6-Methoxyhexylthio)piperidin-1-yl]phenyl]imidazo[2,1-b][1,3,4]thiadiazol-6-yl]benzoic acid ethyl ester trifluroacetic acid salt ESI MASS (m/z) (Positive): 579 ($M^+$).

The following compound was obtained according to a similar manner to that of Preparation 101.

PREPARATION 128

4-[2-[4-[4-(6-Methoxyhexylthio)piperidin-1-yl]phenyl]imidazo[2,1-b][1,3,4]thiadiazol-6-yl]bezoic acid NMR ($CDCl_3$, δ): 1.30–1.80 (10H, m), 1.95–2.25 (2H, m), 2.45–2.70 (2H, m), 2.70–3.20 (4H, m), 3.35 (3H, s), 3.35–3.50 (2H, m), 6.80–7.05 (3H, m), 7.36 (1H, s), 7.63 (1H, d, J=8.19 Hz), 7.75 (1H, d, J=8.21 Hz), 7.89 (1H, d, J=7.52 Hz), 8.00–8.20 (2H, m).

APCI MASS (m/z): 551 ($M^+$).

The following compound was obtained according to a similar manner to that of Preparation 102.

PREPARATION 129

4-[2-[4-[4-(6-Methoxyhexylthio)piperidin-1-yl]phenyl]imidazo[2,1-b][1,3,4]thiadiazol-6-yl]benzoic acid benzotriazol-1-yl ester IR (KBr): 1772, 1603, 1535, 1470 $cm^{-1}$.

PREPARATION 130

To a solution of tetrahydrothiopyran-4-one (1.0 g) in dichloromethane (20 ml) was added 3-chloroperoxybenzoic acid (4.16 g, purity 80%) under ice-cooling with stirring. The mixture was stirred at the same temperature for 20 minutes and then stirred at ambient temperature for 1 hour. The resulting precipitates were filtered off, and the filtrate was concentrated in vacuo. The residue was dissolved in a mixture of ethyl acetate. (50 ml) and water (20 ml) and adjusted to pH 2 with 1N-hydrochloric acid. The organic layer was separated, and the aqueous layer was extracted with ethyl acetate (50 ml). The organic layers were combined, washed in turn with water, saturated aqueous sodium bicarbonate and saturated aqueous sodium chloride, dried over anhydrous magnesium sulfate and evaporated in vacuo. The resulting residue was dissolved in a mixture of dichloromethane (100 ml) and methanol (20 ml), dried over anhydrous magnesium sulfate and evaporated in vacuo to give 1,1-dioxotetrahydrothiopyran-4-one (1.18 g).

NMR ($CD_3CD$, δ): 2.20 (4H, t, J=6.05 Hz), 2.90–3.20 (4H, m).

PREPARATION 131

To a solution of (R,S)-5-hydroxy-2-phenyl-1,3-dioxane (5.0 g) (Acta Chemica Scandinavia, 1996; 50: 185–187) in DMF (50 ml) were added t-butyl dimethylsilyl chloride (12.5 g) and imidazole (9.45 g) with stirring at ambient temperature, and the mixture was allowed to stand at the same temperature overnight. The reaction mixture was poured into pH 6.86 standard buffer solution (500 ml) and extracted twice with ethyl acetate (200 ml). The extracts were combined, washed successively with water and saturated aqueous sodium chloride, dried over anhydrous magnesium sulfate and evaporated in vacuo. The resulting residue was chromatographed on silica gel (400 ml) eluting with a mixture of n-hexane and ethyl acetate (9:1 v/v). The fractions containing the object compound were collected and evaporated under reduced pressure to give (R,S)-5-(tert-butyldimethylsilyloxy)-2-phenyl-1,3-dioxane (10.14 g).

NMR ($CDCl_3$, δ): 0.02–0.12 (6H, m), 0.89–0.94 (9H, m), 3.50–4.25 (5H, m), 5.50–5.95 (1H, m), 7.30–7.55 (5H, m).

ESI MASS (m/z) (Positive): 317.3 ($M^+$+Na).

PREPARATION 132

A solution of (R,S)-5-tert-butyldimethylsilyloxy-2-phenyl-1,3-dioxane (10.1 g) and 10% palladium on carbon (50% including water) (5.0 g) in methanol (100 ml) was hydrogenated under an atmospheric pressure of hydrogen with stirring at ambient temperature for 2 hours. The catalyst was filtered off, and the filtrate was dried over anhydrous magnesium sulfate and evaporated in vacuo. The resulting residue was chromatographed on silica gel (300 ml), eluting with a mixture of n-hexane and ethyl acetate (3:1 v/v). The fractions containing the object compound were collected and evaporated under reduced pressure to give (R,S)-2-(tert-butyldimethylsilyloxy)-3-hydroxypropanol (5.69 g). This compound was immediately used as the starting compound for the next step. To a solution of this compound were successively added diisopropylethylamine (14.4 ml) and acetyl chloride (6.5 ml) with stirring, and the mixture was stirred at 0–5° C. for 2 hours water (10 ml) was added to the reaction mixture, and the organic layer was separated, washed with saturated aqueous sodium chloride, dried over anhydrous magnesium sulfate and evaporated in vacuo. The resulting residue was dissolved in a mixture of methanol (100 ml) and conc. hydrochloric acid (1.0 ml), and the solution was stirred at ambient temperature for 2 hours. The reaction mixture was concentrated in vacuo and chromatographed on silica gel (200 ml) eluting with a mixture of n-hexane and ethyl acetate (2:1 v/v). The fractions containing the object compound were collected and evaporated under reduced pressure to give (R,S)-2-hydroxy-1,3-diacetoxypropane (2.06 g).

NMR (CDCl$_3$, δ): 2.06 (3H, s), 2.11 (3H, s), 3.74 (1H, m), 4.10–4.25 (4H, m).

PREPARATION 133

To a solution of oxalyl chloride (1.09 ml) in dichloromethane (20 ml was added dropwise dimethylsulfoxide (DMSO) (1.93 ml) with stirring at –40–50° C. After stirring at the same temperature for 5 minutes, to the solution was added dropwise a solution of (R,S)-2-hydroxy-1,3-diacetoxypropane (2.0 g) in dichloromethane (20 ml) and stirred at the same temperature for 30 minutes. Triethylamine (5.54 ml) was added dropwise to the reaction mixture with stirring at the same temperature, and then the mixture was stirred at ambient temperature for 30 minutes. The insoluble material was filtered off, and the filtrate was washed successively with 0.5N hydrochloric acid, water, saturated aqueous sodium bicarbonate and saturated aqueous sodium chloride, dried over anhydrous magnesium sulfate and evaporated in vacuo. The resulting residue was chromatographed on silica gel (200 ml) eluting with a mixture of n-hexane and ethyl acetate (1:2 v/v). The fractions containing the object compound were collected and evaporated under reduced pressure to give 2-oxo-1,3-diacetoxypropane (1.17 g).

NMR (CDCl$_3$, δ): 2.18 (6H, s), 4.76 (4H, s).

ESI MASS (m/z) (Positive): 197.3 (M$^+$+Na).

PREPARATION 134

To a solution of (R,S)-5-hydroxy-2-phenyl-1,3-dioxane (10.0 g) (Acta Chemica Scandinavica, 1996; 50: 185–187) in dichloromethane (200 ml) were added molecular sieves 4A powder (28 g) and pyridinium chlorochromic acid (PCC) (23.9 g) with stirring at ambient temperature and the mixture was stirred at the same temperature for 2 hours. To the reaction mixture was added diethyl ether (100 ml), and the insoluble material was filtered off with celite and the filtrates were evaporated in vacuo. The residue was dissolved in a mixture of n-hexane (100 ml) and ethyl acetate (100 ml), dried over anhydrous magnesium sulfate and evaporated in vacuo. The resulting residue was chromatographed on silica gel (600 ml) eluting with a mixture of n-hexane and ethyl acetate (2:1 v/v). The fractions containing the object compound were collected and evaporated under reduced pressure to give 5-oxo-2-phenyl-1,3-dioxane (7.06 g).

NMR (CDCl$_3$, δ): 4.49 (2H, s), 4.50 (2H, s), 5.90 (1H, s), 7.30–7.60 (5H, m).

PREPARATION 135

To a solution of 4-aminobutanol (630 mg), 5-oxo-2,2-dimethyl-1,3-dioxane (1.0 g) and acetic acid (1.20 ml) in MeOH (9 ml)-DMF (4 ml) was added sodium cyanoborohydride (622 mg) with stirring at ambient temperature, and the mixture was stirred at the same temperature overnight. To the reaction mixture was added dropwise a solution of allyloxycarbonyl chloride (0.97 ml) in THF (2 ml) with stirring under ice-cooling, and the mixture was stirred at the same temperature for 1 hour. To the reaction mixture were added ethyl acetate (50 ml) and n-hexane (10 ml), and the solution was washed in turn with water and saturated aqueous sodium chloride, dried over anhydrous magnesium sulfate and evaporated in vacuo. The resulting residue was chromatographed on silica gel (100 ml) eluting with a mixture of n-hexane and ethyl acetate (1:1 v/v). The fractions containing the object compound were collected and evaporated under reduced pressure to give 4-[allyloxycarbonyl-(2,2-dimethyl-1,3-dioxan-5-yl)]aminobutanol (1.04 g).

NMR (CDCl$_3$, δ): 1.42 (3H, s), 1.48 (3H, s), 1.50–1.80 (4H, m), 3.45 (2H, t, J=8.20 Hz), 3.68 (2H, ABq, J=5.84 and 11.36 Hz), 3.80–4.20 (5H, m), 4.50–4.70 (2H, m), 5.15–5.40 (2H, m), 5.80–6.05 (1H, m).

ESI MASS (m/z) (Positive): 310.3 (M$^+$+Na).

PREPARATION 136

To a solution of oxalyl chloride (0.32 ml) in dichloromethane (10 ml) was added DMSO (0.57 ml) dropwise with stirring at –40–50° C. After stirring at the same temperature for 5 minutes, to the solution was added dropwise a solution of 4-[allyloxycarbonyl(2,2-dimethyl-1,3-dioxan-5-yl)]aminobutanol (1.0 g) in dichloromethane (5 ml) and stirred at the same temperature for 30 minutes. Triethylamine (1.46 ml) was added dropwise to the reaction mixture with stirring at the same temperature, and then the mixture was stirred at ambient temperature for 30 minutes. The insoluble material was filtered off, and the filtrate was washed successively with 1N-hydrochloric acid, water, saturated aqueous sodium bicarbonate and saturated aqueous sodium chloride, dried over anhydrous magnesium sulfate and evaporated in vacuo. The resulting residue was dissolved in a mixture of acetic acid (16 ml) and water (4 ml), and the solution was stirred at 90–100° C. for 5 hours. The reaction mixture was concentrated in vacuo. The resulting residue was chromatographed on silica gel (100 ml) eluting with a mixture of dichloromethane and methanol (19:1 v/v). The fractions containing the object compound were collected and evaporated under reduced pressure to give 4-[allyloxycarbonyl-(1,3-dihydropropan-2-yl)]aminobutylaldehyde (321 mg).

NMR (CDCl$_3$, δ): 1.50–1.75 (2H, m), 1.80–2.00 (2H, m), 2.40–2.60 (2H, m), 3.20–4.10 (7H, m), 4.59 (2H, d, J=5.60 Hz), 5.10–5.40 (2H, m), 5.80–6.10 (1H, m).

APCI MASS (m/z) (Positive): 246 (M$^+$).

The following compound was obtained according to a similar manner to that of Preparation 95.

PREPARATION 137

N-t-Butoxycarbonyl-4-allyloxypiperidine

NMR (CDCl$_3$, δ): 1.45 (9H, s), 1.45–1.60 (2H, m), 1.70–1.95 (2H, m), 3.00–3.20 (2H, m), 3.40–3.60 (1H, m), 3.65–3.90 (2H, m), 3.95–4.05 (2H, m), 5.10–5.35 (2H, m), 5.80–6.10 (1H, m).

PREPARATION 138

To a solution of N-t-butoxycarbonyl-4-allyloxypiperidine (2.95 g) in THF (15 ml) was added 9-borobicyclo[3.3.1]nonane (9-BBN, 0.5M solution in THF) (51.3 ml) under ice-cooling with stirring, and the mixture was stirred at ambient temperature for 4 hours. The reaction mixture was cooled at 0–5° C., and 3M aqueous sodium hydroxide (20.4 ml) and 30% hydrogen peroxide aqueous solution (20.4 ml) were added the reaction mixture at 0–5° C. The mixture was stirred at ambient temperature for 1 hour. To a reaction mixture was added ethyl acetate (100 ml), and the solution was washed successively with saturated aqueous sodium chloride, 1N-hydrochloric acid, saturated aqueous sodium bicarbonate and saturated aqueous sodium chloride, dried over anhydrous magnesium sulfate and evaporated in vacuo. The resulting residue was chromatographed on silica gel (200 ml) eluting with a mixture of dichloromethane and methanol (9:1 v/v). The fractions containing the desired compound were collected and evaporated under reduced pressure to give 4-(3-hydroxypropyloxy)-N-t-butoxycarbonylpiperidine (3.83 g).

NMR (CDCl$_3$, δ): 1.43 (9H, s), 1.43–1.60 (2H, m), 1.70–1.90 (4H, m), 2.35–2.45 (1H, m), 3.00–3.20 (2H, m), 3.35–3.55 (1H, m), 3.60–3.90 (5H, m).

PREPARATION 139

To a solution of 4-(3-hydroxypropyloxy)-N-t-butyloxycarbonylpiperidine (3.82 g) in ethyl acetate (40 ml) were added triethylamine (4.1 ml) and methanesulfonyl chloride (1.37 ml) with stirring under ice-cooling, and the mixture was stirred at the same temperature for 1 hour. To the reaction mixture were added water (50 ml) and ethyl acetate (50 ml) with stirring. The organic layer was separated, washed twice with saturated aqueous sodium chloride, dried over anhydrous magnesium sulfate and evaporated in vacuo. The resulting residue was chromatographed on silica gel (150 ml) eluting with a mixture of n-hexane and ethyl acetate (1:1 v/v). The fractions containing the desired compound were collected and evaporated under reduced pressure to give 4-[3-(methanesulfonyloxy)propyloxy]-N-t-butyloxycarbonylpiperidine (3.77 g).

NMR (CDCl$_3$, δ): 1.45 (9H, s), 1.45–1.60 (2H, m), 1.70–1.90 (2H, m), 1.90–2.10 (2H, m), 3.01 (3H, s), 3.03–3.20 (2H, m), 3.30–3.50 (1H, m), 3.57 (2H, t, J=5.87 Hz), 3.65–3.80 (2H, m), 4.35 (2H, t, J=6.18 Hz).

ESI MASS (m/z) (Positive): 360.3 (M$^+$+Na).

PREPARATION 140

To a solution of 4-[3-(methanesulfonyloxy)propyloxy]-N-t-butyloxycarbonylpiperidine (3.76 g) in methanol (20 ml) was added 28% sodium methoxide methanol solution (22.7 ml), and the mixture was stirred under refluxing for 1.5 hours. The reaction mixture was evaporated in vacuo and dissolved in ethyl acetate (200 ml). The solution was washed twice with saturated aqueous sodium chloride, dried over anhydrous magnesium sulfate and evaporated in vacuo. The resulting residue was chromatographed on silica gel (200 ml) eluting with a mixture of n-hexane and ethyl acetate (2:1 v/v). The fractions containing the object compound were collected and evaporated under reduced pressure to give 4-(3-methoxypropyloxy)-N-t-butyloxycarbonylpiperidine (2.66 g).

NMR (CDCl$_3$, δ): 1.45 (9H, s), 1.45–1.60 (2H, m), 1.70–1.90 (4H, m), 3.00–3.15 (2H, m), 3.33 (3H, s), 3.35–3.60 (5H, m), 3.65–3.85 (2H, m).

ELSI MASS (m/z): 296.3 (M$^+$+Na).

PREPARATION 141

A mixture of 1-acetyl-4-(4-hydroxyphenyl)piperazine (5.00 g) in N,N-dimethylformamide (50 ml) was treated with 1,6-dibromohexane (10.5 ml) and potassium carbonate (4.71 g), and the mixture was stirred for 18 hours at ambient temperature. To the reaction mixture was added water (200 ml), and the resulting precipitate was collected by filtration, washed with water and n-hexane successively and dried under reduced pressure to give crude 1-acetyl-4-[4-(6-bromohexyloxy)phenyl]piperazine (10.52 g), that was used in the next reaction directly.

MASS (m/z): 383 (M$^+$+1).

PREPARATION 142

A solution of crude 1-acetyl-4-[4-(6-bromohexyloxy) phenyl]piperazine (10.52 g) in methanol (105 ml) was treated with 28% sodium methoxide in methanol (105 ml), and the solution was refluxed for 7 hours. After cooling, the precipitate was removed by filtration. The filtrate was added to a mixture of methylene chloride and water. The organic layer was taken, dried over magnesium sulfate, filtered and evaporated to give a crude oil. This oil in methylene chloride (20 ml) was treated with acetic anhydride (6.4 ml) under ice-cooling. After 6 hours, the solution was added to a mixture of methylene chloride and water. The organic layer was taken, dried over magnesium sulfate, filtered and evaporated. The residue was purified by silica gel column chromatography eluting with a mixed solvent of methylene chloride-methanol (from 0% to 3% gradient elution) to give 1-acetyl-4-[4-(6-methoxyhexyloxy)phenyl]piperazine (5.38 g) as a pale red solid.

NMR (DMSO-d$_6$, δ): 1.24–1.78 (8H, m), 2.03 (3H, s), 2.86–3.06 (4H, m), 3.21 (3H, s), 3.23–3.36 (2H, m), 3.48–3.65 (4H, m), 3.87 (2H, d, J=6.4 Hz), 6.82 (2H, dd, J=9.2 and 2.6 Hz), 6.88 (2H, dd, J=9.3 and 2.6 Hz).

MASS (m/z): 335 (M$^+$+1).

PREPARATION 143

A mixture of 1-acetyl-4-[4-(6-methoxyhexyloxy)phenyl] piperazine (4.87 g) and 6N-hydrochloric acid (50 ml) was heated at 75° C. for 3 hours. After cooling, the solution was adjusted to pH 11 with 25% sodium hydroxide aqueous solution then the resulting precipitate was collected by filtration, washed with water and dried under reduced pressure to give 4-[4-(6-methoxyhexyloxy)phenyl]piperazine (3.77 g) as a pale brown solid.

NMR (DMSO-d$_6$, δ): 1.25–1.78 (8H, m), 2.74–2.96 (8H, m), 3.21 (3H, s), 3.30 (2H, t, J=6.3 Hz), 3.86 (2H, t, J=6.4 Hz), 6.79 (2H, d, J=9.2 Hz), 6.83 (2H, d, J=9.5 Hz).

MASS (m/z): 293 (M$^+$+1).

PREPARATION 144

A mixture of ethyl 4-fluorobenzoate (1.90 g) and 1-[4-(6-methoxyhexyloxy)phenyl]piperazine (3.00 g) in dimethylsulfoxide (45 ml) was treated with potassium carbonate (4.25 g), and the mixture was heated at 150° C. for 22 hours. After cooling, water (200 ml) was added to the reaction mixture, and the resulting precipitate was collected by filtration, washed with water and dried under reduced pressure at 50° C. for 7 hours to give ethyl 4-[4-[4-(6-methoxyhexyloxy)phenyl]piperazin-1-yl]benzoate (3.20 g) as an ocher solid.

NMR (DMSO-d$_6$, δ): 1.22–1.79 (8H, m), 1.33 (3H, t, J=7.1 Hz), 3.08–3.20 (4H, m), 3.21 (3H, s), 3.27–3.40 (2H, m), 3.40–3.54 (4H, m), 3.68 (2H, t, J=6.4 Hz), 4.24 (2H, q, J=7.1 Hz), 6.83 (2H, d, J=9.0 Hz), 6.94 (2H, d, J=9.1 Hz), 7.04 (2H, d, J=9.0 Hz), 7.81 (2H, d, J=8.9 Hz).

MASS (m/z): 441 (M$^+$+1).

PREPARATION 145

A mixture of ethyl 4-[4-[4-(6-methoxyhexyloxy)phenyl] piperazin-1-yl]benzoate (3.00 g) in ethanol (30 ml) was treated with 1N-sodium hydroxide aqueous solution (6.81 ml) then the mixture was refluxed for 24 hours, during which period tetrahydrofuran (20 ml) and 1N-sodium hydroxide aqueous solution (6.81 ml) was added. After cooling, water was added to the mixture, and the acidity of the mixture was adjusted to pH 1 with 1N-hydrochloric acid. The resulting precipitate was filtered, washed with water and dried under reduced pressure to give 4-[4-[4-(6-methoxyhexyloxy)phenyl]piperazin-1-yl]benzoic acid dihydrochloride (2.25 g) as an ocher solid.

NMR (DMSO-$d_6$, δ): 1.24–1.78 (8H, m), 3.04–3.21 (4H, m), 3.21 (3H, s), 3.30 (2H, t, J=6.3 Hz), 3.34–3.56 (4H, m), 3.88 (2H, t, J=6.4 Hz), 6.83 (2H, d, J=9.2 Hz), 6.94 (2H, d, J=9.2 Hz), 7.01 (2H, d, J=9.0 Hz), 7.79 (2H, d, J=8.8 Hz).

MASS (m/z): 413 ($M^+$+1).

PREPARATION 146

A mixture of 4-[4-[4-(6-methoxyhexyloxy)phenyl]piperazin-1-yl]benzoic acid dihydrochloride (2.00 g) and 1-hydroxybenzotriazole (0.84 g) in methylene chloride (40 ml) was treated with triethylamine (1.44 ml) and 1-ethyl-3-(3'-dimethylaminopropyl)carbodiimide hydrochloride, and the mixture was stirred for 24 hours at ambient temperature. The reaction mixture was added to water. The organic layer was taken, washed with saturated sodium hydrogen carbonate aqueous solution, water and saturated sodium chloride aqueous solution successively, and dried over magnesium sulfate. Magnesium sulfate was filtered off, and the filtrate was evaporated under reduced pressure. To the residue was added diisopropyl ether, and the resulting precipitate was filtered, washed with diisopropyl ether and dried under reduced pressure to give 4-[4-(4-(6-methoxyhexyloxy)phenyl]piperazin-1-yl]benzoic acid benzotriazol-1-yl ester (2.30 g) as a dark yellow solid.

NMR (CDCl$_3$, δ): 1.33–1.87 (8H, m), 3.15–3.28 (4H, m), 3.34 (3H, s), 3.39 (2H, t, J=6.4 Hz), 3.54–3.67 (4H, m), 3.93 (2H, t, J=6.5 Hz), 6.87 (2H, d, J=9.3 Hz), 6.95 (2H, d, J=9.3 Hz), 7.00 (2H, d, J=9.1 Hz), 7.37–7.58 (3H, m), 8.10 (1H, d, J=8.2 Hz), 8.15 (2H, d, J=9.1 Hz).

MASS (m/z): 530 ($M^+$+1).

PREPARATION 147

A mixture of 1-acetyl-4-(4-hydroxyphenyl)piperazine (3.00 g) in N,N-dimethylformamide was treated with 3-bromo-1-propanol (1.60 ml) and potassium carbonate (2.82 g), and the mixture was heated at 60° C. for 8 hours. Then 3-bromo-1-propanol (1.60 ml) was added again, and the mixture was heated at 110° C. for 6 hours. After cooling, water and methylene chloride were added to the reaction mixture, and the organic layer was taken and dried over magnesium sulfate. Magnesium sulfate was filtered off, and the filtrate was evaporated under reduced pressure. The residue was purified by silica gel chromatography eluting with a mixed solvent of methylene chloride-methanol (from 0% to 6% gradient elution) to give 1-acetyl-4-[4-(3-hydroxypropyloxy)phenyl]piperazine (3.53 g) as a pale pink solid.

NMR (DMSO-$d_6$, δ): 1.82 (2H, t, J=6.3 Hz), 2.03 (3H, s), 2.84–3.06 (4H, m), 3.45–3.62 (4H, m), 3.95 (2H, t, J=6.4 Hz), 4.13 (2H, t, J=6.5 Hz), 4.47–4.60 (1H, m), 6.82 (2H, d, J=9.2 Hz), 6.90 (2H, d, J=9.3 Hz).

MASS (m/z): 279 ($M^+$+1).

PREPARATION 148

A solution of 1-acetyl-4-[4-(3-hydroxypropyloxy)phenyl]piperazine (3.47 g) in a mixed solvent of tetrahydrofuran (35 ml) and N,N-dimethylformamide (10 ml) was treated with silver(I) oxide (3.18 g) and 3-bromocyclohexene (1.86 ml), and the mixture was stirred at ambient temperature for 16 hours. To the mixture was added silver(I) oxide (3.18 g) and 3-bromocyclohexene (1.86 ml) again, and the mixture was heated at 60° C. for 3 hours and then at 110° C. for 40 hours. The precipitate was removed by filtration, and the filtrate was evaporated. The residue was purified by silica gel column chromatography eluting with a mixed solvent of methylene chloride-methanol (from 0% to 5% gradient solution) to give crude 1-acetyl-4-[4-[3-(2-cyclohexen-1-yloxy)propyloxy]phenylpiperazine (1.60 g), that was used in the next reaction directly.

MASS (m/z): 359 ($M^+$+1).

PREPARATION 149

A mixture of crude 1-acetyl-4-[4-[3-(2-cyclohexen-1-yloxy)propyloxy]phenyl]piperazine (1.55 g) in ethanol (16 ml) was hydrogenated at atmospheric pressure with 10% palladium-carbon (0.16 g) for 5 hours. After removal of catalyst by filtration, the filtrate was concentrated in vacuo to give crude 1-acetyl-4-[4-(3-cyclohexyloxypropyloxy)phenyl]piperazine (1.18 g), that was used in the next reaction directly, as a brown oil.

MASS (m/z): 361 ($M^+$+1).

The following compound was obtained according to a similar manner to that of Preparation 143.

PREPARATION 150

4-[4-(3-Cyclohexyloxypropyloxy)phenyl]piperazine

NMR (CDCl$_3$, δ): 1.12–1.94 (10H, m), 1.94–2.11 (2H, m), 3.03 (8H, s), 3.57–3.68 (1H, m), 3.86 (2H, t, J=5.9 Hz), 4.09 (2H, t, J=5.9 Hz), 6.86 (2H, d, J=9.0 Hz), 6.89 (2H, d, J=9.0 Hz).

APCI MASS (m/z): 319 ($M^+$+1).

The following compound was obtained according to a similar manner to that of Preparation 144.

PREPARATION 151

Ethyl 4-[4-[4-(3-cyclohexyloxypropyloxy)phenyl]piperazin-1-yl]benzoate

NMR (CDCl$_3$, δ): 1.12–1.95 (10H, m), 1.38 (3H, t, J=7.1 Hz), 1.95–2.14 (2H, m), 3.13–3.30 (4H, m), 3.42–3.56 (4H, m), 3.61 (2H, t, J=6.2 Hz), 3.81–3.94 (1H, m), 4.10 (2H, t, J=5.9 Hz), 4.34 (2H, q, J=7.1 Hz), 6.78–7.01 (6H, m), 7.95 (2H, d, J=8.9 Hz).

MASS (m/z): 467 ($M^+$+1).

PREPARATION 152

A mixture of ethyl 4-[4-[4-(3-cyclohexyloxypropyloxy)phenyl]piperazin-1-yl]benzoate (290 mg) in the mixed solvent of tetrahydrofuran (15 ml) and ethanol (3 ml) was treated with 10% sodium hydroxide aqueous solution (0.50 ml), and the mixture was refluxed for 8 hours. After cooling, water was added to the reaction mixture, and the acidity of the mixture was adjusted to pH 1 with 1N-hydrochloric acid. The resulting precipitate was filtered, washed with water and dried under reduced pressure to give 4-[4-[4-(3-cyclohexyloxypropyloxy)phenyl]piperazin-1-yl]benzoic acid dihydrochloride (96 mg) as a pale brown solid.

NMR (DMSO-$d_6$, δ): 1.08–1.96 (12H, m), 3.07–3.62 (11H, m), 3.95 (2H, t, J=5.5 Hz), 6.84 (2H, d, J=9.1 Hz), 6.94 (2H, d, J=9.2 Hz), 7.03 (2H, d, J=8.9 Hz), 7.79 (2H, d, J=8.7 Hz).

MASS (m/z): 439 ($M^+$+1).

The following compound was obtained according to a similar manner to that of Preparation 146.

PREPARATION 153

4-[4-[4-(3-Cyclohexyloxypropyloxy)phenyl] piperazin-1-yl]benzoic acid benzotriazol-1-yl ester MASS (m/z): 556 (M$^+$+1).

PREPARATION 154

A solution of 4-bromo-2,6-dimethylphenol (2.00 g) and 1,7-dibromoheptane (5.10 g) in N,N-dimethylformamide (20 ml) was treated with potassium carbonate (2.06 g), and the mixture was stirred for 5 hours at ambient temperature. To the reaction mixture was added water and methylene chloride, and the organic layer was separated and dried over magnesium sulfate. Magnesium sulfate was filtered off, and the filtrate was concentrated in vacuo. The residue was purified by silica gel column chromatography eluting successively with the following solvents: (1) n-hexane, (2) n-hexane:ethyl acetate=4:1, (3) n-hexane:ethyl acetate=1:1. The fractions containing the object compound were concentrated in vacuo to give crude 5-bromo-2-(7-bromoheptyloxy)-1,3-dimethylbenzene, that was used in the next reaction directly, as a pale yellow oil.

NMR (CDCl$_3$, δ): 1.28–1.98 (10H, m), 2.23 (6H, s), 3.35–3.50 (2H, m), 3.71 (2H, t, J=6.4 Hz), 7.13 (2H, s).

PREPARATION 155

A solution of crude 5-bromo-2-(7-bromoheptyloxy)-1,3-dimethylbenzene (7.81 g) in methanol (78 ml) was treated with 28% sodium methoxide in methanol (78 ml), and the solution was refluxed for 8 hours. After cooling, the reaction mixture was evaporated under reduced pressure, and the residue was extracted with methylene chloride. The organic layer was dried over magnesium sulfate and magnesium sulfate was filtered off, and then the filtrate was evaporated under reduced pressure. The residue was purified by silica gel column chromatography eluting with a mixed solvent of n-hexane-ethyl acetate (from 0% to 7% gradient elution) to give 5-bromo-2-(7-methoxyheptyloxy)-1,3-dimethylbenzene (3.34 g) as a colorless oil.

NMR (CDCl$_3$, δ): 1.38–1.69 (8H, m), 1.69–1.89 (2H, m), 2.23 (6H, s), 3.35 (3H, s), 3.28–3.44 (2H, m), 3.65–3.78 (2H, m), 7.13 (2H, s).

MASS (m/z): 329 (M$^+$+1).

PREPARATION 156

To a mixture of cesium carbonate (1.39 g), palladium(II) acetate (34.1 mg) and 2,2'-bis(diphenylphosphino)-1,1'-binaphthyl (142 mg) in toluene (3.1 ml) was successively added ethyl 4-(piperazin-1-yl)benzoate (0.85 g) and a solution of 5-bromo-2-(7-methoxyheptyloxy)-1,3-dimethylbenzene (1.00 g) in toluene (3 ml) in a stream of nitrogen. The mixture was stirred at ambient temperature for 30 minutes and refluxed for a further 20 hours. After cooling, the reaction mixture was concentrated in vacuo and to the residue was added water and methylene chloride. The organic layer was separated, washed with saturated aqueous sodium chloride solution, dried over magnesium sulfate, filtered and concentrated in vacuo. The residue was purified by silica gel column chromatography eluting successively with the following solvent: (1) n-hexane, (2) n-hexane;ethyl acetate=9:1, (3) n-hexane:ethyl acetate=5:1. The fractions containing the object compound were concentrated in vacuo to give ethyl 4-[4-[4-(7-methoxyheptyloxy)-3,5-dimethylphenyl]piperazin-1-yl]benzoate (0.53 g) as a pale yellow solid.

NMR (CDCl$_3$, δ): 1.32–1.69 (11H, m), 1.69–1.88 (2H, m), 2.26 (6H, s), 3.17–3.30 (4H, m), 3.33 (3H, s), 3.38 (2H, t, J=6.5 Hz), 3.41–3.54 (4H, m), 3.71 (2H, t, J=6.5 Hz), 4.34 (2H, q, J=7.1 Hz), 6.63 (2H, s), 6.91 (2H, d, J=9.0 Hz), 7.95 (2H, d, J=9.0 Hz).

MASS (m/z): 483 (M$^+$+1).

The following compound was obtained according to a similar manner to that of Preparation 152.

PREPARATION 157

4-[4-[4-(7-Methoxyheptyloxy)-3,5-dimethylphenyl] piperazin-1-yl]benzoic acid dihydrochloride NMR (DMSO-d$_6$, δ): 1.22–1.60 (8H, m), 1.60–1.79 (2H, m), 2.17 (6H, s), 3.10–3.50 (10H, m), 3.21 (3H, s), 3.64 (2H, t, J=6.3 Hz), 6.65 (2H, s), 7.01 (2H, d, J=9.0 Hz), 7.79 (2H, d, J=8.8 Hz), 12.30 (1H, br s).

MASS (m/z): 455 (M$^+$+1).

The following compound was obtained according to a similar manner to that of Preparation 146.

PREPARATION 158

4-[4-[4-(7-Methoxyheptyloxy)-3,5-dimethylphenyl] piperazin-1-yl]benzoic acid benzotriazol-1-yl ester NMR (CDCl$_3$, δ): 1.32–1.89 (10H, m), 2.27 (6H, s), 3.20–3.34 (4H, m), 3.34 (3H, s), 3.38 (2H, t, J=6.5 Hz), 3.54–3.68 (4H, m), 3.72 (2H, t, J=6.5 Hz), 6.64 (2H, s), 7.00 (2H, d, J=9.1 Hz), 7.37–7.62 (3H, m), 8.09 (2H, d, J=8.3 Hz), 8.15 (2H, d, J=9.0 Hz). MASS (m/z): 572 (M$^+$+1).

The following compound was obtained according to a similar manner to that of Preparation 152.

PREPARATION 159

4-[4-(4-Cyclohexylpiperazin-1-yl)phenyl]benzoic acid dihydrochloride

NMR (DMSO-d$_6$, δ): 1.03–2.19 (10H, m), 2.80–2.93 (1H, m), 3.10–3.49 (8H, m), 7.08 (2H, d, J=8.4 Hz), 7.65 (2H, d, J=8.6 Hz), 7.75 (2H, d, J=8.4 Hz), 7.97 (2H, d, J=8.3 Hz).

MASS (m/z): 365 (M$^+$+1).

The following compound was obtained according to a similar manner to that of Preparation 146.

PREPARATION 160

4-[4-(4-Cyclohexylpiperazin-1-yl)phenyl]benzoic acid benzotriazol-1-yl ester

NMR (CDCl$_3$, δ): 1.04–1.43 (6H, m), 1.69–2.04 (4H, m), 2.24–2.47 (1H, s), 2.68–2.88 (4H, m), 3.20–3.43 (4H, m), 7.03 (2H, d, J=8.8 Hz), 7.38–7.66 (3H, m), 7.63 (2H, d, J=8.7 Hz), 7.79 (2H, d, J=8.5 Hz), 8.12 (1H, d, J=8.2 Hz), 8.30 (2H, d, J=8.5 Hz).

MASS (m/z): 482 (M$^+$+1).

PREPARATION 161

To a solution of methyl 4-(4-hydroxyphenyl)benzoate (0.94 g), (S)-(−)-2-(tert-butoxycarbonylamino)-3-cyclohexyl-1-propanol (1.00 g) and triphenylphosphine (1.62 g) in N,N-dimethylformamide (20 ml) was added dropwise diisopropyl azodicarboxylate (1.21 ml) for 10 minutes under ice-cooling in a stream of nitrogen. The solution was stirred for 16 hours at ambient temperature, and then water was added to the reaction mixture, and the mixture was extracted with ethyl acetate. The organic layer was washed with saturated aqueous sodium chloride solution, dried over magnesium sulfate, filtered and concentrated in vacuo. The residue was purified by silica gel column chromatography eluting with a mixed solvent of n-hexane-ethyl acetate (from 0% to 20% gradient elution) to give methyl (S)-4-[4-[2-(tert-butoxycarbonylamino)-3-cyclohexylpropyloxy]phenyl]benzoate (290 mg) as a white solid.

NMR (CDCl$_3$, δ): 1.72–1.93 (13H, m), 1.46 (9H, s), 3.90–4.16 (3H, m), 3.93 (3H, s), 4.63–4.78 (1H, m), 6.93–7.05 (2H, m), 7.50–7.68 (4H, m), 8.06–8.15 (2H, m).

MASS (m/z): 368 (M$^+$+2−Boc).

PREPARATION 162

A solution of methyl (S)-4-[4-[2-(tert-butoxycarbonylamino)-3-cyclohexylpropyloxy]phenyl] benzoate (0.28 g) in a mixed solvent of methanol (14 ml) and tetrahydrofuran (3 ml) was treated with 1N-sodium hydroxide aqueous solution, and the mixture was refluxed for 16 hours. After cooling, water was added to the mixture, and the acidity of the mixture was adjusted to pH 1 with 1N-hydrochloric acid. The resulting precipitate was filtered, washed with water and dried under reduced pressure to give (S)-4-[4-[2-(tert-butoxycarbonylamino)-3-cyclohexylpropyloxy]phenyl]benzoic acid (222 mg) as a white solid.

NMR (DMSO-d$_6$, δ): 0.66–1.48 (8H, m), 1.39 (9H, s), 1.48–1.87 (5H, m), 3.78–3.97 (3H, m), 6.79 (1H, d, J=7.2 Hz), 7.04 (2H, d, J=8.8 Hz), 7.68 (2H, d, J=8.8 Hz), 7.75 (2H, d, J=8.4 Hz), 7.98 (2H, d, J=8.4 Hz), 12.83 (1H, br s).

MASS (m/z): 354 (M$^+$+2−Boc).

The following compound was obtained according to a similar manner to that of Preparation 163.

PREPARATION 163

(S)-4-[4-[2-(tert-Butoxycarbonylamino)-3-cyclohexylpropyloxy]phenyl]benzoic acid benzotriazol-1-yl ester NMR (CDCl$_3$, δ): 0.75–1.96 (13H, m), 1.47 (9H, s), 3.92–4.20 (3H, m), 4.60–4.79 (1H, m), 7.04 (2H, d, J=8.8 Hz), 7.40–7.63 (3H, m), 7.64 (2H, d, J=8.7 Hz), 7.79 (2H, d, J=8.4 Hz), 8.12 (1H, d, J=8.1 Hz), 8.32 (2H, d, J=8.4 Hz).

MASS (m/z): 571 (M$^+$+1).

PREPARATION 164

A mixture of 1-fluoro-4-nitrobenzene (2.71 ml), 1,2,3,6-tetrahydro-4-phenylpyridine hydrochloride (5 g) and potassium carbonate (8.83 g) in dimethylsulfoxide (50 ml) was stirred for 1 hour at 100° C. The reaction mixture was pulverized with water. The precipitate was collected by filtration, and dried under reduced pressure to give 4-(4-phenyl-3,6-dihydro-2H-pyridin-1-yl)nitrobenzene.

IR (KBr): 1589.1, 1311.4, 1108.9 cm$^{-1}$.

NMR (CDCl$_3$, δ): 2.73–2.77 (2H, m), 3.73 (2H, t, J=11.3 Hz), 4.09 (2H, dd, J=2.5 and 5.9 Hz), 6.16–6.20 (1H, m), 6.80–6.88 (2H, m), 7.29–7.45 (5H, m), 8.12–8.20 (2H, m).

MASS (m/z): 281 (M$^+$+1).

PREPARATION 165

To a solution of 4-(4-phenyl-3,6-dihydro-2H-pyridin-1-yl)nitrobenzene (6.4 g) in ethyl alcohol (192 ml) and tetrahydrofuran (192 ml) was added 10% palladium on carbon (0.64 g), and hydrogen gas at atmosphere pressure for 6 hours. The reaction mixture was filtered through celite and evaporated under reduced pressure to give 1-(4-aminophenyl)-4-phenylpiperidine (5.66 g).

IR (KBr): 1604.5, 1511.9, 1382.7, 1207.2 cm$^{-1}$.

NMR (CDCl$_3$, δ): 1.84–1.97 (4H, m), 2.52–2.78 (3H, m), 3.10–3.73 (4H, m), 6.63–6.70 (2H, m), 6.84–6.92 (2H, m), 7.17–7.37 (5H, m).

MASS (m/z): 253 (M$^+$+1).

PREPARATION 166

To a solution of 1-(4-aminophenyl)-4-phenylpiperidine (2 g) in 47% hydrobromic acid (20 ml) and acetic acid (23 ml) was added dropwise sodium nitrite (0.55 g) in water (1 ml) under ice-cooling. The solution was then stirred for 30 minutes at 0° C. The reaction mixture was added dropwise copper(I) bromide (2.27 g) in 47% hydrobromic acid (2.3 ml) under ice-cooling. The reaction mixture was then stirred for 1.5 hours at ambient temperature. The reaction mixture was pulverized with water. The precipitate was collected by filtration. The powder was added 1N-sodium hydroxide (21 ml) and extracted with ethyl acetate. The organic layer was separated, washed with brine, dried over magnesium sulfate. The magnesium sulfate was filtered off, and the filtrate was evaporated under reduced pressure. The residue was purified by column chromatography over silica using dichloromethane/n-hexane (1:1) as the elution to give 1-(4-bromophenyl)-4-phenylpiperidine (1.23 g).

IR (KBr): 1583.3, 1488.8, 1382.7, 1214.9 cm$^{-1}$.

NMR (CDCl$_3$, δ): 1.77–1.96 (4H, m), 2.57–2.71 (1H, m), 2.74–2.88 (2H, m), 3.73–3.79 (2H, m), 6.81–6.89 (2H, m), 7.18–7.38 (7H, m).

MASS (m/z): 316 (M$^+$+1).

PREPARATION 167

A mixture of piperazine-1-carboxylic acid tert-butyl ester (2.02 g), 1-(4-bromophenyl)-4-phenylpiperidine (2.86 g), tris(dibenzylideneacetone)(chloroform)-di-palladium(0) (0.19 g), (S)-(−)-2,2'-bis(diphenylphosphino)-1,1'-binaphthyl (0.28 g) and sodium tert-butoxide (1.74 g) in toluene (29 ml) was stirred for 6 hours at 90° C. The reaction mixture was added to a mixture of water and ethyl acetate. The organic layer was taken and dried over magnesium sulfate. The magnesium sulfate was filtered off, and the filtrate was evaporated under reduced pressure. The residue was purified by column chromatography over silica using dichloromethane/methyl alcohol (50:1) as the elution to give 4-[4-(4-phenylpiperidin-1-yl)phenyl]piperazine-1-carboxylic acid tert-butyl ester (2.93 g).

IR (KBr): 1691.3, 1596.8, 1116.6 cm$^{-1}$.

NMR (CDCl$_3$, δ): 1.48 (9H, s), 1.87–1.99 (4H, m), 2.60–2.90 (3H, m) 3.00–3.16 (4H, m), 3.55–3.71 (6H, m), 6.87–6.99 (4H, m), 7.21–7.53 (5H, m).

MASS (m/z): 422 (M$^+$+1).

PREPARATION 168

To a solution of 4-[4-(4-phenylpiperidin-1-yl)phenyl] piperazine-1-carboxylic acid tert-butyl ester (2.45 g) in 1,4-dioxane (62 ml) was added dropwise 4N-HCl/1,4-dioxane (58 ml) at ambient temperature. The reaction mixture was stirred for 110 minutes at ambient temperature, and stirred for 2 hours at 80° C. The precipitate was filtered and dried to give 1-[4-(4-phenylpiperidin-1-yl)phenyl] piperazine trihydrochloride salt (2.07 g).

IR (KBr): 3494.4, 3237.9, 1635.3, 1498.4 cm$^{-1}$.

NMR (DMSO-d$_6$, δ): 1.98–3.90 (18H, m), 7.02–7.41 (7H, m), 7.82–7.86 (2H, m).

MASS (m/z): 322.4 (M$^+$+1) (free).

PREPARATION 169

A mixture of 4-[4-(4-phenylpiperidin-1-yl)phenyl]piperazine trihydrochloride salt (1.77 g) and 1N-sodium hydroxide (62 ml) in dichloromethane (62 ml) was stirred for 30 minutes at ambient temperature. The organic layer was separated, washed with brine, dried over magnesium sulfate. The magnesium sulfate was filtered off, and the filtrate was evaporated under reduced pressure to give 1-[4-(4-phenylpiperidin-1-yl)phenyl]piperazine (1.19 g).

PREPARATION 170

A mixture of 4-fluorobenzoic acid ethyl ester (1.25 g), 1-[4-(4-phenylpiperidin-1-yl)phenyl]piperazine (1.19 g) and potassium carbonate (1.53 g) in dimethylsulfoxide (18 ml) was stirred for 12 hours at 150° C. The reaction mixture was pulverized with water. The mixture was extracted with dichloromethane. The organic layer was separated, washed with brine, dried over magnesium sulfate. The magnesium sulfate was filtered off, and the filtrate was evaporated under reduced pressure. The residue was purified by column chromatography over silica using dichloromethane/methyl alcohol (200:1) as the elution. The powder was recrystallized from toluene (60 ml). The crystal was collected by filtration, and dried under reduced pressure to give 4-[4-[4-(4-phenylpiperidin-1-yl)phenyl]piperazin-1-yl]benzoic acid ethyl ester (0.80 g).

IR (KBr): 1702.8, 1513.8, 1232.3 cm$^{-1}$.

NMR (CDCl$_3$, δ): 1.37 (3H, t, J=7.1 Hz), 1.89–2.00 (4H, m), 2.55–2.84 (3H, m), 3.22–3.27 (4H, m), 3.46–3.51 (4H, m), 3.66–3.72 (2H, m), 4.34 (2H, q, J=7.1 Hz), 6.90–7.03 (6H, m), 7.18–7.37 (5H, m), 7.93–7.98 (2H, m).

MASS (m/z): 470.

PREPARATION 171

To a mixture of 4-[4-[4-(4-phenylpiperidin-1-yl)phenyl]piperazin-1-yl]]benzoic acid ethyl ester (0.78 g) in ethyl alcohol (39 ml) and 1,4-dioxane (39 ml) was added 10% NaOH aq. (1.3 ml) and refluxed for 16 hours. The reaction mixture was adjusted to pH 1–2 with 1N-HCl and the resulting precipitate was collected by filtration, and dried under reduced pressure to give 4-[4-[4-(4-phenylpiperidin-1-yl)phenyl]piperazin-1-yl]benzoic acid dihydrochloride salt (0.65 g).

IR (KBr): 2840.6, 1670.1, 1602.6, 1232.3 cm$^{-1}$.

NMR (CDCl$_3$+CD$_3$OD, δ): 2.05–2.20 (2H, m), 2.70–3.10 (3H, m), 3.40–3.85 (12H, m), 6.91–7.06 (4H, m), 7.25–7.37 (7H, m), 7.95–7.99 (2H, m).

MASS (m/z): 442 (free).

PREPARATION 172

To a suspension of 4-[4-[4-(4-phenylpiperidin-1-yl)phenyl]piperazin-1-yl]benzoic acid dihydrochloride salt (0.62 g) and 1-hydroxybenzotriazole (0.2 g) in dichloromethane (12 ml) was added 1-ethyl-3-(3'-dimethylaminopropyl)carbodiimide (0.22 g) and stirred for 22 hours at ambient temperature. The reaction mixture was added to a mixture of water and dichloromethane. The organic layer was taken and dried over magnesium sulfate. The magnesium sulfate was filtered off, and the filtrate was evaporated under reduced pressure to give 4-[4-[4-(4-phenylpiperidin-1-yl)phenyl]piperazin-1-yl]benzoic acid benzotriazol-1-yl ester (0.41 g).

IR (KBr): 1780.0, 1600.6, 1513.8, 1230.4 cm$^{-1}$.

NMR (CDCl$_3$, δ): 1.85–2.05 (4H, m), 2.60–2.90 (3H, m), 3.25–3.80 (10H, m), 6.95–7.55 (15H, m), 8.08–8.18 (2H, m).

MASS (m/z): 559 (M$^+$+1).

PREPARATION 173

To a suspension of 4-hydroxy-4-phenylpiperidine (5 g) and triethylamine (4.32 ml) in dichloromethane (50 ml) was added dropwise di-tert-butyldicarbonate (6.16 g) in dichloromethane (6 ml) under ice-cooling. The reaction mixture was then stirred for 4 hours at ambient temperature. The reaction mixture was pulverized with water. The organic layer was separated, washed with brine, dried over magnesium sulfate. The magnesium sulfate was filtered off, and the filtrate was evaporated under reduced pressure. The residue was purified by column chromatography over silica using dichloromethane/methyl alcohol (30:1) as the elution to give 4-hydroxy-4-phenylpiperidine-1-carboxylic acid tert-butyl ester (7.2 g).

IR (KBr): 3463.5, 1675.8, 1664.3, 1170.6 cm$^{-1}$.

NMR (CDCl$_3$, δ): 1.48 (9H, s), 1.63–2.08 (5H, m), 3.19–3.30 (2H, m), 3.90–4.10 (2H, m), 7.27–7.50 (5H, m).

MASS (m/z): 178 (M$^+$−Boc+1).

PREPARATION 174

To a solution of 4-hydroxy-4-phenylpiperidine-1-carboxylic acid tert-butyl ester (7.1 g) in N,N-dimethylformamide (71 ml) was added 60% sodium hydride in mineral oil (1.13 g) under ice-cooling, and stirred for 1 hour at ambient temperature. The suspension was then stirred for 1.5 hours at 60° C. To the reaction mixture was added iodomethane (32 ml) at 40° C., and stirred for 30 minutes at 45° C. Water and ethyl acetate were added with stirring, and the organic layer was separated, washed with brine, dried over magnesium sulfate. The magnesium sulfate was filtered off, and the filtrate was evaporated under reduced pressure. The residue was purified by column chromatography over silica using n-hexane/ethyl acetate (4:1) as the elution to give 4-methoxy-4-phenylpiperidine-1-carboxylic acid tert-butyl ester (6.63 g).

IR (KBr): 1700.9, 1685.5, 1170.6 cm$^{-1}$.

NMR (CDCl$_3$, δ): 1.47 (9H, s), 1.79–2.05 (4H, m), 2.98 (3H, s), 3.12–3.24 (2H, m), 3.90–4.10 (2H, m), 7.28–7.39 (5H, m).

MASS (m/z): 192 (M$^+$−Boc+1).

PREPARATION 175

To a solution of 4-methoxy-4-phenylpiperidine-1-carboxylic acid tert-butyl ester (6.5 g) in ethyl acetate (65 ml) was added dropwise 4N-HCl/ethyl acetate (56 ml) at ambient temperature. The reaction mixture was stirred for 1.5 hours at ambient temperature. To the reaction mixture was added diisopropyl ether. The precipitate was collected by filtration to give powder. The powder was adjusted to pH 11 with 1N-NaOH, and extracted with ethyl acetate. The organic layer was separated, washed with brine, dried over magnesium sulfate. The magnesium sulfate was filtered off, and the filtrate was evaporated under reduced pressure to give 4-methoxy-4-phenylpiperidine (3.47 g).

IR (KBr): 3322.7, 1535.1, 1070.3 cm$^{-1}$.

NMR (CDCl$_3$, δ): 1.80–2.07 (5H, m), 2.88–3.15 (7H, m), 7.28–7.44 (5H, m).

MASS (m/z): 192 (M$^+$+1).

PREPARATION 176

A mixture of 1-acetyl-4-(4-trifluoromethanesulfonyloxyphenyl)piperazine (3 g), 4-methoxy-4-phenylpiperidine (1.63 g), acetic acid palladium(II) salt (0.11 g), racemic-2,2'-bis(diphenylphosphino)-1,1'-binaphthyl (0.42 g) and cesium carbonate (3.88 g) in toluene (17 ml) was stirred for 30 minutes at ambient temperature. After being stirred for a further 17 hours at 100° C., the reaction mixture was diluted with dichloromethane. The suspension was filtered through celite, and the filtrate was evaporated under reduced pressure. The residue was purified by column chromatography over silica using ethyl acetate/methyl alcohol (30:1) as the elution to give 1-acetyl-4-[4-(4-methoxy-4-phenylpiperidin-1-yl)phenyl]piperazine (2.65 g).

IR (KBr): 1643.1, 1321.0, 1074.2 cm$^{-1}$.

NMR (CDCl$_3$, δ): 2.14 (3H, s), 2.14–2.17 (4H, m), 2.98 (3H, s), 2.98–3.45 (8H, m), 3.59–3.79 (4H, m), 6.92–7.00 (4H, m), 7.28–7.47 (5H, m).

MASS (m/z): 394 (M$^+$+1).

PREPARATION 177

A mixture of 1-acetyl-4-[4-(4-methoxy-4-phenylpiperidin-1-yl)phenyl]piperazine (2.5 g) and 10% NaOH aq. (10.2 ml) in ethyl alcohol (50 ml) was refluxed for 23.5 hours. The reaction mixture was evaporated under reduced pressure. The residue was washed with water, and dried to give 1-[4-(4-methoxy-4-phenylpiperidin-1-yl)phenyl]piperazine (2.18 g).

IR (KBr): 3290.0, 1513.8, 1232.3, 1074.2 cm$^{-1}$.

NMR (DMSO-d$_6$, δ): 1.91–2.11 (4H, m), 2.80–3.17 (11H, m), 3.20–3.45 (5H, m), 6.79–6.91 (4H, m), 7.25–7.46 (5H, m).

MASS (m/z): 352 (M$^+$+1).

The following compound was obtained according to a similar manner to that of Preparation 170.

PREPARATION 178

4-[4-[4-(4-Methoxy-4-phenylpiperidin-1-yl)phenyl]piperazin-1-yl]benzoic acid ethyl ester IR (KBr): 1702.8, 1511.9, 1236.1, 1105.0 cm$^{-1}$.

NMR (CDCl$_3$, δ): 1.37 (3H, t, J=7.1 Hz), 2.14–2.18 (4H, m), 3.01 (3H, s), 3.06–3.50 (12H, m), 4.34 (2H, q, J=7.1 Hz), 6.90–7.03 (6H, m), 7.28–7.47 (5H, m), 7.93–7.98 (2H, m).

MASS (m/z): 500 (M$^+$+1).

The following compound was obtained according to a similar manner to that of Preparation 170.

PREPARATION 179

4-[4-[4-(4-Methoxy-4-phenylpiperidin-1-yl)phenyl]piperazin-1-yl]benzoic acid dihydrochloride IR (KBr): 2960.2, 1702.8, 1604.5, 1184.1 cm$^{-1}$.

NMR (DMSO-d$_6$, δ): 2.20–3.70 (19H, m), 7.02–7.62 (11H, m), 7.78–7.83 (2H, m).

MASS (m/z): 472 (M$^+$+1) (free).

The following compound was obtained according to a similar manner to that of Preparation 172.

PREPARATION 180

4-(4-[4-(4-Methoxy-4-phenylpiperidin-1-yl)phenyl]piperazin-1-yl)benzoic acid benzotriazol-1-yl ester IR (KBr): 1762.6, 1600.6, 1230.4, 1184.1 cm$^{-1}$.

NMR (CDCl$_3$, δ): 2.10–2.20 (4H, m), 3.01 (3H, s), 3.05–3.64 (12H, m), 6.98–7.04 (6H, m), 7.32–7.51 (8H, m), 8.07–8.17 (3H, m).

MASS (m/z): 589 (M$^+$+1).

The following compound was obtained according to a similar manner to that of Preparation 176.

PREPARATION 181

1-[4-[4-(1,4-Dioxa-8-azaspiro[4.5]decan-8-yl)phenyl]piperazin-1-yl]ethanone

IR (KBr): 1648.8, 1637.3, 1334.5, 1230.4, 1099.2 cm$^{-1}$.

NMR (DMSO-d$_6$, δ): 1.67–1.73 (4H, m), 2.03 (3H, s), 2.90–3.14 (8H, m), 3.50–3.60 (4H, m), 3.90 (4H, s), 6.86 (4H, s).

MASS (m/z): 346 (M$^+$+1).

The following compound was obtained according to a similar manner to that of Preparation 177.

PREPARATION 182

8-(4-Piperazinylphenyl)-1,4-dioxa-8-azaspiro[4.5]decane

IR (KBr): 3284.2, 1513.8, 1328.7, 1110.8 cm$^{-1}$.

NMR (DMSO-d$_6$, δ): 1.70 (4H, t, J=5.7 Hz), 2.79–2.91 (8H, m), 3.06–3.12 (4H, m), 3.25–3.38 (5H, m), 6.77–6.88 (4H, m).

MASS (m/z): 304 (M$^+$+1).

The following compound was obtained according to a similar manner to that of Preparation 170.

PREPARATION 183

4-[4-[4-(1,4-Dioxa-8-azaspiro[4.5]decan-8-yl)phenyl]piperazin-1-yl]benzoic acid ethyl ester IR (KBr): 1704.8, 1511.9, 1224.6, 1108.9 cm$^{-1}$.

NMR (CDCl$_3$, δ): 1.37 (3H, t, J=7.1 Hz), 1.86 (4H, t, J=5.7 Hz), 3.20–3.25 (8H, m), 3.45–3.50 (4H, m), 3.99 (4H, s), 4.34 (2H, q, J=7.1 Hz), 6.89–6.93 (6H, m), 7.91–7.97 (2H, m).

MASS (m/z): 452 (M$^+$+1).

The following compound was obtained according to a similar manner to that of Preparation 171.

PREPARATION 184

4-[4-[4-(1,4-Dioxa-8-azaspiro[4.5]decan-8-yl)phenyl]piperazin-1-yl]benzoic acid dihydrochloride IR (KBr): 2962.1, 1670.1, 1321.0, 1230.4 cm$^{-1}$.

NMR (DMSO-d$_6$, δ): 1.70–2.00 (4H, m), 3.10–3.70 (16H, m), 7.00–7.20 (6H, m), 7.78–7.82 (2H, m).

MASS (m/z): 424 (M$^+$+1) (free).

The following compound was obtained according to a similar manner to that of Preparation 172.

PREPARATION 185

4-[4-[4-(1,4-Dioxa-8-azaspiro[4.5]decan-8-yl)phenyl]piperazin-1-yl]benzoic acid benzotriazol-1-yl ester IR (KBr): 1781.9, 1600.6, 1232.3 cm$^{-1}$.

NMR (CDCl$_3$, δ): 1.86 (4H, t, J=5.7 Hz), 3.21–3.28 (8H, m), 3.59–3.64 (4H, m), 4.00 (4H, s), 6.95–7.02 (6H, m), 7.40–7.58 (3H, m), 8.07–8.17 (3H, s).

MASS (m/z): 541 (M$^+$+1).

The following compound was obtained according to a similar manner to that of Preparation 176.

PREPARATION 186

1-Acetyl-4-[4-(4-cyclohexyloxypiperidin-1-yl)phenyl]piperazine

IR (KBr): 1621.8, 1236.1, 1101.2 cm$^{-1}$.

NMR (CDCl$_3$, δ): 1.20–2.00 (14H, m), 2.13 (3H, s), 2.75–3.78 (14H, m), 6.78–7.83 (4H, m).

MASS (m/z): 386 (M$^+$+1).

PREPARATION 187

A mixture of 1-acetyl-4-[4-(4-cyclohexyloxypiperidin-1-yl)phenyl]piperazine (0.37 g) and 10% sodium hydroxide (1.9 ml) in ethyl alcohol (7.4 ml) was refluxed for 10 hours. The reaction mixture was evaporated under reduced pressure. The residue was washed with water, and dried to give 1-[4-(4-cyclohexyloxypiperidin-1-yl)phenyl]piperazine (0.32 g).

The following compound was obtained according to a similar manner to that of Preparation 170.

PREPARATION 188

4-[4-[4-(4-Cyclohexyloxypiperidin-1-yl)phenyl]piperazin-1-yl]benzoic acid ethyl ester IR (KBr): 1706.7, 1234.2, 1110.8 cm$^{-1}$.

NMR (CDCl$_3$, δ): 1.23–1.91 (17H, m), 2.77–2.86 (2H, m), 3.19–3.24 (4H, m), 3.30–3.60 (8H, m), 4.34 (2H, q, J=7.1 Hz), 6.89–6.93 (6H, m), 7.93–7.97 (2H, m).

MASS (m/z): 492 (M$^+$+1).

The following compound was obtained according to a similar manner to that of Preparation 171.

PREPARATION 189

4-[4-[4-(4-Cyclohexyloxypiperidin-1-yl)phenyl]piperazin-1-yl]benzoic acid dihydrochloride IR (KBr): 1672.0, 1322.9, 1230.4 cm$^{-1}$.

NMR (DMSO-d$_6$, δ): 1.00–2.20 (14H, m), 3.20–4.00 (14H, m), 6.80–8.00 (8H, m).

MASS (m/z): 464 (M$^+$+1) (free).

The following compound was obtained according to a similar manner to that of Preparation 172.

PREPARATION 190

4-[4-[4-Cyclohexyloxypiperidin-1-yl)phenyl]piperazin-1-yl]benzoic acid benzotriazol-1-yl ester IR (KBr): 1781.9, 1600.6, 1513.8, 1230.4 cm$^{-1}$.

NMR (CDCl$_3$, δ): 1.13–2.10 (14H, m), 2.80–2.88 (2H, m), 3.22–3.64 (12H, m), 6.94–7.02 (6H, m), 7.39–7.58 (3H, m), 8.07–8.17 (3H, m).

MASS (m/z): 581 (M$^+$+1).

PREPARATION 191

To a suspension of 1-(4-hydroxyphenyl)piperazine (50 g) and potassium carbonate (46.5 g) in N,N-dimethylformamide (100 ml) was added dropwise benzyl chloroformate (47.86 g) at 0 to 10° C., and stirred for 4 hours at ambient temperature. The reaction mixture was poured into water, and extracted with ethyl acetate. The organic layer was washed with brine and dried, and the solvent was evaporated under reduced pressure. The residue was chromatographed on a column of silica gel eluting with dichloromethane/methyl alcohol (30:1) to give 4-(4-hydroxyphenyl)piperazine-1-carboxylic acid benzyl ester (60.8 g).

IR (KBr): 3336.2, 1658.5, 1226.5 cm$^{-1}$.

NMR (CDCl$_3$, δ): 3.00 (4H, t, J=4.9 Hz), 3.66 (4H, t, J=5.1 Hz), 5.16 (2H, s), 5.29 (1H, s), 6.74–6.86 (4H, m), 7.30–7.40 (5H, m).

MASS (m/z): 313 (M$^+$+1).

PREPARATION 192

To a solution of 4-(4-hydroxyphenyl)piperazine-1-carboxylic acid benzyl ester (22.38 g) and pyridine (8.7 ml) in dichloromethane (336 ml) was added dropwise trifluoromethanesulfonic anhydride (15.7 ml) at 0 to 10° C., and stirred for 2 hours. The reaction mixture was washed successively with 0.5N hydrochloric acid, saturated sodium hydrogen carbonate, water, brine, dried, and evaporated under reduced pressure. The residue was chromatographed on a column of silica gel eluting with dichloromethane/methyl alcohol (50:1) to give 4-(4-trifluoromethanesulfonyloxyphenyl)piperazine-1-carboxylic acid benzyl ester (21.06 g).

IR (KBr): 1685.5, 1511.9, 1427.1 cm$^{-1}$.

NMR (CDCl$_3$, δ): 3.17 (4H, t, J=5.0 Hz), 3.67 (4H, t, J=5.2 Hz), 5.16 (2H, s), 6.87–7.18 (4H, m), 7.34–7.38 (5H, m).

MASS (m/z): 445 (M$^+$+1).

The following compound was obtained according to a similar manner to that of Preparation 176.

PREPARATION 193

4-[4-(1,4-Dioxa-8-azaspiro[4.5]decan-8-yl)phenyl]piperazine-1-carboxylic acid benzyl ester IR (KBr): 1697.1, 1519.6, 1230.4 cm$^{-1}$.

NMR (CDCl$_3$, δ): 1.85 (4H, t, J=5.7 Hz), 3.00–3.05 (4H, m), 3.21 (4H, t, J=5.7 Hz), 3.65 (4H, t, J=5.1 Hz), 3.99 (4H, s), 5.16 (2H, s), 6.84–6.95 (4H, m), 7.36–7.39 (5H, m).

MASS (m/z): 438 (M$^+$+1).

PREPARATION 194

To a solution of 4-[4-(1,4-dioxa-8-azaspiro[4.5]decan-8-yl)phenyl]piperazine-1-carboxylic acid benzyl ester (30 g) in 1,4-dioxane (450 ml) was added 1N-hydrochloric acid (240 ml) at ambient temperature, and the mixture was stirred for 7 hours at 90° C. The reaction mixture was poured into water. The mixture was adjusted to pH 10–12 with 1N-sodium hydroxide (480 ml), and extracted with ethyl acetate. The organic layer was washed with water, brine, and dried, and evaporated under reduced pressure. The residue was chromatographed on a column of silica gel eluting with dichloromethane/methyl alcohol (50:1) to give 4-[4-(4-oxopiperidin-1-yl)phenyl]piperazine-1-carboxylic acid benzyl ester (21.22 g).

IR (KBr): 1718.3, 1683.6, 1232.3 cm$^{-1}$.

NMR (CDCl$_3$, δ): 2.55 (4H, t, J=6.0 Hz), 3.05 (4H, t, J=4.8 Hz), 3.49 (4H, t, J=6.0 Hz), 3.66 (4H, t, J=5.1 Hz).

MASS (m/z): 394 (M$^+$+1).

PREPARATION 195

To a suspension of 4-(4-chlorophenyl)-4-hydroxypiperidine (8 g) and triethylamine (5.8 ml) in dichloromethane (80 ml) was added di-tert-butyldicarbonate (9.07 g) under ice-cooling. The suspension was then stirred for 5 hours at ambient temperature. The reaction mixture was evaporated under reduced pressure. The residue was diluted with ethyl acetate and washed with water, washed with brine, and dried over magnesium sulfate. The magnesium sulfate was filtered off, and the filtrate was evaporated under reduced pressure. The residue was purified by column chromatography over silica using n-hexane/ethyl acetate (3:1) as the elution to give 4-(4-chlorophenyl)-4-hydroxypiperidine-1-carboxylic acid tert-butyl ester (11.76 g).

IR (KBr): 3461.6, 1675.8, 1662.3, 1166.7 cm$^{-1}$.

NMR (CDCl$_3$, δ): 1.48 (9H, s), 1.62–2.04 (5H, m), 3.16–3.28 (2H, m), 3.97–4.09 (2H, m), 7.30–7.44 (4H, m).

MASS (m/z): 212 (M$^+$–Boc).

The following compound was obtained according to a similar manner to that of Preparation 174.

PREPARATION 196

4-(4-Chlorophenyl-4-methoxypiperidine-1-carboxylic acid tert-butyl ester

IR (KBr): 1695.1, 1423.2, 1170.6 cm$^{-1}$.

NMR (CDCl$_3$, δ): 1.47 (9H, s), 1.72–2.04 (4H, m), 2.97 (3H, s), 3.07–3.22 (2H, m), 3.90–4.04 (2H, m), 7.27–7.37 (4H, m).

MASS (m/z): 348.1 (M$^+$+Na).

The following compound was obtained according to a similar manner to that of Preparation 175.

PREPARATION 197

4-(4-Chlorophenyl)-4-methoxypiperidine

IR (Film): 3305.4, 1490.7, 1135.9, 1072.2 cm$^{-1}$.

NMR (CDCl$_3$, δ): 1.75–2.03 (4H, m), 2.86–3.11 (8H, m), 7.33 (4H, s).

MASS (m/z): 226.2.

The following compound was obtained according to a similar manner to that of Preparation 164.

PREPARATION 198

1-(4-Nitrophenyl)-4-(4-chlorophenyl)-4-methoxypiperidine

IR (KBr): 1594.8, 1319.1, 1066.4 cm$^{-1}$.

NMR (CDCl$_3$, δ): 1.91–2.20 (4H, m), 3.02 (3H, s), 3.34–3.48 (2H, m), 3.79–3.86 (2H, m), 6.83–6.91 (2H, m), 7.29–7.39 (4H, m), 8.09–8.17 (2H, m).

MASS (m/z): 347.2.

PREPARATION 199

A mixture of 1-(4-nitrophenyl)-4-(4-chlorophenyl)-4-methoxypiperidine (8.9 g), iron powder (10.7 g) and ammonium chloride (1.07 g) in ethanol (445 ml) and water (44.5 ml) was stirred at reflux for 5.5 hours. The insoluble material was filtered off, and the filtrate was evaporated under reduced pressure. To the residue was added a mixture of ethyl acetate (150 ml), water (100 ml) and saturated sodium hydrogen carbonate (50 ml). The organic layer was separated, washed with brine, dried over magnesium sulfate. The magnesium sulfate was filtered off, and the filtrate was evaporated under reduced pressure. To the residue was added a mixture of diisopropyl ether (10 ml) and n-hexane (20 ml). The precipitate was collected by filtration, and dried under reduced pressure to give 1-(4-aminophenyl)-4-(4-chlorophenyl)-4-methoxypiperidine (7.3 g).

IR (KBr): 3342.0, 1614.1, 1517.7, 1066.4 cm$^{-1}$.

NMR (CDCl$_3$, δ): 2.04–2.20 (4H, m), 2.99 (3H, s), 3.03–3.34 (6H, m), 6.64–6.70 (4H, m), 7.30–7.45 (4H, m).

MASS (m/z): 317.3.

The following compound was obtained according to a similar manner to that of Preparation 166.

PREPARATION 200

1-(4-Bromophenyl)-4-(4-chlorophenyl)-4-methoxypiperidine

IR (KBr): 1589.1, 1494.6, 1249.6, 1062.6 cm$^{-1}$.

NMR (CDCl$_3$, δ): 1.96–2.15 (4H, m), 2.99 (3H, s), 3.08–3.22 (2H, m), 3.40–3.55 (2H, m), 6.81–6.87 (2H, m), 7.30–7.38 (6H, m).

MASS (m/z): 382 (M$^+$+1).

The following compound was obtained according to a similar manner to that of Preparation 167.

PREPARATION 201

4-[4-[4-(4-Chlorophenyl)-4-methoxypiperidin-1-yl]phenyl]piperazine-1-carboxylic acid tert-butyl ester IR (KBr): 1695.1, 1511.9, 1234.2 cm$^{-1}$.

NMR (CDCl$_3$, δ): 1.48 (9H, s), 2.05–2.15 (4H, m), 2.99 (3H, s), 3.00–3.16 (6H, m), 3.37–3.43 (2H, m), 3.55–3.60 (4H, m), 6.87–6.99 (4H, m), 7.35 (4H, s).

MASS (m/z): 486 (M$^+$+1).

PREPARATION 202

To a solution of 4-[4-[4-(4-chlorophenyl)-4-methoxypiperidin-1-yl]phenyl]piperazine-1-carboxylic acid tert-butyl ester (1.56 g) in ethyl acetate (62 ml) was added dropwise 4N-HCl/ethyl acetate (40 ml) at ambient temperature. The reaction mixture was stirred for 33 hours at ambient temperature. The precipitate was collected by filtration, and dried under reduced pressure to give 4-[4-[4-(4-chlorophenyl)-4-methoxypiperidin-1-yl]phenyl] piperazine trihydrochloride salt (1.52 g).

IR (KBr): 3382.5, 1504.2, 1255.4 cm$^{-1}$.

NMR (DMSO$_6$, δ): 2.24–3.76 (20H, m), 7.12–7.84 (8H, m).

MASS (m/z): 386 (free).

The following compound was obtained according to a similar manner to that of Preparation 169.

PREPARATION 203

4-[4-[4-(4-Chlorophenyl)-4-methoxypiperidin-1-yl]phenyl]piperazine

The following compound was obtained according to a similar manner to that of Preparation 170.

PREPARATION 204

4-[4-[4-[4-(4-Chlorophenyl)-4-methoxypiperidin-1-yl]phenyl]piperazin-1-yl]benzoic acid ethyl ester IR (KBr): 1702.8, 1602.6, 1513.8, 1234.2 cm$^{-1}$.

MASS (m/z): 534 (M$^+$+1).

The following compound was obtained according to a similar manner to that of Preparation 171.

PREPARATION 205

4-[4-[4-[4-(4-Chlorophenyl)-4-methoxypiperidin-1-yl]phenyl]piperazin-1-yl]benzoic acid dihydrochloride IR (KBr): 2962.1, 1697.1, 1602.6, 1515.8, 1224.6 cm$^{-1}$.

MASS (m/z): 506 (M$^+$+1) (free).

The following compound was obtained according to a similar manner to that of Preparation 172.

PREPARATION 206

4-[4-[4-[4-(4-Chlorophenyl)-4-methoxypiperidin-1-yl]phenyl]piperazin-1-yl]benzoic acid benzotriazol-1-yl ester IR (KBr): 1772.3, 1762.6, 1598.7, 1230.4, 1184.1 cm$^{-1}$.

NMR (CDCl$_3$+CD$_3$OD, δ): 2.11–2.17 (3H, m), 3.01 (3H, s), 3.05–3.66 (12H, m), 6.95–7.04 (6H, m), 7.37–7.60 (7H, m), 8.07–8.17 (3H, m).

MASS (m/z): 623 (M$^+$+1).

PREPARATION 207

60% Sodium hydride (1.01 g) was added slowly to a suspension of 4,4'-bicyclohexanol (5 g) in N,N-dimethylformamide (50 ml) at ambient temperature, and the mixture was stirred for 6 hours at 80° C. To the mixture was added dropwise n-propylbromide (2.29 ml) at 0–5° C., and the reaction mixture was stirred for 18.5 hours at 80° C. The reaction mixture was poured into water, and extracted with ethyl acetate. The organic layer was washed with brine and dried, and the solvent was evaporated under reduced pressure. The residue was chromatographed on a column of silica gel eluting with dichloromethane/methyl alcohol (50:1) to give 4'-propyl-4-hydroxy-1,1'-bicyclohexane (1.21 g).

IR (KBr): 3363.2, 1454.1, 1101.2 cm$^{-1}$.

NMR (CDCl$_3$, δ): 0.67–2.08 (24H, m), 2.88–3.60 (4H, m).

PREPARATION 208

To a solution of 4'-propoxybicyclohexyl-4-ol (1 g) and triethylamine (0.81 ml) in dichloromethane (10 ml) was added dropwise methanesulfonyl chloride (0.39 ml) at 0–5° C., and stirred for 3 hours. The reaction mixture was washed with water and brine, and dried, and evaporated under reduced pressure to give 4'-propoxy-4-methylsulfonyloxy-1,1'-bicyclohexane (1.44 g).

IR (KBr): 1454.1, 1351.9, 1338.4, 1164.8, 1110.8 cm$^{-1}$.

NMR (CDCl$_3$, δ): 0.87–2.20 (23H, m), 2.89–3.44 (7H, m).

PREPARATION 209

A mixture of 4-piperazinylbenzoic acid ethyl ester (1.03 g), 4'-propoxy-4-methylsulfonyloxy-1,1'-bicyclohexane (1.4 g), potassium carbonate (0.91 g) in N,N-dimethylformamide (10 ml) was stirred for 8 hours at 130° C. The reaction mixture was poured into water, and extracted with ethyl acetate. The organic layer was washed with brine and dried, and the solvent was evaporated under reduced pressure. The residue was chromatographed on a column of silica gel eluting with dichloromethane/methyl alcohol (200:1) to give 4-[4-(4'-propoxy-1,1'-bicyclohexan-4-yl)piperazin-1-yl] benzoic acid ethyl ester (0.26 g).

IR (KBr): 1706.7, 1286.3, 1108.9 cm$^{-1}$.

NMR (CDCl$_3$, δ): 0.88–2.20 (26H, m), 3.00–3.67 (1H, m), 4.33 (2H, q, J=7.1 Hz), 6.85–6.89 (2H, m), 7.92–7.97 (2H, m).

MASS (m/z): 455.

The following compound was obtained according to a similar manner to that of Preparation 171.

PREPARATION 210

4-[4-(4'-Propoxy-1,1'-bicyclohexan-4-yl)piperazin-1-yl]benzoic acid hydrochloride IR (KBr): 1695.1, 1228.4, 1112.7 cm$^{-1}$.

NMR (CDCl$_3$, δ): 0.88–2.03 (23H, m), 3.10–3.66 (12H, m), 6.86–6.91 (2H, m), 7.98–8.02 (2H, m).

MASS (m/z): 455.

The following compound was obtained according to a similar manner to that of Preparation 172.

PREPARATION 211

4-[4-(4'-Propoxy-1,1'-bicyclohexan-4-yl)piperazin-1-yl]benzoic acid benzotriazol-1-yl ester IR (KBr): 1772.3, 1695.1, 1226.5, 1187.9, 1089.6 cm$^{-1}$.

NMR (CDCl$_3$, δ): 0.88–2.04 (23H, m), 3.10–3.69 (12H, m), 6.93–6.98 (2H, m), 7.39–8.17 (6H, m).

PREPARATION 212

Lithium aluminum hydride (7.94 g) was added slowly to stirred tetrahydrofuran (80 ml) at ambient temperature. To the mixture was added dropwise 3,3-tetramethyleneglutamide (7 g) in tetrahydrofuran (70 ml) at ambient temperature. After refluxed for 5 hours, to the reaction mixture was added dropwise water, and the mixture was filtered. The filtrate was evaporated under reduced pressure to give an oil (4.7 g). To the residue was added tetrahydrofuran (47 ml) and triethylamine (6.12 ml). To the mixture was added dropwise benzyloxycarbonyl chloride (5.76 g) in tetrahydrofuran (6 ml) at ambient temperature. After stirring for 1.5 hours, the reaction mixture was poured into water, and extracted with ethyl acetate. The organic layer was separated, washed with diluted hydrochloric acid, water, brine, and dried, and evaporated under reduced pressure to give an oil (8.52 g). The oil was chromatographed on a silica gel eluting with a mixture of dichloromethane and methyl alcohol (100:1) to give an oil (5.51 g). A solution of this oil (5.51 g) in methyl alcohol (55 ml) was added 10% palladium on carbon (0.55 g), and hydrogen gas at atmospheric pressure for 6 hours. The reaction mixture was filtered through celite and evaporated under reduced pressure to give 8-azaspiro[4.5]decane (2.49 g).

IR (KBr): 3249.5, 1531.2, 1467.6 cm$^{-1}$.

NMR (CDCl$_3$, δ): 1.40–1.64 (13H, m), 2.84 (4H, br s).

MASS (m/z): 140 (M$^+$+1).

The following compound was obtained according to a similar manner to that of Preparation 176.

PREPARATION 213

1-[4-[4-(8-Azaspiro[4.5]decan-8-yl)phenyl]piperazin-1-yl]ethanone

IR (KBr): 2937.1, 1648.8, 1515.8, 1238.1 cm$^{-1}$.

NMR (CDCl$_3$, δ): 1.42–1.67 (12H, m), 2.13 (3H, s), 3.03–3.08 (8H, m), 3.58–3.63 (2H, m), 3.73–3.79 (2H, m), 6.78–7.86 (4H, m).

MASS (m/z): 342 (M$^+$+1).

The following compound was obtained according to a similar manner to that of Preparation 177.

PREPARATION 214

6-(Piperazinylphenyl)-8-azaspiro[4.5]decane

The following compound was obtained according to a similar manner to that of Preparation 170.

PREPARATION 215

4-[4-[4-(8-Azaspiro[4.5]decan-8-yl)phenyl]piperazin-1-yl]benzoic acid ethyl ester IR (KBr): 1706.7, 1322.9, 1282.4, 1236.1, 1105.0 cm$^{-1}$.

NMR (CDCl$_3$, δ): 1.37 (3H, t, J=7.1 Hz), 1.41–1.65 (12H, m), 3.03–3.09 (4H, m), 3.19–3.24 (4H, m), 3.45–3.50 (4H, m), 4.34 (2H, q, J=7.1 Hz), 6.89–6.94 (6H, m), 7.93–7.97 (2H, m).

MASS (m/z): 448 (M$^+$+1).

The following compound was obtained according to a similar manner to that of Preparation 171.

PREPARATION 216

4-[4-[4-(8-Azaspiro[4.5]decan-8-yl)phenyl]piperazin-1-yl]benzoic acid dihydrochloride IR (KBr): 2946.7, 1689.3, 1388.5, 1226.5, 1184.1 cm$^{-1}$.

NMR (DMSO-d$_6$, δ): 1.40–2.40 (12H, m), 3.00–4.20 (12H, m), 7.01–7.15 (4H, m), 7.69–7.74 (2H, m), 7.78–7.83 (2H, m), 12.06 (1H, br s).

MASS (m/z): 420 (M$^+$+1) (free).

The following compound was obtained according to a similar manner to that of Preparation 172.

PREPARATION 217

4-[4-[4-(8-Azaspiro[4.5]decan-8-yl)phenyl]piperazin-1-yl]benzoic acid benzotriazol-1-yl ester IR (KBr): 1781.9, 1598.7, 1513.8, 1228.4 cm$^{-1}$.

NMR (CDCl$_3$, δ): 1.43–1.73 (2H, m), 3.05–3.10 (4H, m), 3.22–3.27 (4H, m), 3.59–3.64 (4H, m), 6.90–7.02 (6H, m), 7.39–7.58 (3H, m), 8.07–8.17 (3H, m).

MASS (m/z): 537 (M$^+$+1).

PREPARATION 218

To a solution of 4-acetyl-1-(4-hydroxyphenyl)piperazine (20 g) and pyridine (11.02 ml) in dichloromethane (60 ml) was added dropwise with stirring trifluoromethanesulfonic acid anhydride (20 ml) at 0° C. The mixture was then stirred for 1 hour at 0° C. and 1 hour at room temperature. The reaction mixture was added to a mixture of 0.5 mol/l hydrochloric acid and dichloromethane. The organic layer was washed with sodium hydrogen carbonate solution and sodium chloride solution. The organic layer was taken and dried over magnesium sulfate. The magnesium sulfate was filtered off, and the filtrate was concentrated under reduced pressure. The residue was purified by silica gel chromatography (30:1 dichloromethane-methanol elution). Diisopropyl ether was added to the residue, and precipitates were filtered, washed with the same solvent, and dried to give trifluoromethanesulfonic acid 4-(4-acetylpiperazin-1-yl)phenyl ester (27.78 g).

NMR (CDCl$_3$, δ): 2.15 (3H, s), 3.20 (4H, m), 3.63 (2H, t, J=5.2 Hz), 3.78 (2H, t, J=5.2 Hz), 6.88–6.95 (2H, m), 7.15–7.20 (2H, m).

MASS (m/z): 353 (M$^+$+1).

PREPARATION 219

To a mixture of cesium carbonate (25.32 g), palladium(II) acetate (0.624 g) and 2,2'-bis(diphenylphosphino)-1,1'-binaphthyl (2.59 g) in toluene (110 ml) was successively added cis-2,6-dimethylmorpholine (8.21 ml) and trifluoromethanesulfonic acid 4-(4-acetylpiperazin-1-yl)phenyl ester (20 g) in stream of nitrogen. The mixture was stirred at ambient temperature for 30 minutes and at 100° C. for further 12 hours. After cooling to room temperature, water was added to the reaction mixture. The resulting precipitates were filtered, washed with water and dried. The residue was purified by silica gel chromatography (50:1 dichloromethane-methanol elution) to give 1-[4-[4-(cis-2,6-dimethylmorpholin-4-yl)phenyl]piperazin-1-yl]ethanone (7.78 g).

NMR (CDCl$_3$, δ): 1.15–1.30 (6H, m), 2.13 (3H, s), 2.36 (2H, t, J=11.1 Hz), 3.00–3.90 (12H, m), 6.85–7.00 (4H, m).

MASS (m/z): 318 (M$^+$+1).

PREPARATION 220

A mixture 1-[4-[4-(cis-2,6-dimethylmorpholin-4-yl)phenyl]piperazin-1-yl]ethanone (11.37 g) and 1.0 mol/l hydrochloric acid (225 ml) in ethanol (220 ml) was refluxed for 23 hours. The reaction mixture was added to a mixture of 1.0 mol/l sodium hydroxide solution and dichloromethane. The organic layer was taken and dried over magnesium sulfate. The magnesium sulfate was filtered off, and the filtrate was concentrated under reduced pressure to give cis-2,6-dimethyl-4-(4-piperazinylphenyl)morpholine (3.64 g).

NMR (CDCl$_3$, δ): 1.24 (6H, d, J=6.3 Hz), 2.35 (2H, t, J=11.1 Hz), 2.95–3.40 (11H, m), 3.70–3.9 (2H, m), 6.8–6.95 (4H, m).

MASS (m/z): 276 (M$^+$+1).

PREPARATION 221

A solution of cis-2,6-dimethyl-4-(4-piperazinylphenyl)morpholine (2.00 g), 4-fluorobenzoic acid ethyl ester (1.43 g) and potassium carbonate (1.01 g) in dimethylsulfoxide (40 ml) was stirred for 8 hours at 150° C., during which period additional 4-fluorobenzoic acid ethyl ester (1.35 g) and potassium carbonate (1.0 g) was added to the mixture. The reaction mixture was added to a mixture of water and dichloromethane. The organic layer was taken and dried over magnesium sulfate. The magnesium sulfate was filtered off, and the filtrate was concentrated under reduced pressure. The residue was purified by silica gel chromatography (25:1 dichloromethane-methanol elution) to give 4-[4-[4-(cis-2,6-dimethylmorpholin-4-yl)phenyl]piperazin-1-yl]benzoic acid ethyl ester (2.5 g).

IR (KBr): 1705, 1697 1605, 1513, 1282, 1234 cm$^{-1}$.

NMR (DMSO-d$_6$, δ): 1.25 (6H, d, J=6.3 Hz), 1.36 (3H, t, J=7.1 Hz), 2.37 (2H, t, J=11.1 Hz), 3.15–3.55 (10H, m), 3.7–3.9 (2H, m), 4.34 (2H, q, J=7.1 Hz), 6.85–7.00 (6H, m), 7.95 (2H, d, J=8.9 Hz).

MASS (m/z): 424 (M$^+$+1).

PREPARATION 222

A mixture of 4-[4-[4-(cis-2,6-dimethylmorpholin-4-yl)phenyl]piperazin-1-yl]benzoic acid ethyl ester (2.46 g) and 1.0 mol/l sodium hydroxide solution (11.6 ml) in a mixed solvent of ethanol (50 ml) and tetrahydrofuran (125 ml) was refluxed for 33 hours, during which period additional 1.0 mol/l sodium hydroxide solution (24 ml) was added to the mixture. After cooling to ambient temperature, the reaction mixture was poured into cold water, and the mixture was adjusted to pH 2 with 1.0 mol/l hydrochloric acid. The resulting precipitates were filtered, washed with water and dried to give 4-[4-[4-(cis-2,6-dimethylmorpholin-4-yl)phenyl]piperazin-1-yl]benzoic acid (1.05 g).

IR (KBr): 1664, 1603, 1514, 1234 cm$^{-1}$.

NMR (DMSO-d$_6$, δ): 1.14 (6H, d, J=6.21 Hz), 2.16 (2H, t, J=11.0 Hz), 3.05–3.80 (12H, m), 6.80–7.15 (6H, m), 7.79 (2H, d, J=8.8 Hz).

MASS (m/z): 472 (M$^+$+1).

PREPARATION 223

A mixture of 4-[4-[4-(cis-2,6-dimethylmorpholin-4-yl)phenyl]piperazin-1-yl]benzoic acid (1.01 g), 1-hydroxybenzotriazole (370 mg) and 1-ethyl-3-(3'-dimethylaminopropyl)carbodiimide hydrochloride (986 mg) in methylene chloride (100 ml) was stirred for 4 hours at room temperature then evaporated under reduced pressure. Water was added to the residue and the resulting precipitate collected by filtration, washed with water, then dried under hi-vacuum to give 4-[4-[4-(cis-2,6-dimethylmorpholin-4-yl)phenyl]piperazin-1-yl]benzoic acid benzotriazol-1-yl ester (1.197 g).

IR (KBr): 1784, 1603, 1512, 1232 cm$^{-1}$.

NMR (CDCl$_3$, δ): 1.26 (6H, d, J=6.3 Hz), 2.38 (2H, t, J=11.0 Hz), 3.15–3.45 (6H, m), 3.62 (4H, t, J=5.1 Hz), 3.7–3.95 (2H, m), 6.8–7.1 (6H, m), 7.3–7.6 (3H, m), 8.0–8.25 (3H, m).

MASS (m/z): 589 (M$^+$+1).

PREPARATION 224

To a mixture of cesium carbonate (6.33 q), palladium(II) acetate (156 mg) and 2,2'-bis(diphenylphosphino)-1,1'-binaphthyl (648 mg) in dioxane (28 ml) was successively added cis-2,6-dimethyl-4-(4-piperazinylphenyl)morpholine (4.59 g) and 4'-trifluoromethanesulfonyloxy-1,1'-biphenyl-4-carboxylic acid methyl ester (5 g) in a stream of nitrogen. The mixture was stirred at ambient temperature for 30 minutes and at 80° C. for a further 28 hours. After cooling to room temperature, water was added to the reaction mixture. The resulting precipitates were filtered, washed with water and dried to give 4'-[4-[4-(cis-2,6-dimethylmorpholin-4-yl)phenyl]piperazin-1-yl]-1,1'-biphenyl-4-carboxylic acid methyl ester (3.72 g).

NMR (CDCl$_3$, δ): 1.26 (6H, d, J=6.3 Hz), 2.37 (2H, t, J=11.0 Hz), 3.2–3.5 (10H, m), 3.75–3.9 (2H, m), 3.93 (3H, s), 6.8–7.15 (6H, m), 7.5–7.7 (4H, m), 8.07 (2H, d, J=8.3 Hz).

MASS (m/z): 486 (M$^+$+1).

PREPARATION 225

A mixture of 4'-[4-[4-(cis-2,6-dimethylmorpholin-4-yl)phenyl]piperazin-1-yl]-1,1'-biphenyl-4-carboxylic acid methyl ester (3.70 g) and 1.0 mol/l sodium hydroxide solution (30 ml) in a mixed solvent of methanol (75 ml) and tetrahydrofuran (185 ml) was refluxed for 15.5 hours. After cooling to ambient temperature, the reaction mixture was poured into cold water, and the mixture was adjusted to pH 2 with 1.0 mol/l hydrochloric acid. The resulting precipitates were filtered, washed with water and diisopropyl ether and dried to give 4'-[4-[4-(cis-2,6-dimethylmorpholin-4-yl)phenyl]piperazin-1-yl]-1,1'-biphenyl-4-carboxylic acid (3.68 g).

MASS (m/z): 472 (M$^+$+1).

The following compound was obtained according to a similar manner to that of Preparation 223.

PREPARATION 226

4'-[4-[4-(2,6-Dimethylmorpholin-4-yl)phenyl]piperazin-1-yl]-1,1'-biphenyl-4-carboxylic acid benzotriazol-1-yl ester NMR (DMSO-d$_6$, δ): 1.26 (6H, d, J=6.3 Hz), 2.38 (2H, t, J=11.0 Hz), 3.2–3.6 (10H, m), 3.7–3.95 (2H, m), 6.85–7.15 (6H, m), 7.4–7.9 (7H, m), 8.12 (2H, d, J=8.1 Hz), 8.31 (2H, d, J=8.5 Hz).

MASS (m/z): 589 (M$^+$+1).

PREPARATION 227

A solution of 4-fluorobenzoic acid ethyl ester (3 g), cis-2,6-dimethylmorpholine (2.26 g) and potassium carbonate (2.47 g) in dimethylsulfoxide (60 ml) was stirred for 18 hours at 80° C. The reaction mixture was added to a mixture of water and ethyl acetate. The organic layer was taken and dried over magnesium sulfate. The magnesium sulfate was filtered off, and the filtrate was concentrated under reduced pressure. The residue was purified by silica gel chromatography (5:1 hexane-ethyl acetate elution) to give 4-(cis-2,6-dimethylmorpholin-4-yl)benzoic acid ethyl ester (555 mg).

IR (KBr): 1695, 1605, 1518, 1244 cm$^{-1}$.

NMR (CDCl$_3$, δ): 1.27 (6H, d, J=6.3 Hz), 1.37 (3H, t, J=7.1 Hz), 2.51 (2H, t, J=11.4 Hz), 3.5–3.9 (4H, m), 4.33 (2H, q, J=7.1 Hz), 6.85 (2H, d, J=9 Hz), 7.93 (2H, d, J=8.9 Hz).

MASS (m/z): 250 (M$^+$+1).

PREPARATION 228

To a solution of 4-(cis-2,6-dimethylmorpholin-4-yl)benzoic acid ethyl ester (0.55 g) in a mixed solvent of methanol (3 ml) and tetrahydrofuran (6 ml) was added hydrazine monohydrate (1.6 ml). The solution was refluxed for 20 hours, during which period additional hydrazine monohydrate (1.6 ml) was added to the mixture. After cooling to ambient temperature, the reaction mixture was added to a mixture of water and ethyl acetate. The organic layer was washed with sodium chloride solution. The organic layer was taken and dried over magnesium sulfate. The magnesium sulfate was filtered off, and the filtrate was concentrated under reduced pressure to give 4-(cis-2,6-dimethylmorpholin-4-yl)benzoic acid hydrazide (489.7 mg).

IR (KBr): 1632, 1606, 1506, 1331, 1246 cm$^{-1}$.

NMR (DMSO-d$_6$, δ): 1.15 (6H, d, J=6.1 Hz), 2.3 (2H, t, J=11.4 Hz), 3.55–3.8 (4H, m), 4.36 (2H, br s), 6.94 (2H, d, J=8.9 Hz), 7.71 (2H, d, J=8.8 Hz).

MASS (m/z): 250 (M$^+$+1).

PREPARATION 229

A mixture of 4-(cis-2,6-dimethylmorpholin-4-yl)benzoic acid hydrazide (458 mg), 4-methoxycarbonylbenzoyl chloride (622 mg) and pyridine (5 ml) in tetrahydrofuran (10 ml) was stirred for 6 hours at 0° C. The reaction mixture was added to water. The resulting precipitates were filtered, washed with water and dried to give 4-[N'-[4-(cis-2,6-dimethylmorpholin-4-yl)benzoyl]hydrazinocarbonyl] benzoic acid methyl ester (662.8 mg).

IR (KBr): 1724, 1606, 1279, 1242 cm$^{-1}$.

NMR (DMSO-d$_6$, δ): 1.17 (6H, d, J=6.1 Hz), 2.35 (2H, t, J=11.2 Hz), 3.6–3.85 (4H, m), 3.9 (3H, s), 7.02 (2H, d, J=8.9 Hz), 7.83 (2H, d, J=8.8 Hz), 8.0–8.2 (4H, m), 10.28 (1H, s), 10.58 (1H, s).

MASS (m/z): 412 (M$^+$+1).

PREPARATION 230

To a solution of 4-[N'-[4-(cis-2,6-dimethylmorpholin-4-yl)benzoyl]hydrazinocarbonyl]benzoic acid methyl ester (100 mg) in dimethoxyethane (3 ml) was added phosphorus pentasulfide (82 mg). The mixture was refluxed for 5 hours. After cooling to ambient temperature, the reaction mixture was poured into cold water and the mixture was adjusted to pH 11 with 1N-sodium hydroxide aqueous solution. The resulting precipitates were filtered, washed with water and dried to give 4-[5-[4-(cis-2,6-dimethylmorpholin-4-yl)phenyl][1,3,4]thiadiazol-2-yl]benzoic acid methyl ester (97.4 mg).

IR (KBr): 1716, 1605, 1437, 1412, 1277, 1238 cm$^{-1}$.

NMR (CDCl$_3$, δ): 1.29 (6H, d, J=6.2 Hz), 2.54 (2H, t, J=11.3 Hz), 3.61 (2H, d, J=11.9 Hz), 3.7–3.9 (2H, m), 3.96 (3H, s), 6.96 (2H, d, J=8.9 Hz), 7.91 (2H, d, J=8.8 Hz), 8.0–8.25 (4H, m).

MASS (m/z): 410 (M$^+$+1).

PREPARATION 231

A mixture of 4-[5-[4-(cis-2,6-dimethylmorpholin-4-yl)phenyl][1,3,4]thiadiazol-2-yl]benzoic acid methyl ester (527 mg) and 1.0 mol/l sodium hydroxide solution (2.6 ml) in a mixed solvent of methanol (10 ml) and tetrahydrofuran (25 ml) was refluxed for 6 hours. After cooling to ambient temperature, the reaction mixture was poured into cold water and the mixture was adjusted with 1.0 mol/l hydrochloric acid. The resulting precipitates were filtered, washed with water and dried to give 4-[5-[4-(cis-2,6-dimethylmorpholin-4-yl)phenyl][1,3,4]thiadiazol-2-yl]benzoic acid (429.1 mg).

IR (KBr): 1686, 1605, 1412, 1236 cm$^{-1}$.

NMR (DMSO-d$_6$, δ): 1.18 (6H, d, J=6.1 Hz), 2.39 (2H, t, J=11.2 Hz), 3.6–3.9 (4H, m), 7.11 (2H, d, J=9.1 Hz), 7.87 (2H, d, J=8.8 Hz), 8.11 (4H, s), 13.3 (1H, br s).

MASS (m/z): 396 (M$^+$+1).

The following compound was obtained according to a similar manner to that of Preparation 223.

PREPARATION 232

4-[5-[4-(cis-2,6-bimethylmorpholin-4-yl)phenyl][1,3,4]thiadiazol-2-yl]benzoic acid benzotriazol-1-yl ester IR (KBr): 1780, 1603, 1441, 1414, 1230 cm$^{-1}$.

NMR (CDCl$_3$, δ): 1.3 (6H, d, J=6.2 Hz), 2.45–2.65 (2H, m), 3.55–3.95 (4H, m), 6.97 (2H, d, J=8.9 Hz), 7.4–7.7 (3H, m), 7.85–8.5 (7H, m).

MASS (m/z): 513 (M$^+$+1).

PREPARATION 233

A mixture of cesium trichloride (5.0 g) in tetrahydrofuran (45 ml) was stirred at room temperature for 6 hours. 1,4-Dioxaspiro[4.5]decan-8-one (1.4 g) was added to the solution and stirred at room temperature for 1 hour. To the solution was added dropwise with stirring cyclohexylmagnesium chloride (2.0M solution in diethyl ether) (6.7 ml) at 0° C. The reaction mixture was quenched with 10% acetic acid aqueous solution. Diethyl ether was added to the solution. The organic layer was taken, washed with brine, sodium hydrogen carbonate solution, brine and dried over magnesium sulfate. The magnesium sulfate was filtered off, and the filtrate was concentrated under reduced pressure. The residue was purified by silica gel chromatography to give 8-cyclohexyl-1,4-dioxaspiro[4.5]decan-8-ol (1.266 g).

NMR (CDCl$_3$, δ): 0.9–2.1 (19H, m), 3.85–4.05 (4H, m).

PREPARATION 234

To a solution of 8-cyclohexyl-1,4-dioxaspiro[4.5]decan-8-ol (1.143 g) and iodomethane (0.59 ml) in N,N-dimethylformamide (11 ml) was added sodium hydride (60% dispersion in mineral oil) (342 mg) at 0° C. The solution was stirred for 9 hours at 0° C., during which period additional iodomethane (0.59 ml) and sodium hydride (60% dispersion in mineral oil) (344 mg) was added to the mixture. The reaction mixture was added to a mixture of water and dichloromethane. The organic layer was washed with water. The organic layer was taken and dried over magnesium sulfate. The magnesium sulfate was filtered off, and the filtrate was concentrated under reduced pressure. The residue was purified by silica gel chromatography (ethyl acetate elution) to give 8-cyclohexyl-8-methoxy-1,4-dioxaspiro[4.5]decane (1.201 g).

IR (NaCl): 1448, 1377, 1250 cm$^{-1}$.

NMR (CDCl$_3$, δ): 0.9–1.9 (19H, m), 3.11 (3H, s), 3.85–4.0 (4H, m).

MASS (m/z): 277 (M$^+$+Na).

PREPARATION 235

A solution of 8-cyclohexyl-8-methoxy-1,4-dioxaspiro[4.5]decane (1.15 g) and acetic acid (40 ml) in water was stirred at 100° C. for 6 hours. After cooling to room temperature, the reaction mixture was added to a mixture of sodium hydrogen carbonate solution and diethyl ether. The organic layer was taken, washed with sodium hydrogen carbonate solution and dried over magnesium sulfate. The magnesium sulfate was filtered off, and the filtrate was concentrated under reduced pressure to give 1-methoxy-1,1'-bicyclohexane-4-one (1.018 g).

NMR (CDCl$_3$, δ): 0.8–2.7 (19H, m), 3.22 (3H, s).

MASS (m/z): 233 (M$^+$+Na).

PREPARATION 236

To an ice cooled solution of ethyl 4-(piperazin-1-yl)benzoate (1.23 g) and 1-methoxy-1,1'-bicyclohexane-4-one (916 mg) in a mixed solvent of methanol (20 ml), tetrahydrofuran (15 ml) and acetic acid (0.74 ml) was added sodium cyanoborohydride (301 mg) in a stream of nitrogen. The mixture was stirred at this temperature for 1.5 hours and at room temperature for 7.5 hours. The reaction mixture was quenched with saturated aqueous sodium hydrogen carbonate solution. Dichloromethane was added to the solution. The organic layer was taken, washed with sodium hydrogen carbonate solution and dried over magnesium sulfate. The magnesium sulfate was filtered off, and the filtrate was concentrated under reduced pressure. The residue was purified by silica gel chromatography (3:1 hexane-methanol elution) to give 4-[4-(1-methoxy-1,1'-bicyclohexan-4-yl)piperazinyl]benzoic acid ethyl ester (801 mg).

IR (KBr): 1701, 1608, 1520 cm$^{-1}$.

NMR (CDCl$_3$, δ): 0.7–1.9 (22H, m), 2.1–2.4 (1H, m), 2.65–2.85 (4H, m), 3.10 (3H, s), 3.25–3.4 (4H, m), 4.32 (2H, q, J=7.1 Hz), 6.86 (2H, d, J=8.8 Hz), 7.92 (2H, d, J=8.9 Hz).

MASS (m/z): 429 (M$^+$+1).

The following compound was obtained according to a similar manner to that of Preparation 231.

PREPARATION 237

4-[4-(1-Methoxy-1,1'-bicyclohexyl-4-yl)piperazin-1-yl]benzoic acid

IR (KBr): 1689, 1610, 1232, 1186 cm$^{-1}$.

MASS (m/z): 401 (M$^+$+1).

The following compound was obtained according to a similar manner to that of Preparation 223.

PREPARATION 238

4-[4-(1-Methoxy-1,1'-bicyclohexyl-4-yl)piperazinyl]benzoic acid benzotriazol-1-yl ester IR (KBr): 1782, 1603, 1522, 1232, 1186 cm$^{-1}$.

NMR (CDCl$_3$, δ): 0.7–2.1 (19H, m), 2.2–2.3 (1H, m), 2.7–2.9 (4H, m), 3.11 (3H, s), 3.4–3.55 (4H, m), 6.94 (2H, d, J=9.1 Hz), 7.3–7.6 (3H, m), 8.0–8.2 (3H, m).

MASS (m/z): 518 (M$^+$+1).

The following compound was obtained according to a similar manner to that of Preparation 236.

PREPARATION 239

4-[4-(1-Methoxy-1,1'-bicyclohexyl-4-yl)piperazinyl]benzoic acid ethyl ester

IR (KBr): 1703, 1606, 1518, 1450, 1282, 1238 cm$^{-1}$.

NMR (CDCl$_3$, δ): 0.7–2.3 (23H, m), 2.55–2.7 (4H, m), 3.14 (3H, s), 3.25–3.45 (4H, m), 4.33 (2H, q, J=7.1 Hz), 6.8–6.95 (2H, m), 7.85–8.05 (2H, m).

MASS (m/z): 429 (M$^+$+1).

The following compound was obtained according to a similar manner to that of Preparation 231.

PREPARATION 240

4-[4-(1-Methoxy-1,1'-bicyclohexyl-4-yl)piperazinyl]benzoic acid

IR (KBr): 1668, 1603, 1228, 1186 cm$^{-1}$.

MASS (m/z): 401 (M$^+$+1).

The following compound was obtained according to a similar manner to that of Preparation 223.

PREPARATION 241

4-[4-(1-Methoxy-1,1'-bicyclohexyl-4-yl)piperazin-1-yl]benzoic acid benzotriazol-1-yl ester IR (KBr): 1767, 1603, 1524, 1232, 1186 cm$^{-1}$.

NMR (CDCl$_3$, δ): 0.7–2.1 (19H, m), 2.15–2.3 (1H, m), 2.55–2.7 (4H, m), 3.15 (3H, s), 3.35–3.55 (4H, m), 6.95 (2H, d, J=9.1 Hz), 7.35–7.6 (3H, m), 8.0–8.2 (3H, m).

MASS (m/z): 518 (M$^+$+1).

PREPARATION 242

A solution of piperazine (30.37 g), 4-fluorobenzoic acid ethyl ester (20 g) and potassium carbonate (65.75 g) in dimethylsulfoxide (100 ml) was stirred for 5.5 hours at 150° C. After cooling to the room temperature, water was added to the solution. The resulting precipitate was collected by filtration and dried to give ethyl 4-piperazinylbenzoate (18.48 g).

NMR (CDCl$_3$, δ): 1.37 (3H, t, J=7.1 Hz), 2.95–3.1 (4H, m), 3.2–3.4 (4H, m), 4.33 (2H, q, J=7.1 Hz), 6.87 (2H, d, J=9.0 Hz), 7.85–8.0 (2H, m).

MASS (m/z): 235 (M$^+$+1).

The following compound was obtained according to a similar manner to that of Preparation 236.

PREPARATION 243

4-[4-(4-tert-Butylcyclohexyl)piperazinyl]benzoic acid ethyl ester

IR (KBr): 1699, 1606, 1282, 1234, 1190 cm$^{-1}$.

NMR (CDCl$_3$, δ): 0.85 (9H, s), 0.9–1.45 (8H, m), 1.75–2.05 (4H, m), 2.1–2.4 (1H, m), 2.71 (4H, t, J=5.1 Hz), 3.33 (4H, t, J=5.1 Hz), 4.25–4.4 (2H, m), 6.86 (2H, d, J=9.0 Hz), 7.85–8.0 (2H, m).

MASS (m/z): 373 (M$^+$+1).

The following compound was obtained according to a similar manner to that of Preparation 231.

PREPARATION 244

4-[4-(4-tert-Butylcyclohexyl)piperazinyl]benzoic acid

IR (KBr): 1680, 1603 cm$^{-1}$.

MASS (m/z): 345 (M$^+$+1).

The following compound was obtained according to a similar manner to that of Preparation 223.

PREPARATION 245

4-4-(4-tert-Butylcyclohexyl)piperazinyl]benzoic acid benzotriazol-1-yl ester

IR (KBr): 1788, 1593, 1232 cm$^{-1}$.

NMR (CDCl$_3$, δ): 0.86 (9H, s), 0.9–1.4 (5H, m), 1.7–2.4 (5H, m), 2.75 (4H, t, J=5.0 Hz), 3.47 (4H, t, J=5.1 Hz), 6.8–7.05 (2H, m), 7.35–7.6 (3H, m), 8.0–8.25 (3H, m).

MASS (m/z): 462 (M$^+$+1).

The following compound was obtained according to a similar manner to that of Preparation 236.

PREPARATION 246

4-[4-(4-tert-Butylcyclohexyl)piperazinyl]benzoic acid ethyl ester

IR (KBr): 1701, 1606, 1282, 1248, 1192 cm$^{-1}$.

NMR (CDCl$_3$, δ): 0.84 (9H, s), 1.0–1.5 (10H, m), 1.9–2.25 (3H, m), 2.58 (4H, t, J=5.1 Hz), 3.31 (4H, t, J=5.1 Hz), 4.33 (2H, q, J=7.1 Hz), 6.8–6.95 (2H, m), 7.85–8.0 (2H, m).

MASS (m/z): 373 (M$^+$+1).

The following compound was obtained according to a similar manner to that of Preparation 231.

PREPARATION 247

4-[4-(4-tert-Butylcyclohexyl)piperazinyl]benzoic acid

IR (KBr): 1664, 1606, 1240 cm$^{-1}$.

MASS (m/z): 345 (M$^+$+1).

The following compound was obtained according to a similar manner to that of Preparation 223.

PREPARATION 248

4-[4-(4-tert-Butylcyclohexyl)piperazinyl]benzoic acid benzotriazol-1-yl ester

IR (KBr): 1778, 1603, 1232 cm$^{-1}$.

NMR (DMSO-d$_6$, δ): 0.86 (9H, s), 1.0–1.5 (7H, m), 1.95–2.3 (3H, m), 2.62 (4H, t, J=5.1 Hz), 3.45 (4H, t, J=5.1 Hz), 6.95 (2H, d, J=9.2 Hz), 7.35–7.6 (3H, m), 8.05–8.2 (3H, m).

MASS (m/z): 462 (M$^+$+1).

PREPARATION 249

A mixture of 4-bromo-4'-hydroxy-1,1'-biphenyl (5 g), cis-2,6-dimethylmorpholine, dichlorobis(tri-o-tolylphosphine)-palladium(II) and lithium bis(trimethylsilyl)amide (1.0 M solution in hexanes) (44 ml) in toluene (25 ml) was stirred for 6 hours at 100° C. The reaction mixture was added to a mixture of 1.0 mol/l hydrochloric acid and dichloromethane. The organic layer was washed with 1.0 mol/l hydrochloric acid, sodium hydrogen carbonate solution and sodium chloride solution. The organic layer was taken and dried over magnesium sulfate. The magnesium sulfate was filtered off, and the filtrate was concentrated under reduced pressure. The residue was purified by silica gel chromatography (50:1 dichloromethane-methanol elution) to give 4'-(cis-2,6-dimethylmorpholin-4-yl)-1,1'-biphenyl-4-ol (1.49 g).

NMR (CDCl$_3$, δ): 1.28 (6H, d, J=6.3 Hz), 2.45 (2H, t, J=11.2 Hz), 3.49 (2H, d, J=10.6 Hz), 3.75–3.95 (2H, m), 4.89 (1H, s), 6.8–7.0 (4H, m), 7.4–7.5 (4H, m).

MASS (m/z): 284 (M$^+$+1).

The following compound was obtained according to a similar manner to that of Preparation 218.

PREPARATION 250

Trifluoromethanesulfonic acid 4'-(cis-2,6-dimethylmorpholin-4-yl)-1,1'-biphenyl-4-yl ester NMR (CDCl$_3$, δ): 1.28 (6H, d, J=6.3 Hz), 2.47 (2H, t, J=11.3 Hz), 3.52 (2H, d, J=10.4 Hz), 3.7–3.95 (2H, m), 6.98 (2H, d, J=8.8 Hz), 7.30 (2H, d, J=8.8 Hz), 7.48 (2H, d, J=8.7 Hz), 7.60 (2H, d, J=8.8 Hz).

MASS (m/z): 416 (M$^+$+1).

PREPARATION 251

To a mixture of cesium carbonate (1.43 g), palladium(II) acetate (35 mg) and 2,2'-bis(diphenylphosphino)-1,1'-binaphthyl (146 mg) in dioxane (6 ml) was successively added trifluoromethanesulfonic acid 4'-(cis-2,6-dimethylmorpholin-4-yl)-1,1'-biphenyl-4-yl ester (1.30 g) and ethyl 4-piperazinylbenzoate (0.88 g) in a stream of nitrogen. The mixture was stirred at ambient temperature for 30 minutes and at 100° C. for further 6.5 hours. After cooling to room temperature, water was added to the reaction mixture. The resulting precipitates were filtered, washed with water and dried. The residue was pulverized with acetone and collected by filtration to give 4-[4-[4'-(cis-2,6-dimethylmorpholin-4-yl)-1,1'-biphenyl-4-yl]piperazinyl]benzoic acid ethyl ester (1.17 g).

IR (KBr): 1703, 1608, 1504, 1284, 1230 cm$^{-1}$.

NMR (CDCl$_3$, δ): 1.28 (6H, d, J=6.3 Hz), 1.38 (3H, t, J=7.1 Hz), 2.45 (2H, t, J=10.9 Hz), 3.3–3.6 (10H, m), 3.7–3.95 (2H, m), 4.34 (2H, q, J=7.1 Hz), 6.85–7.1 (6H, m), 7.45–7.6 (4H, m), 7.96 (2H, d, J=8.9 Hz).

MASS (m/z): 500 (M$^+$+1).

The following compound was obtained according to a similar manner to that of Preparation 222.

PREPARATION 252

4-[4-[4'-(cis-2,6-Dimethylmorpholin-4-yl)-1,1'-biphenyl-4-yl]piperazinyl]benzoic acid IR (KBr): 1668, 1603, 1504, 1230 cm$^{-1}$.

MASS (m/z): 472 (M$^+$+1).

The following compound was obtained according to a similar manner to that of Preparation 223.

PREPARATION 253

4-[4-[4'-(cis-2,6-Dimethylmorpholin-4-yl)-1,1'-biphenyl-4-yl]piperazinyl]benzoic acid benzotriazol-1-yl ester IR (KBr): 1765, 1601, 1502, 1230, 1184 cm$^{-1}$.

NMR (CDCl$_3$, δ): 1.28 (6H, d, J=6.3 Hz), 2.45 (2H, t, J=11.2 Hz), 3.35–3.95 (12H, m), 6.9–7.1 (6H, m), 7.4–7.6 (7H, m), 8.05–8.2 (3H, m).

MASS (m/z): 589 (M$^+$+1).

PREPARATION 254

A solution of 4-bromophenol (3 g) and 1,4-dibromobutane (6.2 ml) in N,N-dimethylformamide (30 ml) was treated with potassium carbonate (2.89 g) at room temperature for 27 hours. The mixture was diluted with ethyl acetate and washed with brine. The organic layer was dried over magnesium sulfate, filtered, and evaporated. The residue was purified by silica gel chromatography (25:1 hexane-ethyl acetate elution) to give 1-bromo-4-(4-bromobutoxy)benzene (3.09 g).

NMR (CDCl$_3$, δ): 1.8–2.15 (4H, m), 3.48 (2H, t, J=6.4 Hz), 3.96 (2H, t, J=5.9 Hz), 6.7–6.85 (2H, m), 7.3–7.45 (2H, m).

PREPARATION 255

A solution of 1-bromo-4-(4-bromobutoxy)benzene (3.05 g) in methanol (30 ml) was treated with 28% sodium methoxide in methanol (2.43 ml), and the solution was refluxed for 5 hours. After cooling, the reaction mixture was added to a mixture of water and ethyl acetate. The organic layer was washed with brine. The organic layer was taken and dried over magnesium sulfate. The magnesium sulfate was filtered off, and the filtrate was concentrated under reduced pressure. The residue was purified by silica gel chromatography (10:1 hexane-ethyl acetate elution) to give 1-bromo-4-(4-methoxybutoxy)benzene (1.95 g).

IR (NaCl): 1591, 1489, 1286, 1244 cm$^{-1}$.

NMR (CDCl$_3$, δ): 1.65–1.95 (4H, m), 3.35 (3H, s), 3.44 (2H, t, J=6.1 Hz), 3.95 (2H, t, J=6.1 Hz), 6.77 (2H, d, J=8.9 Hz), 7.36 (2H, d, J=8.9 Hz).

MASS (m/z): 282 (M$^+$+Na).

PREPARATION 256

To the solution of 1-bromo-4-(4-methoxybutoxy)benzene (4.94 g) and magnesium (463 mg) in tetrahydrofuran (50 ml) was added iodine at room temperature. The solution was refluxed for 7.5 hours, during which period diiodoethane was added to the mixture. After cooling to 0° C., 4-[4-(4-oxopiperidin-1-yl)phenyl]piperazine-1-carboxylic acid benzyl ester (4.94 g) in tetrahydrofuran (20 ml) was added dropwise with stirring to the solution. The mixture was stirred at room temperature for 2 hours. The reaction mixture was added to a mixture of ammonium chloride solution and ethyl acetate. The organic layer was taken, washed with brine, sodium hydrogen carbonate solution and brine and dried over magnesium sulfate. The magnesium sulfate was filtered off, and the filtrate was concentrated under reduced pressure. The residue was purified by silica gel chromatography (50:1 dichloromethane-methanol elution) to give 4-[4-[4-hydroxy-4-[4-(4-methoxybutoxy)phenyl]piperidin-1-yl]phenyl]piperazine-1-carboxylic acid benzyl ester (3.42 g).

NMR (CDCl$_3$, δ): 1.65–2.0 (6H, m), 2.1–2.4 (2H, m), 2.95–3.3 (6H, m), 3.35 (3H, s), 3.35–3.75 (8H, m), 3.99 (2H, t, J=5.9 Hz), 5.16 (2H, s), 6.8–7.05 (6H, m), 7.3–7.5 (9H, m).

MASS (m/z): 574 (M$^+$+1).

PREPARATION 257

To a solution of 4-[4-[4-hydroxy-4-[4-(4-methoxybutoxy)phenyl]piperidin-1-yl]phenyl]piperazine-1-carboxylic acid benzyl ester (3.41 g) in dichloromethane (50 ml) was added trifluoroacetic acid (8.5 ml) at 0° C. The reaction mixture was stirred at 0° C. for 1 hour and at room temperature for further 6 hours. To the reaction mixture was added 1 mol/ml sodium hydroxide solution (170 ml), dichloromethane (136 ml) and methanol (14 ml). The organic layer was washed with water and brine, dried over magnesium sulfate, filtered, and the filtrate was concentrated under reduced pressure. The residue was purified by silica gel chromatography (50:1 dichloromethane-methanol elution) to give 4-[4-[4-[4-(4-methoxybutoxy)phenyl]-3,6-dihydro-2H-pyridin-1-yl]phenyl]piperazine-1-carboxylic acid benzyl ester (2.23 g).

IR (KBr): 1701, 1514, 1232 cm$^{-1}$.

NMR (CDCl$_3$, δ): 1.7–2.0 (4H, m), 2.65 (2H, br s), 2.95–3.15 (4H, m), 3.35 (3H, s), 3.35–3.9 (10H, m), 3.99 (2H, t, J=6.0 Hz), 5.16 (2H, s), 6.18 (1H, m), 6.8–7.0 (6H, m), 7.3–7.45 (7H, m).

MASS (m/z): 556 (M$^+$+1).

PREPARATION 258

To a mixture of 4-[4-[4-[4-(4-methoxybutoxy)phenyl]-3,6-dihydro-2H-pyridin-1-yl]phenyl]piperazine-1-carboxylic acid benzyl ester (2.20 g) and ammonium formate (1.25 g) in 90% methanol (44 ml) and dioxane was added 10% palladium on carbon at room temperature. The reaction mixture was heated at 100° C. for 2 hours. After cooling, the reaction mixture was filtered and evaporated. Sodium hydrogen carbonate solution was added to the residue. And the resulting precipitate was collected by filtration, washed with water and dried under hi-vacuum to give 1-[4-[4-[4-(4-methoxybutoxy)phenyl]piperidin-1-yl]phenyl]piperazine (1.36 g).

IR (KBr): 1514, 1234 cm$^{-1}$.

NMR (DMSO-d$_6$, δ): 1.5–1.9 (8H, m), 2.5–3.0 (7H, m), 3.23 (3H, s), 3.1–4.1 (11H, m), 6.8–7.25 (5H, m).

MASS (m/z): 424 (M$^+$+1).

The following compound was obtained according to a similar manner to that of Preparation 221.

PREPARATION 259

4-[4-[4-[4-[4-(4-Methoxybutoxy)phenyl]piperidin-1-yl]phenyl]piperazin-1-yl]benzoic acid methyl ester IR (KBr): 1711, 1606, 1514, 1282, 1227 cm$^{-1}$.

NMR (CDCl$_3$, δ): 1.38 (3H, t, J=7.1 Hz), 1.65–2.0 (8H, m), 2.5–2.9 (3H, m), 3.5–3.8 (12H, m), 3.35 (3H, s), 3.97 (2H, t, J=6.0 Hz), 4.34 (2H, q, J=7.0 Hz), 6.8–7.2 (10H, m), 7.95 (2H, d, J=8.8 Hz).

MASS (m/z): 572 (M$^+$+1).

The following compound was obtained according to a similar manner to that of Preparation 222.

PREPARATION 260

4-[4-[4-[4-(4-Methoxybutoxy)phenyl]piperidin-1-yl]phenyl]piperazin-1-yl]benzoic acid IR (KBr): 1514, 1228 cm$^{-1}$.

MASS (m/z): 544 (M$^+$+1).

The following compound was obtained according to a similar manner to that of Preparation 223.

PREPARATION 261

4-[4-[4-[4-(4-Methoxybutoxy)phenyl]piperidin-1-yl]phenyl]piperazin-1-yl]benzoic acid benzotriazol-1-yl ester IR (KBr): 1514, 1230 cm$^{-1}$.

NMR (CDCl$_3$, δ): 1.6–2.0 (8H, m), 2.5–2.9 (3H, m), 3.2–3.8 (15H, m), 3.9–4.05 (2H, m), 6.8–7.3 (10H, m), 7.35–7.6 (3H, m), 8.05–8.25 (3H, m).

MASS (m/z): 661 (M$^+$+1).

The following compound was obtained according to a similar manner to that of Preparation 219.

PREPARATION 262

1-[4-[4-[4-(6-Methoxyhexylthio)piperidin-1-yl]phenyl]piperazin-1-yl]ethanone

IR (KBr): 1622, 1516, 1448, 1242 cm$^{-1}$.

NMR (CDCl$_3$, δ): 1.3–1.9 (10H, m), 1.95–2.15 (5H, m), 2.57 (2H, t, J=7.3 Hz), 2.6–2.85 (3H, m), 2.95–3.15 (4H, m), 3.25–3.85 (11H, m), 6.89 (4H, s).

MASS (m/z): 434 (M$^+$+1).

The following compound was obtained according to a similar manner to that of Preparation 220.

PREPARATION 263

1-[4-[4-(6-Methoxyhexylthio)piperidin-1-yl]phenyl]piperazine

IR (KBr): 1622, 1514, 1454, 1242, 1120 cm$^{-1}$.

NMR (CDCl$_3$, δ): 1.3–1.9 (10H, m), 1.95–2.15 (2H, m), 2.57 (2H, t, J=7.3 Hz), 2.6–2.85 (3H, m), 3.04 (8H, s), 3.3–3.6 (7H, m), 6.89 (4H, s).

MASS (m/z): 392 (M$^+$+1).

The following compound was obtained according to a similar manner to that of Preparation 221.

PREPARATION 264

4-[4-[4-[4-(6-Methoxyhexylthio)piperidin-1-yl]phenyl]piperazin-1-yl]benzoic acid ethyl ester NMR (CDCl$_3$, δ): 1.3–1.9 (13H, m), 1.95–2.15 (2H, m), 2.57 (2H, t, J=7.3 Hz), 2.6–2.85 (3H, m), 3.15–3.6 (15H, m), 4.34 (2H, q, J=7.0 Hz), 6.85–7.0 (6H, m), 7.95 (2H, d, J=8.8 Hz).

MASS (m/z): 540 (M$^+$+1).

The following compound was obtained according to a similar manner to that of Preparation 222.

PREPARATION 265

4-[4-[4-[4-(6-Methoxyhexylthio)piperidin-1-yl]phenyl]piperazin-1-yl]benzoic acid IR (KBr): 1605, 1587, 1546, 1514, 1408, 1225 cm$^{-1}$.

MASS (m/z): 512 (M$^+$+1).

The following compound was obtained according to a similar manner to that of Preparation 223.

PREPARATION 266

4-[4-[4-[4-(6-Methoxyhexylthio)piperidin-1-yl]phenyl]piperazin-1-yl]benzoic acid benzotriazol-1-yl ester IR (KBr): 1782, 1601, 1514, 1446, 1230, 1184 cm$^{-1}$.

NMR (CDCl$_3$, δ): 1.3–1.9 (10H, m), 1.95–2.15 (2H, m), 2.58 (2H, t, J=7.3 Hz), 2.65–2.85 (3H, m), 3.15–3.7 (15H, m), 6.85–7.1 (6H, m), 7.35–7.6 (3H, m), 8.05–8.2 (3H, m).

MASS (m/z): 629 (M$^+$+1).

The following compound was obtained according to a similar manner to that of Preparation 254.

PREPARATION 267

4-(4-Bromobutoxy)benzonitrile

IR (KBr): 2222, 1605, 1506, 1302, 1252 cm$^{-1}$.

NMR (CDCl$_3$, δ): 1.9–2.2 (4H, m), 3.49 (2H, t, J=6.2 Hz), 4.05 (2H, t, J=5.7 Hz), 6.85–7.0 (2H, m), 7.5–7.65 (2H, m).

MASS (m/z): 254 (M$^+$).

The following compound was obtained according to a similar manner to that of Preparation 256.

PREPARATION 268

4-(4-Methoxybutoxy)benzonitrile

IR (KBr): 2216, 1605, 1570, 1510, 1468, 1308, 1261 cm$^{-1}$.

NMR (CDCl$_3$, δ): 1.65–2.0 (4H, m), 3.35 (3H, s), 3.44 (2H, t, J=6.1 Hz), 4.00 (2H, t, J=6.2 Hz), 6.85–7.0 (2H, m), 7.5–7.65 (2H, m).

MASS (m/z): 206 (M$^+$+1).

PREPARATION 269

To a solution of 4-(4-methoxybutoxy)benzonitrile (21.8 g) and trifluoroacetic acid (109 ml) in toluene (218 ml) was added thiosemicarbazide (11.62 g). The solution was stirred for 31 hours at 60° C., during which period additional thiosemicarbazide (2.90 g) and trifluoroacetic acid was added to the mixture. The reaction mixture was pulverized with ethyl acetate. The precipitate was collected by filtration and dried to give 5-[4-(4-methoxybutoxy)phenyl][1,3,4]thiadiazol-2-ylamine trifluoroacetic acid salt (15.10 g).

IR (KBr): 1674, 1606, 1400 cm$^{-1}$.

NMR (CDCl$_3$, δ): 1.55–2.0 (4H, m), 3.36 (3H, s), 3.45 (2H, t, J=6.0 Hz), 4.04 (2H, t, J=6.1 Hz), 4.41 (4H, br s), 6.95 (2H, d, J=8.7 Hz), 7.63 (2H, d, J=8.7 Hz).

MASS (m/z): 280.

PREPARATION 270

To a suspension of 5-[4-(4-methoxybutoxy)phenyl][1,3,4]thiadiazol-2-ylamine trifluoroacetic acid salt (45.00 g) in ethanol (450 ml) was added ethyl 4-bromoacetylbenzoate (28.85 g), and the mixture was stirred under reflux for 4 hours. The reaction mixture was pulverized with ethyl acetate. The precipitate was collected by filtration and dried. To a suspension of the powder in xylene (450 ml) was added trifluoroacetic acid (67.5 ml), and the mixture was stirred at 130° C. for 4 hours. The reaction mixture was pulverized with diisopropyl ether. The precipitate was collected by filtration and dried. The residue was pulverized with ethyl acetate, and the precipitate was collected by filtration and dried to give 4-[2-[4-(4-methoxybutoxy)phenyl]imidazo[2,1-b][1,3,4]thiadiazol-6-yl]benzoic acid ethyl ester (29.85 g).

NMR (CDCl$_3$, δ): 1.41 (3H, t, J=7.1 Hz), 1.65–2.0 (4H, m), 3.36 (3H, s), 3.4–3.55 (2H, m), 4.0–4.15 (2H, m), 4.39 (2H, q, J=7.1 Hz), 6.99 (2H, d, J=8.8 Hz), 7.55–8.15 (7H, m).

MASS (m/z): 452 (M$^+$+1).

The following compound was obtained according to a similar manner to that of Preparation 231.

PREPARATION 271

4-[2-[4-(4-Methoxybutoxy)phenyl]imidazo[2,1-b][1,3,4]thiadiazol-6-yl]benzoic acid IR (KBr): 1680, 1608, 1591, 1549, 1468, 1404, 1257 cm$^{-1}$.

NMR (DMSO-d$_6$, δ): 1.55–1.9 (4H, m), 3.24 (3H, s), 3.3–3.5 (2H, m), 4.10 (2H, t, J=5.9 Hz), 7.14 (2H, d, J=8.7 Hz), 7.8–8.05 (6H, m), 8.84 (1H, s).

MASS (m/z): 424 (M$^+$+1).

The following compound was obtained according to a similar manner to that of Preparation 223.

PREPARATION 272

4-[2-[4-(4-Methoxybutoxy)phenyl]imidazo[2,1-b][1,3,4]thiadiazol-6-yl]benzoic acid benzotriazol-1-yl ester IR (KBr): 1768, 1606, 1547, 1470, 1404, 1255, 1176 cm$^{-1}$.

NMR (CDCl$_3$, δ): 1.6–2.0 (4H, m), 3.37 (3H, s), 3.47 (3H, t, J=6.0 Hz), 4.08 (3H, t, J=6.1 Hz), 7.02 (2H, d, J=8.7 Hz), 7.4–7.65 (3H, m), 7.7–8.4 (8H, m).

MASS (m/z): 541 (M$^+$+1).

PREPARATION 273

A solution of oxalyl dichloride (597 μl) in dry dichloromethane (7 ml) was cooled to −70° C. in nitrogen atmosphere, and a solution of dimethylsulfoxide (1.15 ml) in dry dichloromethane (1.5 ml) was added slowly and stirred for 30 minutes at −70° C. To the reaction mixture was added a solution of (3-hydroxypropyl)carbamic acid tert-butyl ester (1.0 g) in dry dichloromethane (7 ml) slowly to maintain the reaction temperature at −60° C. and stirred for 30 minutes at −70° C. To the reaction mixture was added triethylamine (3.98 ml) slowly to maintain the reaction temperature at −60° C. Then the reaction mixture was allowed to warm to room temperature. To the reaction mixture was added water (10 ml) and stirred for 10 minutes, then the organic layer was separated. The aqueous layer was extracted with dichloromethane (50 ml×2). The organic layer was combined and washed with brine, dried over magnesium sulfate. Magnesium sulfate was filtered off, and the filtrate was evaporated under reduced pressure to give 3-tert-butoxycarbonylaminopropionaldehyde (1.28 g), that was used crude in the next reaction.

The following compound was obtained according to a similar manner to that of Preparation 273.

PREPARATION 274

5-tert-Butoxycarbonylaminovaleraldehyde, that was used crude in the next reaction.

The following compound was obtained according to a similar manner to that of Preparation 273.

PREPARATION 275

6-tert-Butoxycarbonylaminohexanaldehyde, that was used crude in the next reaction.

The following compound was obtained according to a similar manner to that of Preparation 273.

PREPARATION 276

4-tert-Butoxycarbonylaminobutylaldehyde, that was used crude in the next reaction.

PREPARATION 277

To an ice-cooled solution of 5-aminopentan-1-ol (5.0 g) in water (40 ml) and acetone (40 ml) was added triethylamine (8.78 g) and di-tert-butyl dicarbonate (13.75 g), then the solution was stirred at 30° C. for 3 hours. The solvent was evaporated under reduced pressure and extracted with ethyl acetate. The organic layer was washed with water and brine, then dried over magnesium sulfate. Magnesium sulfate was filtered off, and the filtrate was evaporated under reduced pressure to give a crude yellow oil (12.7 g). The crude oil was purified by silica gel chromatography (50:1–4:1 dichloromethane-methanol) to give 5-hydroxypentylcarbamic acid tert-butyl ester (8.68 g), as a pale yellow oil.

IR (KBr): 3344.0, 2975.6, 2935.1, 2665.7, 1706.7, 1695.1, 1529.3, 1280.5, 1249.6, 1178.3, 1168.7 cm$^{-1}$.

NMR (DMSO-$d_6$, δ): 1.1–1.6 (15H, m), 2.88 (2H, dd, J=6.5 and 12.6 Hz), 3.2–3.5 (2H, m), 4.33 (1H, t, J=5.1 Hz), 6.75 (1H, m).

The following compound was obtained according to a similar manner to that of Preparation 277.

PREPARATION 278

6-Hydroxyhexylcarbamic acid tert-butyl ester

IR (KBr): 3351.7, 2977.6, 2937.1, 2859.9, 1714.4, 1679.7, 1533.1, 1276.6, 1249.6, 1180.2, 1164.8 cm$^{-1}$.

NMR (DMSO-$d_6$, δ): 1.0–1.6 (17H, m), 4.83 (2H, dd, J=6.5 and 12.8 Hz), 3.2–3.59 (2H, m), 4.32 (1H, t, J=5.2 Hz), 6.75 (1H, m).

The following compound was obtained according to a similar manner to that of Preparation 277.

PREPARATION 279

(S)-(-)-4-tert-Butoxycarbonylamino-2-hydroxybutyric acid

NMR (DMSO-$d_6$, δ): 1.37 (9H, s), 1.4–1.9 (2H, m), 3.00 (2H, dd, J=7.0 and 13.3 Hz), 3.92 (1H, dd, J=4.0 and 8.4 Hz), 6.78 (1H, m).

PREPARATION 280

To a solution of pyridinium chlorochromate (2.0 g) in dichloromethane (15 ml) was added a solution of 6-hydroxyhexanoic acid ethyl ester (1.0 g) in dichloromethane (1.5 ml) in one portion and stirred for 1.5 hours at ambient temperature. Ether (15 ml) was added to the reaction mixture, and the insoluble material removed by filtration and discarded. The filtrate was purified by silica gel chromatography (diethyl ether) to give 6-oxohexanoic acid ethyl ester (884.6 mg), as a pale green oil.

IR (KBr): 2981.4, 2940.9, 2871.5, 2827.1, 2723.0, 1731.8, 1184.1 cm$^{-1}$.

NMR (CDCl$_3$, δ): 1.26 (3H, t, J=7.1 Hz), 1.5–1.8 (4H, m), 2.2–2.6 (4H, m), 4.13 (2H, q, J=7.1 Hz), 9.77 (1H, t, J=1.6 Hz).

The following compound was obtained according to a similar manner to that of Preparation 280.

PREPARATION 281

9-Oxo-nonanic acid methyl ester

IR (KBr): 2933.2, 2858.0, 2721.1, 1743.3, 1724.0, 1538.6, 1245.8, 1199.5, 1172.5 cm$^{-1}$.

NMR (CDCl$_3$, δ): 1.24 (6H, s), 1.3–1.7 (4H, m), 2.18 (2H, t, J=7.3 Hz), 2.29 (2H, t, J=7.3 Hz), 3.58 (3H, s), 11.97 (1H, s).

PREPARATION 282

A solution of N-t-butoxycarbonyl-L-glutamic acid α-t-butyl ester (600 mg) and 4-piperidone hydrochloride monohydrate (455.6 mg) in dichloromethane (6 ml)-DMF (6 ml), was treated with 1-hydroxybenzotriazole (294 mg) and 1-ethyl-3-(3'-dimethylaminopropyl)carbodiimide (460.5 mg) and stirred 15 hours at room temperature. The reaction was diluted with ethyl acetate and washed with water, dried over magnesium sulfate, evaporated, and the residue was purified by silica gel column chromatography (EtOAc elution) to give 4-(4-piperidon-1-yl)carbonyl-2-tert-butoxycarbonylaminobutanoic acid tert-butyl ester (450 mg) as a white solid.

IR (KBr): 3381, 2931, 2883, 1707, 1631.5, 1510, 1448, 1367, 1321 cm$^{-1}$.

NMR (CDCl$_3$, δ): 1.43 (9H, s), 1.48 (9H, s), 1.85–2.10 (1H, m), 2.15–2.4 (1H, m), 2.4–2.6 (6H, m), 3.6–4.1 (4H, m), 4.1–4.3 (1H, m), 5.19 (1H, br d, J=8.4 Hz).

The following compound was obtained according to a similar manner to that of Preparation 282.

PREPARATION 283

1-(1-tert-Butoxycarbonylazetidin-3-yl)carbonyl-4-piperidone

IR (KBr): 2979.5, 2891, 1712.5, 1691.3, 1649 cm$^{-1}$.

NMR (CDCl$_3$, δ): 1.44 (9H, s), 2.44–2.53 (4H, m), 3.54–3.61 (3H, m), 3.89–3.95 (2H, m), 4.06–4.22 (4H, m).

MASS (m/z): 305.2 (M$^+$+Na).

Elemental Analysis Calcd. for $C_{14}H_{22}N_2O_4 \cdot 0.6H_2O$: C, 57.36, H, 7.98, N, 9.56. Found: C, 57.29, H, 7.65, N, 9.58.

PREPARATION 284

To a solution of 1,3-dioxy-5-hydroxymethyl-4-methyl-2-oxo-4-cyclopentene (2 g) and N,N'-disuccinimidyl carbonate (4.33 g) in dimethylformamide (10 ml) was added pyridine (1.37 ml) and stirred at ambient temperature. The reaction mixture was added to a mixture of water and ethyl acetate. The organic layer was taken and dried over magnesium sulfate. The magnesium sulfate was filtered off, and the filtrate was evaporated under reduced pressure to give (1,3-dioxy-2-oxo-4-cyclopenten-5-yl)methoxycarbonyloxysuccinimido (2.477 g).

IR (KBr): 1808.8, 1785.8, 1741.4, 1733.7, 1259.3, 1228.4, 1209.1 cm$^{-1}$.

NMR (CDCl$_3$, δ): 2.20 (3H, s), 2.86 (4H, s), 5.06 (2H, s).

ESI-MASS (m/z): 294.1 (M$^+$+Na+1).

PREPARATION 285

To a solution of 1-methyl-4-piperidone (1.0 g) in N,N-dimethylformamide (10 ml) was added 2-iodoethanol (0.70 ml-1.5 g) and stirred overnight at ambient temperature. The reaction mixture was evaporated under reduced pressure and washed by ethyl acetate to afford 1-(2-hydroxyethyl)-1-methyl-4-oxopiperidinium iodide (0.94 g).

MASS (m/z): 158 (M$^+$–I$^-$).

PREPARATION 286

To a solution of 1-methyl-4-piperidone (1.0 g) in dichloromethane (5 ml) was slowly added iodomethane (1 ml) at 0° C. and stirred for 30 minutes at ambient temperature. To the reaction mixture was added isopropyl ether (10 ml), and the resulting precipitate was collected by filtration to give 1,1-dimethyl-4-oxopiperidinium iodide (1.416 g).

NMR (DMSO-d$_6$, δ): 1.87 (2H, t, J=5.4 Hz), 2.71 (2H, t, J=6.4 Hz), 3.09 (3H, s), 3.27 (3H, s), 3.30–3.40 (2H, m), 3.75 (2H, t, J=6.6 Hz).

The Starting Compounds (287) to (290) used and the Object Compounds (287) to (290) obtained in the following Preparations 287 to 20 are given in the table as below, in which the formulas of the starting compounds are in the upper column and the formulas of the object compounds are in the lower column, respectively.

| Preparation No. | Formula |
|---|---|
| 287 | 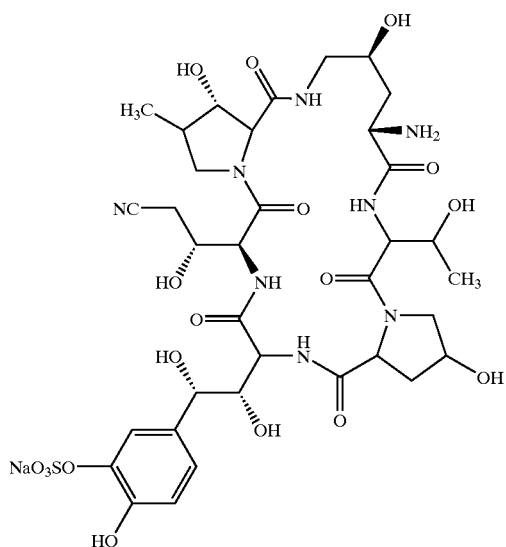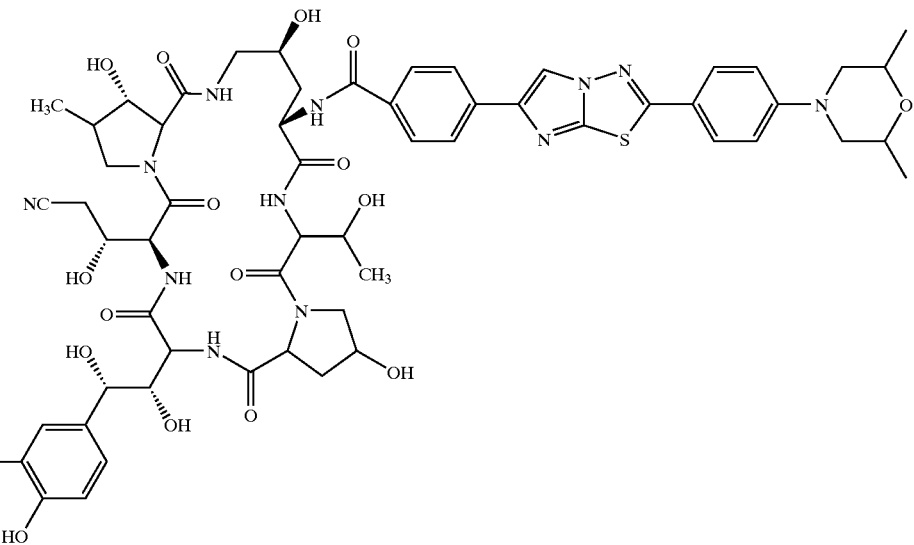 |

| Preparation No. | Formula |
|---|---|
| 288 | 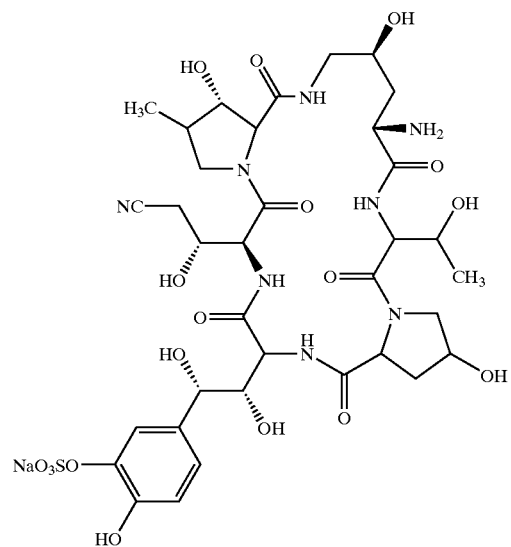 |
| | 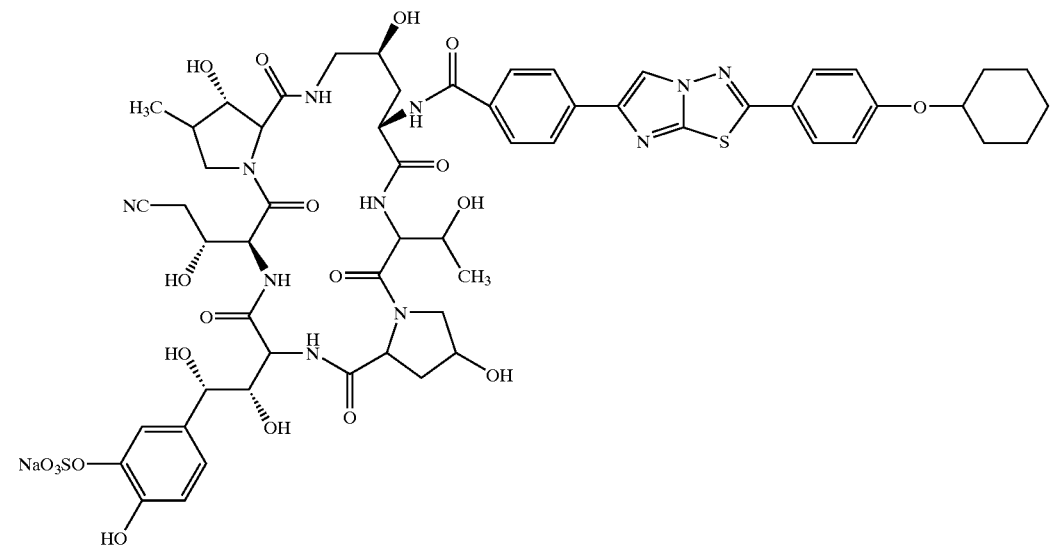 |

-continued
| Preparation No. | Formula |
|---|---|
| 289 | 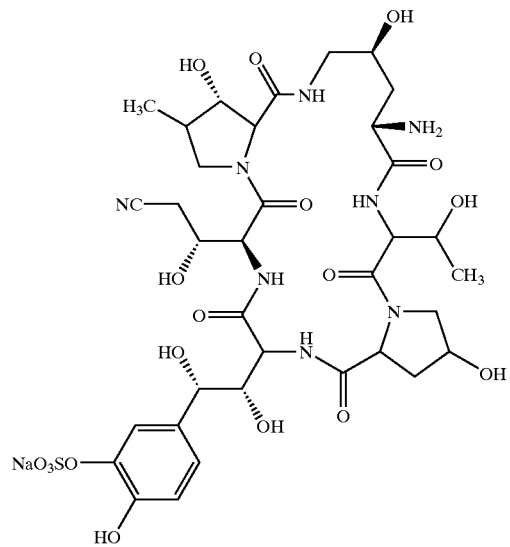 |
| | 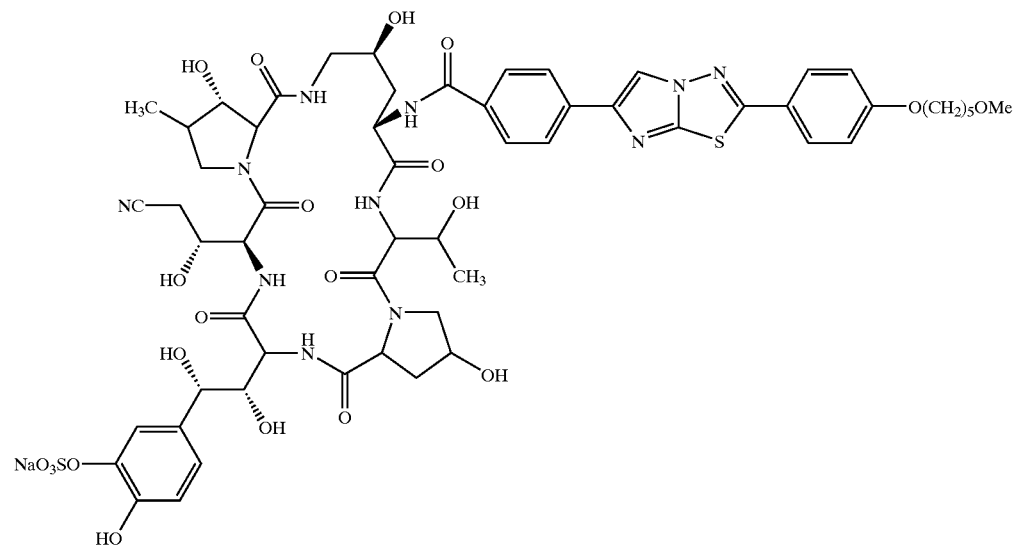 |

-continued

| Preparation No. | Formula |
|---|---|
| 290 | 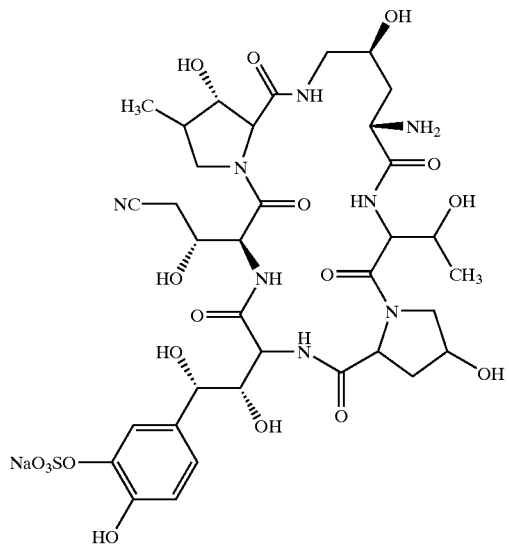<br>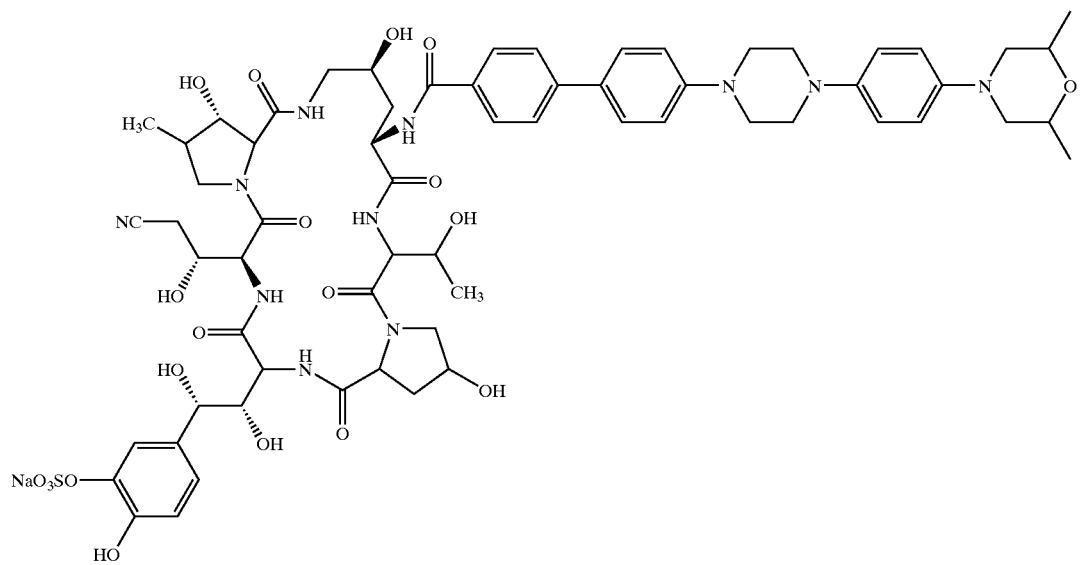 |

The following compounds [Preparations 287 to 290] were obtained according to a similar manner to that of Preparation

PREPARATION 287

MASS (m/z): 1317.3 (M$^+$–Na).

PREPARATION 288

MASS (m/z): 1302.3 (M$^+$–Na).

PREPARATION 289

MASS (m/z): 1320.3 (M$^+$–Na).

PREPARATION 290

The object compound was used directly in the next reaction without purification.

The Starting Compounds (291) to (338) used and the Object Compounds (291) to (338) obtained in the following Preparation 291 to 338 are given in the table as below, in which the formulas of the starting compounds are in the upper column and the formulas of the object compounds are in the lower column, respectively.

| Preparation No. | Formula |
|---|---|
| 291 | 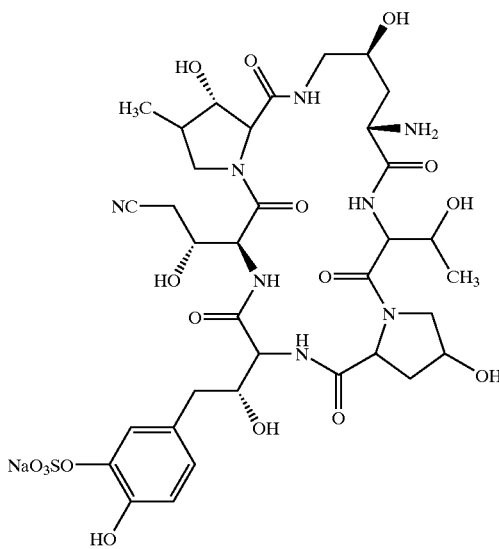 |
| | 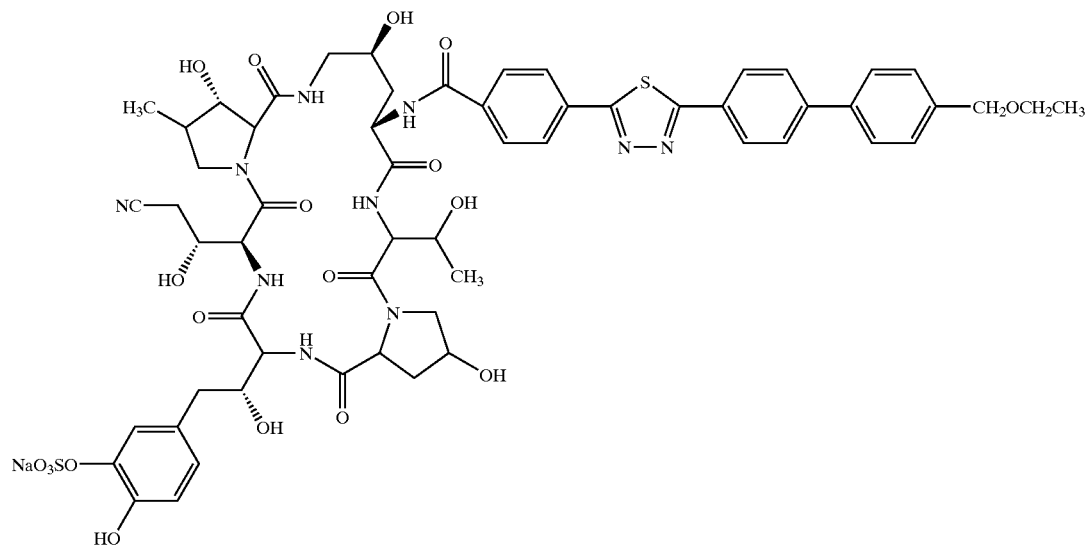 |

| Preparation No. | Formula |
|---|---|
| 292 | 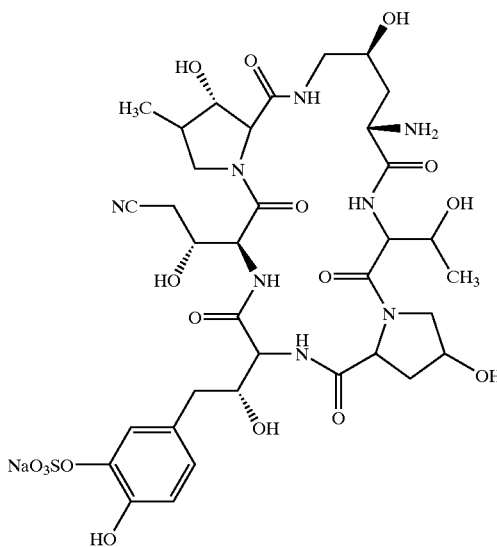 |
| | 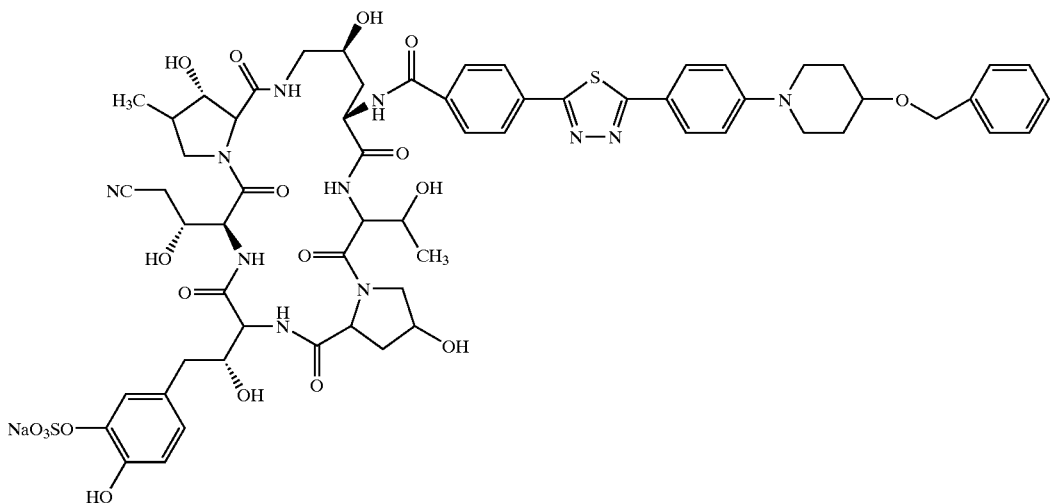 |

-continued
| Preparation No. | Formula |
|---|---|
| 293 | 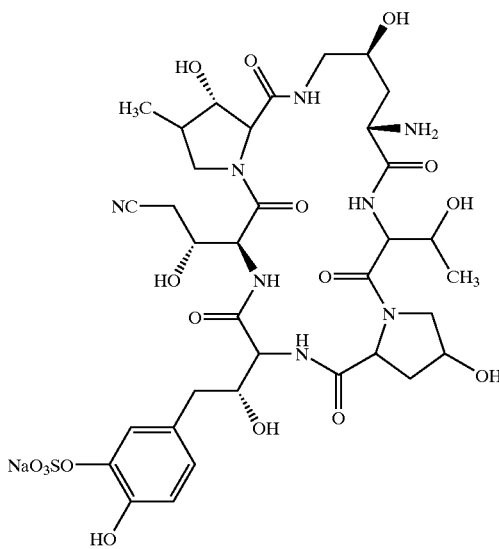 |
| | 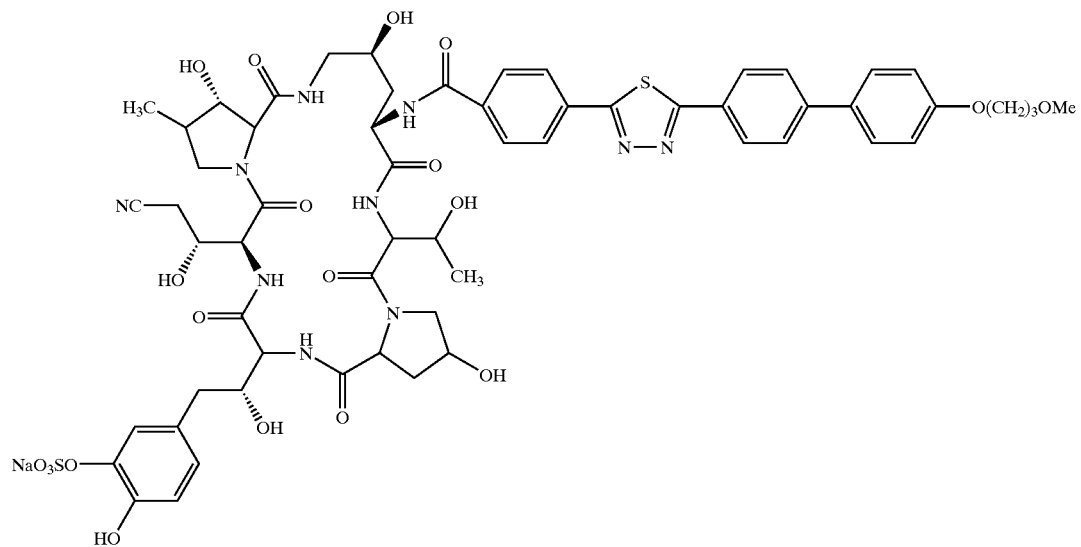 |

| Preparation No. | Formula |
|---|---|
| 294 | 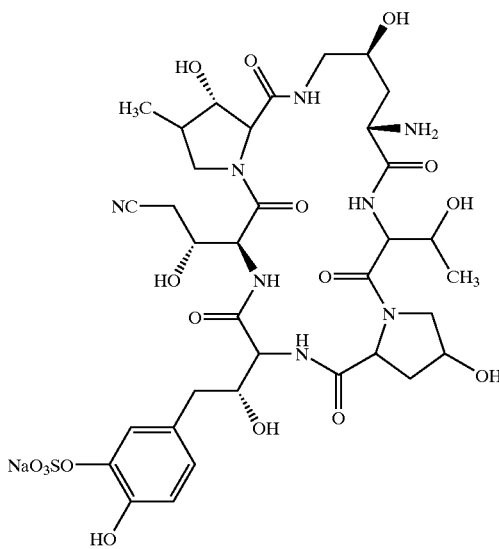 |
| | 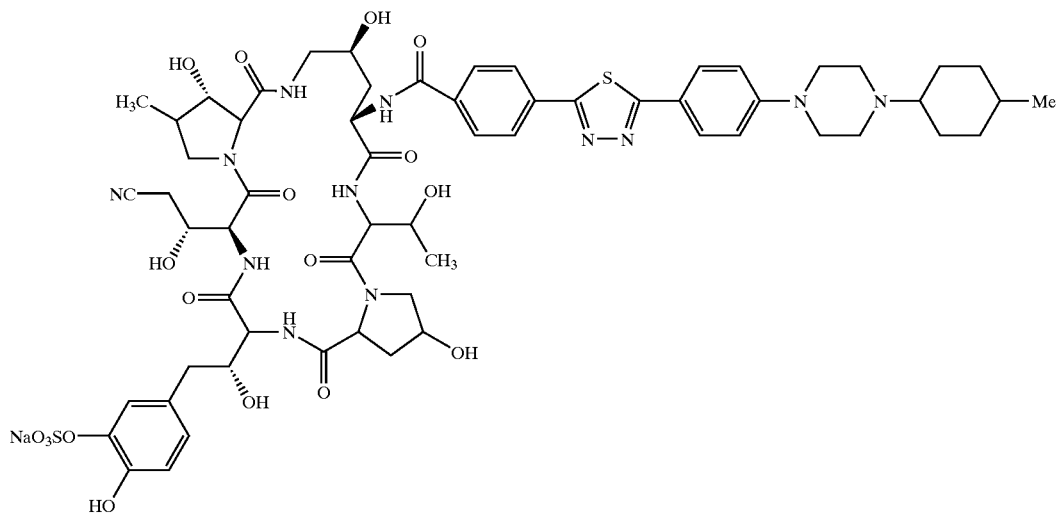 |

| Preparation No. | Formula |
|---|---|
| 295 | 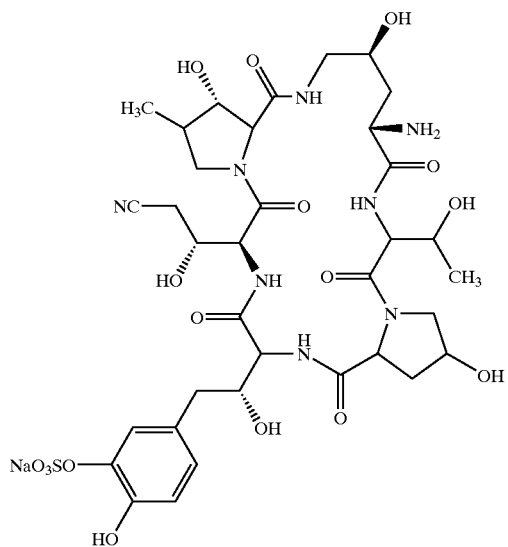 |
| | 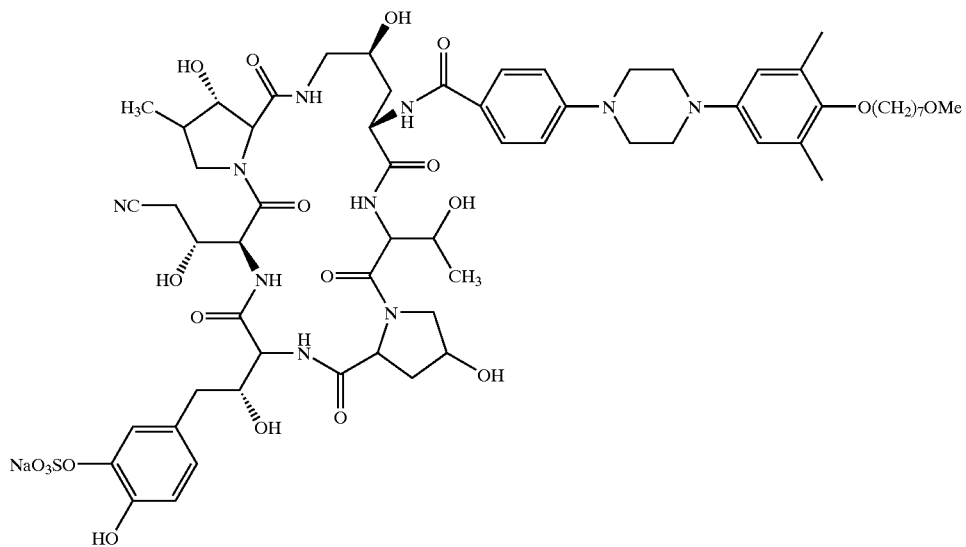 |

| Preparation No. | Formula |
|---|---|
| 296 | 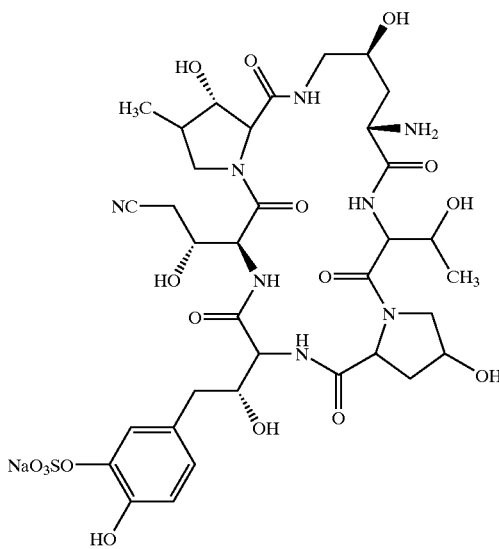 |
| | 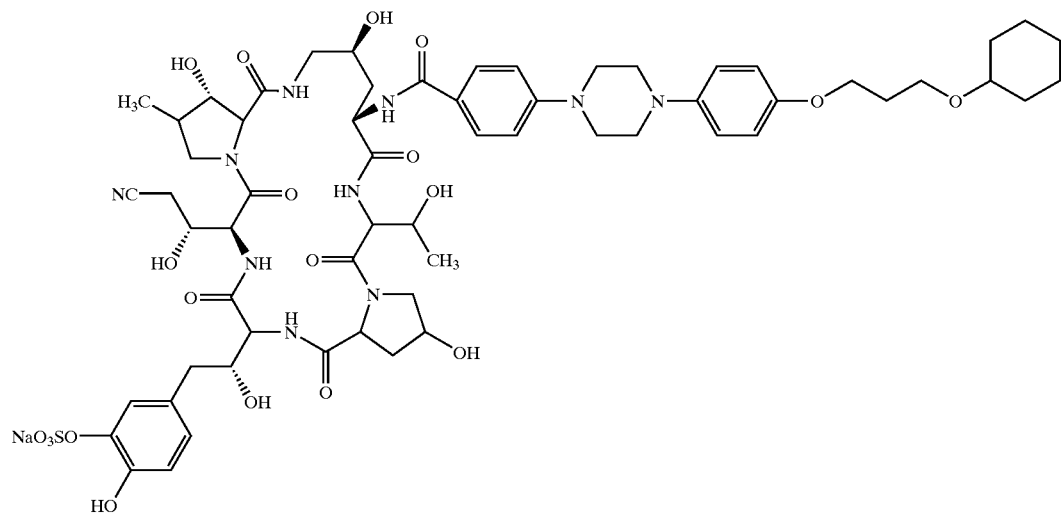 |

-continued
| Preparation No. | Formula |
|---|---|
| 297 | 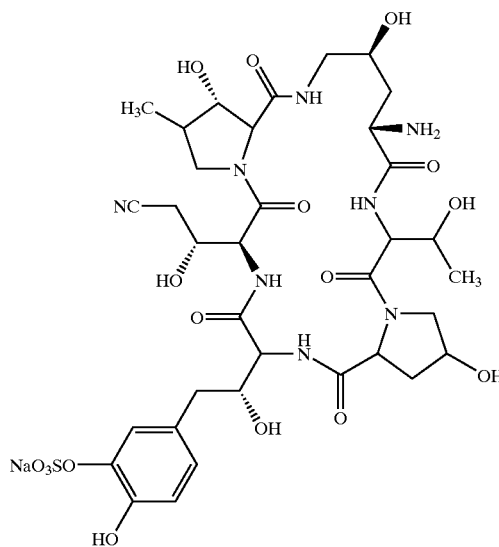 |
| | 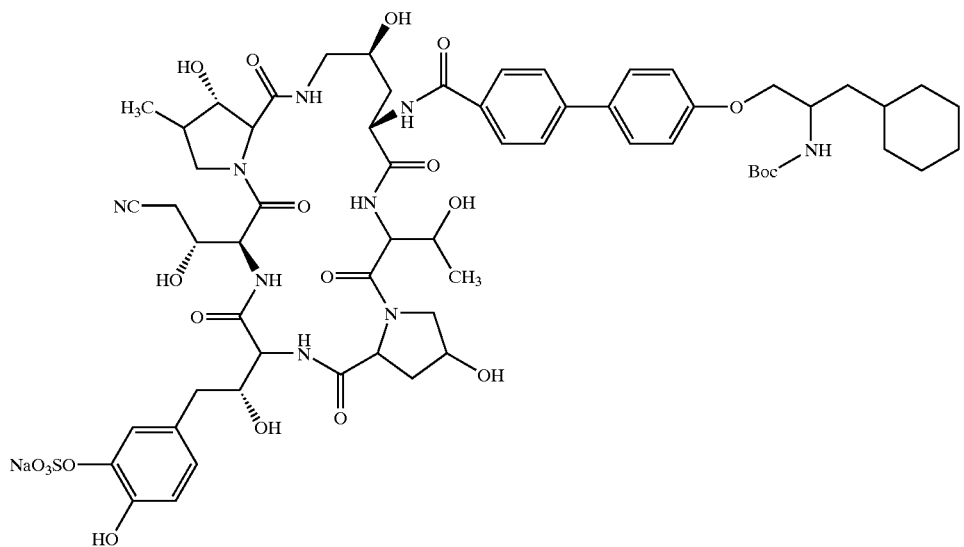 |

| Preparation No. | Formula |
|---|---|
| 298 | 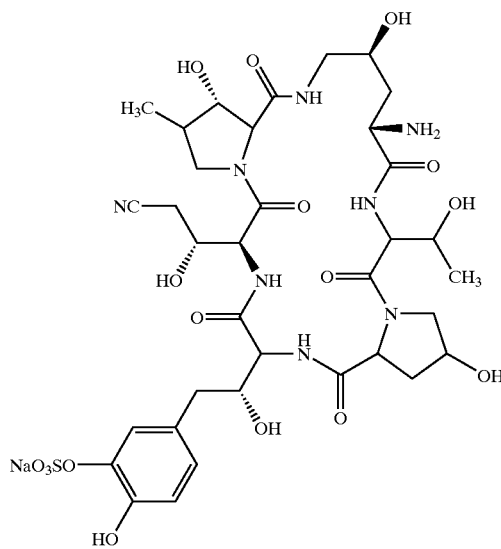 |
| | 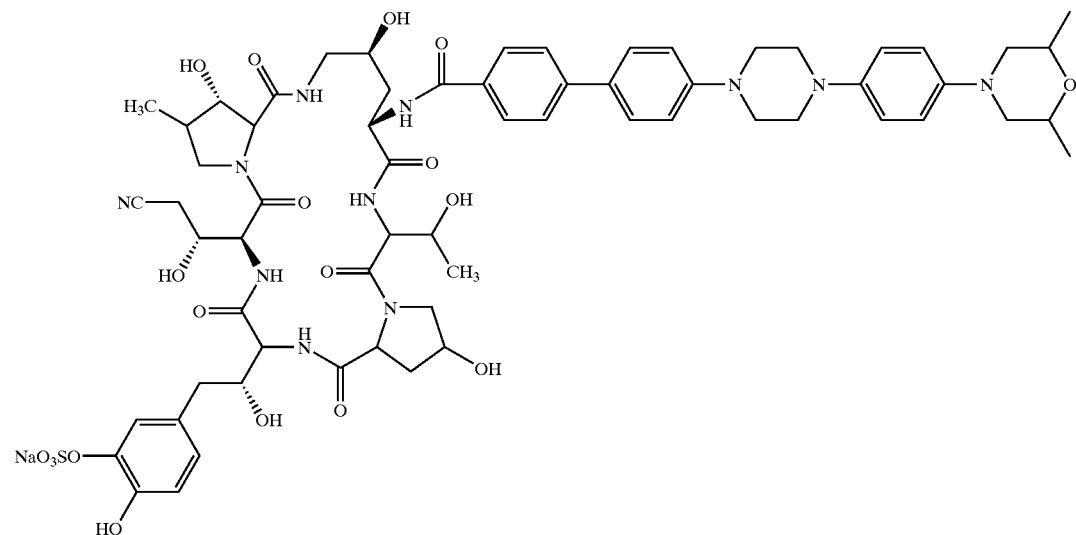 |

| Preparation No. | Formula |
|---|---|
| 299 | 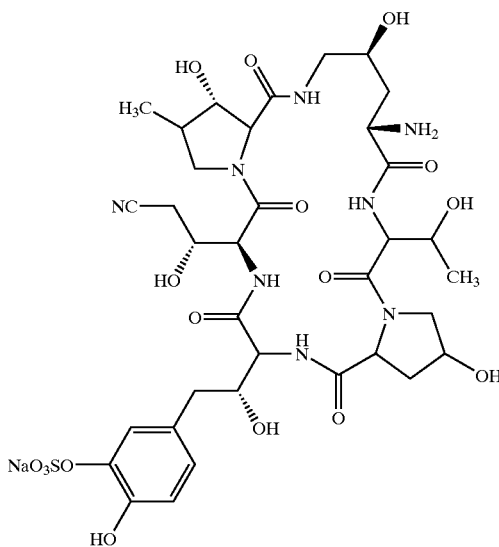 |
| | 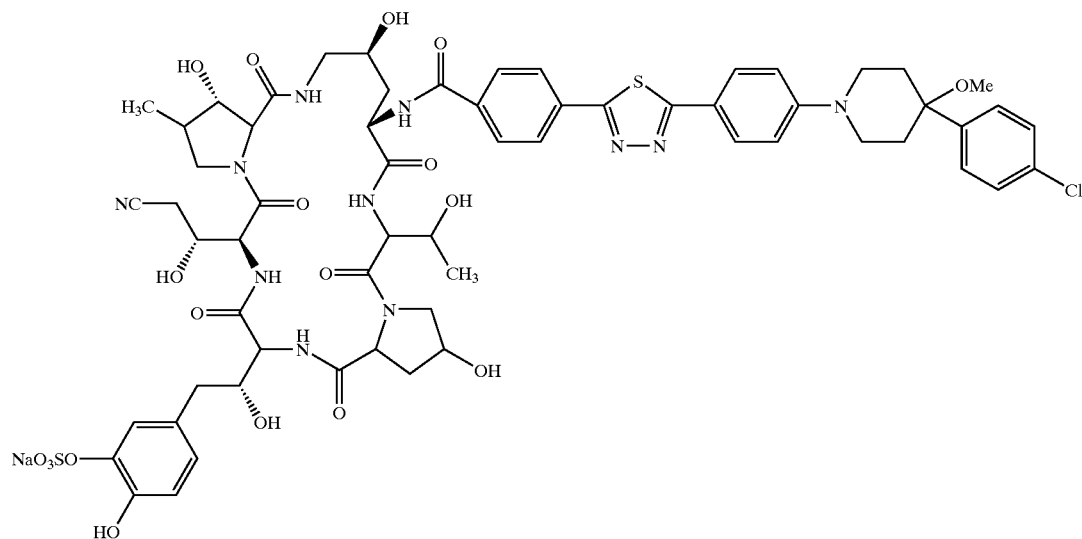 |

-continued
| Preparation No. | Formula |
|---|---|
| 300 | 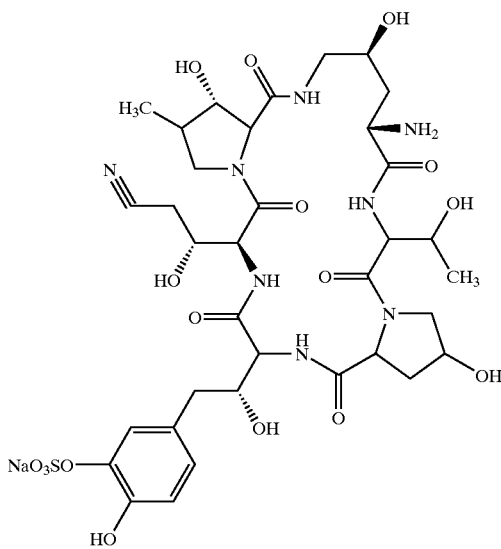 |
| | 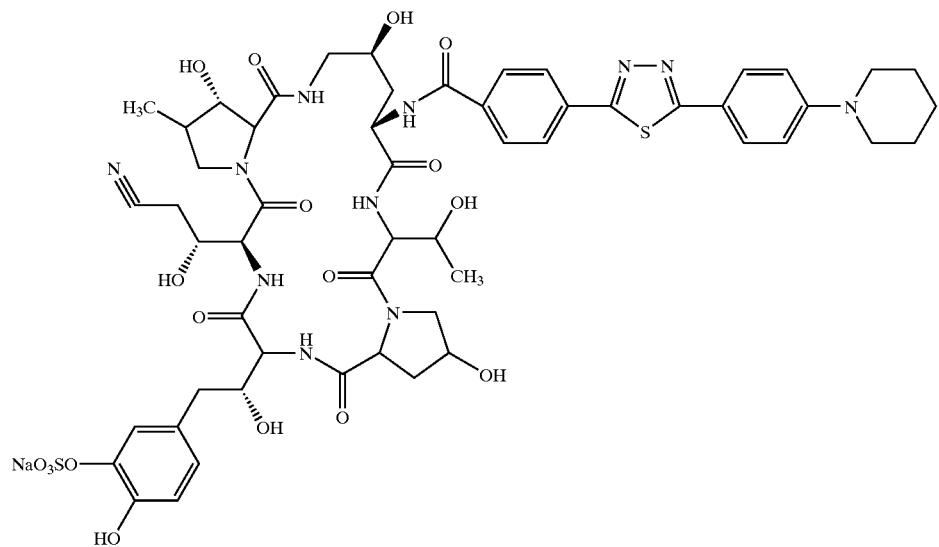 |

| Preparation No. | Formula |
|---|---|
| 301 | 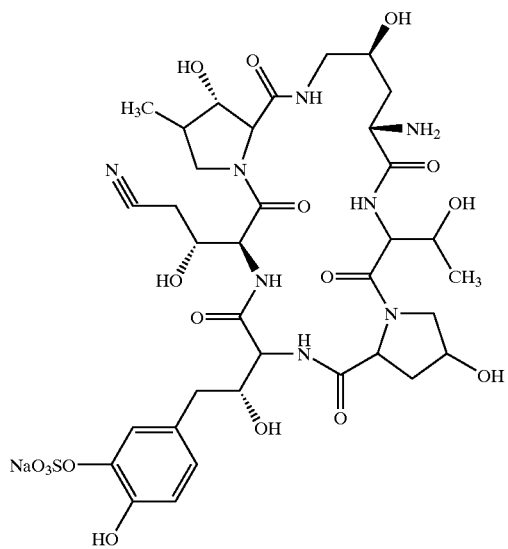 |
| | 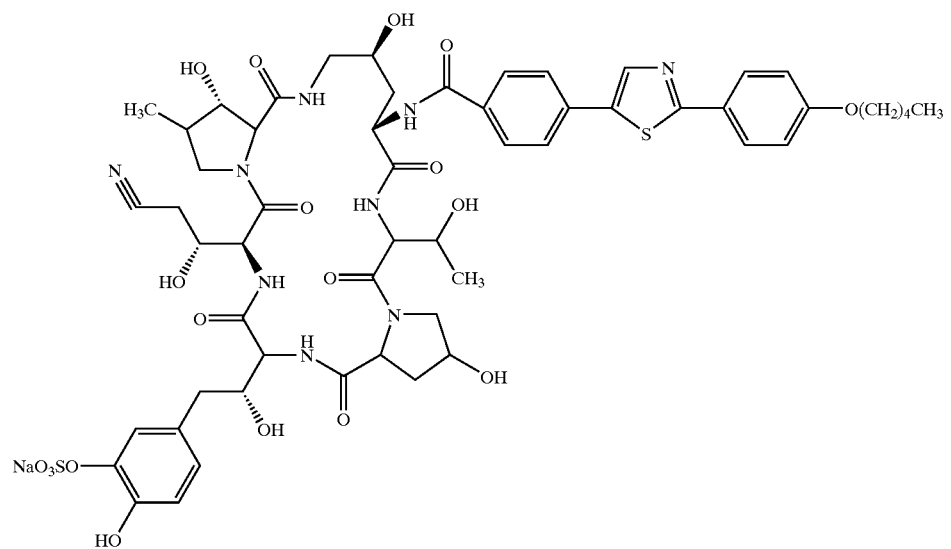 |

| Preparation No. | Formula |
|---|---|
| 302 | 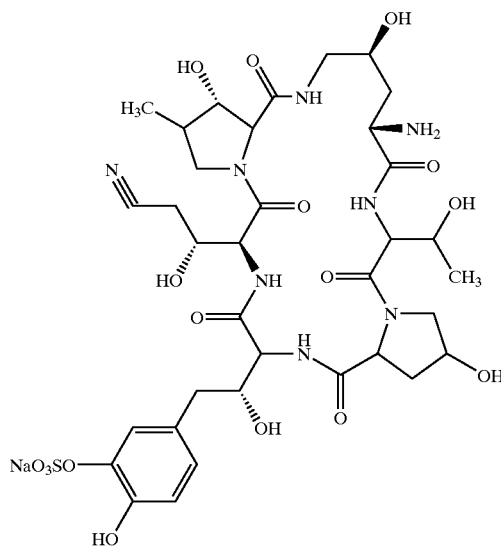 |
| | 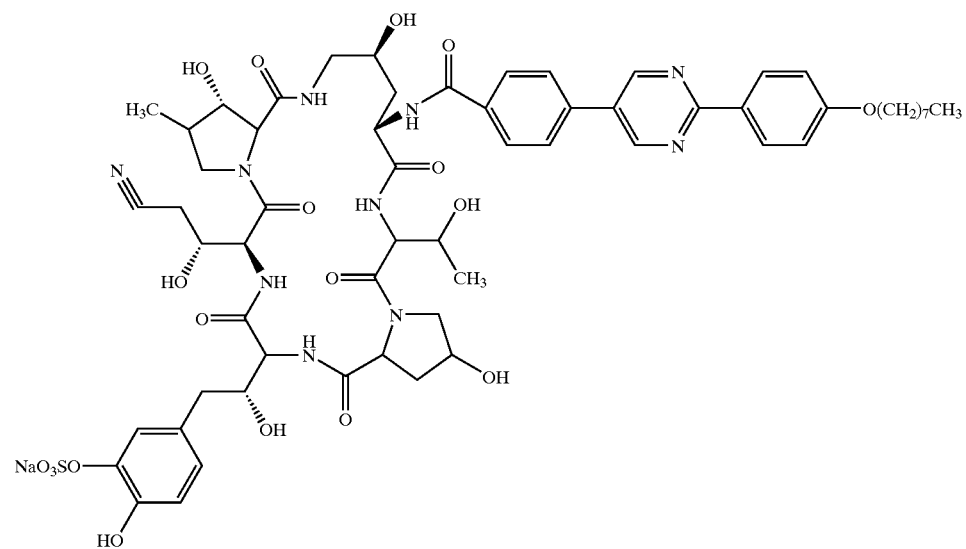 |

| Preparation No. | Formula |
|---|---|
| 303 | 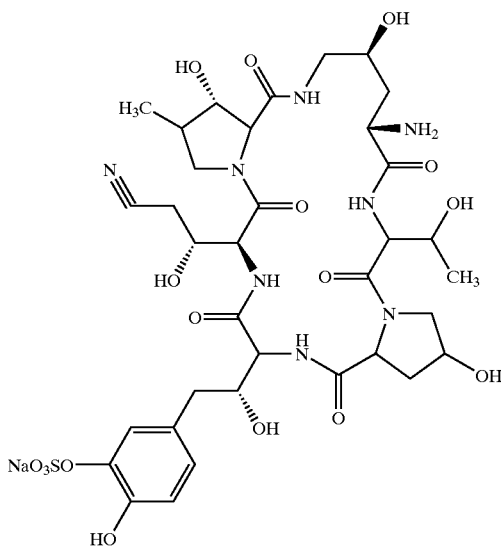 |
| | 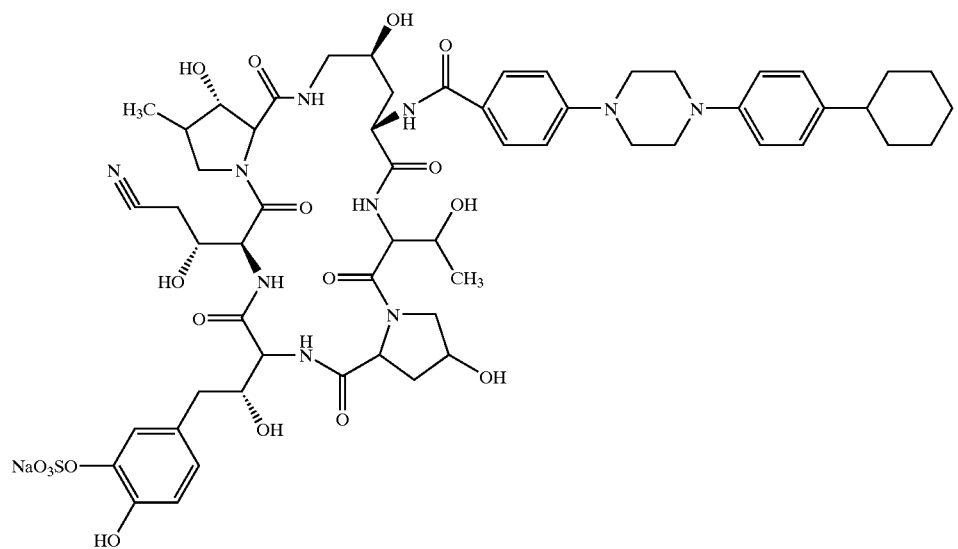 |

| Preparation No. | Formula |
|---|---|
| 304 | 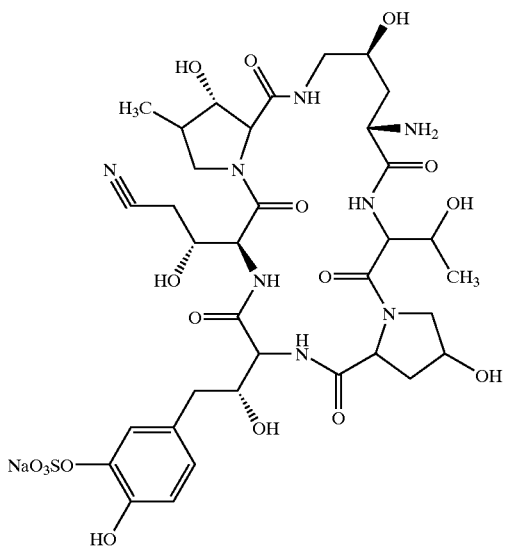 |
| | 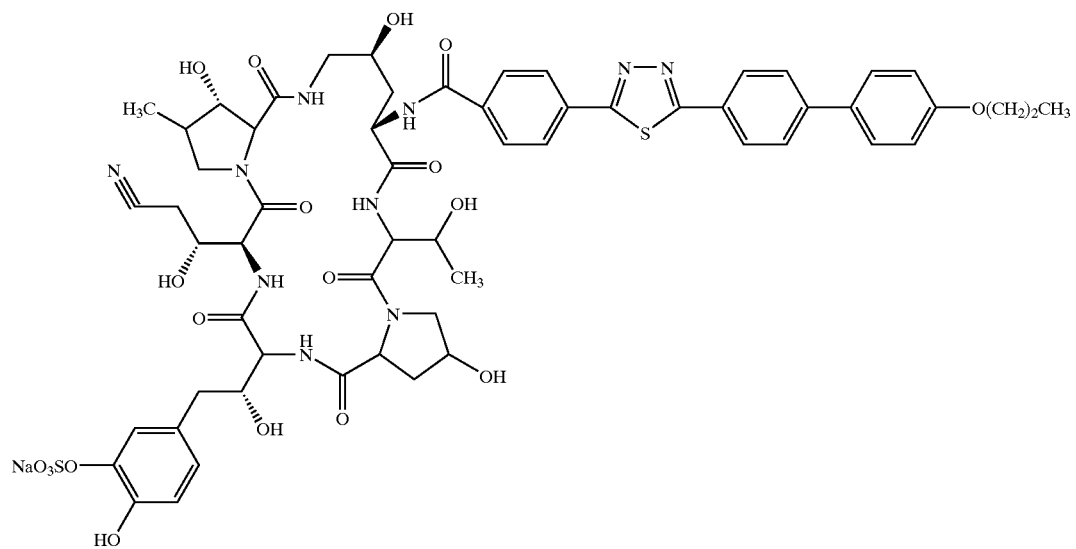 |

| Preparation No. | Formula |
|---|---|
| 305 | 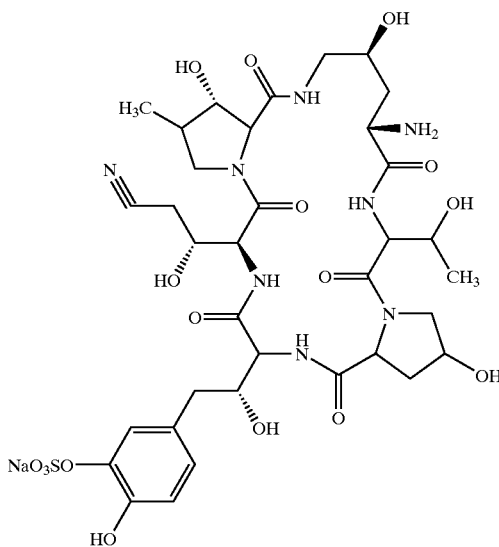 |
| | 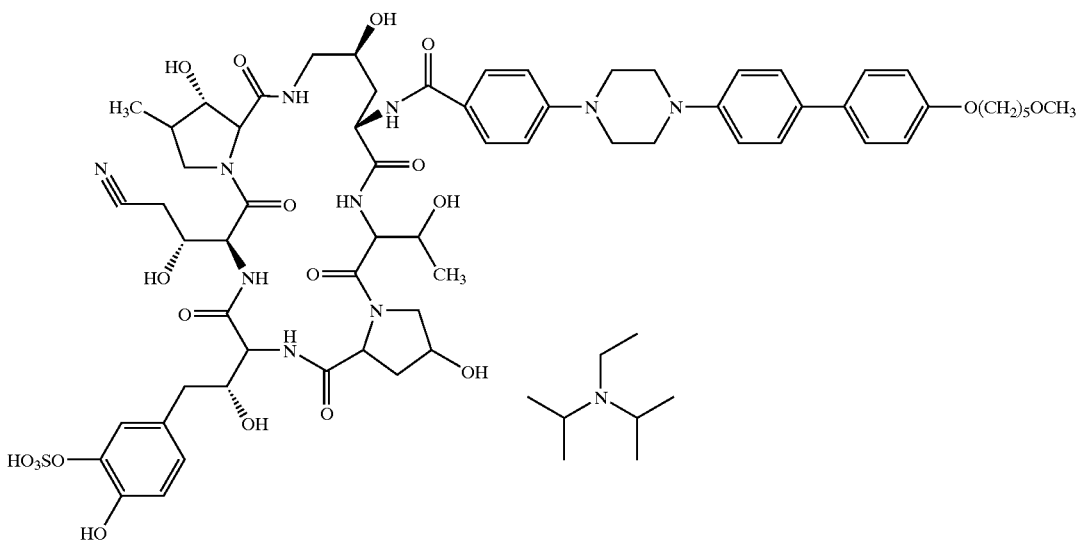 |

| Preparation No. | Formula |
|---|---|
| 306 | 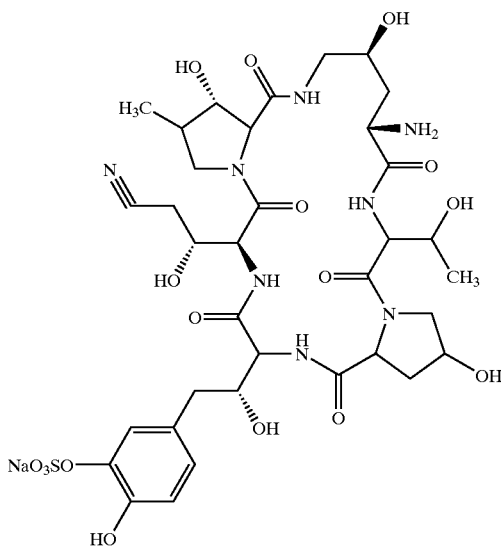 |
| | 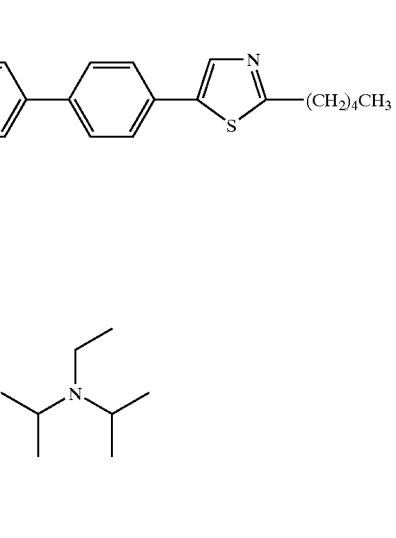 |

| Preparation No. | Formula |
|---|---|
| 307 | 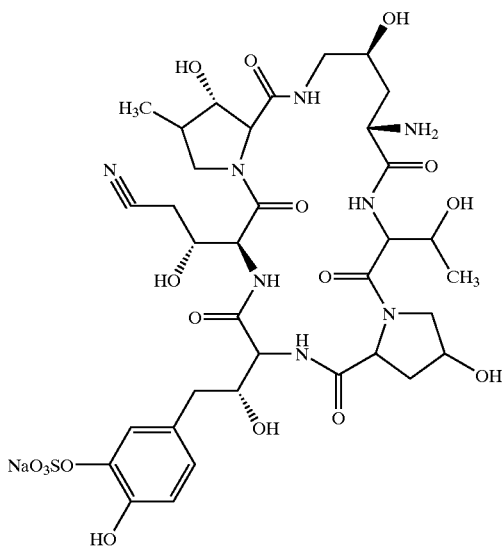 |
| | 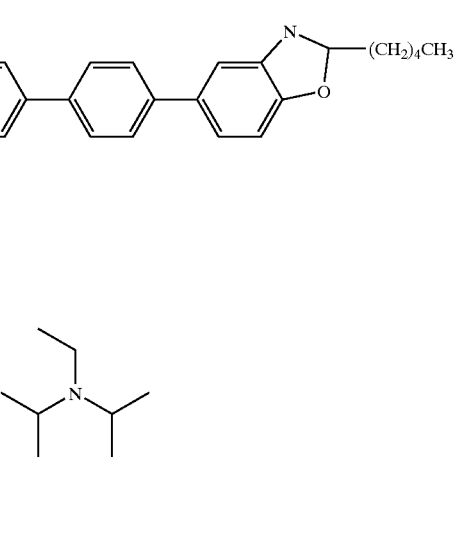 |

| Preparation No. | Formula |
|---|---|
| 308 | 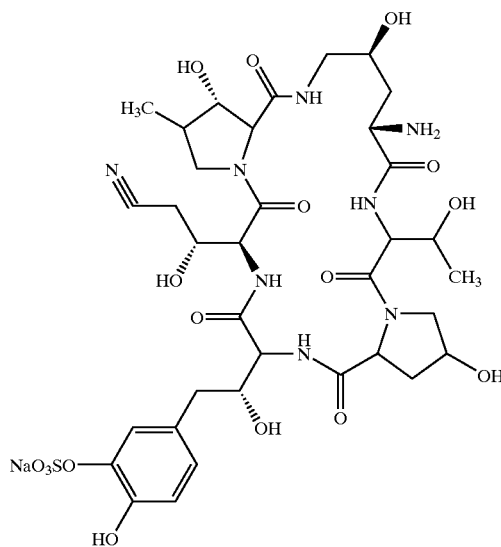 |
| | 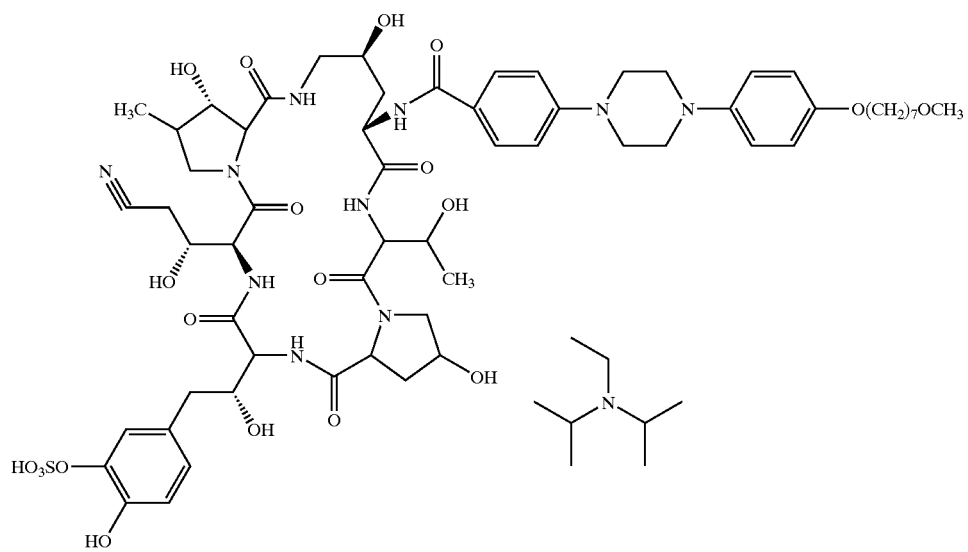 |

-continued
| Preparation No. | Formula |
|---|---|
| 309 | 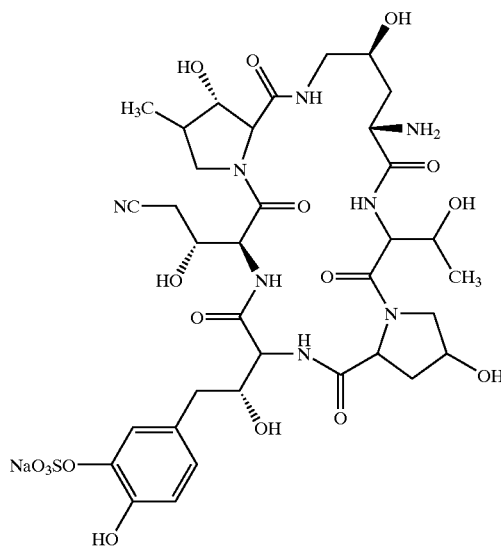 |
| | 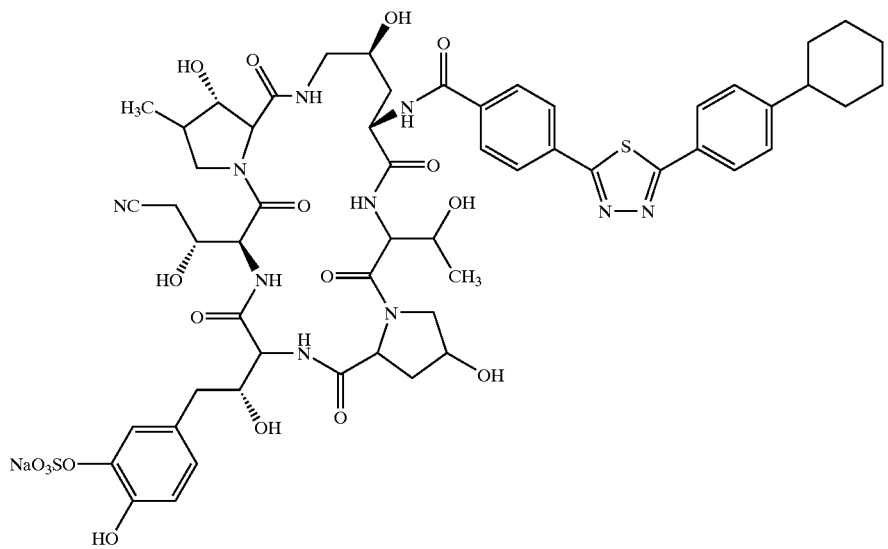 |

| Preparation No. | Formula |
|---|---|
| 310 | 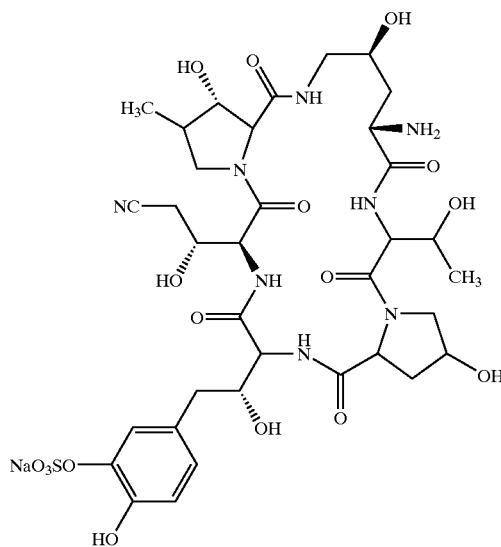 |
| | 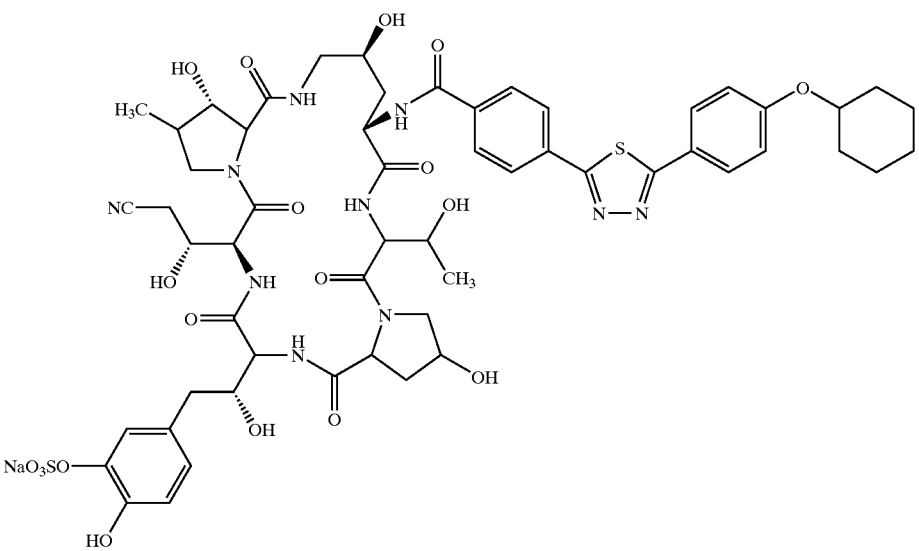 |

-continued
| Preparation No. | Formula |
|---|---|
| 311 | 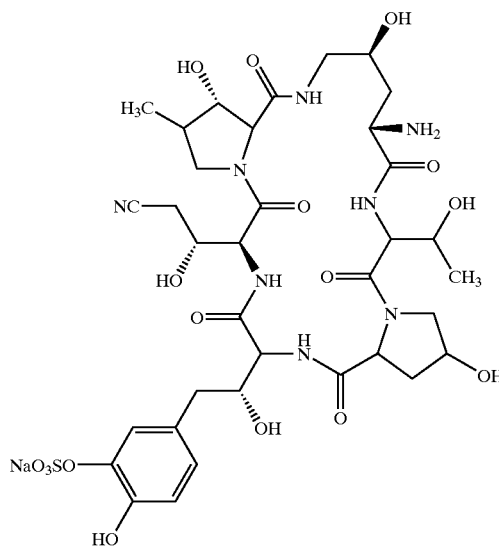 |
| | 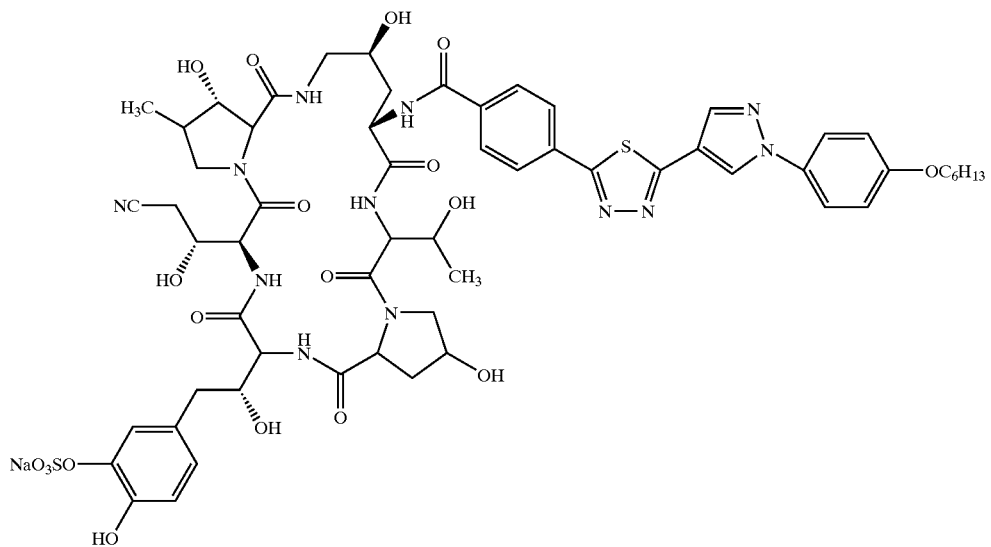 |

| Preparation No. | Formula |
|---|---|
| 312 | 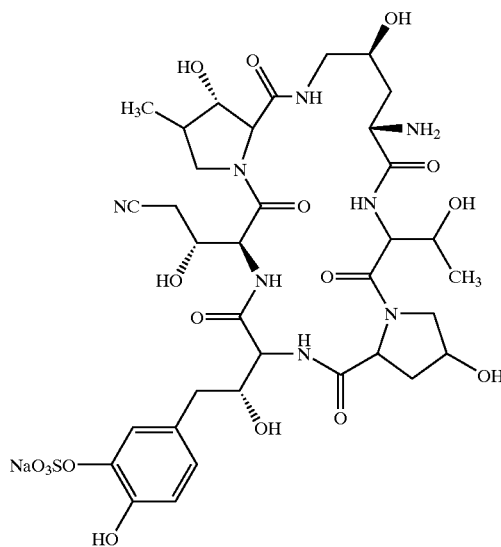 |
| | 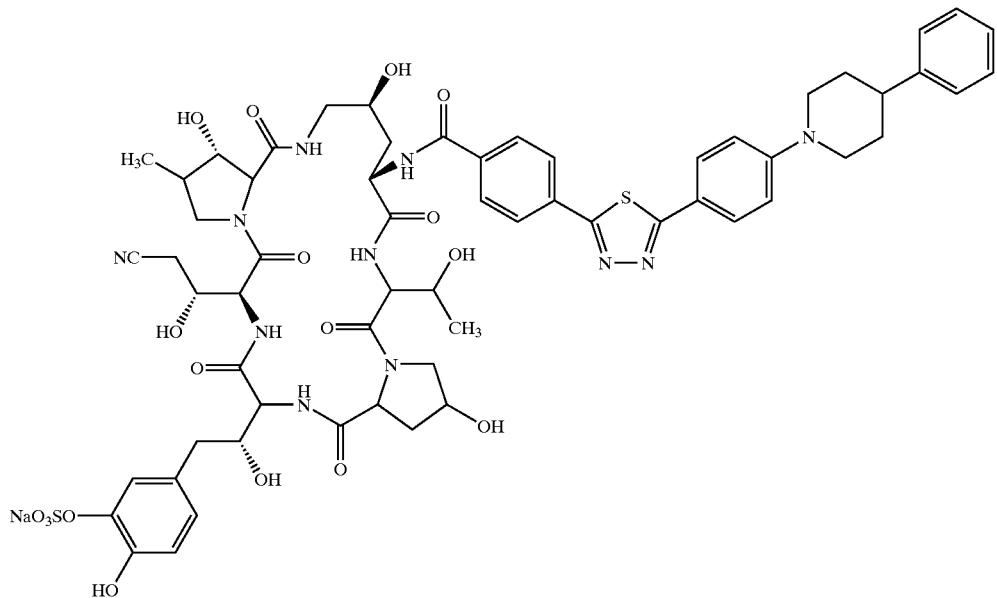 |

-continued
| Preparation No. | Formula |
|---|---|
| 313 | 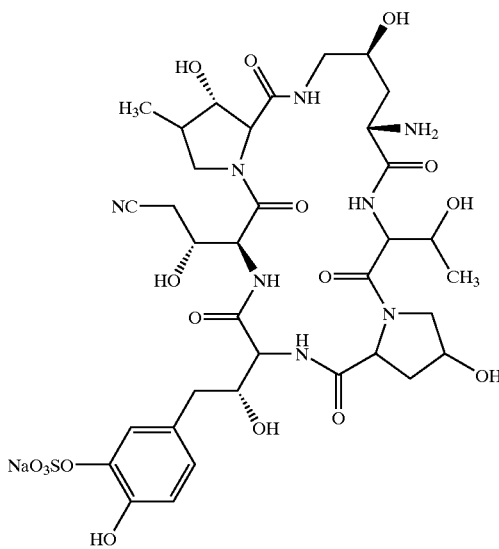 |
| | 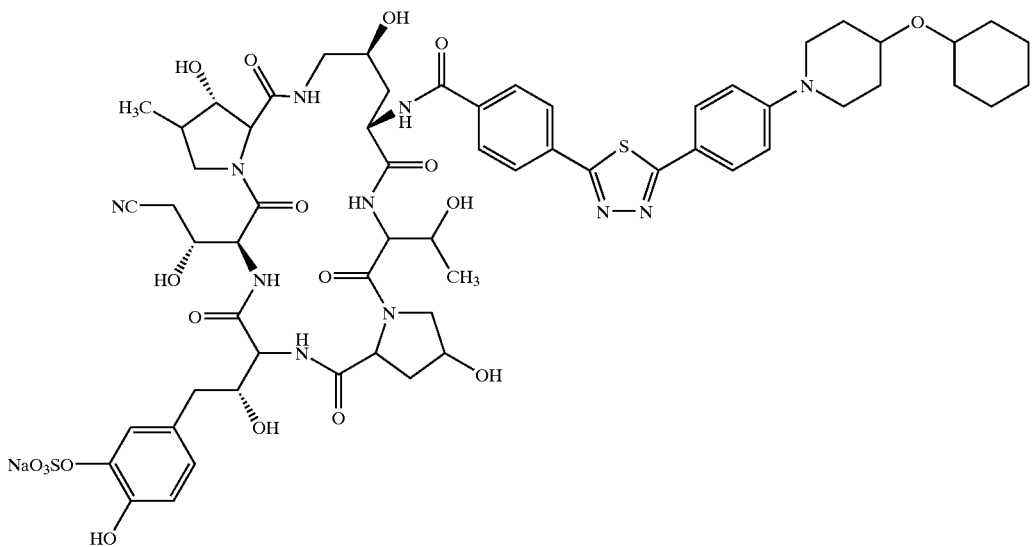 |

-continued
| Preparation No. | Formula |
|---|---|
| 314 | 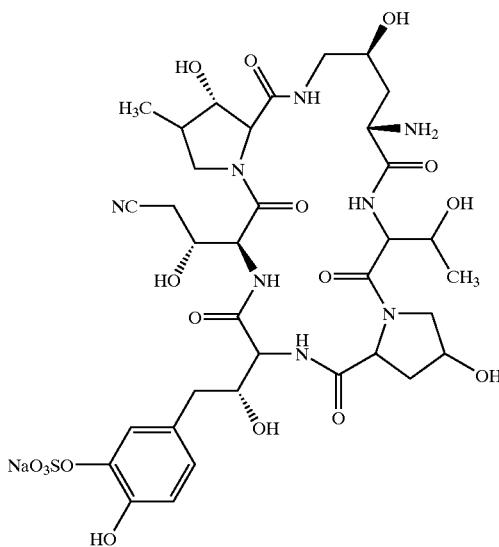 |
| | 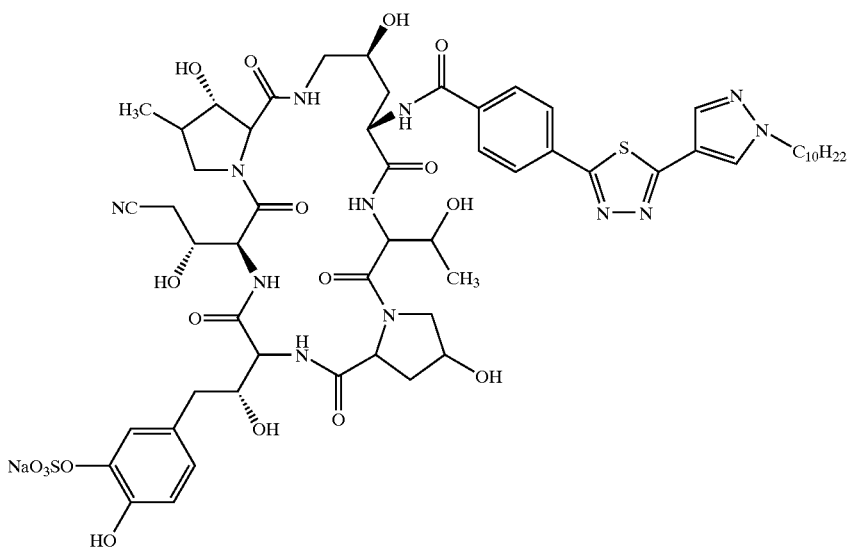 |

-continued
| Preparation No. | Formula |
|---|---|
| 315 | 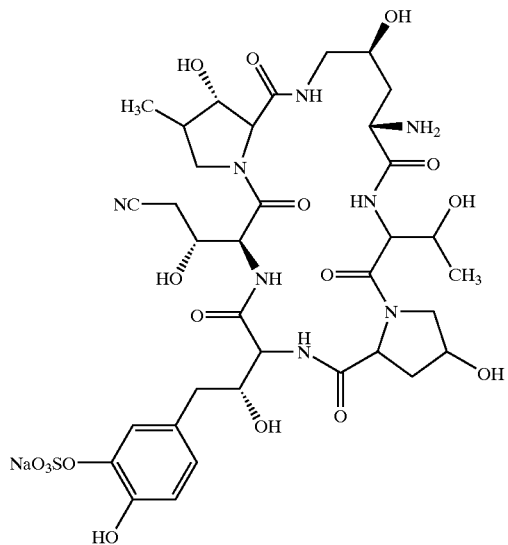 |
| | 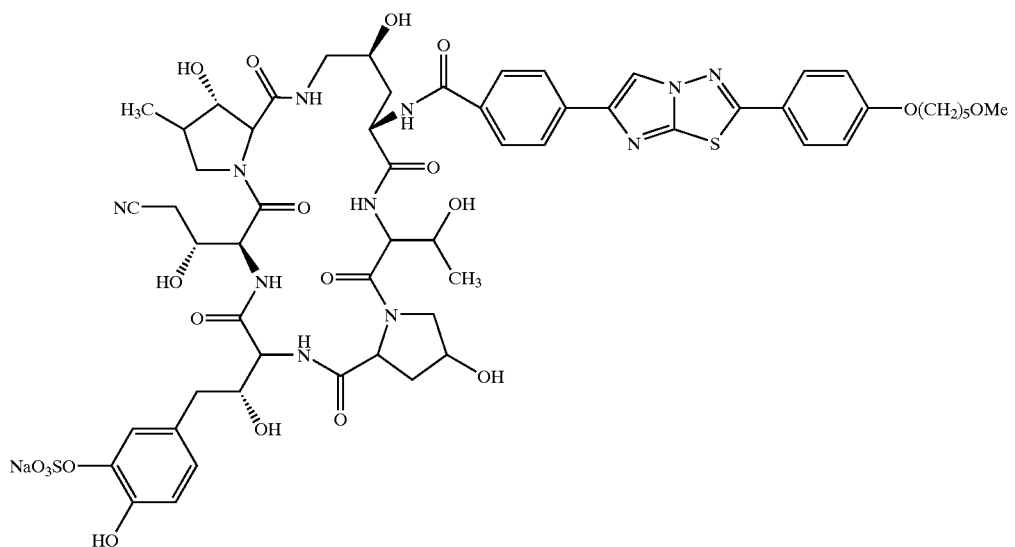 |

-continued
| Preparation No. | Formula |
|---|---|
| 316 | 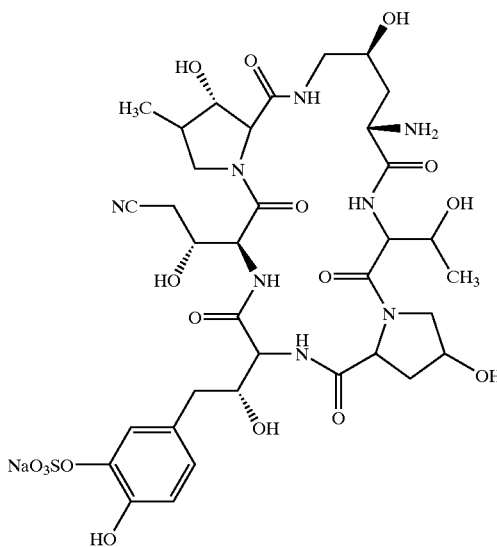 |
| | 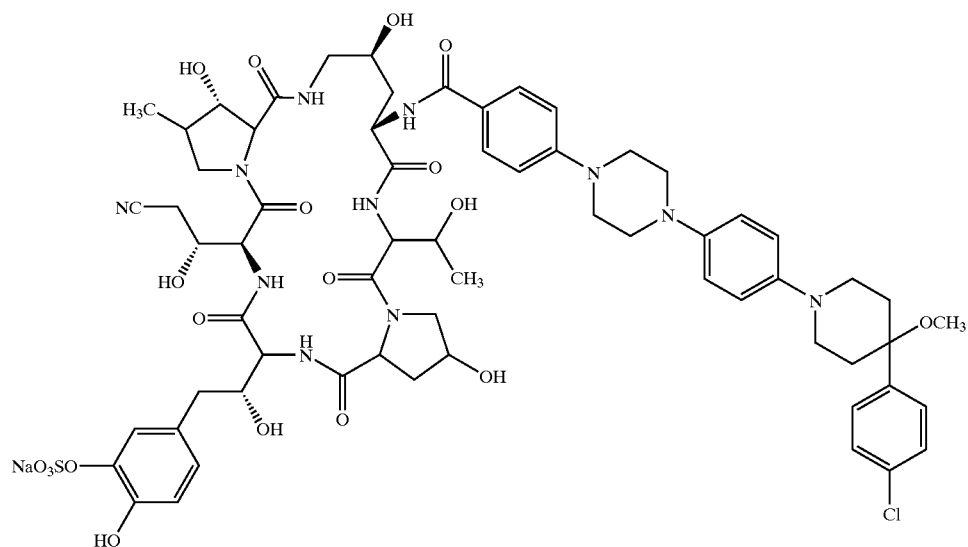 |

| Preparation No. | Formula |
|---|---|
| 317 | 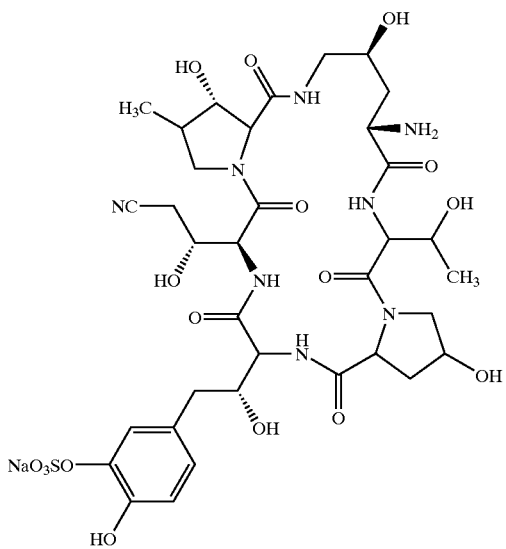 |
| | 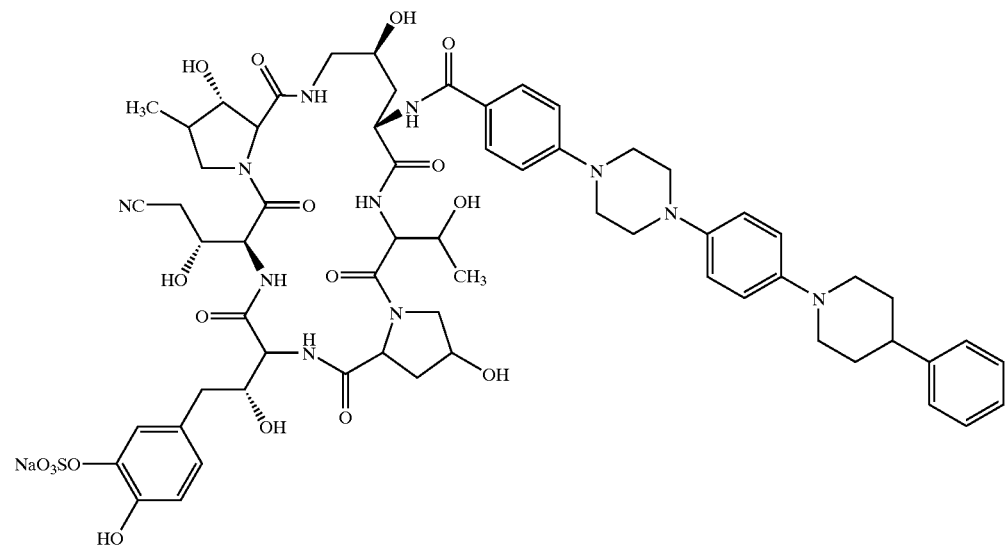 |

| Preparation No. | Formula |
|---|---|
| 318 | 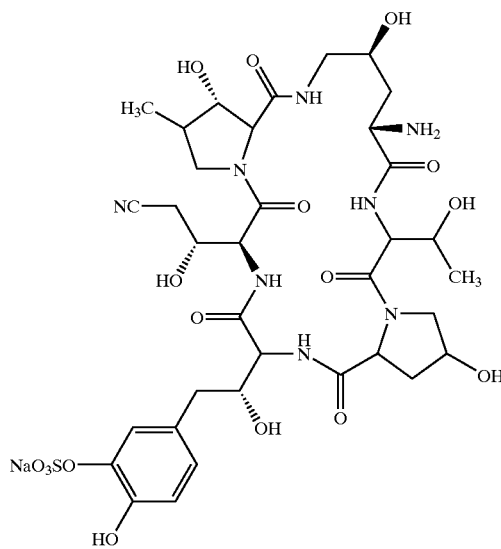 |
| | 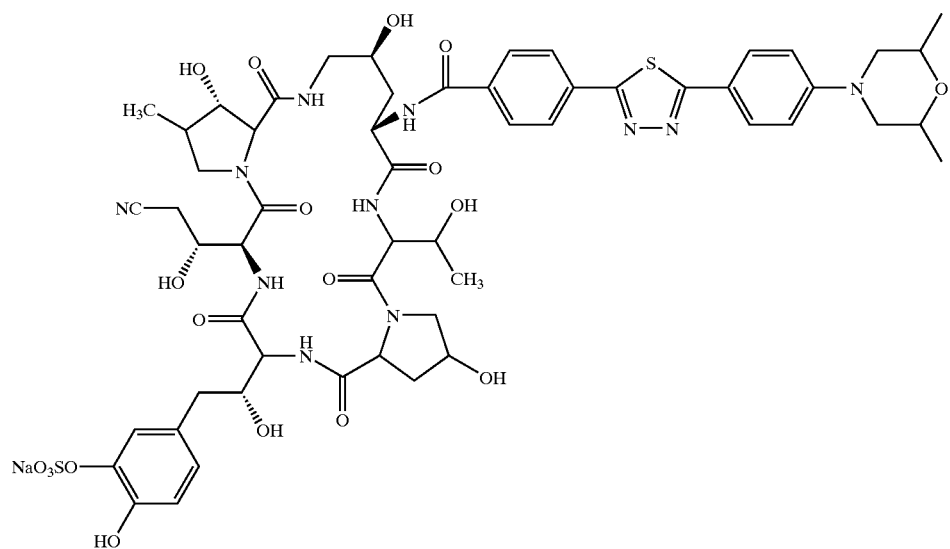 |

-continued
| Preparation No. | Formula |
|---|---|
| 319 | 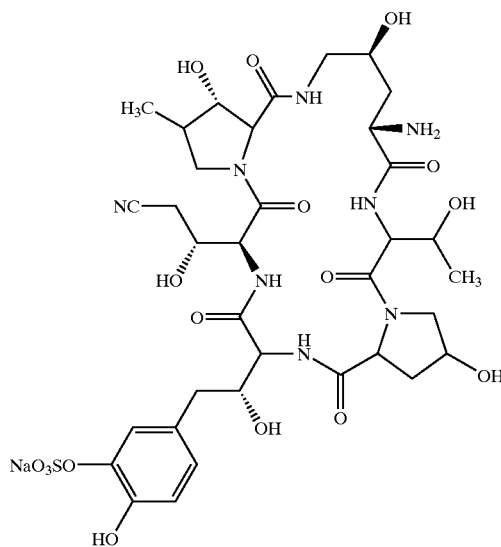 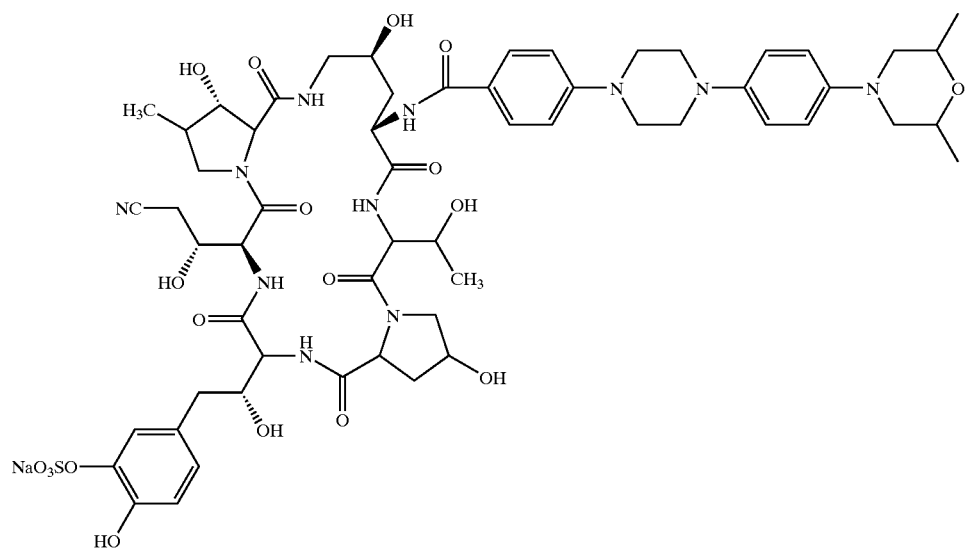 |

-continued
| Preparation No. | Formula |
|---|---|
| 320 | 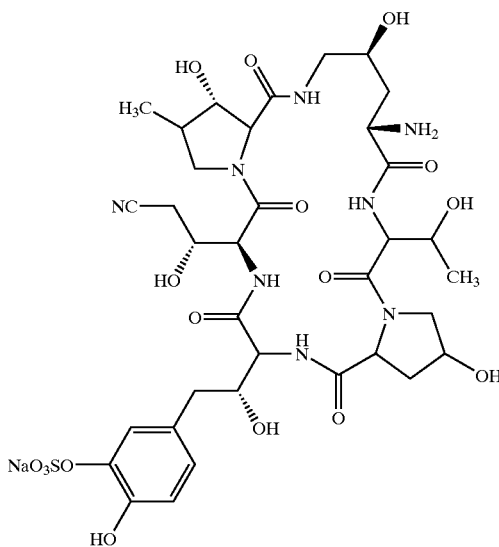 |
| | 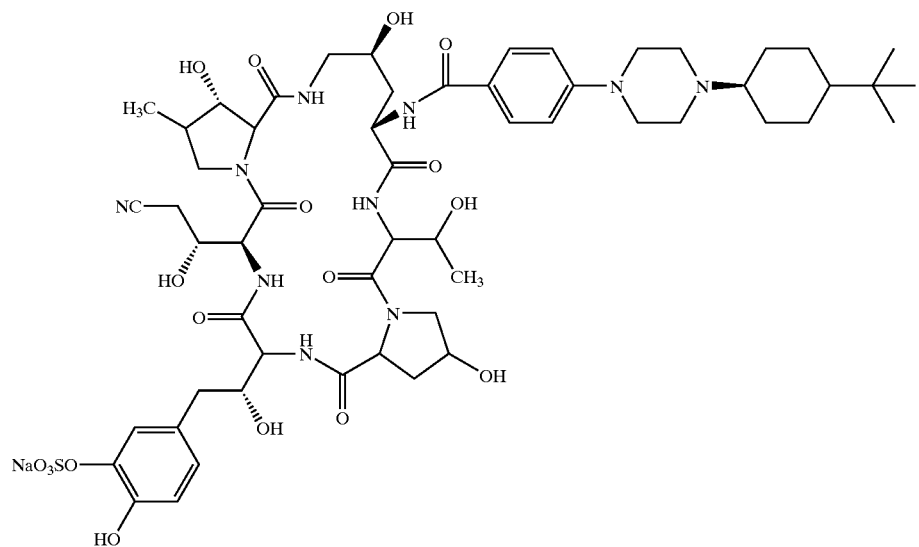 |

| Preparation No. | Formula |
|---|---|
| 321 | 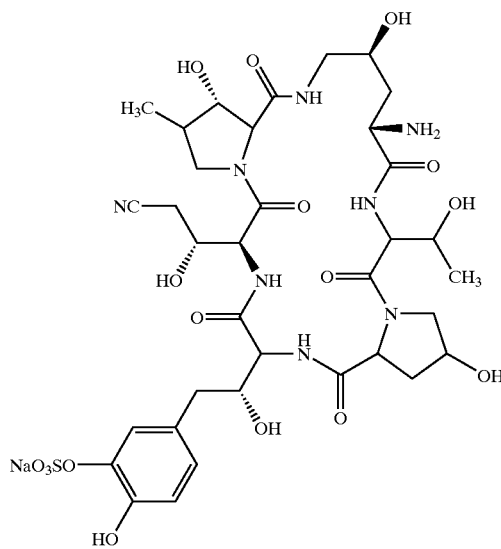 |
| | 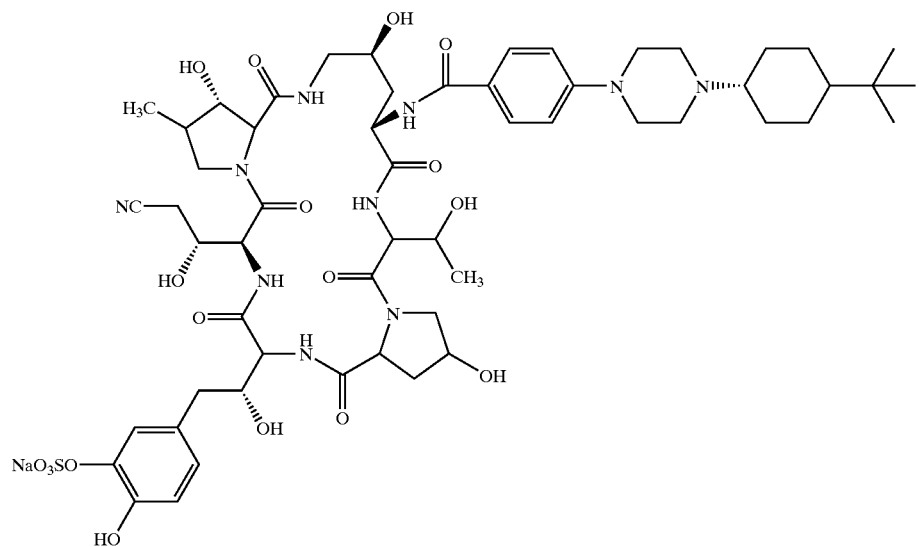 |

-continued
| Preparation No. | Formula |
|---|---|
| 322 | 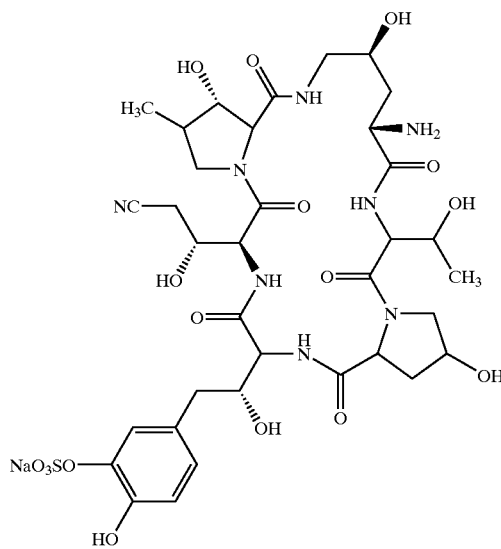 |
| | 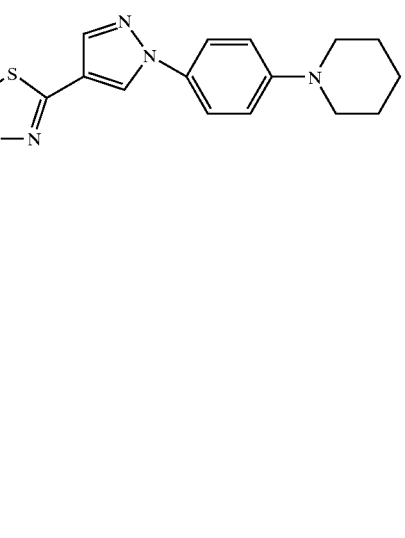 |

| Preparation No. | Formula |
|---|---|
| 323 | 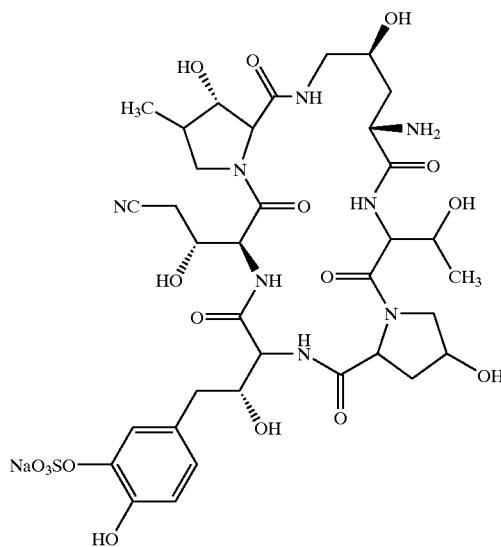 |
| | 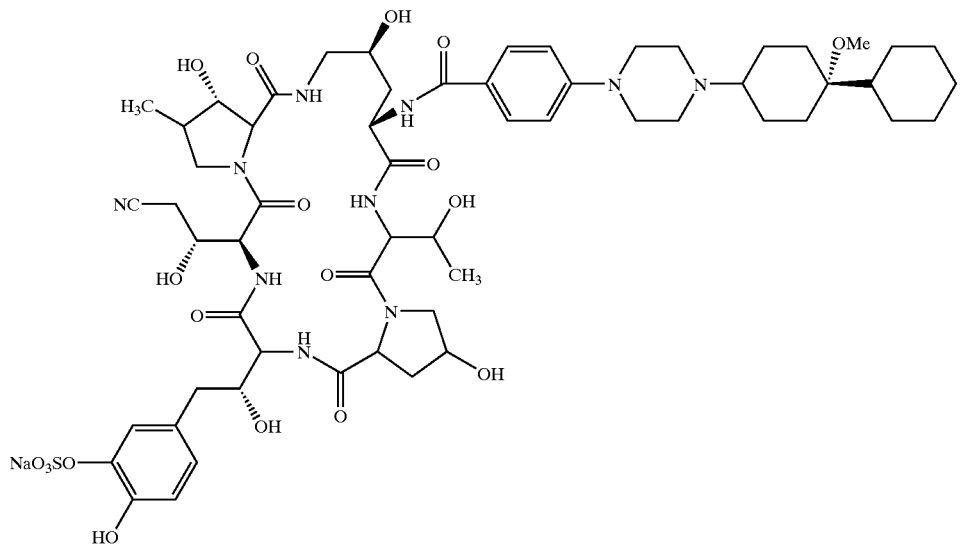 |

-continued
| Preparation No. | Formula |
|---|---|
| 324 | 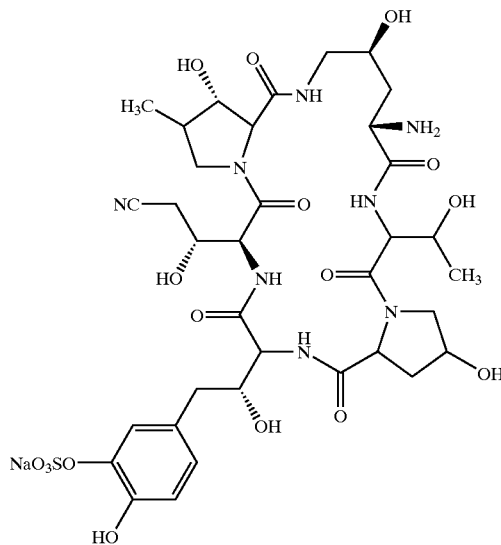 |
| | 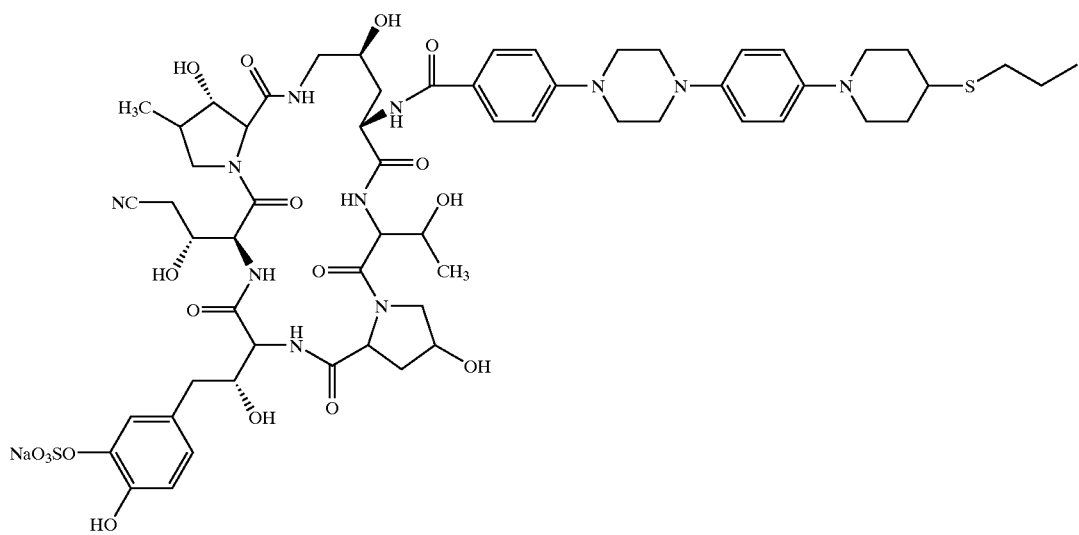 |

| Preparation No. | Formula |
|---|---|
| 325 | 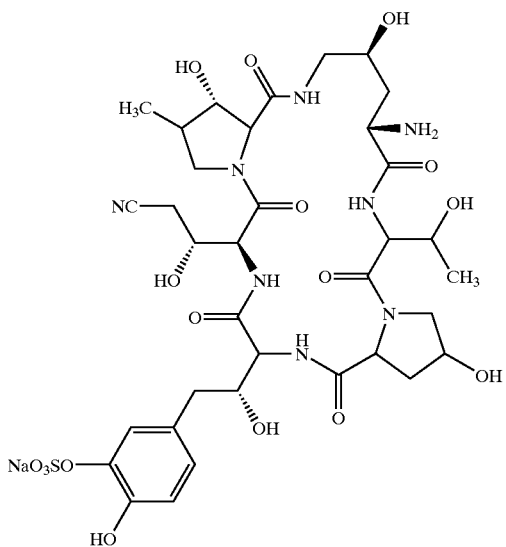 |
| | 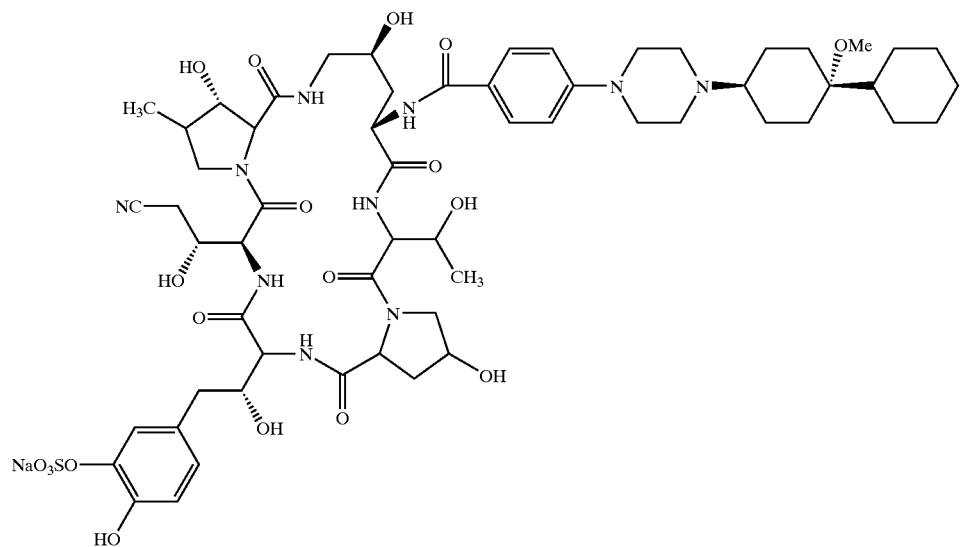 |

-continued
| Preparation No. | Formula |
|---|---|
| 326 | 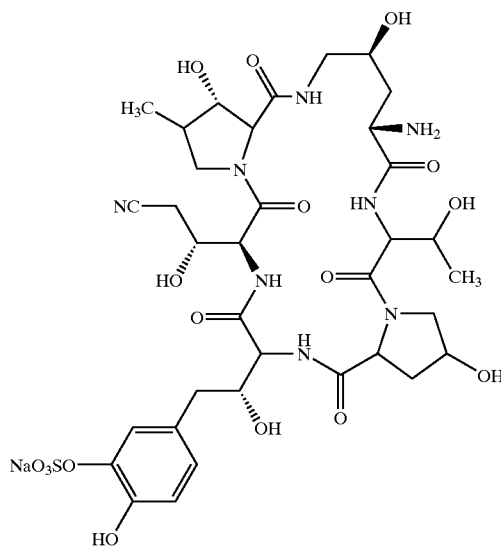 |
| | 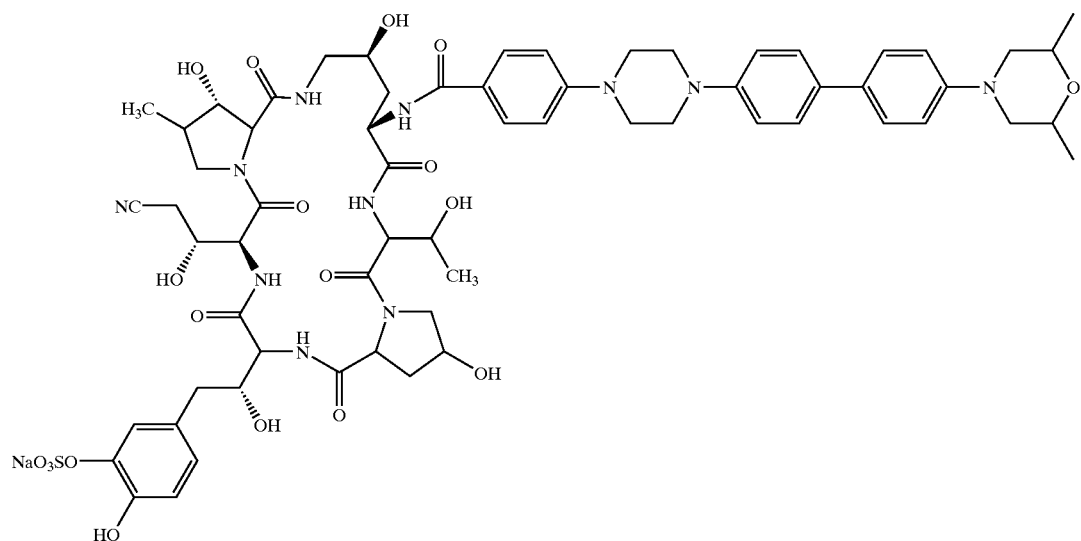 |

-continued
| Preparation No. | Formula |
|---|---|
| 327 | 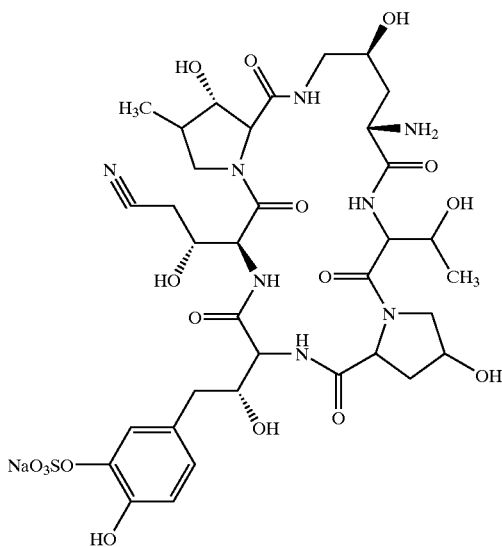 |
| | 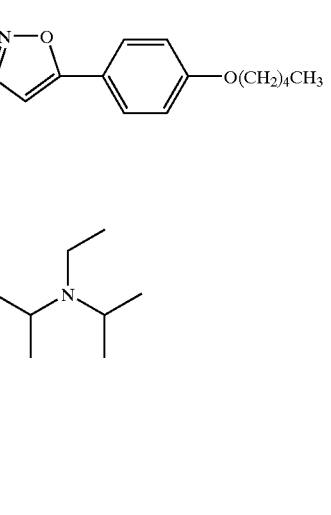 |

-continued
| Preparation No. | Formula |
|---|---|
| 328 | 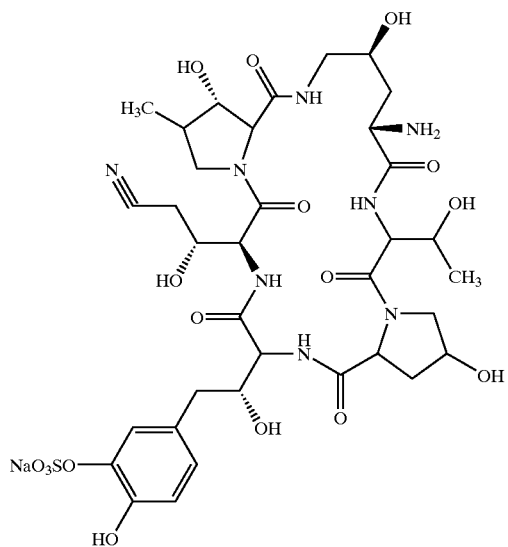 |
| | 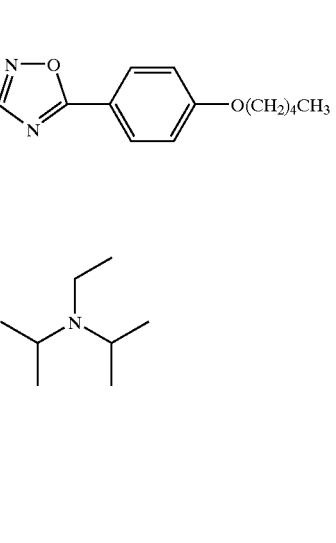 |

-continued
| Preparation No. | Formula |
|---|---|
| 329 | 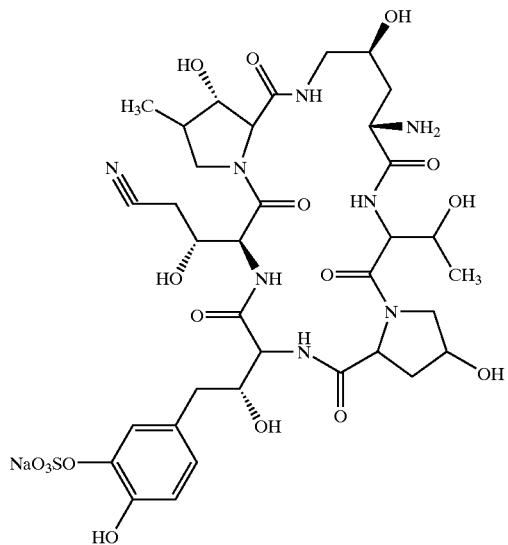 |
| | 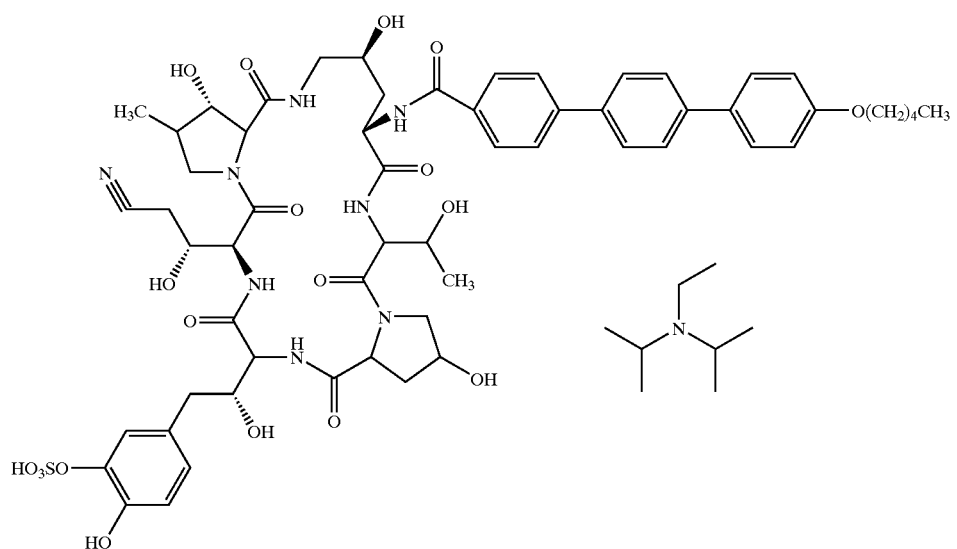 |

| Preparation No. | Formula |
|---|---|
| 330 | 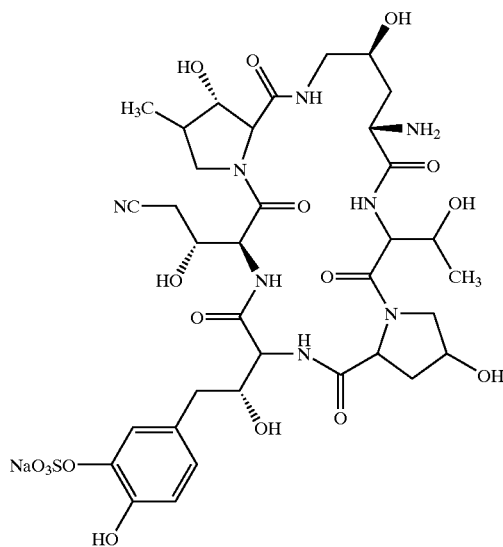 |
| | 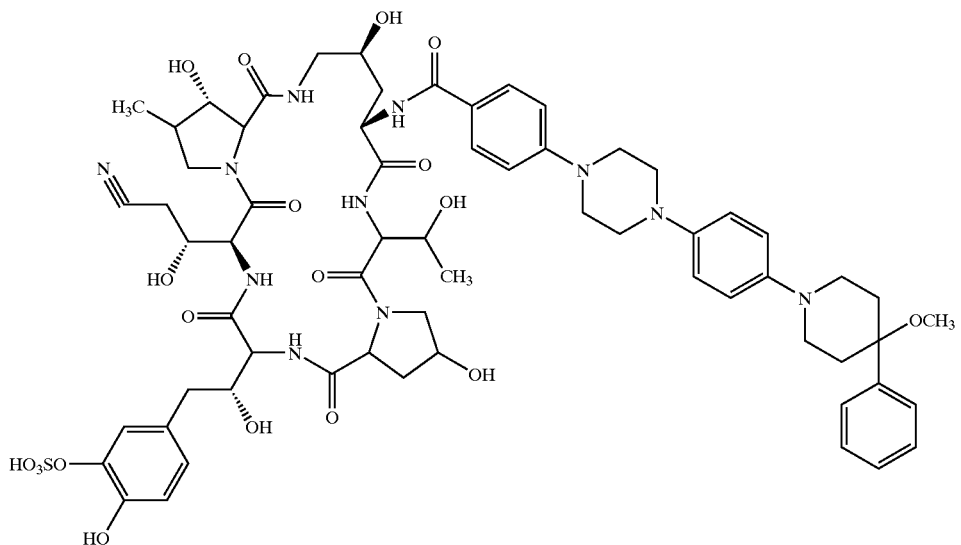 |

| Preparation No. | Formula |
|---|---|
| 331 | 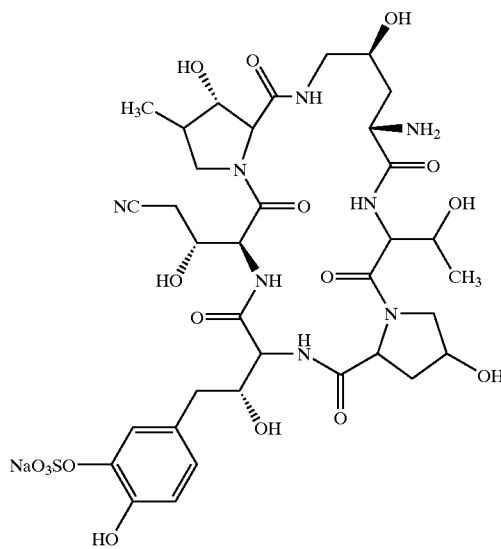 |
| | 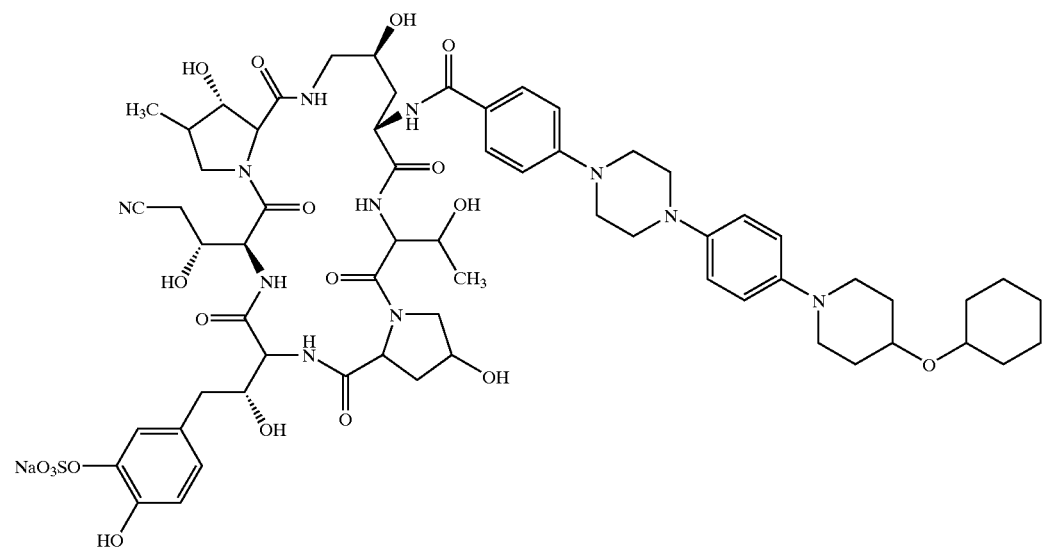 |

| Preparation No. | Formula |
|---|---|
| 332 | 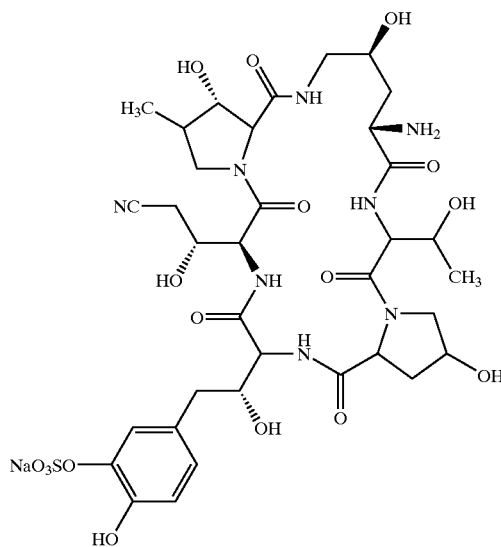 |
| | 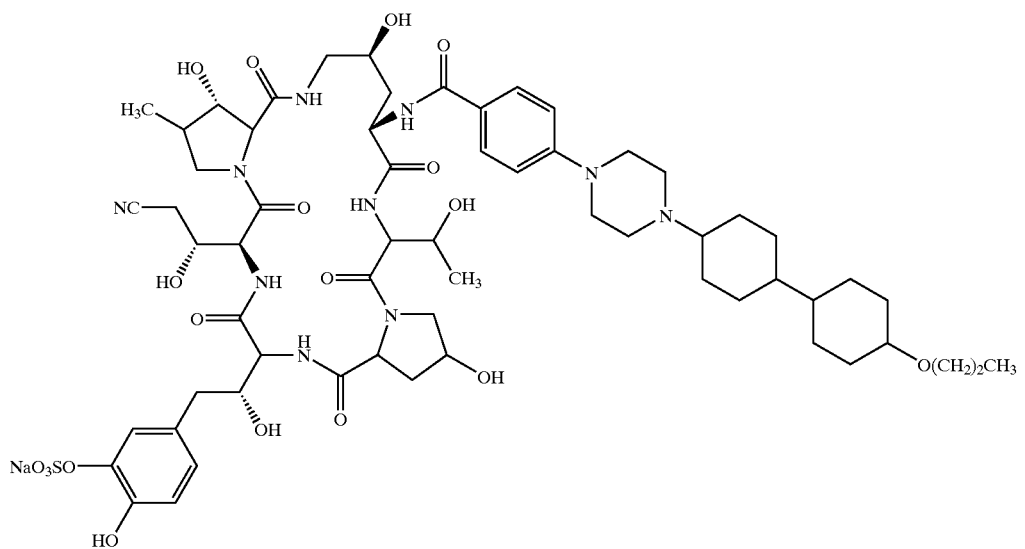 |

| Preparation No. | Formula |
|---|---|
| 333 | 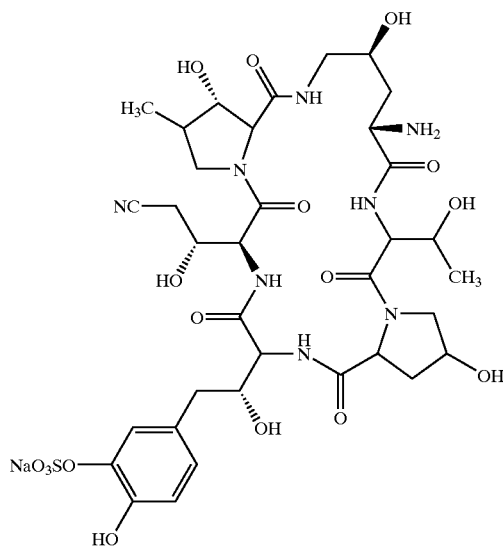 |
| | 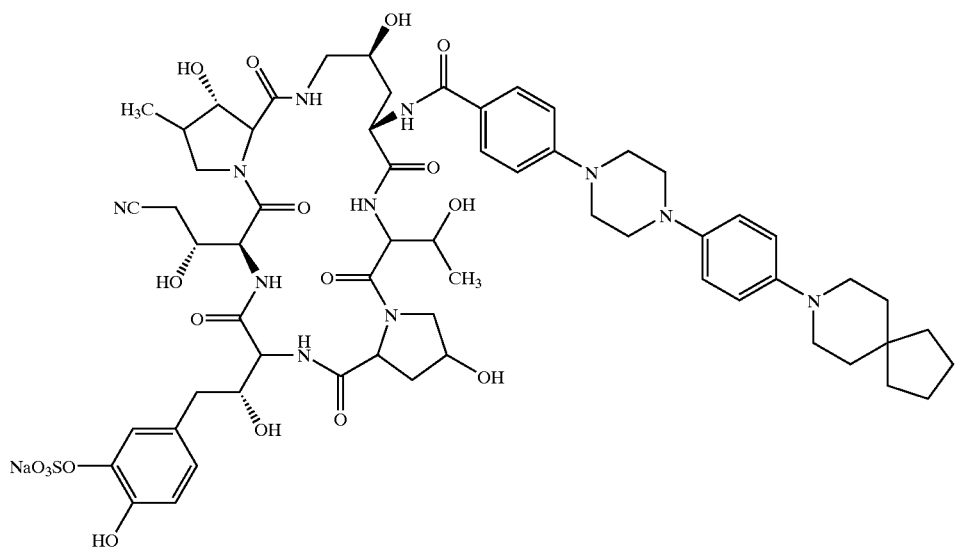 |

| Preparation No. | Formula |
|---|---|
| 334 | 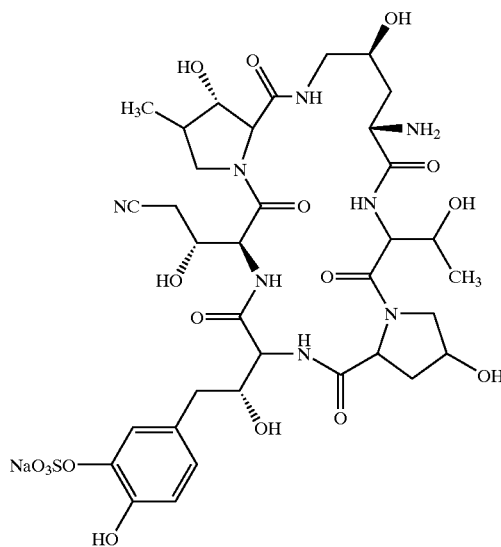 |
| | 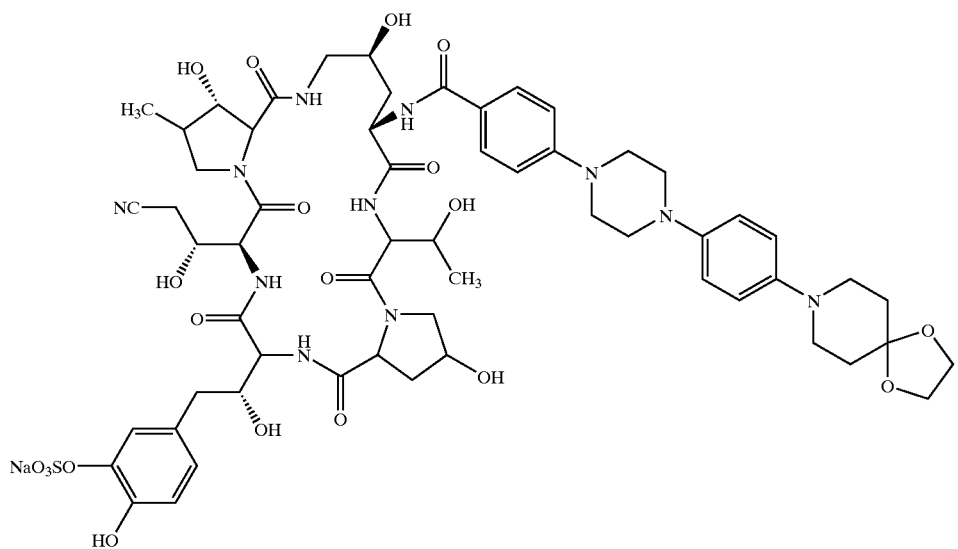 |

| Preparation No. | Formula |
|---|---|
| 335 | 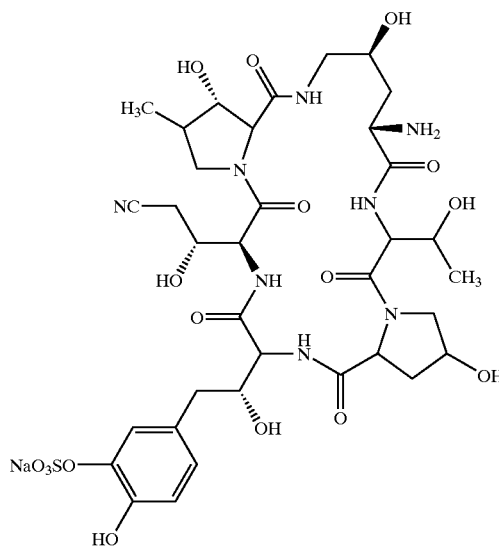 |
| | 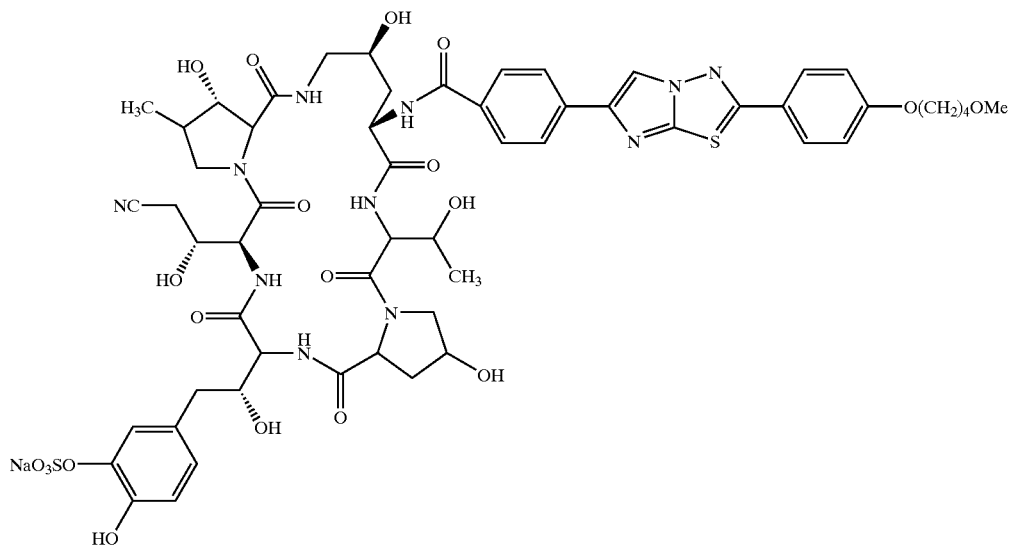 |

| Preparation No. | Formula |
|---|---|
| 336 | 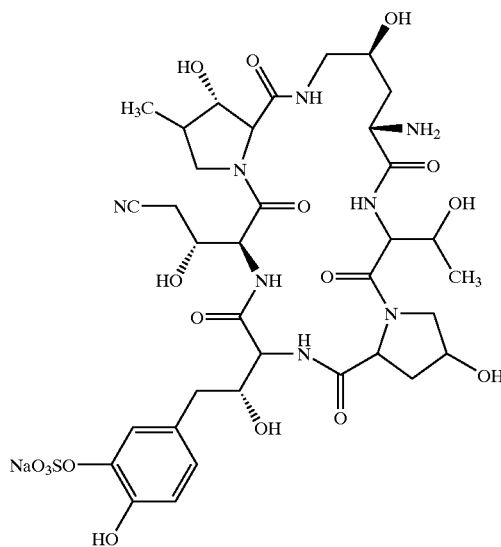 |
| | 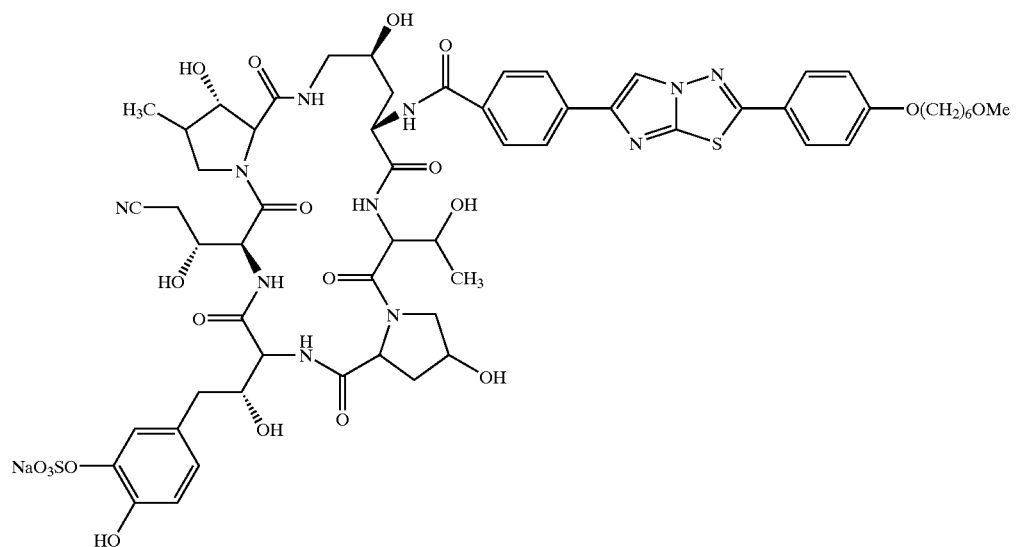 |

-continued
| Preparation No. | Formula |
|---|---|
| 337 | 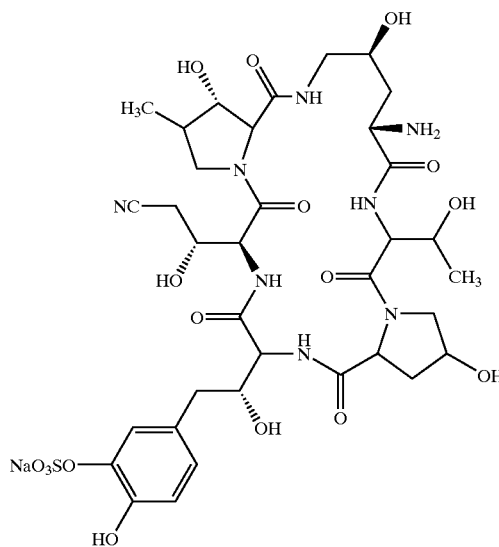 |
| | 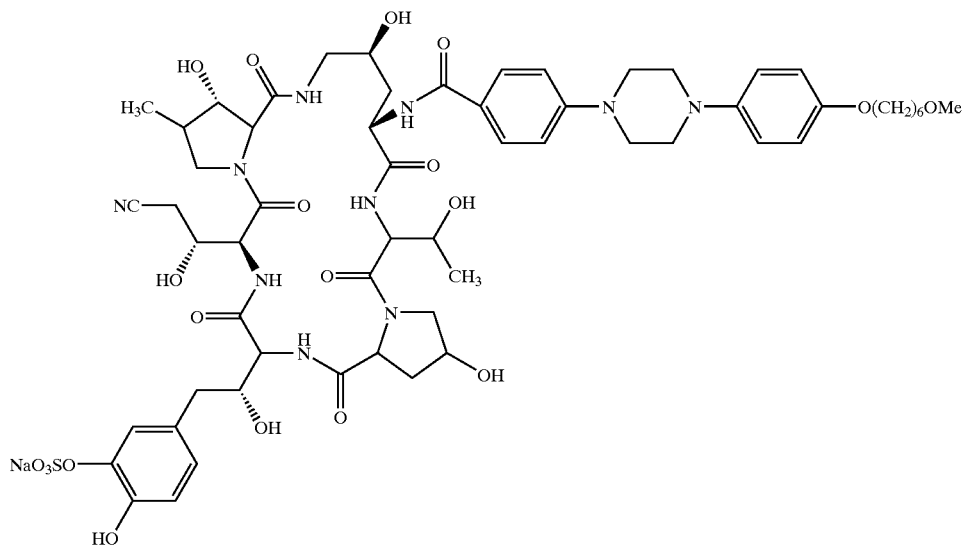 |

| Preparation No. | Formula |
|---|---|
| 338 | 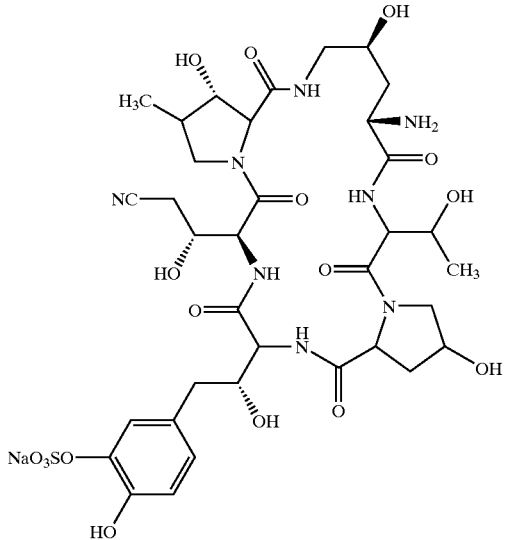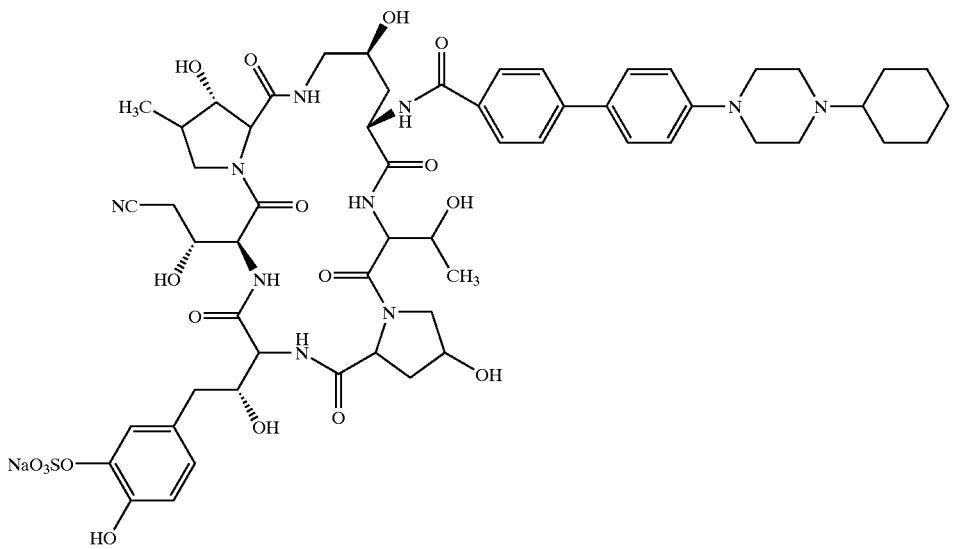 |

The following compounds [Preparations 291 to 338] were obtained according to a similar manner to that of Preparation 10.

PREPARATION 291

MASS (m/z): 1283.3 (M$^+$–Na).

PREPARATION 292

MASS (m/z): 1338.3 (M$^+$–Na).

PREPARATION 293

MASS (m/z): 1313.2 (M$^+$–Na).

PREPARATION 294

MASS (m/z): 1329.3 (M$^+$–Na).

PREPARATION 295

MASS (m/z): 1321.5 (M$^+$–Na).

PREPARATION 296

The object compound was used directly in the next reaction without purification.

PREPARATION 297

MASS (m/z): 1320–4 (M$^+$–Na).

PREPARATION 298

The object compound was used directly in the next reaction without purification.

PREPARATION 299

IR (KBr): 1605, 1444 cm$^{-1}$.

MASS (m/z): 1372 (M–2).

PREPARATION 300

MASS (m/z): 1232.2 (M$^+$–Na).

PREPARATION 301

The object compound was used directly in the next reaction without purification.

PREPARATION 302

The object compound was used directly in the next reaction without purification.

PREPARATION 303

The object compound was used directly in the next reaction without purification.

PREPARATION 304

The object compound was used directly in the next reaction without purification.

PREPARATION 305

The object compound was used directly in the next reaction without purification.

PREPARATION 306

The object compound was used directly in the next reaction without purification.

PREPARATION 307

The object compound was used directly in the next reaction without purification.

PREPARATION 308

The object compound was used directly in the next reaction without purification.

PREPARATION 309

The object compound was used directly in the next reaction without purification.

PREPARATION 310

The object compound was used directly in the next reaction without purification.

PREPARATION 311

MASS (m/z): 1361 (M$^+$+23).

PREPARATION 312

MASS (m/z): 1308 (M$^+$−23).

PREPARATION 313

The object compound was used directly in the next reaction without purification.

PREPARATION 314

The object compound was used directly in the next reaction without purification.

PREPARATION 315

MASS (m/z): 1304.3 (M$^+$−Na).

PREPARATION 316

IR (KBr): 3345.9, 1633.4, 1511.9, 1232.3 cm$^{-1}$.

NMR (DMSO-d$_6$, δ): 0.96 (3H, d, J=6.8 Hz), 1.08 (3H, d, J=6.1 Hz), 1.23–1.26 (2H, m), 2.80–5.21 (51H, m), 6.66–8.72 (20H, m).

MASS (m/z): 1372.3 (M$^+$−Na).

PREPARATION 317

IR (KBr): 3336.2, 1631.5, 1510.0, 1230.4 cm$^{-1}$.

NMR (DMSO-d$_6$, δ): 0.95 (3H, d, J=7.1 Hz), 1.08 (3H, d, J=5.8 Hz), 1.24–5.21 (50H, m), 6.68–8.72 (22H, m).

MASS (m/z): 1308.4 (M$^+$−Na).

PREPARATION 318

MASS (m/z): 1262 (M$^+$−23).

PREPARATION 319

MASS (m/z): 1262 (M$^+$−23).

PREPARATION 320

The object compound was used directly in the next reaction without purification.

PREPARATION 321

The object compound was used directly in the next reaction without purification.

PREPARATION 322

The object compound was used directly in the next reaction without purification.

PREPARATION 323

The object compound was used directly in the next reaction without purification.

PREPARATION 324

The object compound was used directly in the next reaction without purification.

PREPARATION 325

The object compound was used directly in the next reaction without purification.

PREPARATION 326

The object compound was used directly in the next reaction without purification.

PREPARATION 327

The object compound was used directly in the next reaction without purification.

PREPARATION 328

The object compound was used directly in the next reaction without purification.

PREPARATION 329

The object compound was used directly in the next reaction without purification.

PREPARATION 330

IR (KBr): 3351.7, 2256.3, 1633.4, 1232.3, 1116.6 cm$^{-1}$.

NMR (DMSO-d$_6$, δ): 0.96 (3H, d, J=6.7 Hz), 1.08 (3H, d, J=5.9 Hz), 1.80–5.20 (52H, m), 5.91–5.94 (1H, m), 6.68–8.72 (21H, m).

MASS (m/z): 1338.4 (M$^+$–Na).

PREPARATION 331

IR (KBr): 2256.3, 1633.4, 1510.0, 1085.7 cm$^{-1}$.

NMR (DMSO-d$_6$, δ): 0.94–5.93 (68H, m), 6.69–8.72 (16H, m).

MASS (m/z): 1330.5 (M$^+$–Na).

PREPARATION 332

IR (KBr): 3351.7, 2256.3, 1666.2, 1633.4, 1230.4 cm$^{-1}$.

NMR (DMSO-d$_6$, δ): 0.81–5.20 (74H, m), 5.88–5.91 (1H, m), 6.68–8.72 (12H, m).

PREPARATION 333

IR (KBr): 2256.3, 1633.4, 1510.0, 1322.9, 1232.3 cm$^{-1}$.

NMR (DMSO-d$_6$, δ): 0.96 (3H, d, J=6.7 Hz), 1.09 (3H, d, J=5.6 Hz), 1.24–5.20 (57H, m), 5.89–5.93 (1H, m), 6.68–8.79 (16H, m).

MASS (m/z): 1286.3 (M$^+$–Na).

PREPARATION 334

IR (KBr): 3349.7, 2256.3, 1633.4, 1232.3 cm$^{-1}$.

NMR (DMSO-d$_6$, δ): 0.96 (3H, d, J=6.7 Hz), 1.08 (3H, d, J=5.5 Hz), 1.70–5.21 (53H, m), 5.90–5.93 (1H, m), 6.68–8.72 (16H, m).

MASS (m/z): 1336.3 (M$^+$+Na).

PREPARATION 335

NMR (DMSO-d$_6$, δ): 0.96 (3H, d, J=6.7 Hz), 1.10 (3H, d, J=5.7 Hz), 1.6–2.0 (8H, m), 2.2–2.5 (3H, m), 2.7 (1H, m), 2.9 (2H, m), 3.23 (3H, s), 3.34 (2H, m), 3.74 (2H, m), 3.6–4.6 (15H, m), 4.85 (3H, m), 5.03 (1H, d, J=6.2 Hz), 5.10 (1H, m), 5.20 (2H, m), 5.88 (1H, m), 6.71 (1H, d, J=8.2 Hz), 6.78 (1H, d, J=8.2 Hz), 6.98 (1H, s), 7.14 (2H, d, J=8.9 Hz), 7.42 (1H, d, J=8.3 Hz), 7.51 (1H, d, J=9.3 Hz), 7.79 (1H, m), 7.90 (2H, d, J=8.9 Hz), 7.97 (4H, s), 8.32 (1H, d, J=7.7 Hz), 8.51 (1H, d, J=7.5 Hz), 8.71 (1H, m), 8.84 (1H, s).

MASS (m/z): 1290.3 (M$^+$+Na).

PREPARATION 336

MASS (m/z): 1318.3 (M$^+$–Na).

PREPARATION 337

MASS (m/z): 1279.4 (M$^+$–Na).

PREPARATION 338

MASS (m/z): 1231.4 (M$^+$–Na).

The Starting Compounds (339) to (343) used and the Object Compounds (339) to (343) obtained in the following Preparations 339 to 343 are given in the table as below, in which the formulas of the starting compounds are in the upper column and the formulas of the object compounds are in the lower column, respectively.

| Preparation No. | Formula |
| --- | --- |
| 339 | 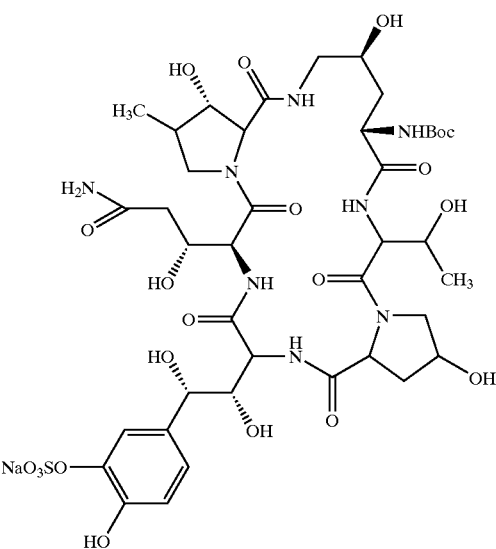 |

-continued
| Preparation No. | Formula |
|---|---|
| | 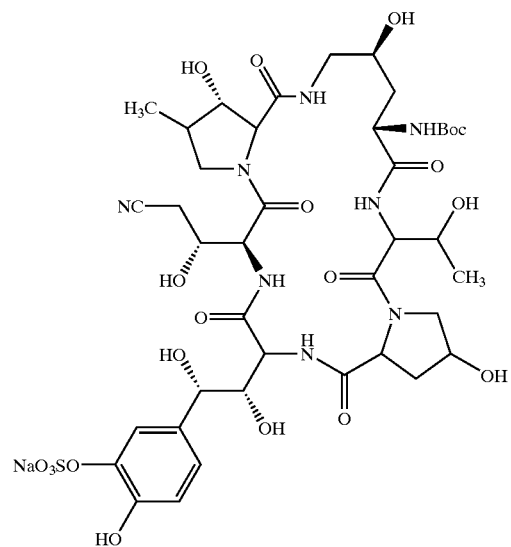 |
| 340 | 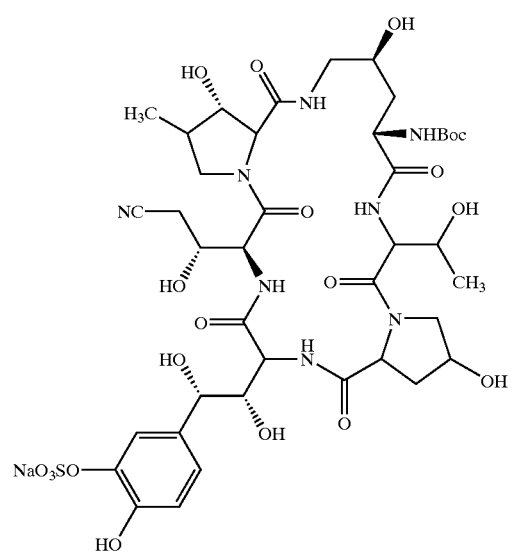 |

-continued
| Preparation No. | Formula |
|---|---|
| | 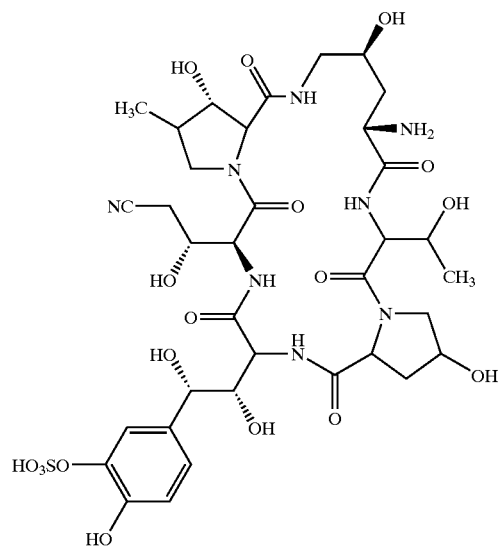 |
| 341 | 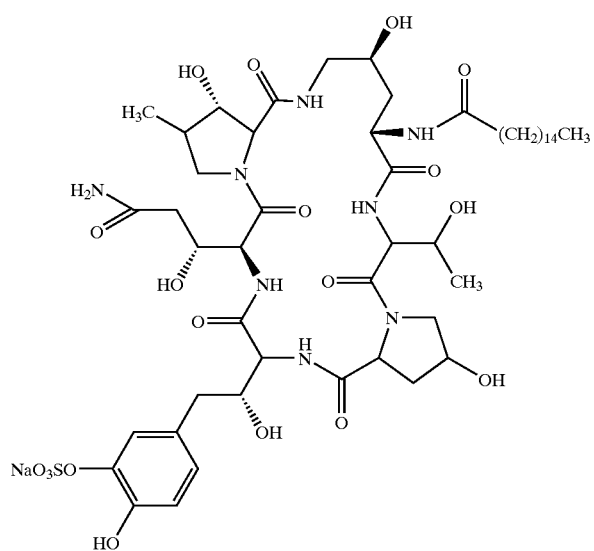 |

-continued
| Preparation No. | Formula |
|---|---|
| | 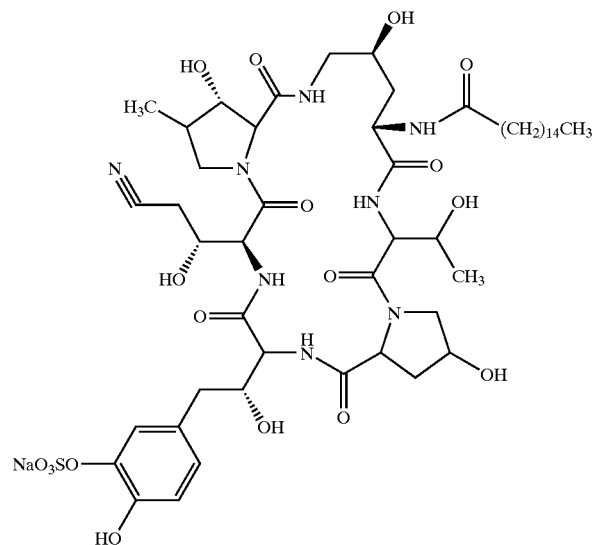 |
| 342 | 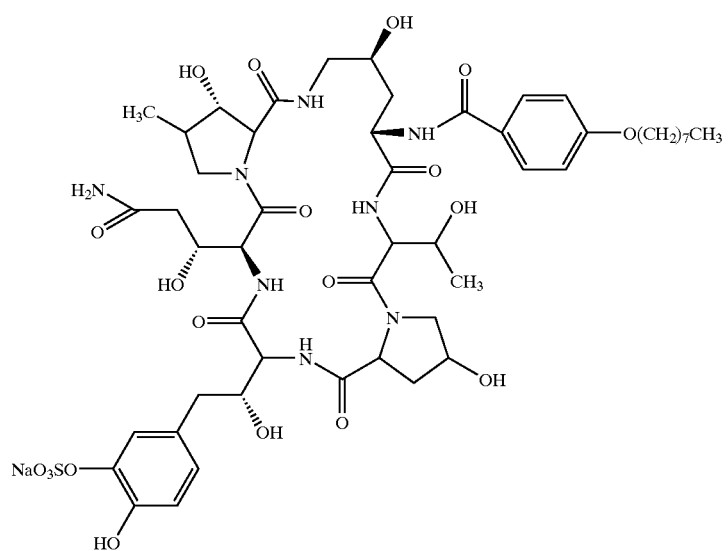 |

-continued
| Preparation No. | Formula |
|---|---|
|  | 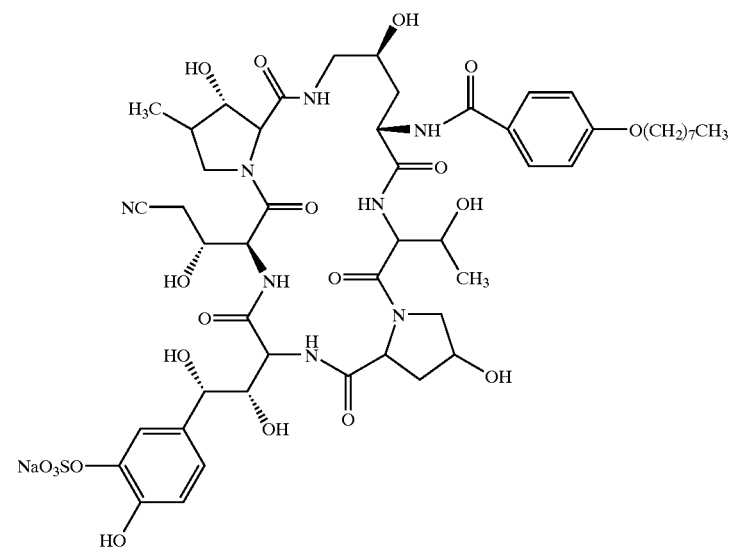 |
| 343 | 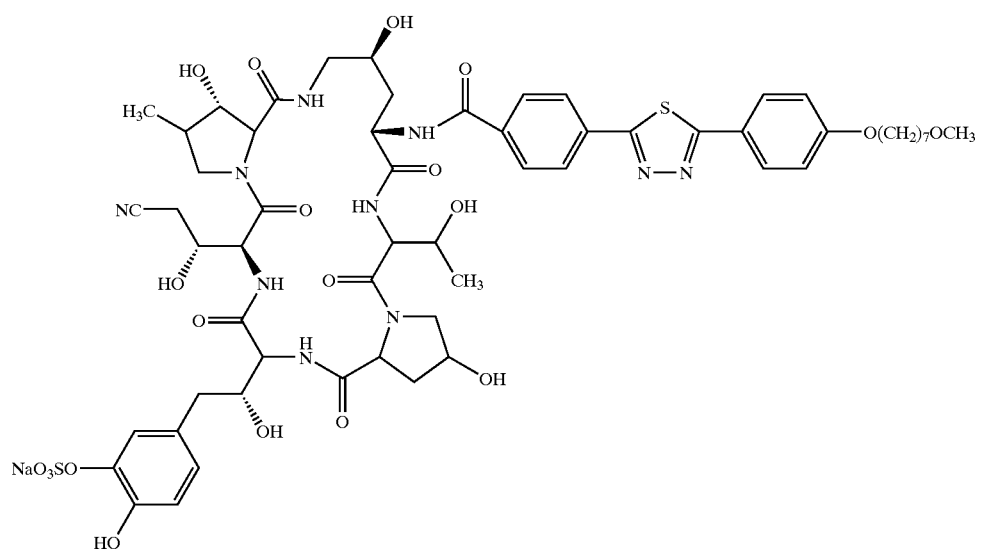 |

| Preparation No. | Formula |
|---|---|
| | (complex macrocyclic peptide structure with thiadiazole and O(CH$_2$)$_7$OCH$_3$ substituent) |

The following compound was obtained according to a similar manner to that of Preparation 2.

PREPARATION 339

IR (KBr): 1666, 1633, 1516, 1443, 1279, 1254 cm$^{-1}$.

NMR (DMSO-d$_6$+D$_2$O, δ): 0.94 (3H, d, J=6.74 Hz), 1.09 (3H, d, J=5.59 Hz), 1.36 (9H, s), 1.50–2.00 (3H, m), 2.10–2.40 (3H, m), 2.55–3.40 (5H, m), 3.55–4.50 (12H, m), 4.70–4.90 (2H, m), 6.73 (1H, d, J=8.20 Hz), 6.82 (1H, d, J=9.80 Hz), 7.06 (1H, s).

ESI MASS (m/z) (Positive): 1047.2 (M$^+$+Na).

Elemental Analysis Calcd. for C$_{40}$H$_{57}$N$_8$O$_{20}$SNa.5H$_2$O: C, 43.09, H, 6.06, N, 10.05. Found: C, 43.05, H, 6.09, N, 9.98.

HPLC (20% CH$_3$CN-pH 6.86 standard buffer solution; YMC-ODS 150×4.6mm): LT 5.38 min.

The following compound was obtained according to a similar manner to that of Preparation 9.

PREPARATION 340

NMR (DMSO-d$_6$+D$_2$O, δ): 0.94 (3H, d, J=6.74 Hz), 1.14 (3H, d, J=5.89 Hz), 1.30–1.55 (1H, m), 1.70–2.00 (1H, m), 2.05–2.45 (3H, m), 2.50–2.90 (3H, m), 3.05–3.35 (1H, m), 3.50–4.50 (16H, m), 4.65–4.95 (2H, m), 6.70–6.85 (2H, m), 7.09 (1H, d, J=1.56 Hz).

ESI-MASS (m/z) (Positive): 925.2 (M$^+$). HPLC (20% CH$_3$CN-pH 6.86 standard buffer solution; YMC-ODS 150× 4.6mm): LT 2.01 min.

The following compounds [Preparation 341 to 342] were obtained according to a similar manner to that of Preparation 2.

PREPARATION 341

IR (KBr): 3354, 2925.5, 2854, 2256, 1631.5, 1535, 1516, 1448, 1267, 1246, 1084, 1047 cm$^{-1}$.

MASS (m/z): 1123.5 (M$^+$-Na).

Elemental Analysis Calcd. for C$_{51}$H$_{79}$N$_8$O$_{18}$SNa.7H$_2$O: C, 48.10, H, 7.36, N, 8.80. Found: C, 48.31, H, 7.26, N, 8.72.

The following compound was obtained according to a similar manner to that of Preparation 2.

PREPARATION 342

IR (KBr): 2931, 1659, 1635, 1531, 1506, 1439, 1387, 1350 cm$^{-1}$.

MASS (m/z): 1133.4 (M$^+$-Na).

PREPARATION 343

To a solution of Starting Compound (343) (1 g) in trifluoroacetic acid (20 ml) was added 1N HCl aq. (4 ml) and stirred for 7 hours at ambient temperature. The reaction mixture was pulverized with water (90 ml). The precipitate was collected by filtration and dried under reduced pressure. The powder was added to 36% acetonitrile aq. (190 ml) and subjected to column chromatography on ODS (YMC-gel ODS-AM X S-50) (Trademark: prepared by Yamamura Chemical Lab.) and eluted with 35% acetonitrile aq. The fractions containing the object compound were combined and evaporated under reduced pressure to remove acetonitrile. The residue was lyophilized to give Object Compound (343) (319 mg).

IR (KBr): 3344.0, 2254, 1658.5, 1635.3, 1444.4, 1257.4 cm$^{-1}$.

ESI-MASS (m/z): 1213 (M$^+$-1).

PREPARATION 344

Dimethylformamide (485 l), p-pentyloxyacetophenone (30.3 kg) and dimethyl terephthalate (45.6 kg) were charged in 2000-liter reactor and stirred. To this mixture was added potassium tert-butoxide (24.7 kg) in several portions and, after that, a reaction was carried out at the inner temperature of 20 to 25° C. for 3.5 hours. After completion of the reaction, methanol (1210 l) was added to the reaction solution at 20 to 30° C. and then 6N hydrochloric acid (49 l) at 5 to 15° C. The mixture was stirred at room temperature for 1 hour, and the resulting appeared crystals were filtered and washed with methanol (152 l) and then water (152 l). The crystals were dried overnight in vacuo to give 1-(4-methoxycarbonylphenyl)-3-(4-pentyloxyphenyl)propane-1, 3-dione (49.6 kg).

NMR (CDCl$_3$, δ): 0.95 (3H, t, J=1.4 Hz), 1.30–1.60 (4H, m), 1.76–1.89 (2H, m), 3.95 (3H, s), 4.03 (2H, t, J=1.3 Hz), 6.84 (1H, s), 6.98 (2H, d, J=1.4 Hz), 7.99 (2H, d, J=1.4 Hz), 8.01 (2H, d, J=1.7 Hz), 8.13 (2H, d, J=1.7 Hz).

MASS (m/z): 369 (M$^+$+1).

PREPARATION 345

Dimethylformamide (123 l), 1-(4-methoxycarbonylphenyl)-3-(4-pentyloxyphenyl)propane-1,3-dione (24.5 kg) and ammonium formate (21.0 kg) were charged in 2000-liter reactor at room temperature and heated, and a reaction was carried out at the inner temperature of 100 to 105° C. for 5 hours. After completion of the reaction, the mixture was cooled down to room temperature, ethyl acetate (613 l) and water (613 l) were added, the mixture was stirred, and an ethyl acetate layer was separated, and then washed with 10% sodium chloride solution (613 l) and with 20% sodium chloride solution (613 l). The ethyl acetate layer was concentrated in vacuo to 125 l and then diluted with n-heptane (625 l) at the inner temperature of 40 to 45° C. to separate crystals of 1-amino-1-(4-methoxycarbonylphenyl)-3-oxo-3-(4-pentyloxyphenyl)-1-propene. The cyrstals were filtered at room temperature and washed with a mixture of n-heptane (104 l) and ethyl acetate (21 l). The crystals were dried overnight in vacuo and purified by suspending in a 70% aqueous acetone (158 l) to give 1-amino-1-(4-methoxycarbonylphenyl)-3-oxo-3-(4-pentyloxyphenyl)-1-propene (14.3 kg).

NMR (CDCl$_3$, δ): 0.94 (3H, t, J=1.4 Hz), 1.30–1.55 (4H, m), 1.70–1.90 (2H, m), 3.96 (3H, s), 4.01 (2H, t, J=1.3 Hz), 6.13 (1H, br s), 6.92 (2H, d, J=1.8 Hz), 7.70 (2H, d, J=1.7 Hz), 7.92 (2H, d, J=1.8 Hz), 8.13 (2H, d, J=1.7 Hz).

MASS (m/z): 368 (M$^+$+1).

The Starting Compounds used and the Object Compounds obtained in the following Examples 1 to 17 are given in the table as below, in which the formulas of the starting compounds are in the upper column and the formulas of the object compounds are in the lower column, respectively.

| Example No. | Formula |
|---|---|
| 1 | 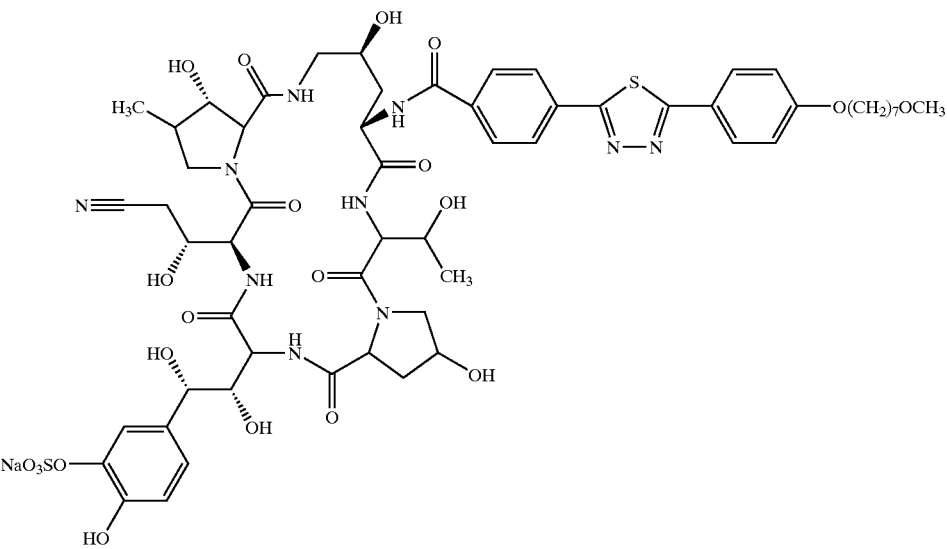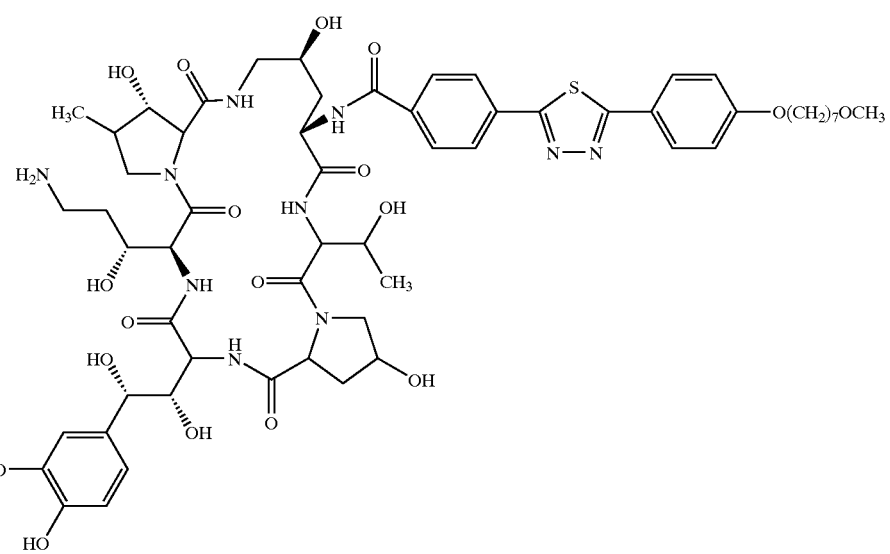 |

2
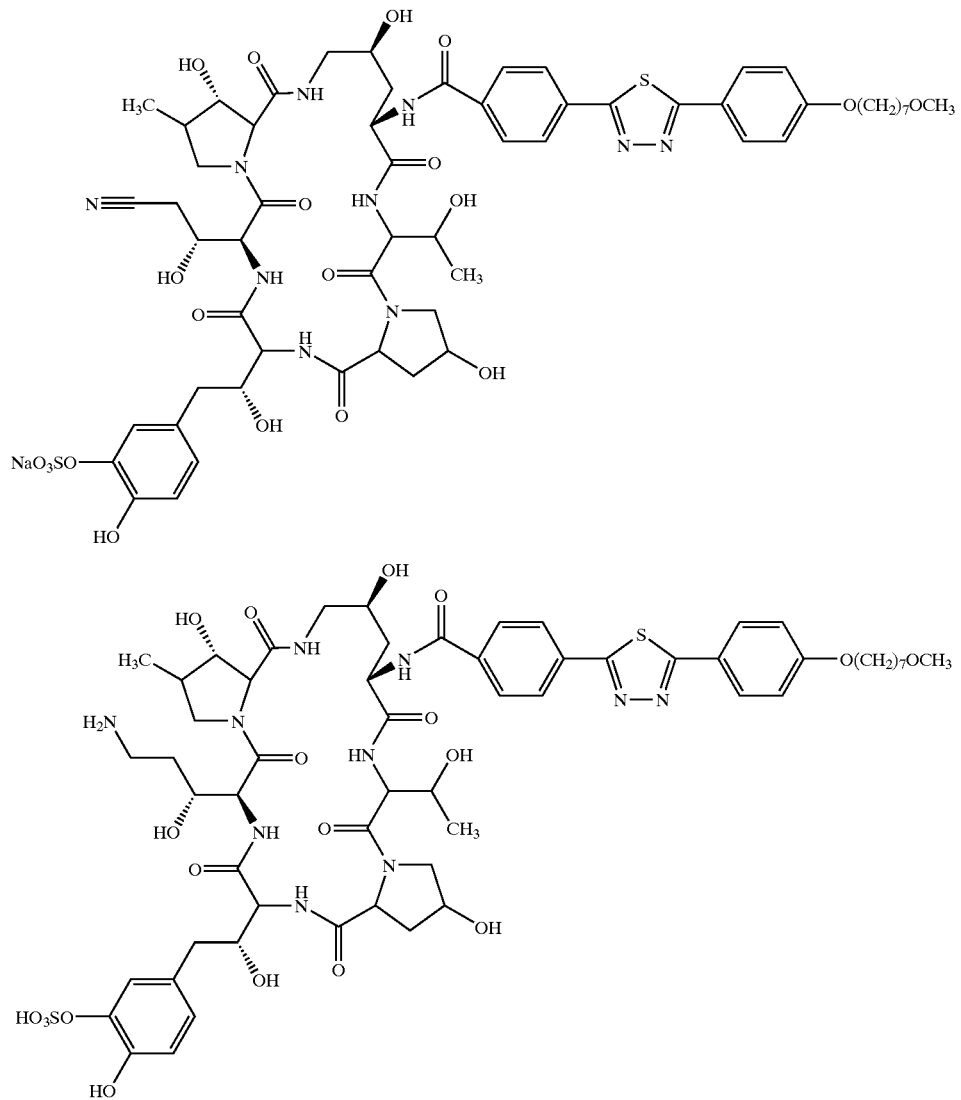
3~13
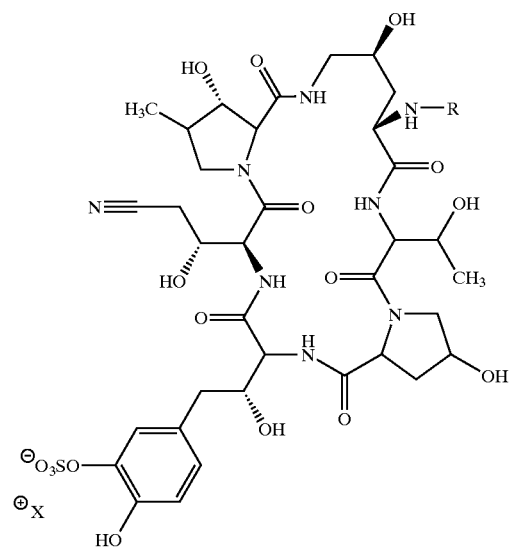

-continued
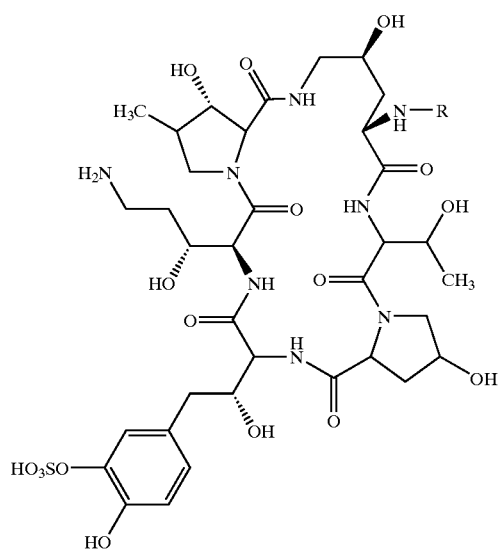
| Example No. | R | X |
|---|---|---|
| 3 | -C(O)-C6H4-[1,3,4-thiadiazole]-C6H4-O(CH2)8OCH3 | Na |
| 4 | -C(O)-C6H4-[1,3,4-thiadiazole]-C6H4-O(CH2)6OCH3 | Na |
| 5 | -C(O)-C6H4-[1,3,4-thiadiazole]-C6H4-C6H4-O(CH2)2OCH3 | Na |
| 6 | -C(O)-C6H4-[1,3,4-thiadiazole]-C6H4-C6H4-O(CH2)4OCH3 | Na |
| 7 | -C(O)-C6H4-[1,3,4-thiadiazole]-C6H4-N(piperazinyl)-cyclohexyl | HN(iPr)(tBu) |
| 8 | -C(O)-C6H4-[imidazo-thiadiazole]-C6H4-O(CH2)4CH3 | HN(iPr)(tBu) |
| 9 | -C(O)-C6H4-[imidazo-thiadiazole]-C6H4-O-cyclohexyl | Na |
| 10 | -C(O)-C6H4-[imidazo-thiadiazole]-C6H4-N(piperazinyl)-cyclohexyl | Na |

-continued
| | | |
|---|---|---|
| 11 | 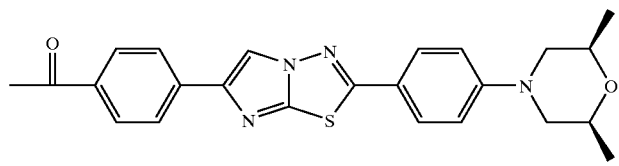 | Na |
| 12 | 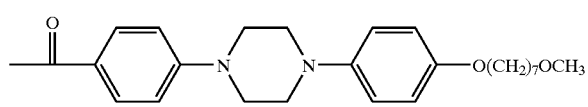 | 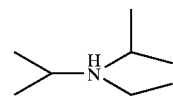 |
| 13 | 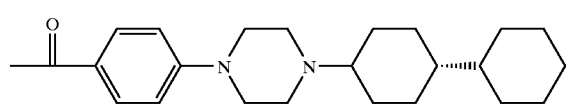 | Na |
| Example No. | Formula |
|---|---|
| 14 | 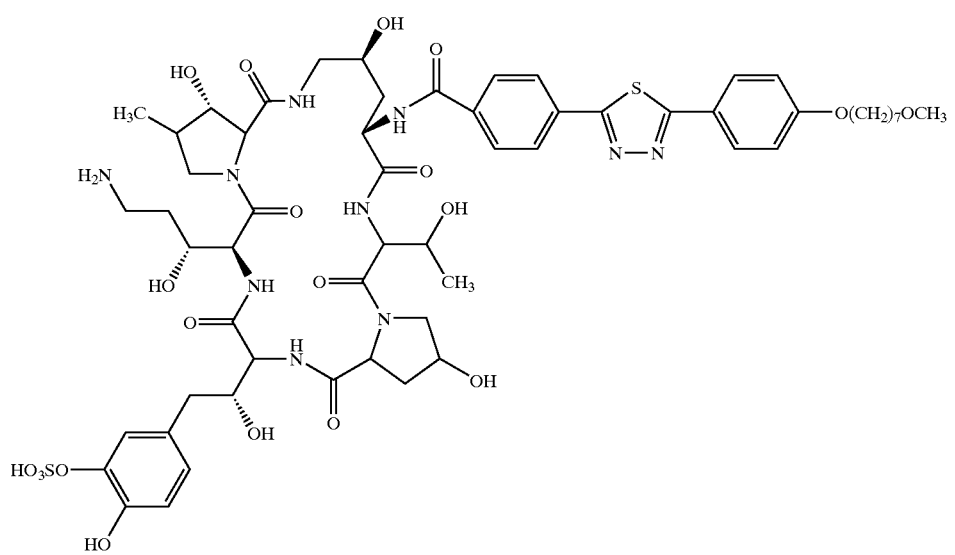 |
| | 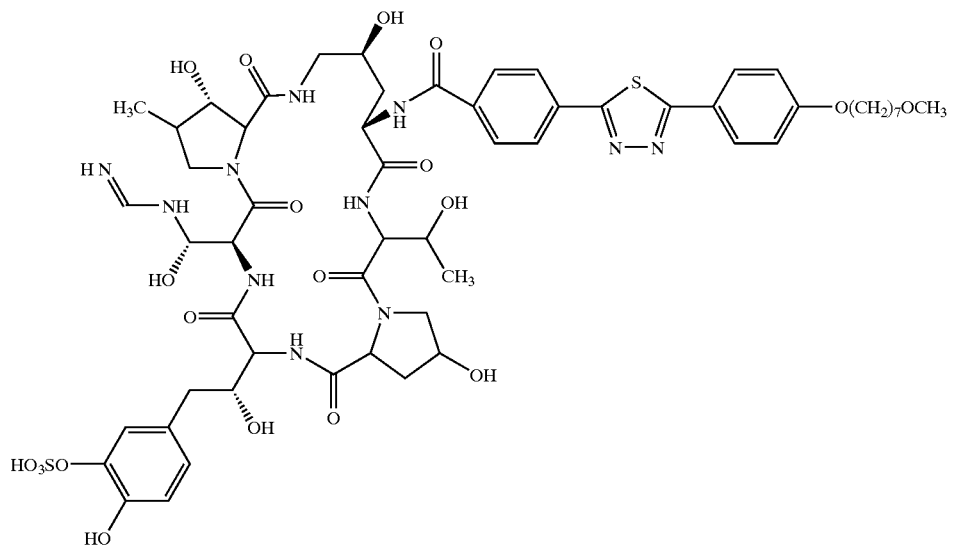 |

15
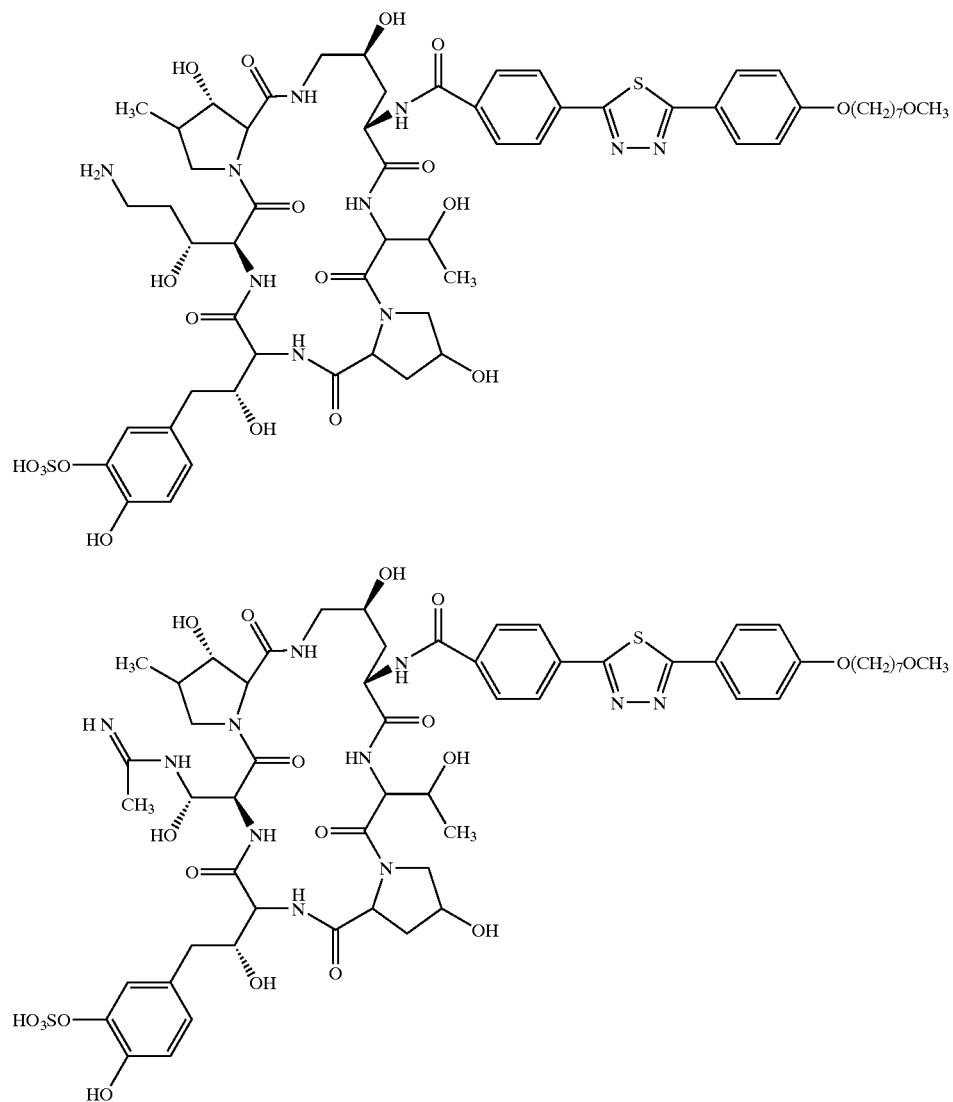
16
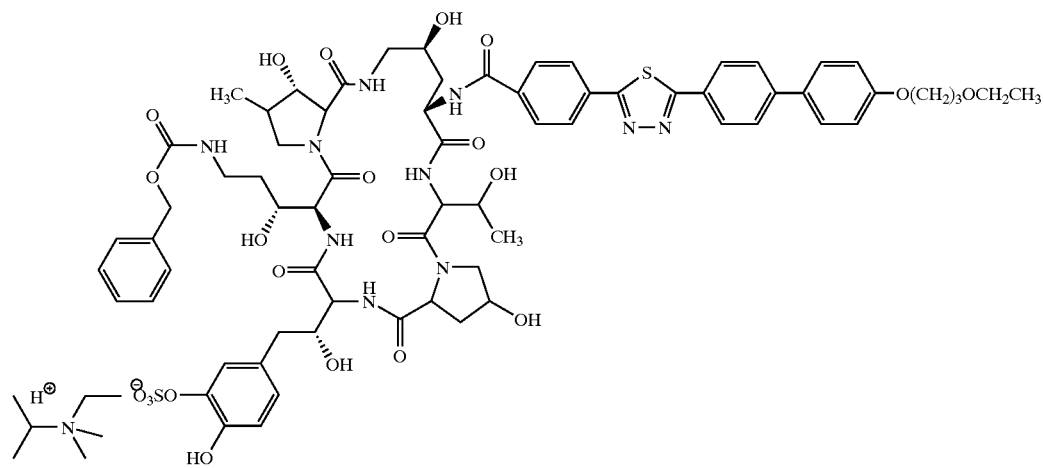

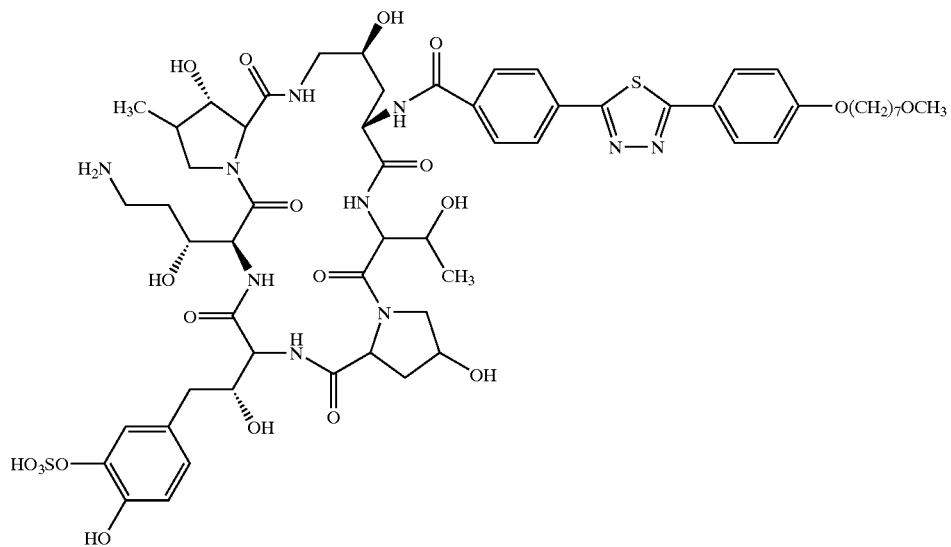
17
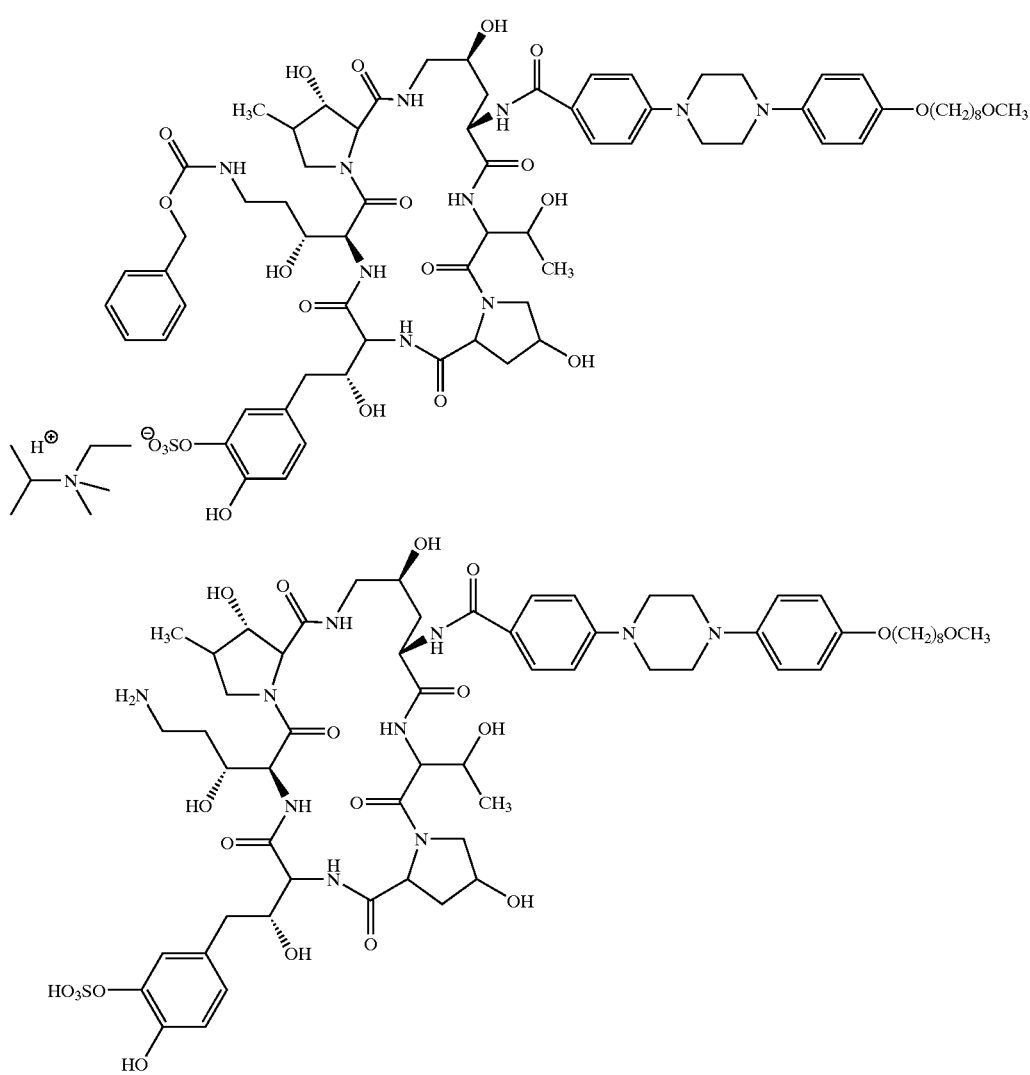

EXAMPLE 1

A solution of crude Starting compound (5.6 g) in methanol (168 ml)-water (336 ml) was treated with cobalt chloride hexahydrate (3.08 g) and the mixture stirred to give a pink colored solution. Sodium borohydride (2.46 g) was then added portionwise over 1 hour. Additional cobalt chloride (1.54 g) was added followed by sodium borohydride (1.23 g, portionwise). After a total reaction time of 2 hours 50% aqueous acetonitrile (600 ml) was added and insoluble material removed by filtration. The filtrate was evaporated to remove organic solvent and sufficient 1N-sodium hydroxide was added to the remaining aqueous layer to effect solution. This clear aqueous solution was then purified by ODS column chromatography eluting with aqueous acetonitrile. Object compounds-containing fractions were pooled, evaporated, and lyophilized to give Object compound (1.4 g) as an amorphous white powder.

IR (KBr): 1658.5, 1635.3, 1546.6, 1529.3, 1517.7, 1444.4, 1257.4 cm$^{-1}$.

NMR (DMSO-d$_6$, δ): 0.96 (3H, d, J=6.8 Hz), 1.10 (3H, d, J=6 Hz), 1.30–1.60 (8H, m), 1.60–2.50 (15H, m), 3.21 (3H, s), 2.80–5.40 (29H, m), 6.74 (1H, d, J=8.2 Hz), 6.80–6.85 (1H, m), 7.07 (1H, br s), 7.14 (2H, d, J=8.9 Hz), 7.40–7.80 (4H, m), 7.97 (2H, d, J=8.8 Hz), 8.09 (4H, ABq like, br m), 8.20–8.30 (1H, m), 8.80–8.90 (1H, m).

MASS (m/z): 1313.3 (M$^+$–1).

Elemental Analysis Calcd. for $C_{58}H_{78}N_{10}O_{21}S_2 \cdot 9H_2O$: C, 47.34, H, 6.16, N, 9.52. Found: C, 47.42, H, 6.26, N, 9.47.

The following compounds [Examples 2 to 13] were obtained according to a similar manner to that of Example 1.

EXAMPLE 2

IR (KBr): 1648.8, 1631.5, 1538.9, 1515.8, 1442.5, 1257.4 cm$^{-1}$.

NMR (DMSO-d$_6$, δ): 0.98 (3H, d, J=6.7 Hz), 1.24 (3H, d, J=5.6 Hz), 1.40–1.60 (8H, m), 1.60–2.65 (15H, m), 2.80–5.50 (27H, m), 3.21 (3H, s), 3.30 (2H, t, J=6.3 Hz), 6.72 (1H, d, J=8.1 Hz), 6.78 (1H, dd, J=1.6 and 8.3 Hz), 7.00 (1H, d, J=1.6 Hz), 7.13 (2H, d, J=8.9 Hz), 7.46 (1H, d, J=8.1 Hz), 7.60–7.90 (2H, m), 7.97 (2H, d, J=8.7 Hz), 8.04–8.14 (4H, m), 8.24–8.27 (1H, m), 8.70–9.00 (2H, m).

MASS (m/z): 1297.3 (M$^+$–1).

Elemental Analysis Calcd. for $C_{58}H_{78}N_{10}O_{20}S_2 \cdot 7.5H_2O$: C, 48.56, H, 6.53, N, 9.76. Found: C, 48.56, H, 6.31, N, 9.63.

EXAMPLE 3

IR (KBr): 1633.4, 1517.7, 1444.4, 1257.4 cm$^{-1}$.

NMR (DMSO-d$_6$, δ): 0.97 (3H, d, J=6.8 Hz), 1.13 (3H, d, J=5.7 Hz), 1.20–1.65 (10H, m), 1.65–2.65 (15H, m), 2.70–5.50 (27H, m), 3.21 (3H, s), 4.07 (2H, t, J=6.5 Hz), 6.71 (1H, d, J=8 Hz), 6.75–6.80 (1H, m), 6.98 (1H, d, J=1.6 Hz), 7.13 (2H, d, J=8.9 Hz), 7.46 (1H, d, J=8 Hz), 7.55–7.85 (2H, m), 7.97 (2H, d, J=8.8 Hz), 8.07 (4H, ABq, J=10.8 Hz), 8.09–8.13 (1H, m), 8.79 (1H, d, J=7.9 Hz), 8.55–9.00 (1H, br s).

MASS (m/z): 1311.3 (M$^+$–1).

Elemental Analysis Calcd. for $C_{59}H_{80}N_{10}O_{20}S_2 \cdot 10H_2O$: C, 47.45, H, 6.75, N, 9.38. Found: C, 47.68, H, 6.27, N, 9.21.

EXAMPLE 4

IR (KBr): 1648.8, 1631.5, 1540.8, 1513.8, 1452.1 cm$^{-1}$.

NMR (DMSO-d$_6$, δ): 0.95 (3H, d, J=6.6 Hz), 1.07 (3H, d, J=6 Hz), 1.1–2.7 (21H, m), 2.7–5.5 (32H, m), 6.68–6.74 (2H, m), 6.9–6.94 (1H, m), 7.13 (2H, d, J=8.9 Hz), 7.2–7.5 (1H, m), 7.5–7.8 (2H, m), 7.97 (2H, d, J=8.8 Hz), 8.09 (4H, s), 8.29 (1H, d, J=7.3 Hz), 8.5–8.9 (2H, m).

MASS (m/z): 1283.3 (M$^+$–1).

EXAMPLE 5

IR (KBr): 1635.3, 1531.2, 1444.4, 1251.6 cm$^{-1}$.

NMR (DMSO-d$_6$, δ): 0.96 (3H, d, J=6.7 Hz), 1.14 (3H, d, J=6 Hz), 1.40–5.30 (41H, m), 3.67–3.70 (2H, m), 4.15–4.23 (2H, m), 6.66 (1H, d, J=8 Hz), 6.64–6.72 (1H, m), 6.96 (1H, br s), 7.09 (2H, d, J=8.9 Hz), 7.4–7.8 (4H, m), 7.57 (2H, d, J=6.3 Hz), 7.74 (2H, d, J=8.8 Hz), 8.0–8.3 (7H, m), 8.73 (1H, d, J=7.5 Hz).

MASS (m/z): 1304.3 (M$^+$).

Elemental Analysis Calcd. for $C_{59}H_{72}N_{10}O_{20}S_2 \cdot 11H_2O$: C, 47.13, H, 6.30, N, 9.32. Found: C, 47.22, H, 5.90, N, 8.82.

EXAMPLE 6

IR (KBr): 1635.3, 1531.2, 1508.1, 1444.4, 1251.6 cm$^{-1}$.

NMR (DMSO-d$_6$, δ): 0.97 (3H, d, J=6.7 Hz), 1.14 (3H, d, J=5.4 Hz), 1.3–5.3 (44H, m), 3.25 (3H, s), 4.05 (2H, t, J=6 Hz), 6.70 (1H, d, J=8.2 Hz), 6.75–6.79 (1H, m), 6.96 (1H, br s), 7.07 (2H, d, J=8.9 Hz), 7.4–7.8 (4H, m), 7.73 (2H, d, J=8.8 Hz), 7.87 (2H, d, J=8.5 Hz), 8.08–8.16 (7H, m), 8.7–8.8 (1H, m).

MASS (m/z): 1332.4 (M$^+$).

Elemental Analysis Calcd. for $C_{61}H_{76}N_{10}O_{20}S_2 \cdot 11H_2O$: C, 47.84, H, 6.45, N, 9.15. Found: C, 48.10, H, 6.00, N, 8.94.

EXAMPLE 7

IR (KBr): 1635.3, 1606.4, 1531.2, 1496.5, 1444.4, 1419.4 cm$^{-1}$.

NMR (DMSO-d$_6$, δ): 0.97 (3H, d, J=6.8 Hz), 1.11 (3H, d, J=5.7 Hz), 1.05–1.04 (5H, m), 1.50–5.30 (52H, complex m), 6.67 (1H, d, J=5.7 Hz), 6.73–6.80 (1H, m), 7.01 (1H, d, J=1.6 Hz), 7.08 (2H, d, J=9 Hz), 7.4–7.8 (3H, m), 7.85 (2H, d, J=8.7 Hz), 8.07 (4H, ABq, J=9 Hz), 8.31 (1H, d, J=6.9 Hz), 8.71 (1H, s), 8.91 (1H, d, J=7.4 Hz).

MASS (m/z): 1319.4 (M$^+$–1).

Elemental Analysis Calcd. for $C_{60}H_{80}N_{12}O_{18}S_2 \cdot 9H_2O$: C, 48.57, H, 6.66, N, 11.33. Found: C, 48.77, H, 6.54, N, 11.25.

EXAMPLE 8

IR (KBr): 1635.3, 1529.3, 1519.6, 1467.6, 1446.4, 1257.4 cm$^{-1}$.

NMR (DMSO-d$_6$, δ): 0.91 (3H, t, J=7 Hz), 0.96 (3H, d, J=8.3 Hz), 1.12 (3H, d, J=5.6 Hz), 1.2–2.6 (17H, m), 2.6–5.4 (29H, m), 6.71 (1H, d, J=8 Hz), 6.77 (1H, br d, J=8 Hz), 6.98 (1H, d, J=1.7 Hz), 7.14 (2H, d, J=8.9 Hz), 7.45 (1H, d, J=8.5 Hz), 7.4–7.8 (3H, m), 7.90 (2H, d, J=8.8 Hz), 8.05 (4H, s), 8.1–8.3 (1H, s), 8.64 (1H, d, J=6.9 Hz), 8.85 (1H, s).

MASS (m/z): 1278.3 (M$^+$–1).

Elemental Analysis Calcd. for $C_{57}H_{73}N_{11}O_{19}S_2 \cdot 9H_2O$: C, 47.46, H, 6.36, N, 10.68. Found: C, 47.58, H, 6.17, N, 10.62.

EXAMPLE 9

IR (KBr): 3361.3, 2937.1, 1635.3, 1523.5, 1461.8, 1251.6 cm$^{-1}$.

NMR (DMSO-d$_6$, δ): 0.97 (3H, d, J=6.8 Hz), 1.10 (3H, d, J=5.9 Hz), 1.2–5.3 (49H, m), 6.67–6.80 (2H, m), 7.01 (1H, d, J=1.6 Hz), 7.15 (2H, d, J=9 Hz), 7.4–7.8 (3H, m), 7.88 (2H, d, J=8.8 Hz), 7.96 (4H, s), 8.35 (1H, d, J=8.3 Hz), 8.7–8.8 (2H, m), 8.86 (1H, s).

API-ES MASS (Negative): 1290.3 (M$^+$−1).

Elemental Analysis Calcd. for $C_{58}H_{73}N_{11}O_{19}S_2 \cdot 8H_2O$: C, 48.29 H 6.26, N, 10.53. Found: C, 48.49 H 6.24, N, 10.73.

EXAMPLE 10

IR (KBr): 1637.3, 1523.5, 1459.9, 1238.1 cm$^{-1}$.

MASS (m/z): 1358.4 (M$^+$−1).

EXAMPLE 11

IR (KBr): 3357.5, 1631.5, 1517.7, 1465.6, 1450.2, 1241.9 cm$^{-1}$.

NMR (DMSO-d$_6$, δ): 0.98 (3H, d, J=6.8 Hz), 1.10 (3H, d, J=6 Hz), 1.18 (6H, d, J=6 Hz), 1.5–2.7 (11H, m), 2.8–5.4 (33H, m), 6.71 (1H, d, J=8.2 Hz), 6.78 (1H, dd, J=8 and 1.6 Hz), 7.01 (1H, d, J=1.6 Hz), 7.12 (2H, d, J=9 Hz), 7.44 (1H, d, J=8.7 Hz), 7.6–7.9 (1H, m), 7.67 (1H, d, J=8 Hz), 7.78 (2H, d, J=8.8 Hz), 7.96 (4H, s), 8.35 (1H, d, J=7 Hz), 7.6–8.8 (1H, br s), 8.75 (1H, d, J=7 Hz), 8.81 (1H, s).

API-ES MASS (Negative): 1305.3 (M$^+$−1).

Elemental Analysis Calcd. for $C_{58}H_{74}N_{12}O_{19}S_2 \cdot 8H_2O$: C, 48.05, H, 6.24, N, 11.55. Found: C, 47.99, H, 6.25, N, 11.58.

EXAMPLE 12

IR (KBr): 1631.5, 1510.0, 1446.4, 1234.2 cm$^{-1}$.

NMR (DMSO-d$_6$, δ): 0.96 (3H, d, J=6.7 Hz), 1.09 (3H, d, J=5.8 Hz), 1.2–2.65 (15H, m), 2.7–5.3 (41H, m), 3.21 (3H, s), 3.30 (2H, t, J=6.4 Hz), 3.85 (2H, t, J=6.5 Hz), 6.70 (1H, d, J=8.2 Hz), 6.74–6.80 (1H, m), 6.83 (2H, d, J=9 Hz), 6.94 (2H, d, J=9 Hz), 6.99 (1H, s), 7.01 (2H, d, J=8.8 Hz), 7.44 (1H, d, J=8.6 Hz), 7.6–7.9 (2H, m), 7.80 (2H, d, J=8.7 Hz), 8.1–8.3 (2H, m), 8.37 (1H, d, J=7.7 Hz).

MASS (m/z): 1297.5 (M$^+$−Na).

Elemental Analysis Calcd. for $C_{60}H_{86}N_{10}O_{20}S \cdot 7H_2O$: C, 50.55, H, 7.07, N, 9.83. Found: C, 50.68, H, 7.08, N, 9.82.

EXAMPLE 13

IR (KBr): 1648.8, 1631.5, 1540.8, 1511.9, 1454.1, 1238.1 cm$^{-1}$.

NMR (DMSO-d$_6$, δ): 0.8–1.3 (18H, m), 1.5–2.5 (24H, m), 2.61 (4H, br s), 2.8–5.4 (27H, m), 6.70 (1H, d, J=8.1 Hz), 6.77 (1H, br d, J=10 Hz), 6.92 (2H, d, J=9 Hz), 7.00 (1H, d, J=1.6 Hz), 7.42 (1H, d, J=8.6 Hz), 7.5–7.7 (2H, m), 7.76 (2H, d, J=8.6 Hz), 8.30 (1H, d, J=7.1 Hz), 8.44 (1H, d, J=6.9 Hz), 8.46–9.00 (1H, br s).

MASS (m/z): 1241.3 (M$^+$−1).

Elemental Analysis Calcd. for $C_{58}H_{86}N_{10}O_{18}S \cdot 10H_2O$: C, 48.94, H, 7.50, N, 9.84. Found: C, 49.19, H, 7.33, N, 9.73.

EXAMPLE 14

A solution of Starting compound (150 mg) in N,N-dimethylformamide (1.5 ml) was treated with diisopropylethylamine (166.5 mg) and ethyl formimidate hydrochloride (64.8 mg) and stirred 2 days at room temperature. Additional ethyl formimidate hydrochloride (39 mg) was added and stirring continued a further 3 hours 15 minutes. The reaction mixture was diluted with water and purified by ODS column chromatography, eluting with aqueous acetonitrile. Product-containing fractions were pooled, evaporated, and lyophilized to give Object compound as an amorphous white powder.

IR (KBr): 1658.5, 1635.3, 1444.4, 1257.4 cm$^{-1}$.

NMR (DMSO-d$_6$, δ): 0.97 (3H, d, J=6.7 Hz), 1.10 (3H, d, J=6.1 Hz), 1.20–1.60 (8H, m), 1.60–2.50 (15H, m), 3.21 (3H, s), 2.80–5.30 (27H, m), 6.71 (1H, d, J=8.1 Hz), 6.78 (1H, d, J=6 Hz), 7.00 (1H, br s), 7.14 (2H, d, J=8.9 Hz), 7.40–7.84 (4H, m), 7.84 (1H, s), 7.97 (2H, d, J=8.8 Hz), 8.08 (4H, ABq, J=8.9 Hz), 8.30–8.40 (2H, m), 8.90–9.10 (2H, m).

MASS (m/z): 1325.4 (M$^+$−1).

Elemental Analysis Calcd. for $C_{58}H_{79}N_{11}O_{19}S_2 \cdot 8H_2O$: C, 48.29, H, 6.64, N, 10.68. Found: C, 48.01, H, 6.34, N, 10.38.

The following compounds [Examples 15 to 17] were obtained according to a similar manner to that of Example 14.

EXAMPLE 15

IR (KBr): 1658, 1635, 1628, 1444, 1257 cm$^{-1}$.

NMR (DMSO-d$_6$, δ): 0.97 (3H, d, J=6.7 Hz), 1.11 (3H, d, J=6.1 Hz), 1.25–1.60 (8H, m), 1.60–2.50 (15H, m), 2.05 (3H, s), 3.21 (3H, s), 2.80–5.30 (27H, m), 6.71 (1H, d, J=8.1 Hz), 6.77 (1H, d, J=8 Hz), 7.00 (1H, br s), 7.13 (2H, d, J=8.9 Hz), 7.30–7.90 (4H, m), 7.97 (2H, d, J=8.7 Hz), 8.08 (4H, ABq, J=8.8 Hz), 8.50–9.00 (4H, m).

MASS (m/z): 1362.3 (M$^+$−Na).

Elemental Analysis Calcd. for $C_{59}H_{81}N_{11}O_{19}S_2 \cdot 9H_2O$: C, 48.06, H, 6.77, N, 10.45. Found: C, 48.02, H, 6.48, N, 10.11.

EXAMPLE 16

IR (KBr): 1643.1, 1633.4, 1535.1, 1513.8, 1442.5, 1249.6 cm$^{-1}$.

NMR (DMSO-d$_6$, δ): 0.97 (3H, d, J=6.8 Hz), 1.1–1.16 (3H, m), 1.12 (3H, t, J=7 Hz), 1.4–2.6 (12H, m), 2.8–5.2 (34H, m), 6.71 (1H, d, J=8 Hz), 6.78 (1H, dd, J=8 and 2 Hz), 7.00 (1H, d, J=2 Hz), 7.08 (2H, d, J=8.8 Hz), 7.45 (1H, d, J=8.9 Hz), 7.6–7.8 (2H, m), 7.73 (2H, d, J=8.8 Hz), 7.87 (2H, d, J=8.5 Hz), 8.0–8.2 (6H, m), 8.28 (1H, d, J=7 Hz), 8.91 (1H, d, J=7.6 Hz), 8.5–9.05 (1H, br s).

MASS (m/z): 1331.2 (M$^+$−1).

Elemental Analysis Calcd. for $C_{61}H_{76}N_{10}O_{20}S_2 \cdot 10H_2O$: C, 48.41, H, 6.39, N, 9.25. Found: C, 48.63, H, 6.13, N, 9.13.

EXAMPLE 17

IR (KBr): 1631.5, 1537.0, 1510.0, 1448.3, 1234.2 cm$^{-1}$.

NMR (DMSO-d$_6$+D$_2$O, δ): 0.96 (3H, d, J=6.7 Hz), 1.05–1.15 (3H, m), 1.2–3.0 (33H, m), 3.15 (3H, s), 3.29 (2H, t, J=6.4 Hz), 3.88 (2H, t, J=6.4 Hz), 3.6–4.5 (14H, m), 4.7–4.85 (2H, m), 6.73–7.04 (9H, m), 7.75–7.9 (2H, m).

MASS (m/z): 1311.4 (M$^+$−1).

Elemental Analysis Calcd. for $C_{61}H_{88}N_{10}O_{20}S \cdot 10H_2O$: C, 49.05, H, 7.29, N, 9.38. Found: C, 48.78, H, 6.83, N, 9.27.

The Starting Compounds (18) to (21) used and the Object Compounds (18) to (21) obtained in the following Examples 18 to 21 are given in the table as below, in which the formulas of the starting compounds are in the upper column and the formulas of the object compounds are in the lower column, respectively.

| Example No. | Formula |
| --- | --- |
| 18 | 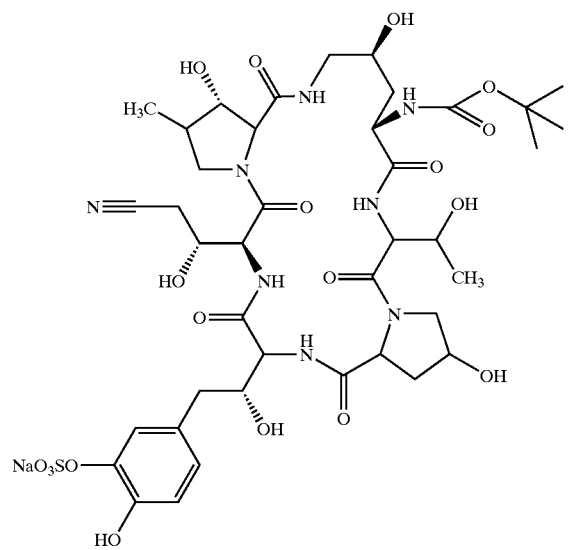 |
| | 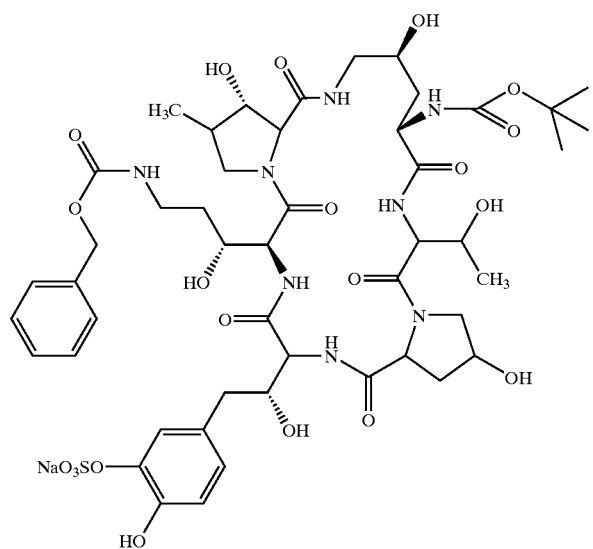 |

-continued
| Example No. | Formula |
|---|---|
| 19 | 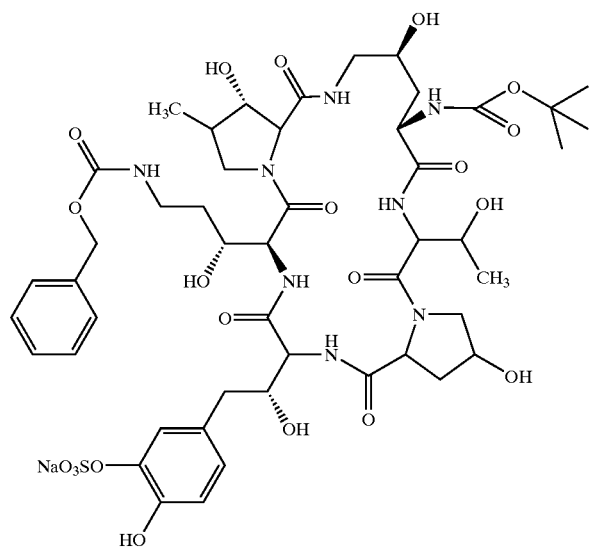 |
| | 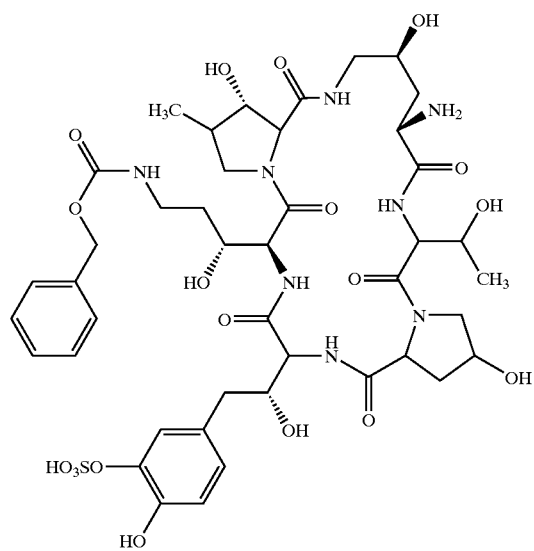 |

| Example No. | Formula |
| --- | --- |
| 20 | 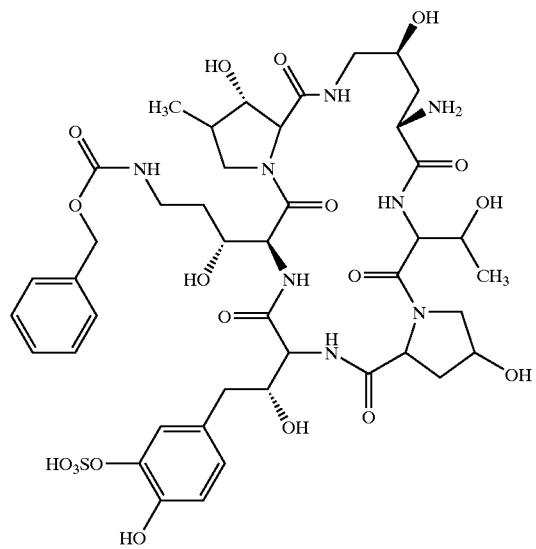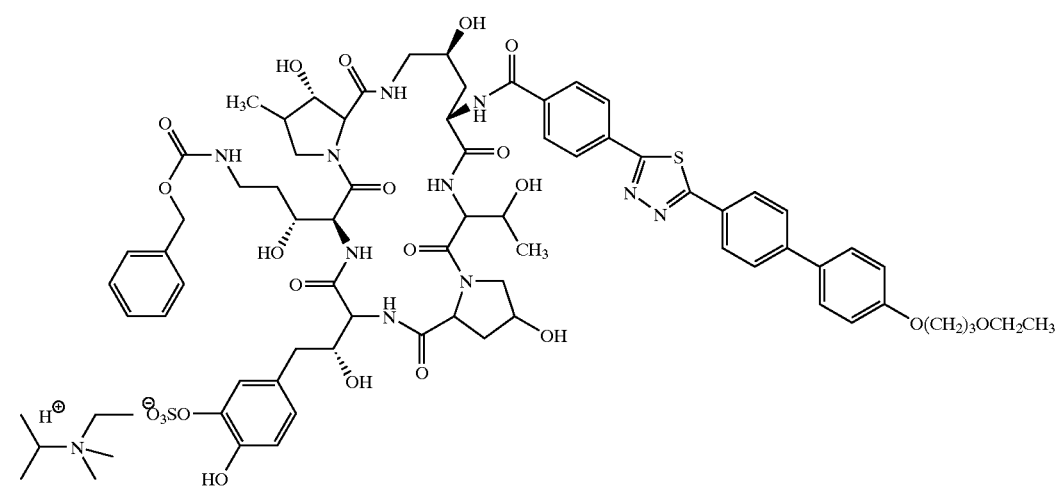 |
| 21 | 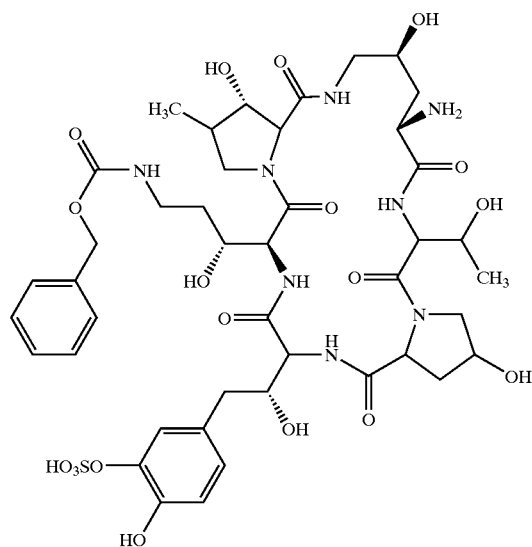 |

| Example No. | Formula |
|---|---|

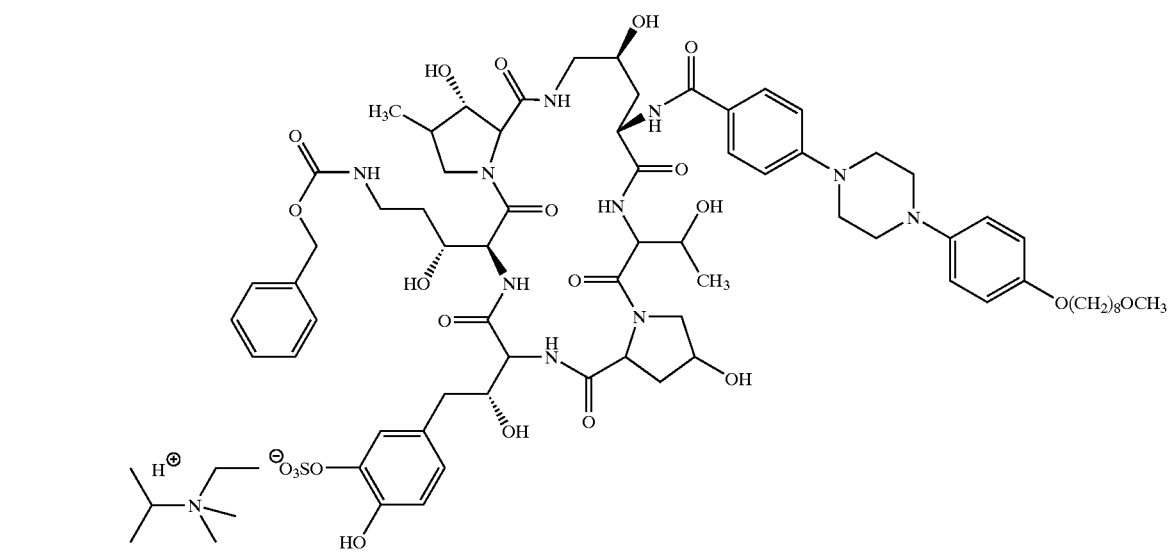

EXAMPLE 18

A solution of Starting compound (2.0 g) in methanol (100 ml)-water (20 ml) was treated with cobalt(II) chloride hexahydrate (1.89 g) and then stirred to give a pink solution. Sodium borohydride (1.5 g) was then added portionwise and then stirred for 1 hour at room temperature. The reaction mixture was filtered through a bed of celite, washing with methanol (100 ml)-water (30 ml) solution. The ice-cooled filtrate was then treated dropwise with a solution of benzyloxy carbonyl chloride (Z-chloride) (0.34 ml) in tetrahydrofuran (5 ml) and stirred for 1 hour at the same temperature. Ethyl acetate (50 ml) was added followed by water (200 ml) and after stirring-5 minutes, the separated organic layer was discarded. The aqueous layer was adjusted to pH 8.8 and evaporated to remove organic solvent and then purified by ODS column chromatography, eluting with aqueous acetonitrile (10–30%). Object compound containing fractions were pooled, evaporated, and lyophilized to give Object compound (1.61 g) as an amorphous white powder.

IR (KBr): 1666.2, 1631.5, 1517.7, 1444.4, 1267.0 cm$^{-1}$.

NMR (DMSO-$d_6$, δ): 0.94 (3H, d, J=6.7 Hz), 1.00–1.15 (3H, m), 1.33 (9H, s), 1.35–2.10 (6H, m), 2.10–2.50 (4H, m), 2.80–3.30 (4H, m), 3.60–4.55 (12H, m), 4.60–4.90 (2H, m), 4.99 (2H, s), 4.50–5.30 (4H, m), 6.60–7.10 (4H, m), 7.33 (5H, s), 7.35–7.90 (3H, m), 8.72 (1H, br s).

MASS (m/z): 1123.3 ($M^+$–Na).

Elemental Analysis Calcd. for $C_{48}H_{67}N_8O_{21}SNa.6H_2O$: C, 45.93, H, 6.34, N, 8.93. Found: C, 45.68, H, 6.33, N, 8.82.

EXAMPLE 19

A suspension of Starting compound (1.6 g) in dichloromethane (41 ml) was stirred with cooling at 5° C. and treated with triethylsilane (1.1 ml), followed by trifluoroacetic acid (5.3 ml) dropwise over 30 minutes. After warming to room temperature, the clear solution was stirred for 2 hours, then poured into 450 ml of pH 6.86 phosphate buffer and adjusted to pH 8.5 with 4N-sodium hydroxide solution. Organic solvent was removed by evaporation and the remaining aqueous solution purified by ODS column chromatography, eluting with aqueous acetonitrile (5–20%). Object compound-containing fractions were pooled, evaporated, and lyophilized to give Object compound (1.25 g) as an amorphous white powder.

IR (KBr): 1633.4, 1537.0, 1517.7, 1440.6, 1267.0 cm$^{-1}$.

NMR (DMSO-$d_6$, δ): 0.95 (3H, d, J=6.7 Hz), 1.12 (3H, d, J=5.8 Hz), 1.27 (2H, d, J=6.6 Hz), 1.28–1.70 (2H, m), 1.75–2.45 (4H, m), 2.65–3.30 (5H, m), 3.50–4.50 (11H, m), 4.60–4.90 (2H, m), 5.00 (2H, s), 5.05–5.40 (5H, m), 6.70 (2H, d, J=8.2 Hz), 6.76 (2H, d, J=8.2 Hz), 6.96 (1H, s), 7.00–7.15 (1H, m), 7.34 (5H, s), 7.40–7.95 (3H, m), 8.60–8.90 (1H, m).

MASS (m/z): 1023.3 ($M^+$–H).

Elemental Analysis Calcd. for $C_{43}H_{60}N_8O_{19}S.6H_2O$: C, 45.5H, H, 6.40, N, 9.89. Found: C, 45.49, H, 6.24, N, 9.70.

EXAMPLE 20

NMR (DMSO-$d_6$, δ): 0.95 (3H, d, J=6.6 Hz), 6.67 (1H, d, J=6.9 Hz), 6.73–6.75 (1H, m), 6.96 (1H, br s), 7.07 (2H, d, J=8.8 Hz), 7.32 (5H, s), 7.73 (2H, d, J=8.7 Hz), 7.87 (2H, d, J=8.5 Hz), 8.06–8.14 (6H, m), 8.72 (1H, s), 8.80 (1H, d, J=7.1 Hz).

MASS (m/z): 1465.5 ($M^+$–Na).

EXAMPLE 21

The Object Compound (21) was used directly in the next reaction without purification.

The Starting compounds (22) to (206) used and the Object Compounds (22) to (206) obtained in the following Example 22 to 206 are given in the table as below, in which the formulas of the starting compounds are in the upper column and the formulas of the object compounds are in the lower column, respectively.

| Example No. | Formula |
|---|---|
| 22 | 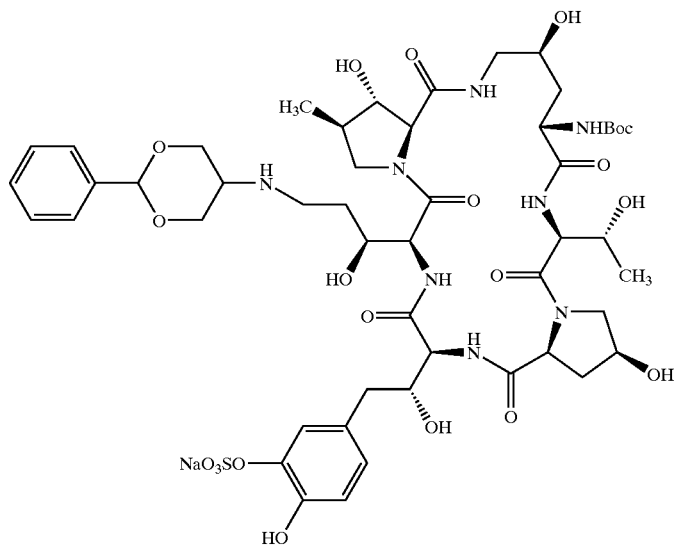 |
| | 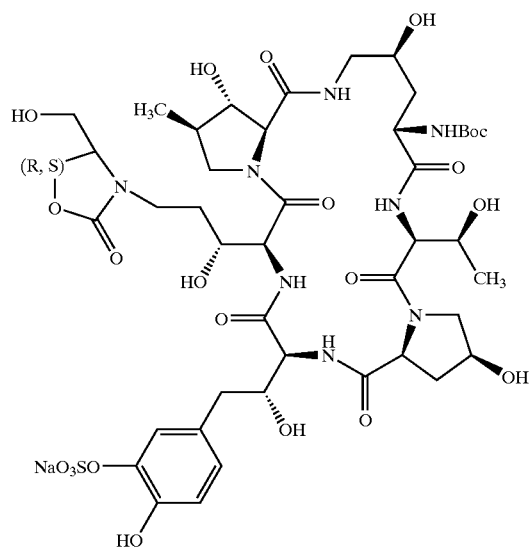 |

| Example No. | Formula |
|---|---|
| 23 | 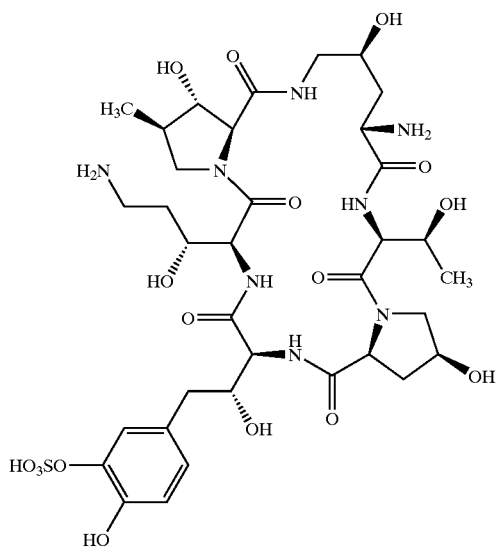 |
| | 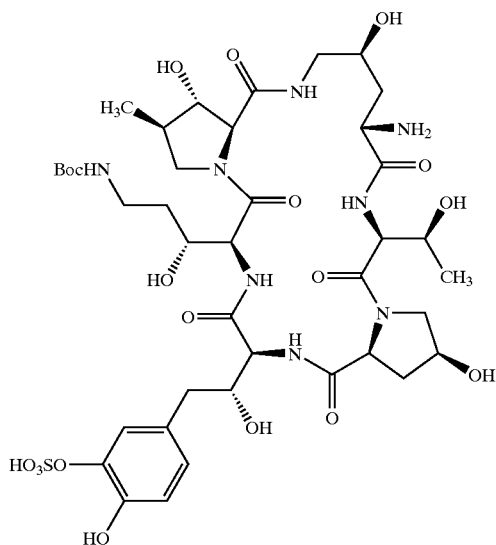 |

| Example No. | Formula |
|---|---|
| 24 | 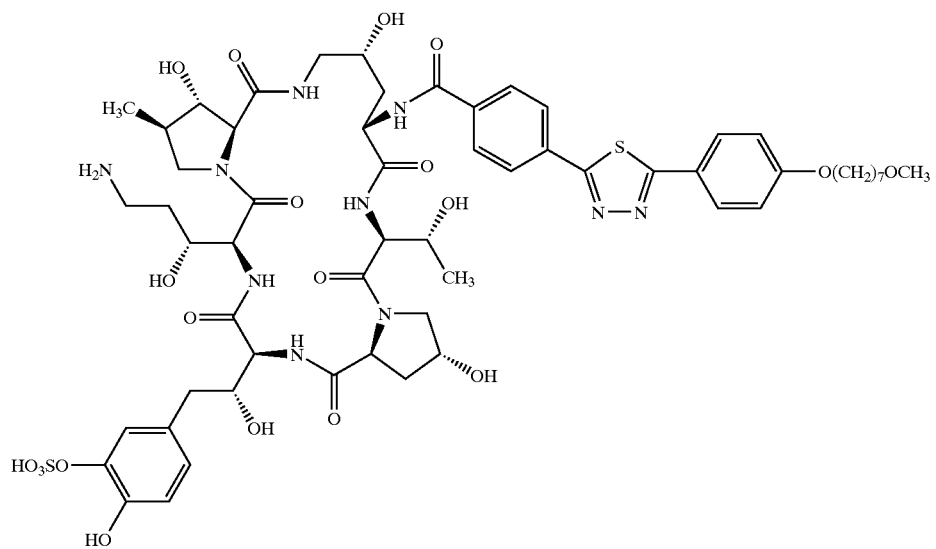 |
| | 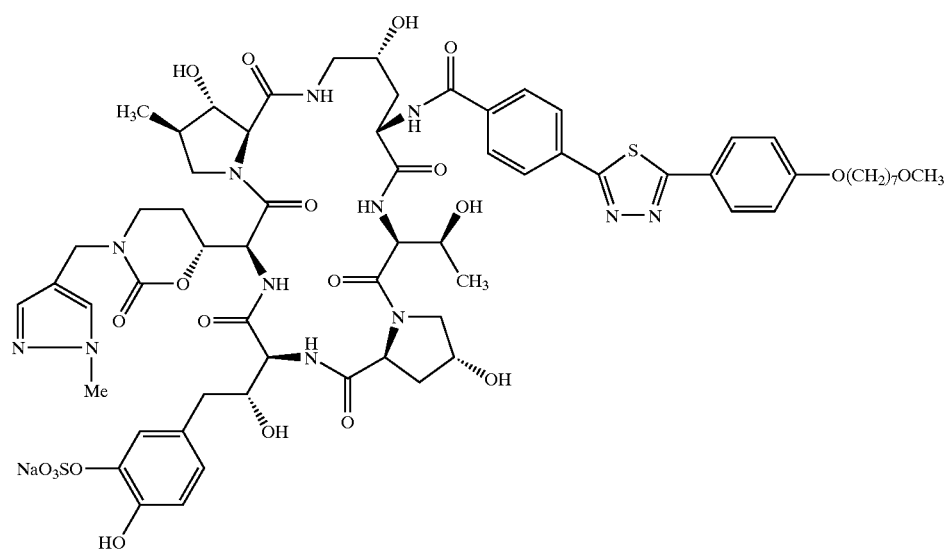 |

| Example No. | Formula |
|---|---|
| | 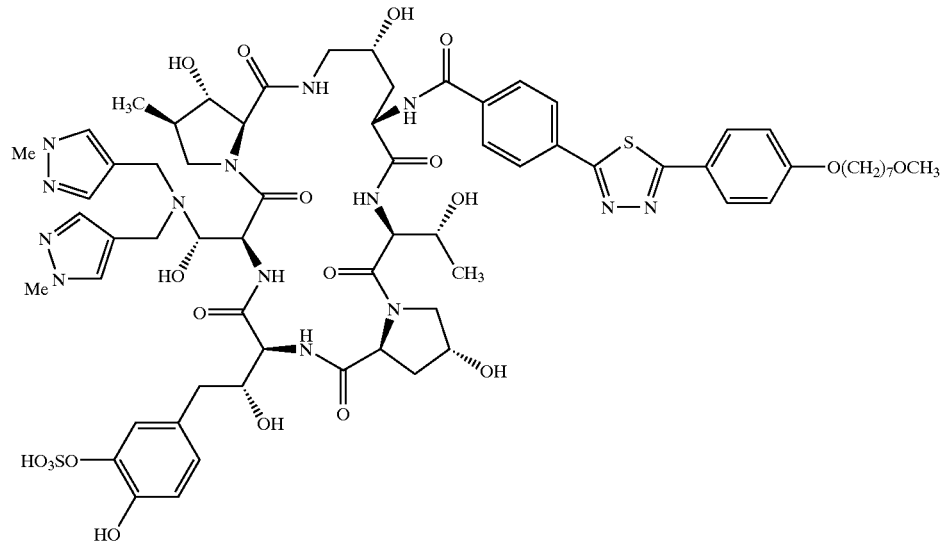 |
| 25 | 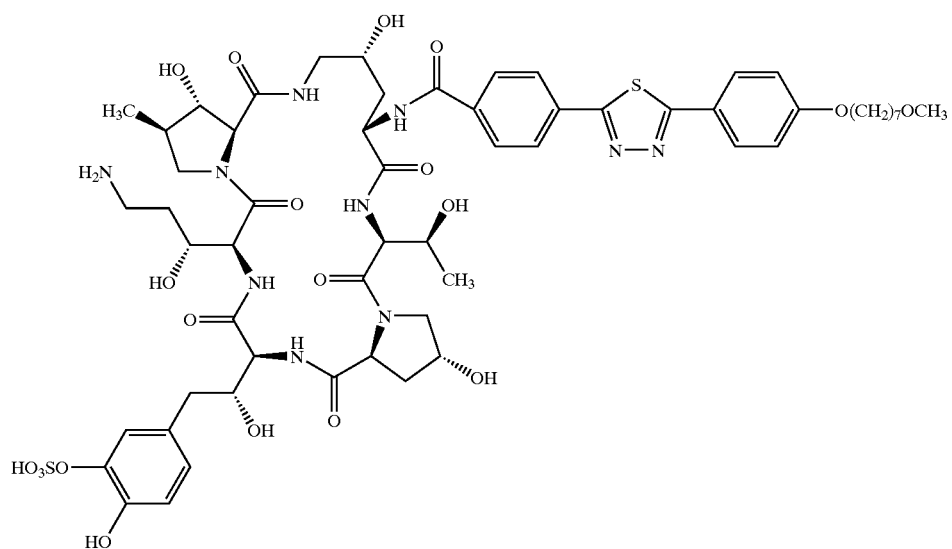 |

| Example No. | Formula |
|---|---|
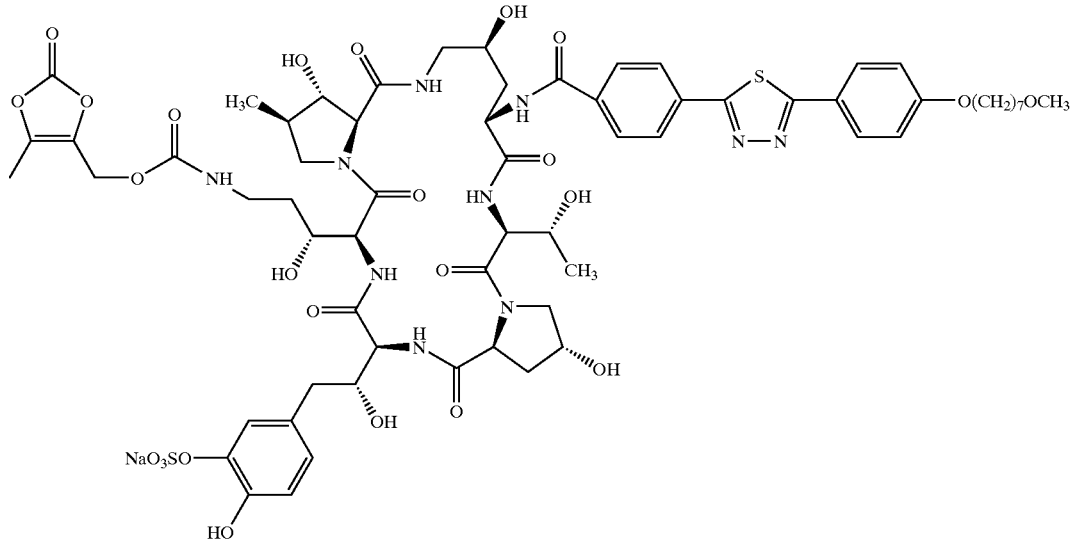
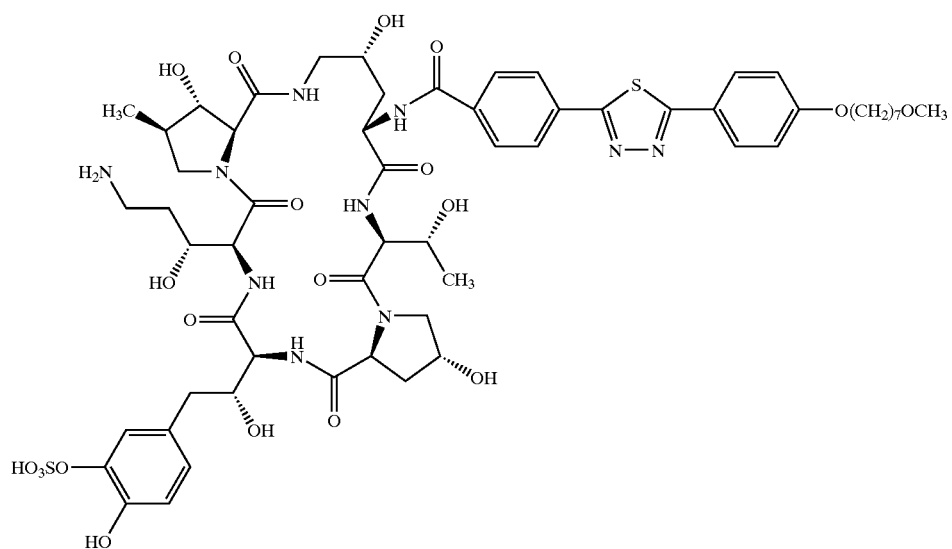
26

-continued
| Example No. | Formula |
|---|---|
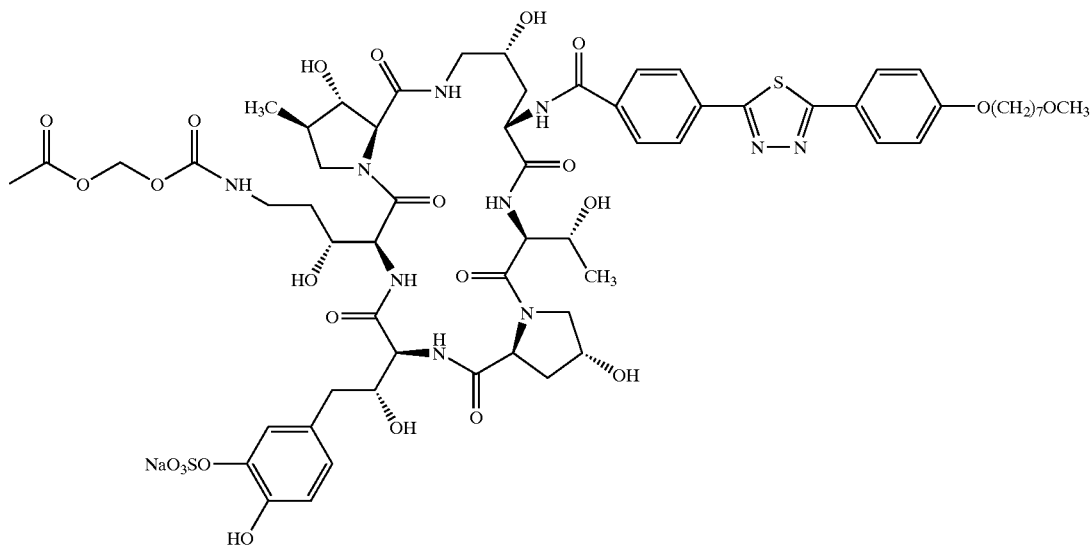
27 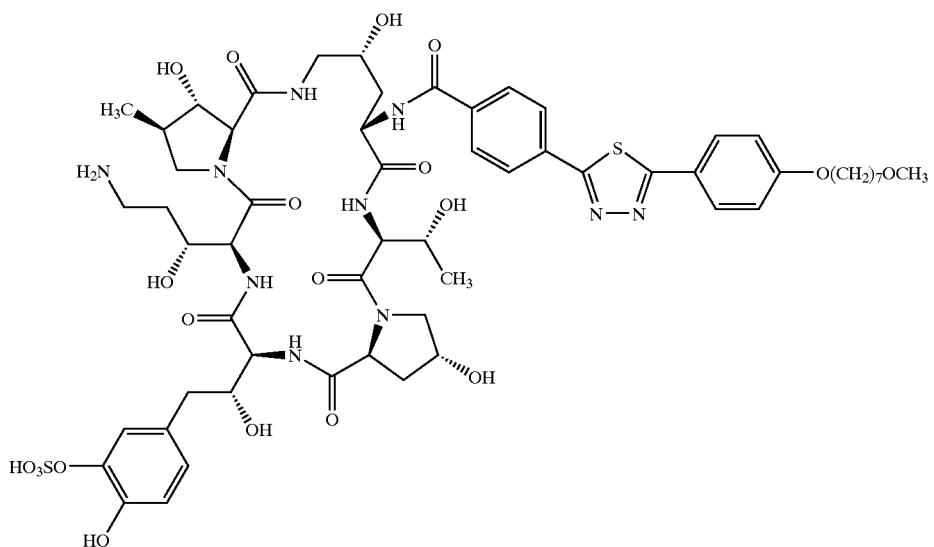

| Example No. | Formula |
|---|---|
| | 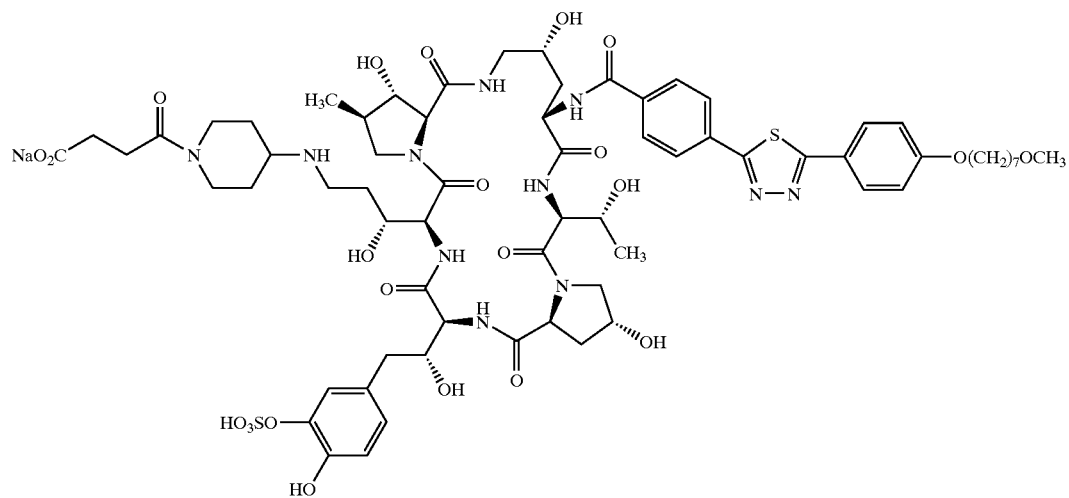 |
| 28 | 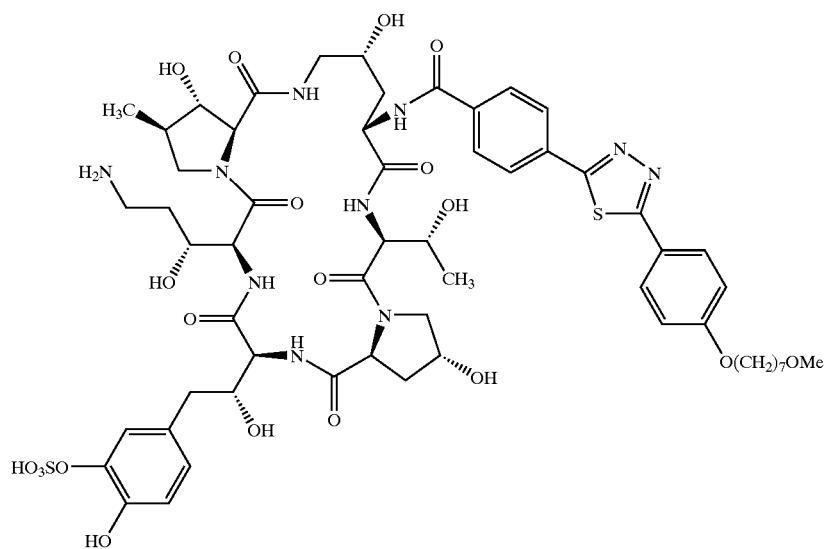 |

| Example No. | Formula |
|---|---|
| | 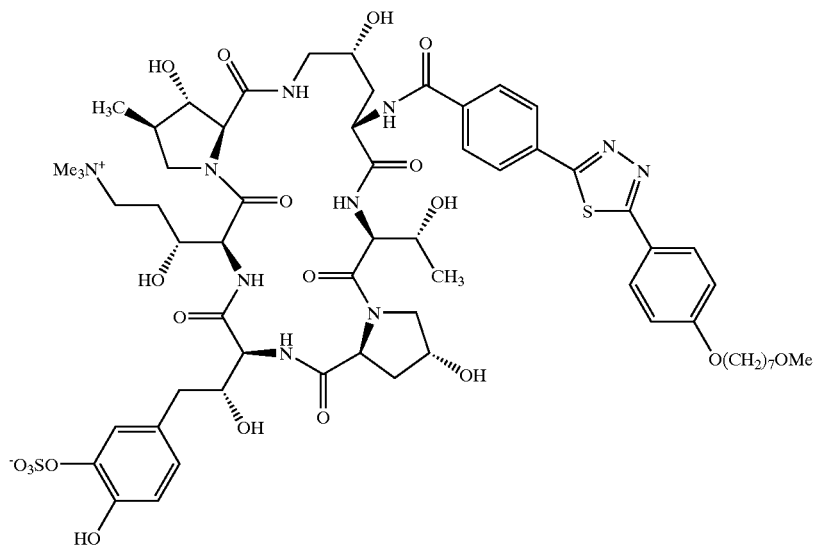 |
| 29 | 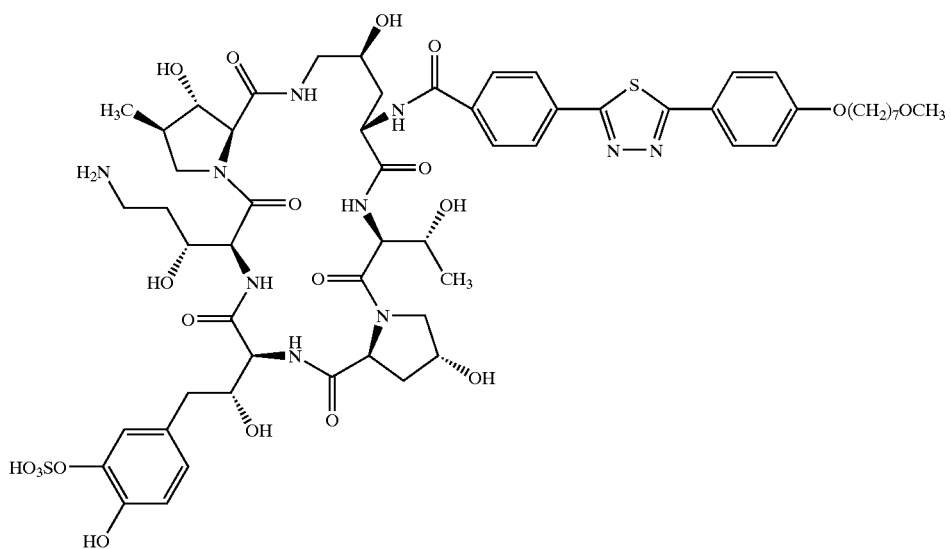 |

-continued
| Example No. | Formula |
|---|---|
| | 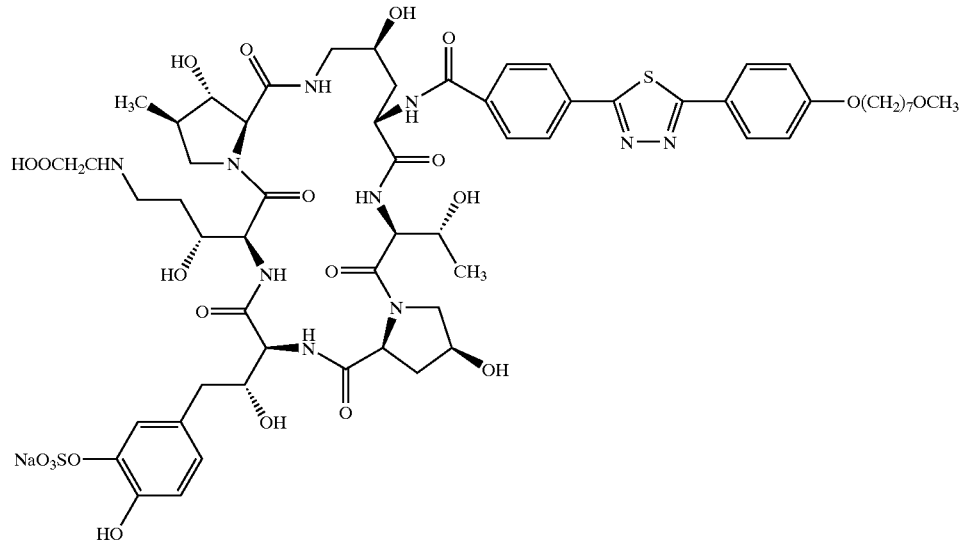 |
| 30 | 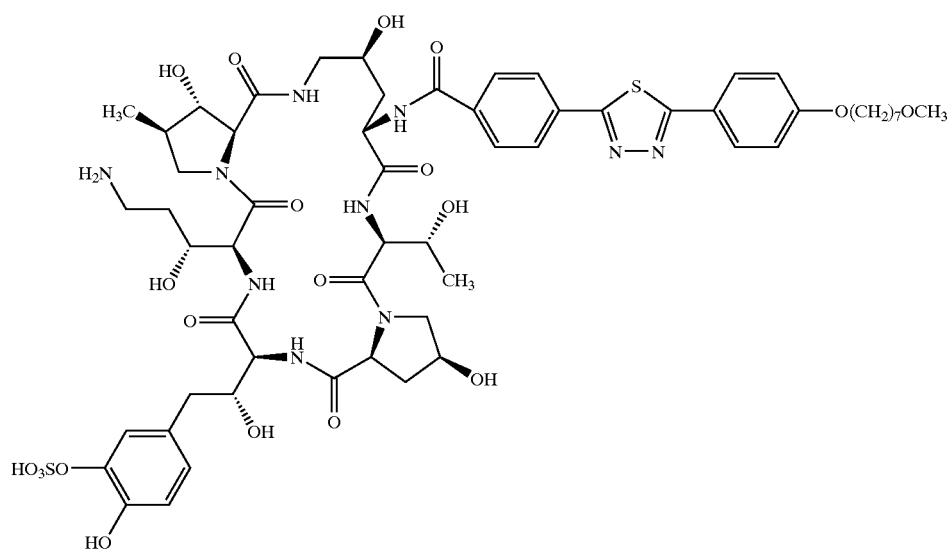 |

| Example No. | Formula |
|---|---|
| | 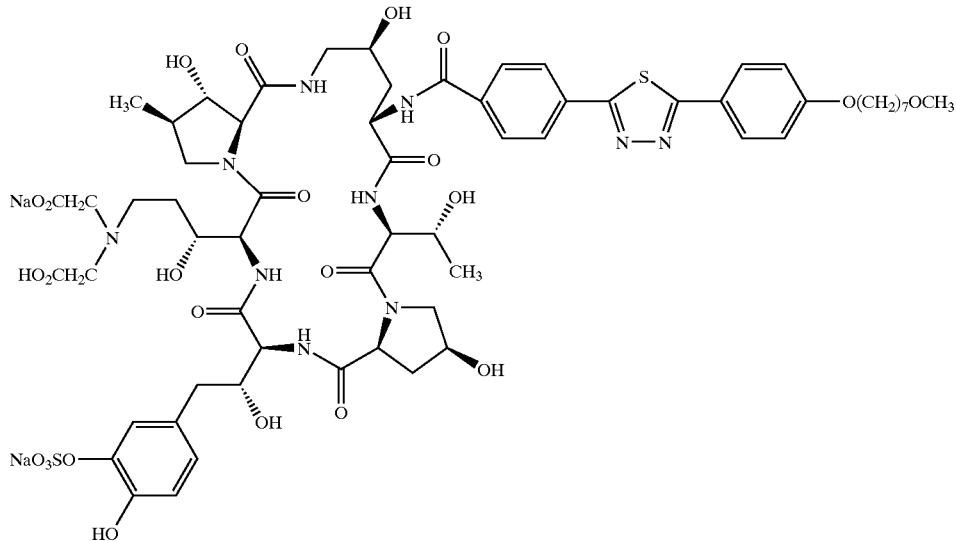 |
| 31 | 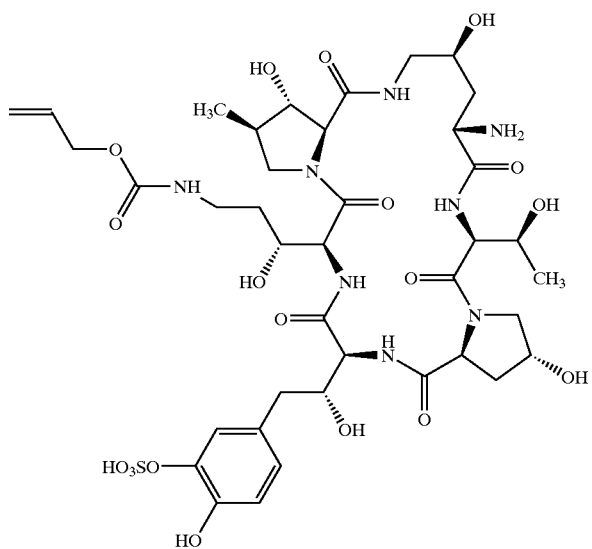 |

| Example No. | Formula |
|---|---|
| | 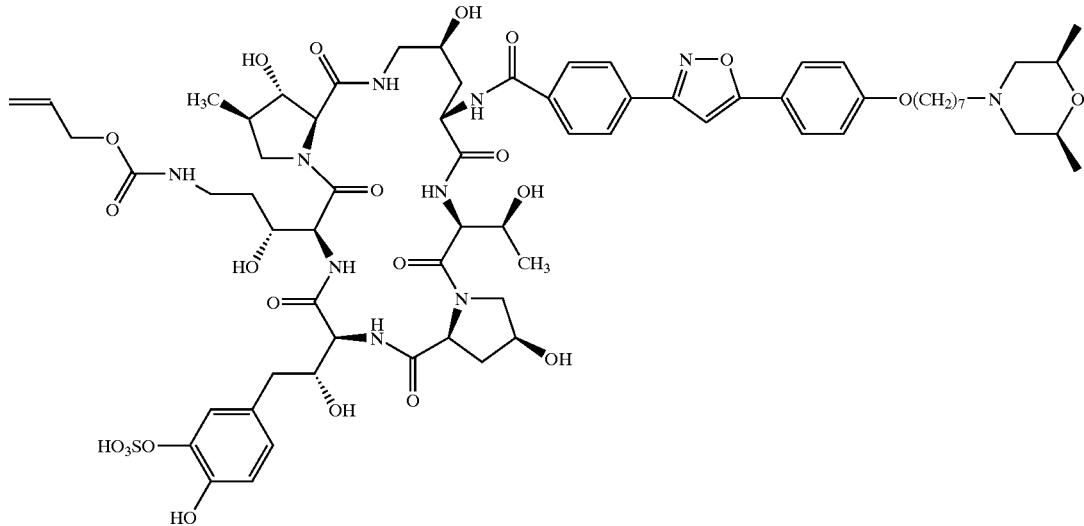 |
| 32 | 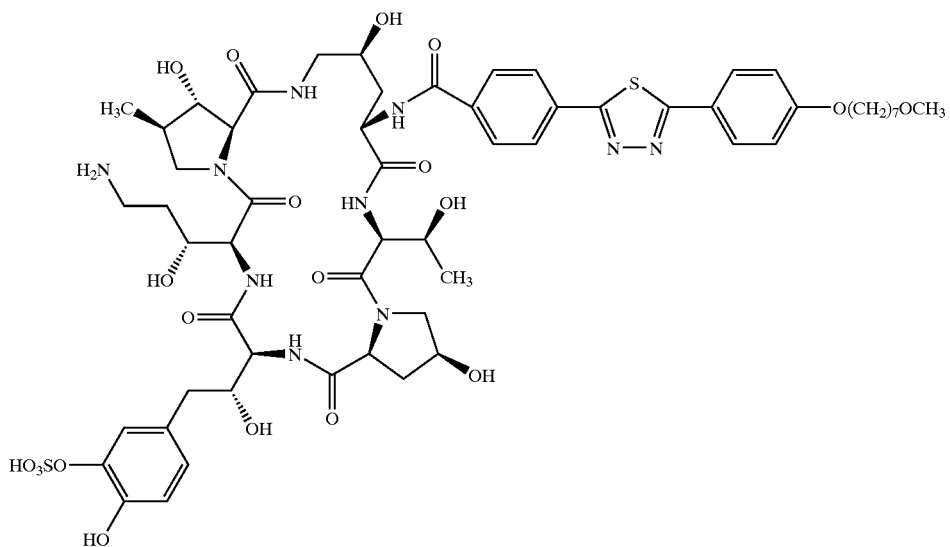 |

| Example No. | Formula |
|---|---|
| | 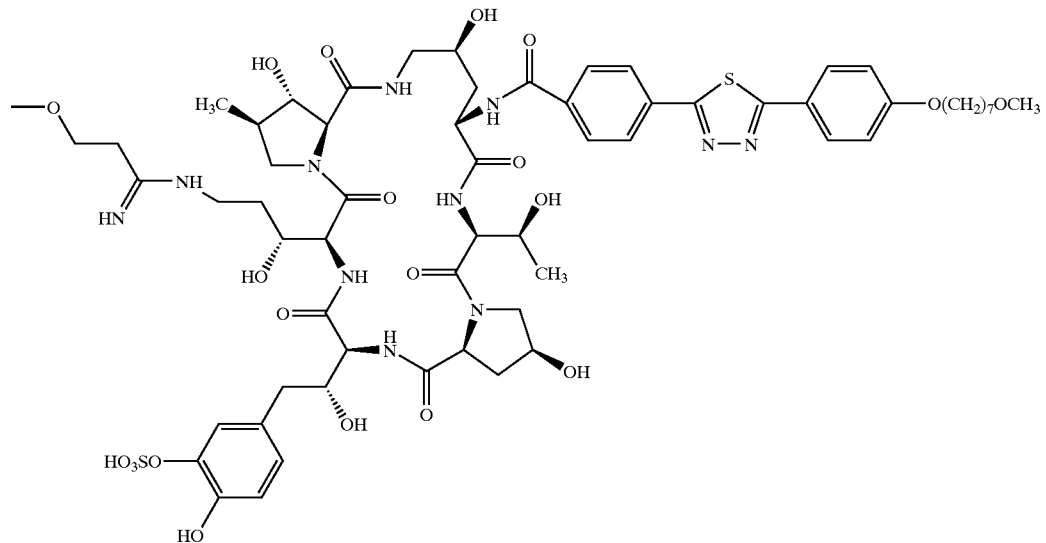 |
| 33 | 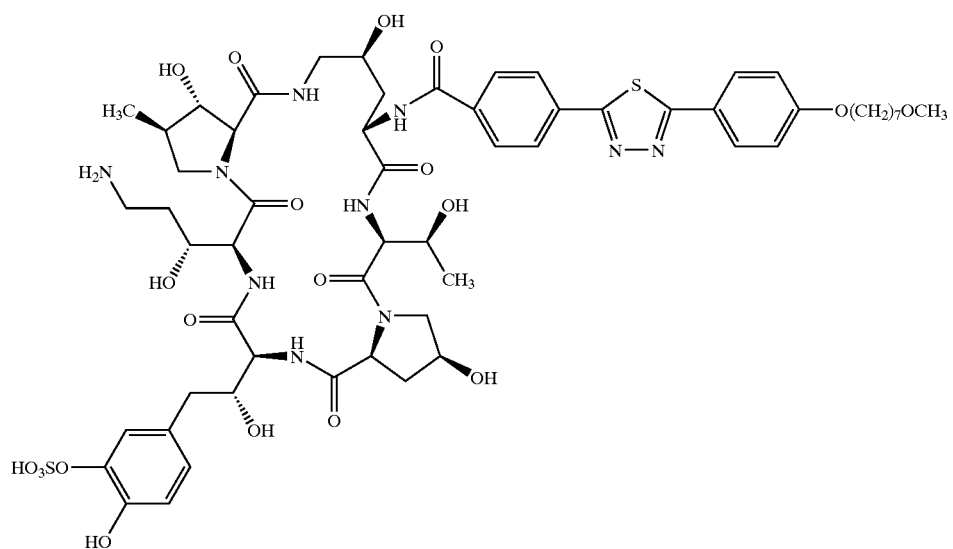 |

| Example No. | Formula |
|---|---|
| | 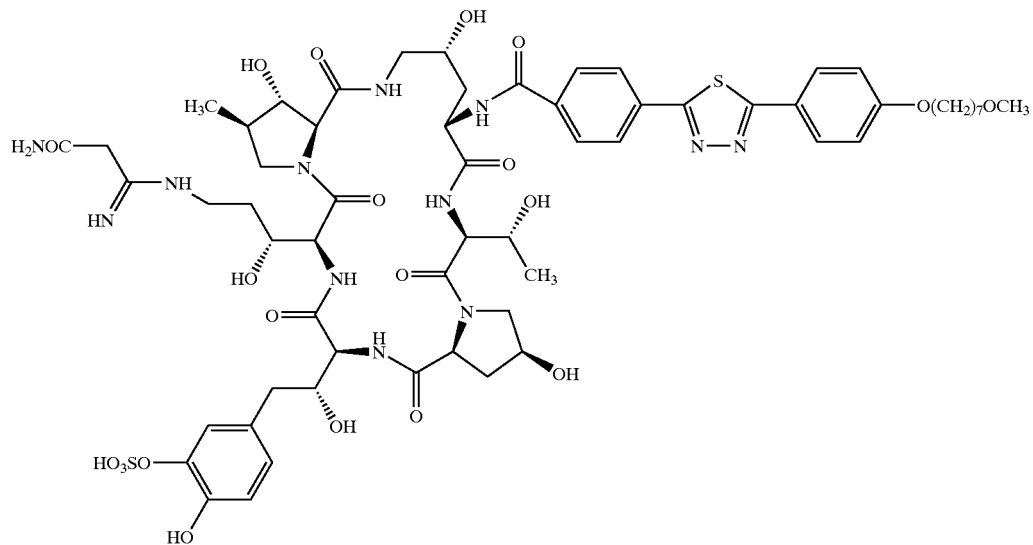 |
| 34 | 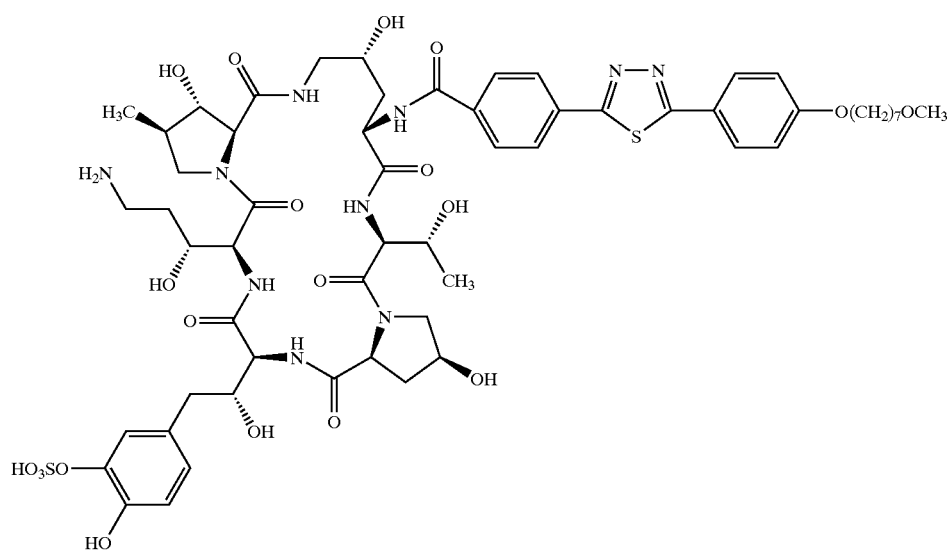 |

| Example No. | Formula |
|---|---|
| | 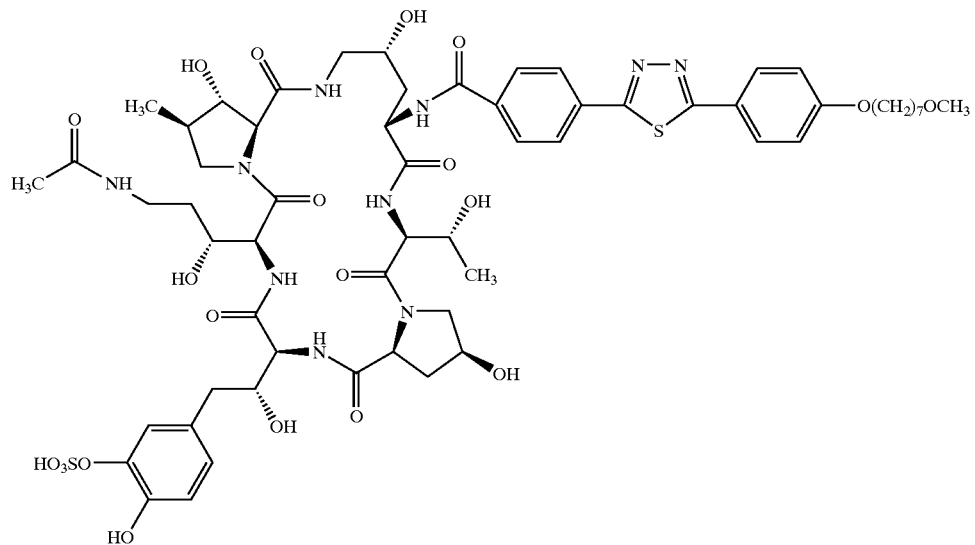 |
| 35 | 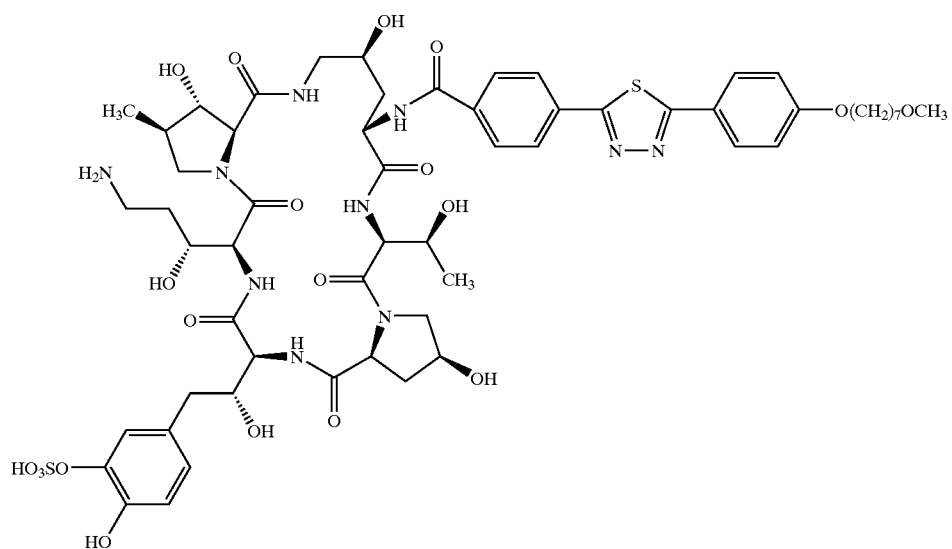 |

| Example No. | Formula |
|---|---|
| | 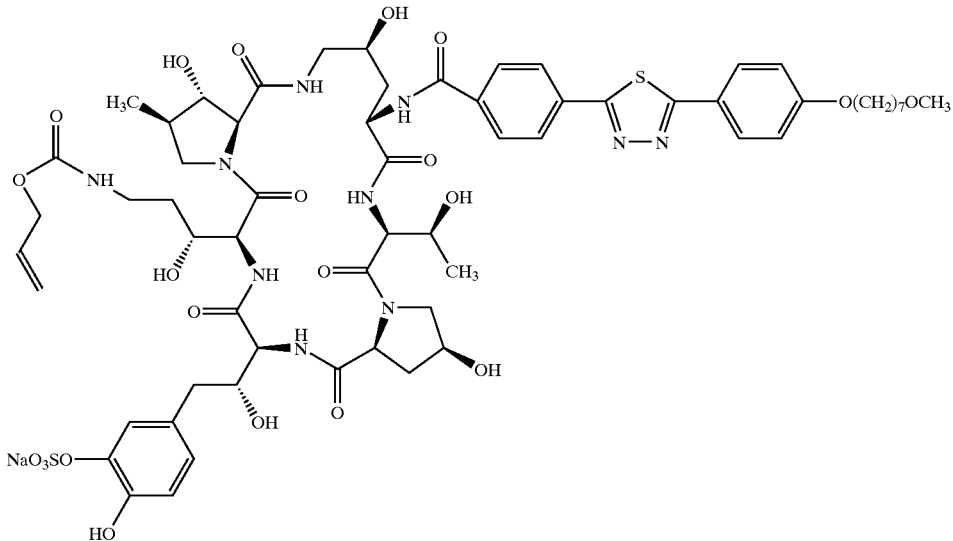 |
| 36 | 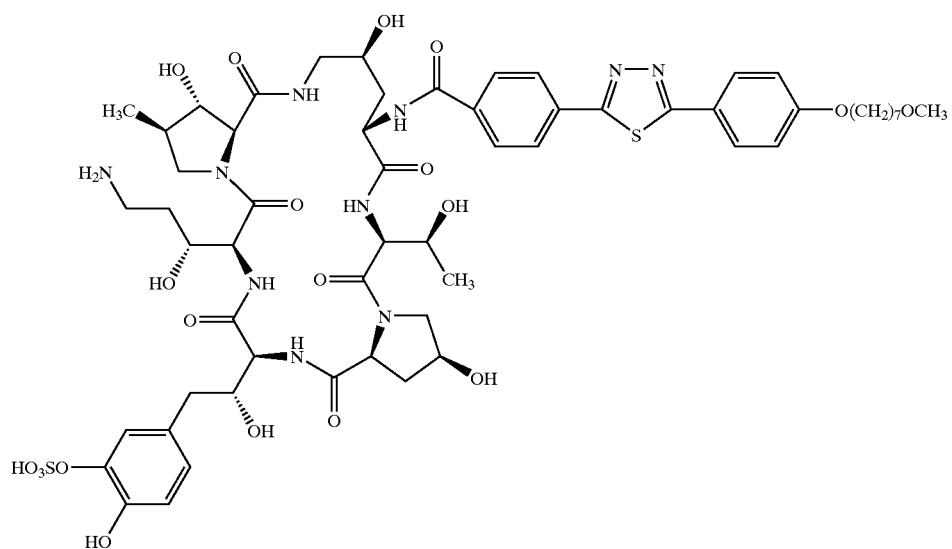 |

| Example No. | Formula |
|---|---|
| | 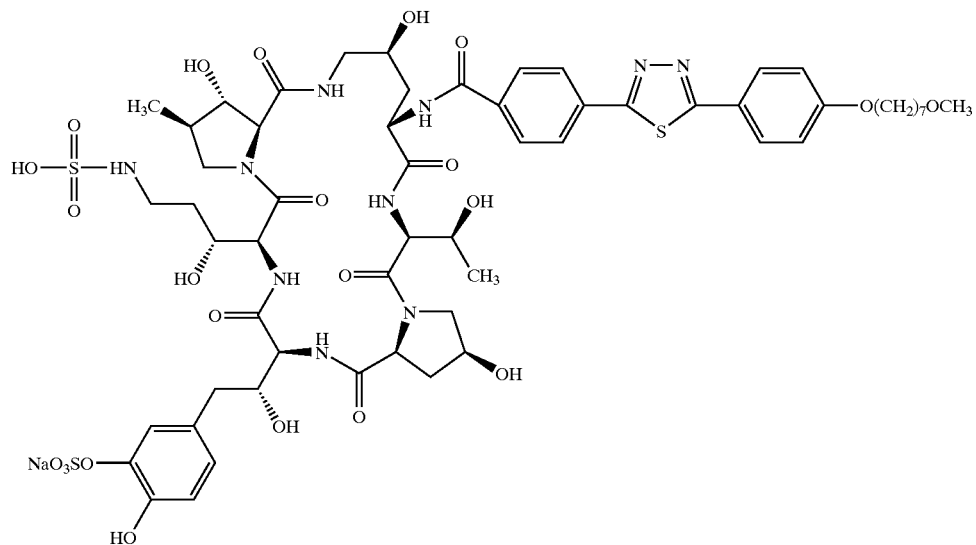 |
| 37 | 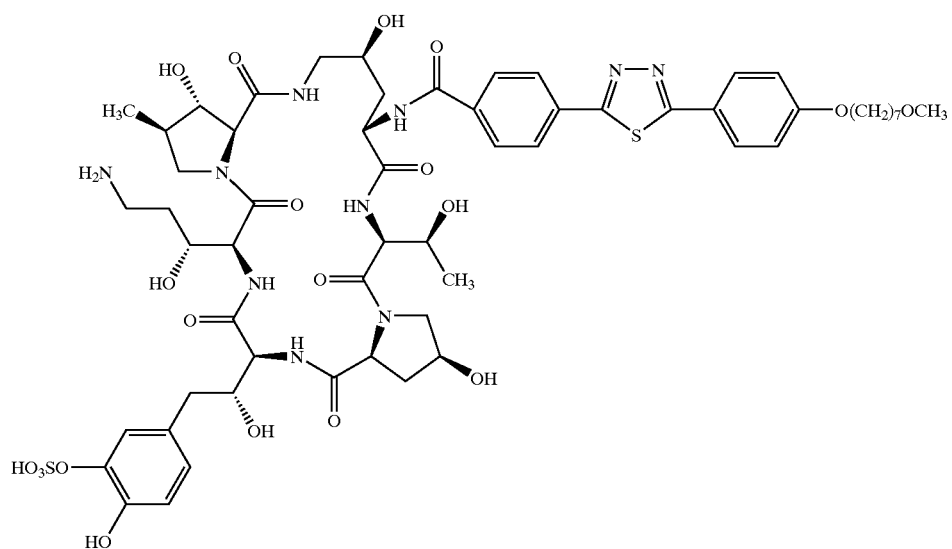 |

| Example No. | Formula |
|---|---|
| | 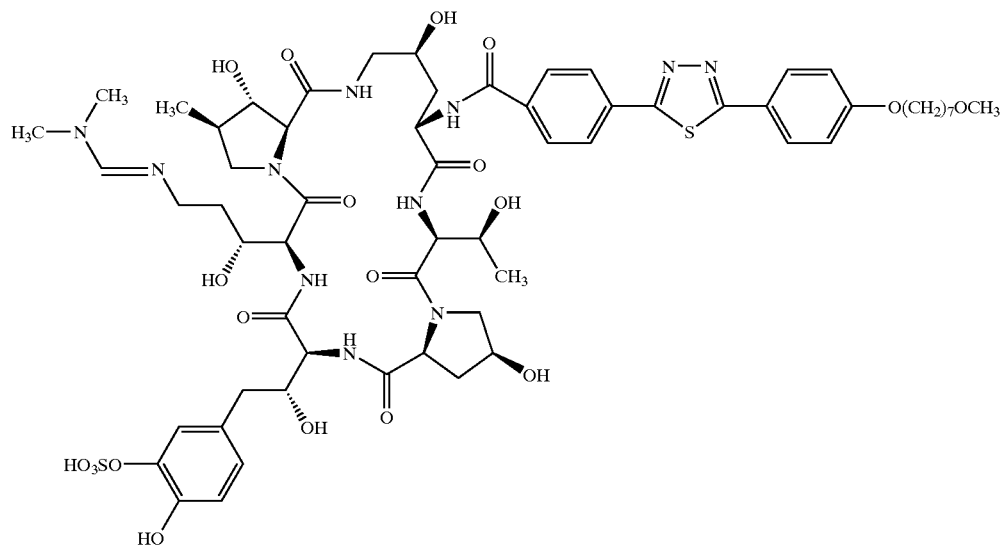 |
| 38 | 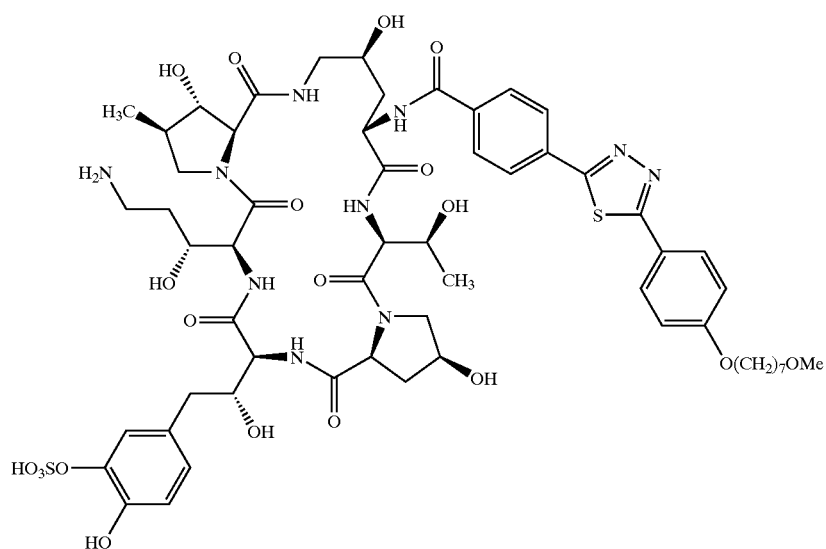 |

| Example No. | Formula |
|---|---|
| | 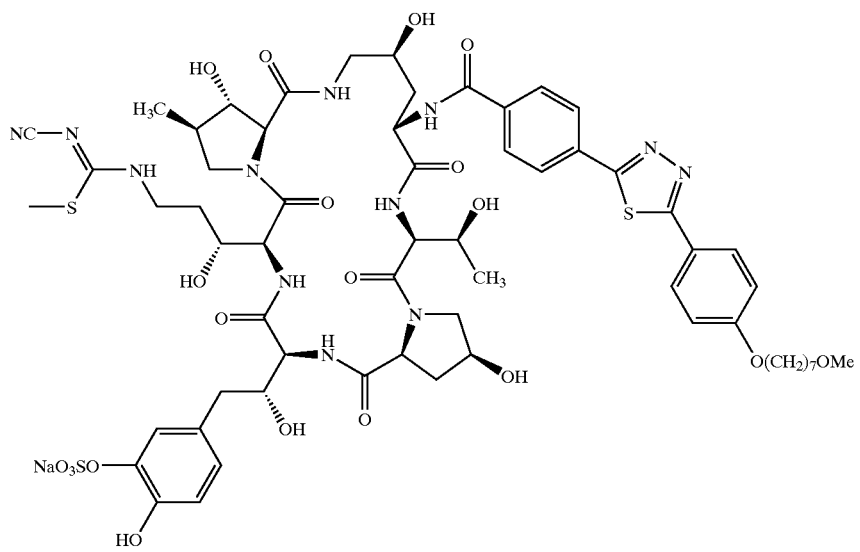 |
| 39 | 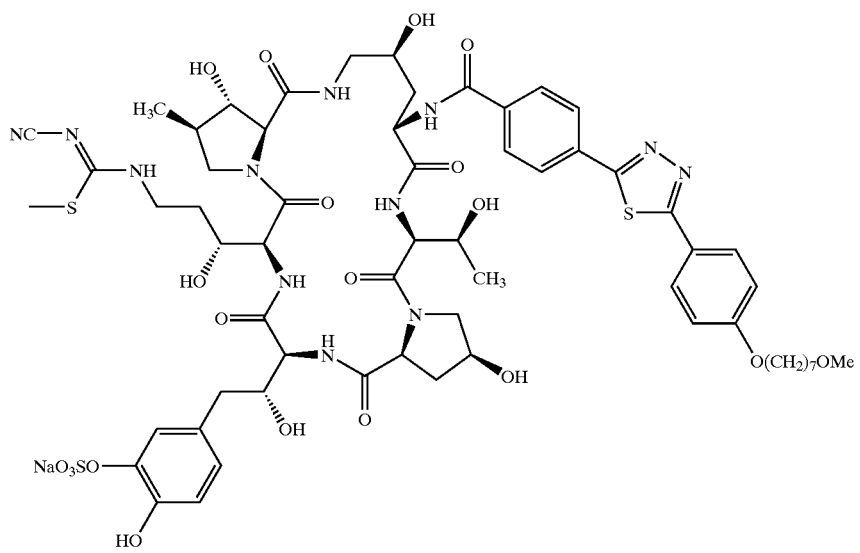 |

| Example No. | Formula |
|---|---|
| | 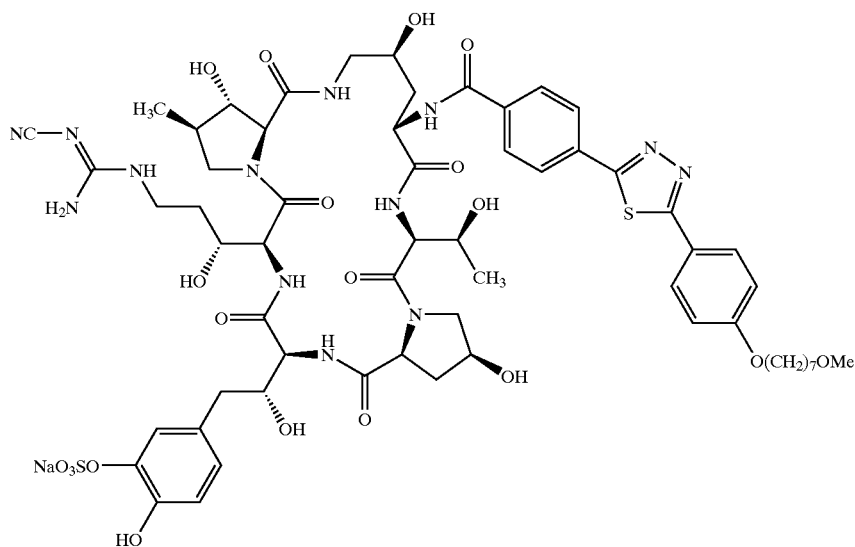 |
| 40 | 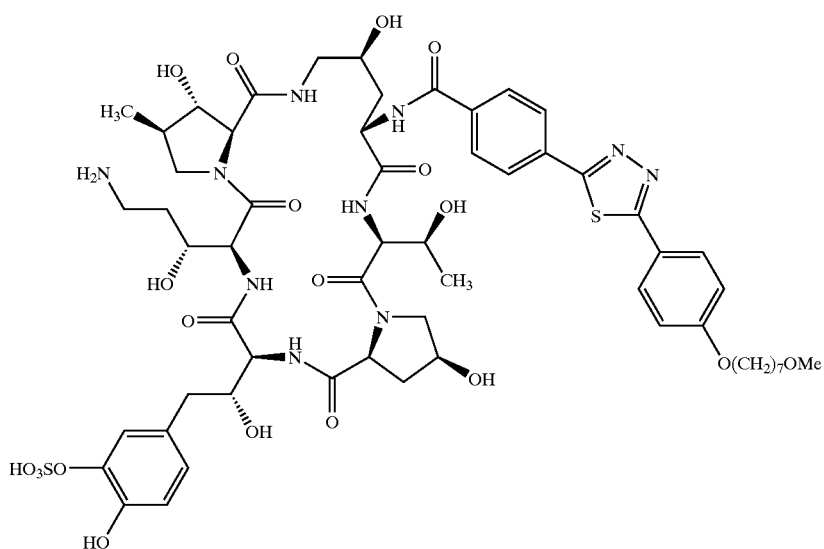 |

-continued
| Example No. | Formula |
|---|---|
| | 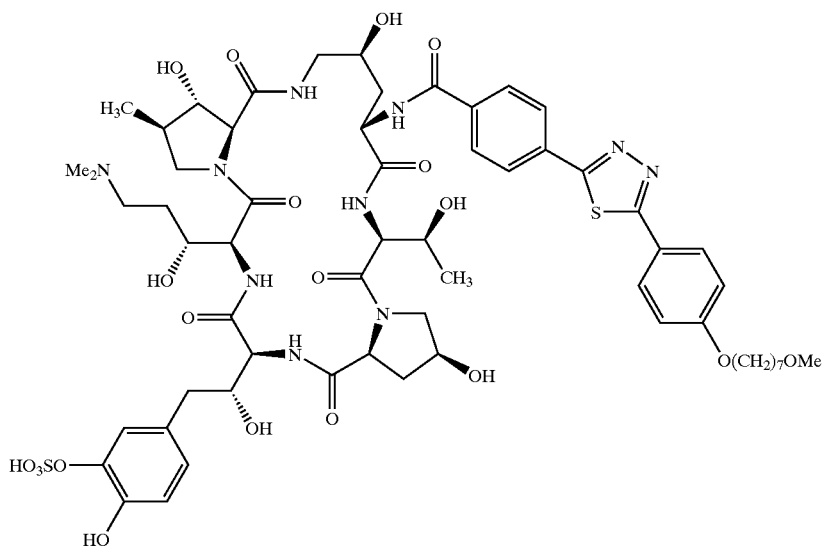 |
| 41 | 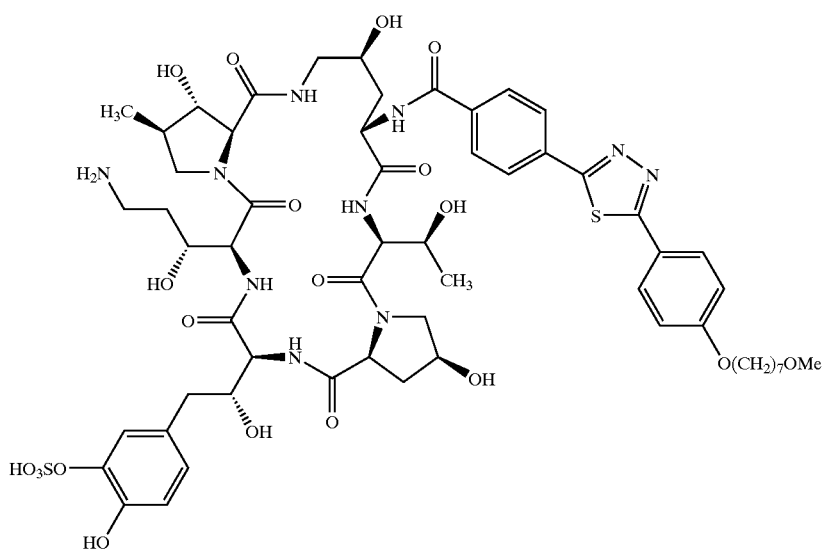 |

-continued
| Example No. | Formula |
|---|---|
| | 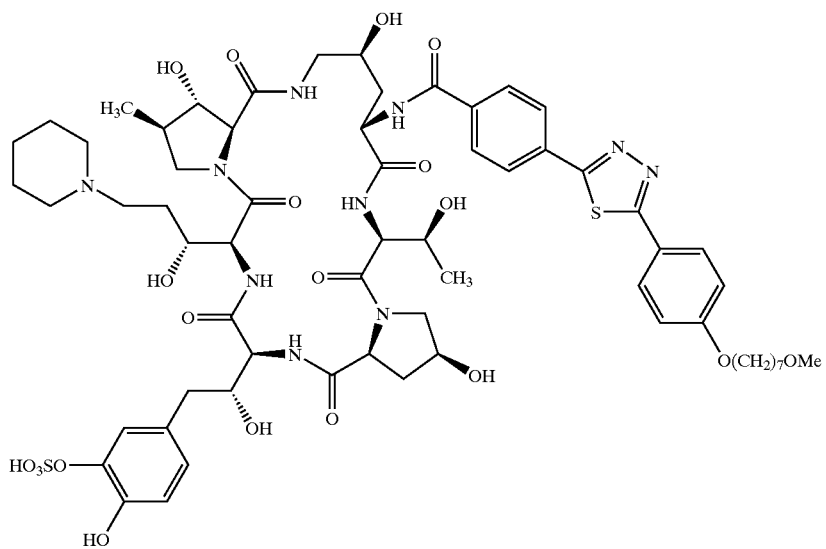 |
| 42 | 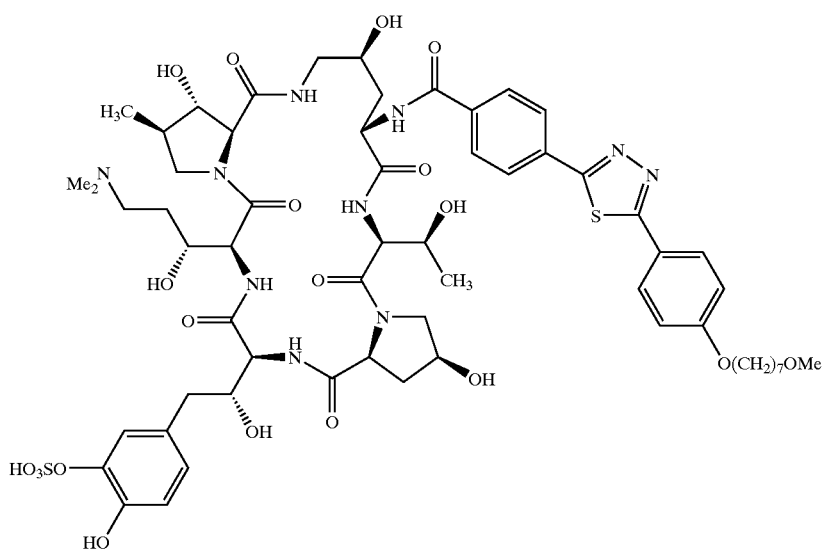 |

-continued
| Example No. | Formula |
|---|---|
| | 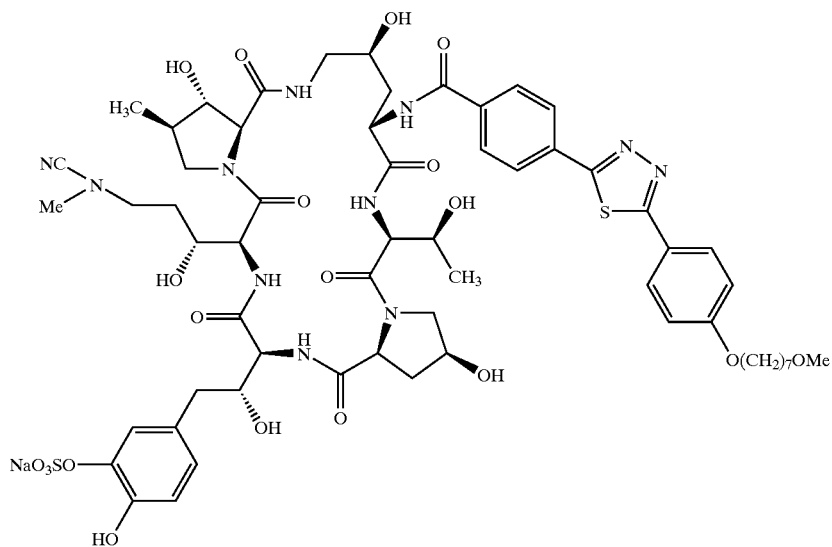 |
| 43 | 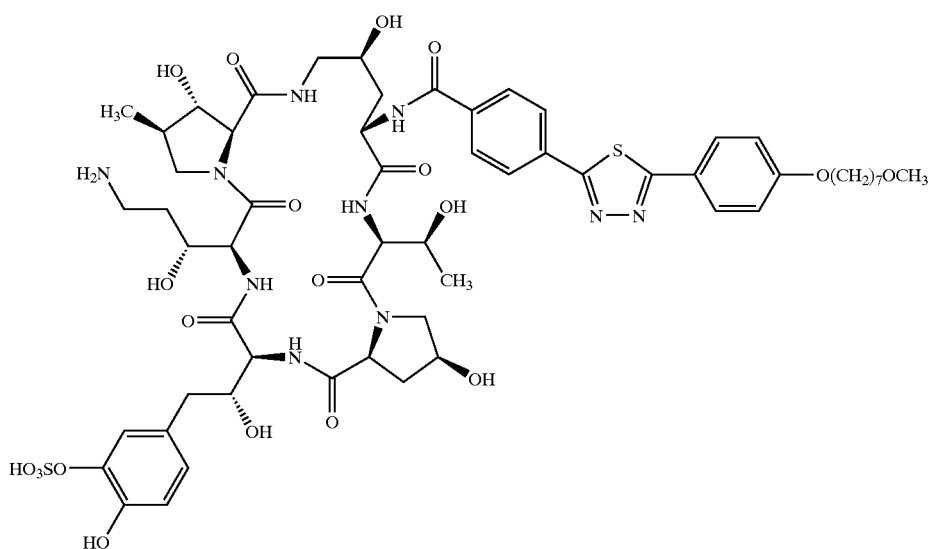 |

| Example No. | Formula |
|---|---|
| | 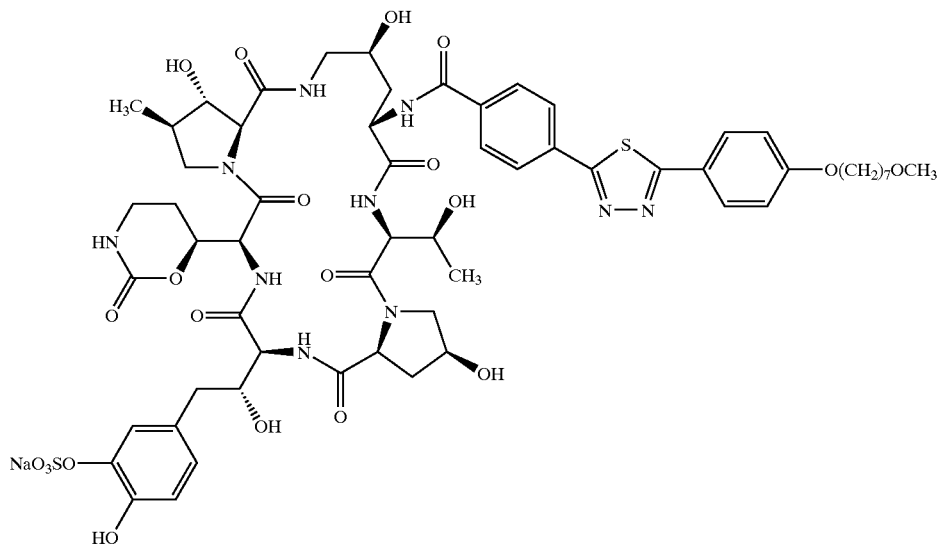 |
| 44 | 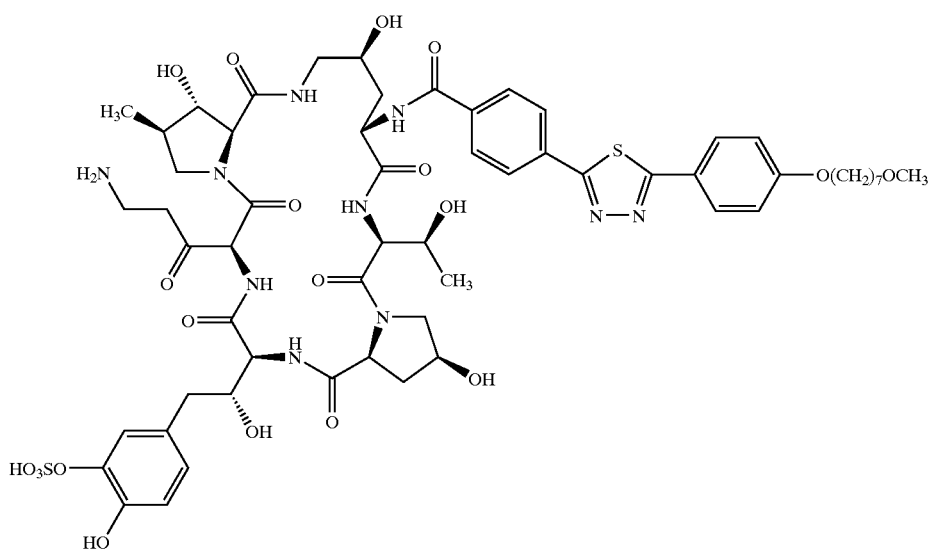 |

-continued
| Example No. | Formula |
|---|---|
| | 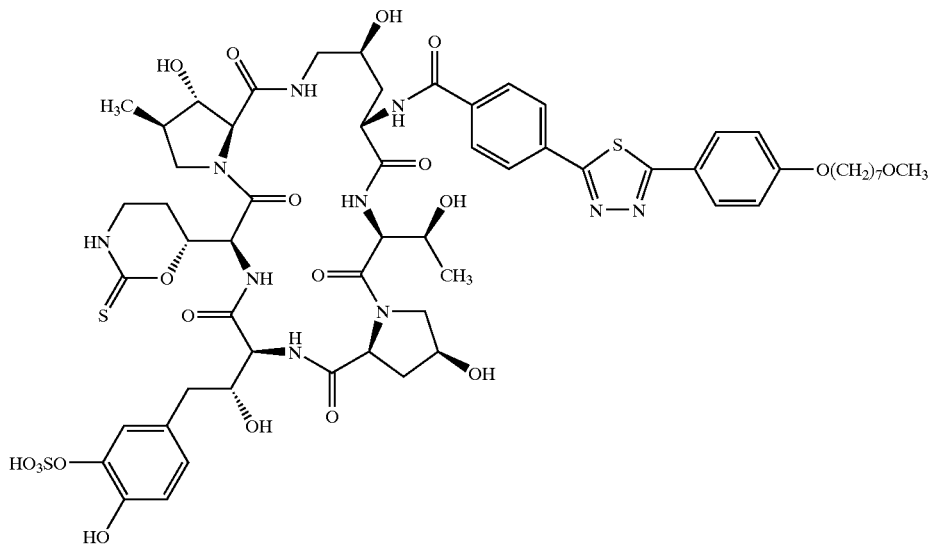 |
| 45 | 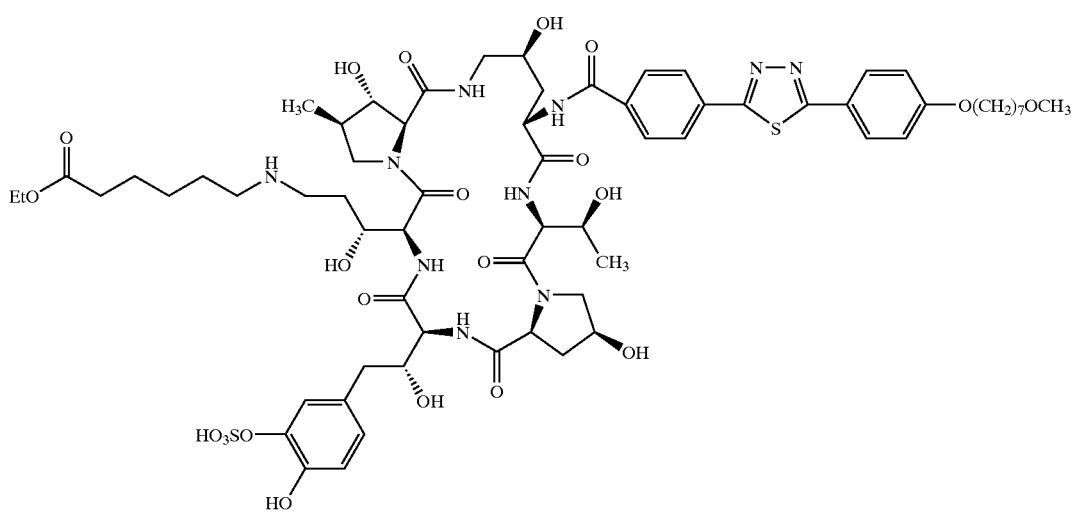 |
| | 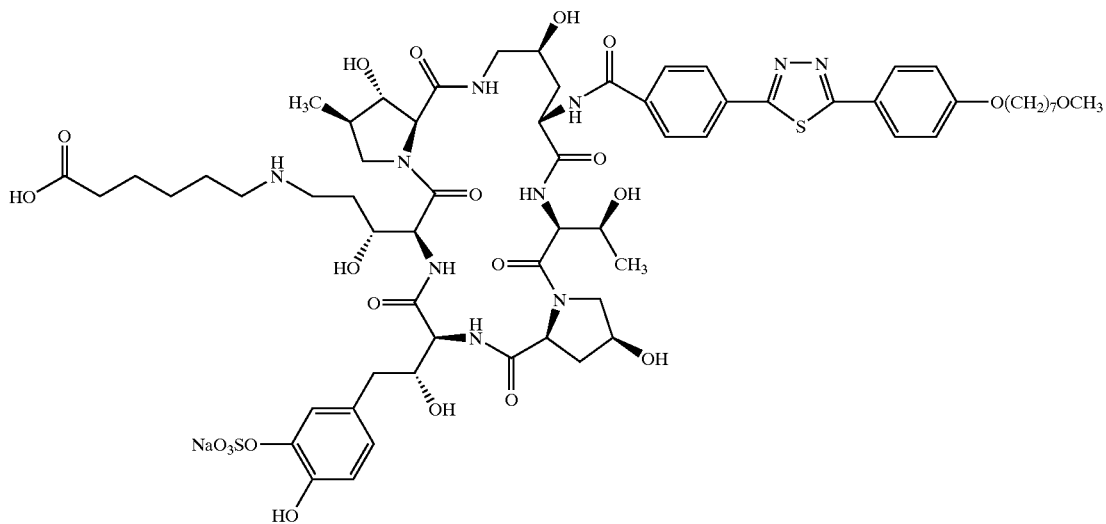 |

-continued
| Example No. | Formula |
|---|---|
| 46 | 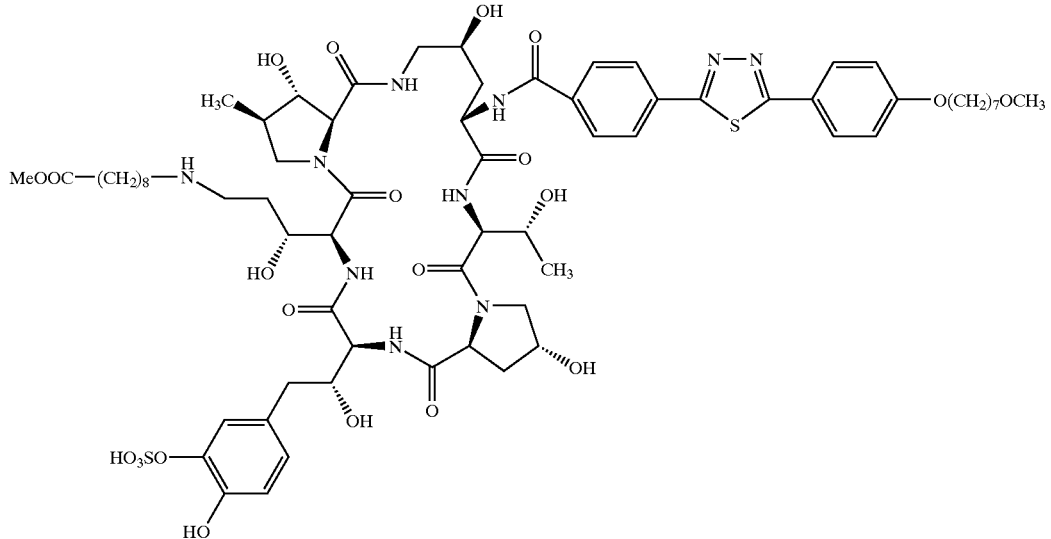<br>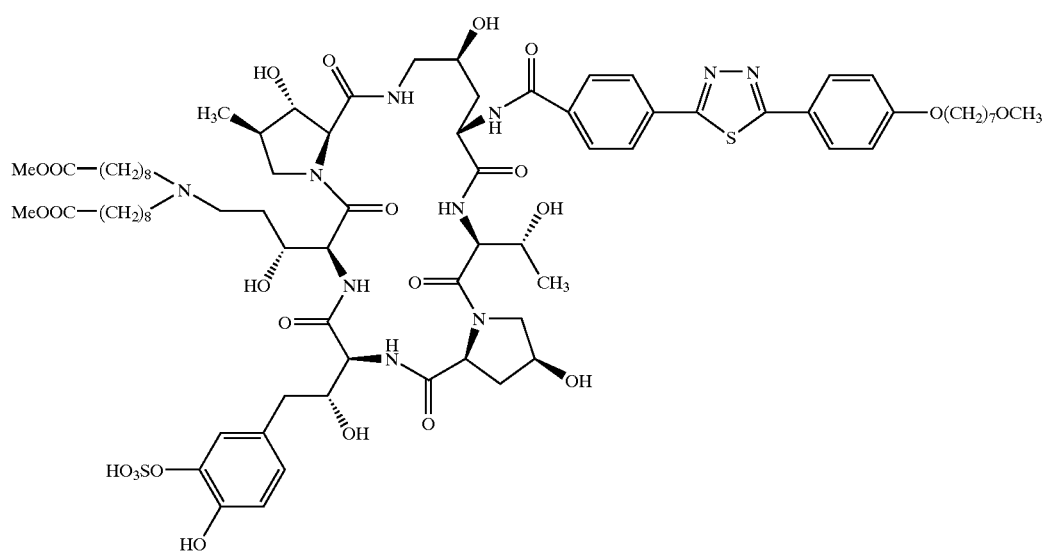 |

-continued
| Example No. | Formula |
|---|---|
| | 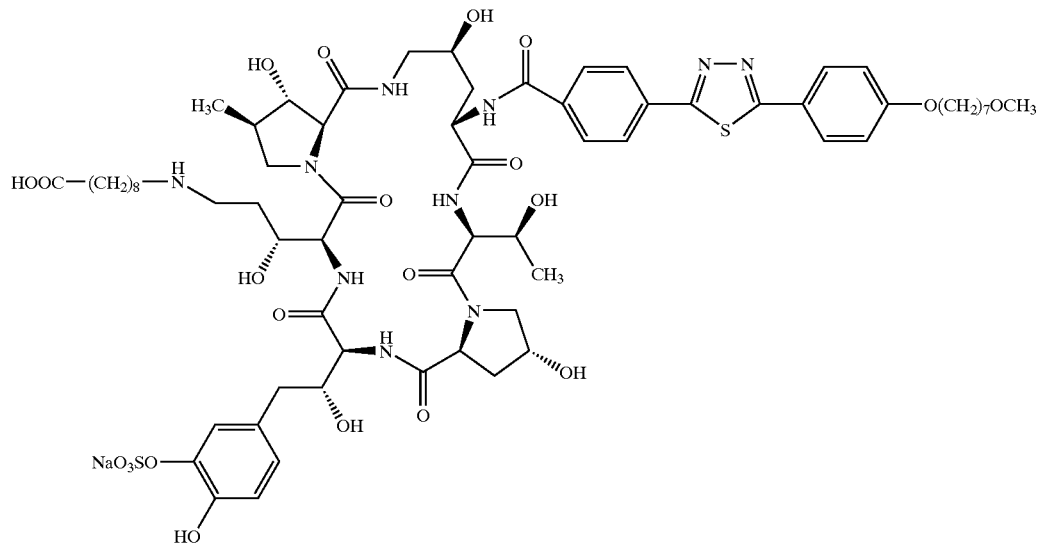 |
| 47 | 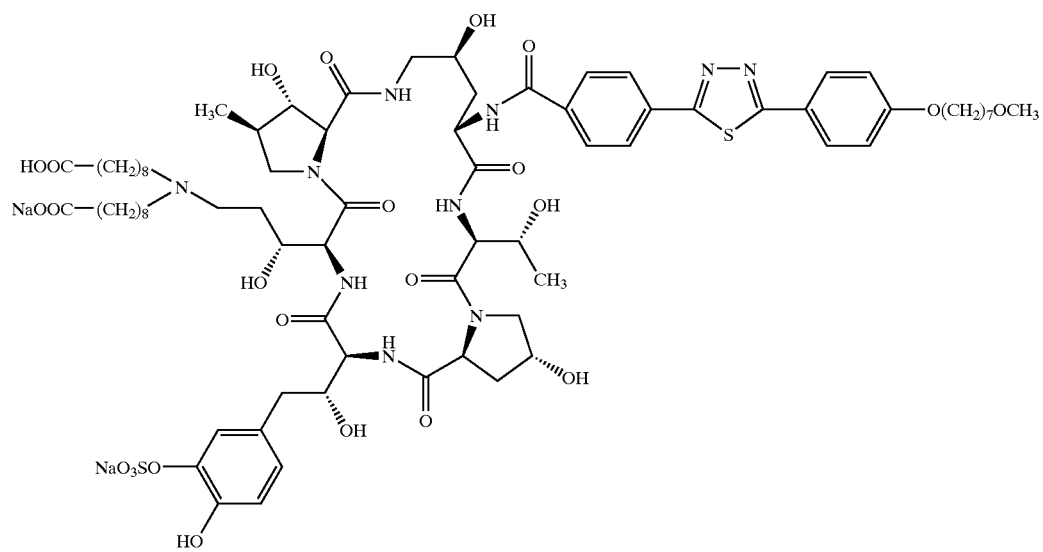 |
| | deleted |
| | deleted |

-continued
| Example No. | Formula |
|---|---|
| 48 | 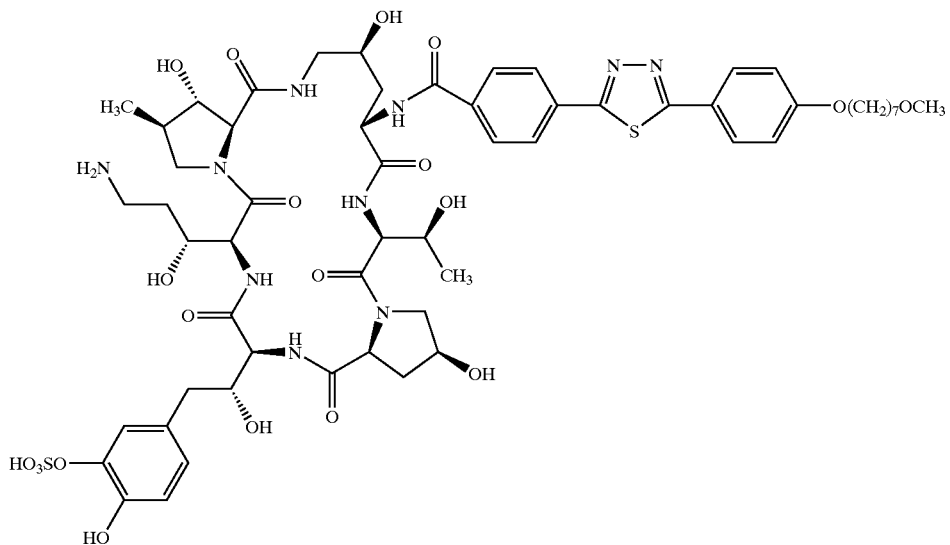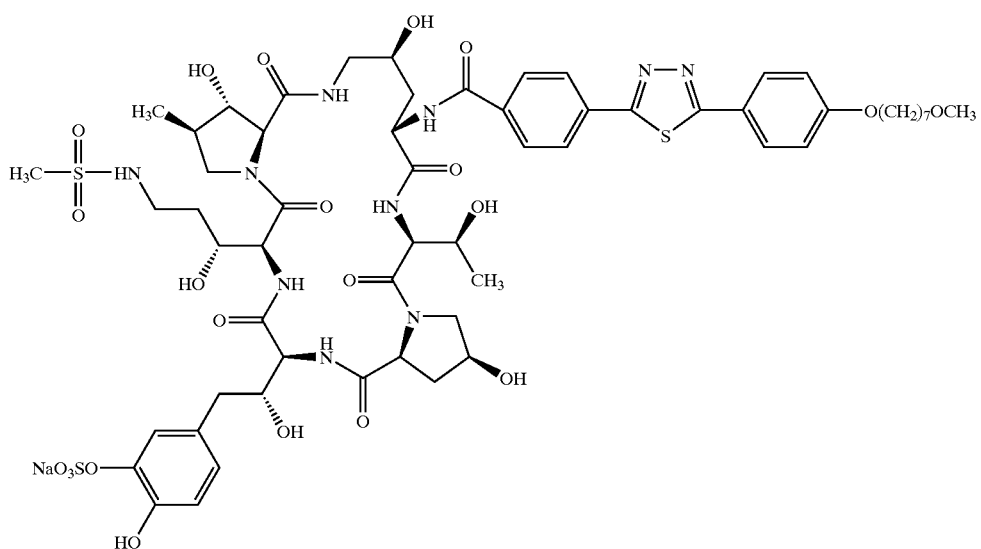 |

-continued
| Example No. | Formula |
|---|---|
| 49 | 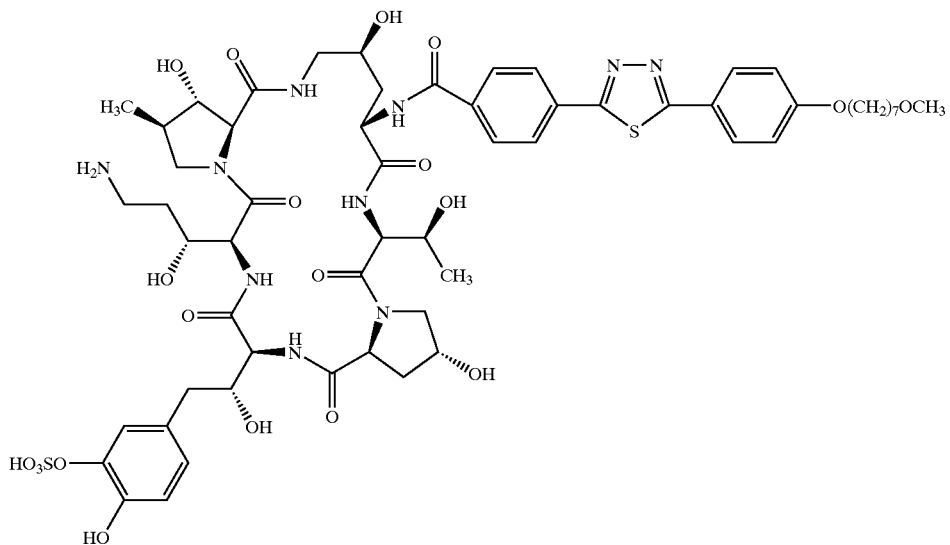 |
| | 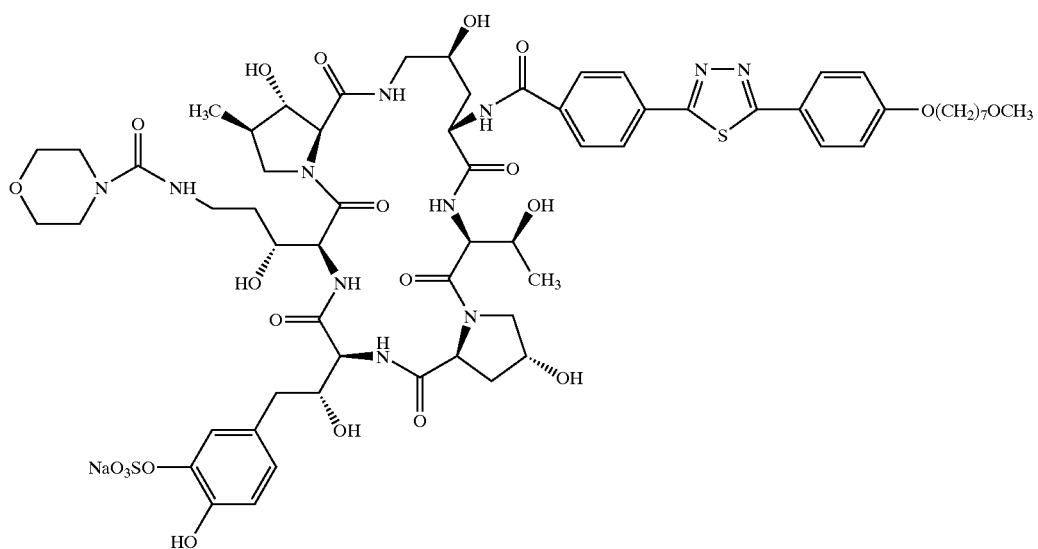 |

| Example No. | Formula |
|---|---|
| 50 | 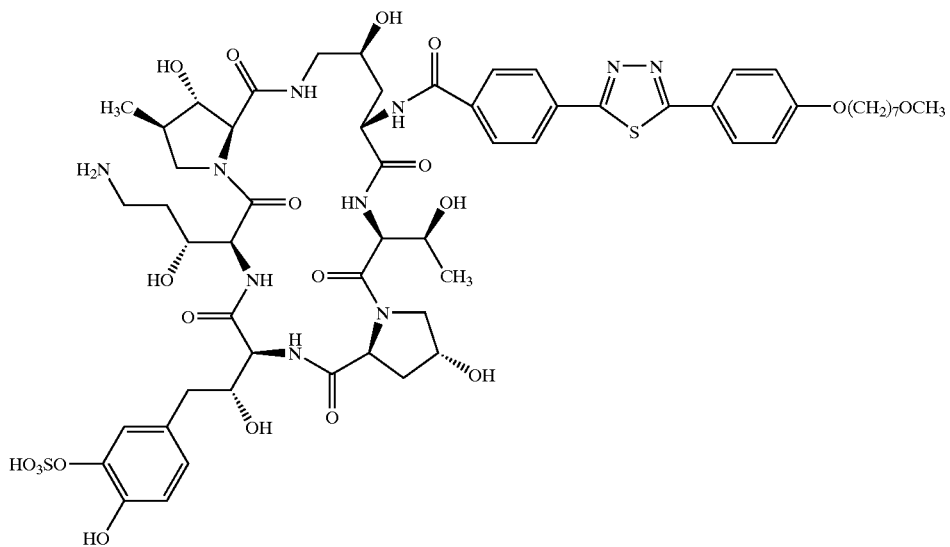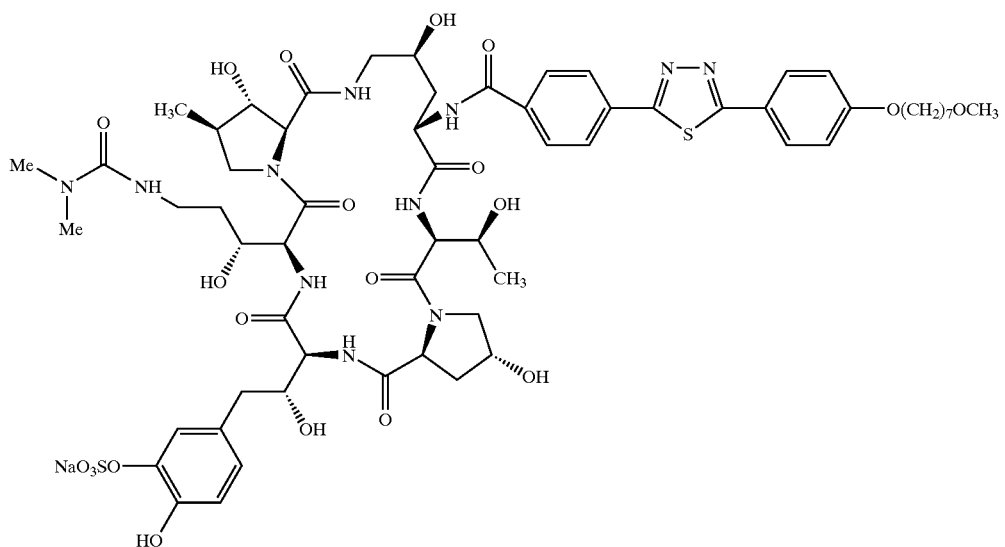 |

-continued
| Example No. | Formula |
|---|---|
| 51 | 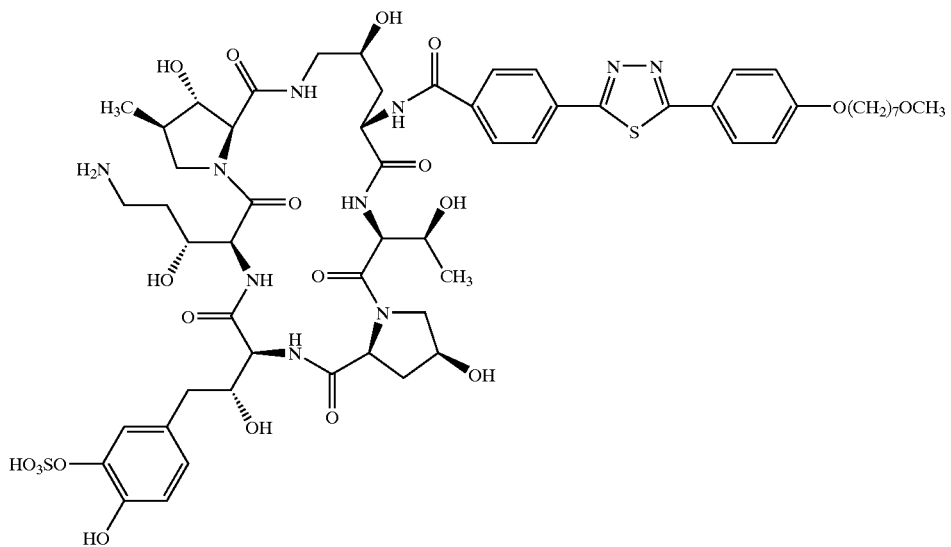 |
| | 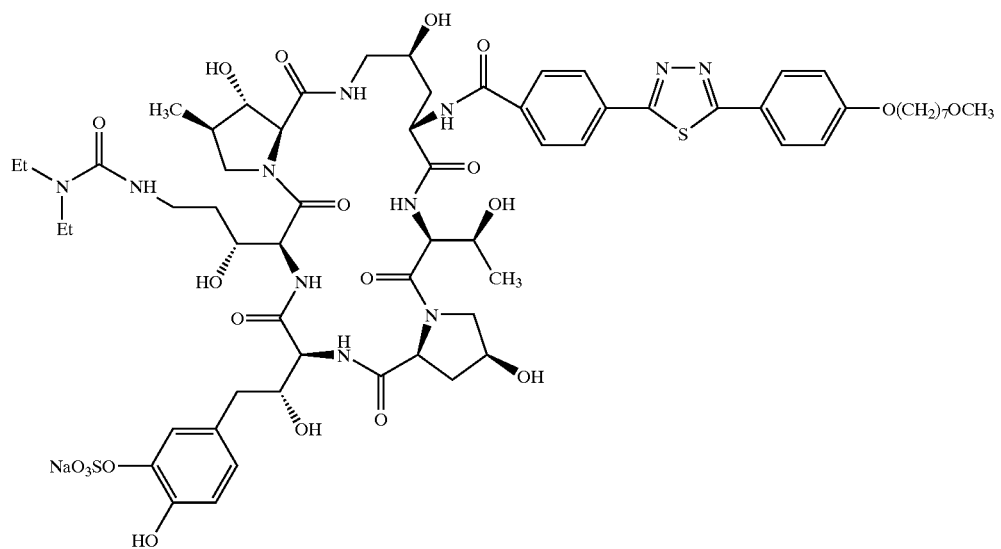 |

| Example No. | Formula |
|---|---|
| 52 | 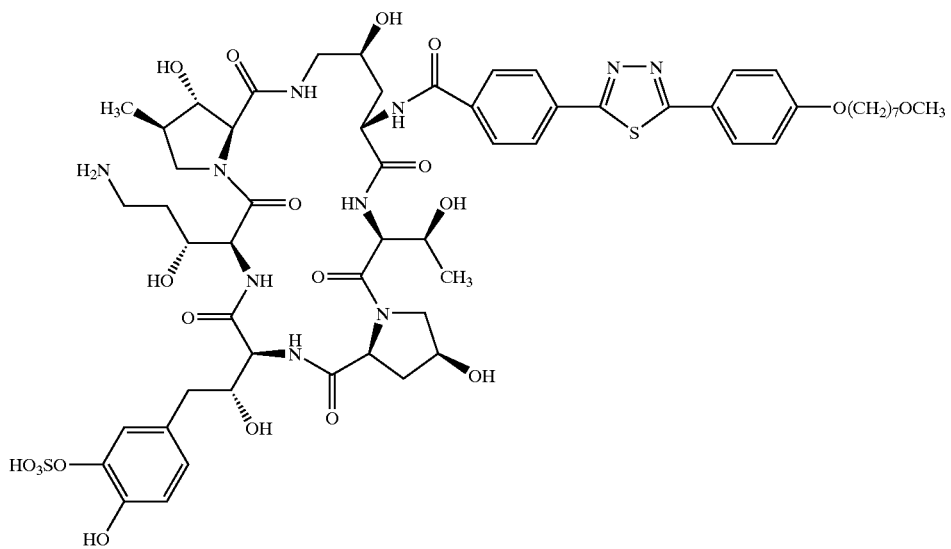 |
| | 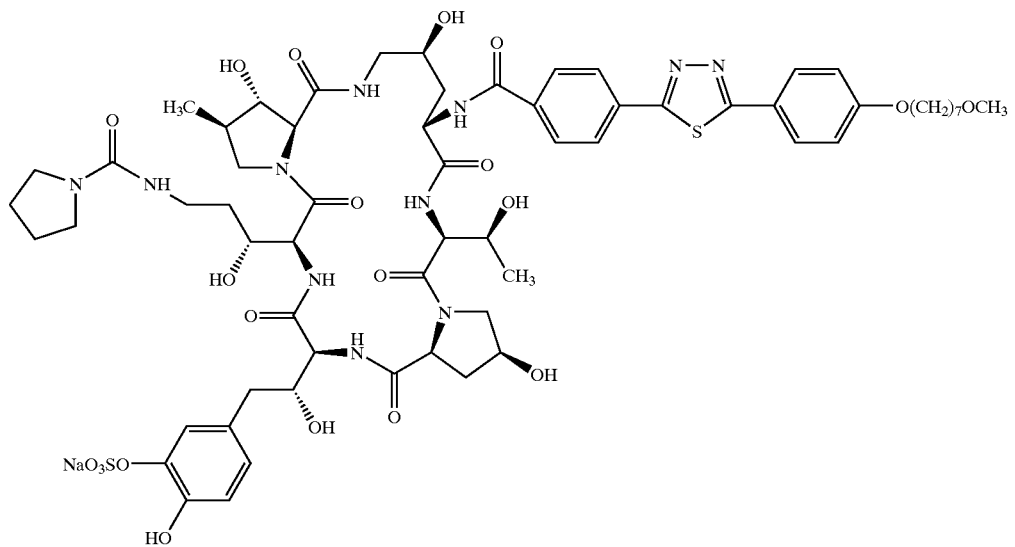 |

-continued
| Example No. | Formula |
|---|---|
| 53 | 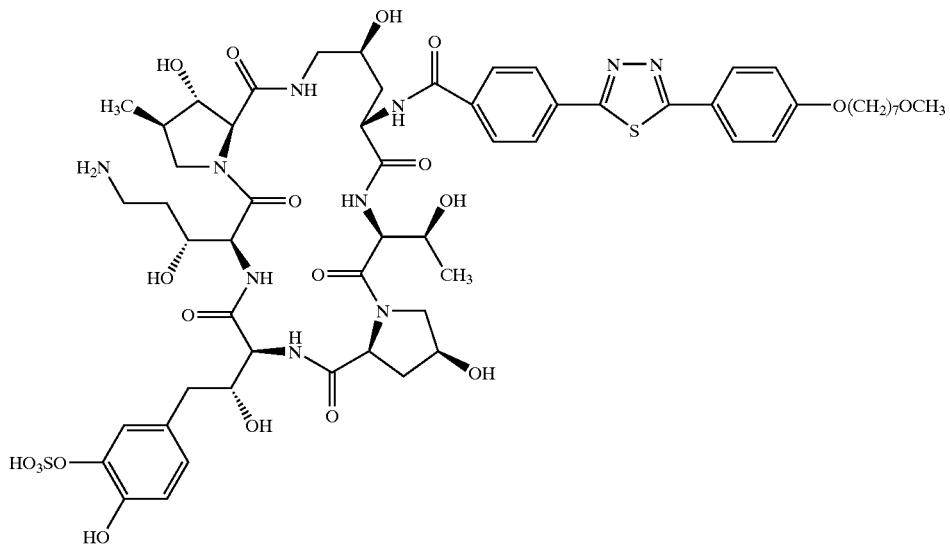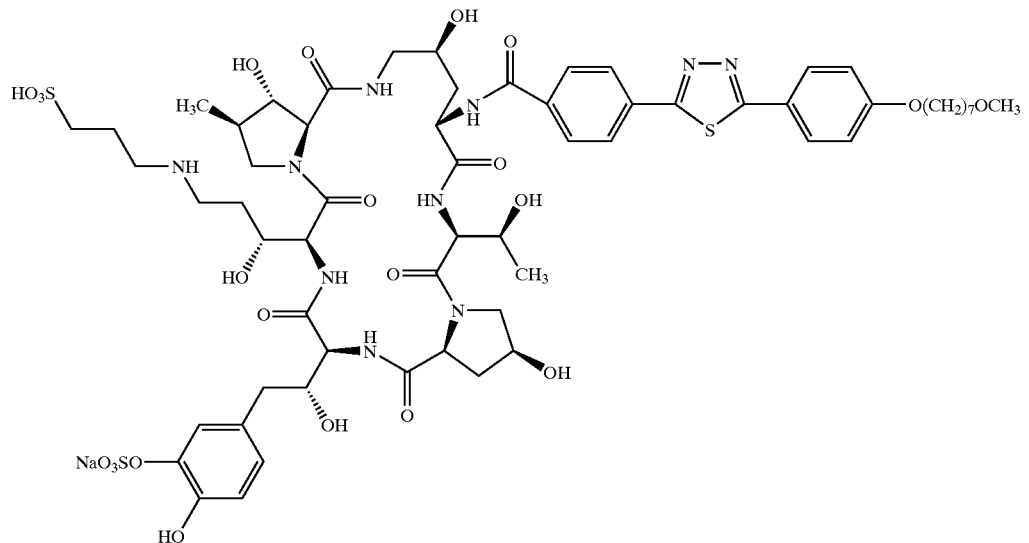 |

| Example No. | Formula |
|---|---|
| 54 | 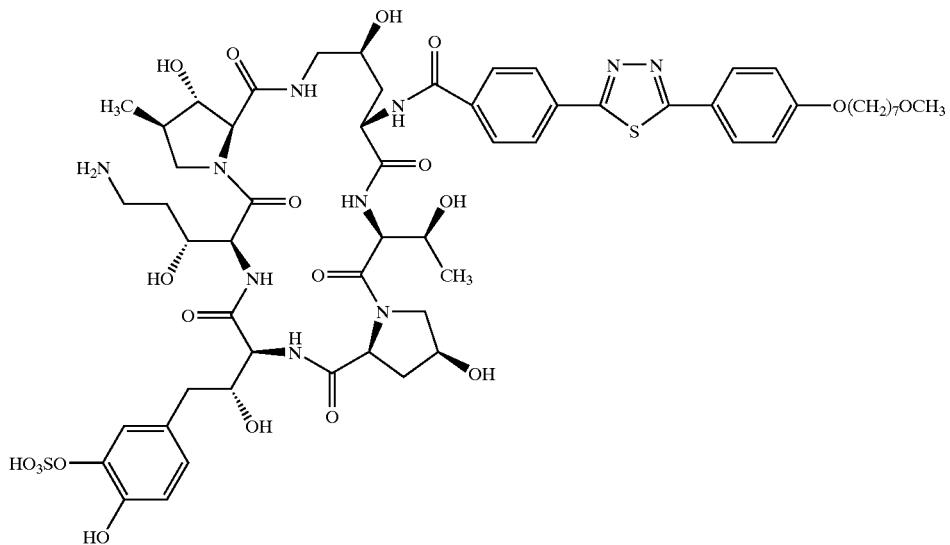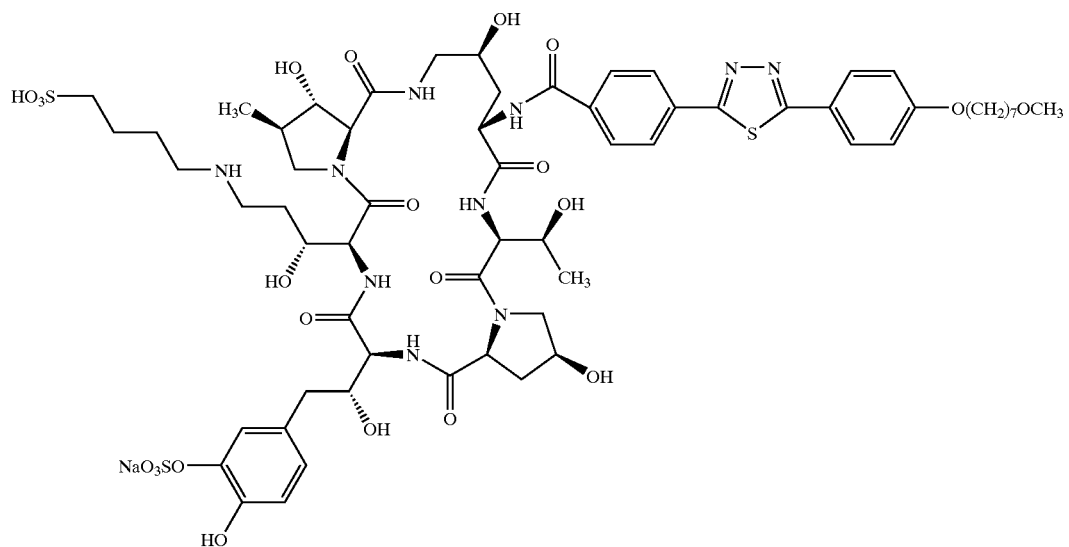 |

-continued
| Example No. | Formula |
|---|---|
| 55 | 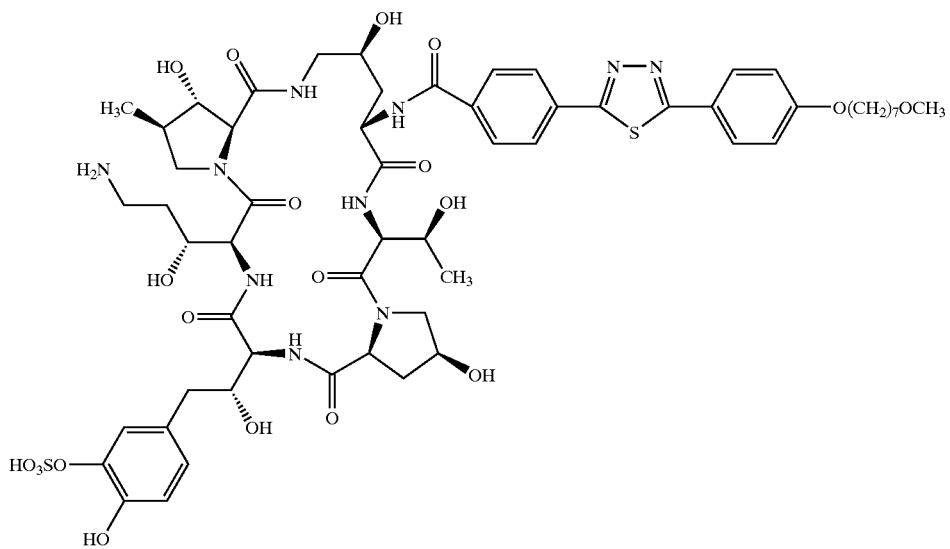<br>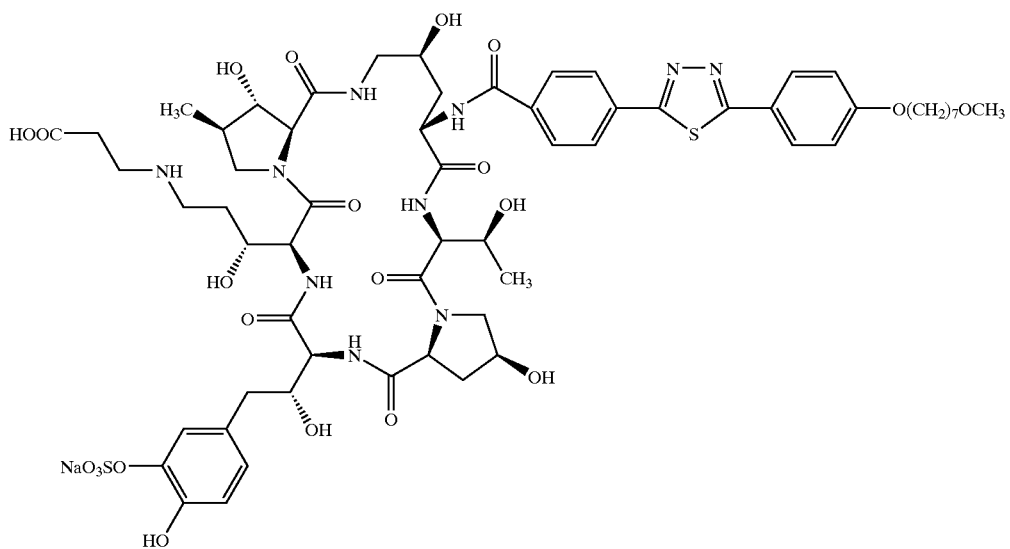 |

| Example No. | Formula |
|---|---|
| 56 | 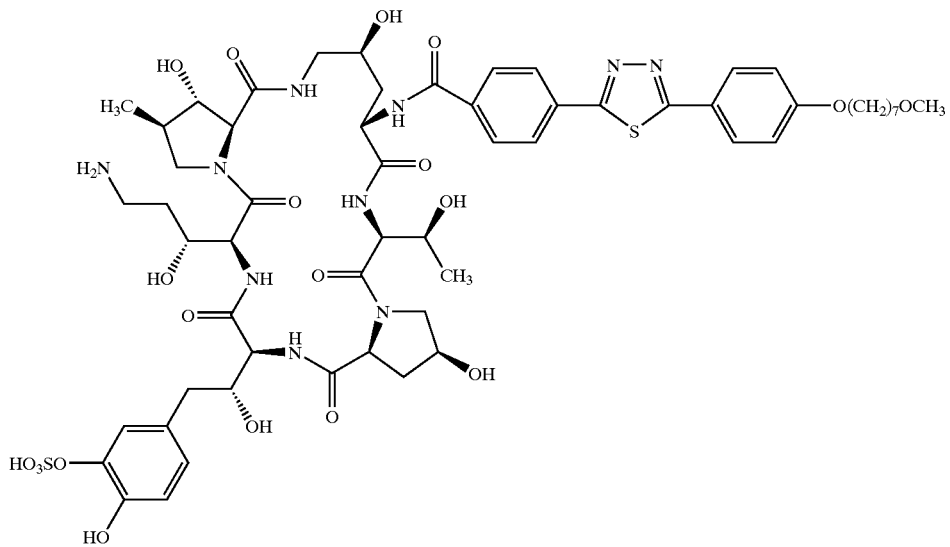 |
| | 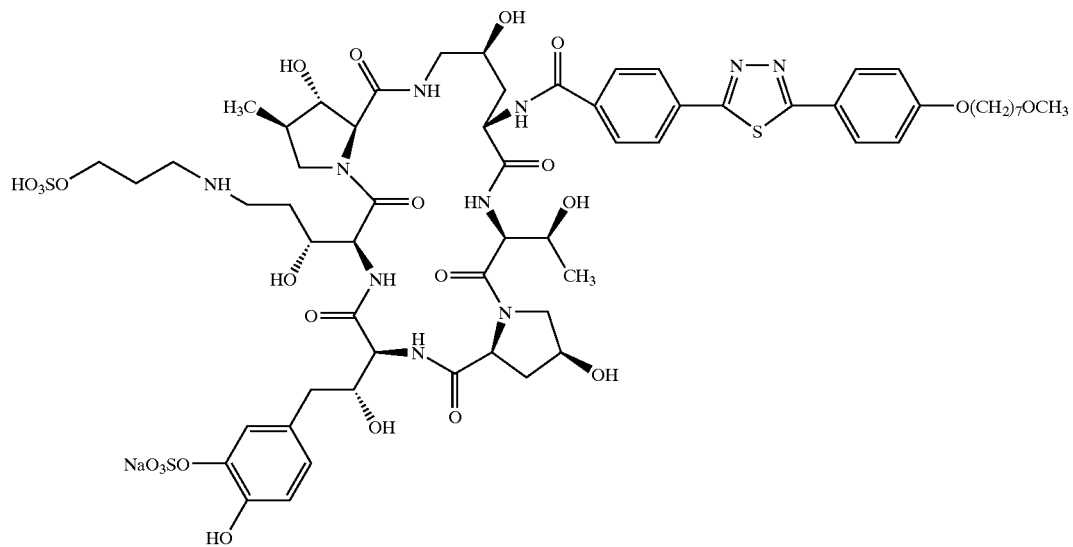 |

-continued
| Example No. | Formula |
|---|---|
| 57 | 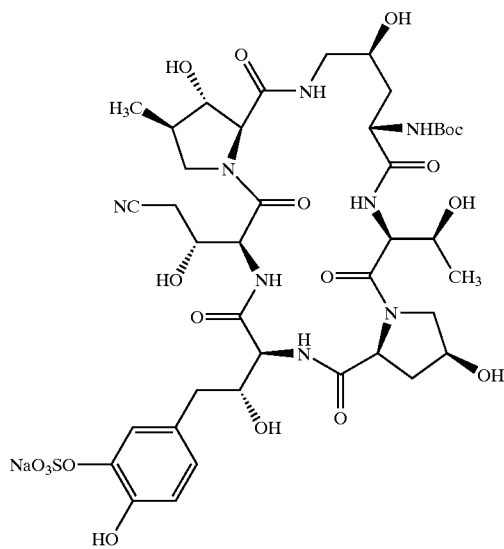 |
| | 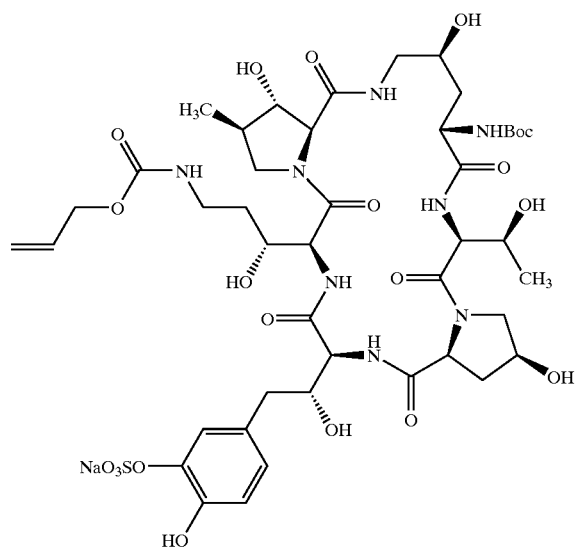 |

-continued
| Example No. | Formula |
|---|---|
| 58 | 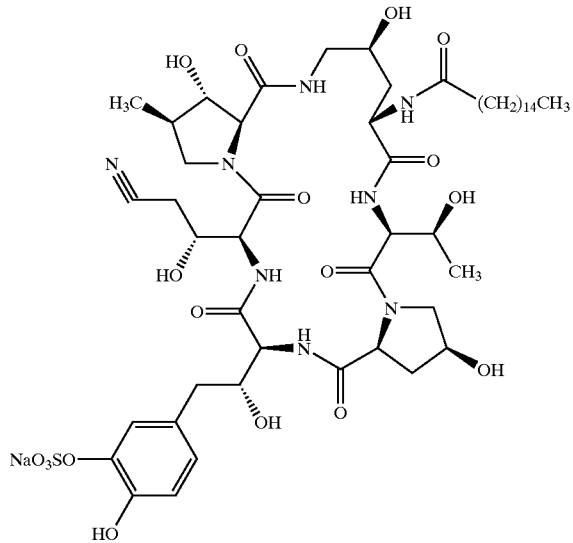 |
| | 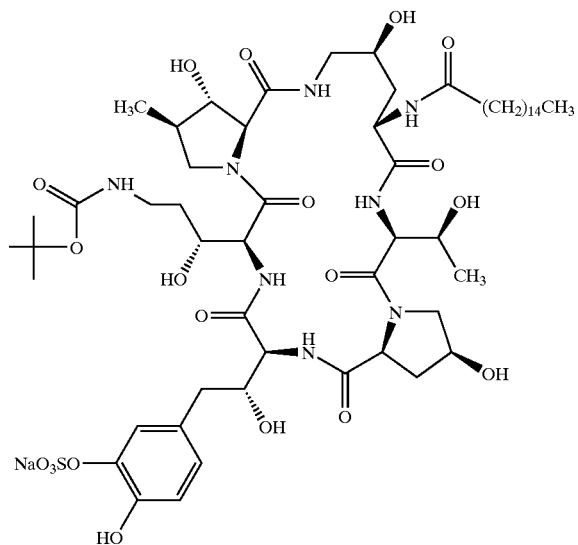 |

-continued
| Example No. | Formula |
|---|---|
| 59 | 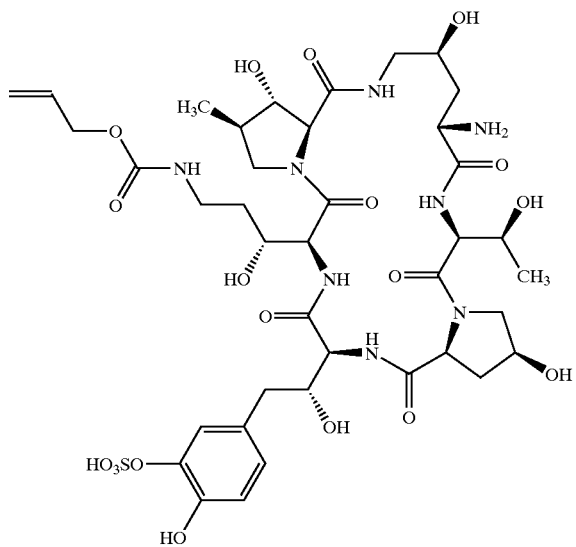 |
| | 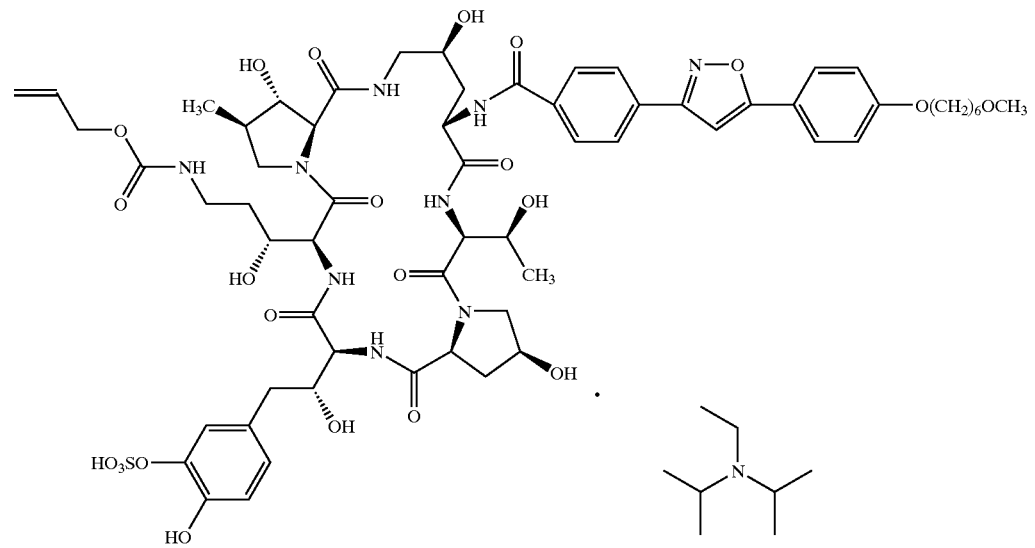 |

-continued
| Example No. | Formula |
|---|---|
| 60 | 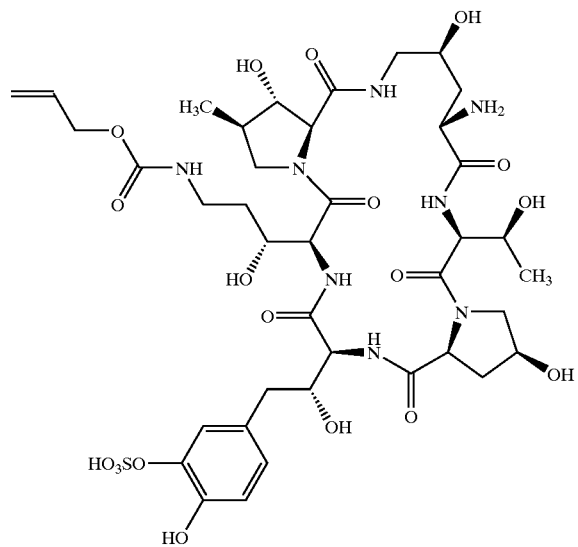 |
| | 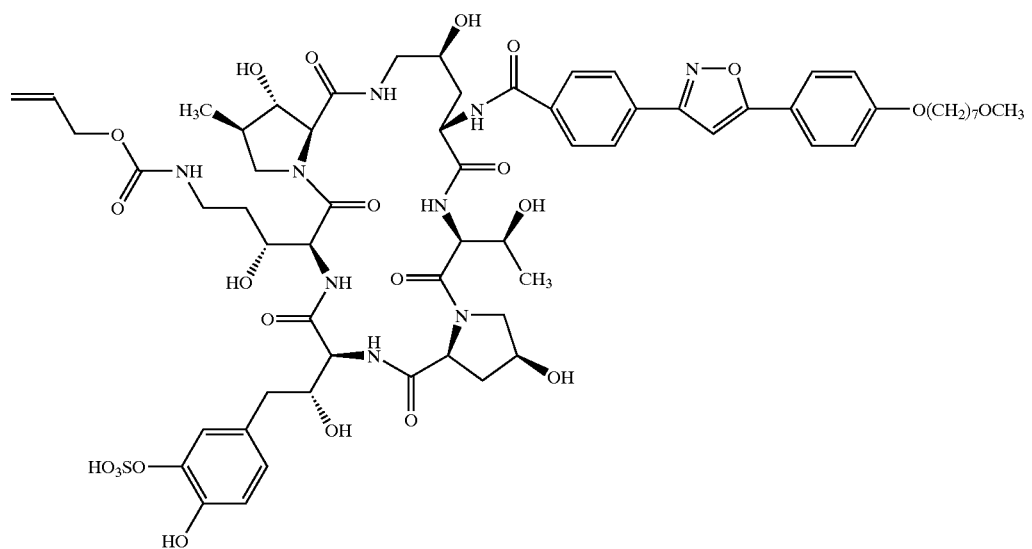 |

-continued
| Example No. | Formula |
|---|---|
| 61 | 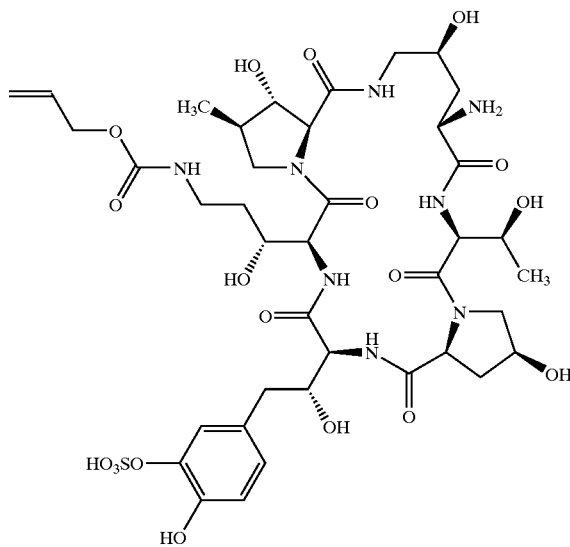 |
| | 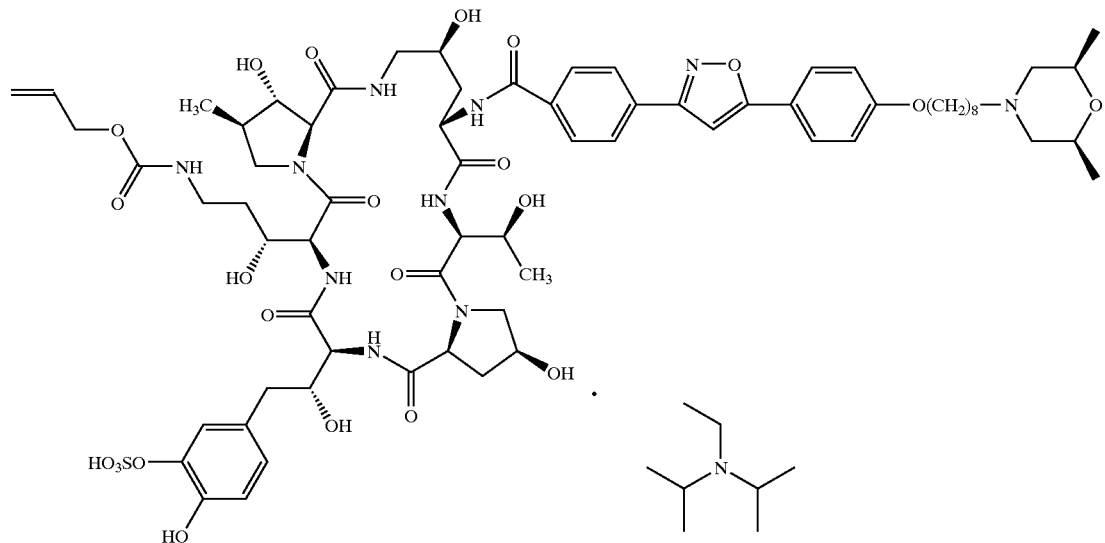 |

-continued
| Example No. | Formula |
|---|---|
| 62 | 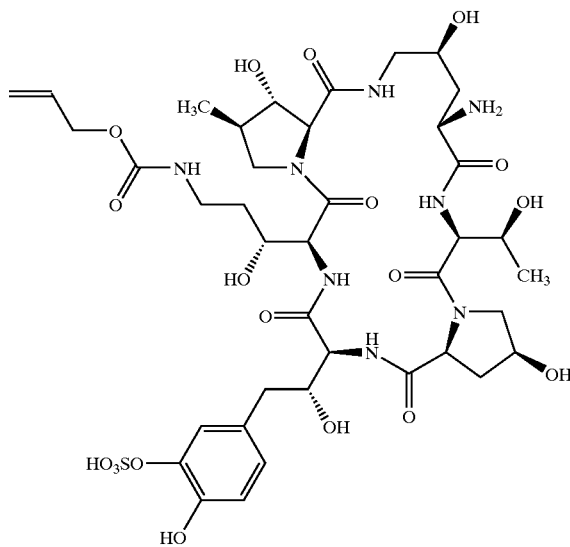 |
| | 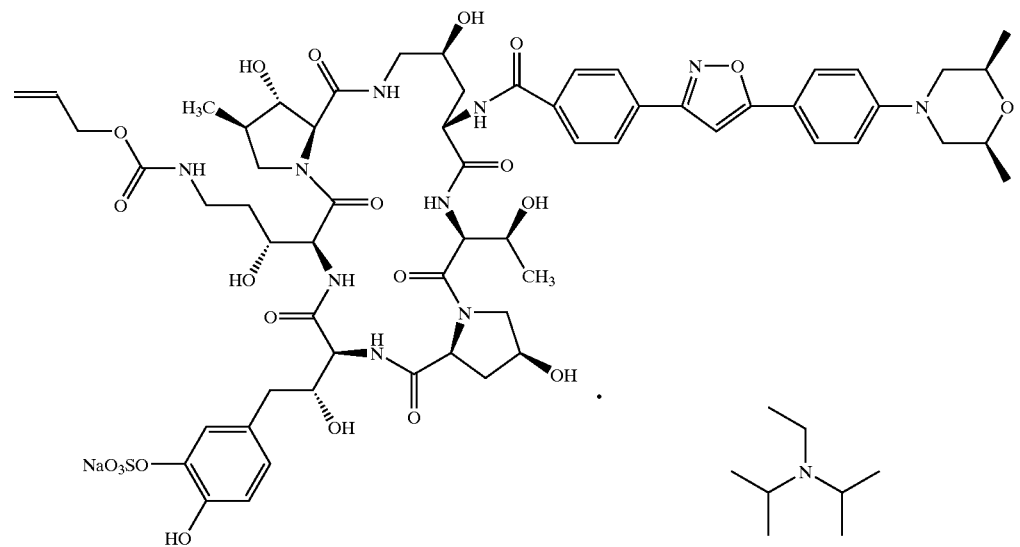 |

| Example No. | Formula |
|---|---|
| 63 | 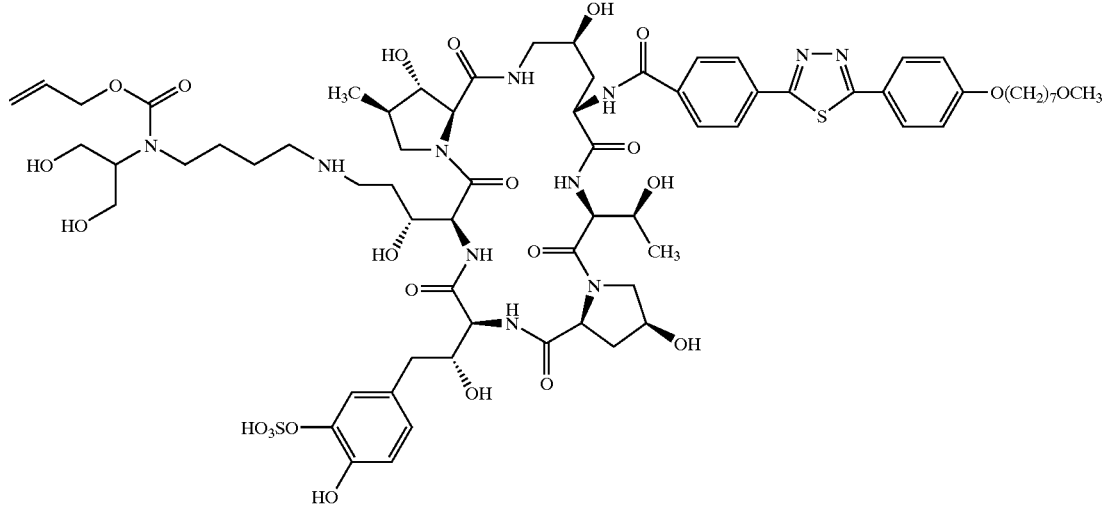 |
| | 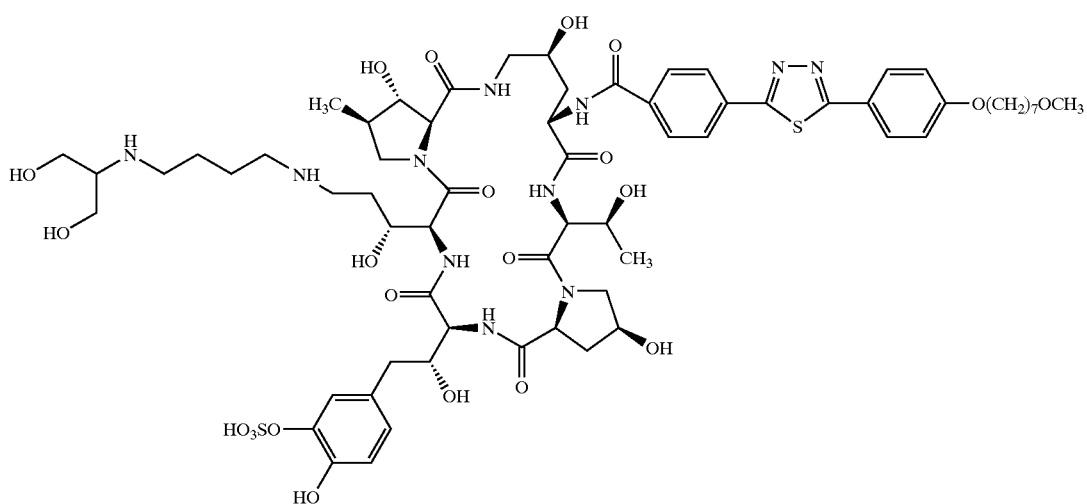 |
| 64 | 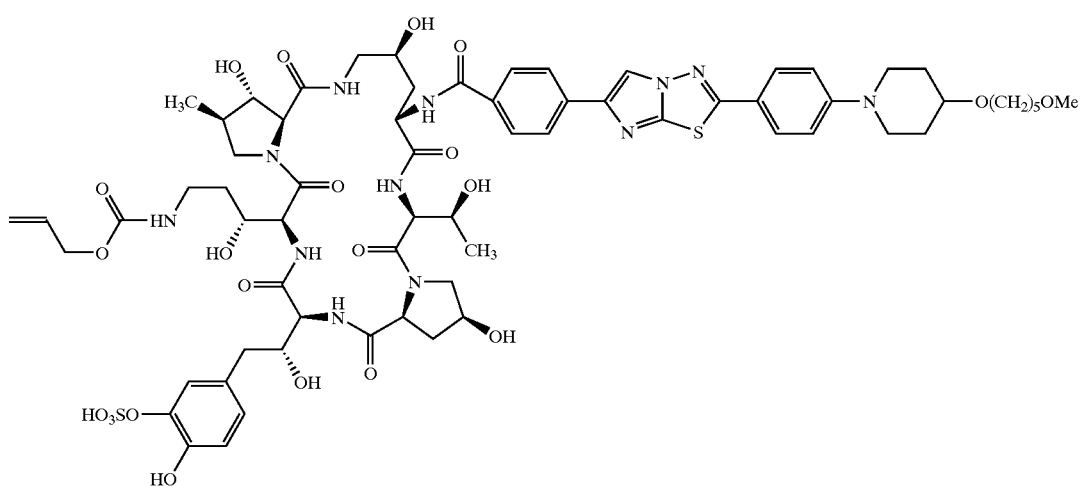 |

-continued
| Example No. | Formula |
|---|---|
| | 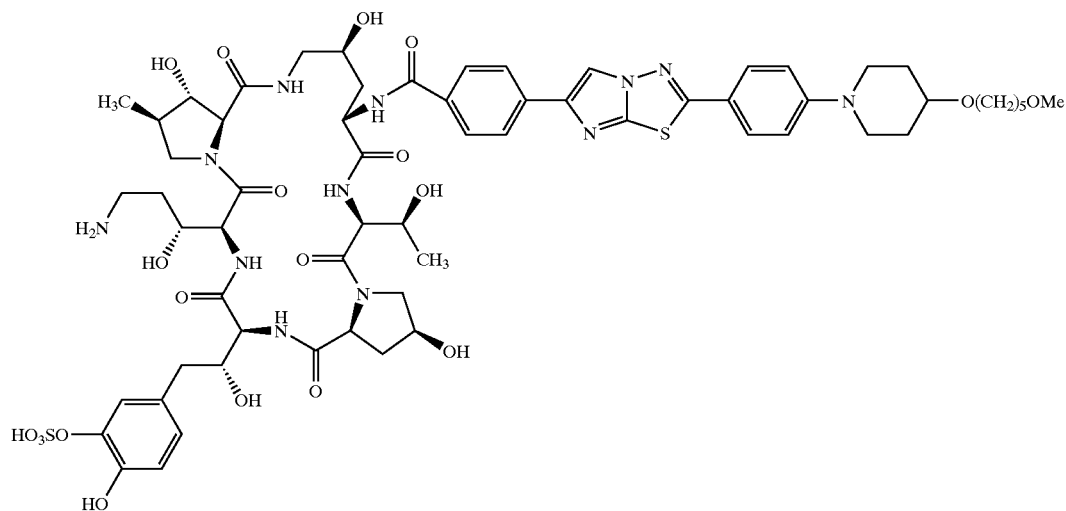 |
| 65 | 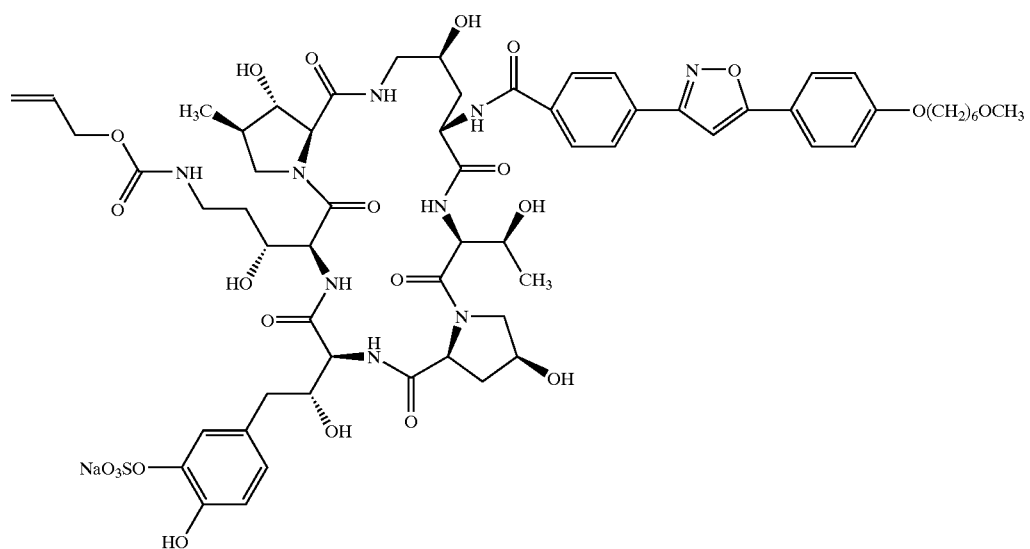 |

| Example No. | Formula |
|---|---|
| | 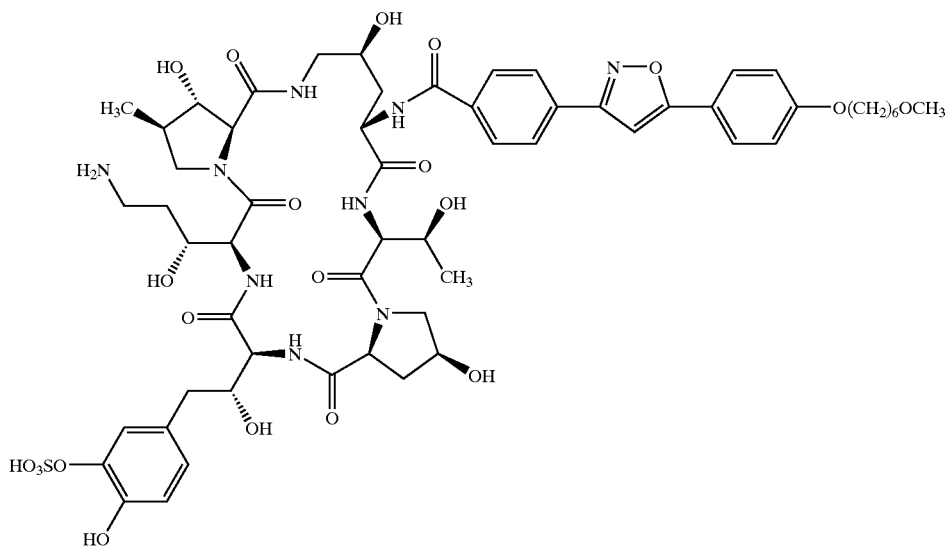 |
| 66 | 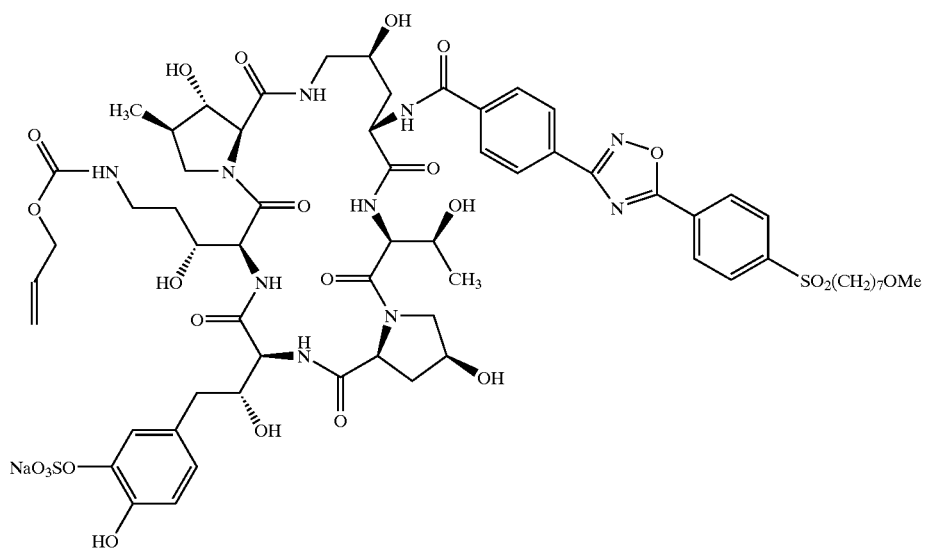 |

| Example No. | Formula |
|---|---|
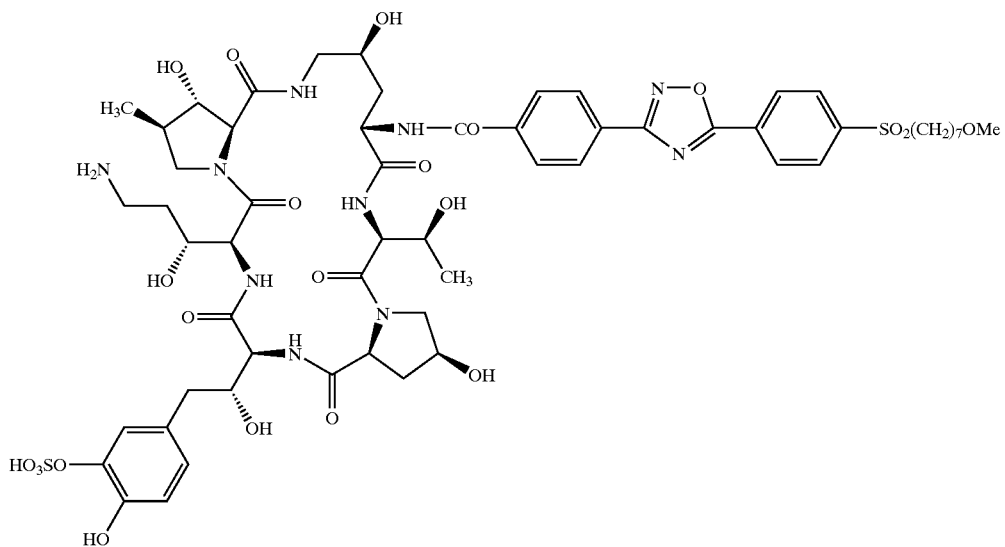
67
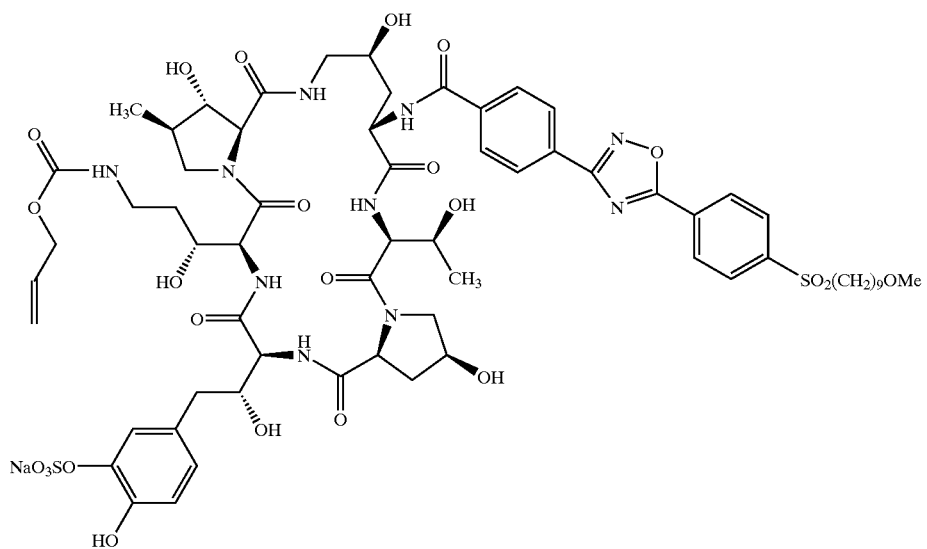

-continued
| Example No. | Formula |
|---|---|
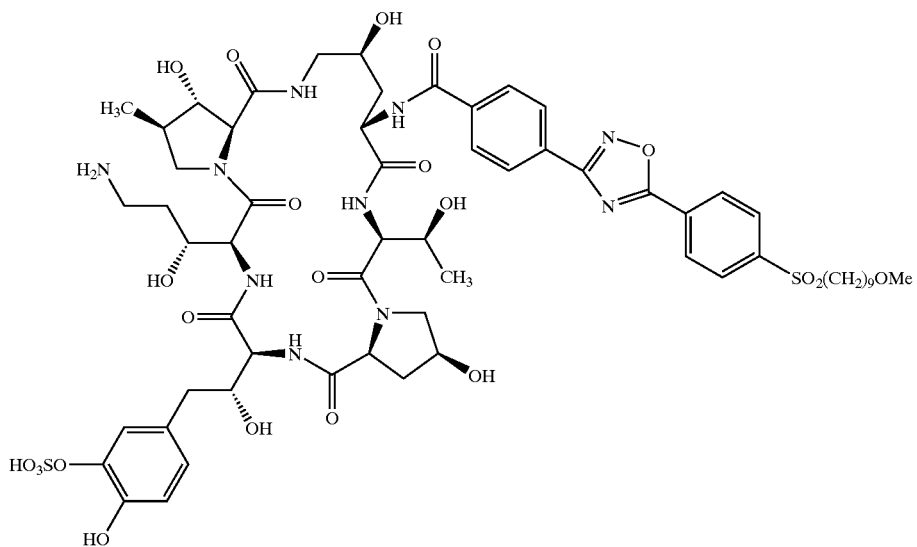
68
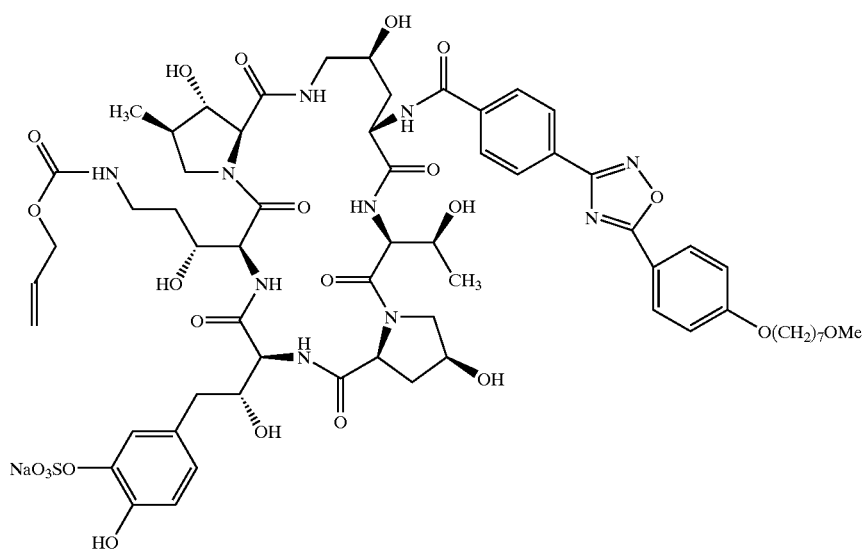

-continued
| Example No. | Formula |
|---|---|
| | 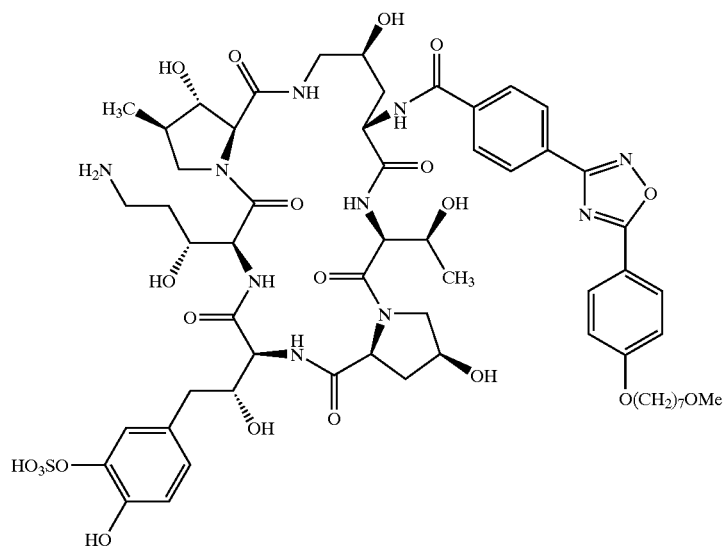 |
| 69 | 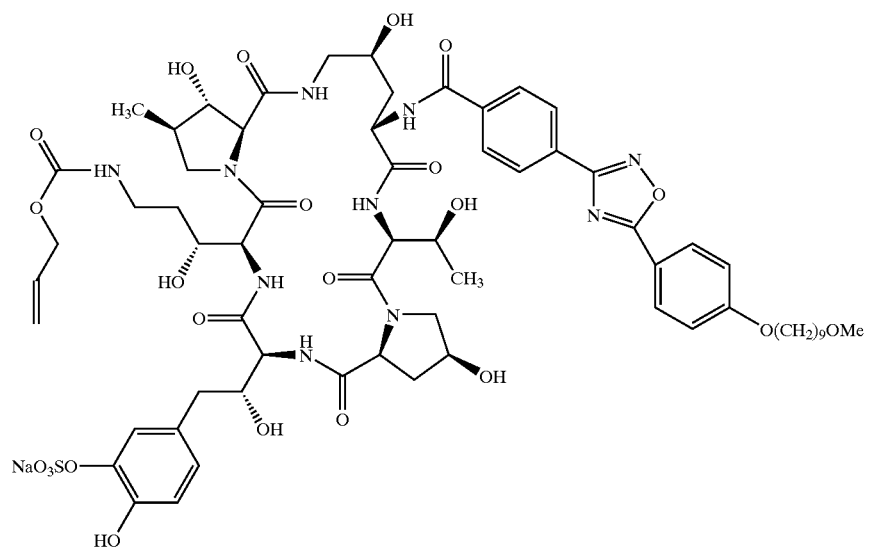 |

| Example No. | Formula |
|---|---|
| | 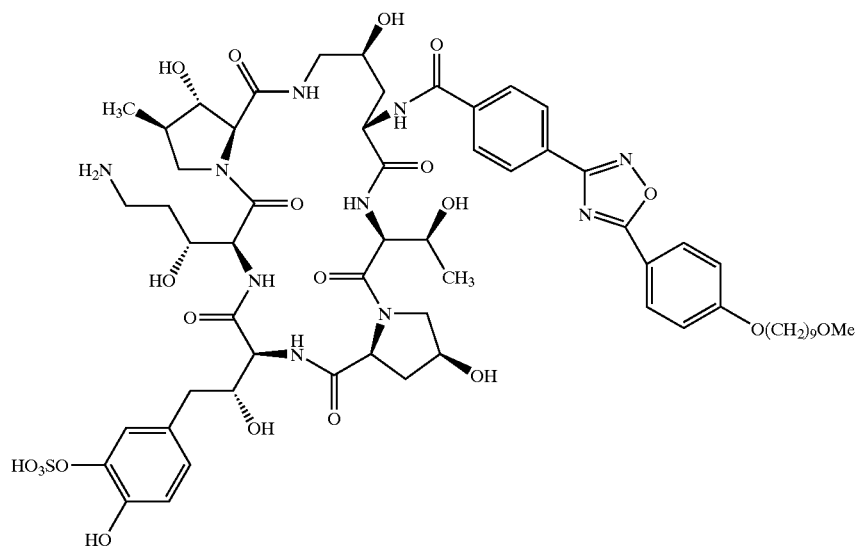 |
| 70 | 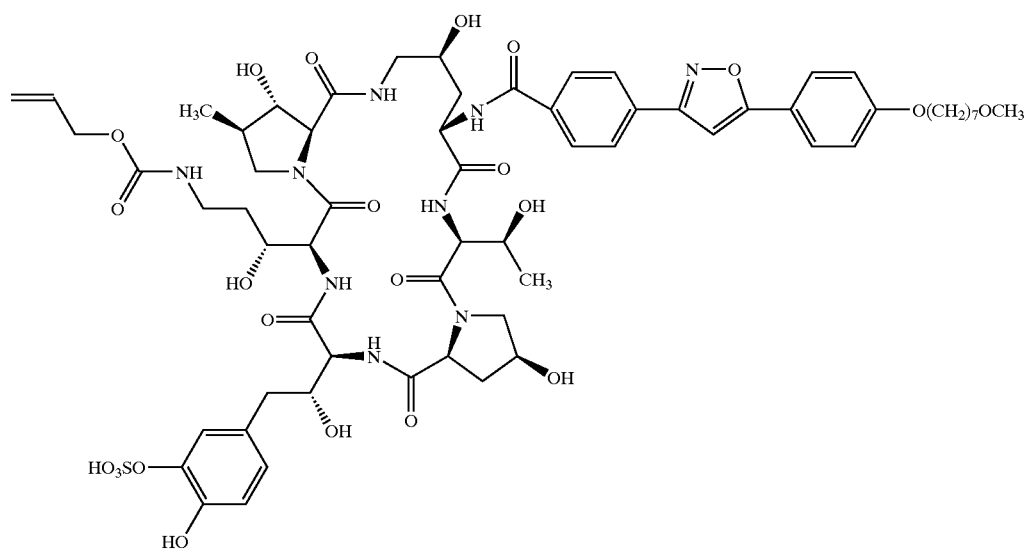 |

-continued
| Example No. | Formula |
|---|---|
| | 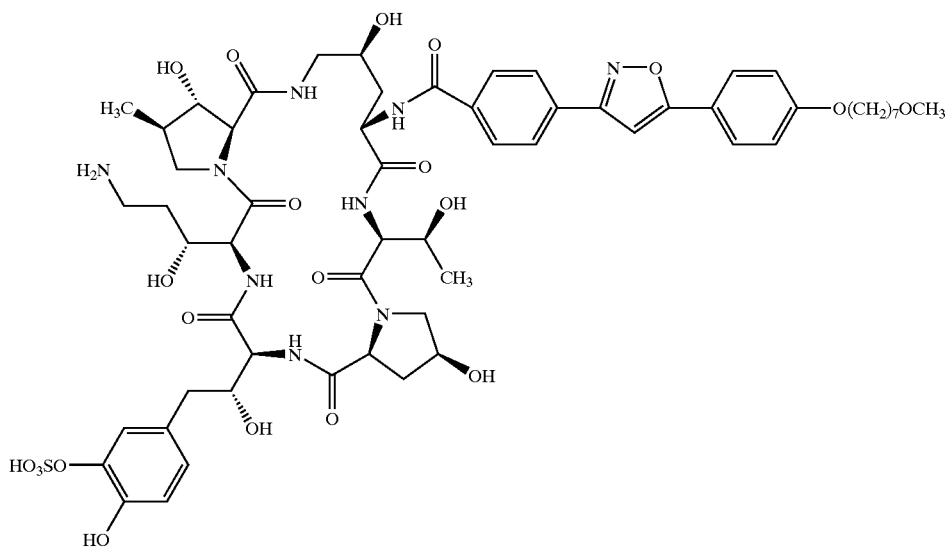 |
| 71 | 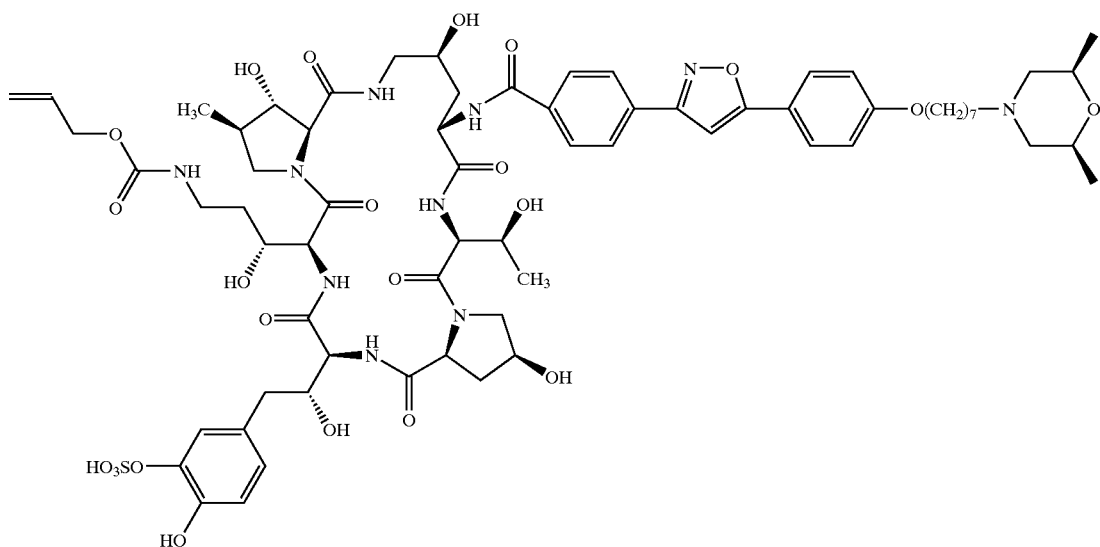 |

| Example No. | Formula |
|---|---|
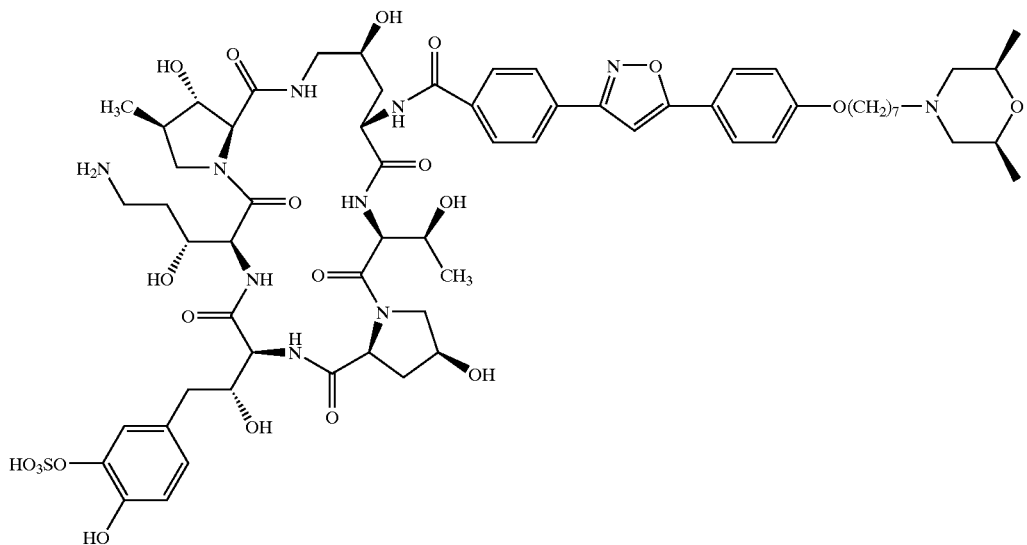
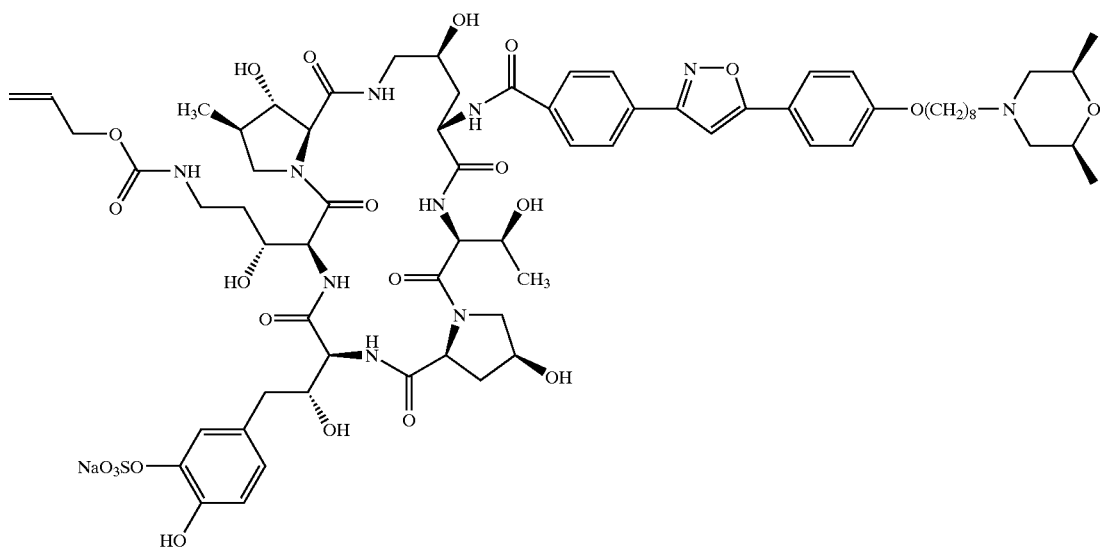
72

-continued
| Example No. | Formula |
|---|---|
| | 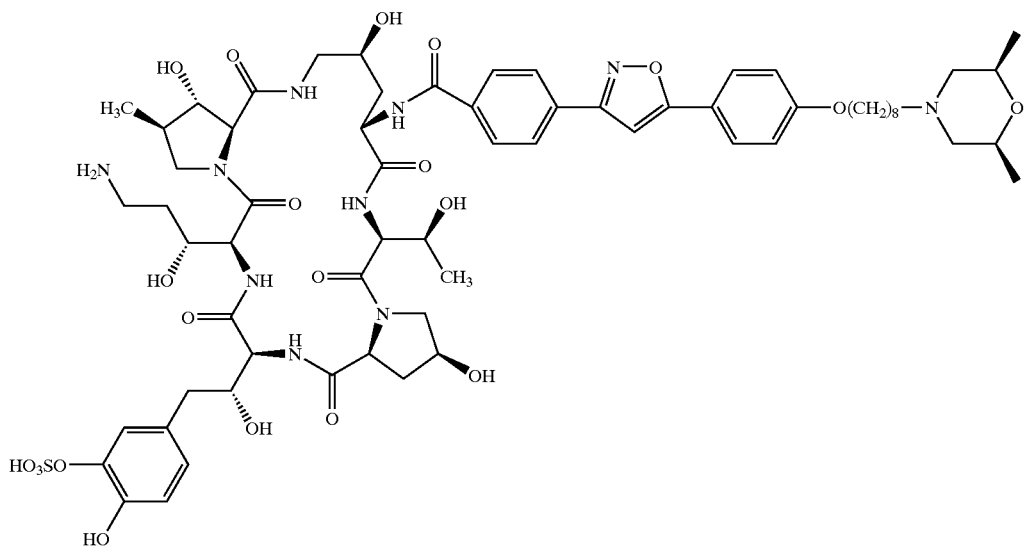 |
| 73 | 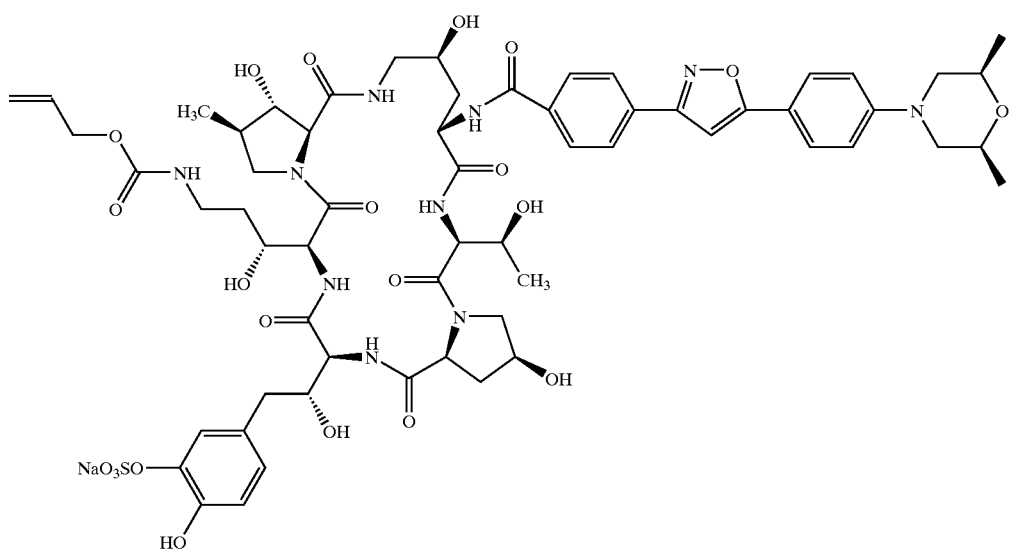 |

-continued
| Example No. | Formula |
|---|---|
| | 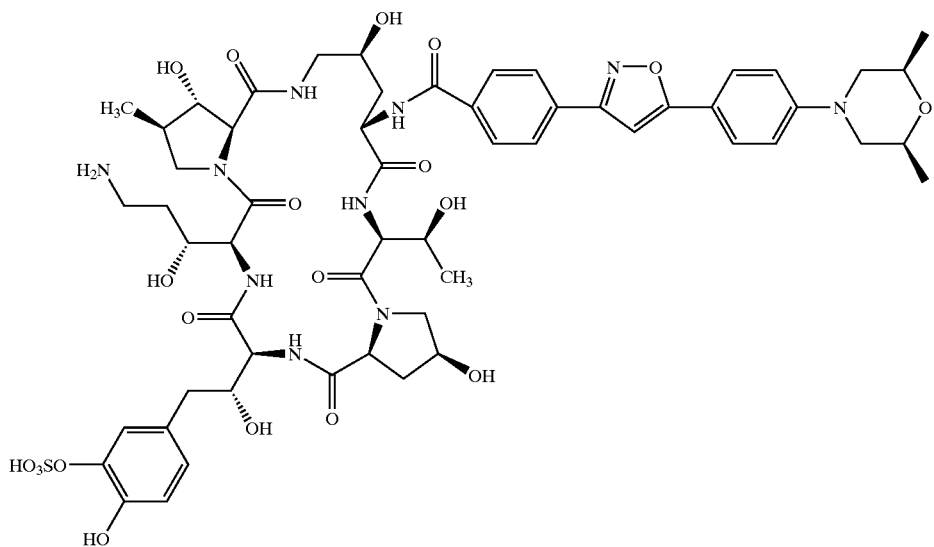 |
| 74 | 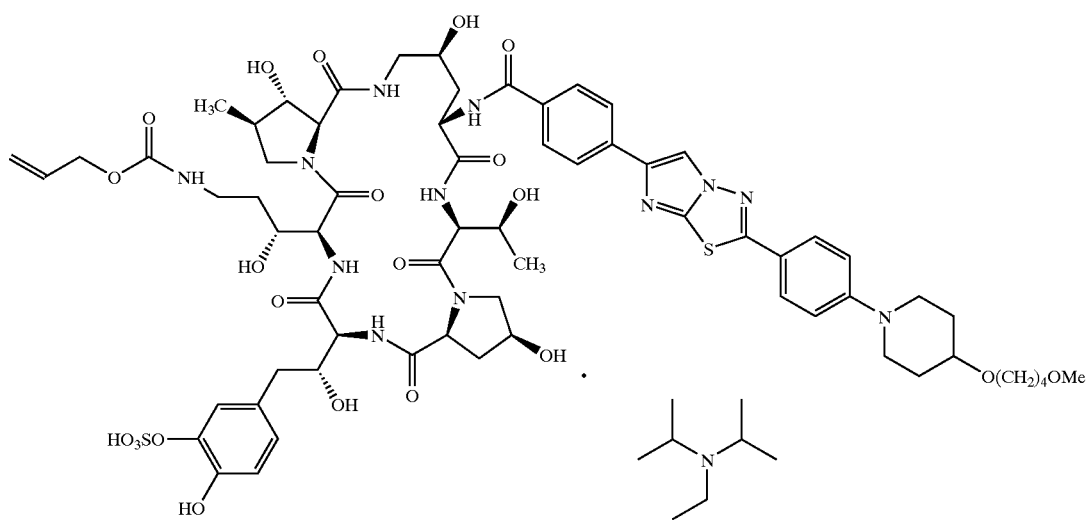 |

-continued
| Example No. | Formula |
|---|---|
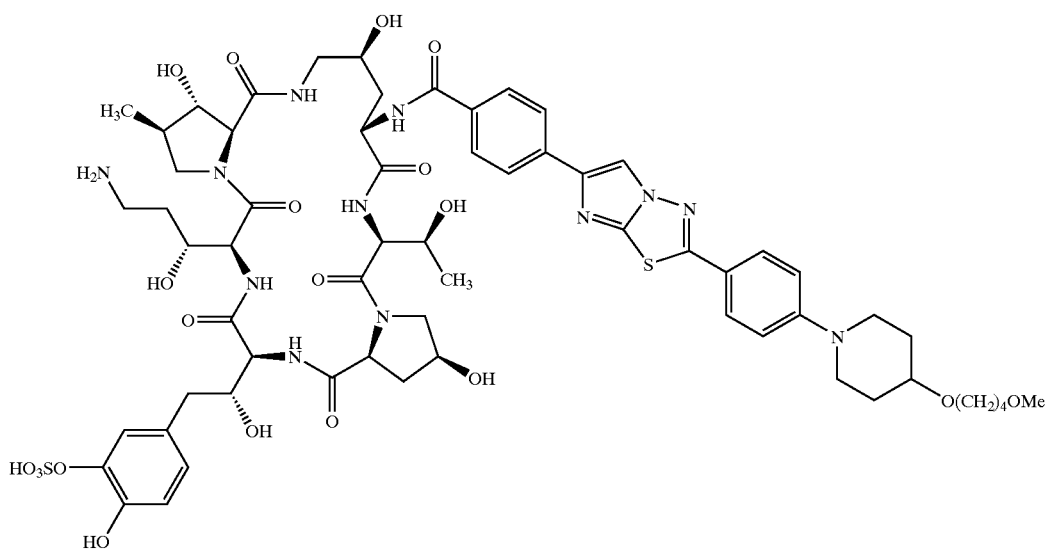
75
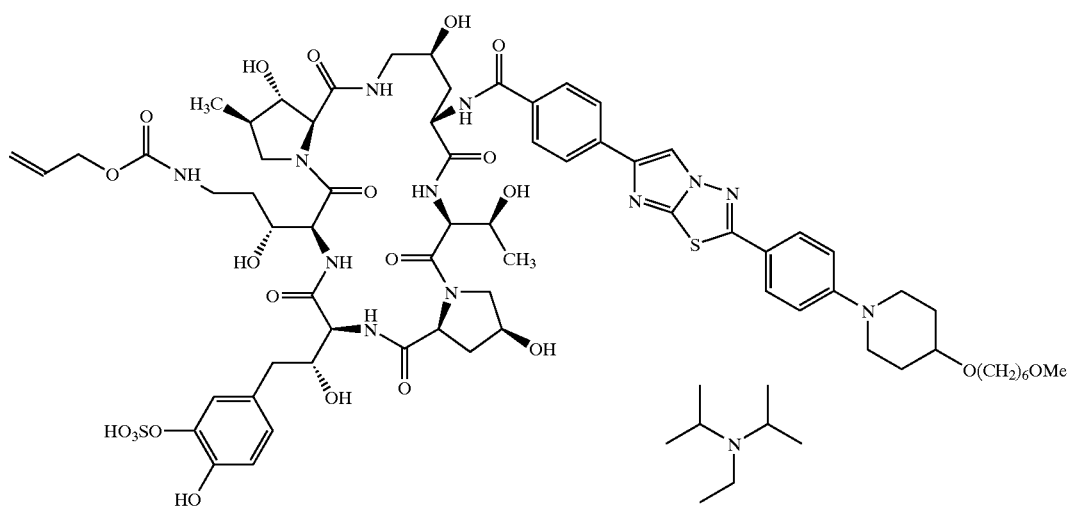

| Example No. | Formula |
|---|---|
|  | 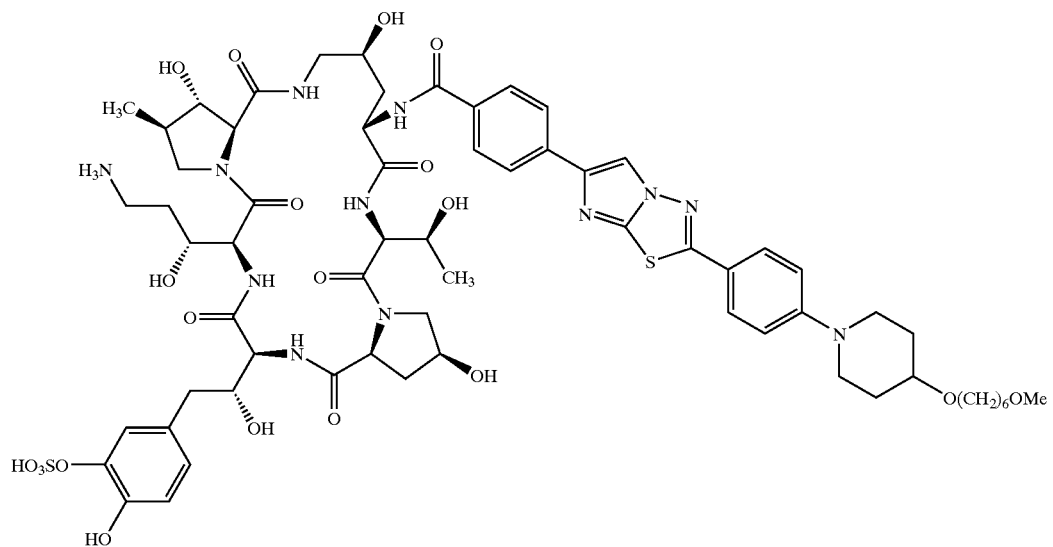 |
| 76 | 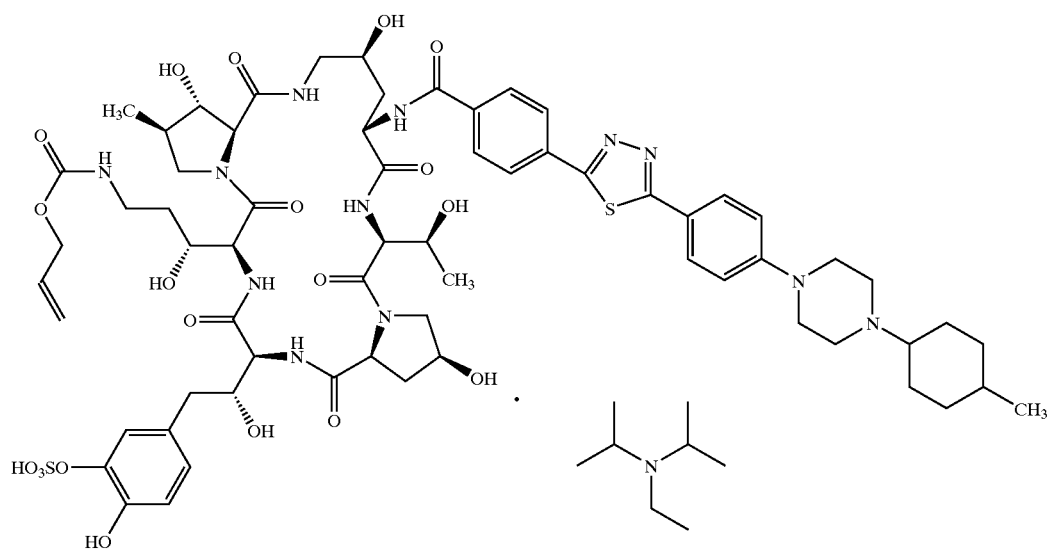 |

-continued
| Example No. | Formula |
|---|---|
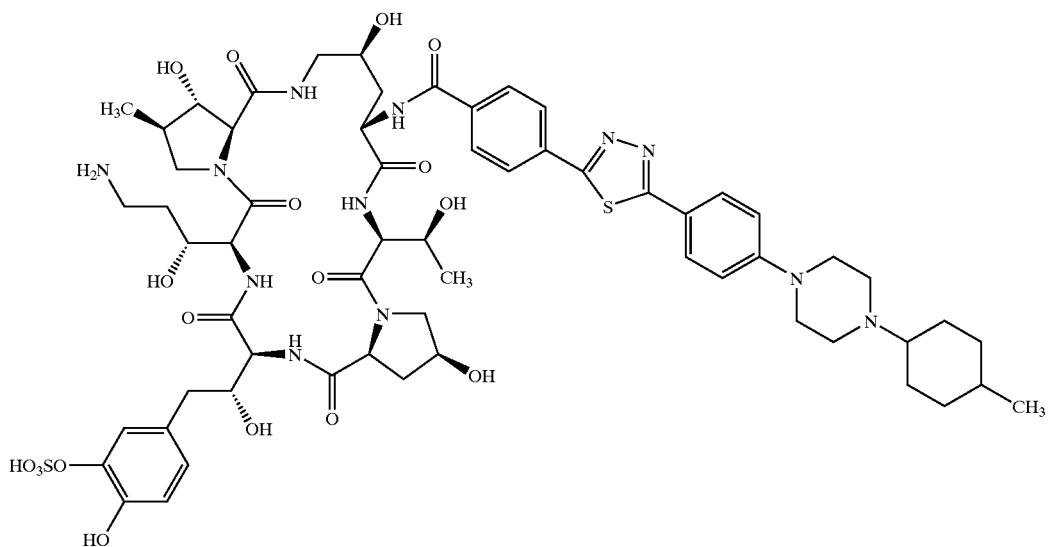
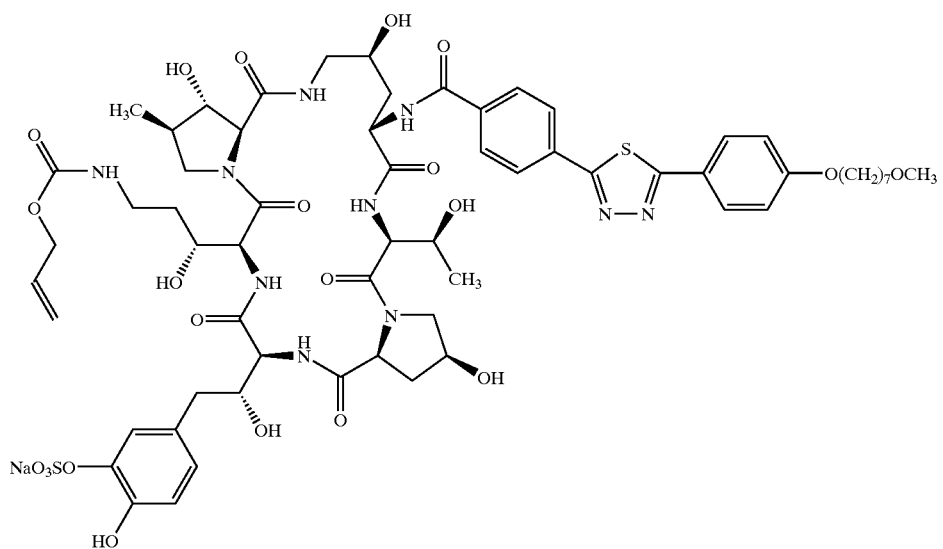
77

-continued
| Example No. | Formula |
|---|---|
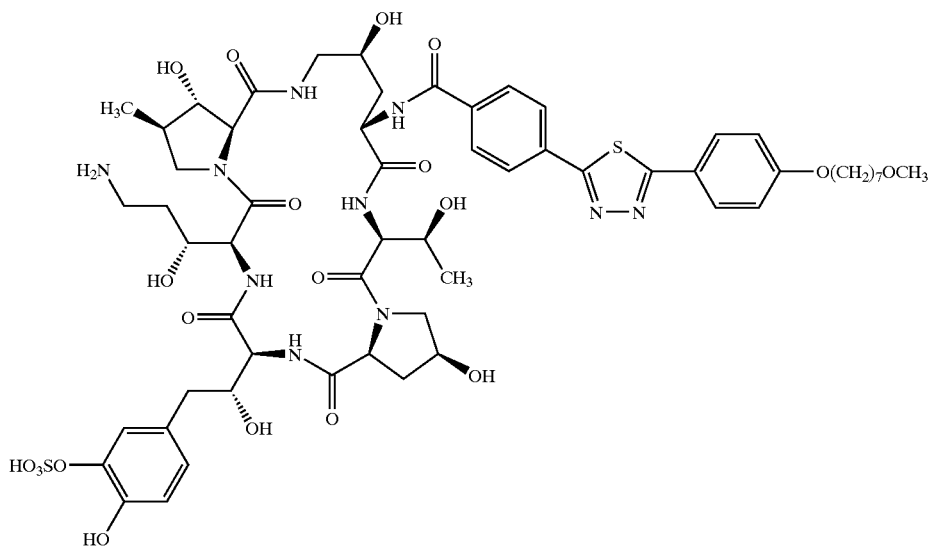
78
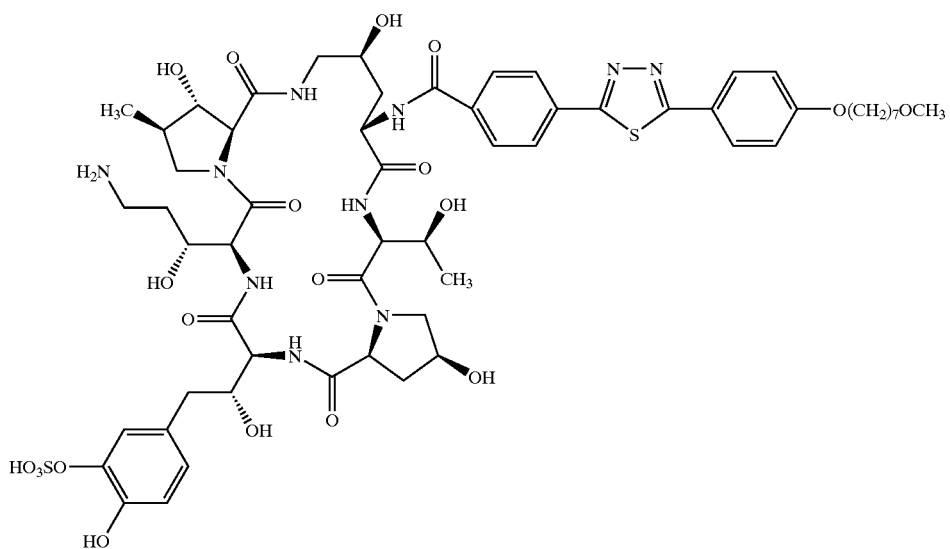

| Example No. | Formula |
|---|---|
| | 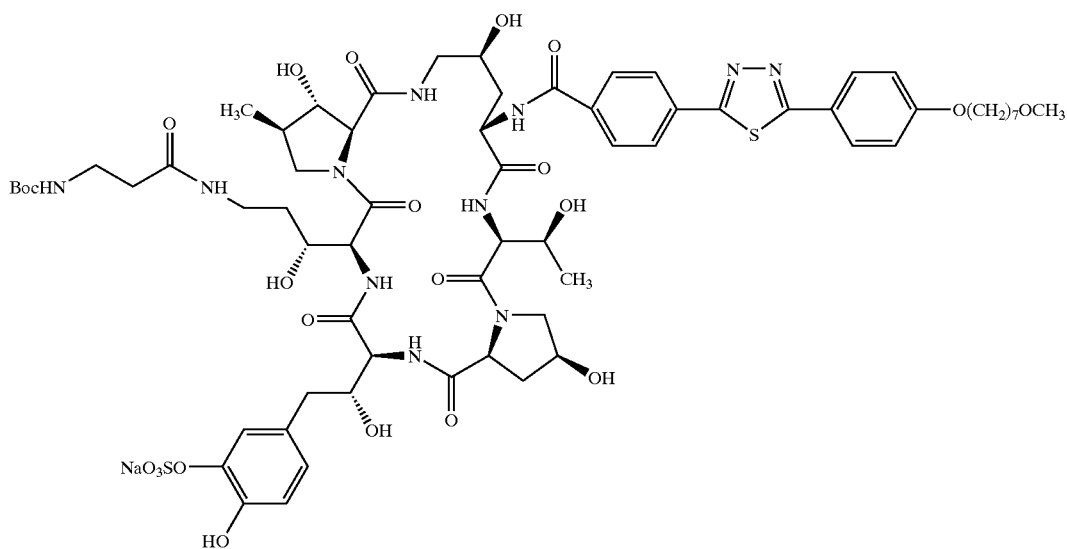 |
| 79 | 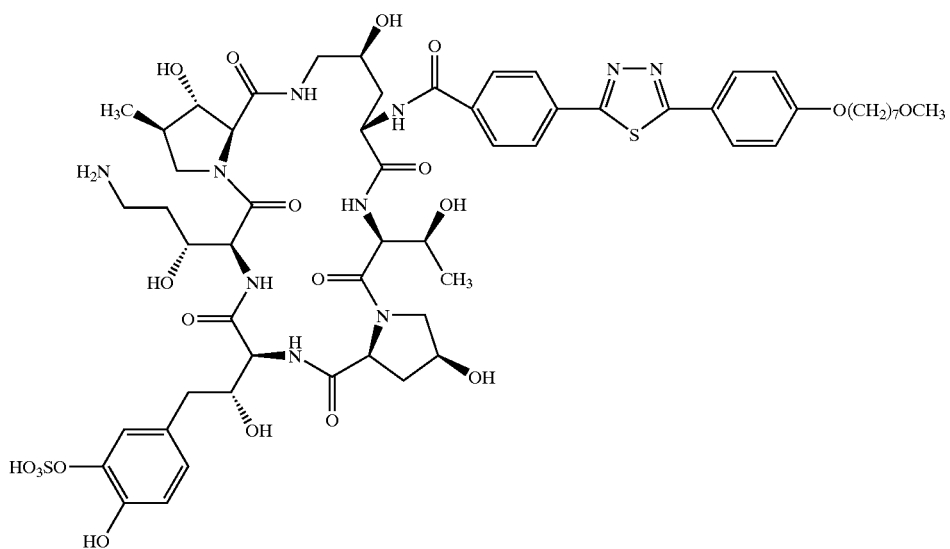 |

-continued
| Example No. | Formula |
|---|---|
| | 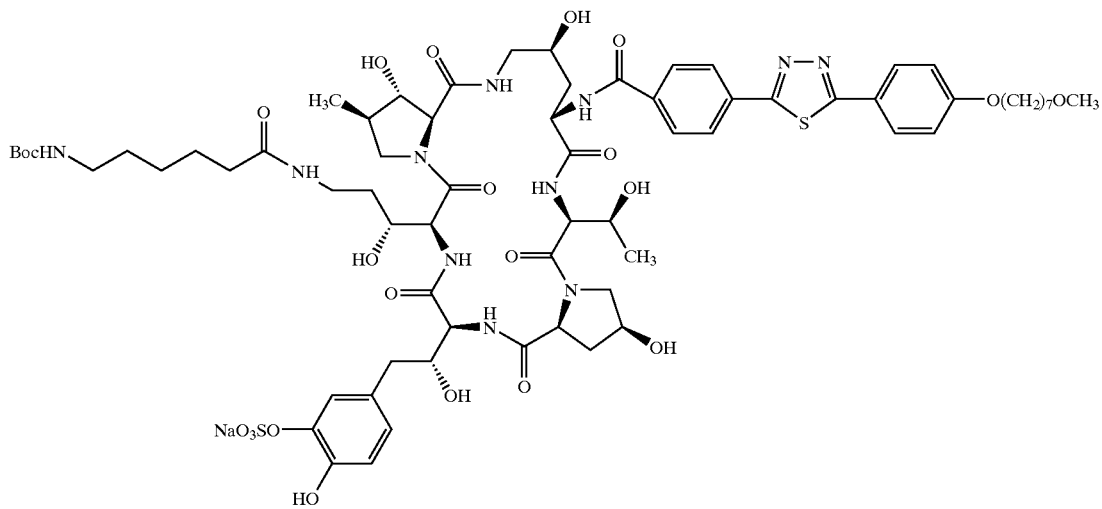 |
| 80 | 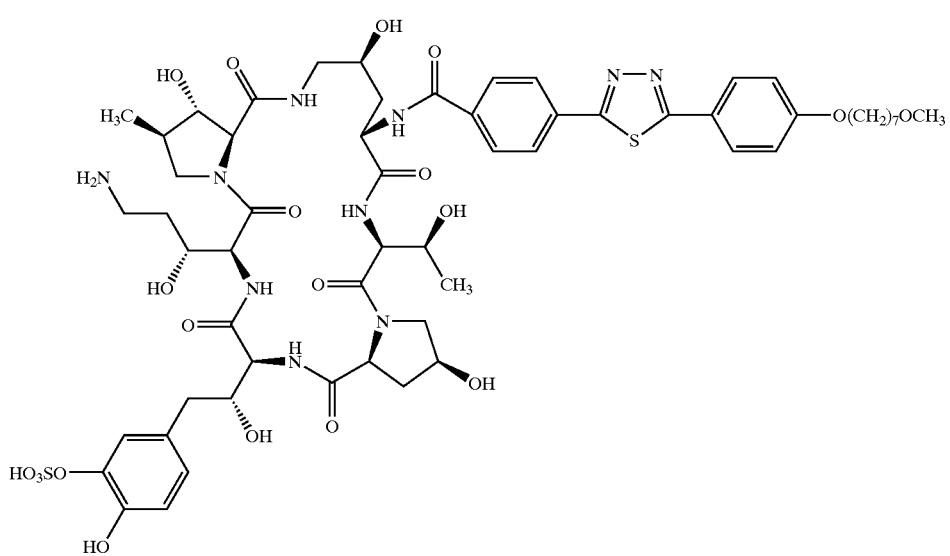 |
| | 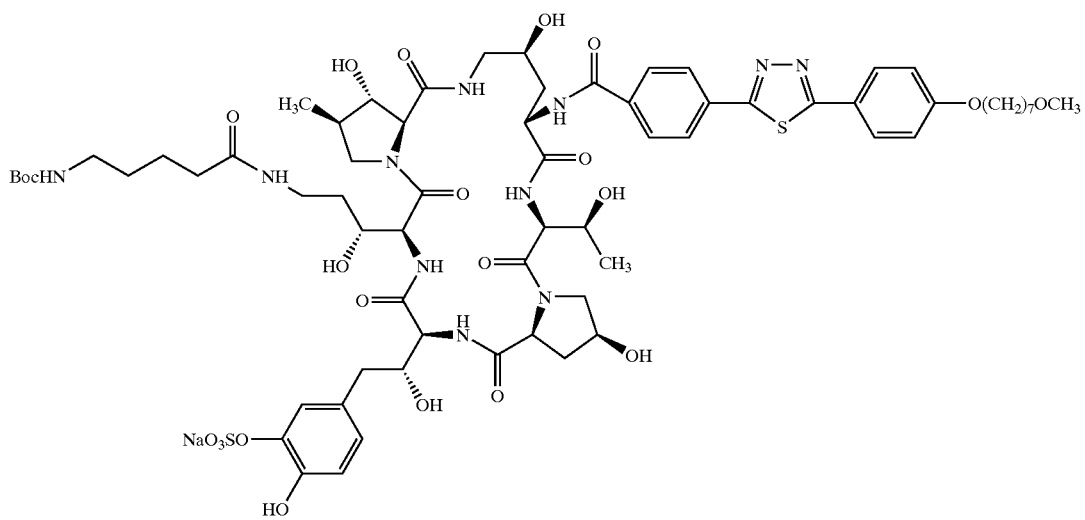 |

| Example No. | Formula |
|---|---|
| 81 | 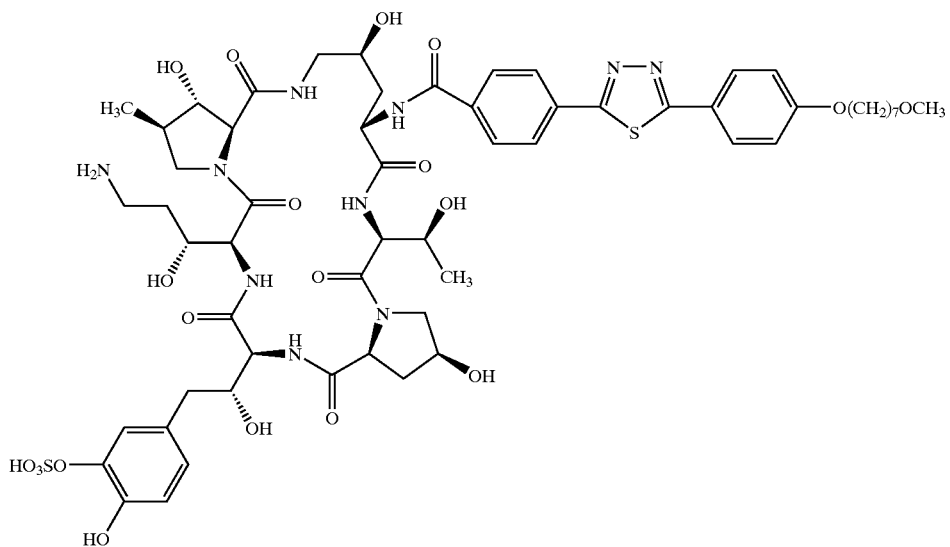 |
| | 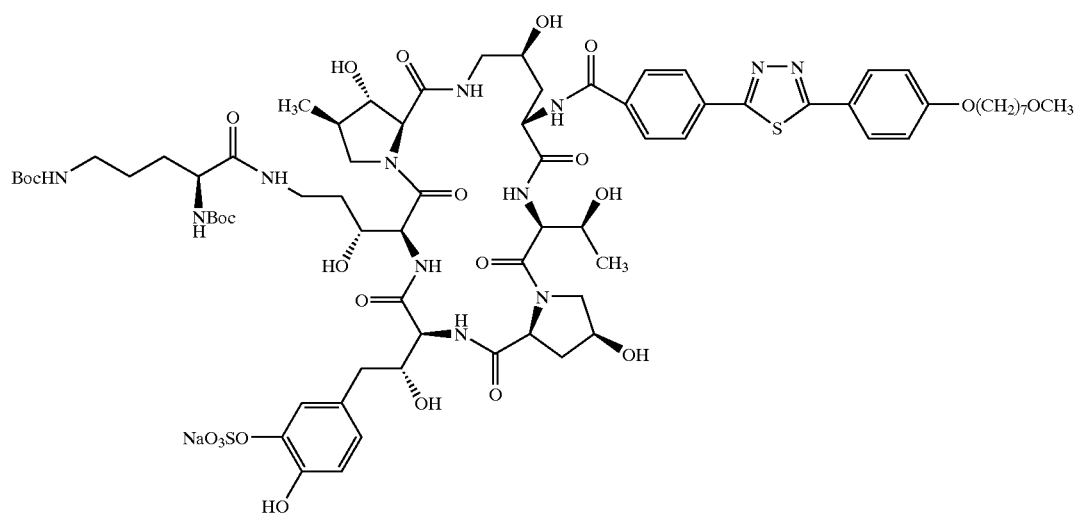 |

-continued
| Example No. | Formula |
|---|---|
| 82 | 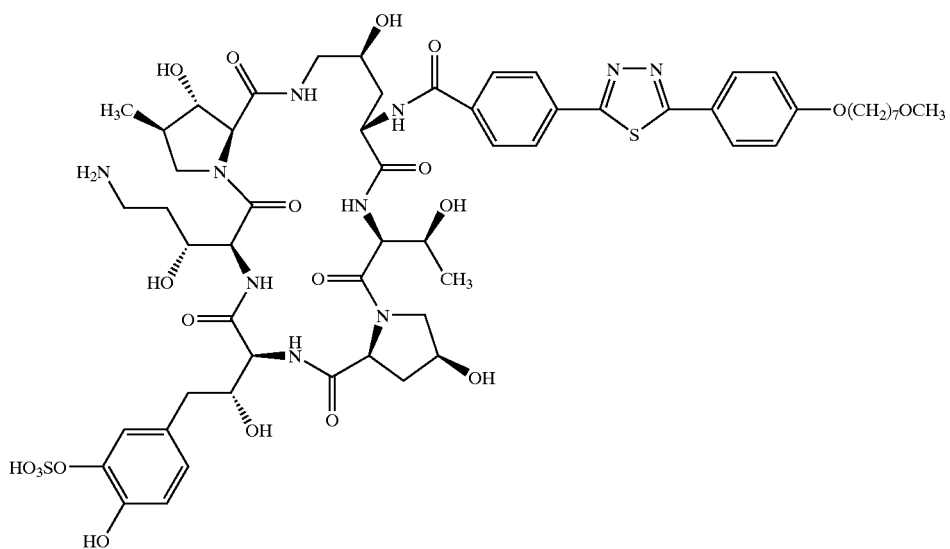 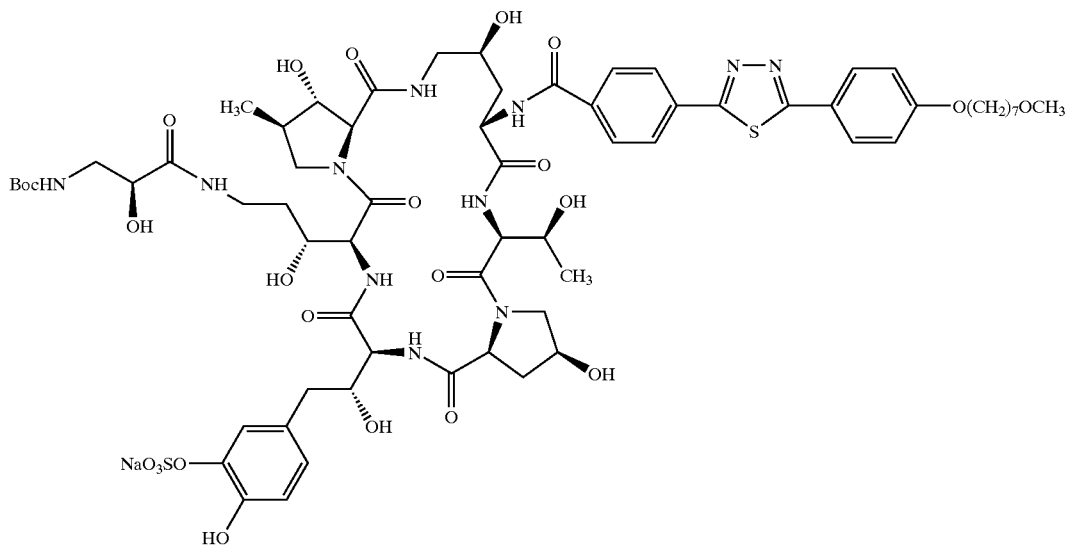 |

| Example No. | Formula |
|---|---|
| 83 | 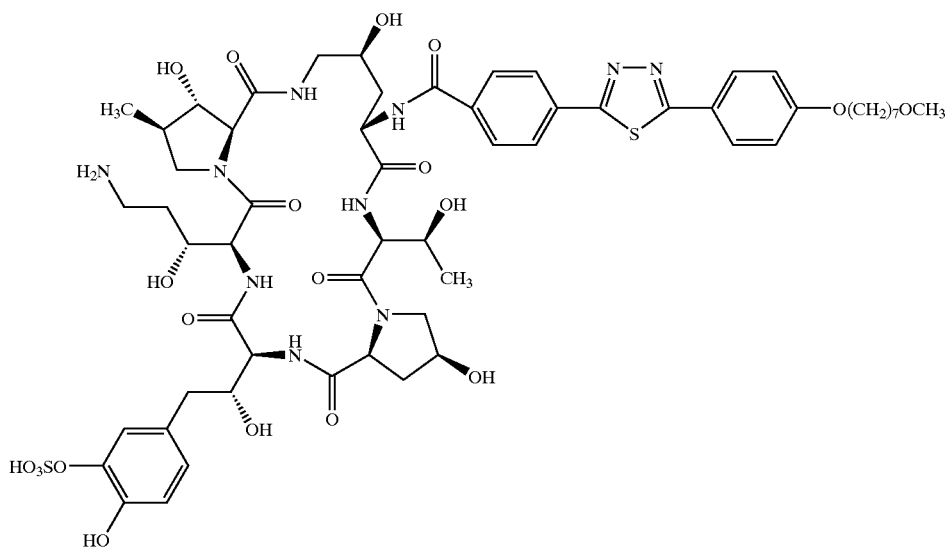 |
| | 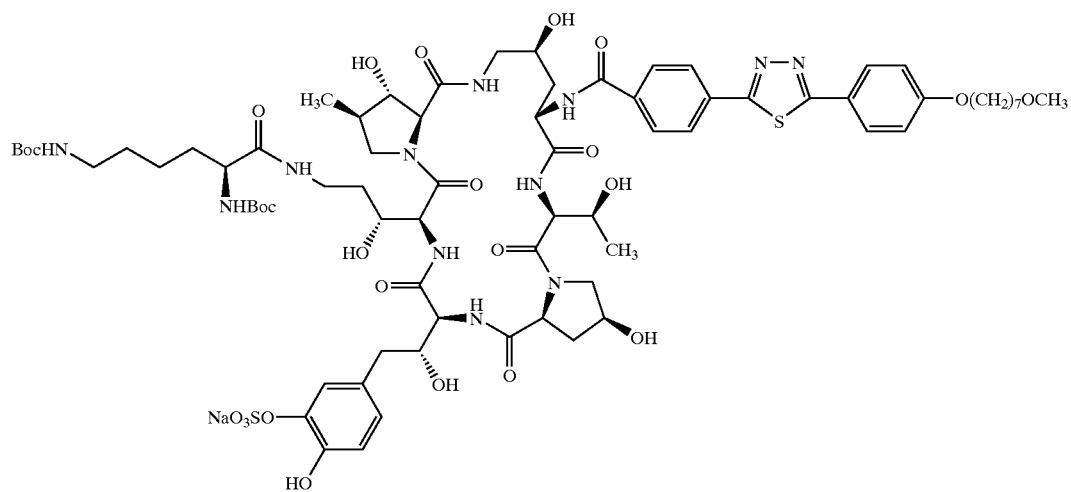 |
| 84 | 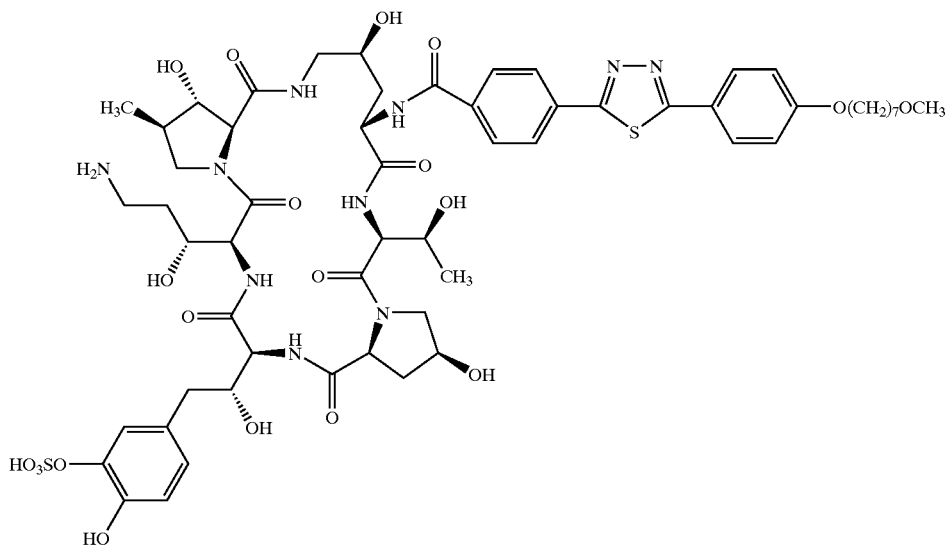 |

| Example No. | Formula |
|---|---|
| | 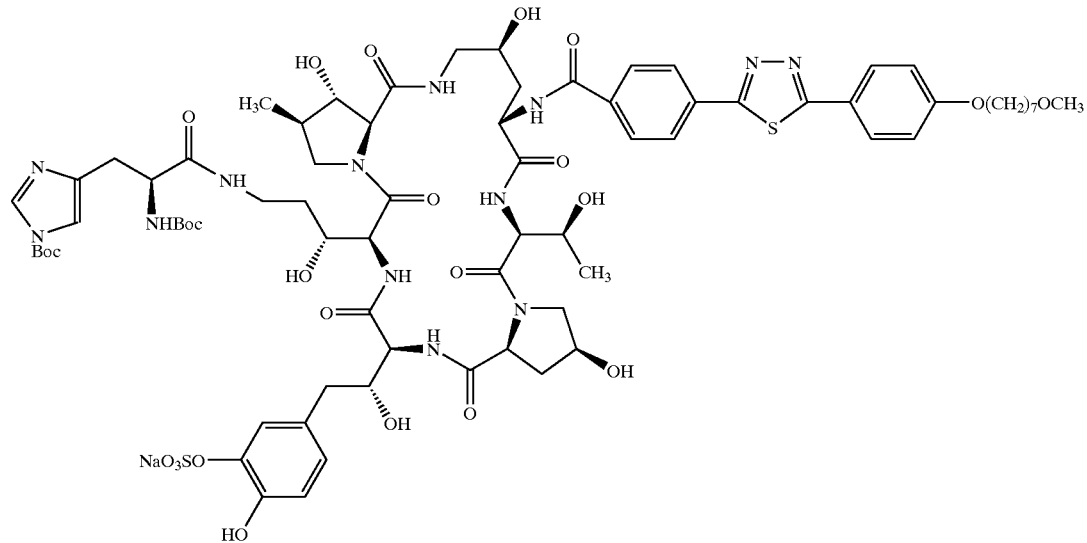 |
| 85 | 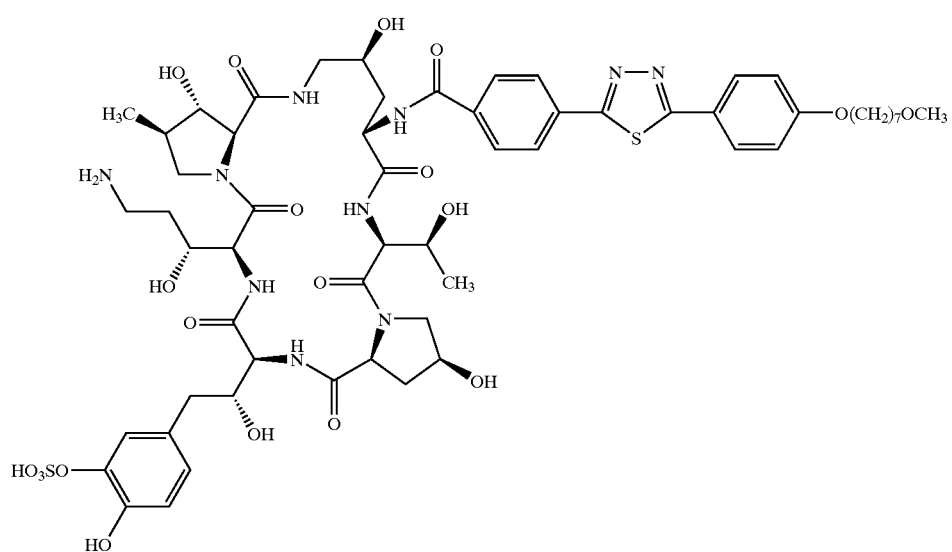 |

-continued
| Example No. | Formula |
|---|---|
| | 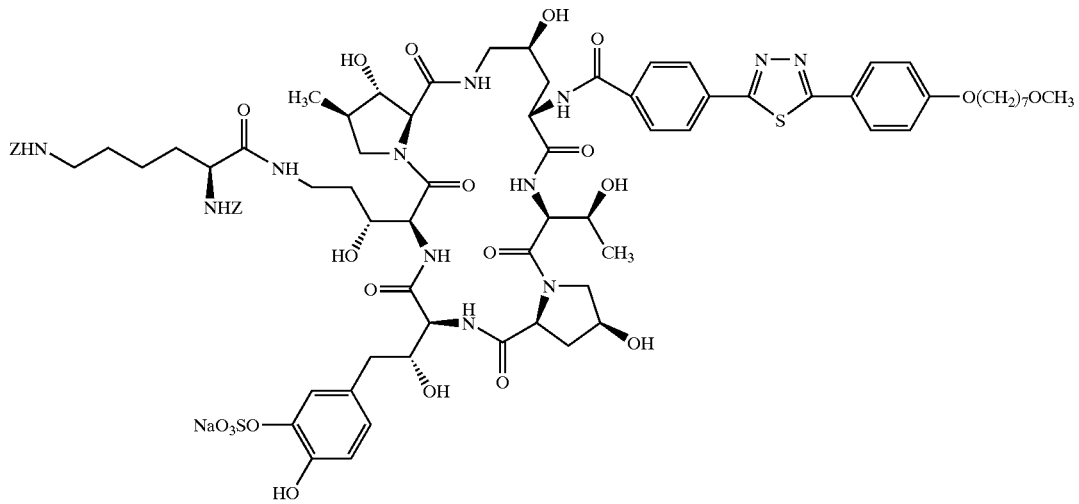 |
| 86 | 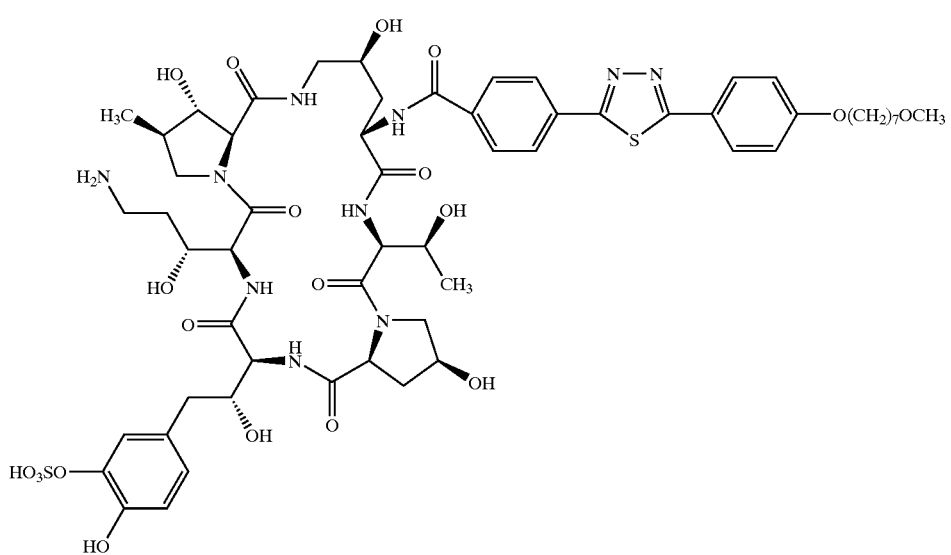 |
| | 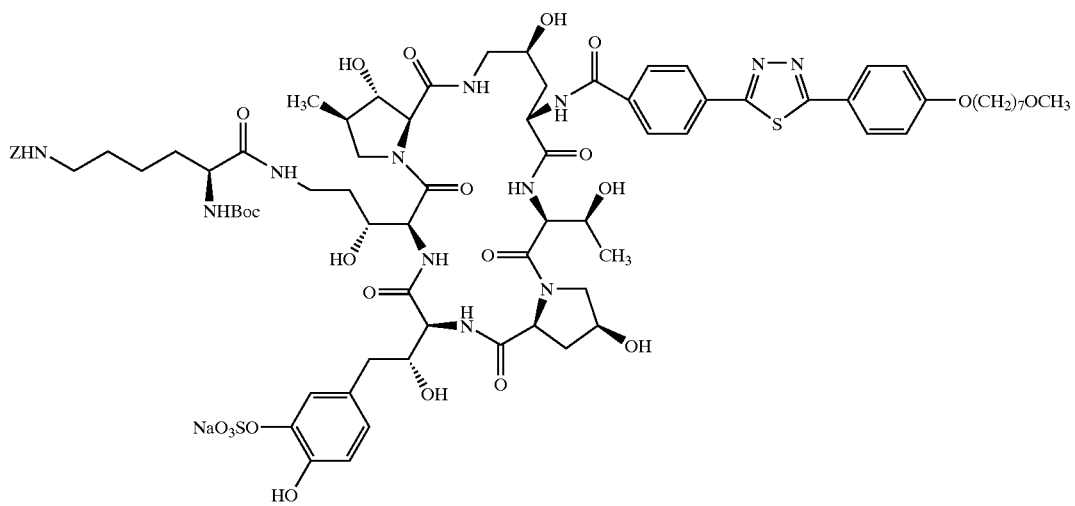 |

-continued
| Example No. | Formula |
|---|---|
| 87 | 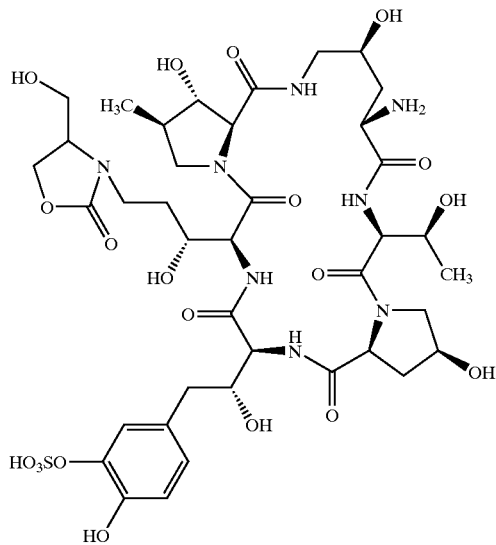 |
| | 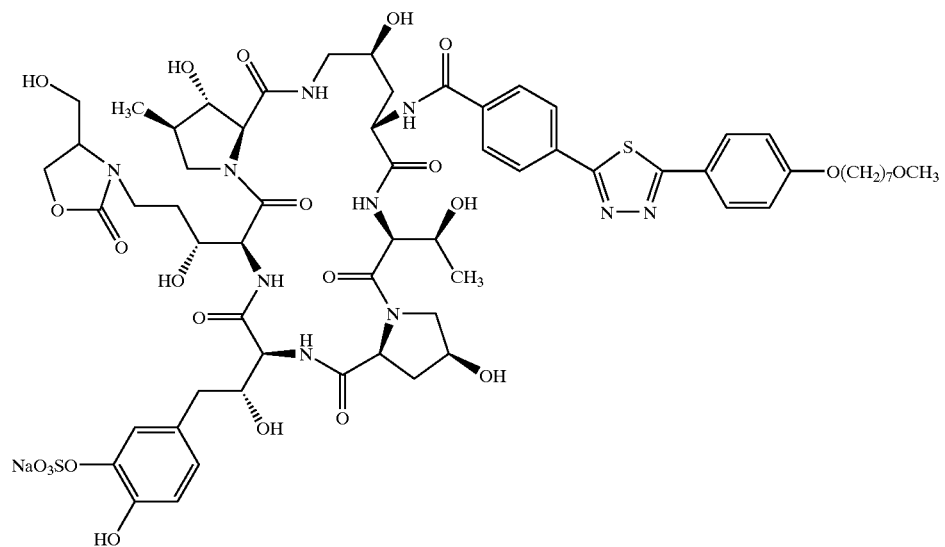 |

-continued
| Example No. | Formula |
|---|---|
| 88 | 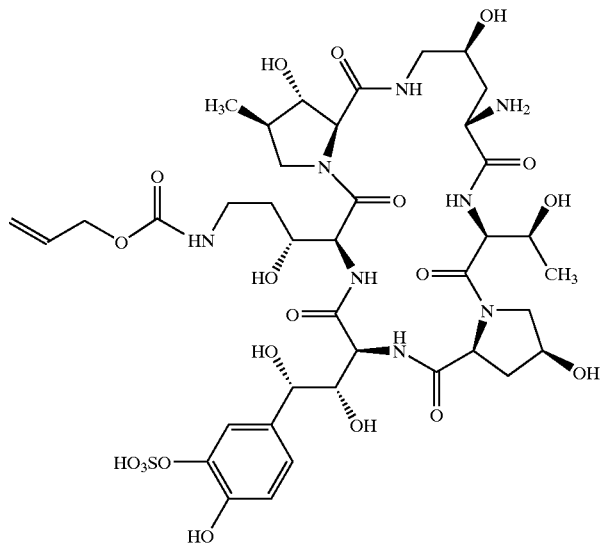 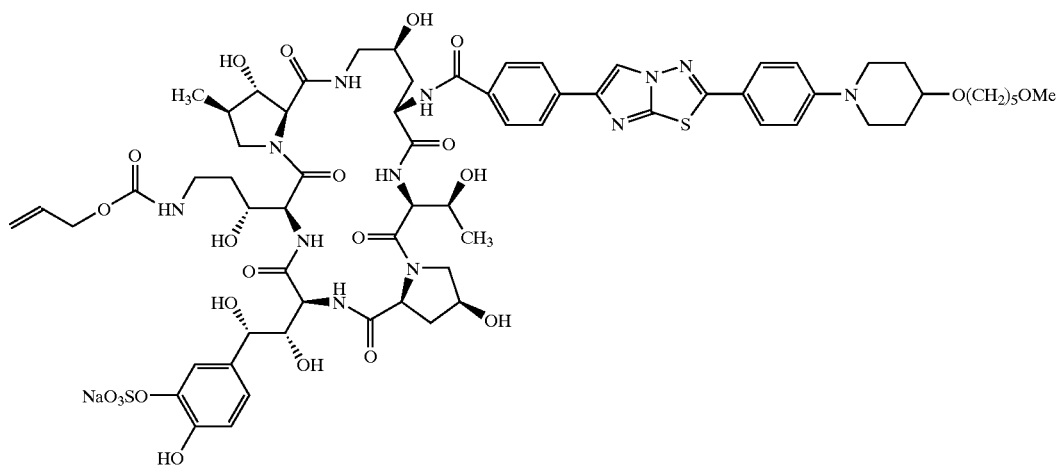 |
| 89 | 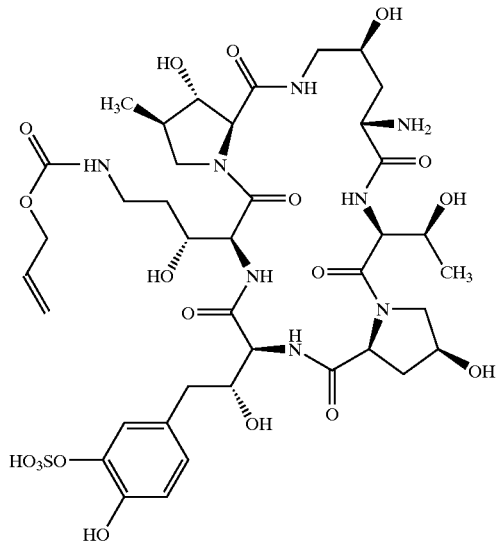 |

-continued
| Example No. | Formula |
|---|---|
| | 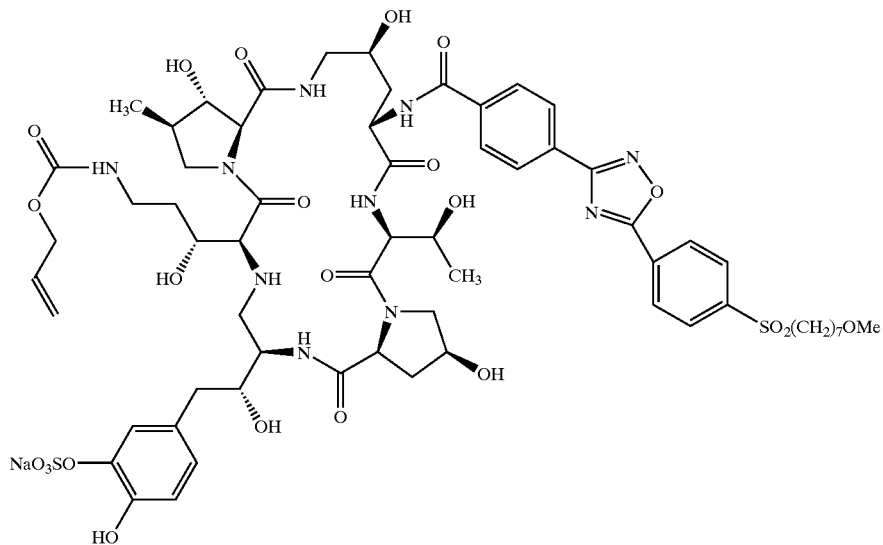 |
| 90 | 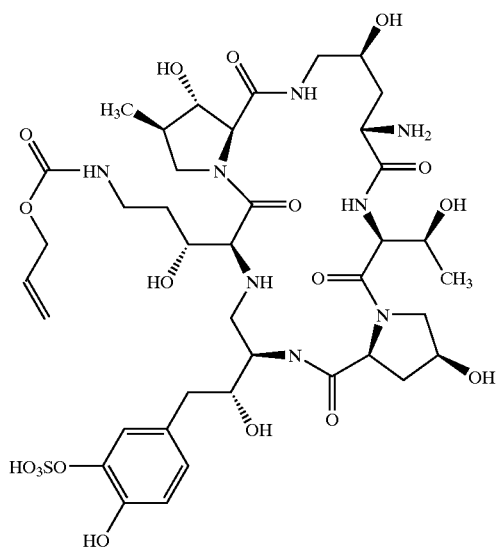 |

| Example No. | Formula |
|---|---|
| | 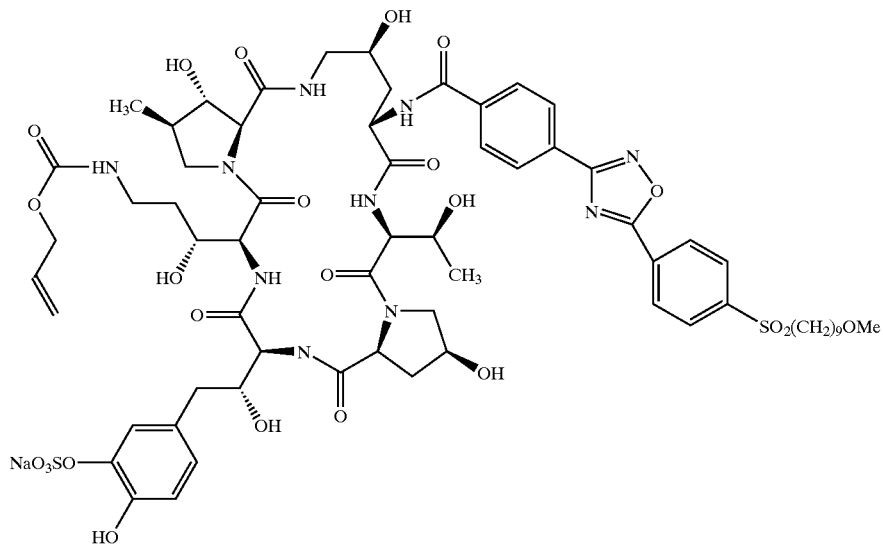 |
| 91 | 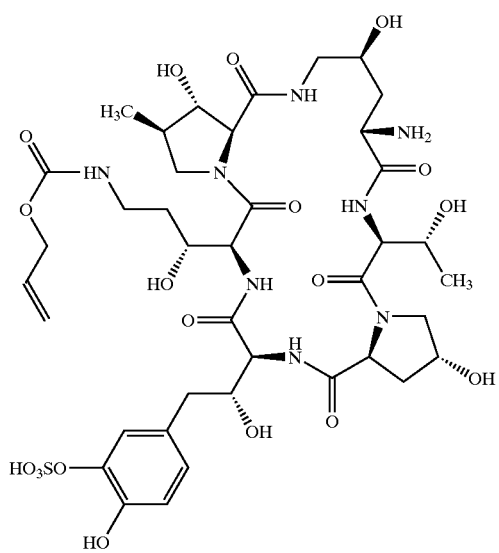 |

-continued
| Example No. | Formula |
|---|---|
| | 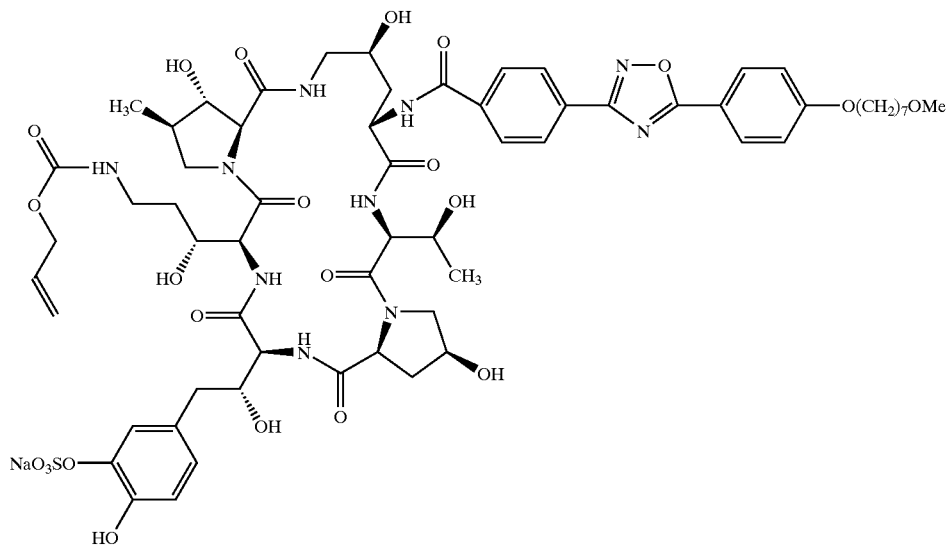 |
| 92 | 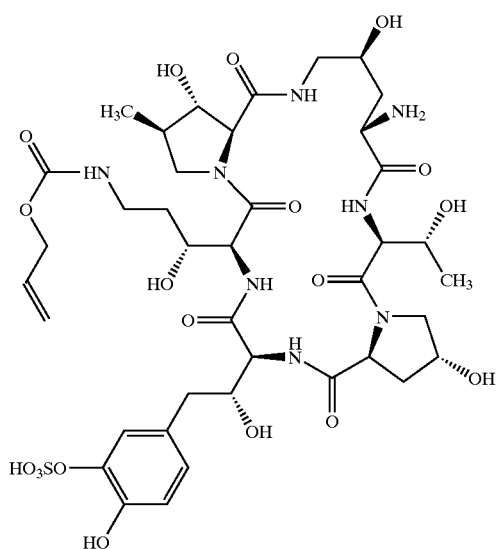 |

| Example No. | Formula |
|---|---|
| | 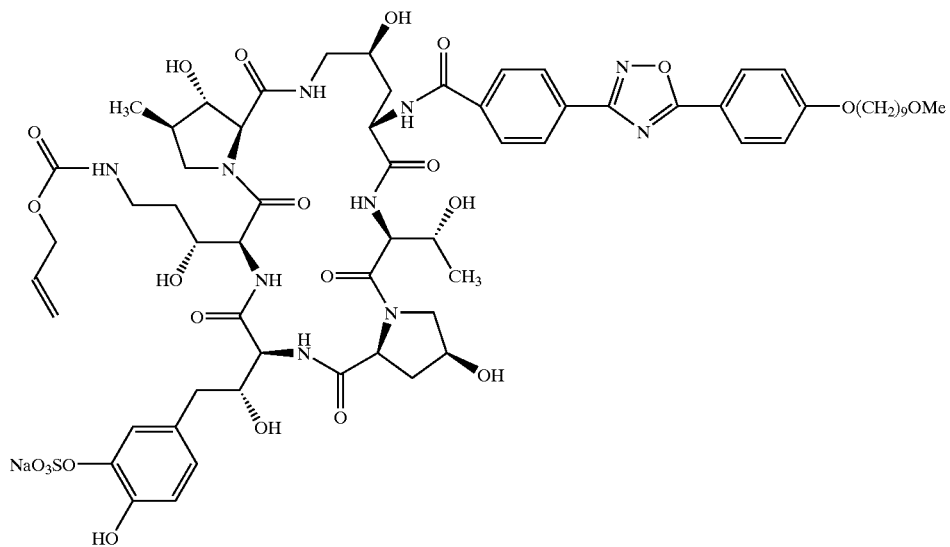 |
| 93 | 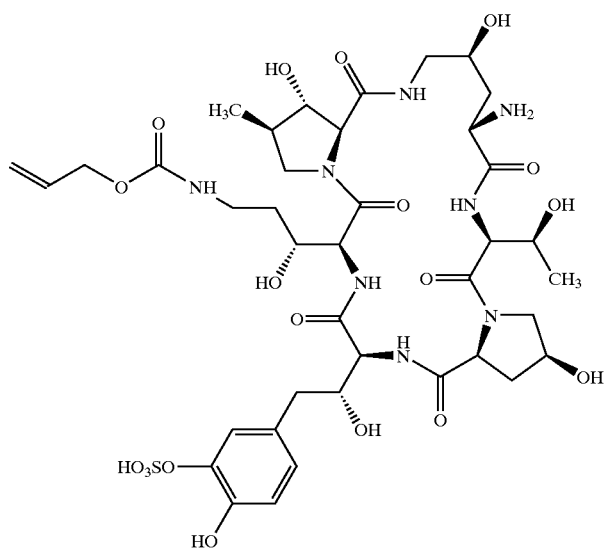 |

| Example No. | Formula |
|---|---|
| | 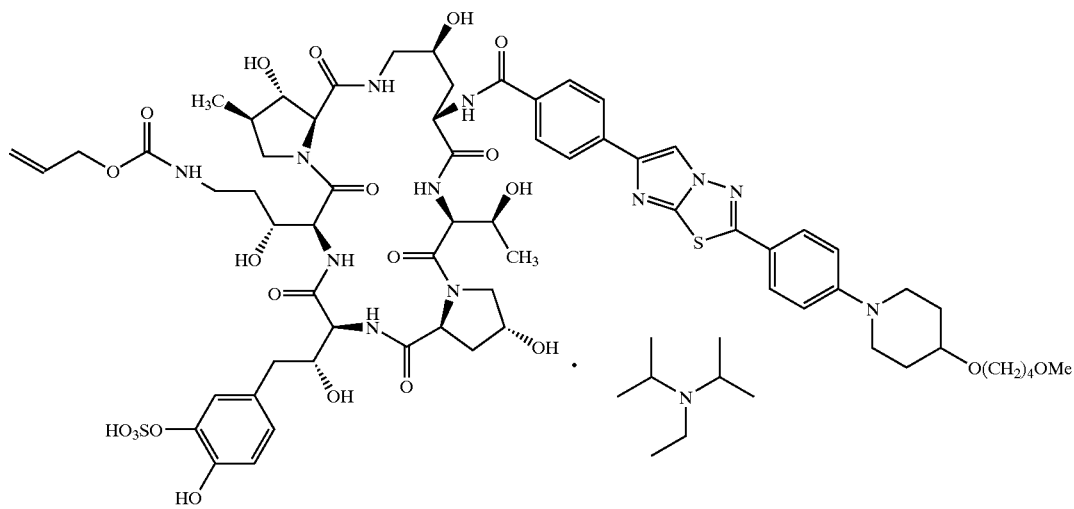 |
| 94 | 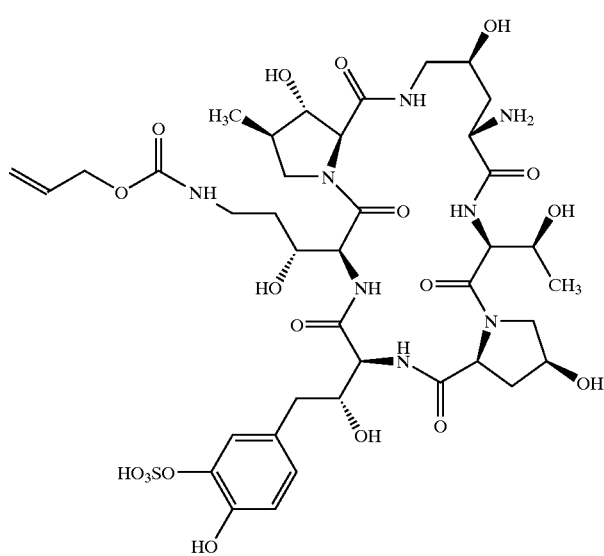 |
| | 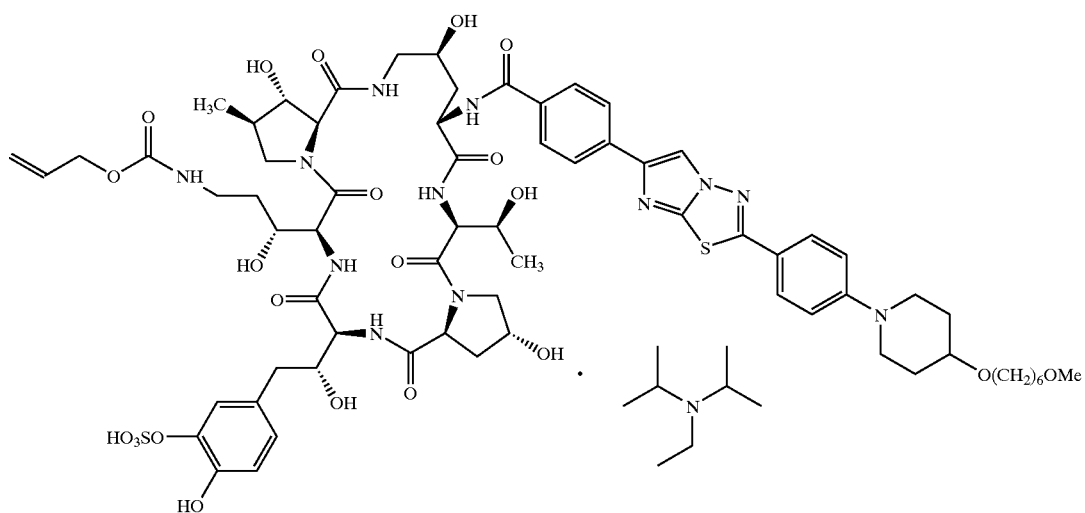 |

| Example No. | Formula |
|---|---|
| 95 | 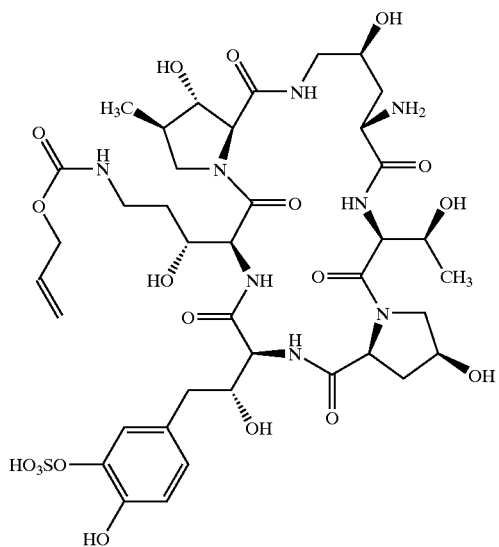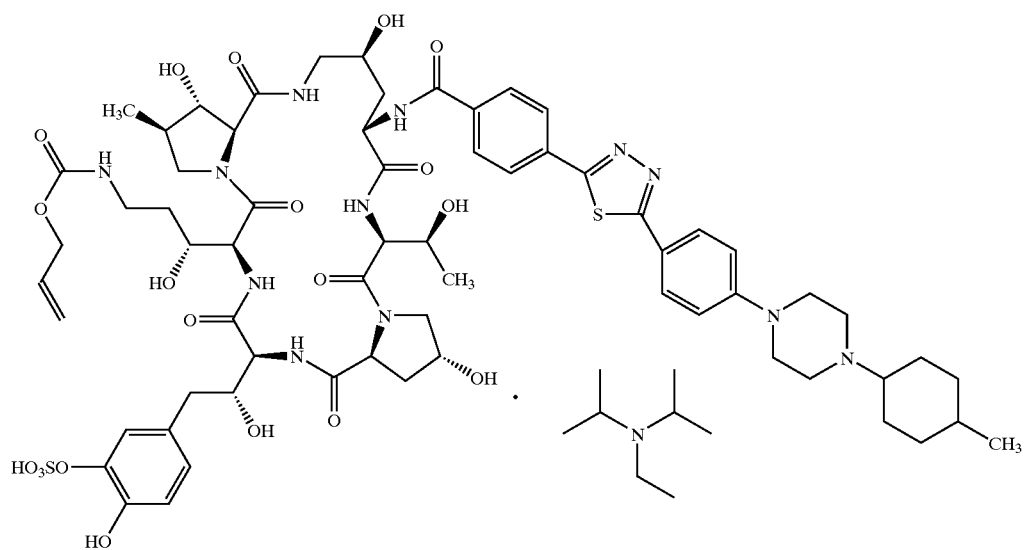 |

| Example No. | Formula |
|---|---|
| 96 | 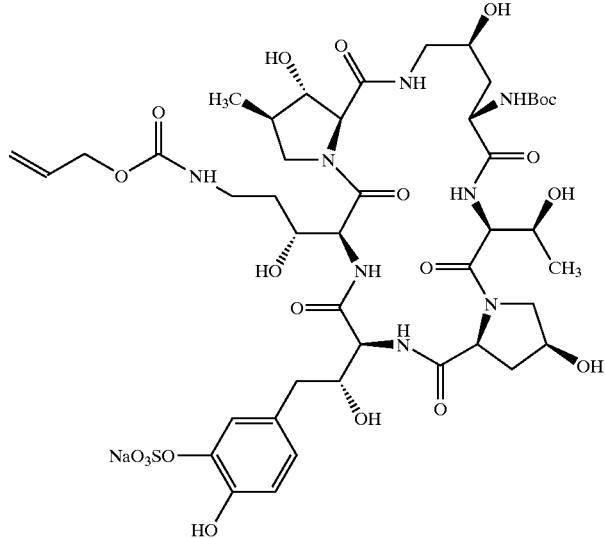 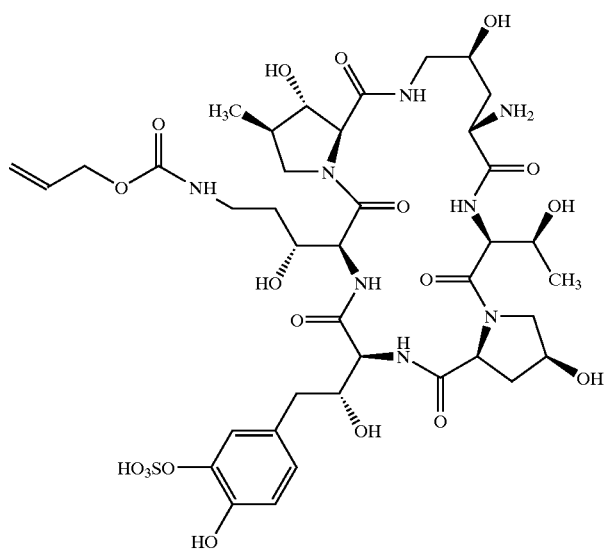 |

-continued
| Example No. | Formula |
|---|---|
| | 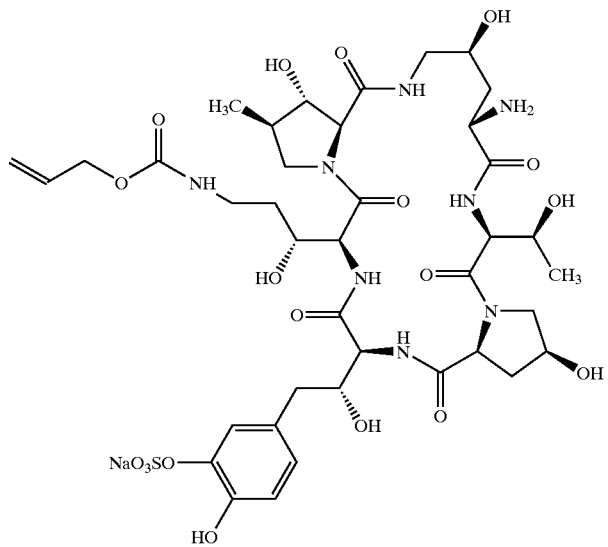 |
| 97 | 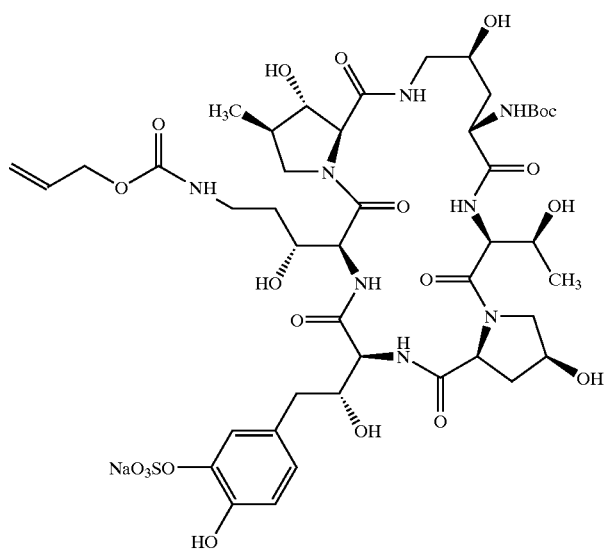 |

| Example No. | Formula |
|---|---|
| | 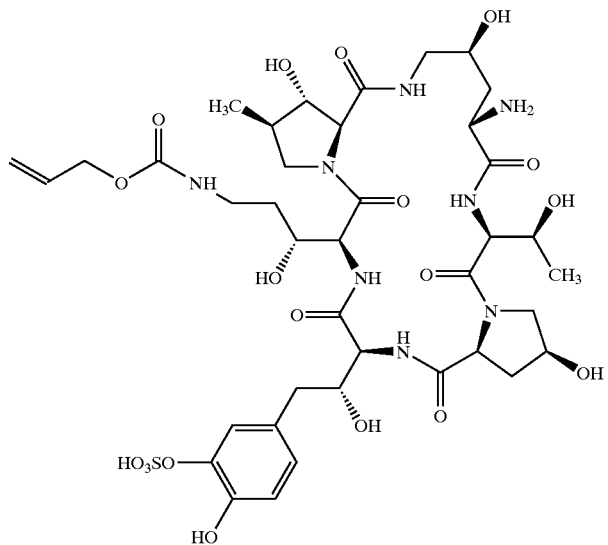 |
| 98 | 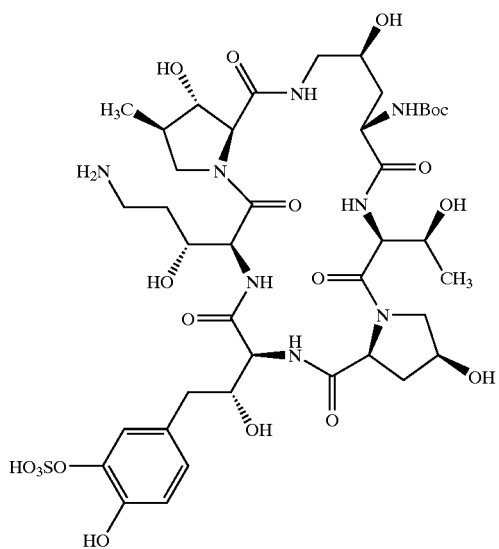 |

| Example No. | Formula |
|---|---|
| | 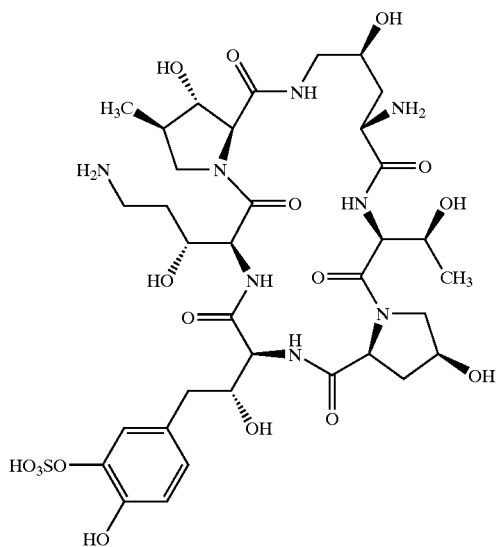 |
| 99 | 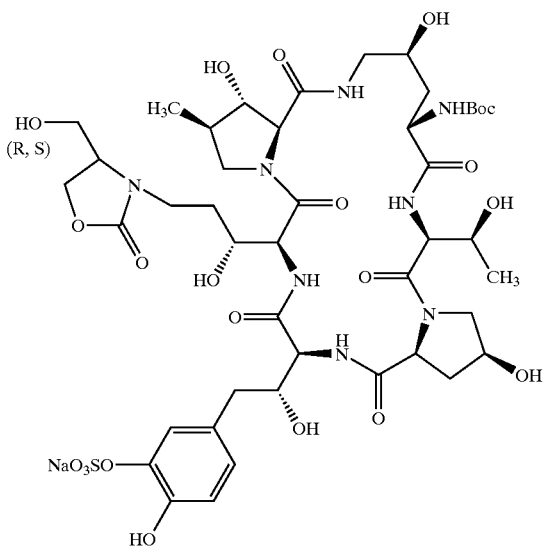 |

| Example No. | Formula |
|---|---|
| | 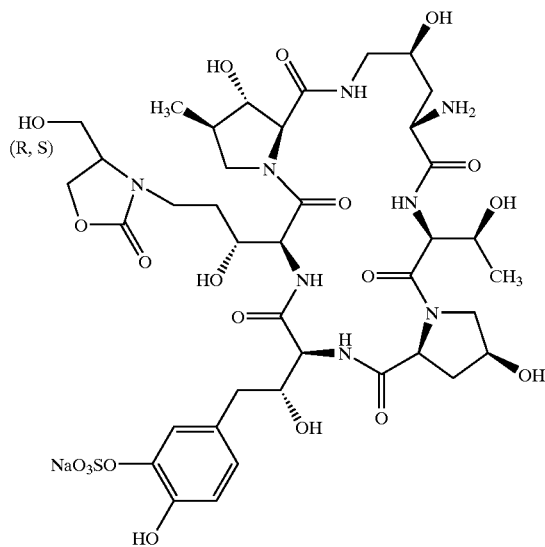 |
| 100 | 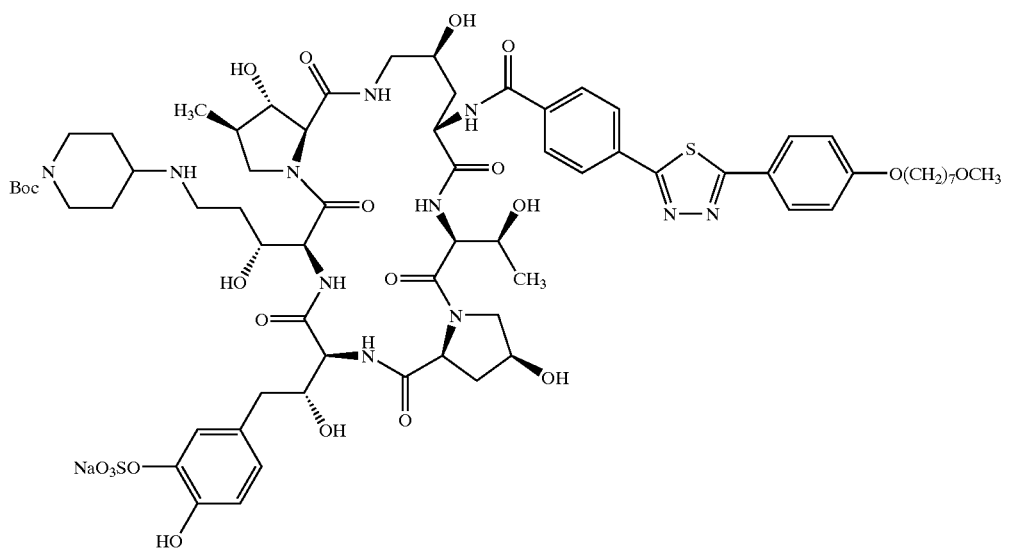 |

| Example No. | Formula |
|---|---|
| | 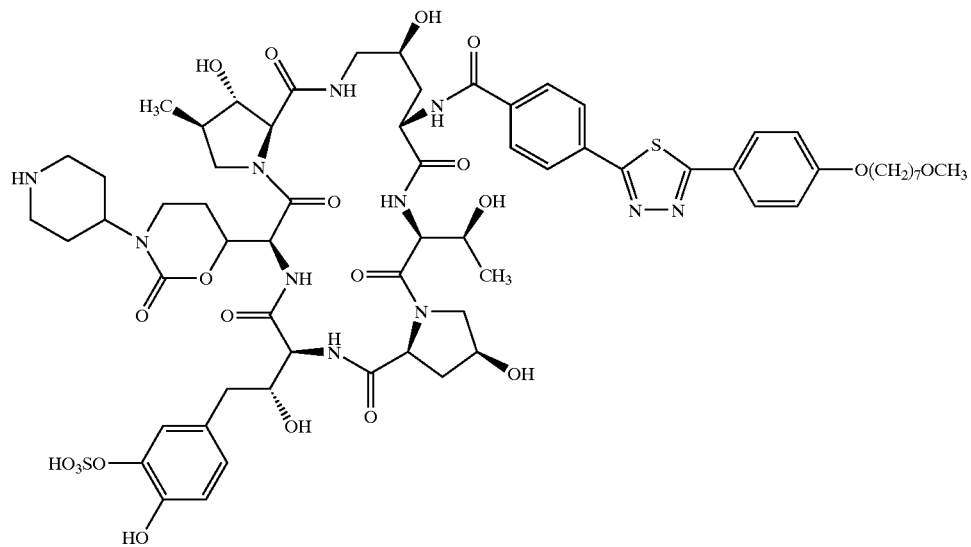 |
| 101 | 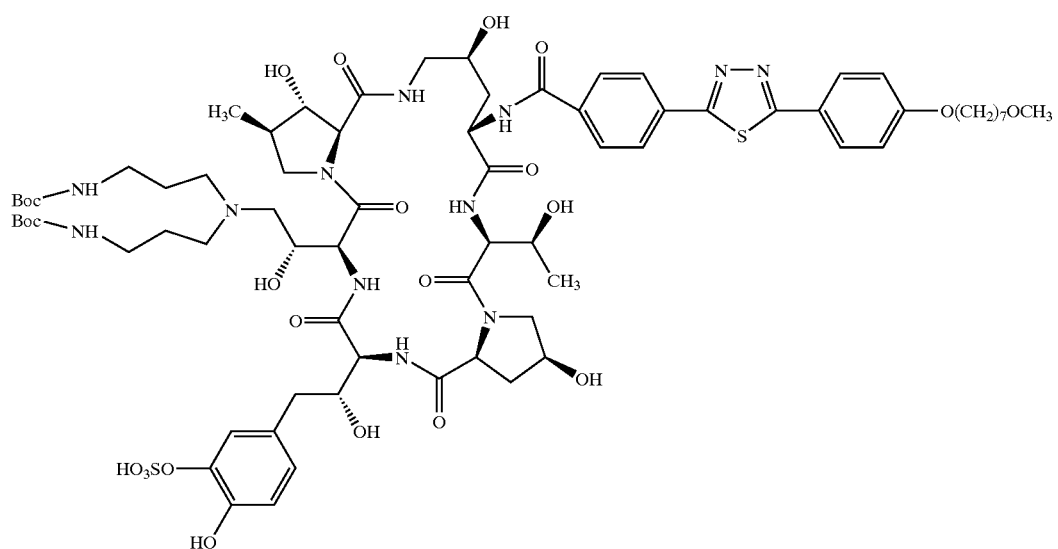 |

-continued
| Example No. | Formula |
|---|---|
| | 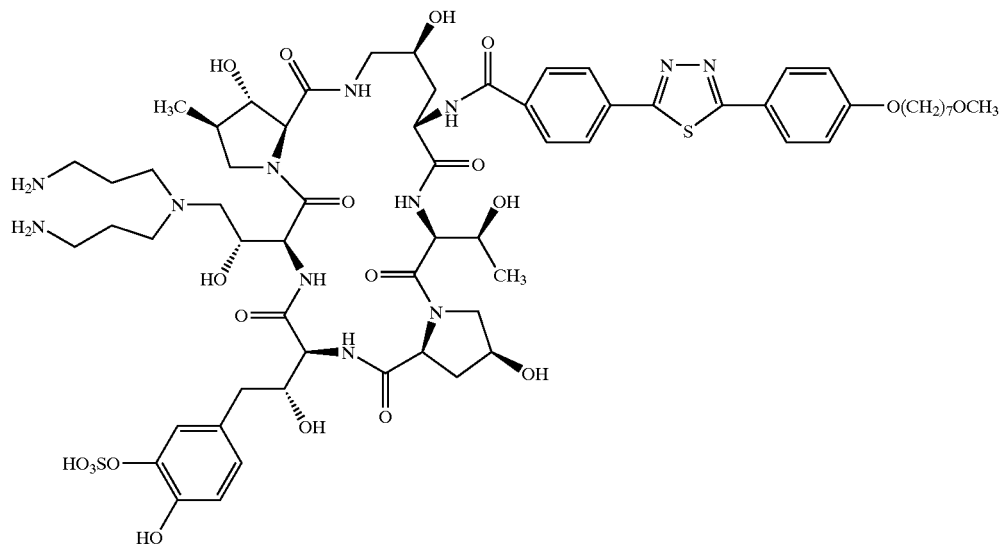 |
| 102 | 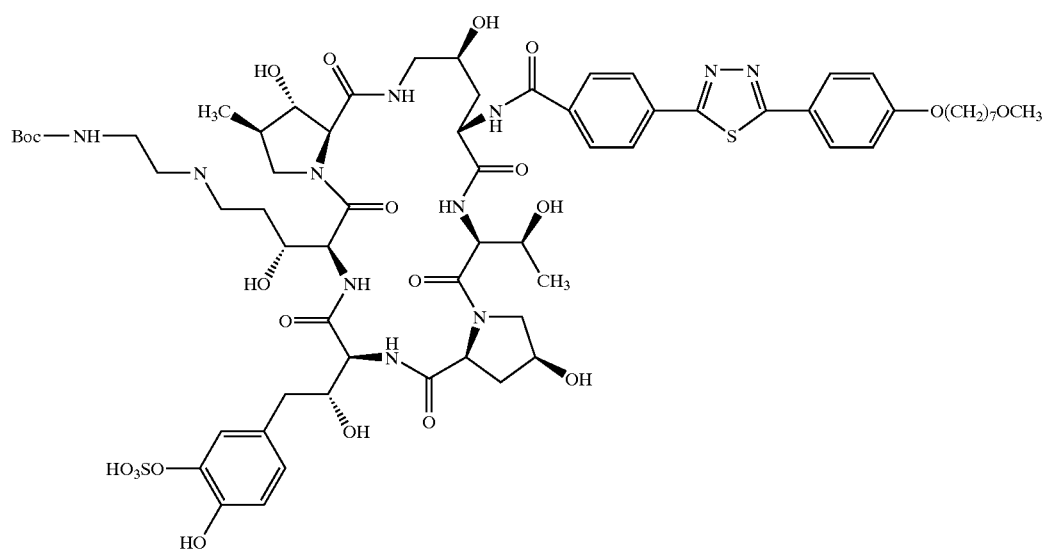 |

| Example No. | Formula |
|---|---|
| | 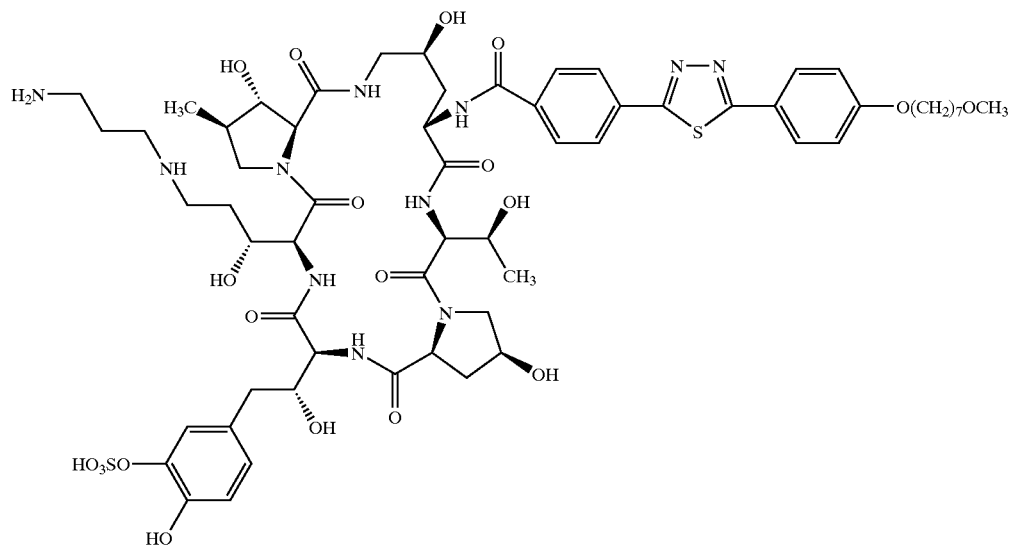 |
| 103 | 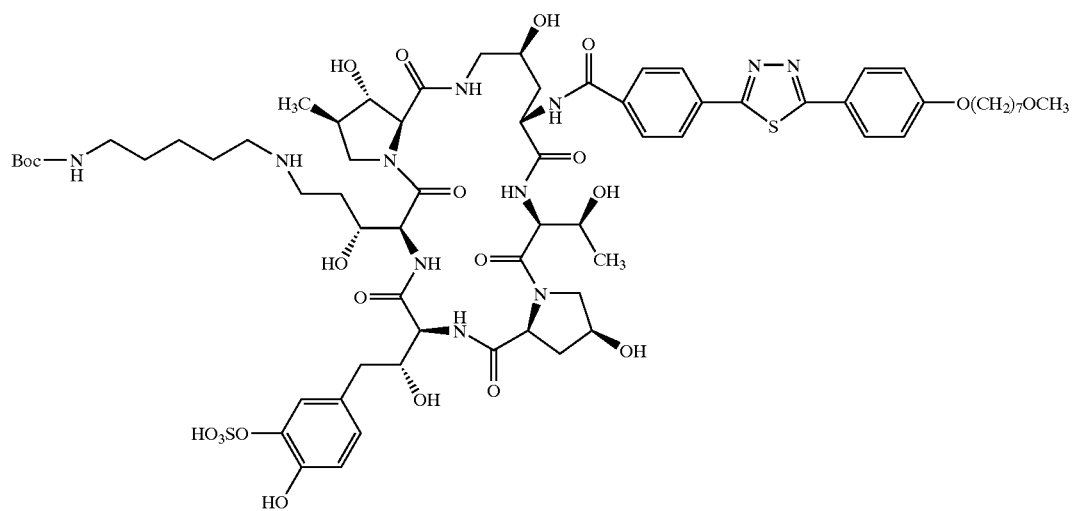 |

-continued
| Example No. | Formula |
|---|---|
| | 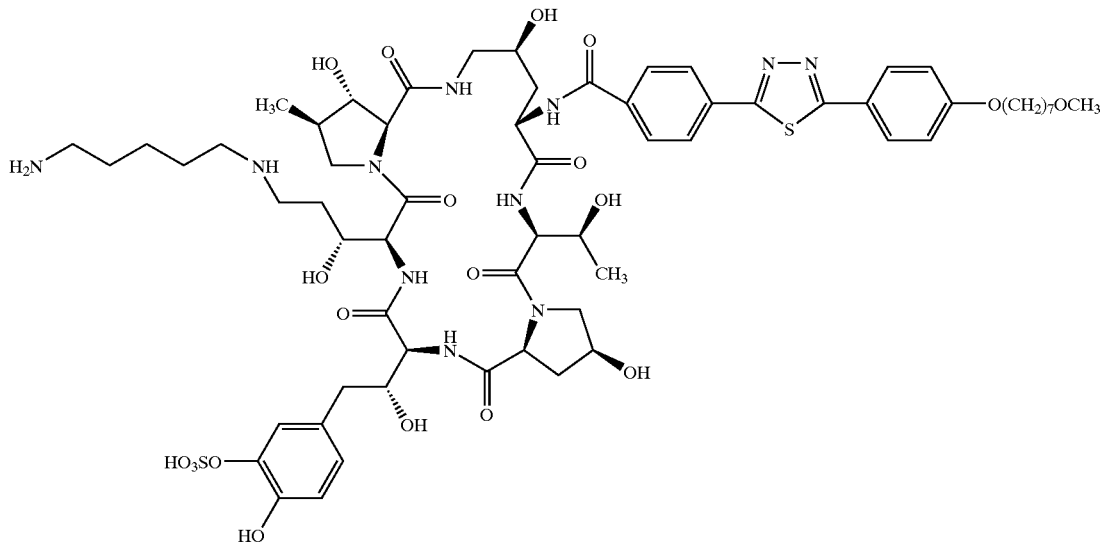 |
| 104 | 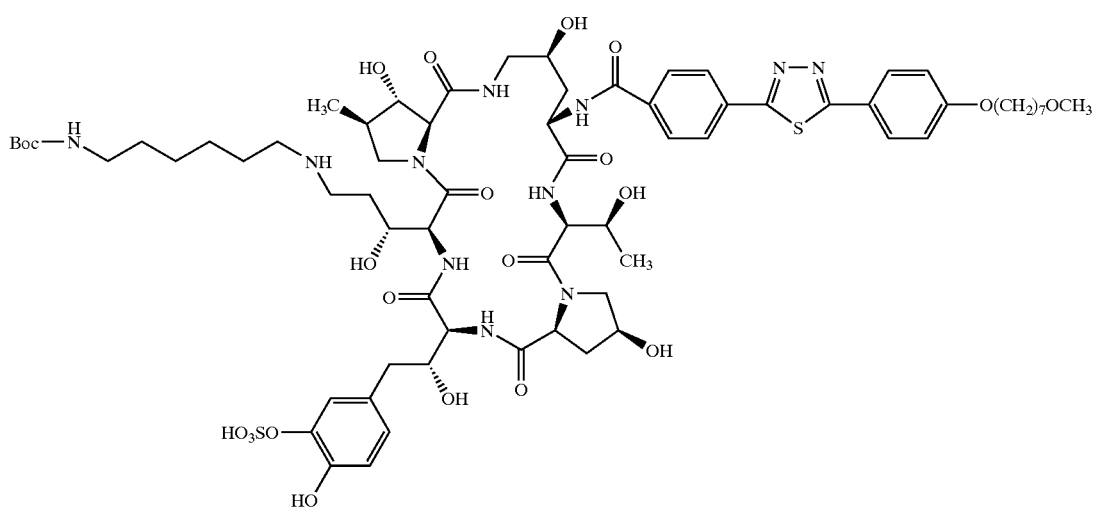 |
| | 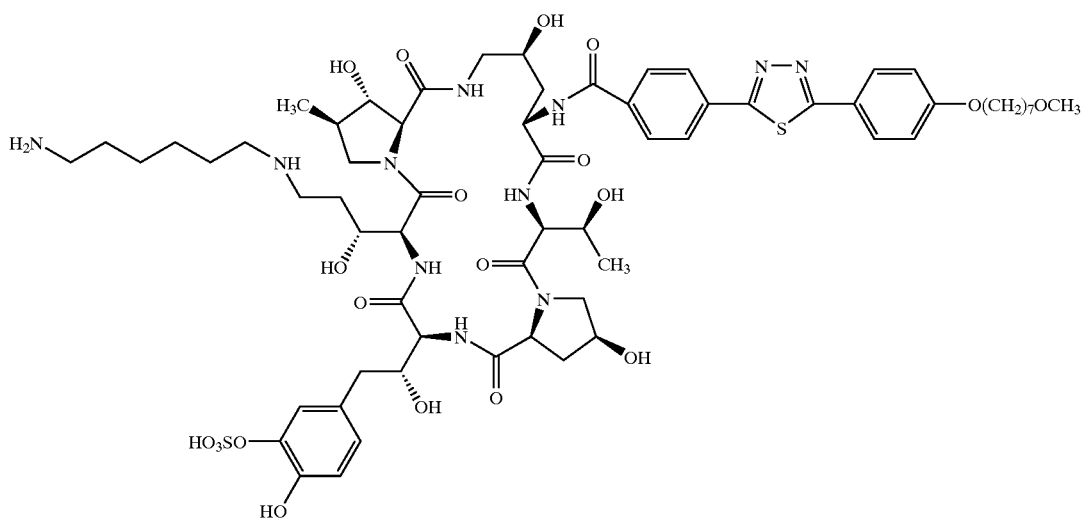 |

-continued
| Example No. | Formula |
|---|---|
| 105 | 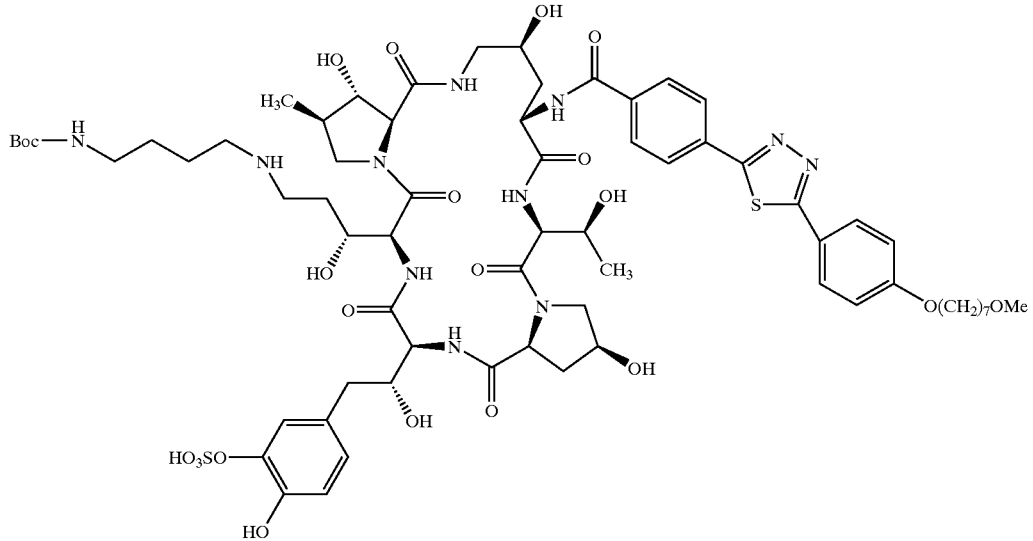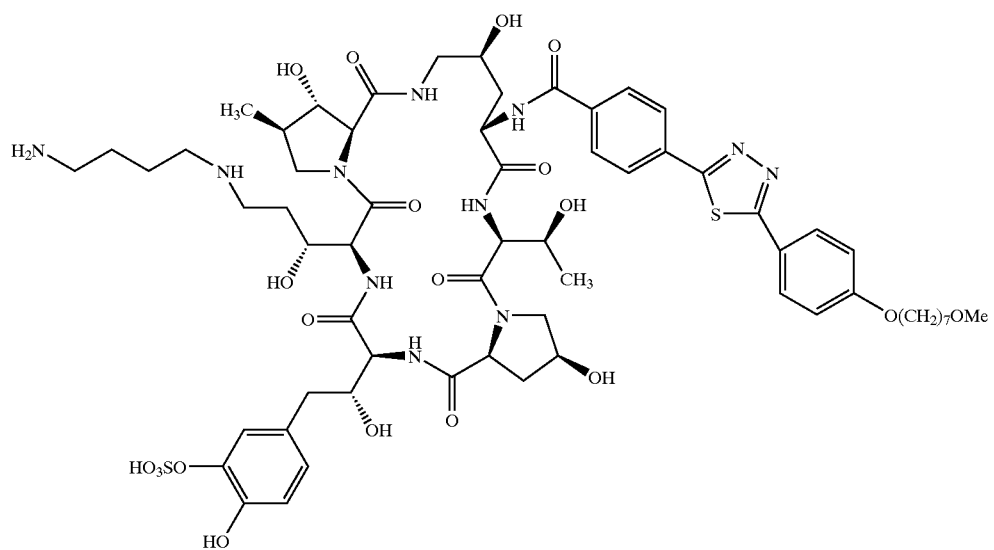 |

-continued
| Example No. | Formula |
|---|---|
| 106 | 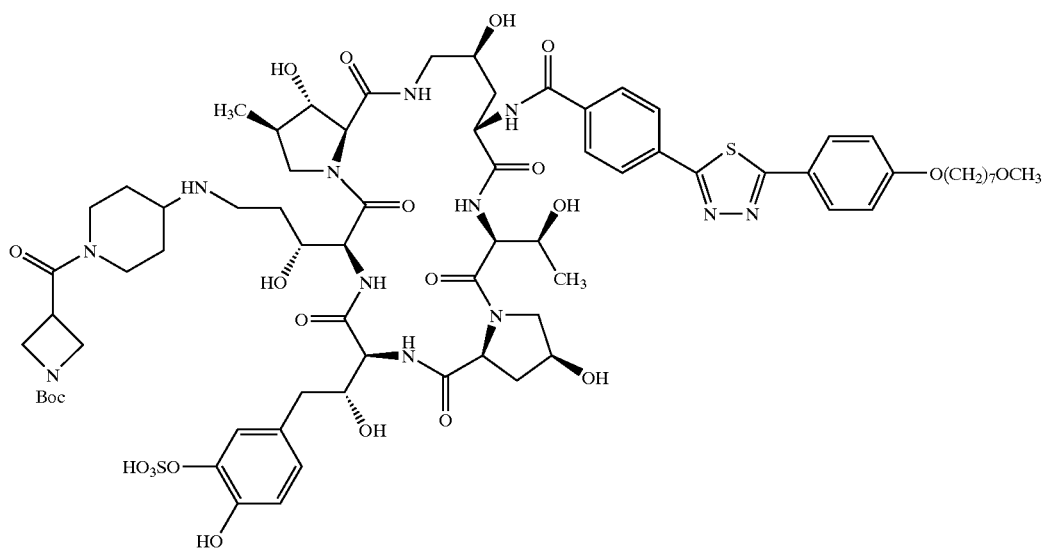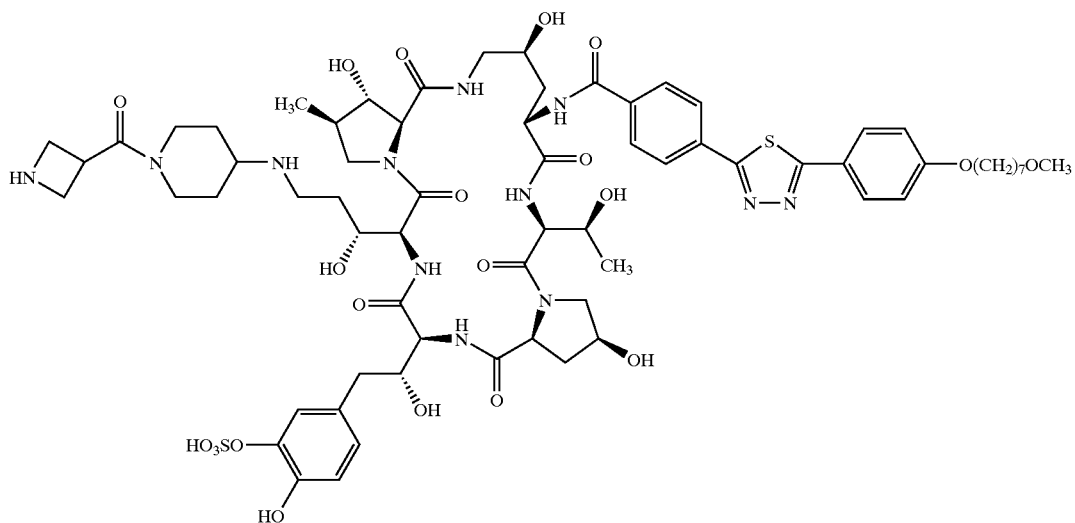 |

-continued
| Example No. | Formula |
|---|---|
| 107 | 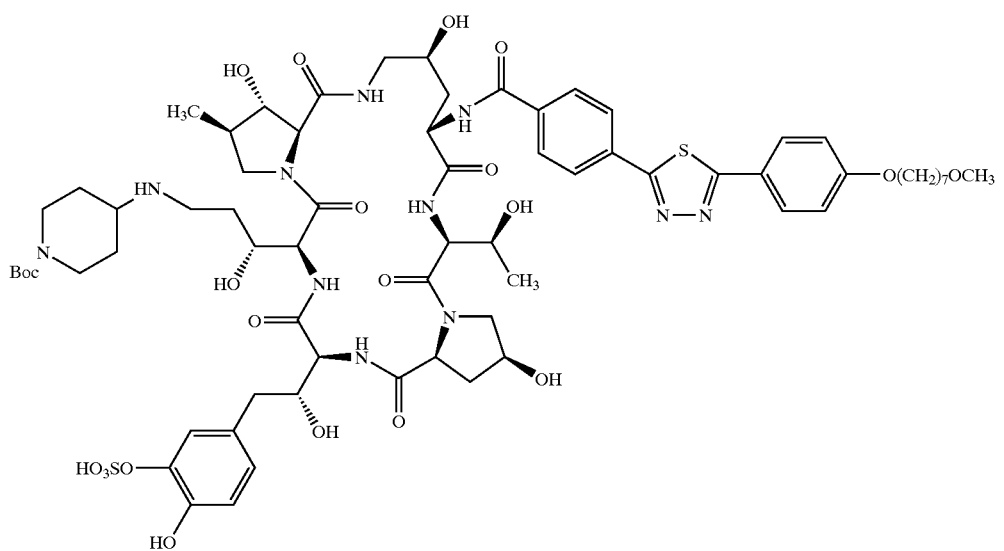 |
| | 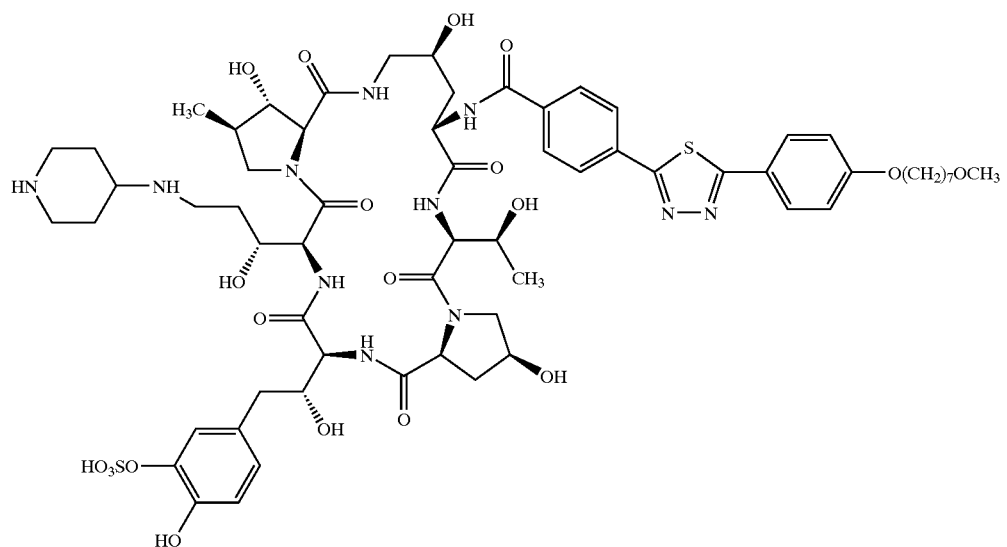 |

-continued
| Example No. | Formula |
|---|---|
| 108 | 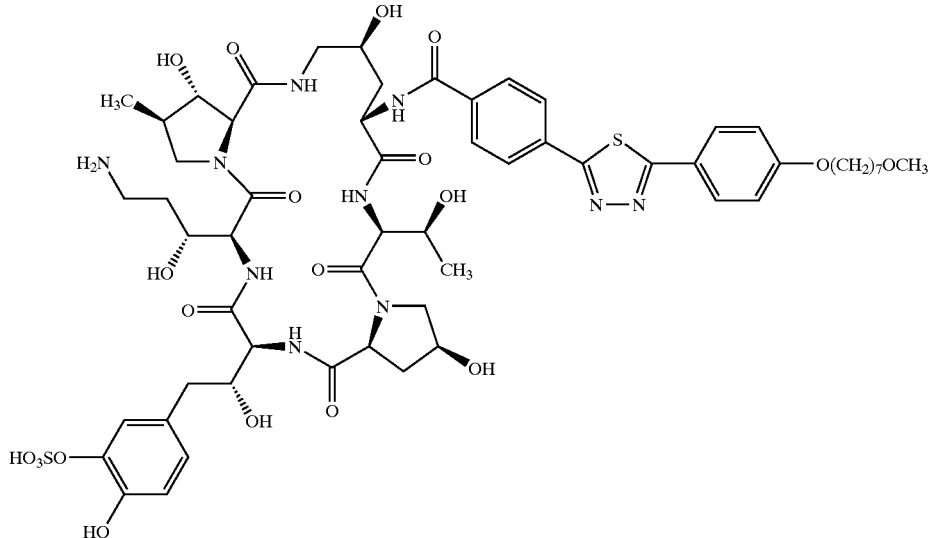 |
| | 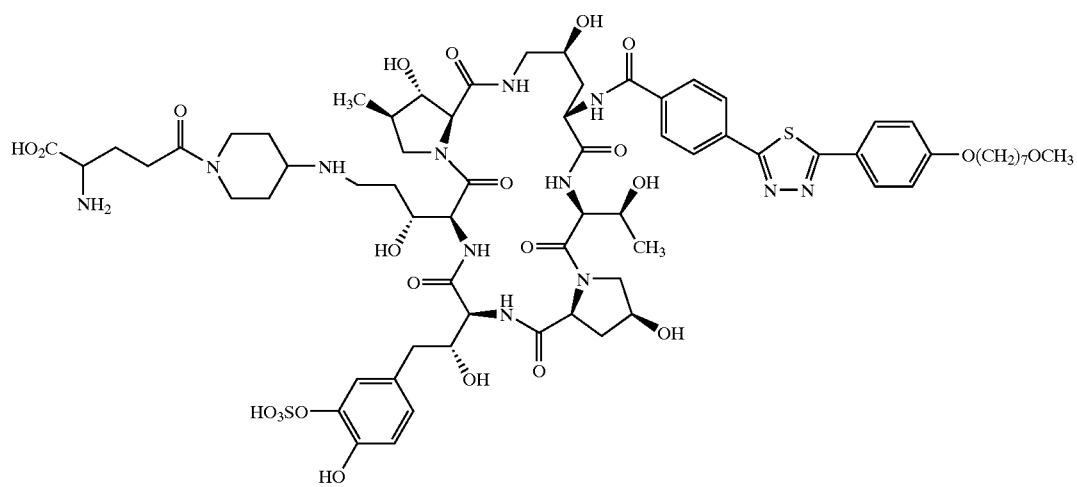 |
| 109 | 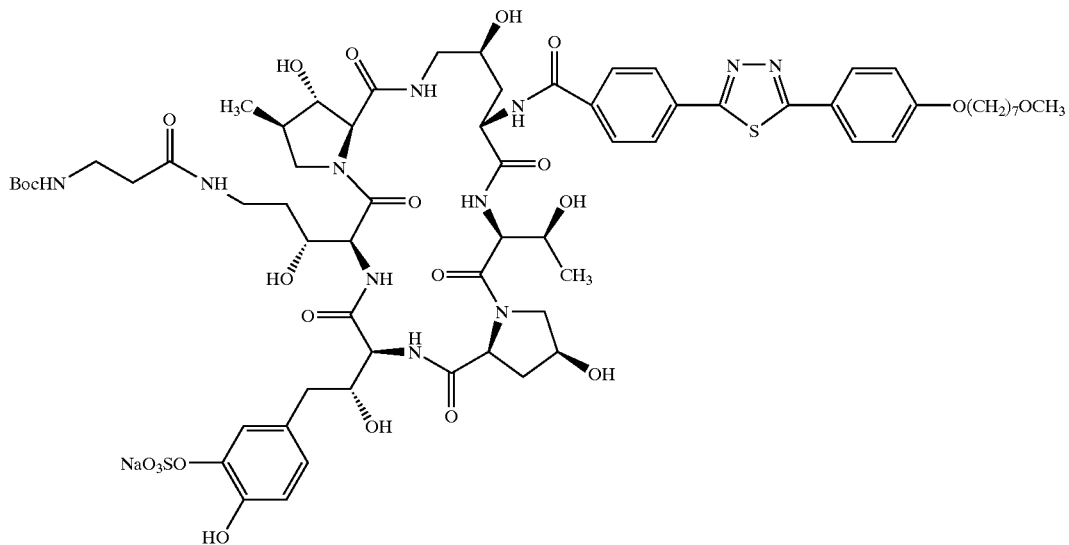 |

| Example No. | Formula |
|---|---|
| | 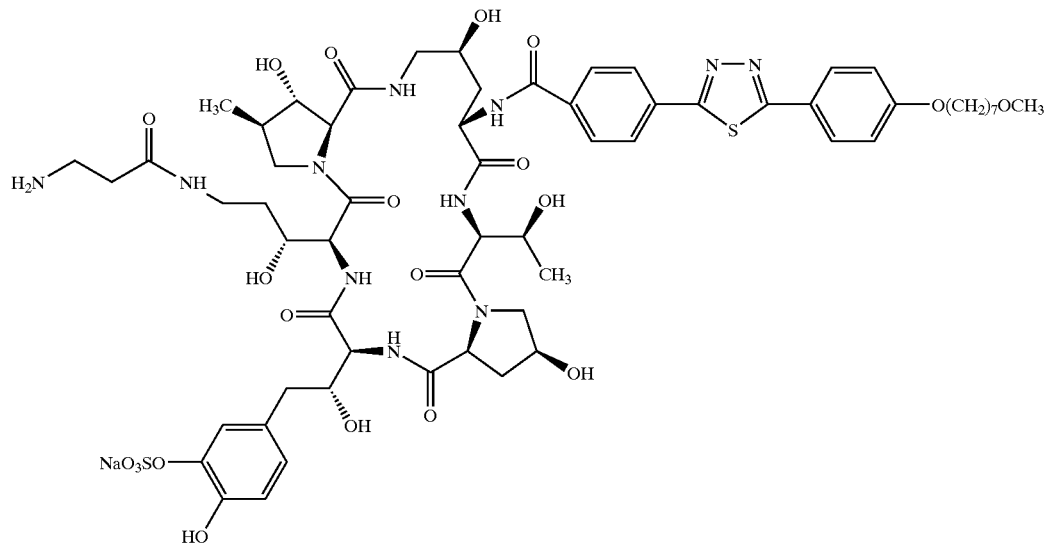 |
| 110 | 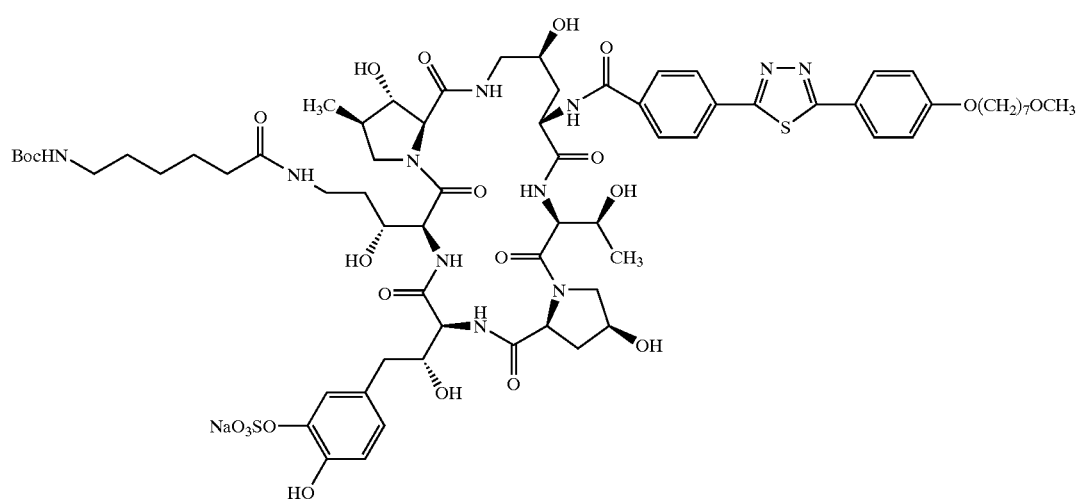 |
| | 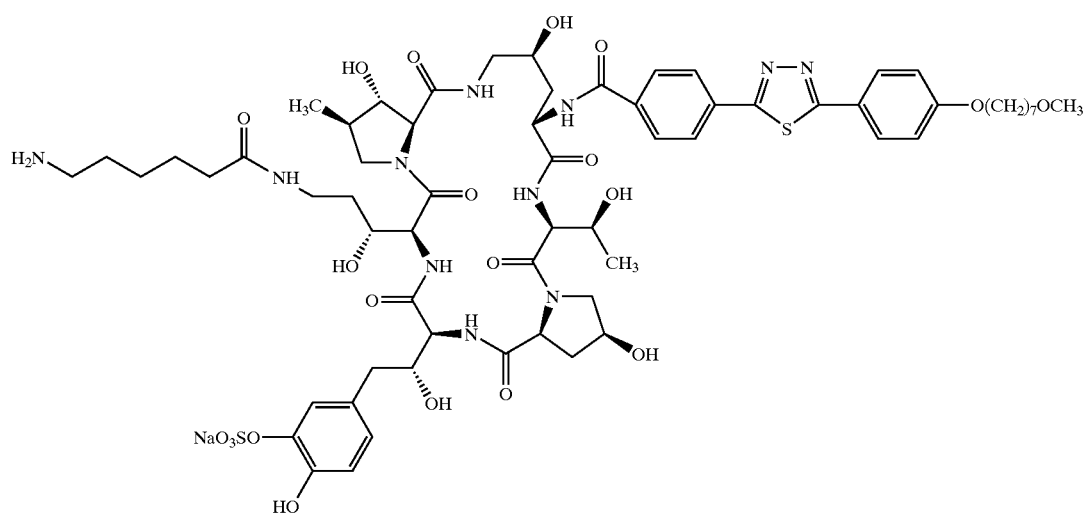 |

| Example No. | Formula |
|---|---|
| 111 | 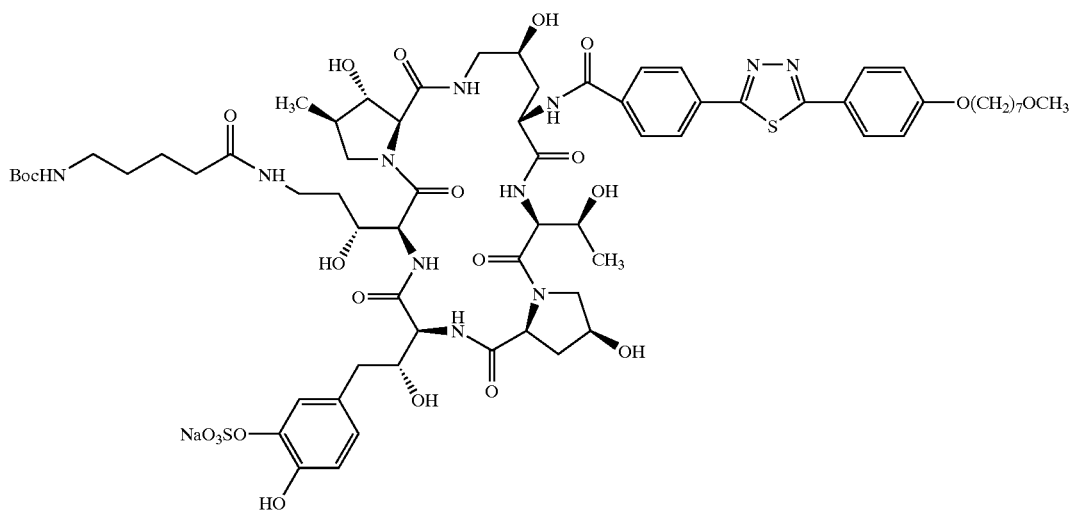 |
| | 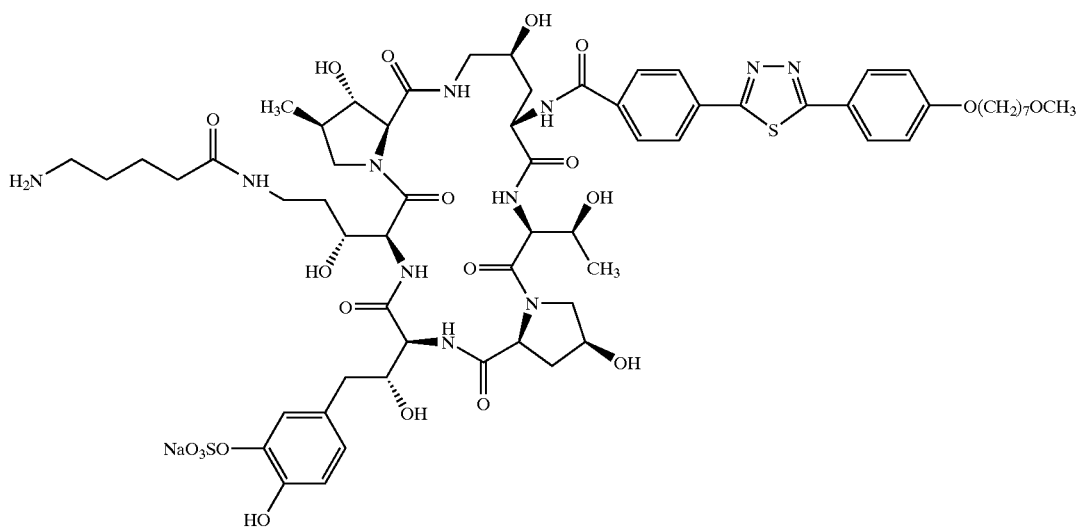 |
| 112 | 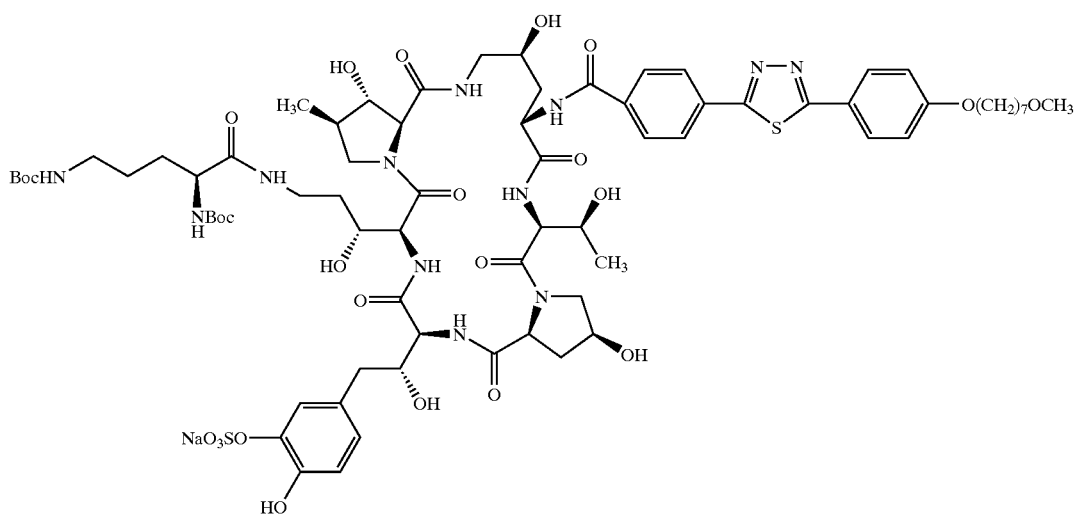 |

-continued
| Example No. | Formula |
|---|---|
| | 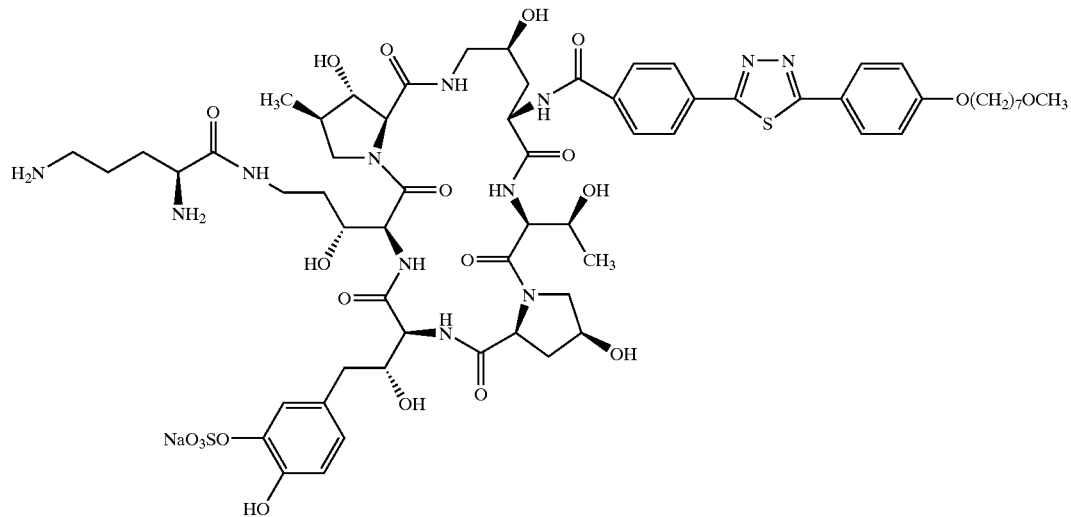 |
| 113 | 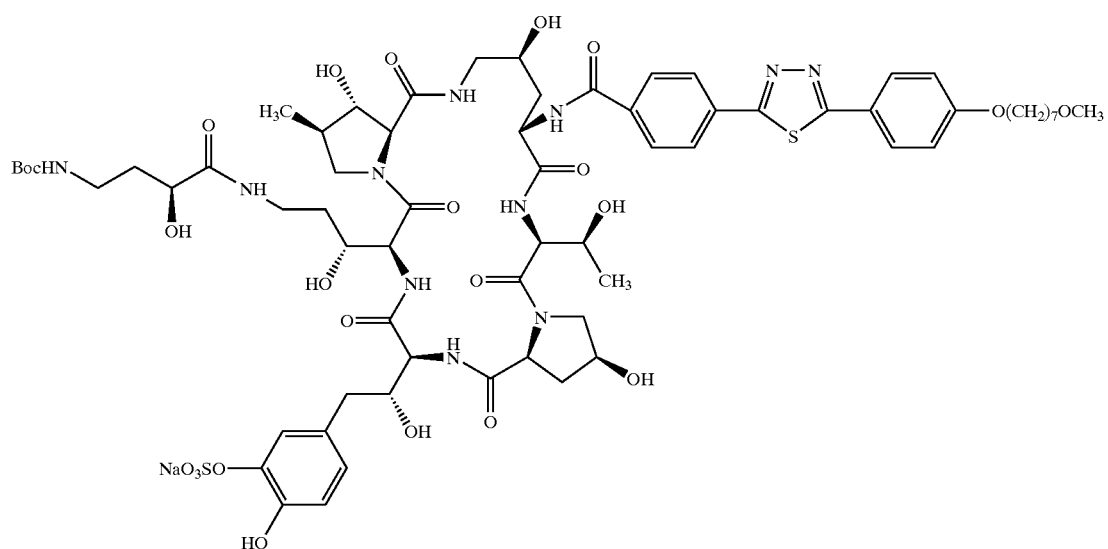 |

| Example No. | Formula |
|---|---|
| | 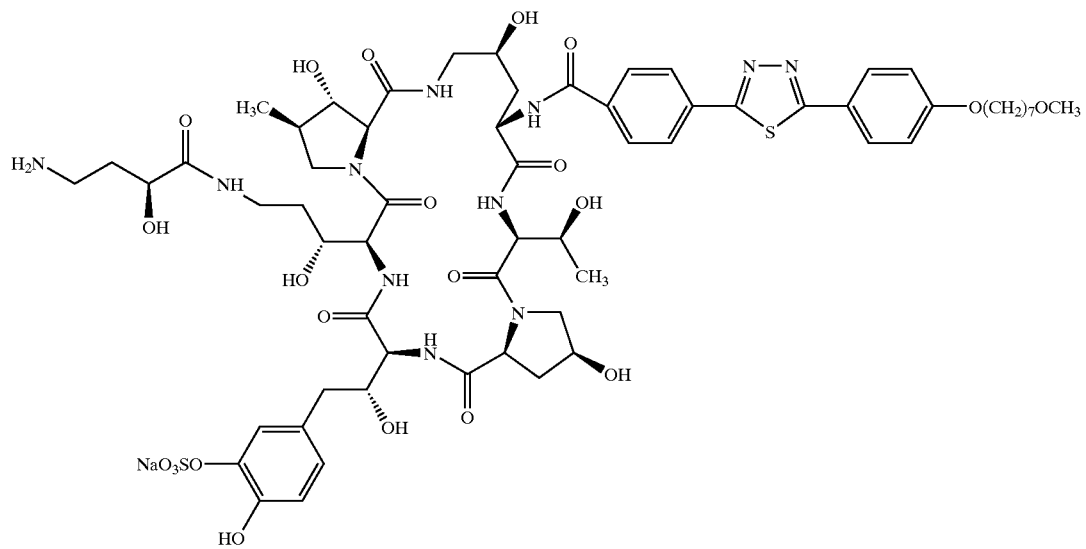 |
| 114 | 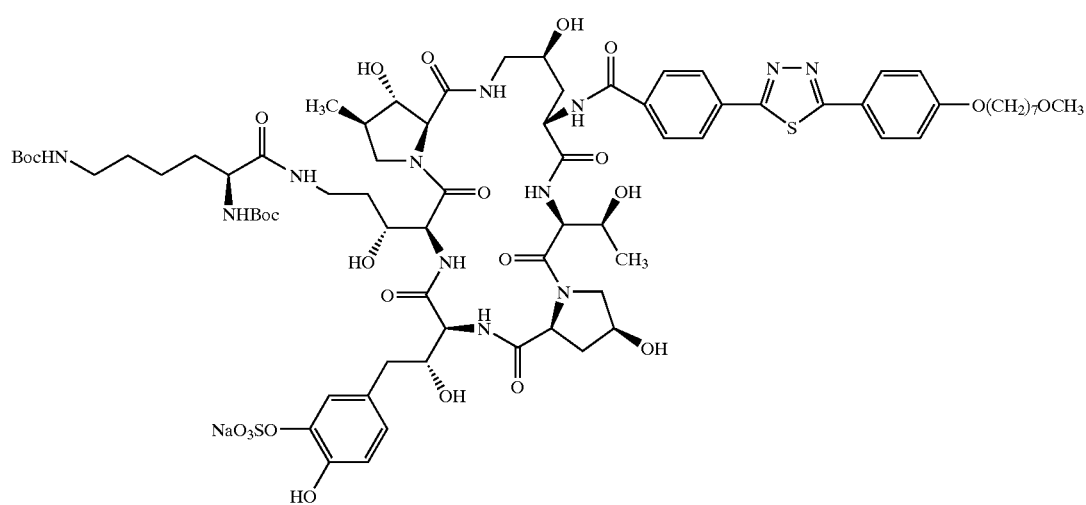 |
| | 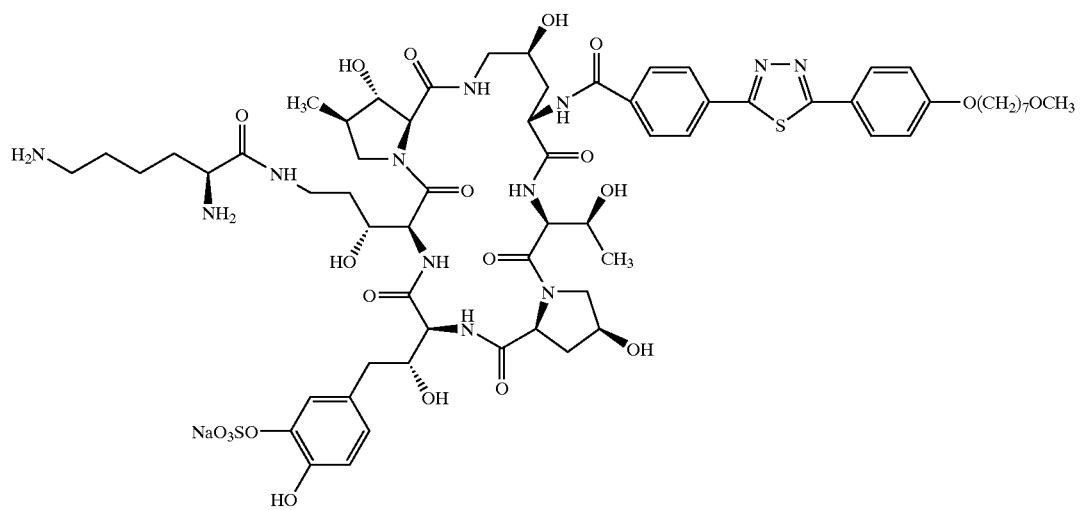 |

| Example No. | Formula |
|---|---|
| 115 | 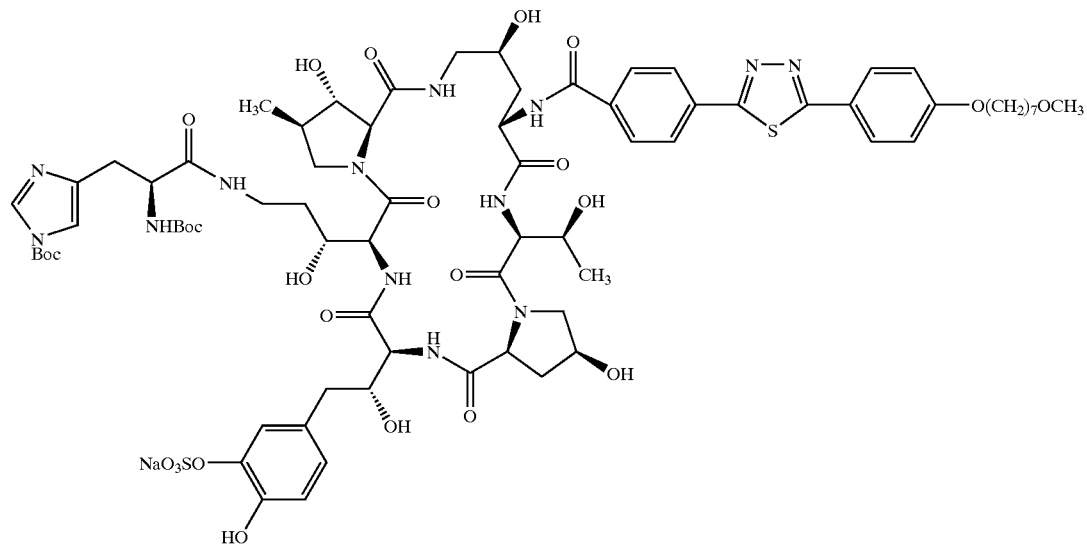<br>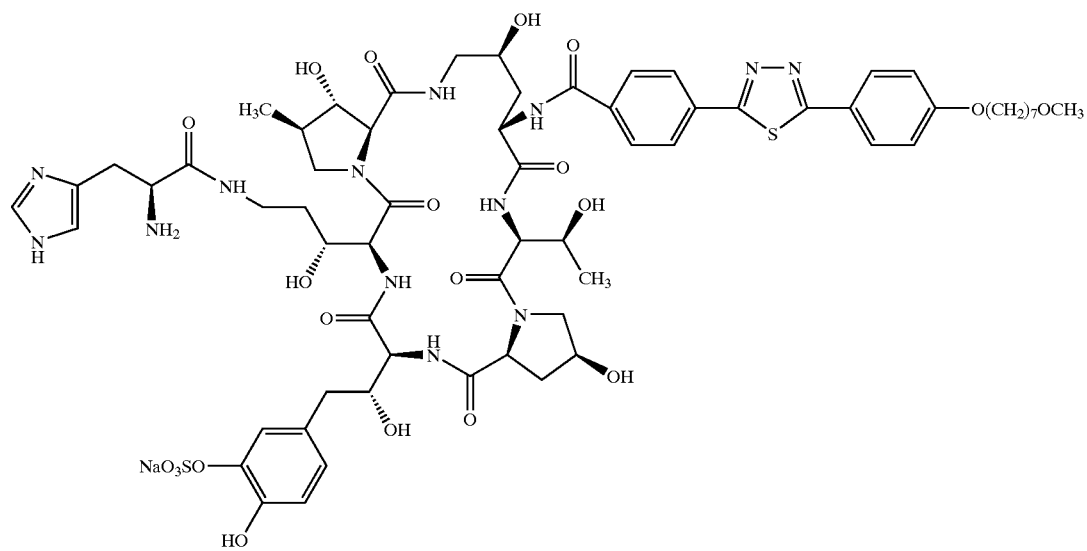 |

-continued
| Example No. | Formula |
|---|---|
116 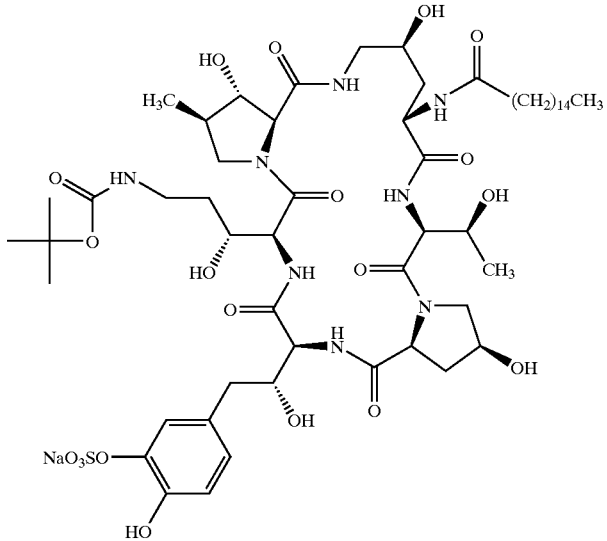
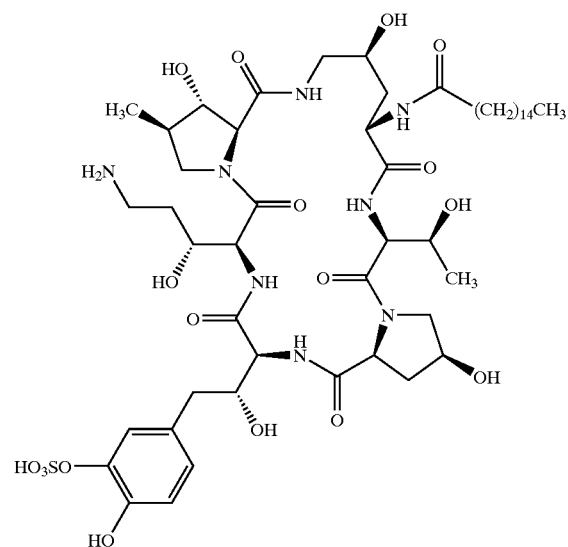

-continued
| Example No. | Formula |
|---|---|
| 117 | 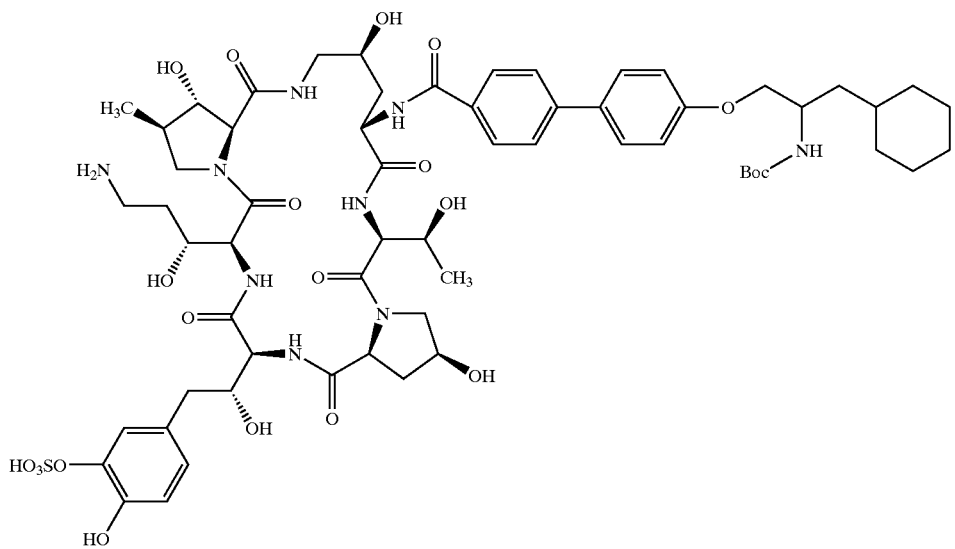 |
| | 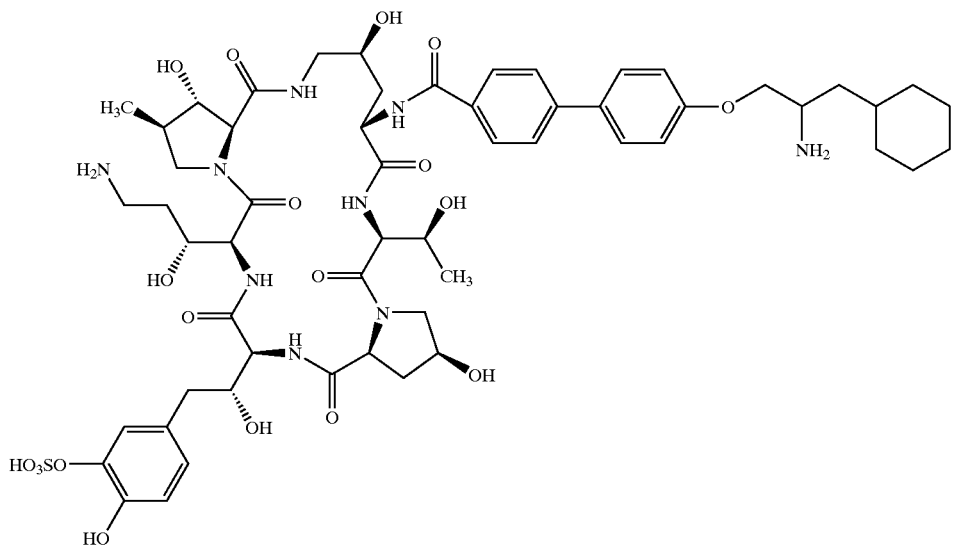 |

-continued
| Example No. | Formula |
|---|---|
| 118 | 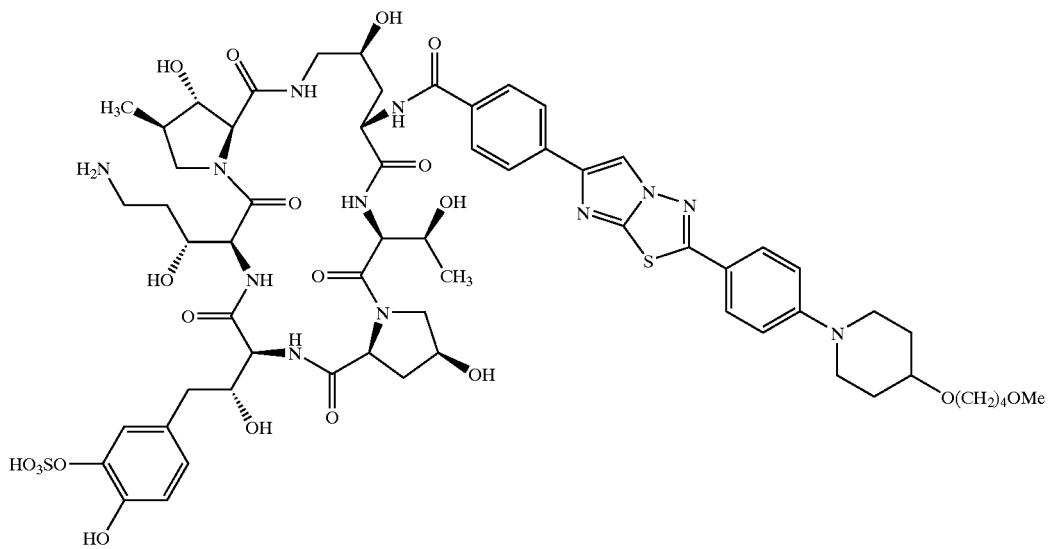<br>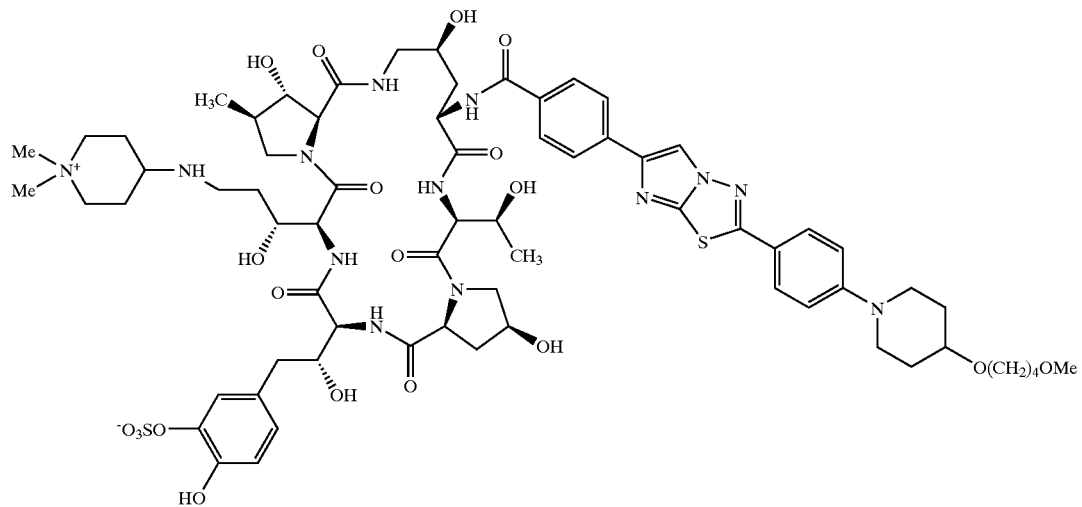 |

-continued
| Example No. | Formula |
|---|---|
| 119 | 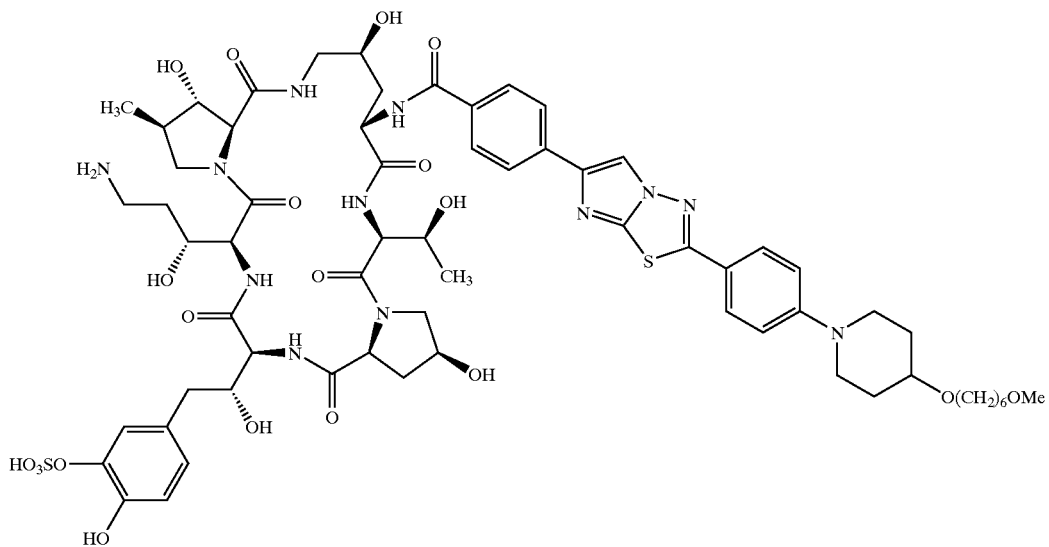 |
| | 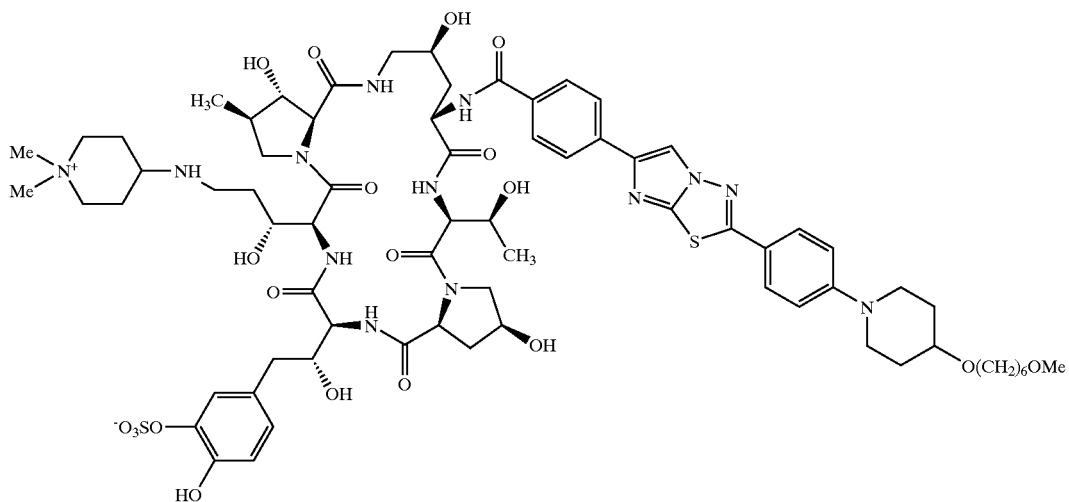 |

-continued
| Example No. | Formula |
|---|---|
| 120 | 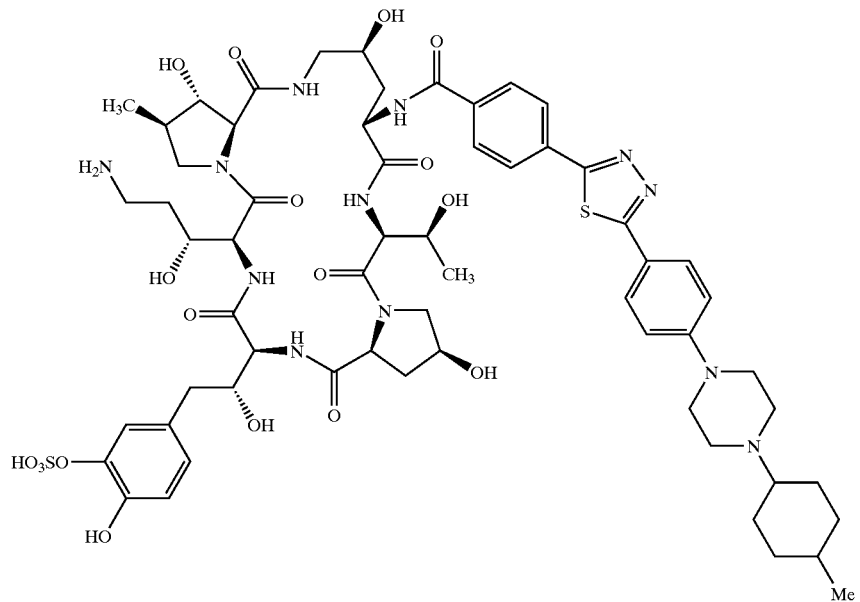 |
| 121 | 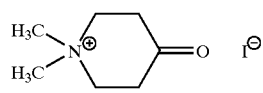 |

-continued
| Example No. | Formula |
|---|---|
| | 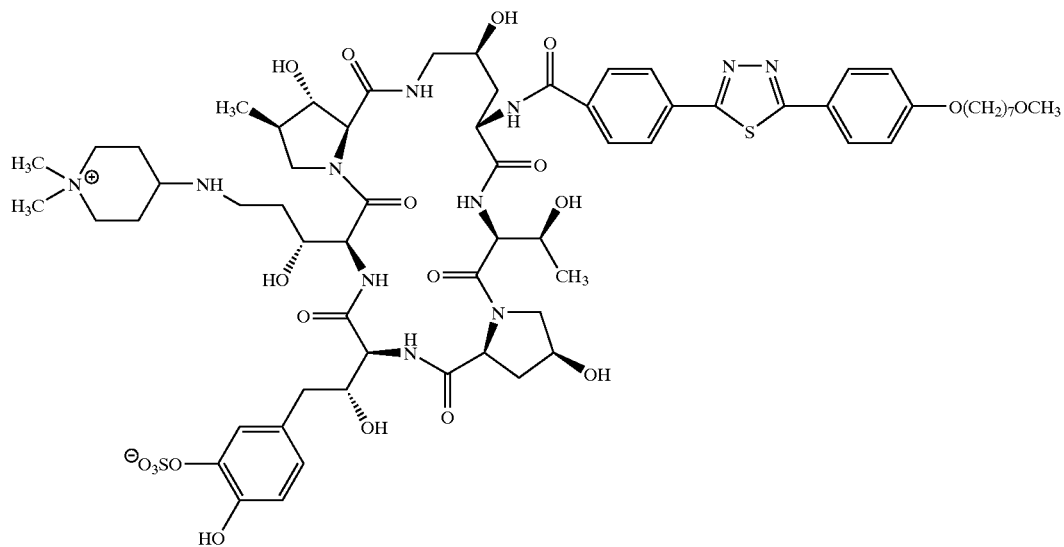 |
| 122 | 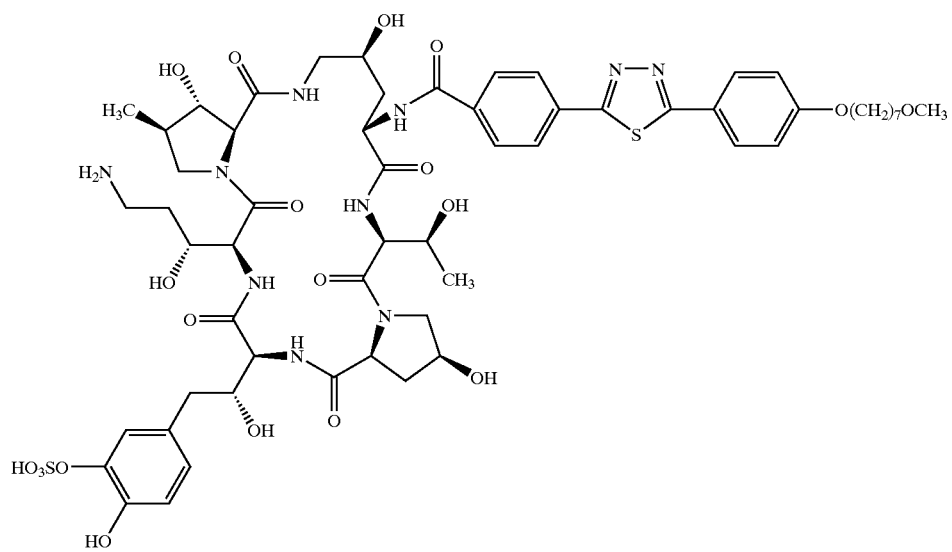 |

-continued
| Example No. | Formula |
|---|---|
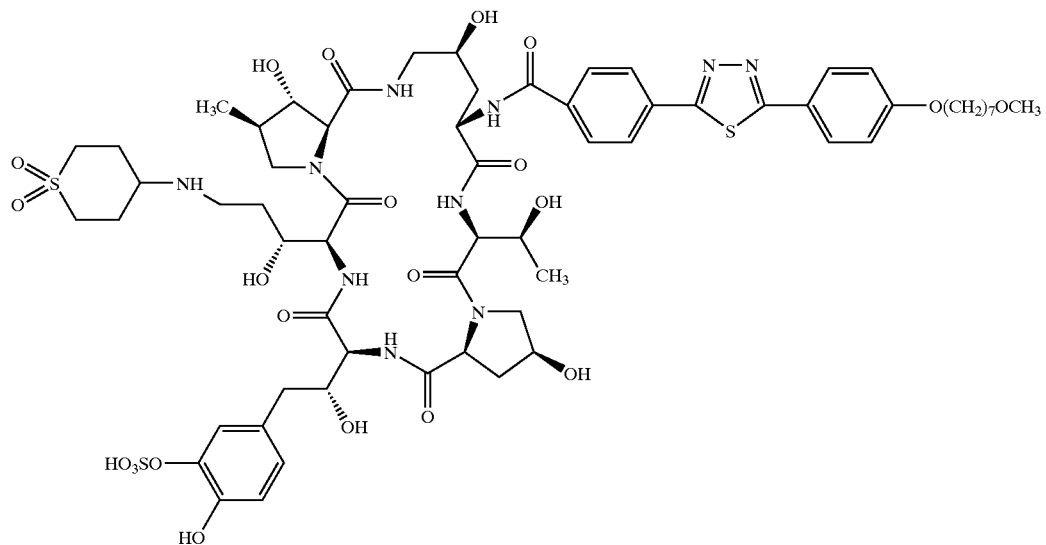
123
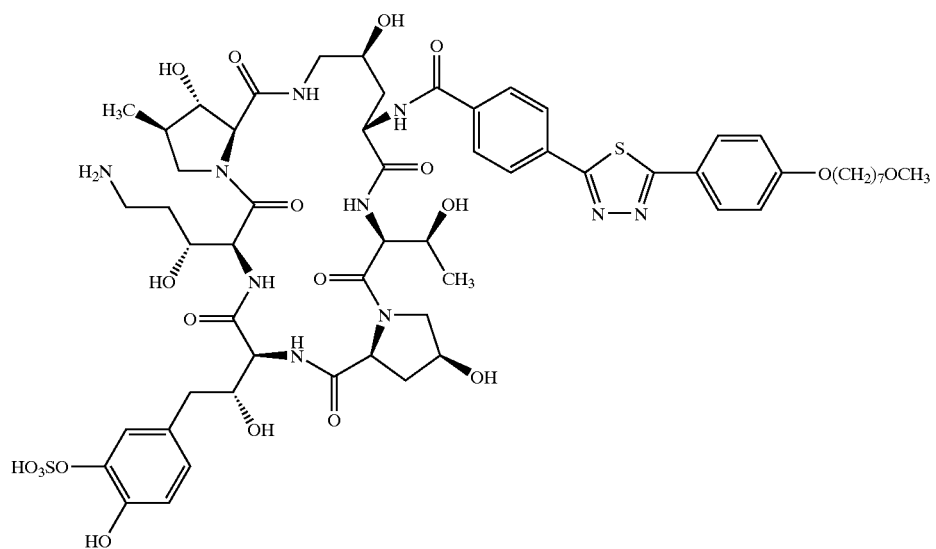

-continued
| Example No. | Formula |
|---|---|
| | 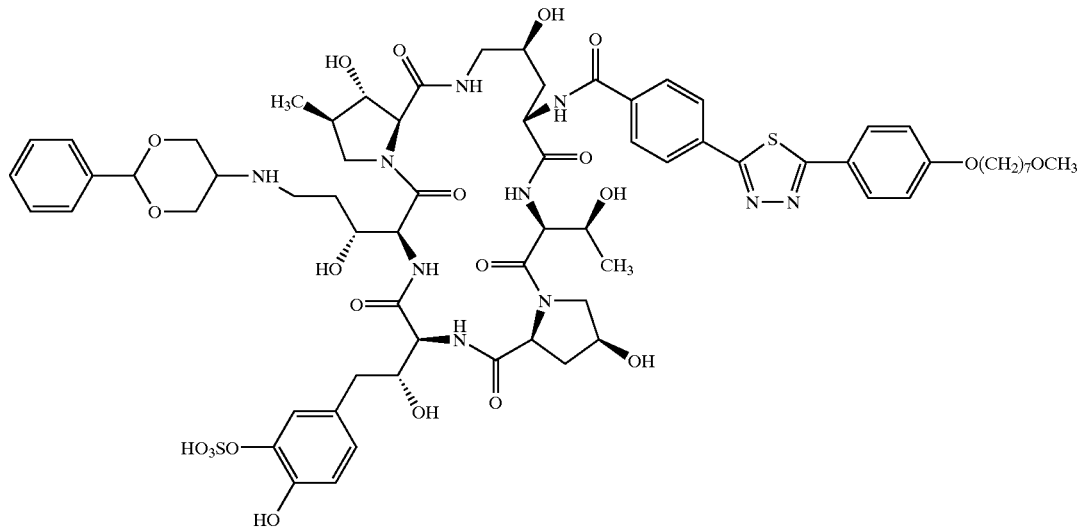 |
| 124 | 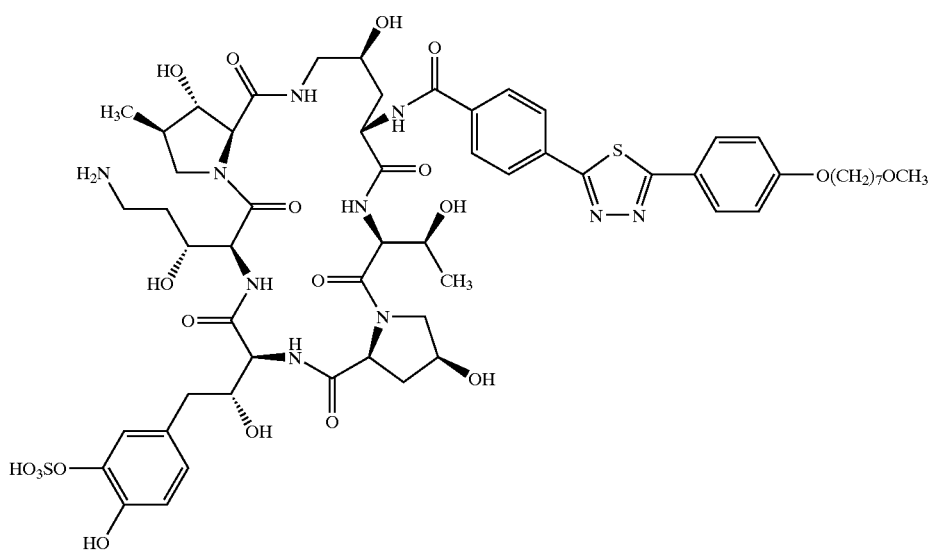 |

| Example No. | Formula |
|---|---|
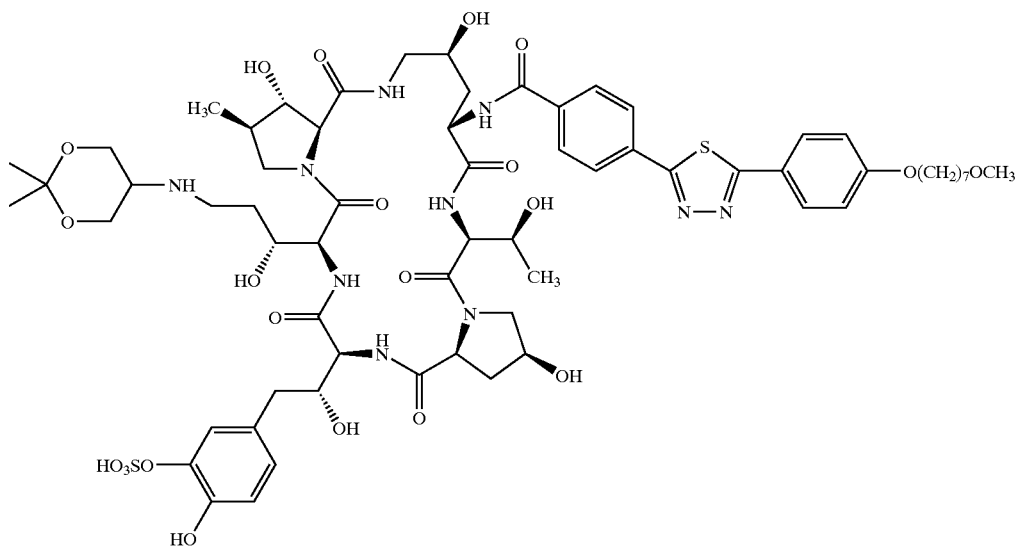
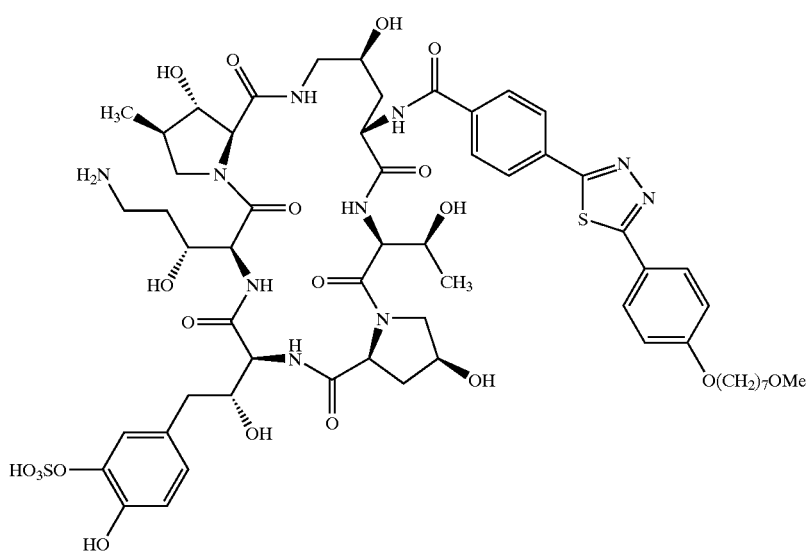
125

| Example No. | Formula |
|---|---|
| | 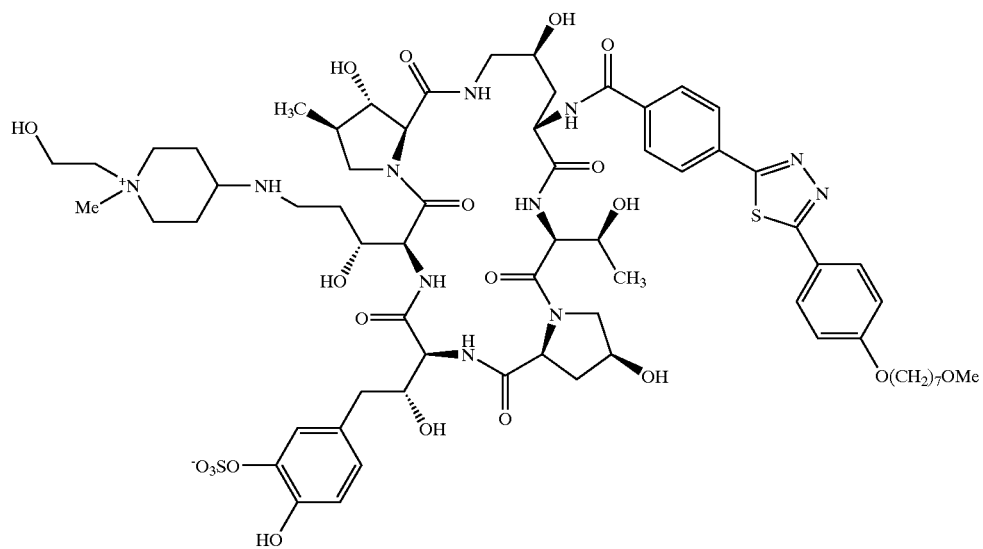 |
| 126 | 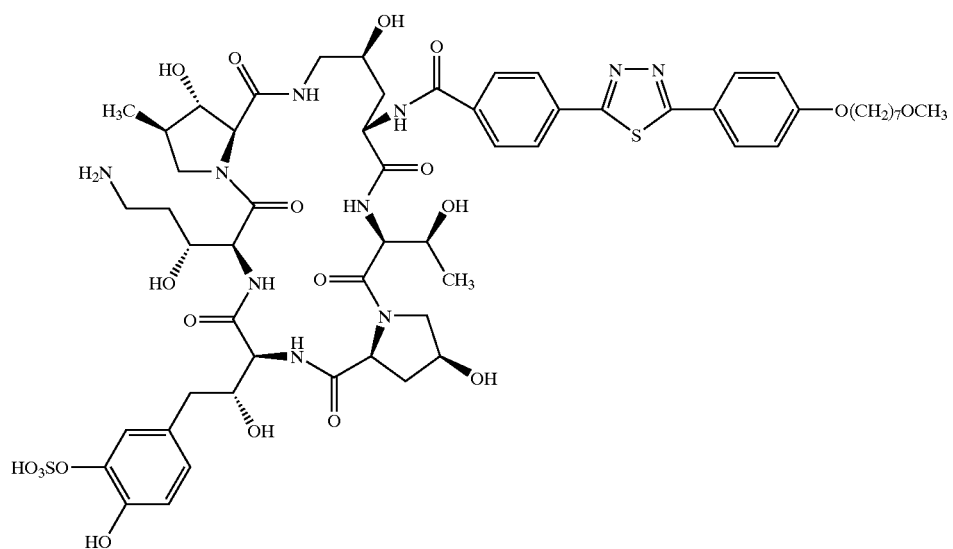 |

| Example No. | Formula |
|---|---|
| | 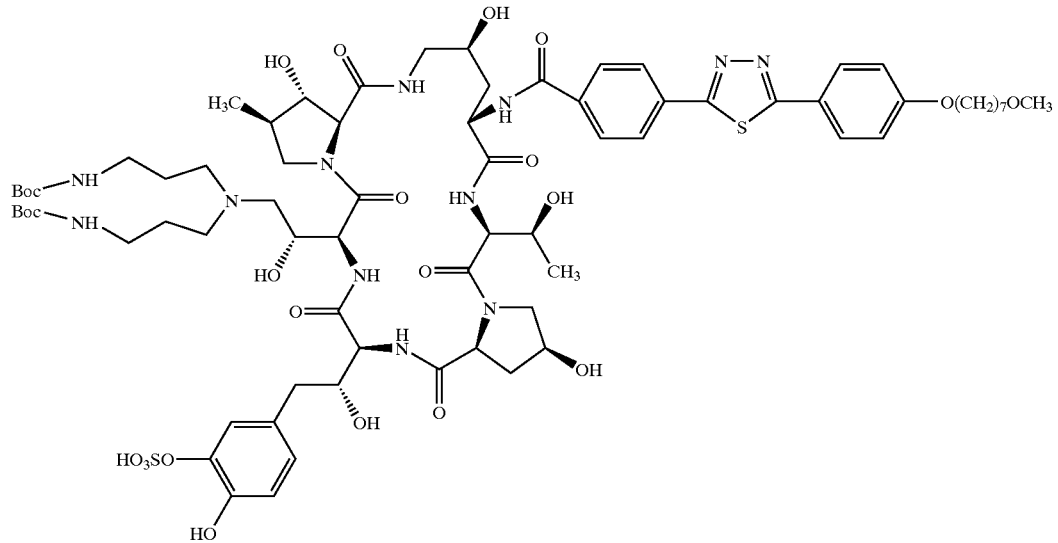 |
| 127 | 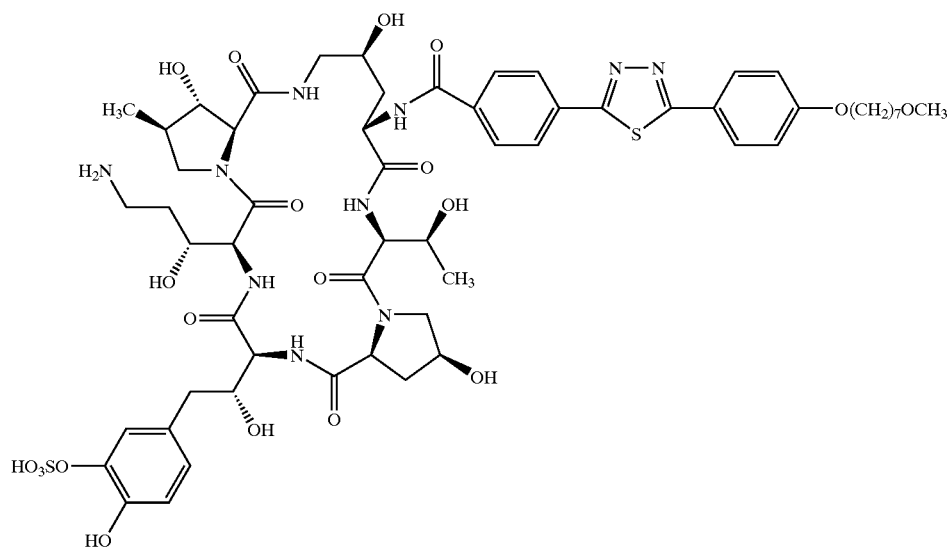 |

| Example No. | Formula |
|---|---|
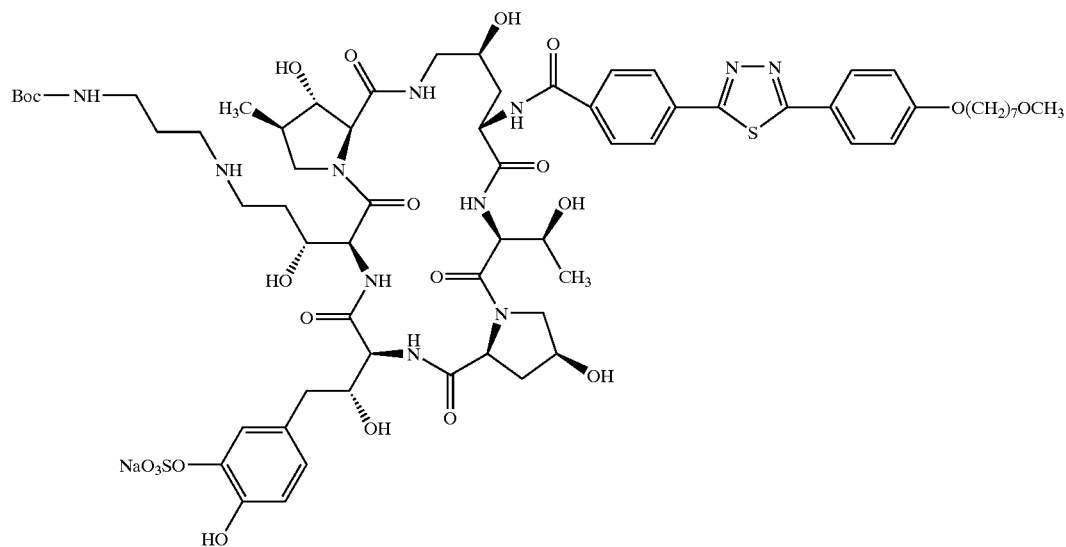
128
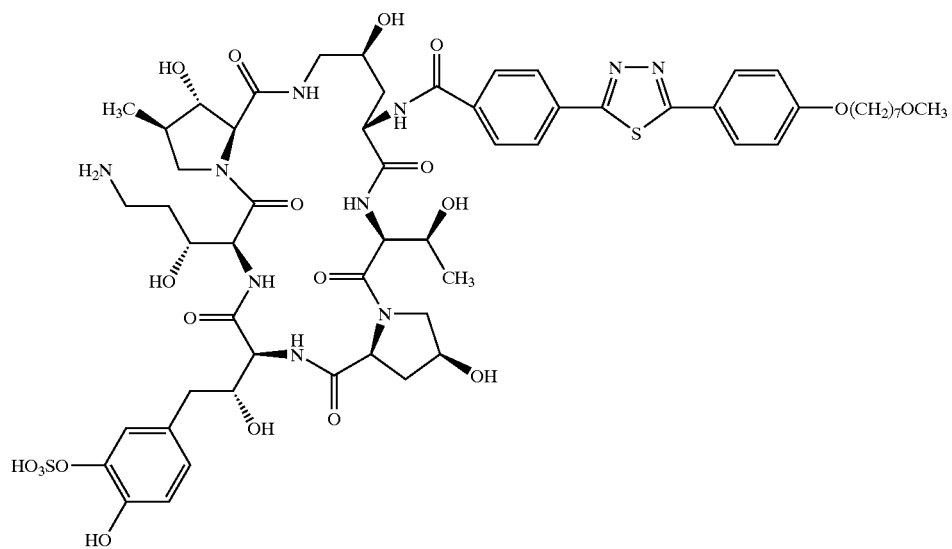

| Example No. | Formula |
|---|---|
| | 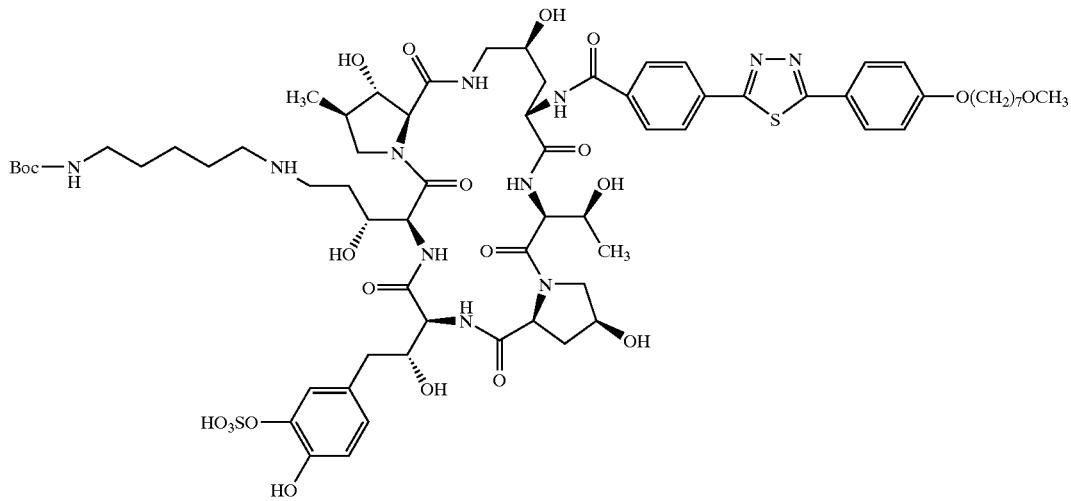 |
| 129 | 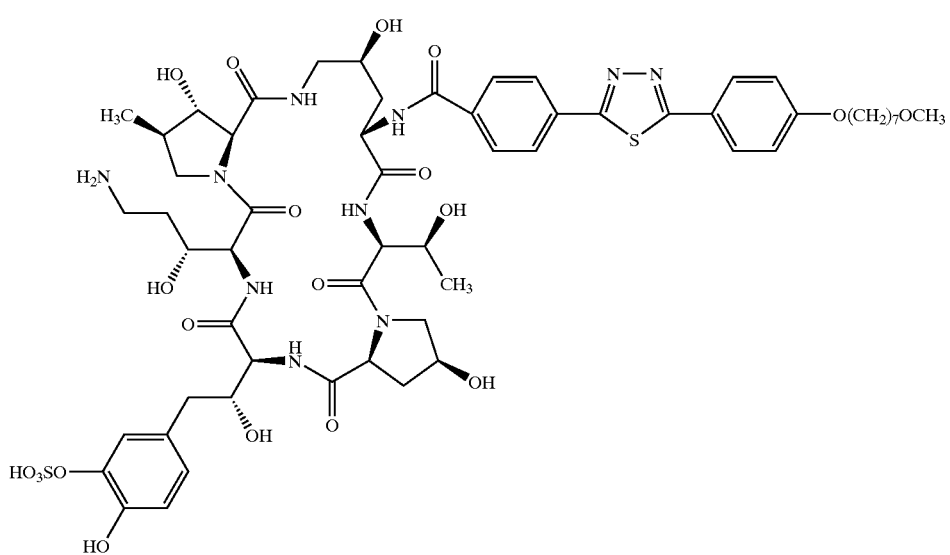 |
| | 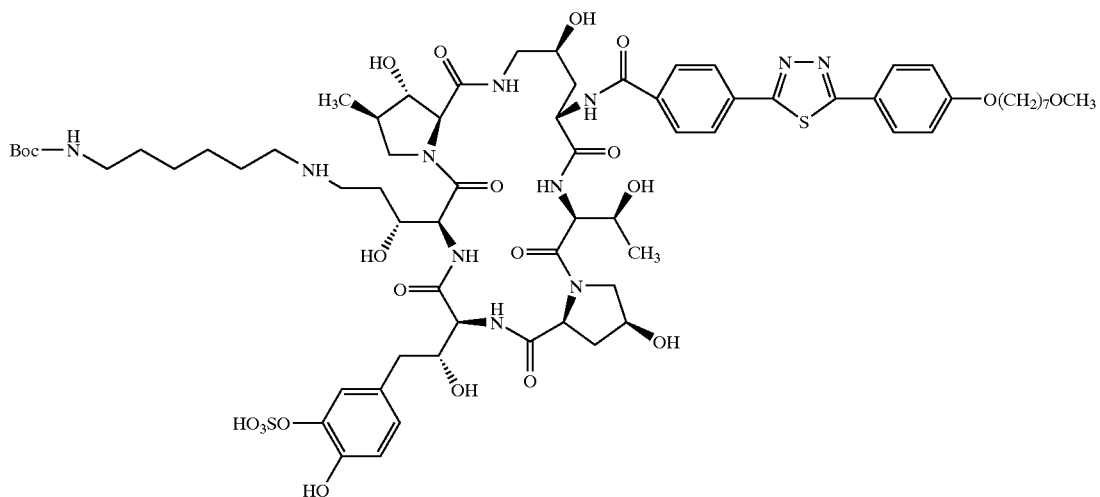 |

-continued
| Example No. | Formula |
|---|---|
| 130 | 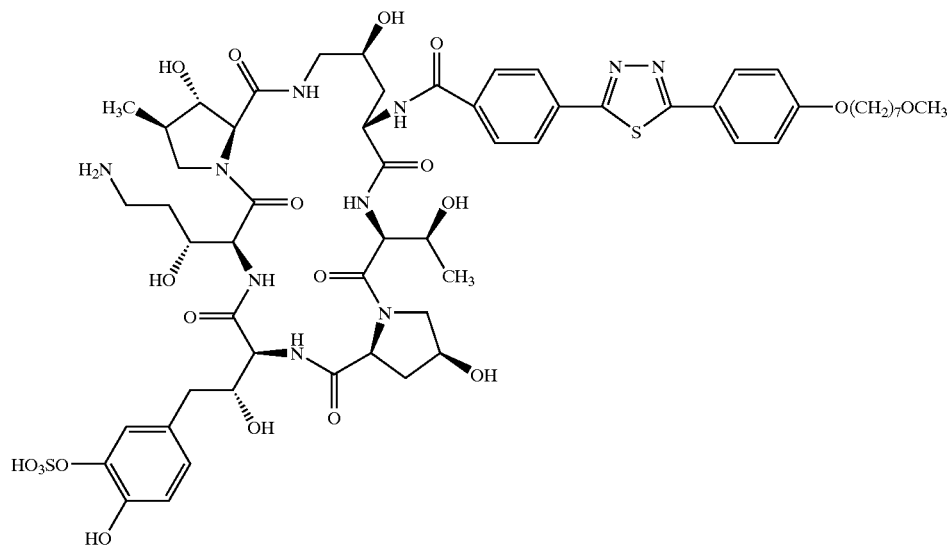 |
| | 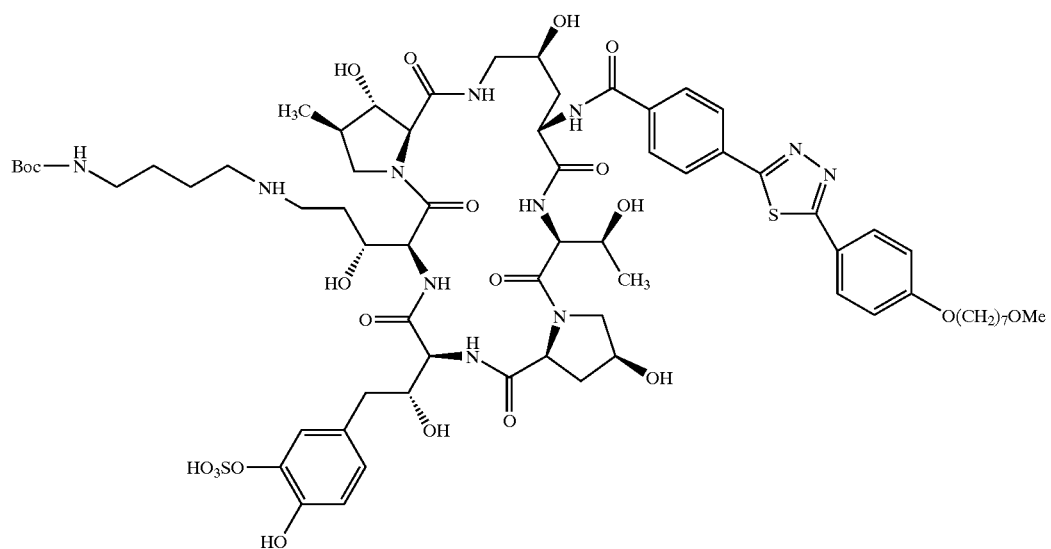 |

| Example No. | Formula |
|---|---|
| | 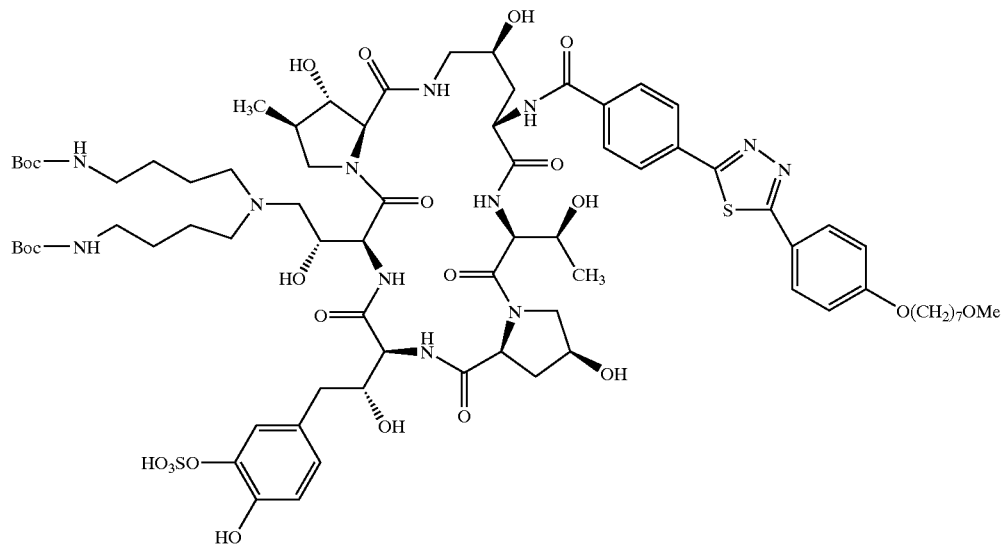 |
| 131 | 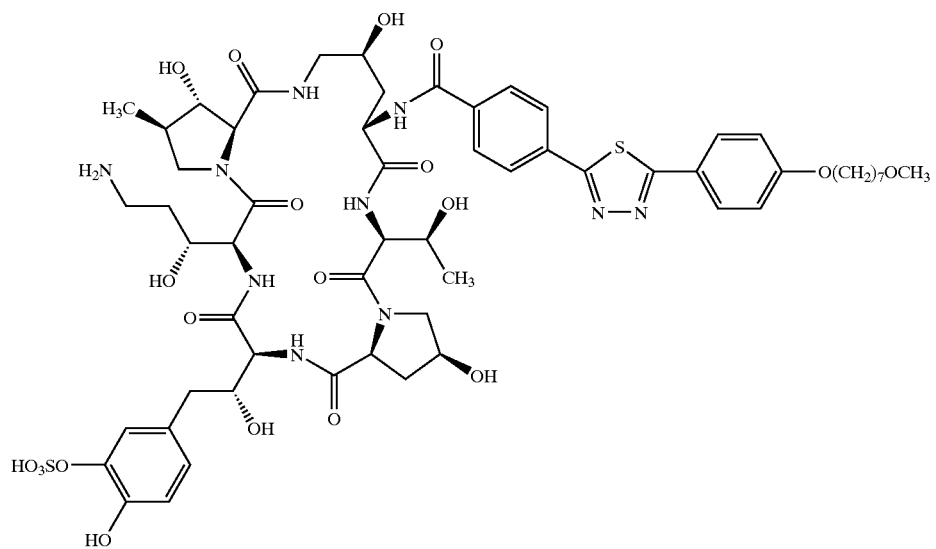 |

| Example No. | Formula |
|---|---|
| | 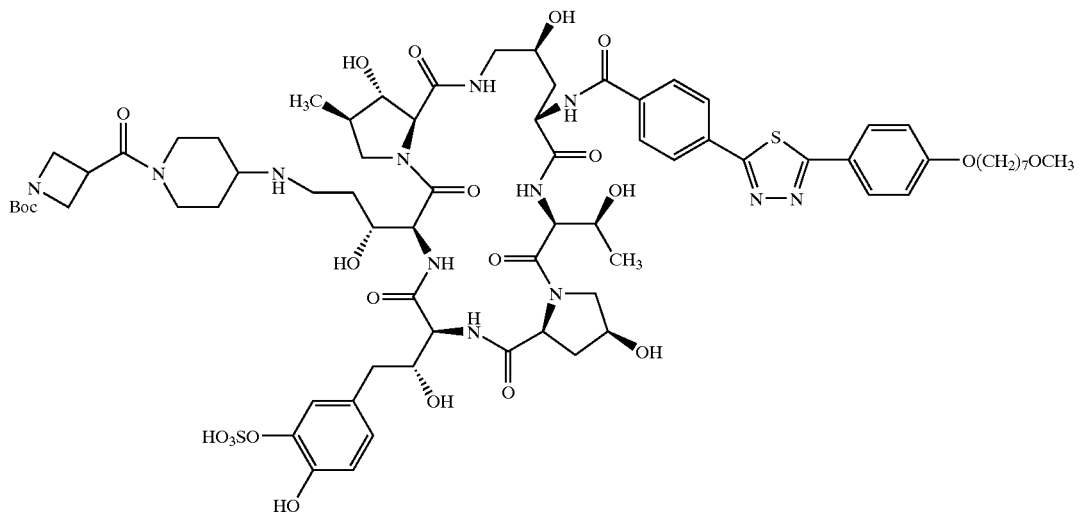 |
| 132 | 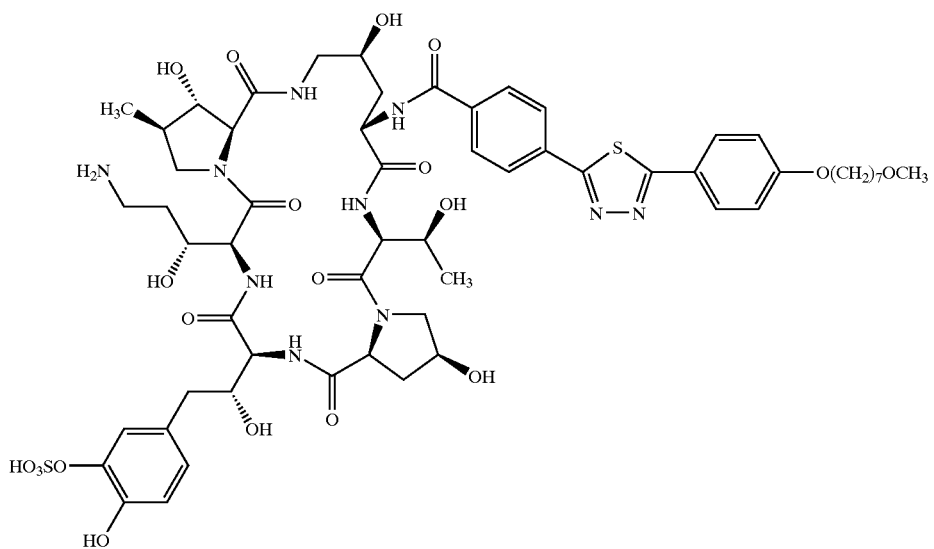 |

| Example No. | Formula |
|---|---|
| | 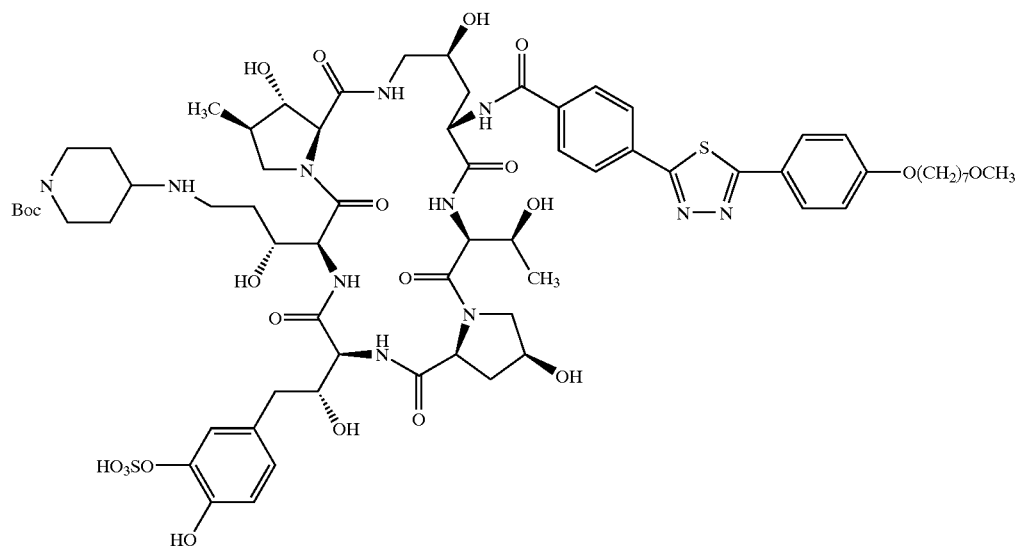 |
| 133 | 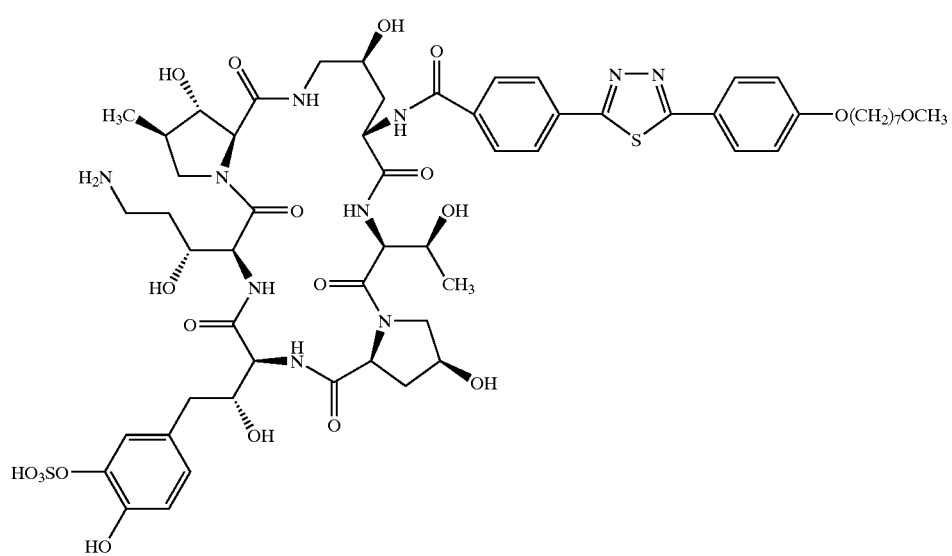 |
| | 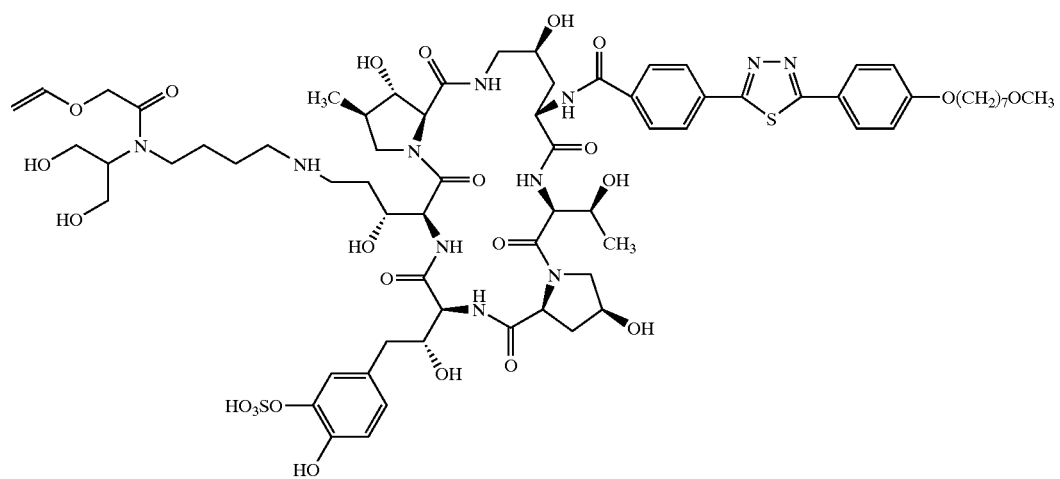 |

-continued
| Example No. | Formula |
|---|---|
| 134 | 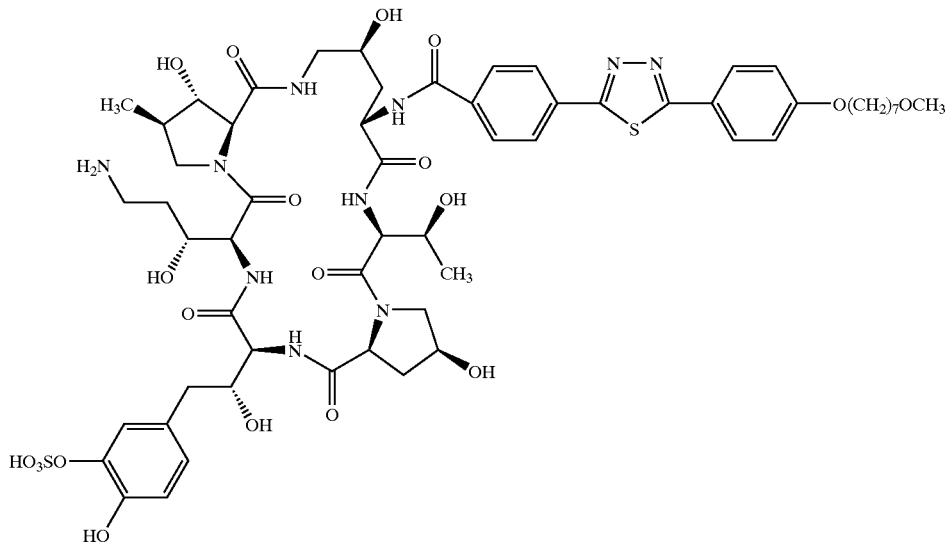 |
| | 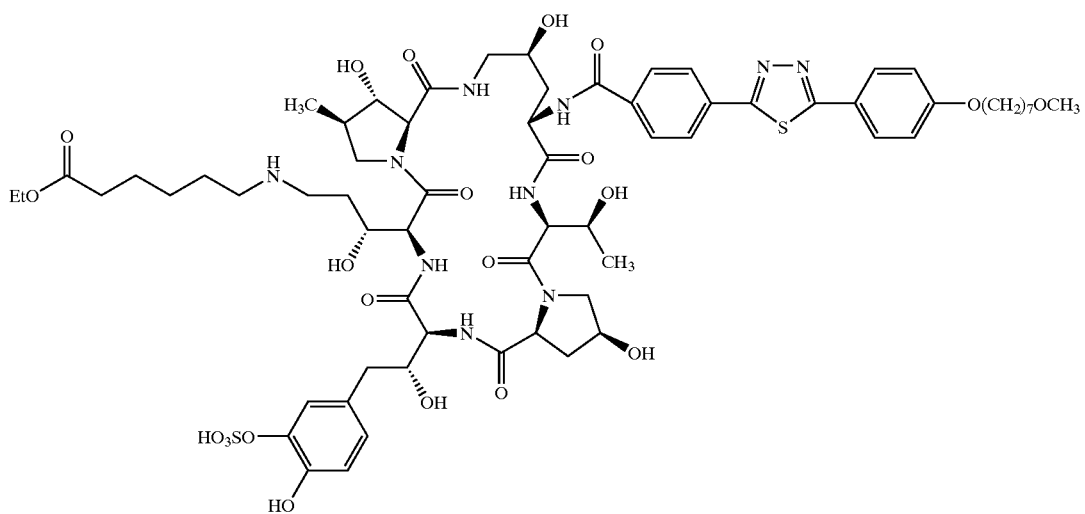 |

-continued
| Example No. | Formula |
|---|---|
| 135 | 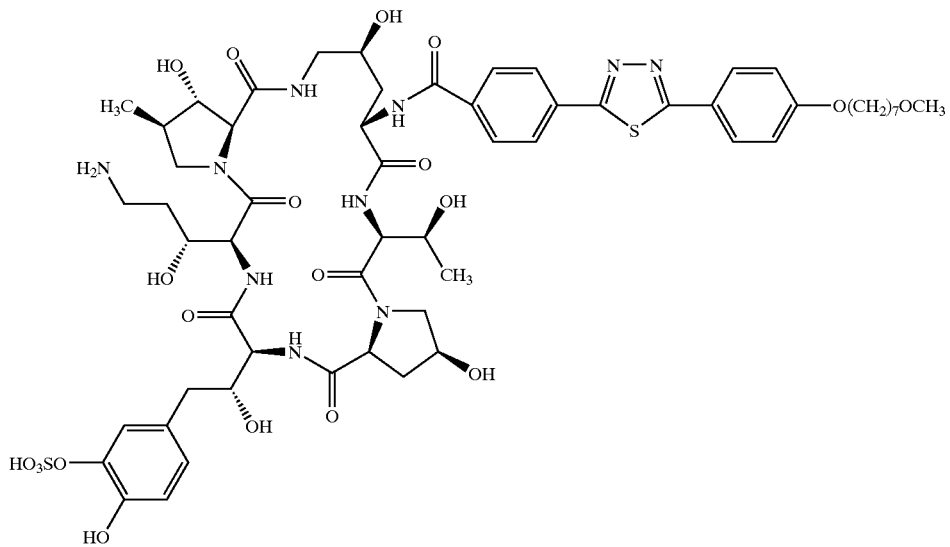 |
| | 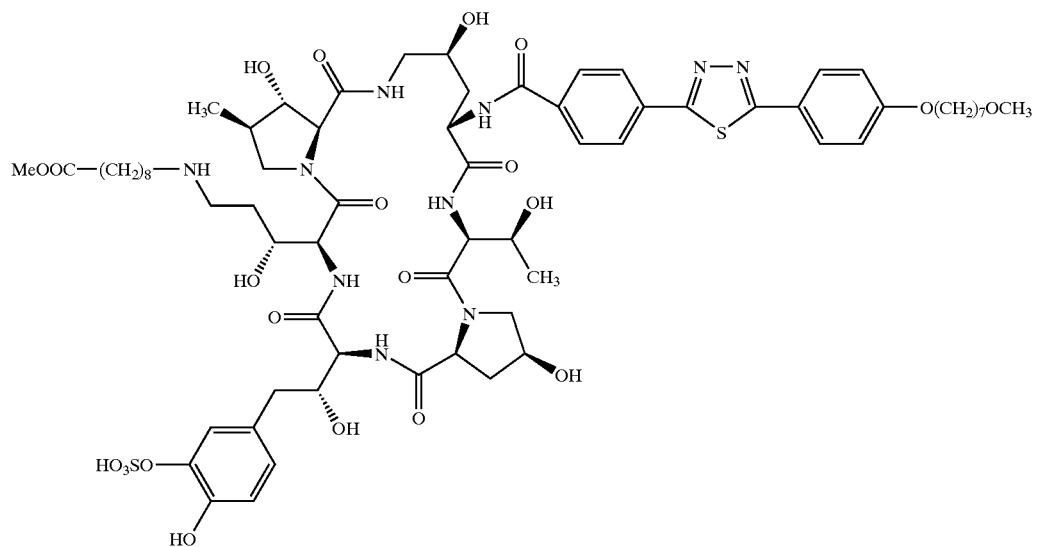 |

| Example No. | Formula |
|---|---|
| | 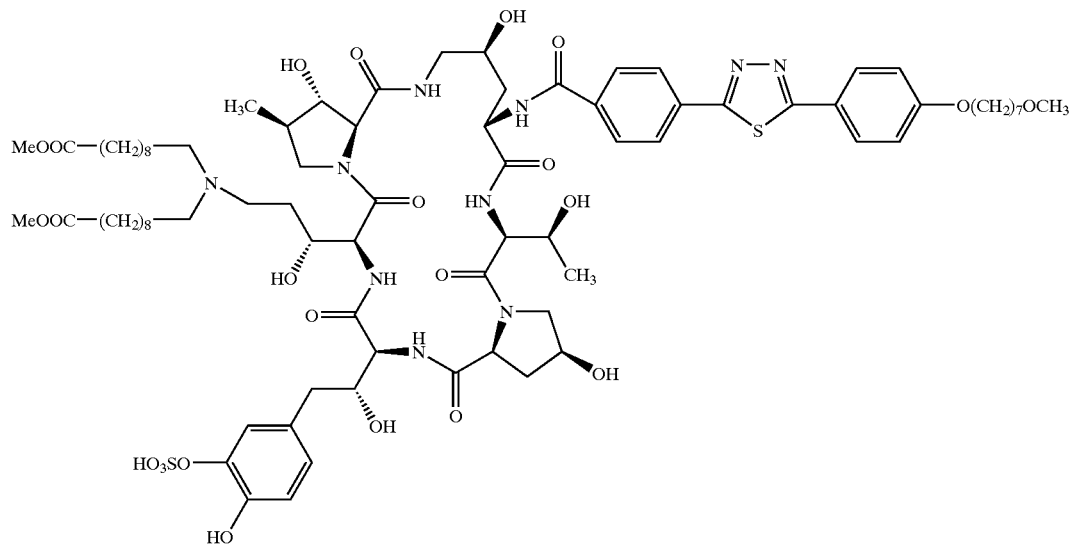 |
| 136 | 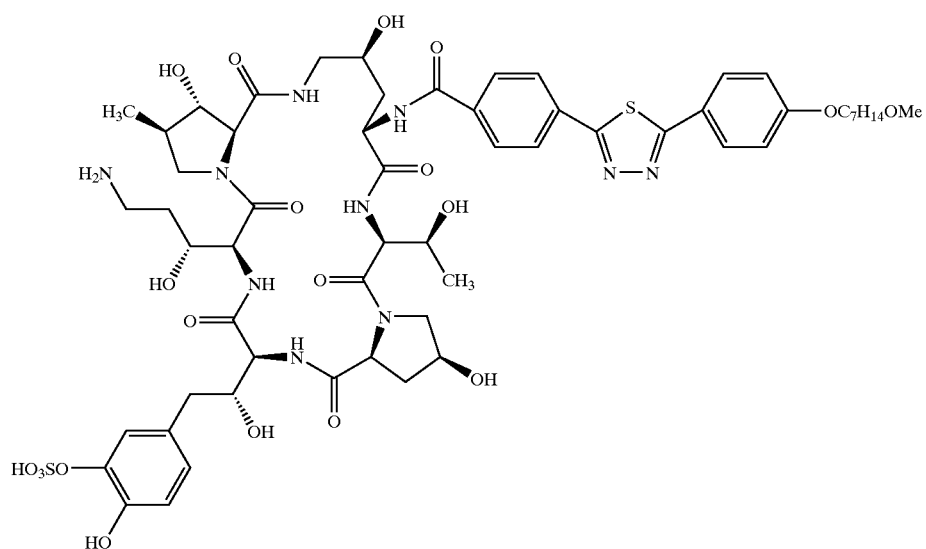 |

| Example No. | Formula |
|---|---|
| | 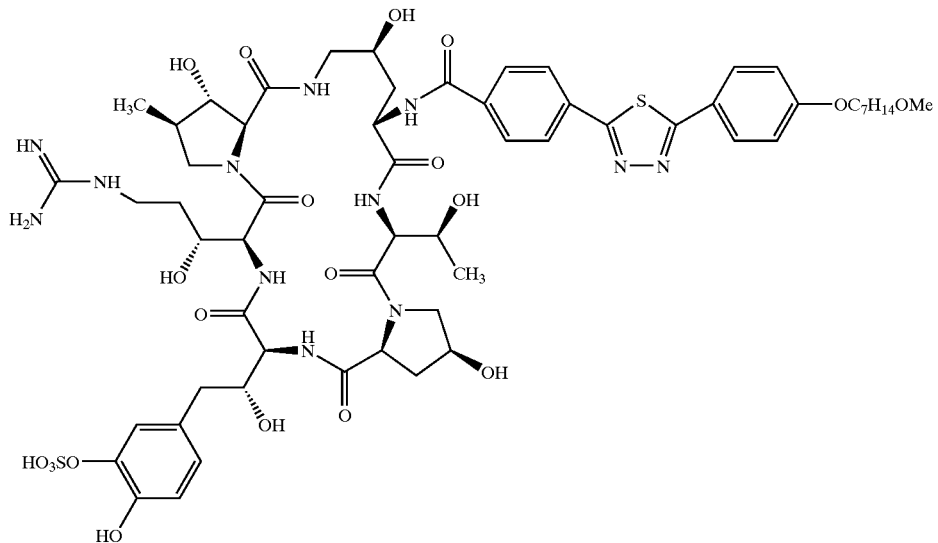 |
| 137 | 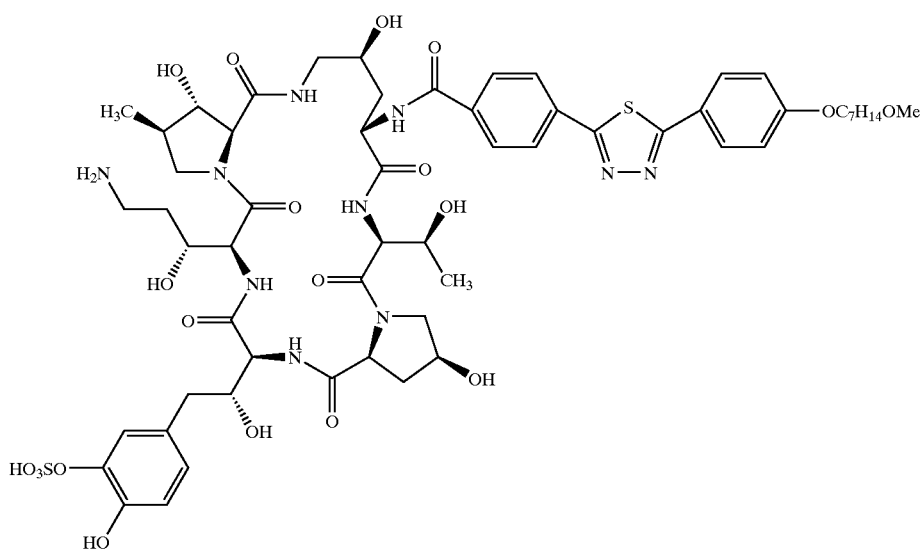 |

-continued
| Example No. | Formula |
|---|---|
| | 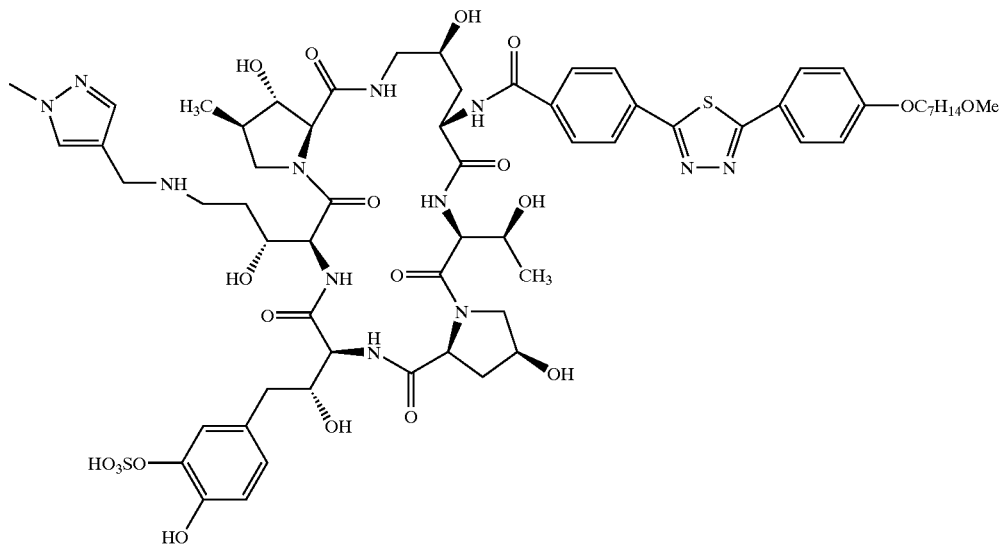 |
| 138 | 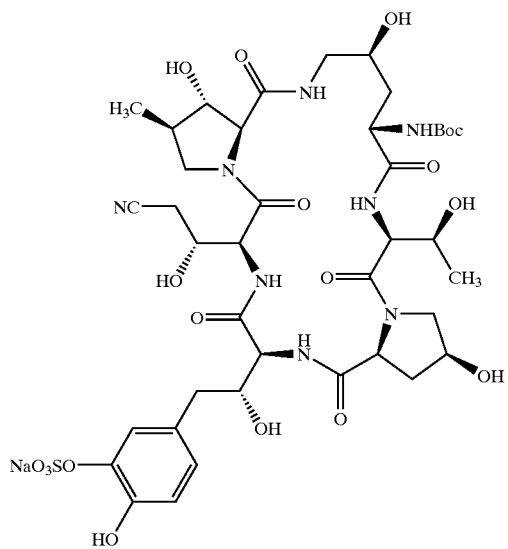 |

-continued
| Example No. | Formula |
|---|---|
| | 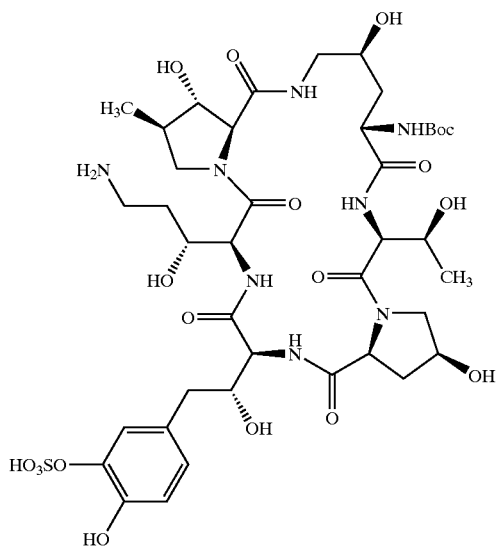 |
| 139 | 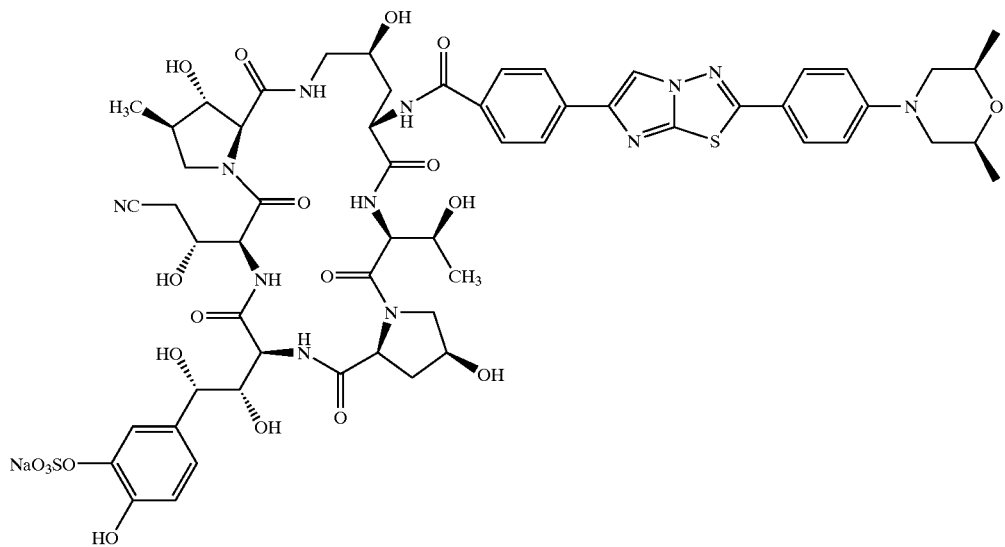 |

-continued
| Example No. | Formula |
|---|---|
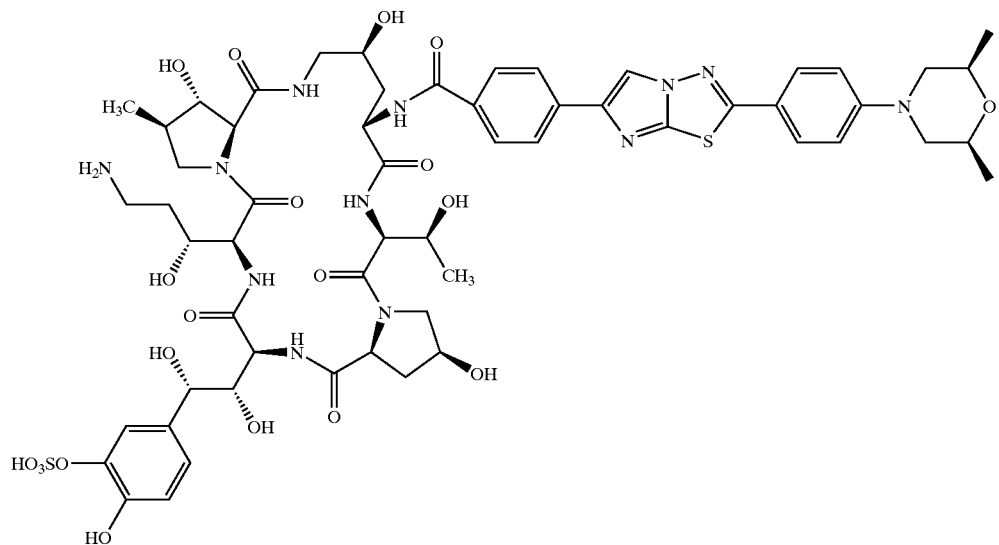
140
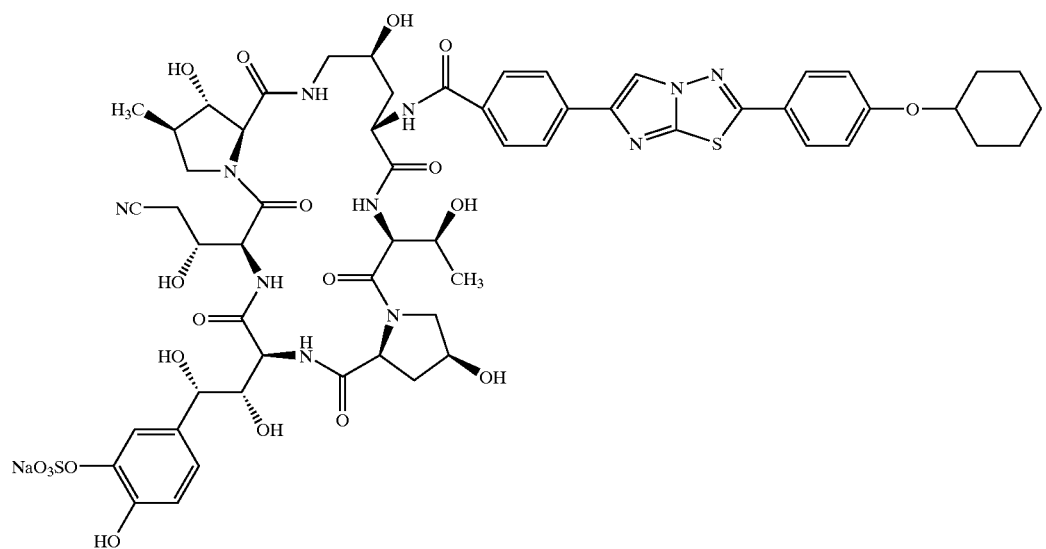

| Example No. | Formula |
|---|---|
| | 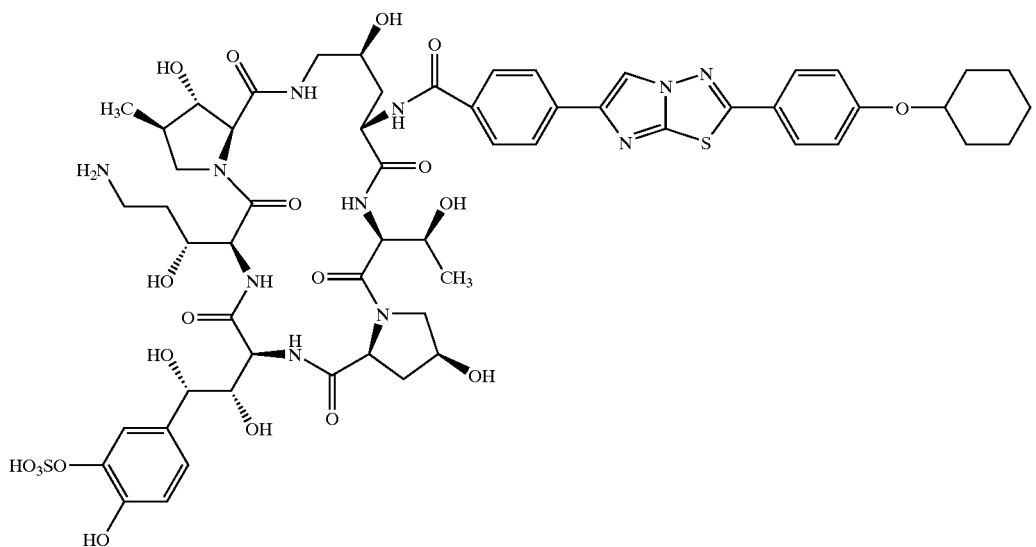 |
| 141 | 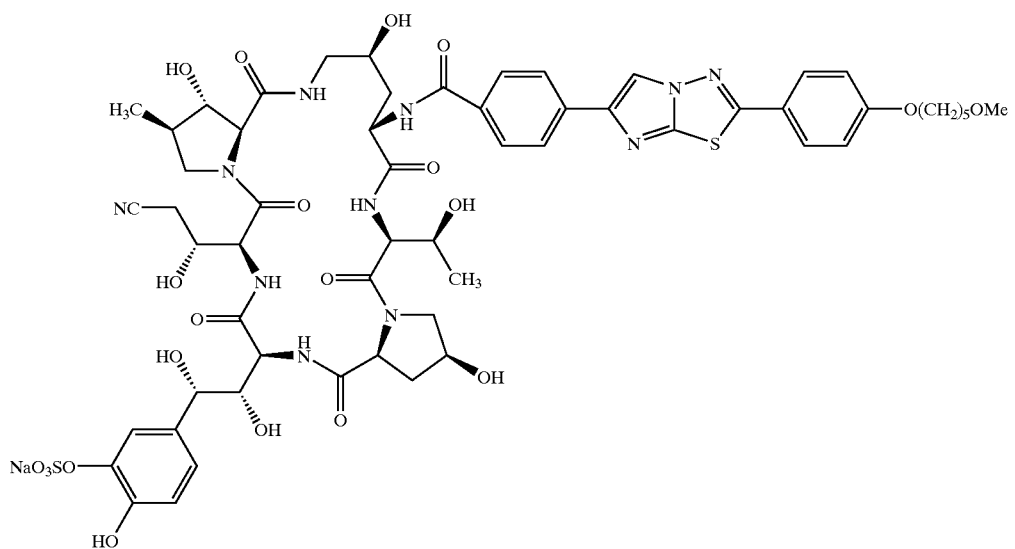 |

| Example No. | Formula |
|---|---|
| | 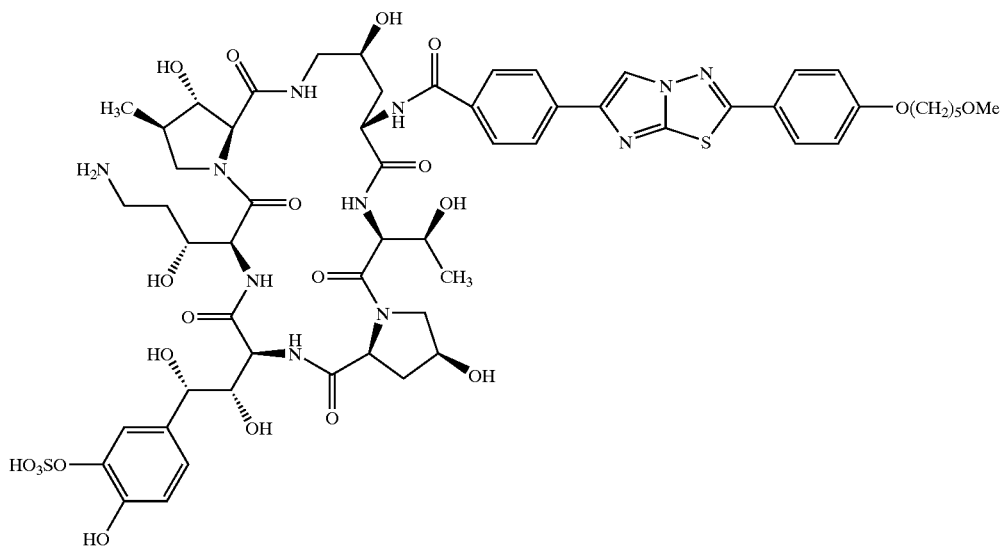 |
| 142 | 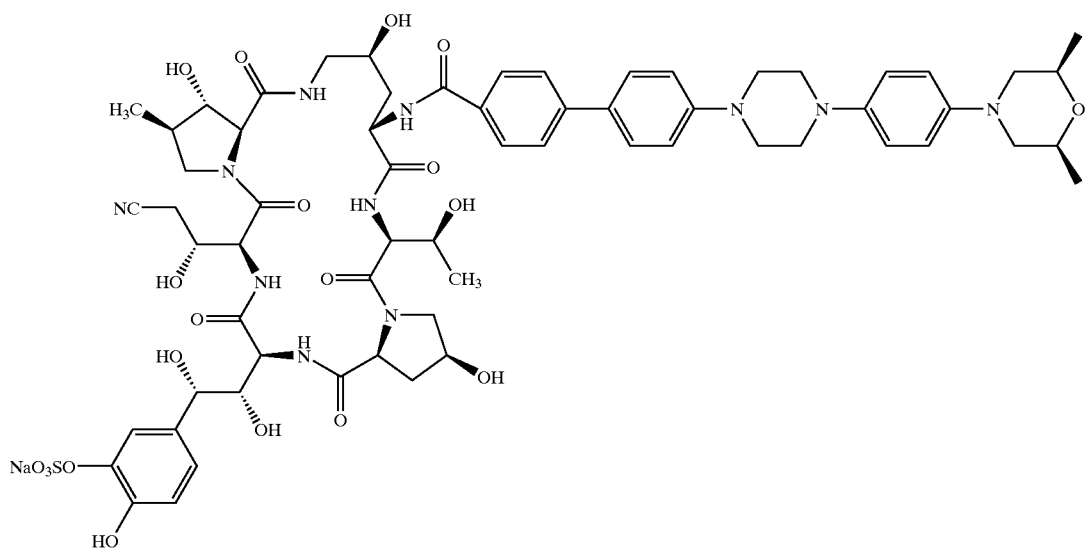 |

-continued
| Example No. | Formula |
|---|---|
| | 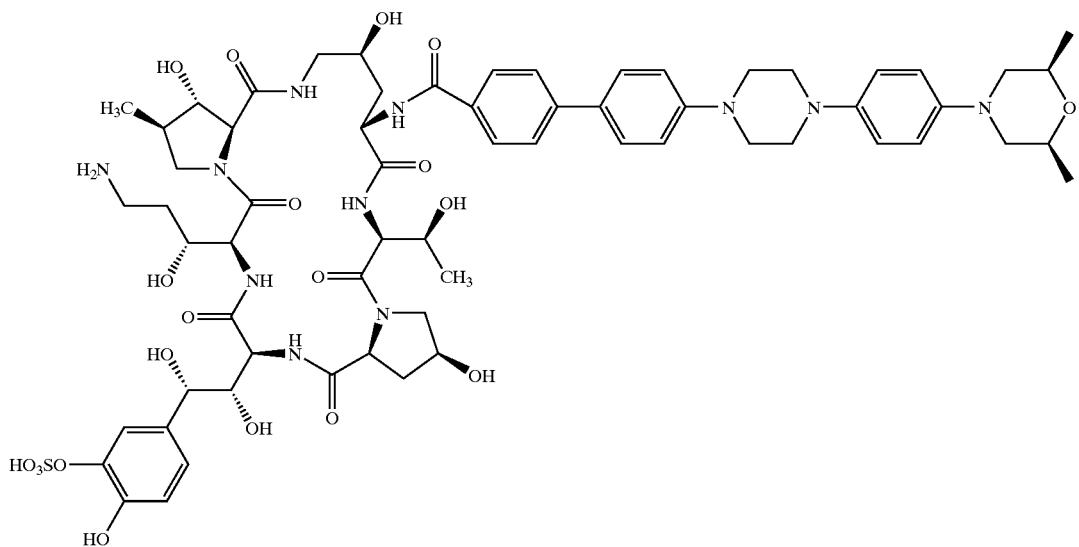 |
| 143 | 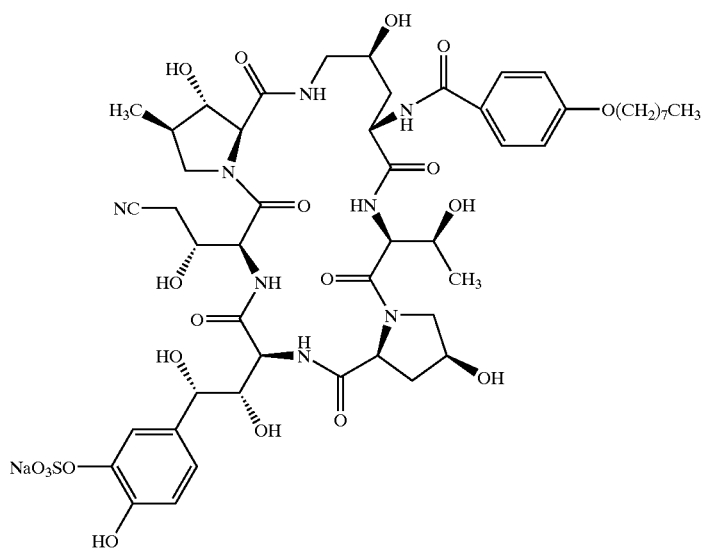 |

| Example No. | Formula |
|---|---|
| | 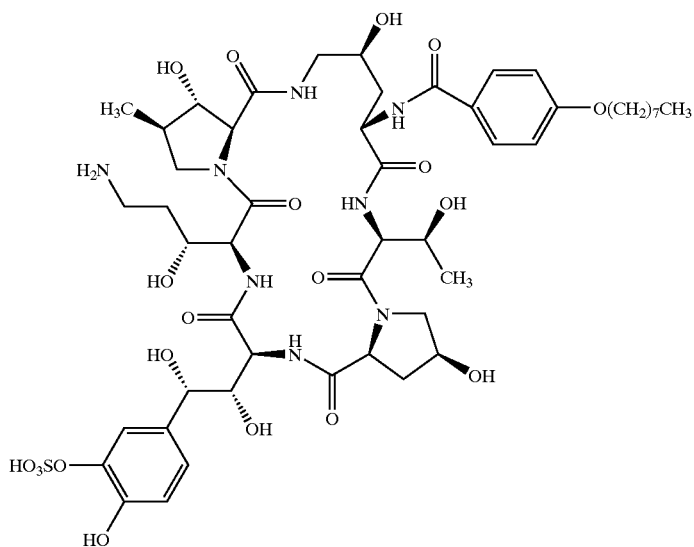 |
| 144 | 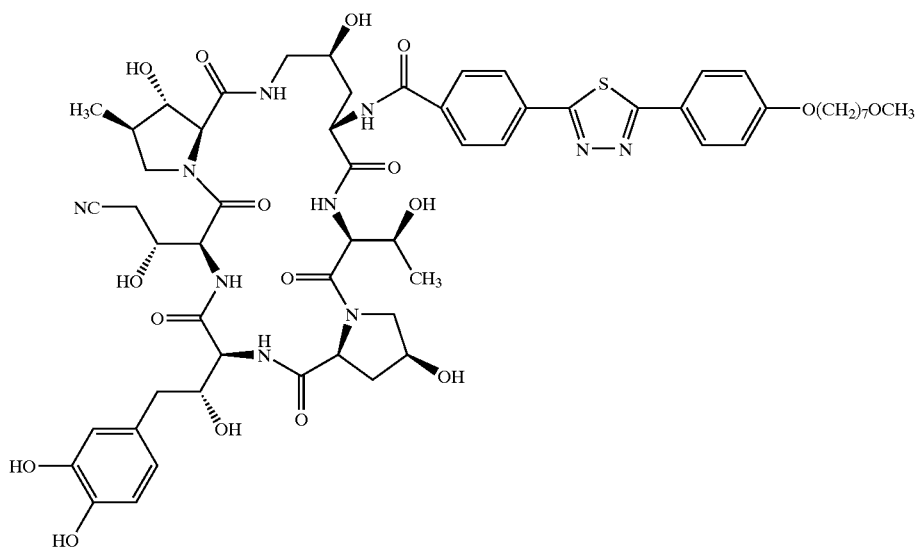 |

| Example No. | Formula |
|---|---|
| | 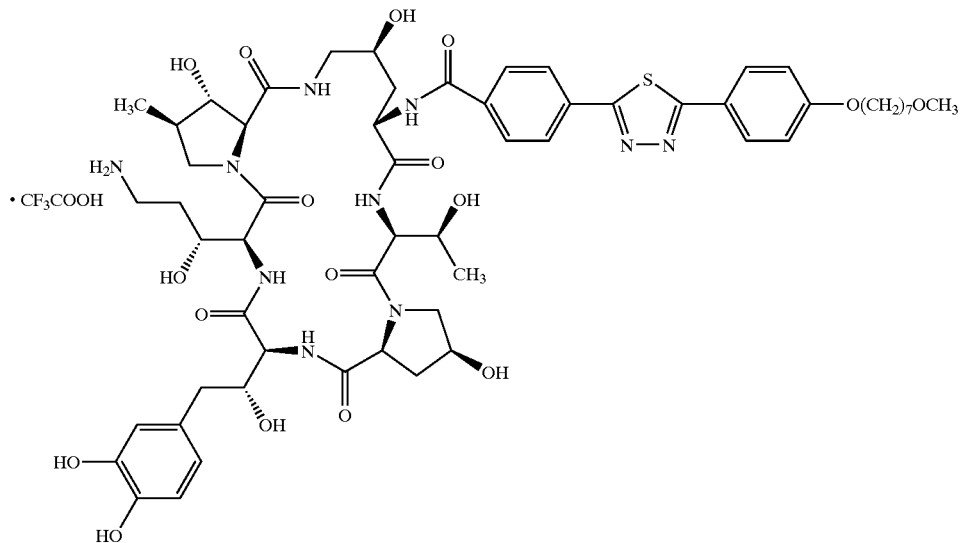 |
| 145 | 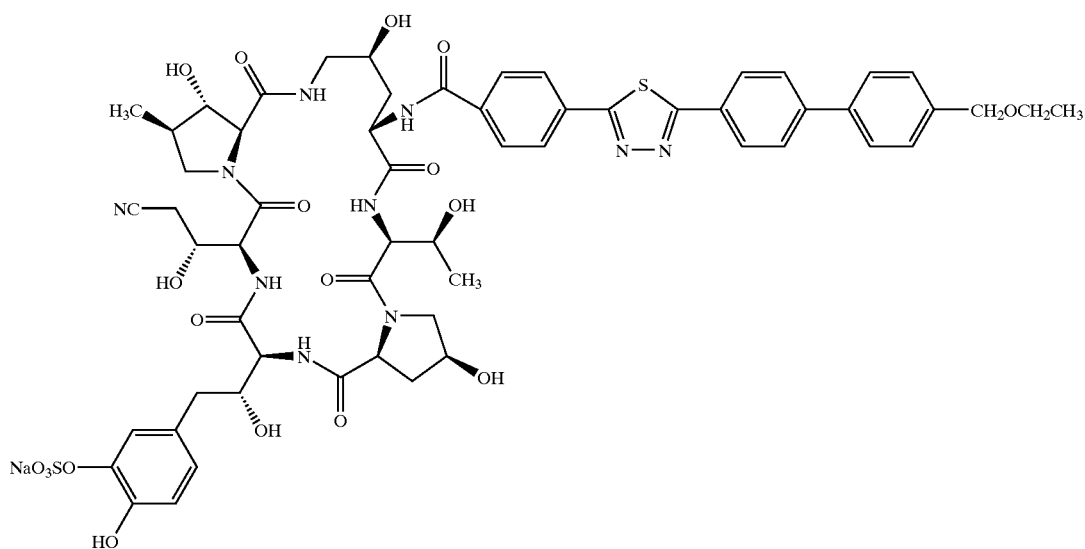 |

-continued
| Example No. | Formula |
|---|---|
| | 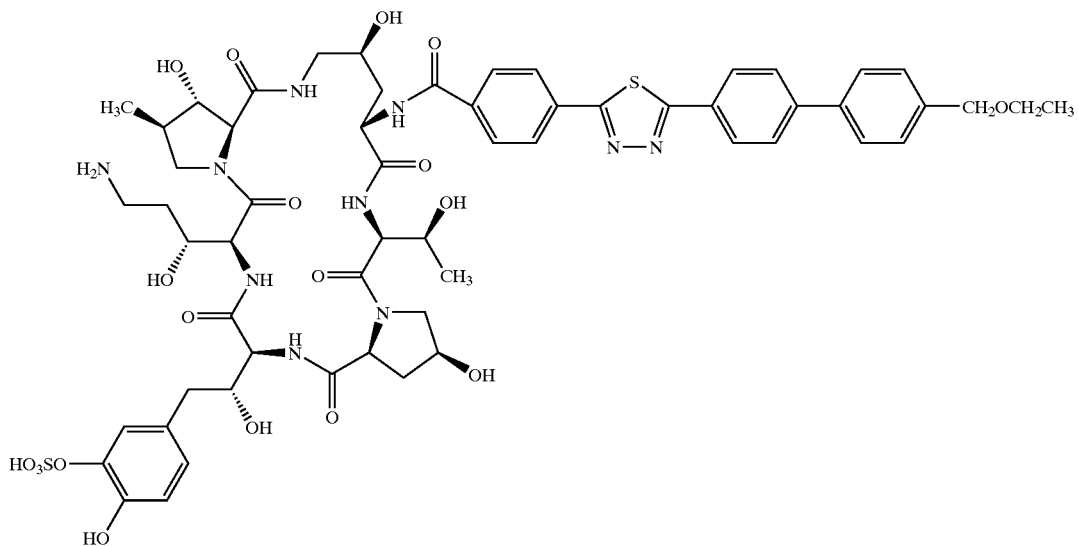 |
| 146 | 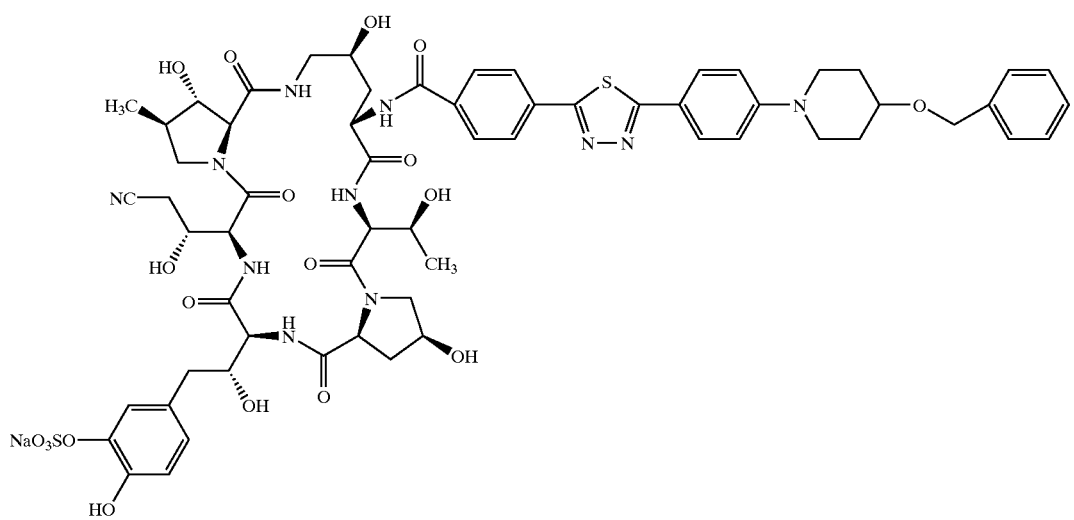 |
| | 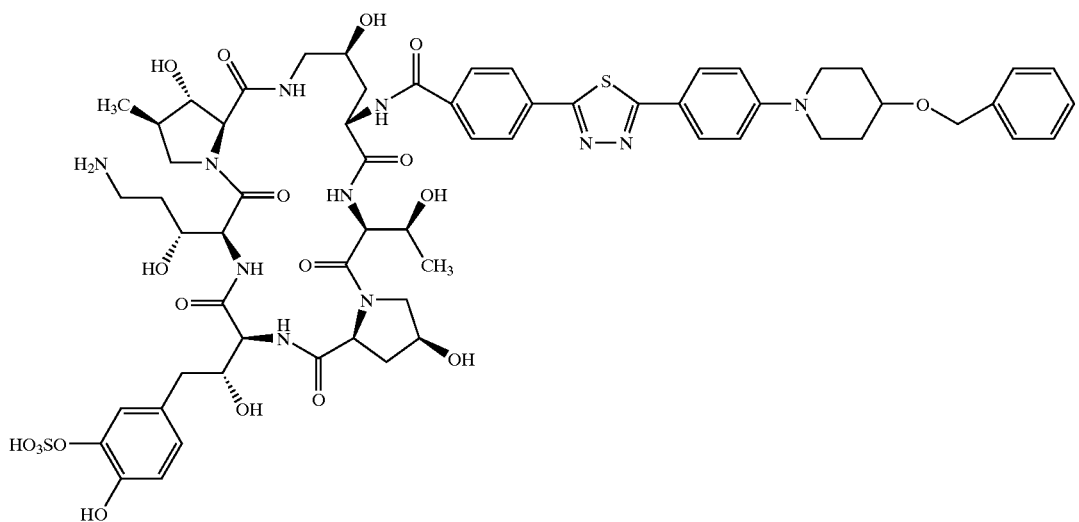 |

-continued
| Example No. | Formula |
|---|---|
| 147 | 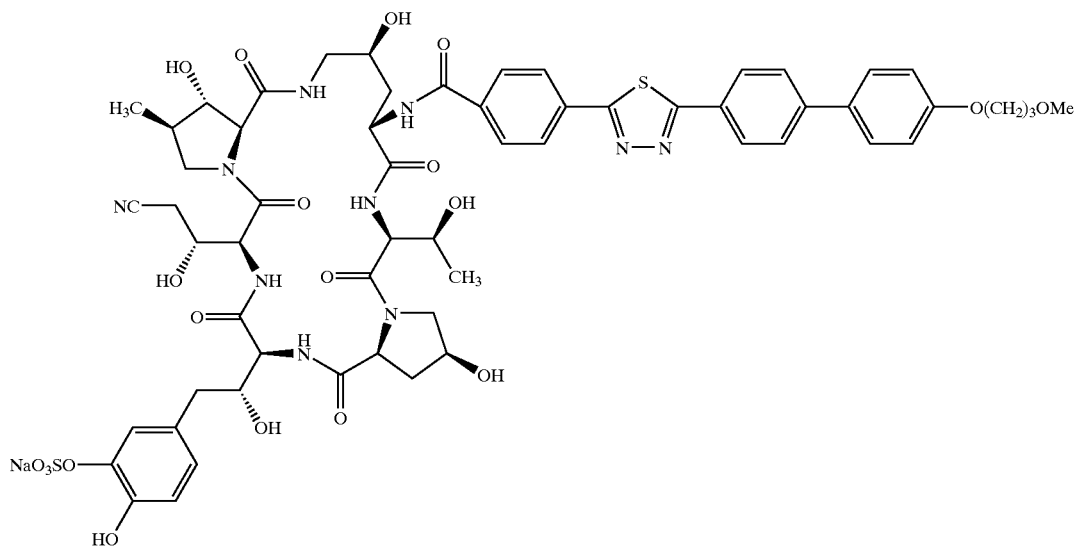 |
| | 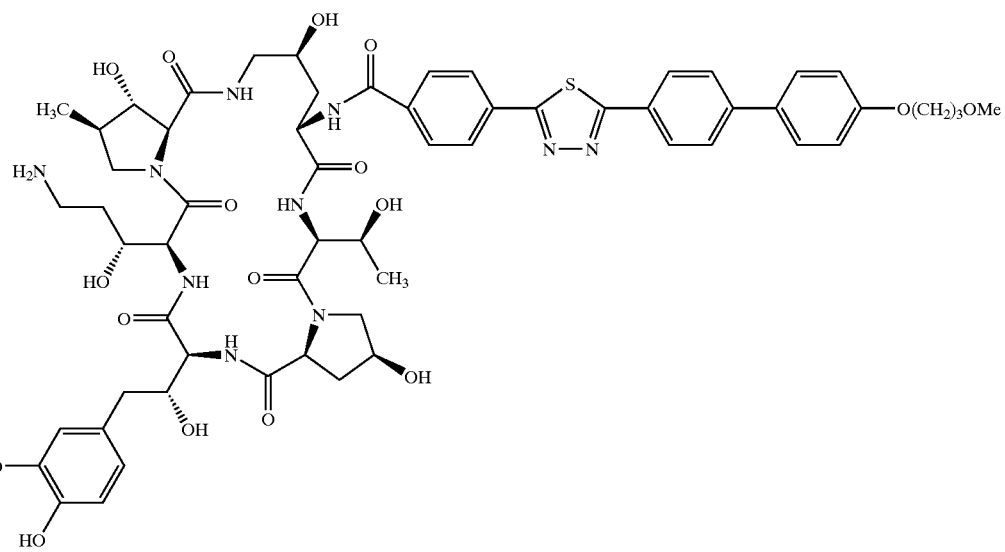 |

-continued
| Example No. | Formula |
|---|---|
| 148 | 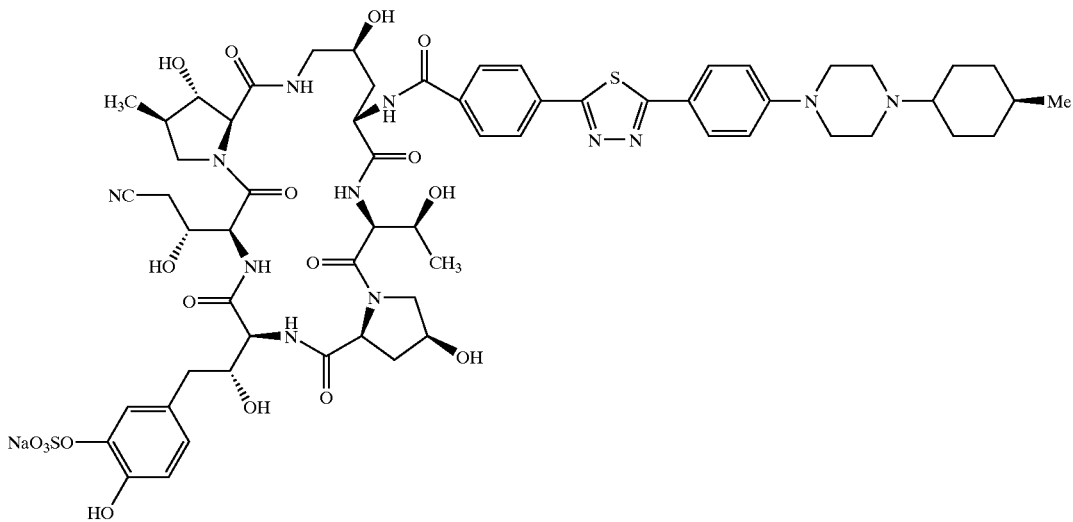 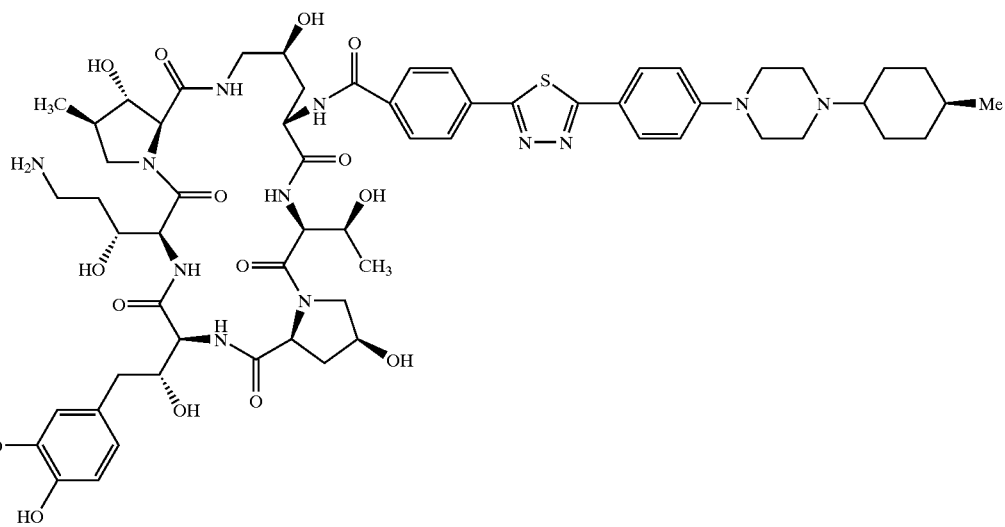 |

-continued
| Example No. | Formula |
|---|---|
| 149 | 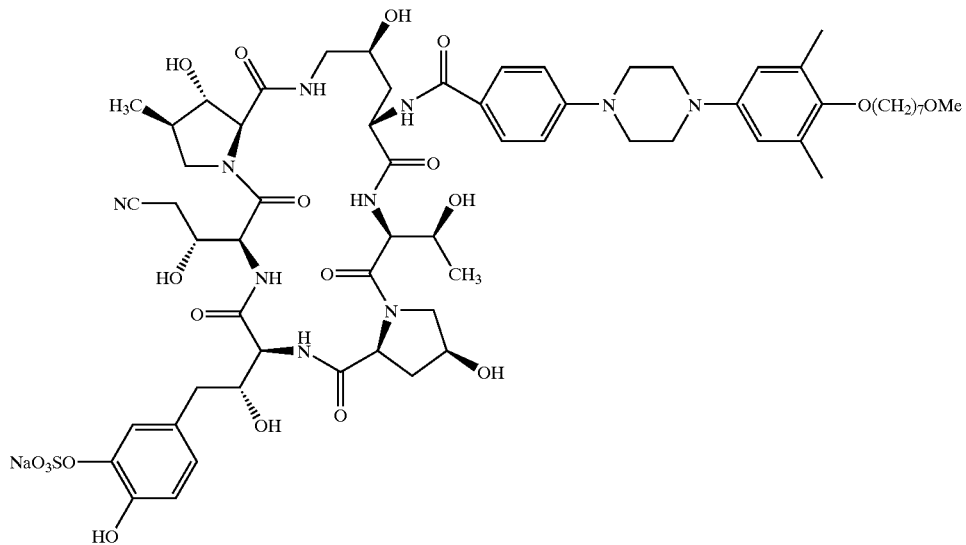 |
| | 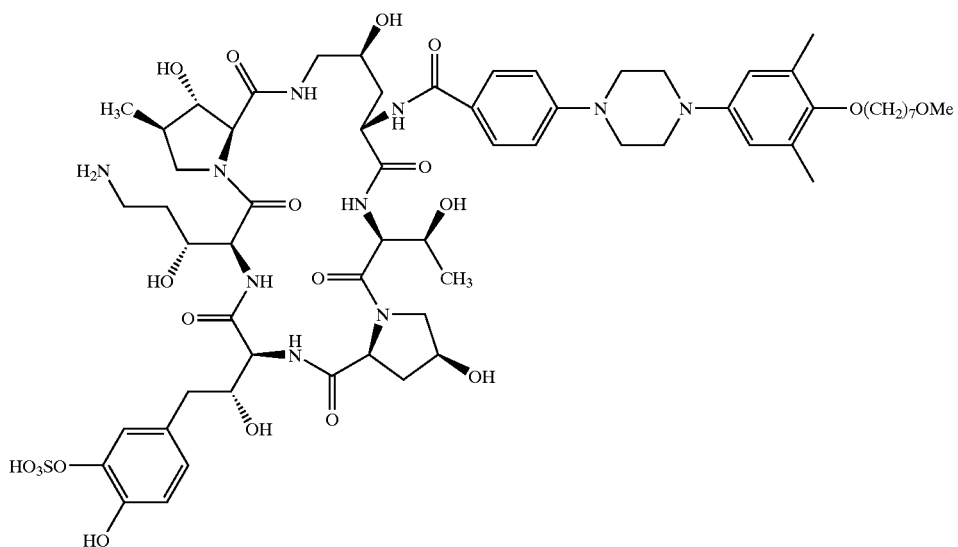 |

-continued
| Example No. | Formula |
|---|---|
150 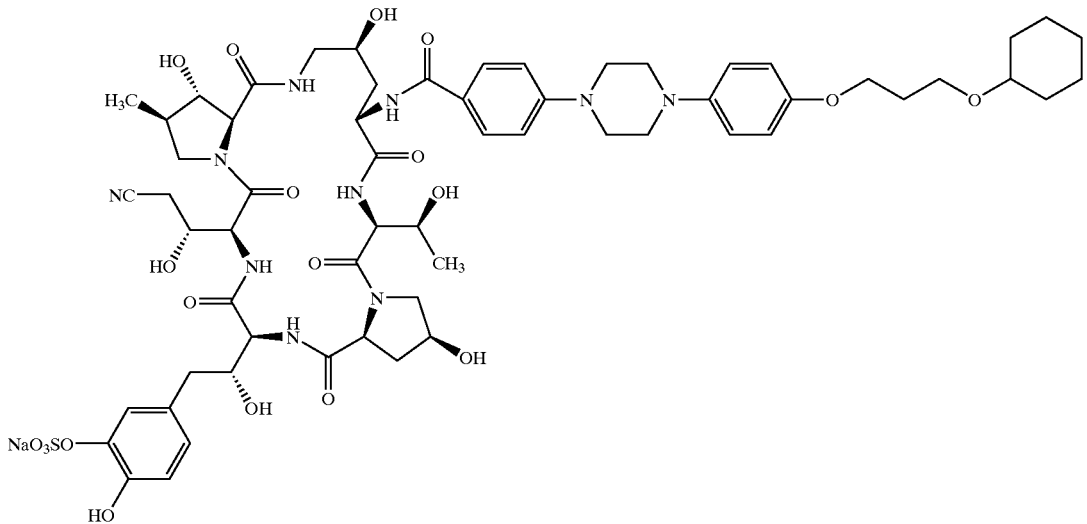
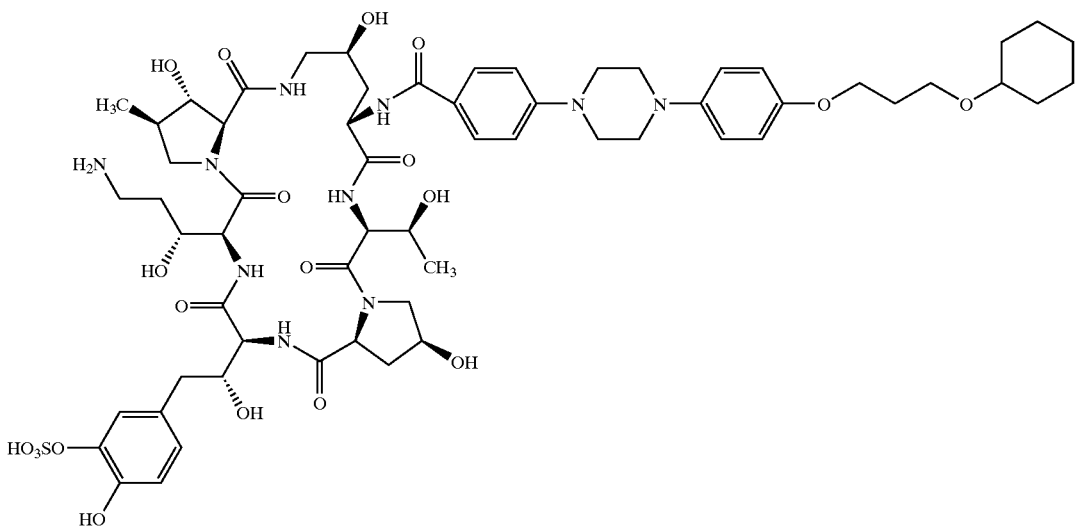

-continued
| Example No. | Formula |
|---|---|
| 151 | 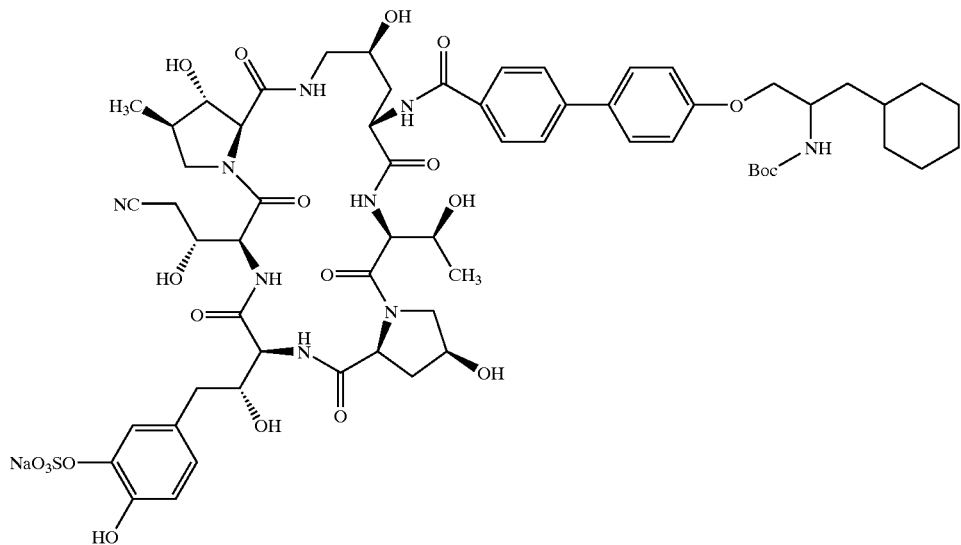 |
| | 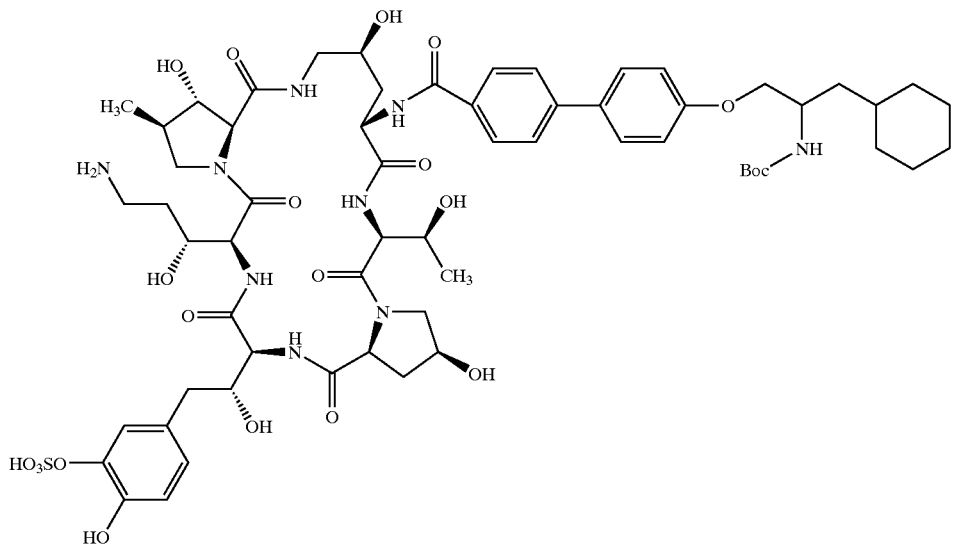 |

-continued
| Example No. | Formula |
|---|---|
| 152 | 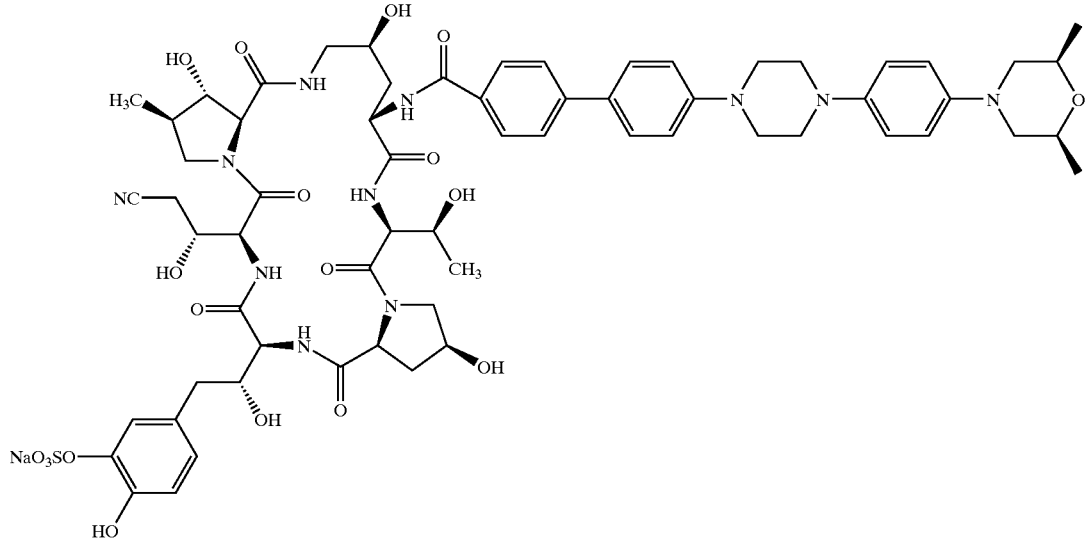 |
| | 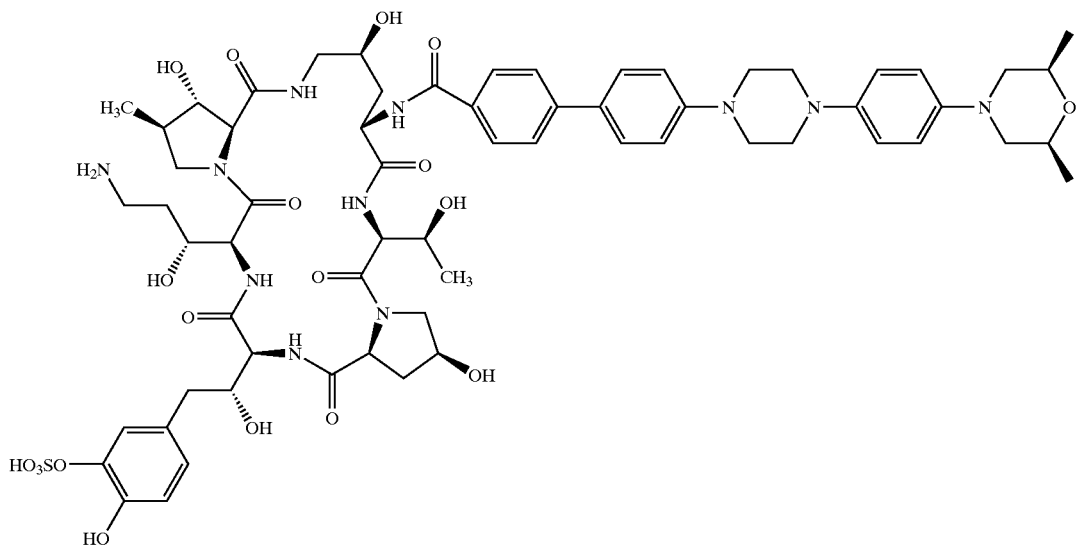 |

-continued
| Example No. | Formula |
|---|---|
| 153 | 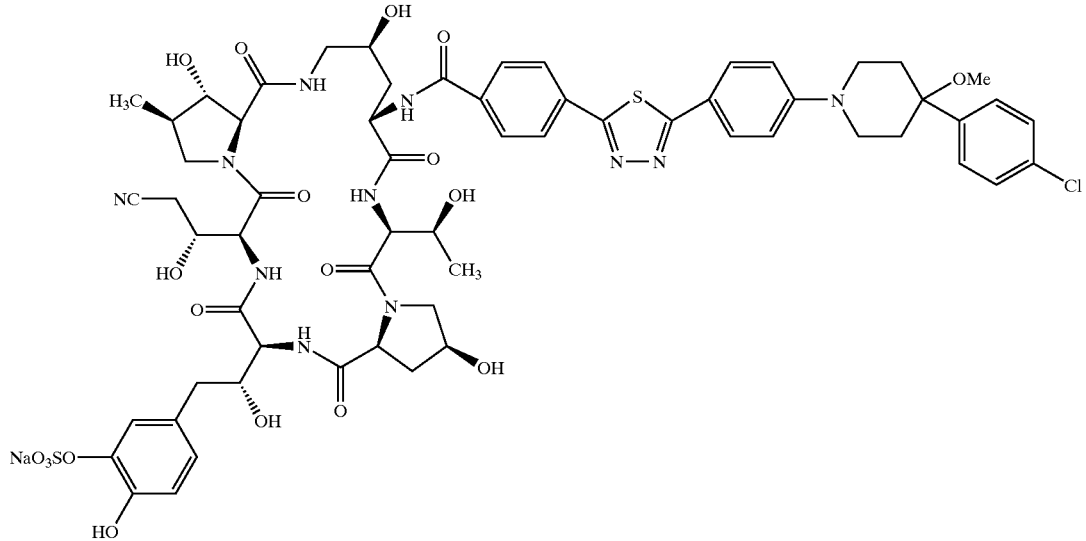 |
| | 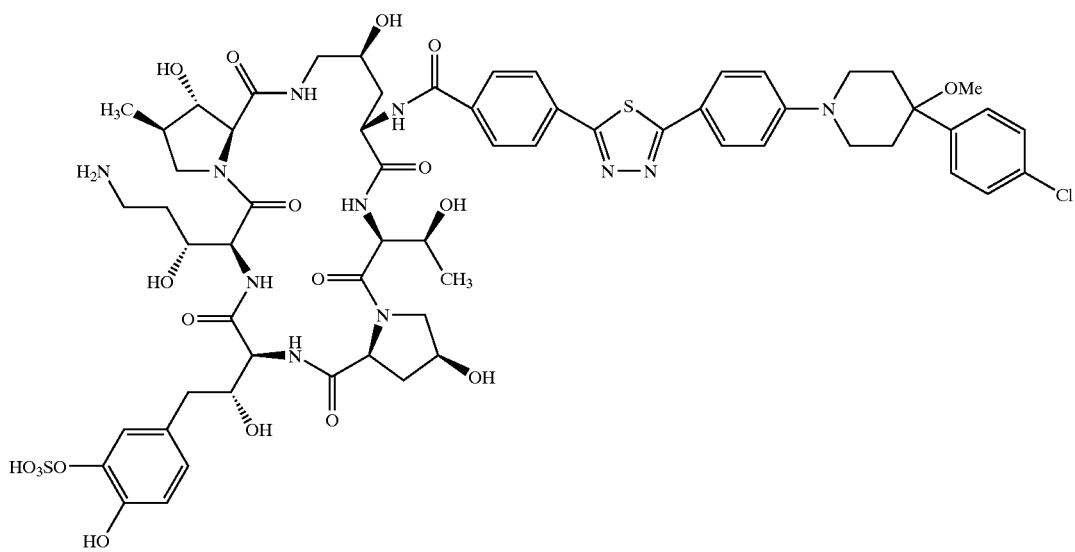 |

-continued
| Example No. | Formula |
|---|---|
| 154 | 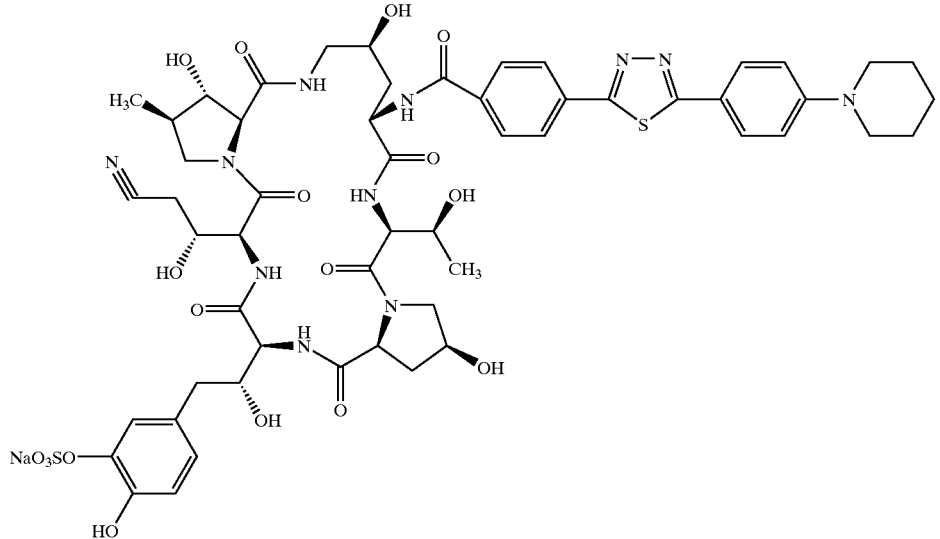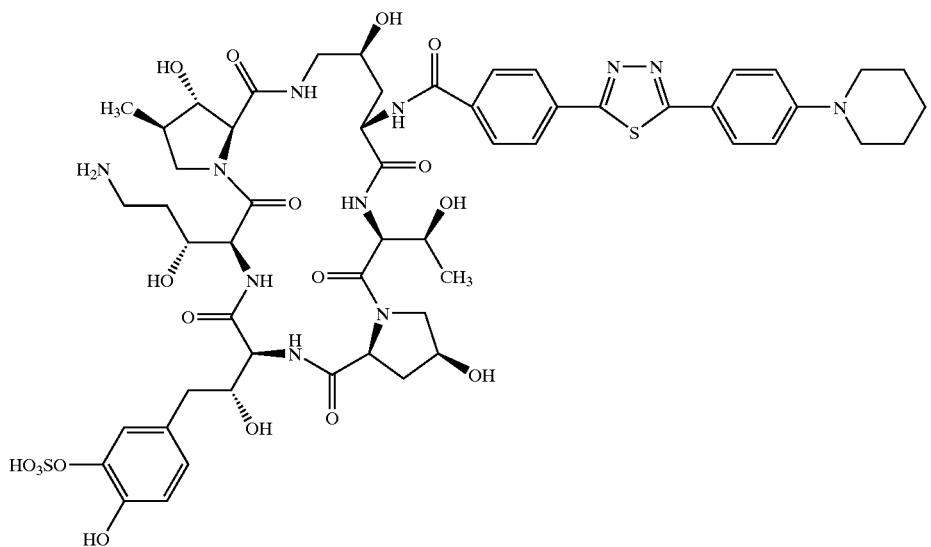 |

| Example No. | Formula |
|---|---|
| 155 | 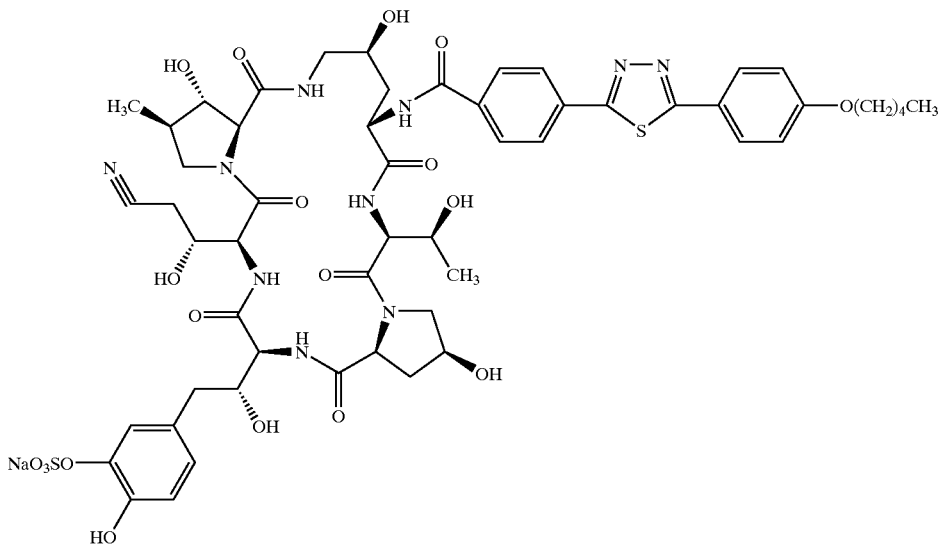 |
| | 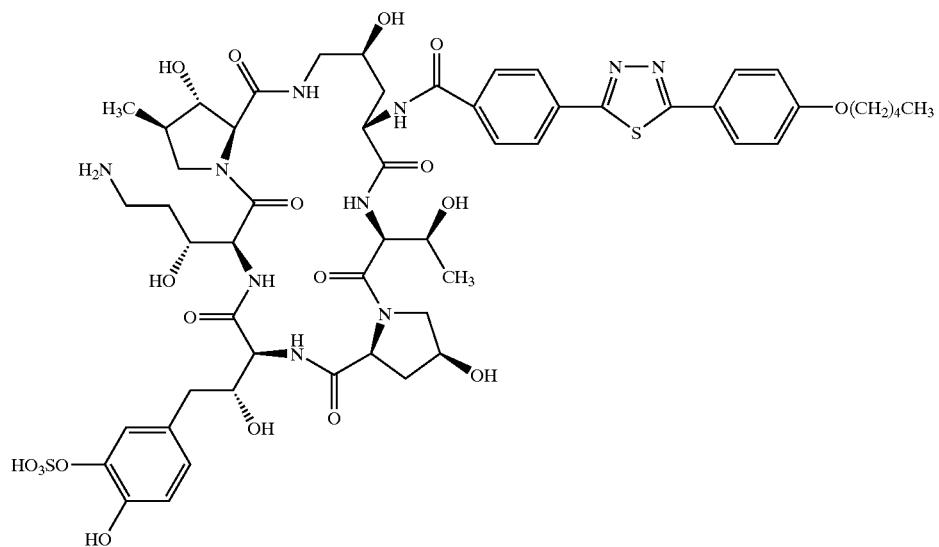 |

-continued
| Example No. | Formula |
|---|---|
| 156 | 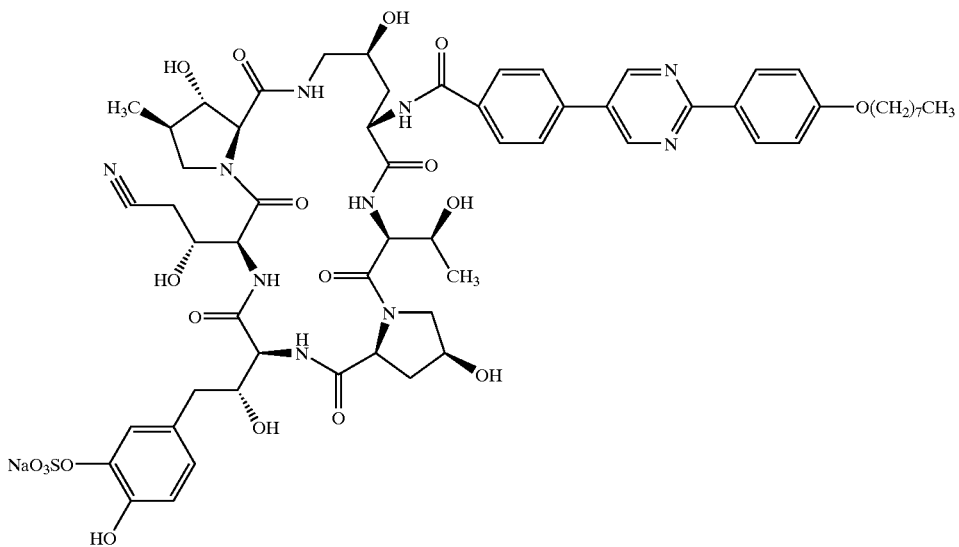 |
| | 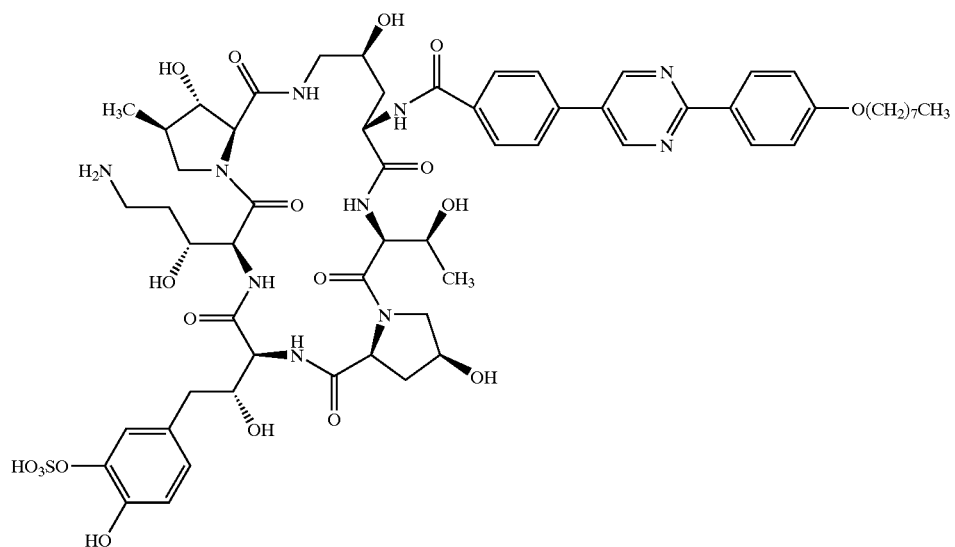 |

| Example No. | Formula |
|---|---|
| 157 | 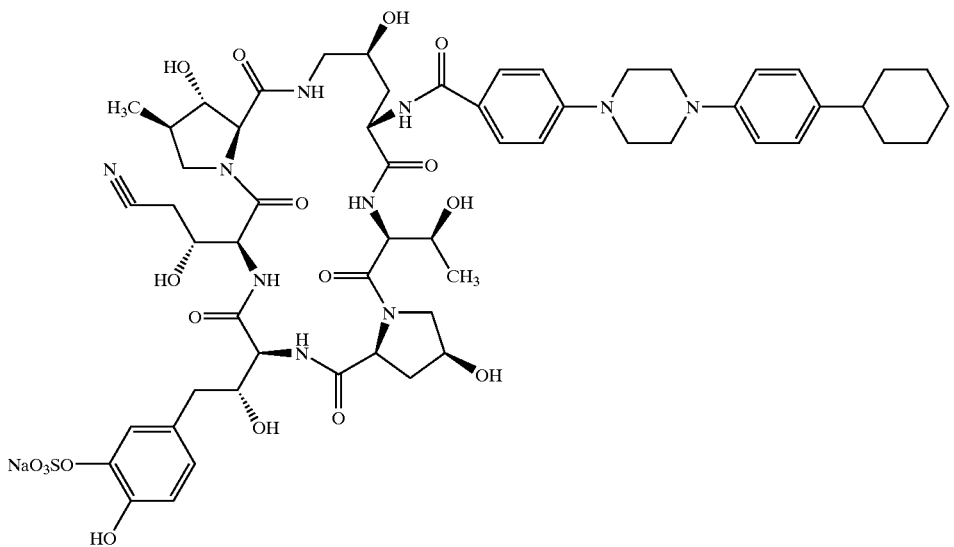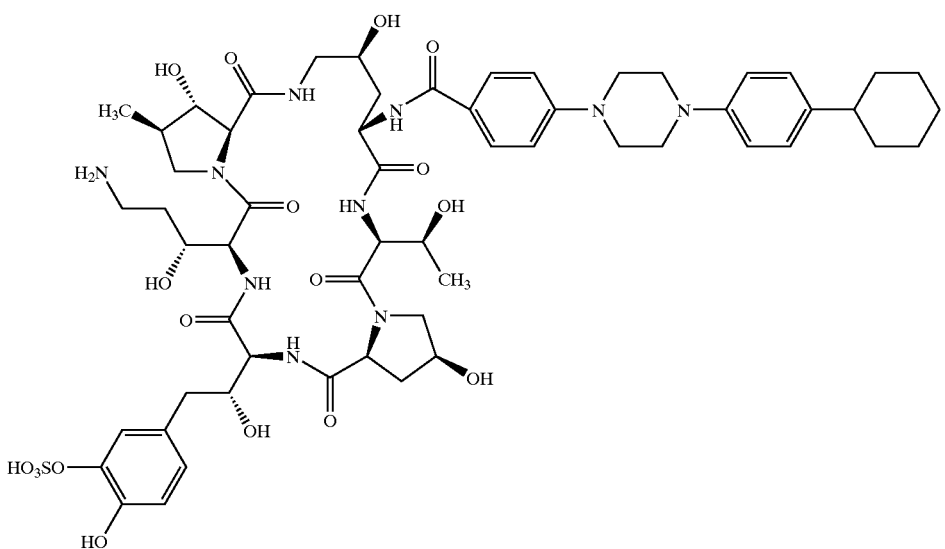 |

-continued
| Example No. | Formula |
|---|---|
| 158 | 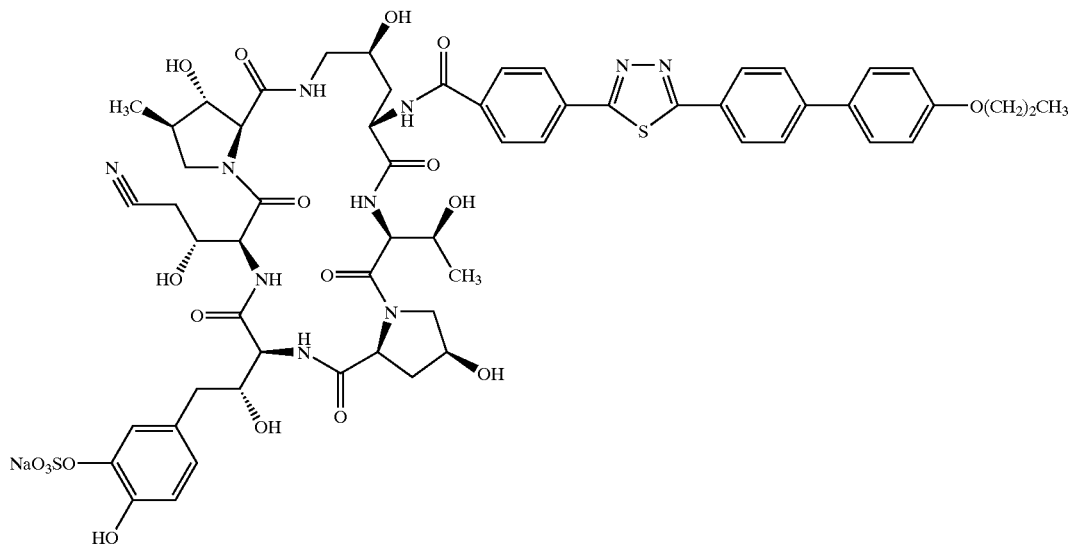<br>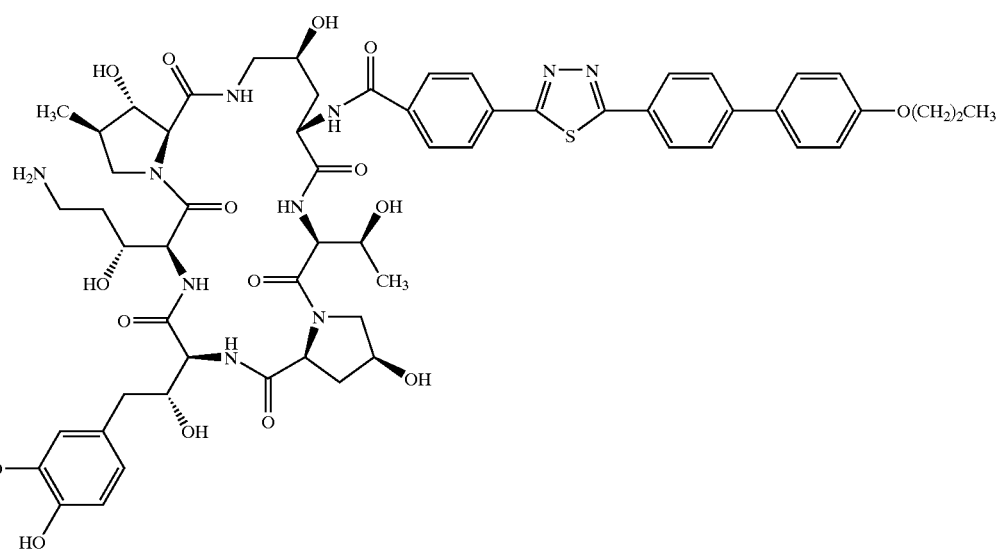 |

-continued
| Example No. | Formula |
|---|---|
| 159 | 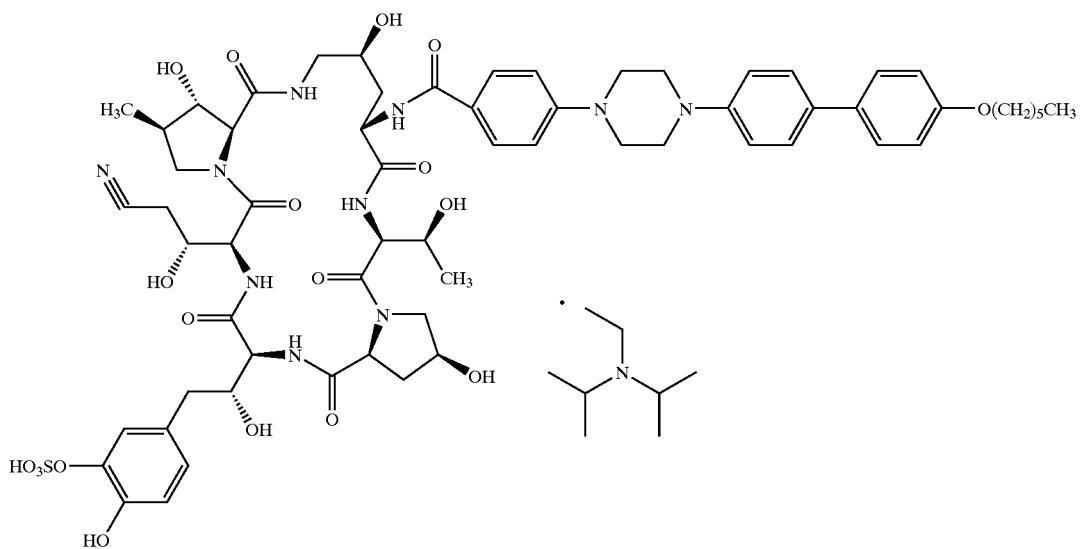 |
| | 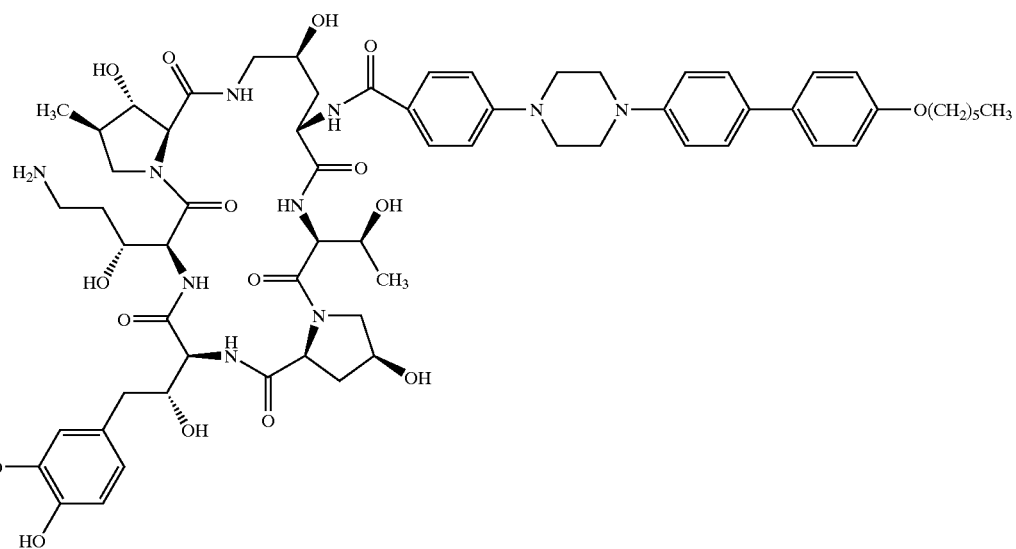 |

-continued
| Example No. | Formula |
|---|---|
| 160 | 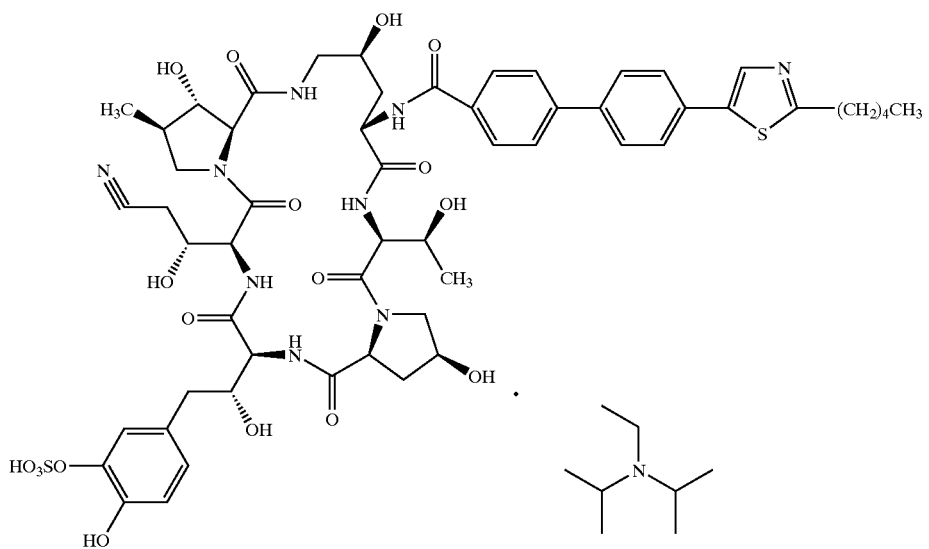 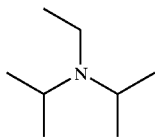 |
| | 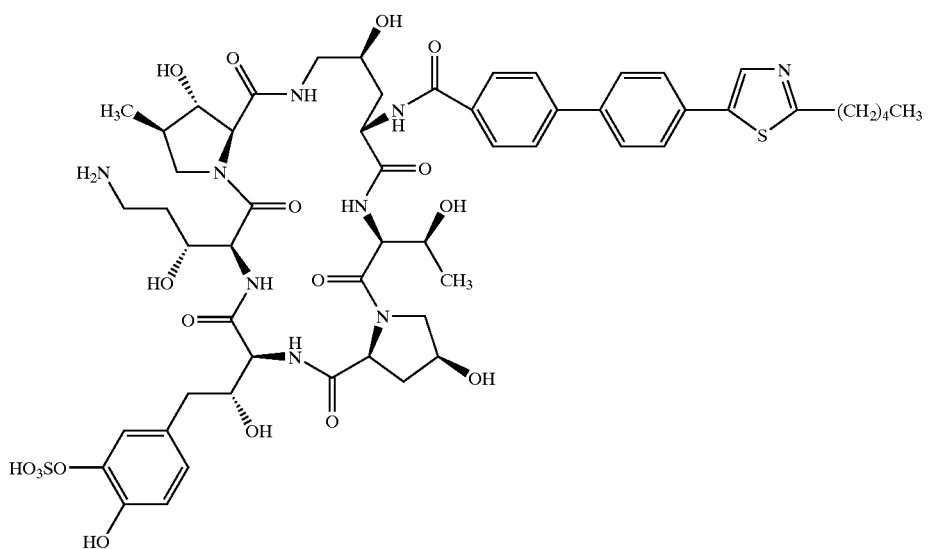 |

| Example No. | Formula |
|---|---|
| 161 | 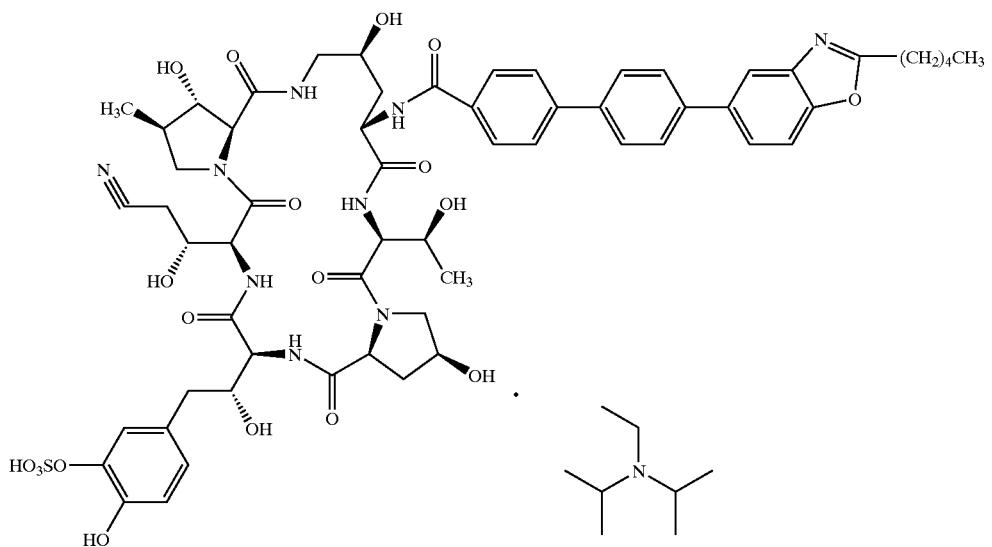 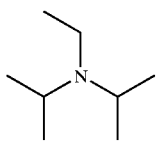 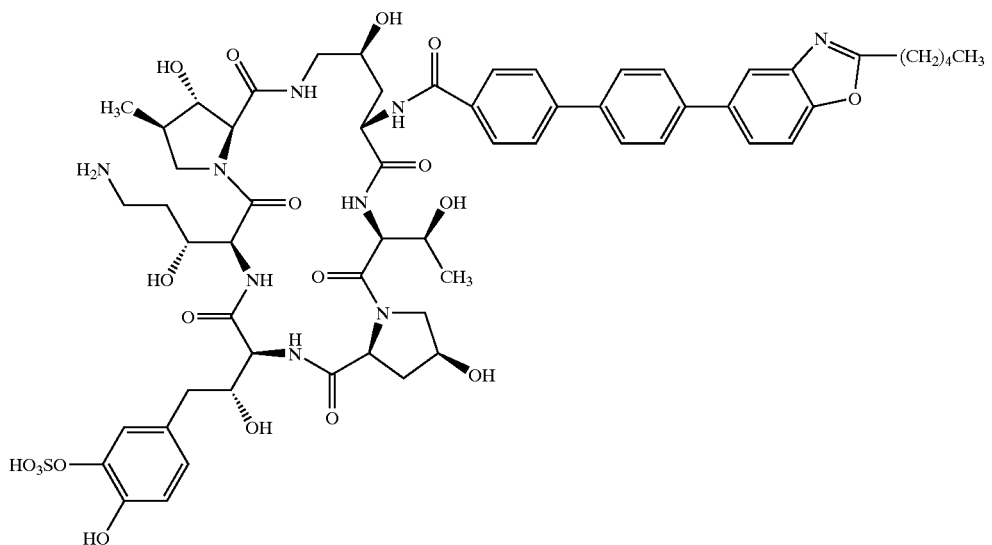 |

-continued
| Example No. | Formula |
|---|---|
| 162 | 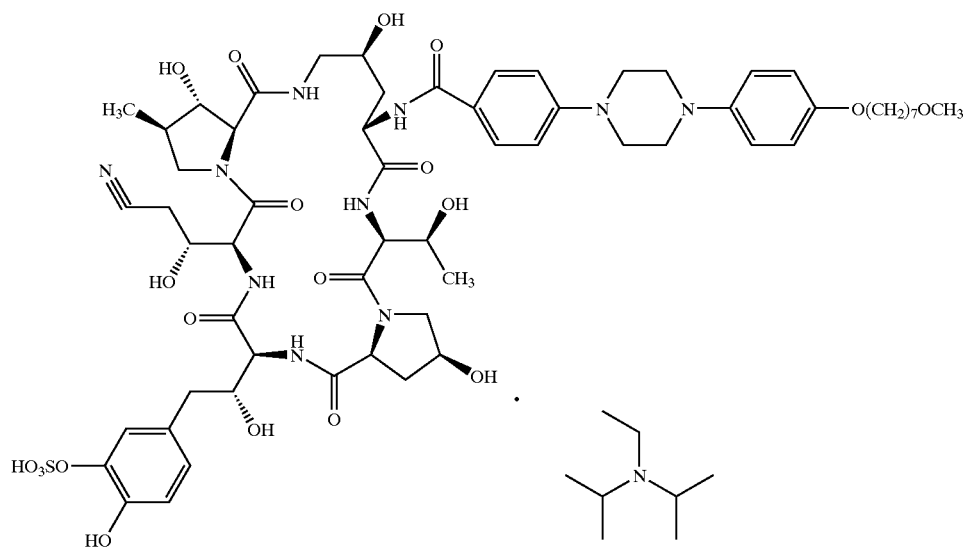 |
| | 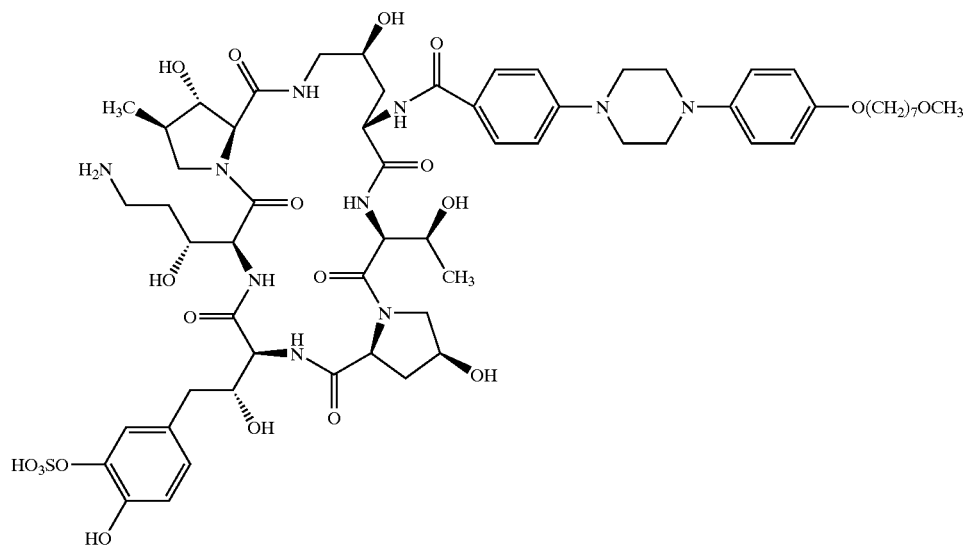 |

-continued
| Example No. | Formula |
|---|---|
| 163 | 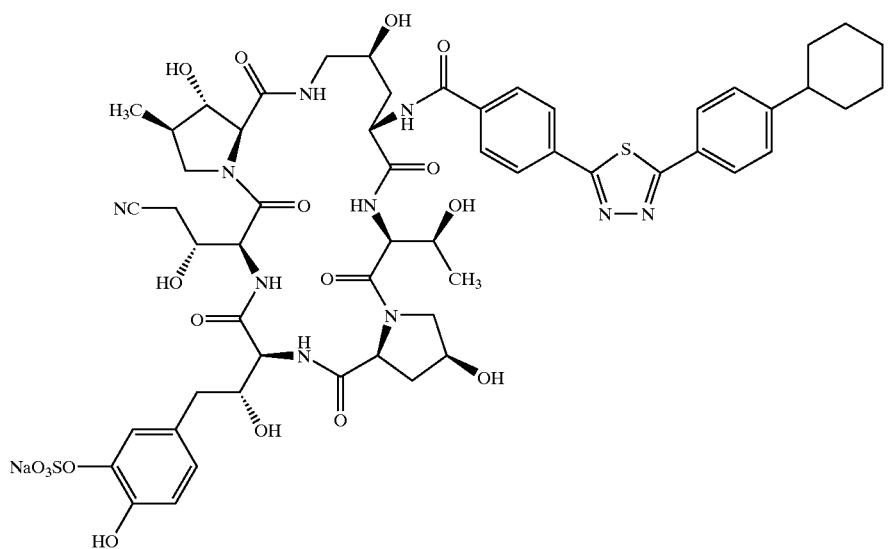<br>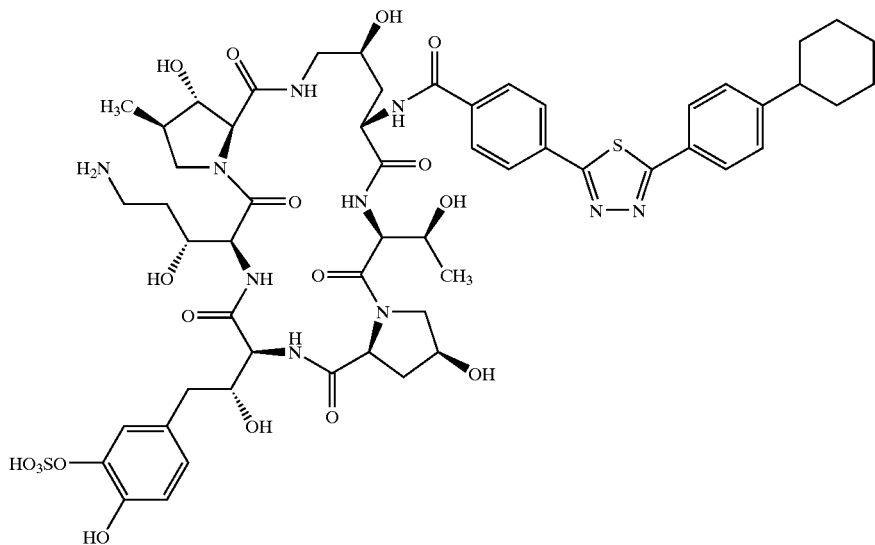 |

-continued
| Example No. | Formula |
|---|---|
| 164 | 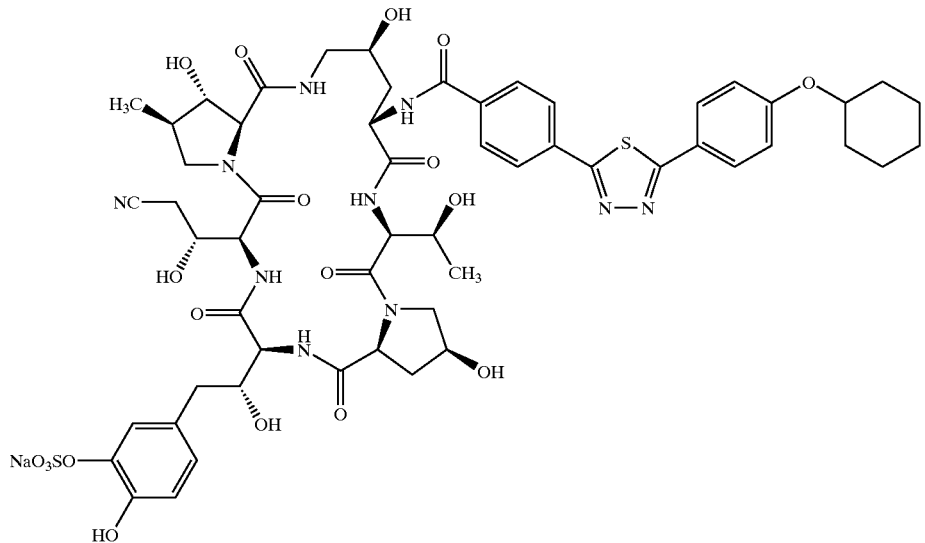 |
| | 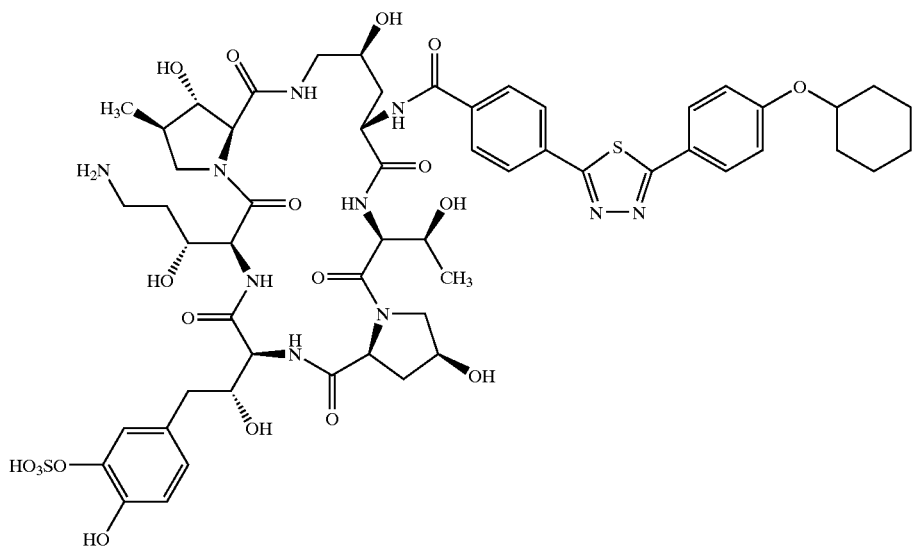 |

| Example No. | Formula |
|---|---|
| 165 | 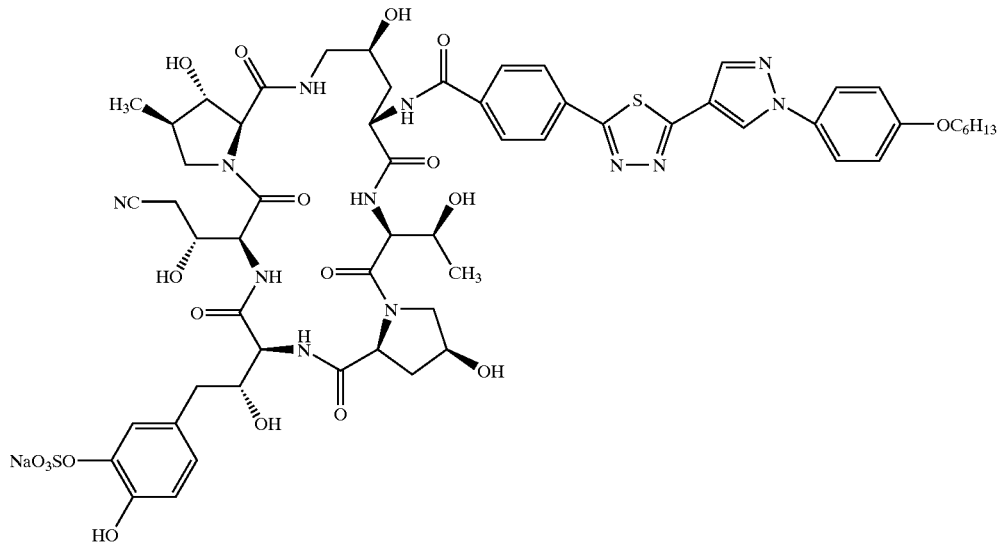 |
| | 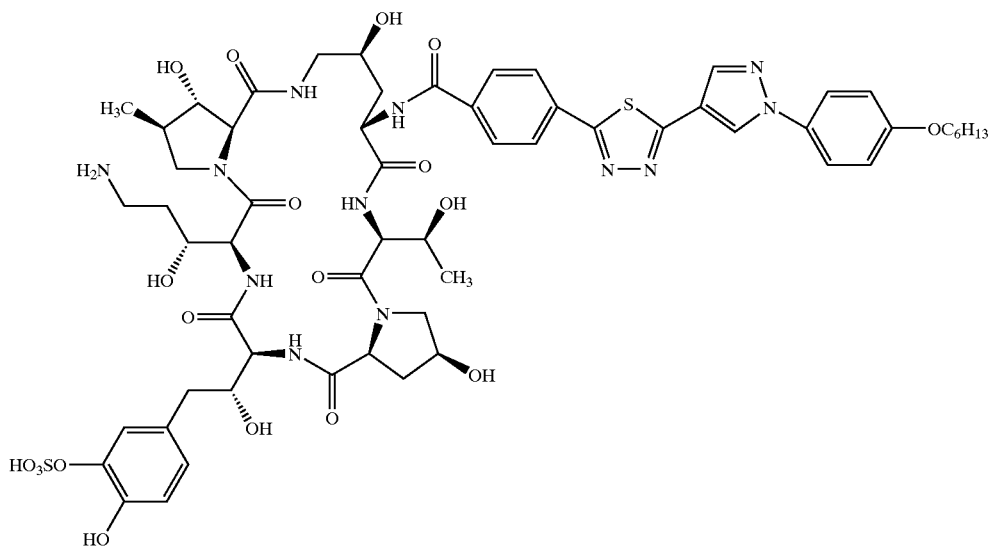 |

-continued
| Example No. | Formula |
|---|---|
| 166 | 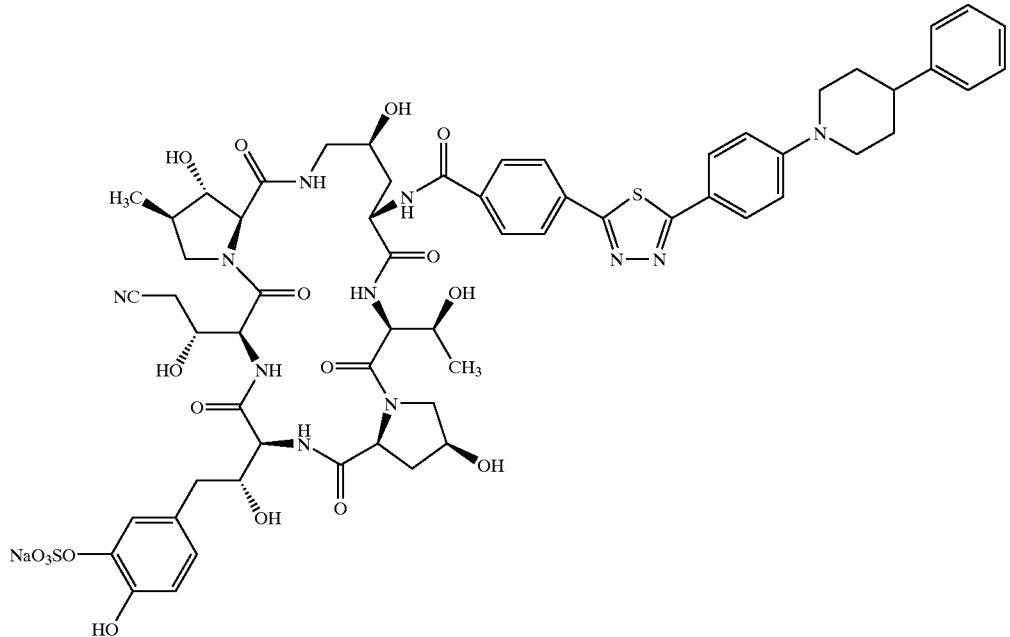 |
| | 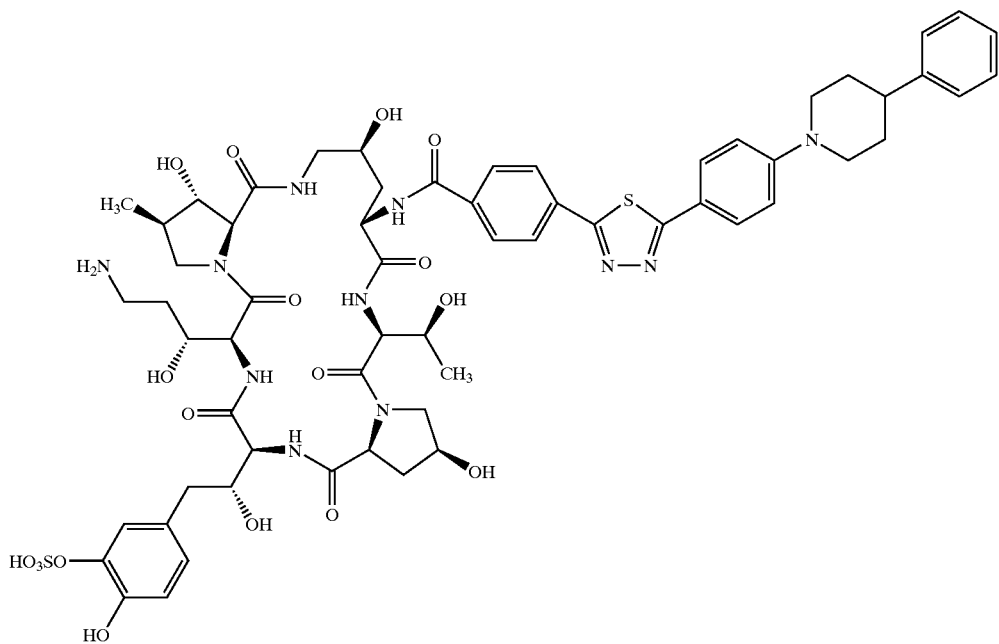 |

| Example No. | Formula |
|---|---|
| 167 | 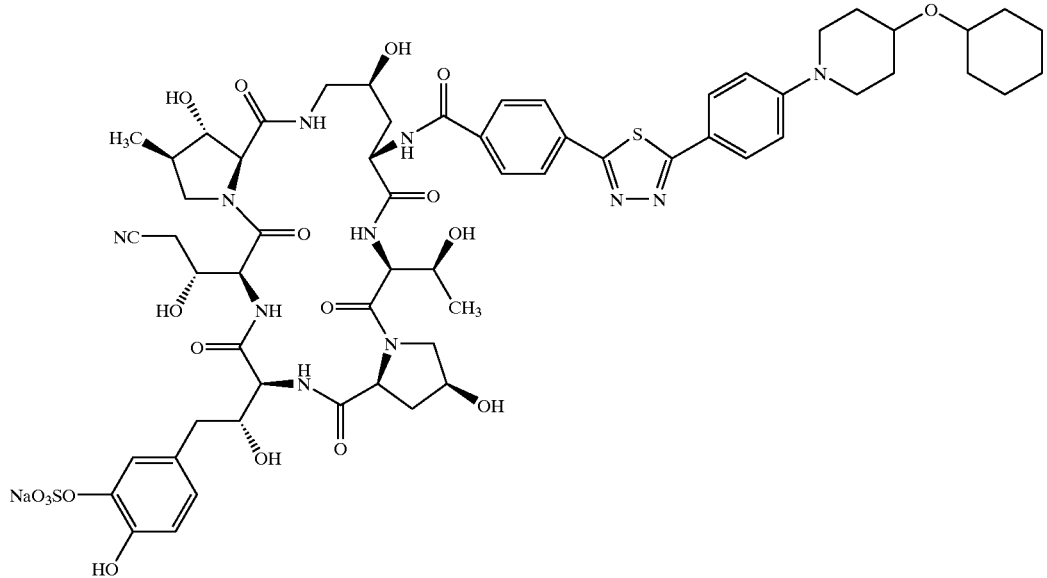 |
| | 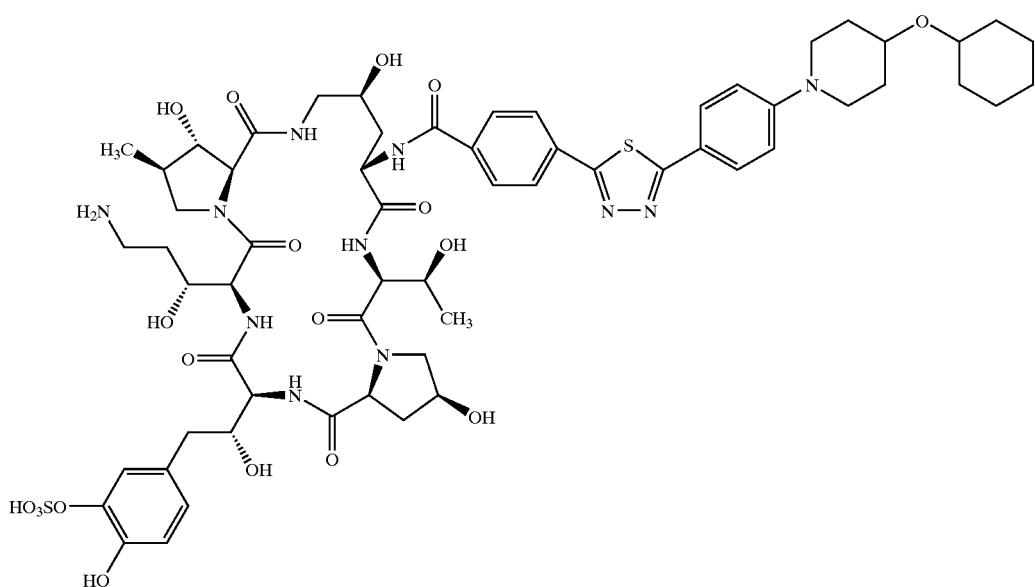 |

-continued
| Example No. | Formula |
|---|---|
| 168 | 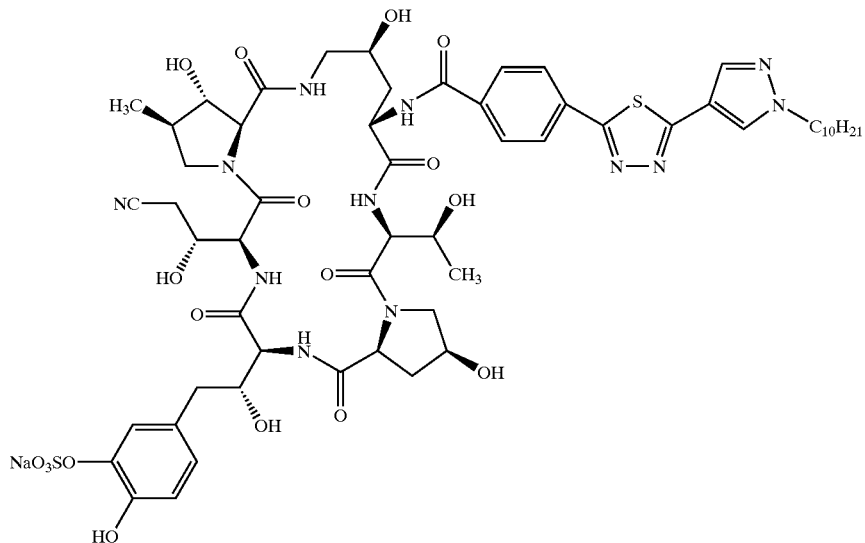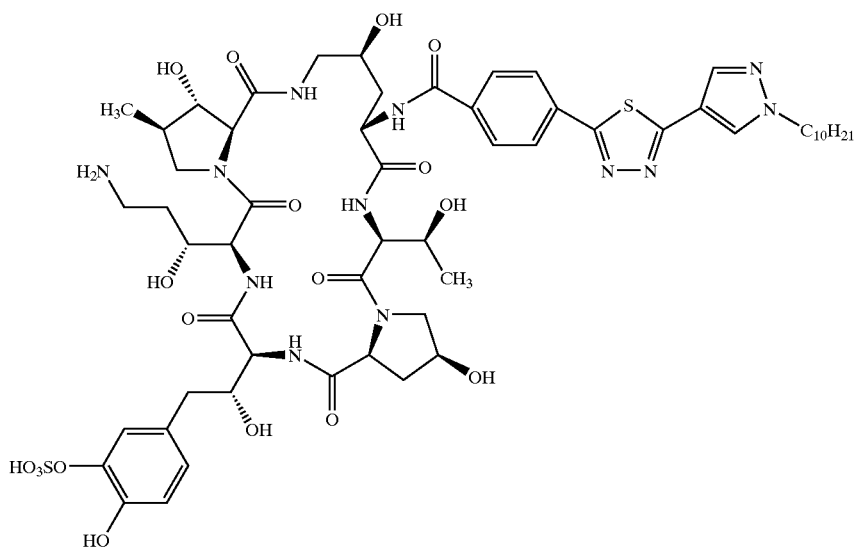 |

-continued
| Example No. | Formula |
|---|---|
| 169 | 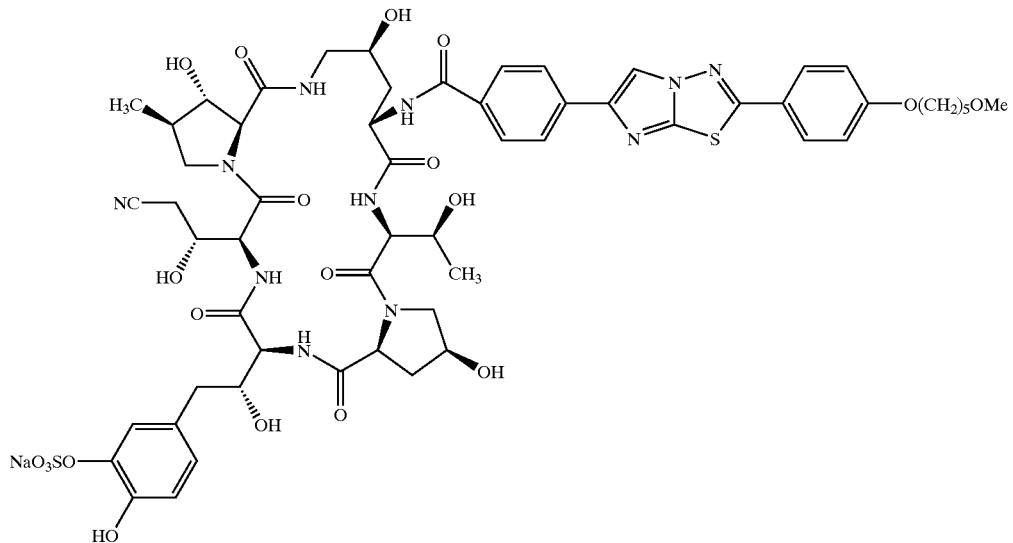 |
| | 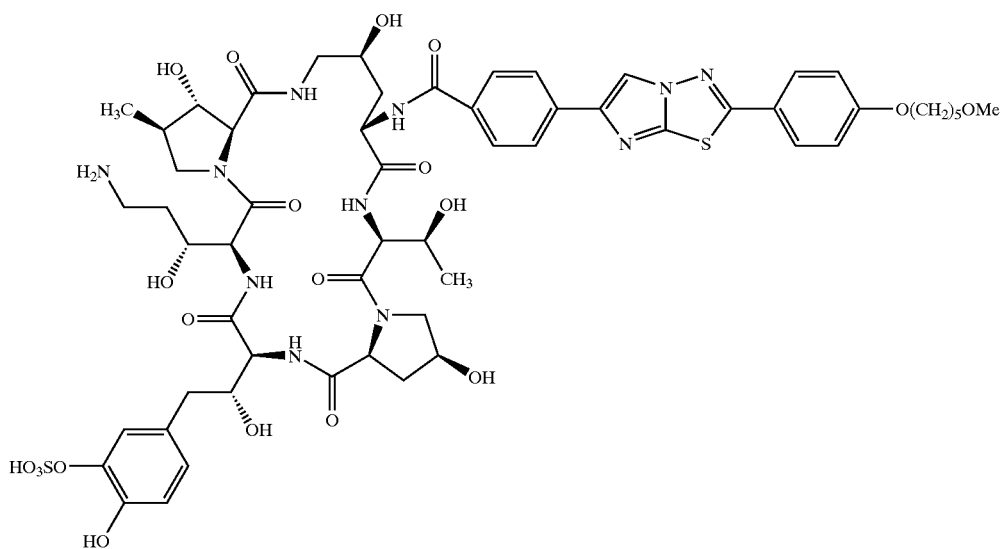 |

-continued
| Example No. | Formula |
|---|---|
| 170 | 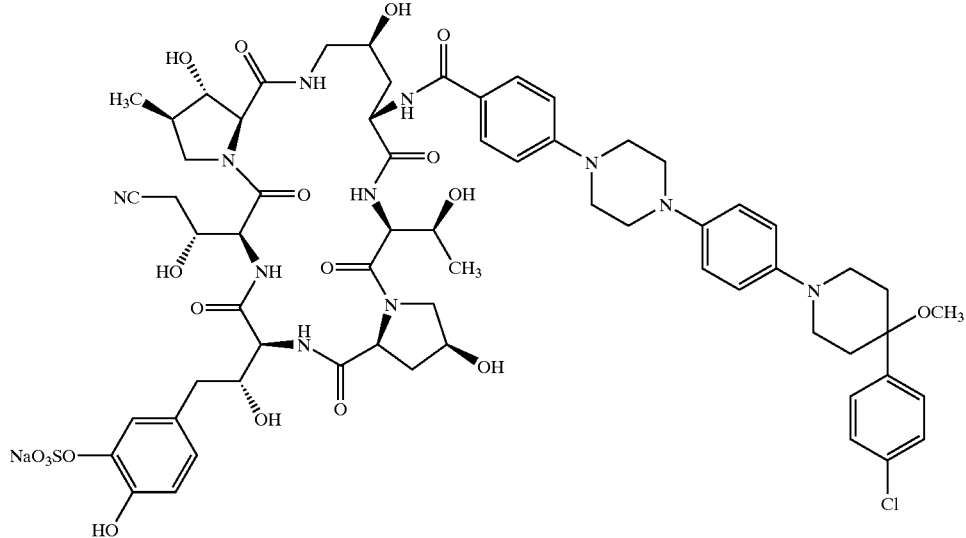 |
| | 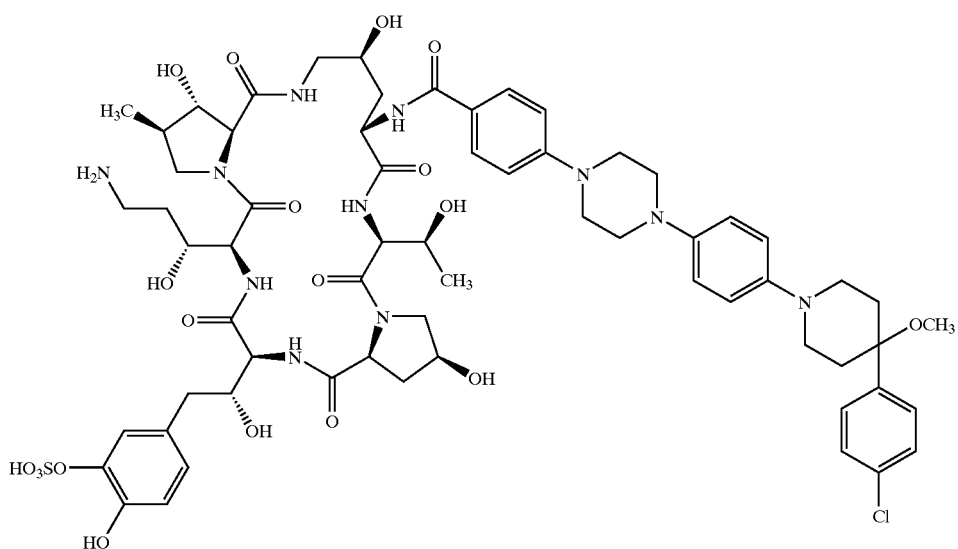 |

-continued
| Example No. | Formula |
|---|---|
| 171 | 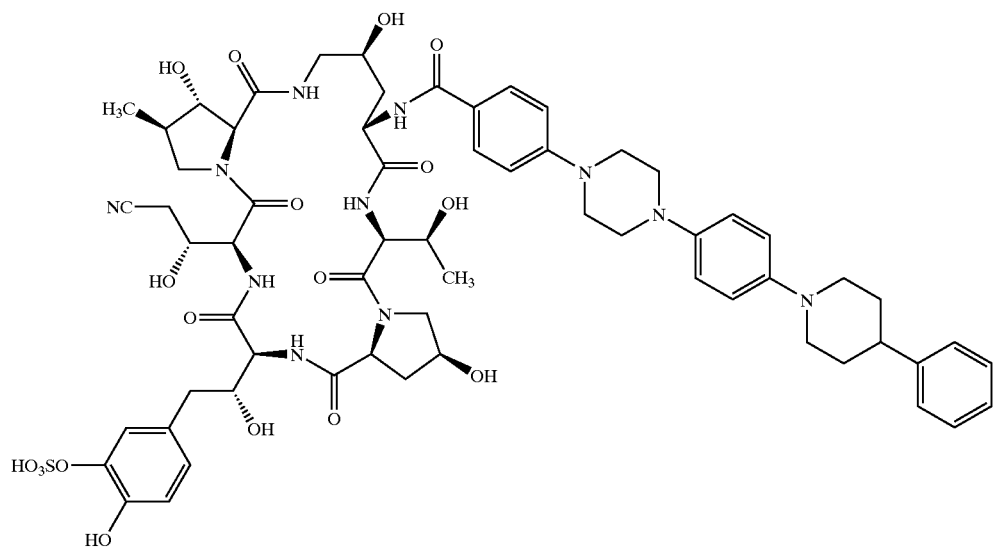 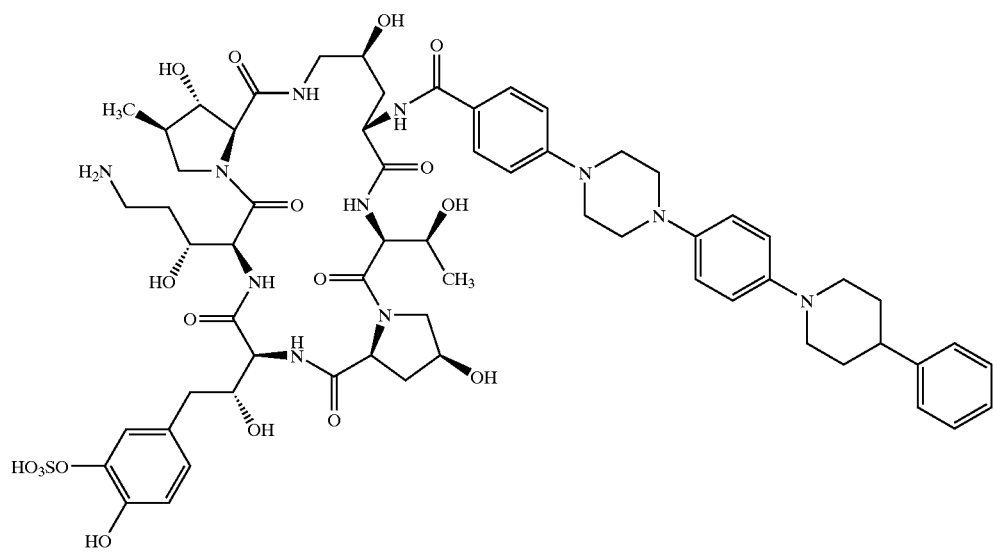 |

-continued
| Example No. | Formula |
|---|---|
| 172 | 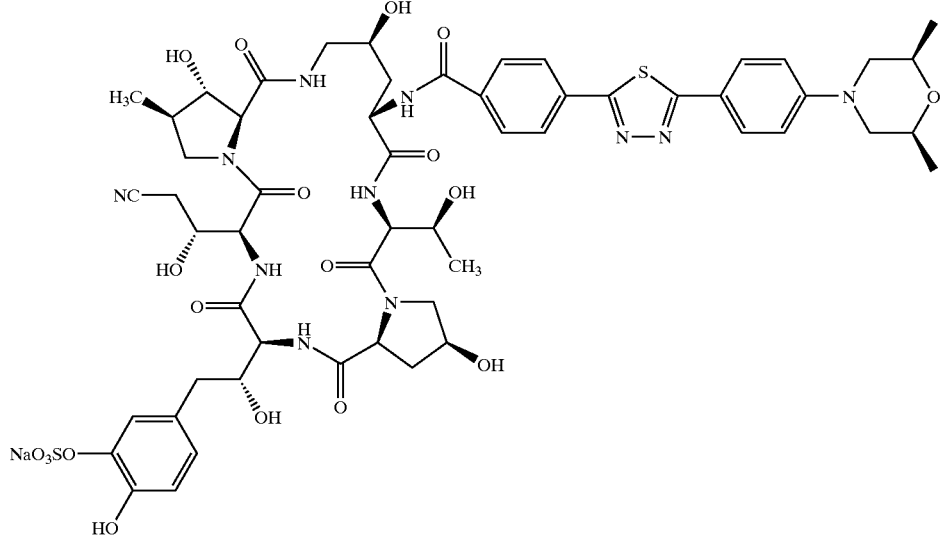<br>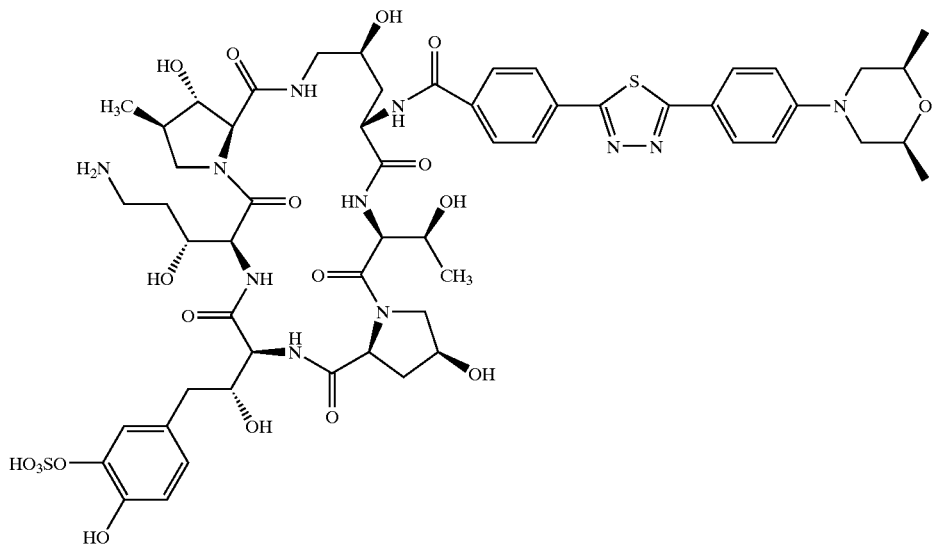 |

-continued
| Example No. | Formula |
|---|---|
| 173 | 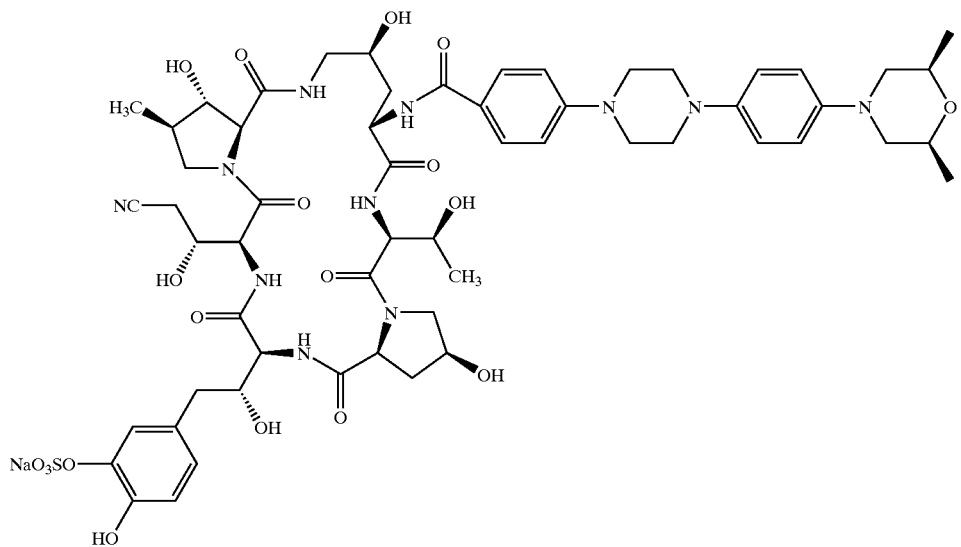 |
| | 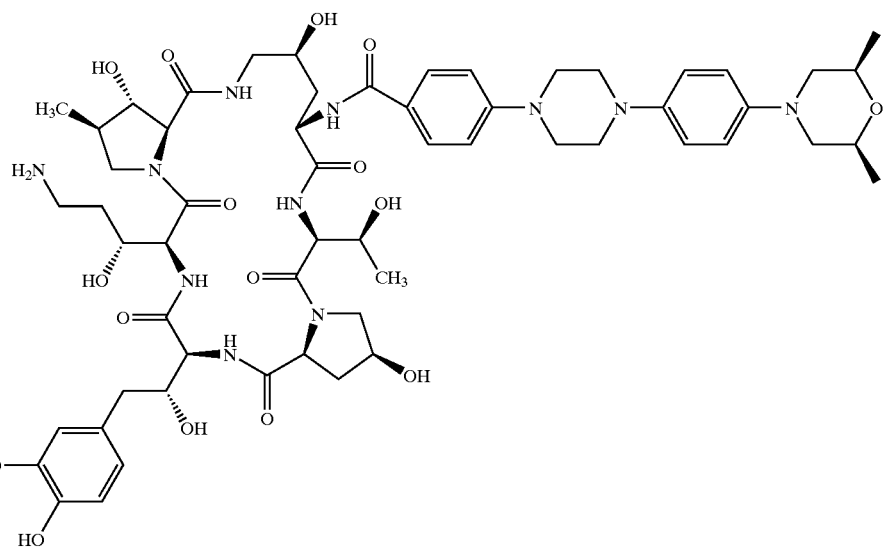 |

-continued
| Example No. | Formula |
|---|---|
| 174 | 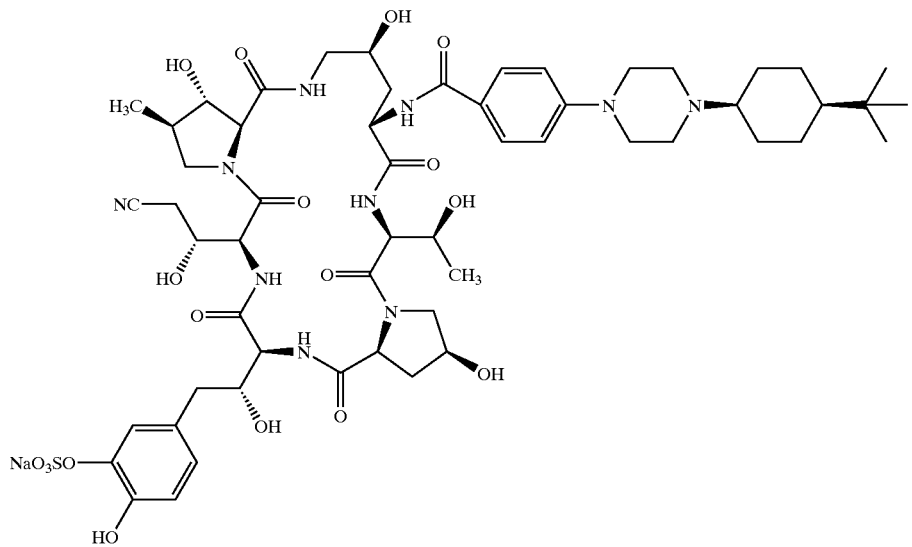 |
| | 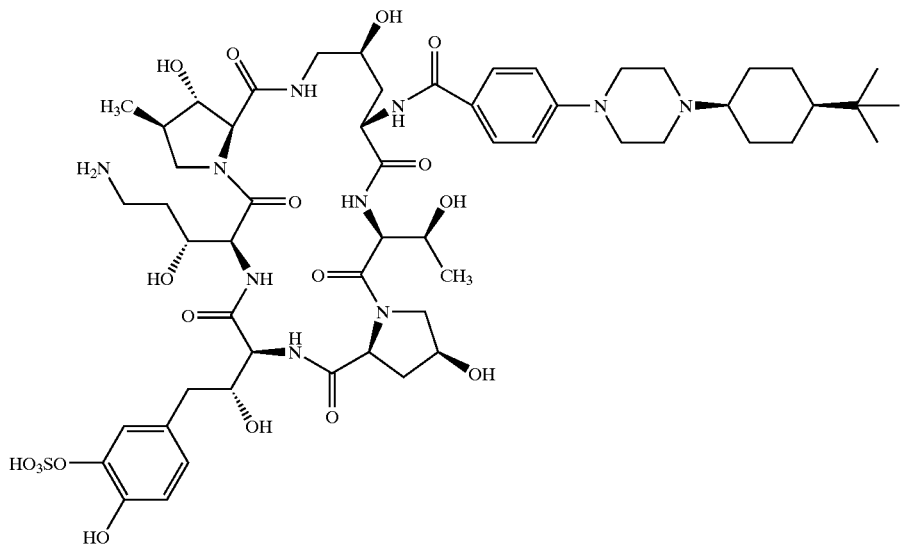 |

-continued
| Example No. | Formula |
|---|---|
| 175 | 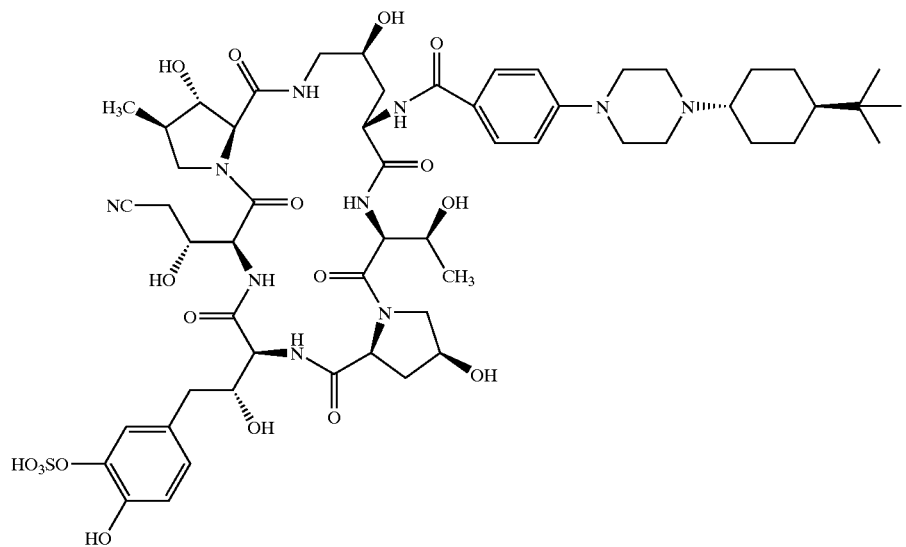 |
| | 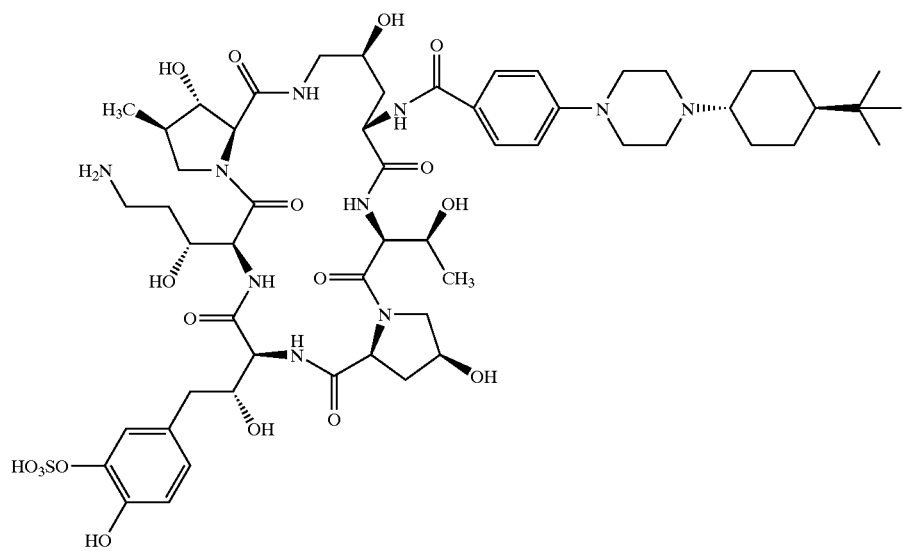 |

| Example No. | Formula |
|---|---|
| 176 | 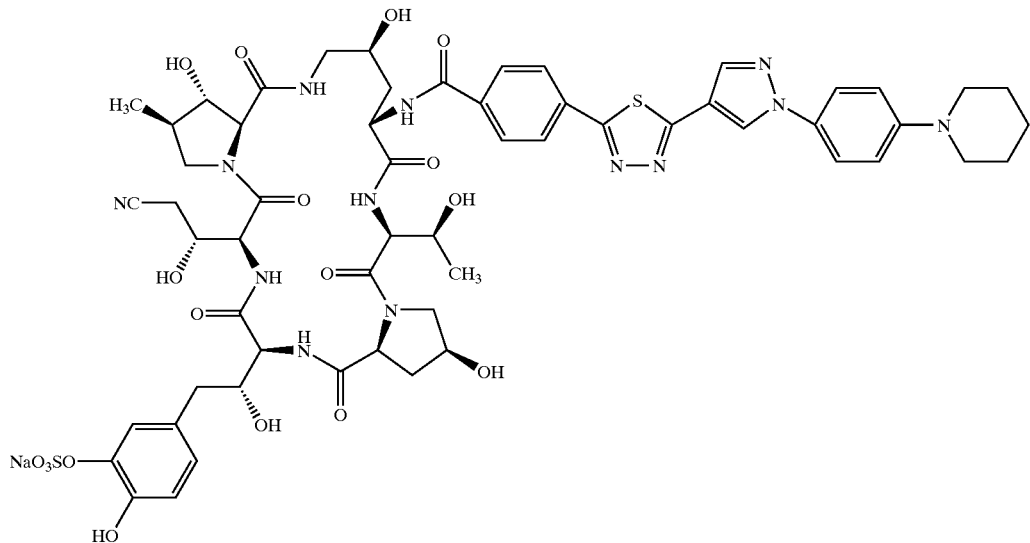<br>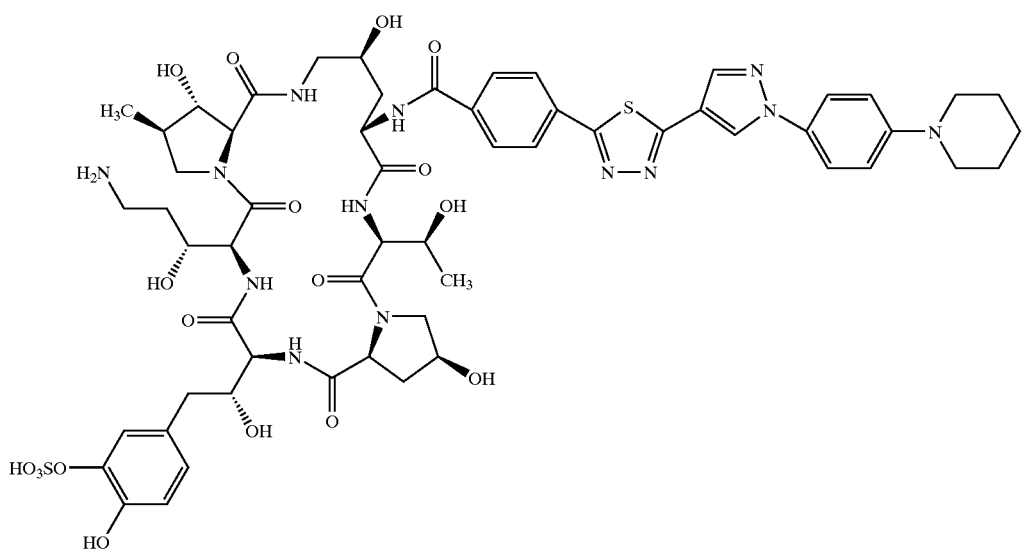 |

| Example No. | Formula |
|---|---|
| 177 | 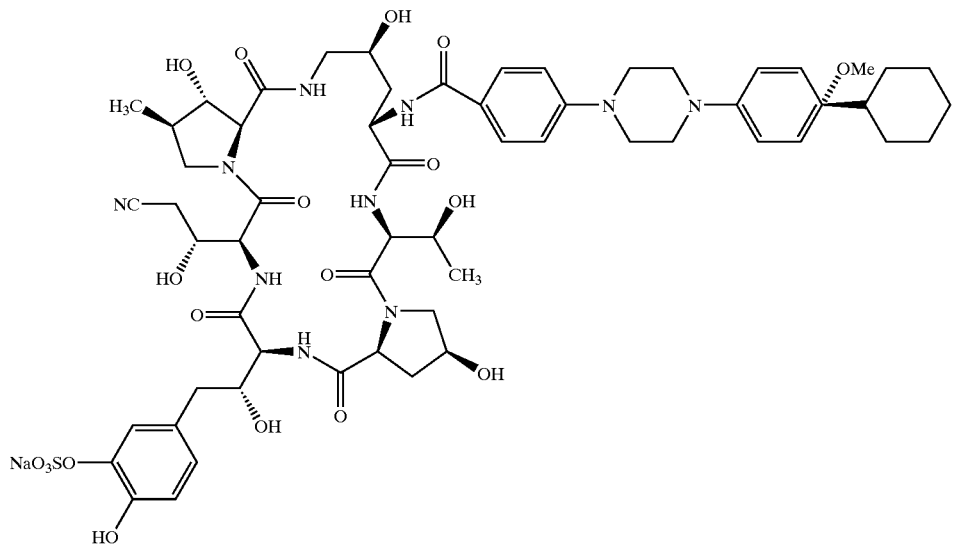 |
| | 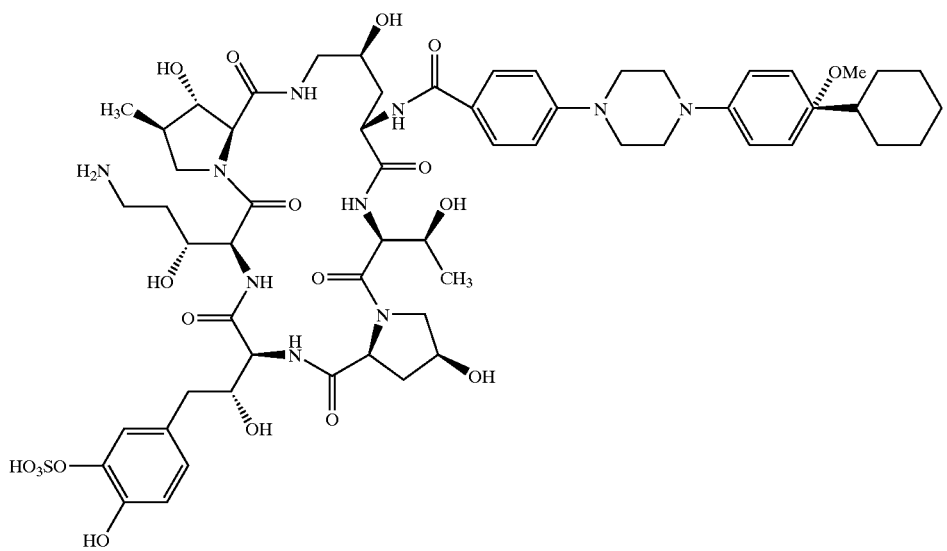 |

-continued
| Example No. | Formula |
|---|---|
| 178 | 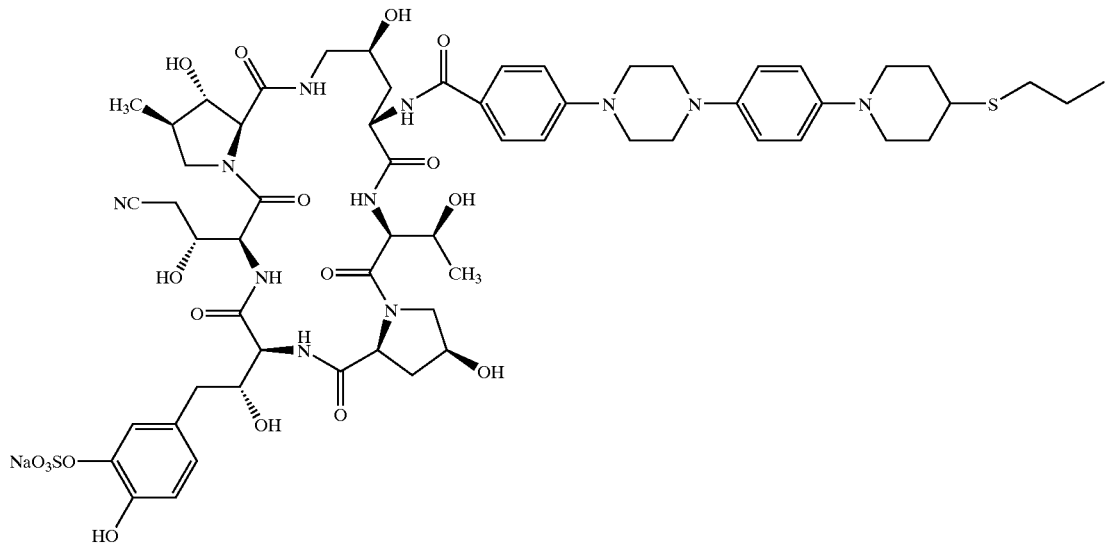<br>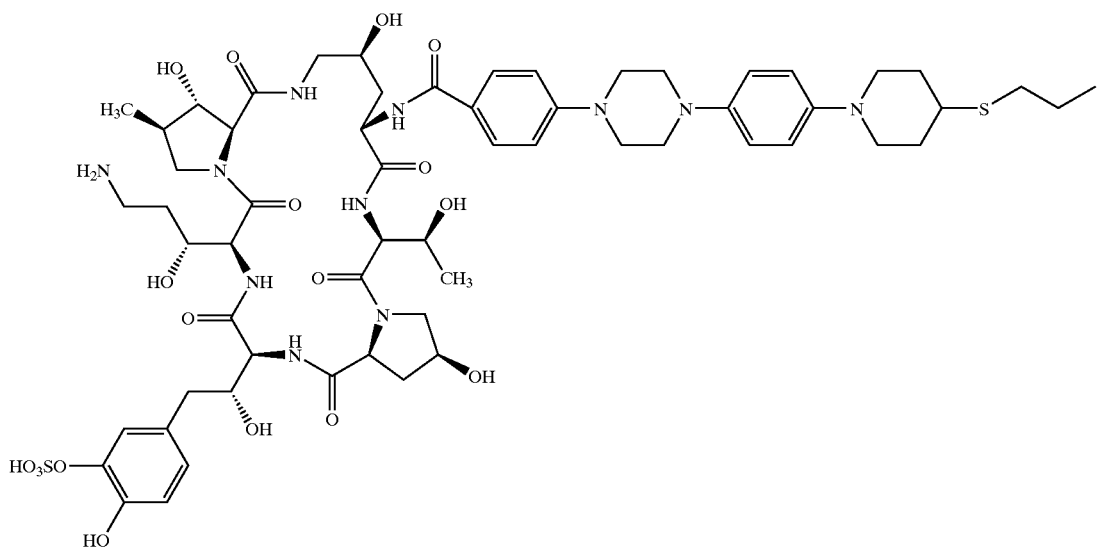 |

-continued
| Example No. | Formula |
|---|---|
| 179 | 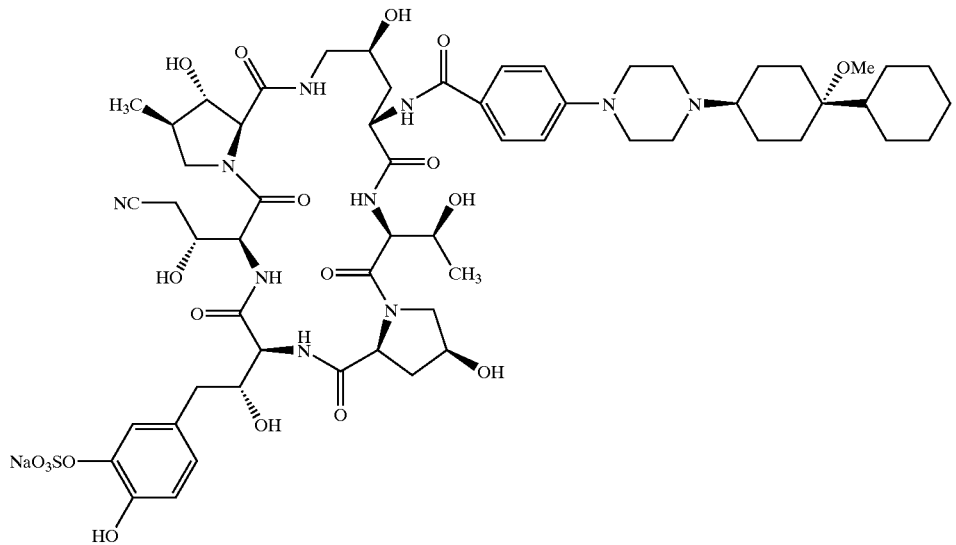 |
| | 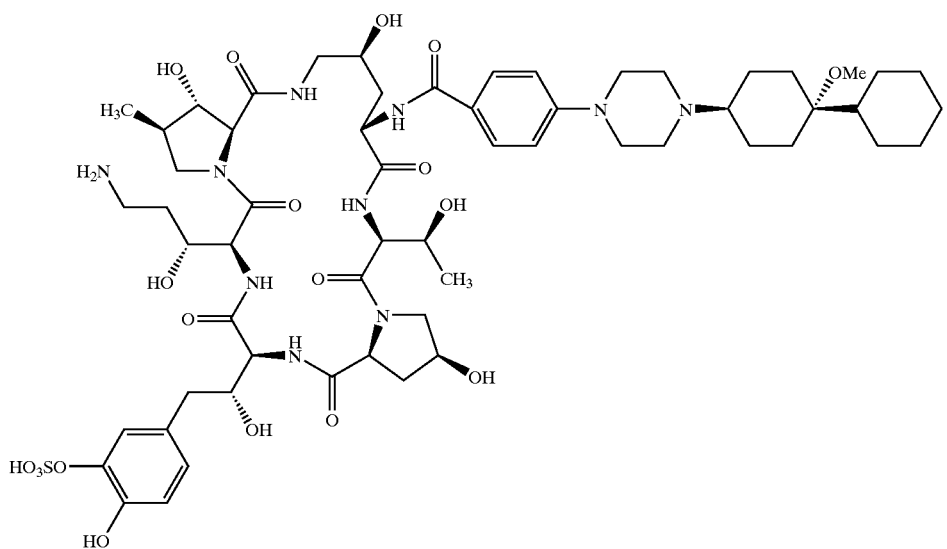 |

-continued
| Example No. | Formula |
|---|---|
| 180 | 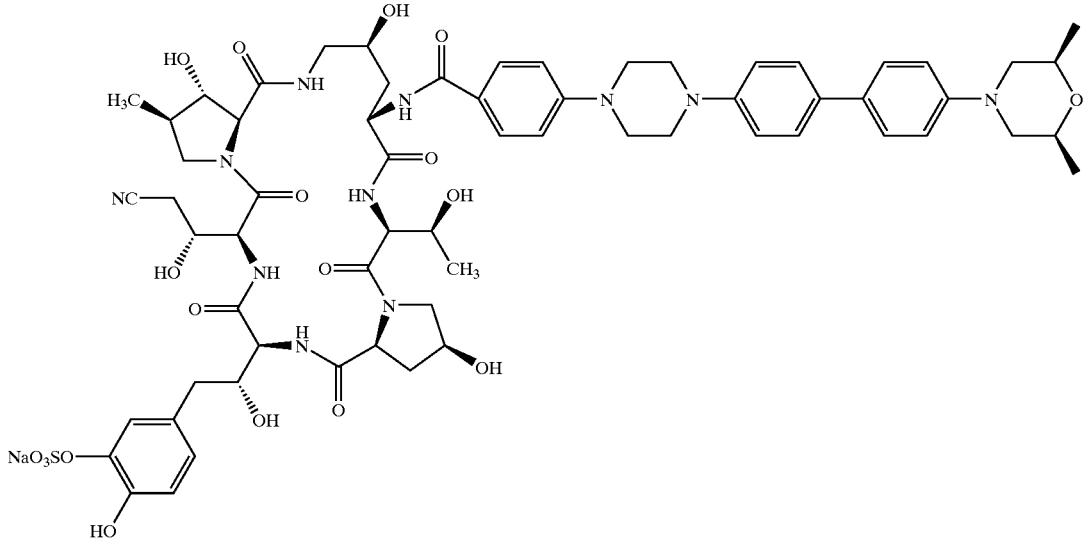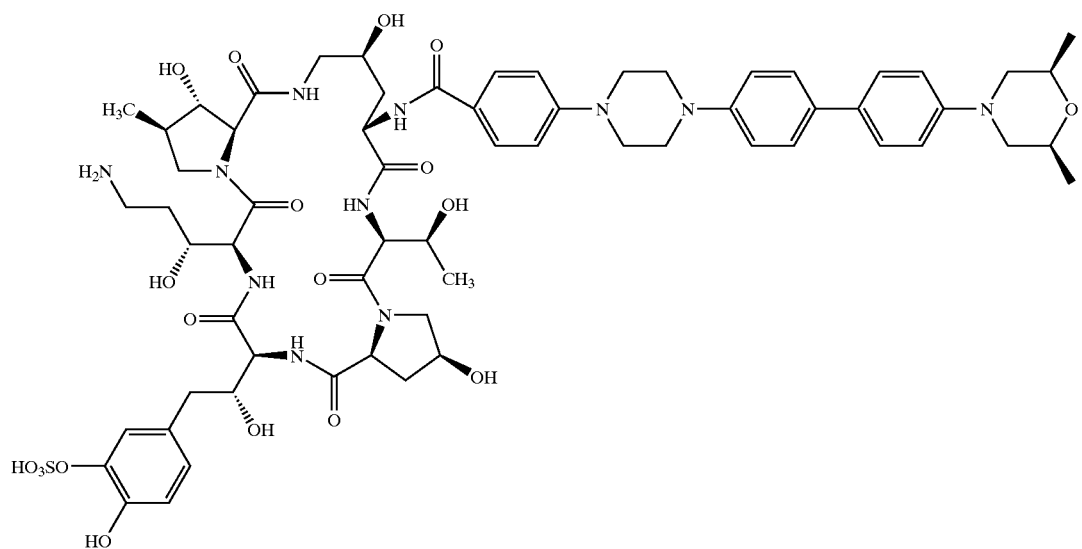 |

-continued
| Example No. | Formula |
|---|---|
| 181 | 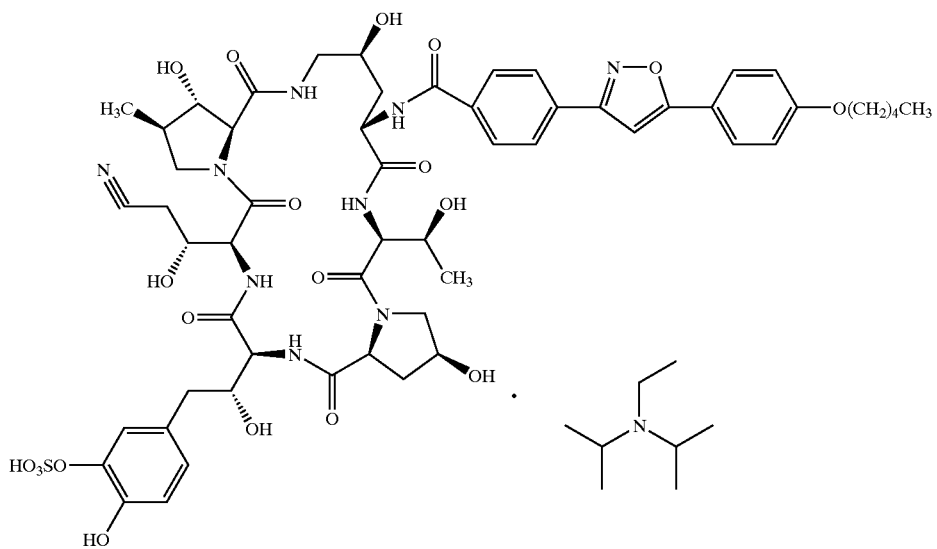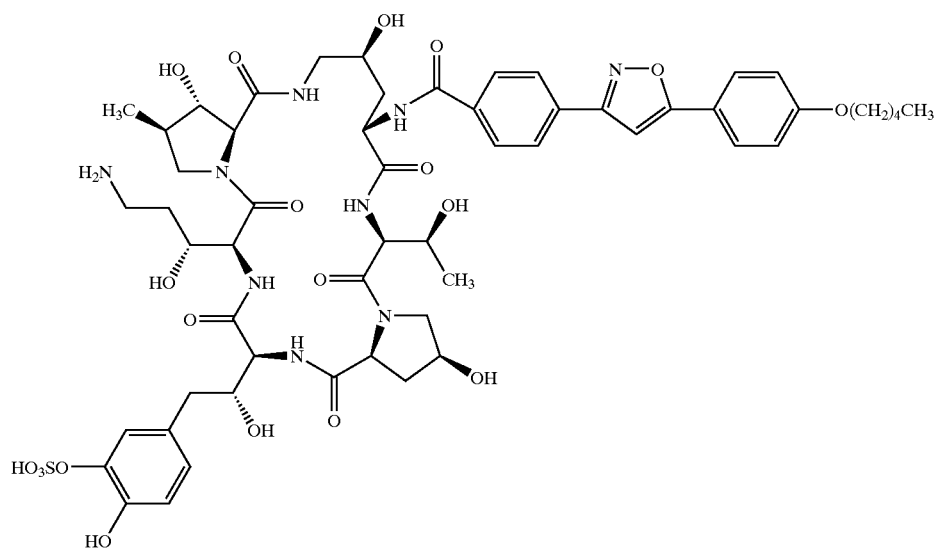 |

| Example No. | Formula |
|---|---|
| 182 | 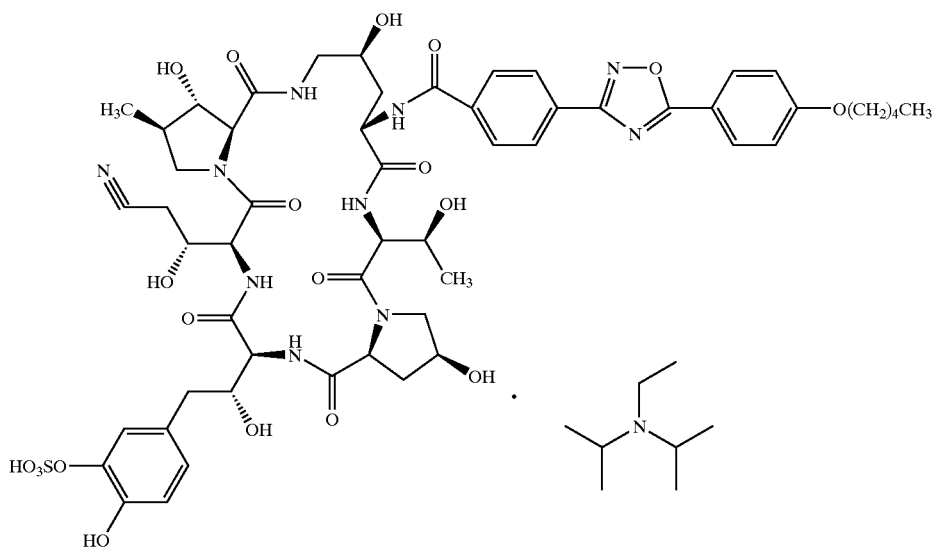 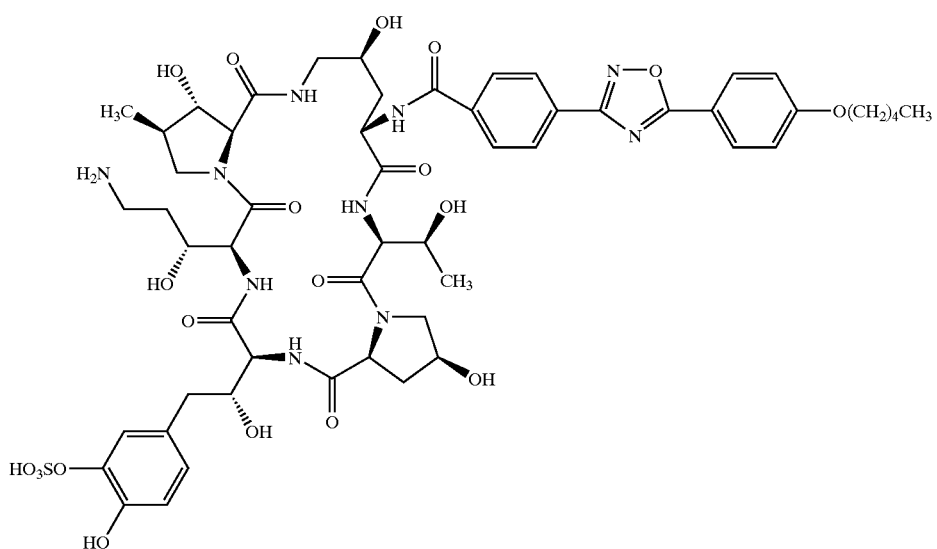 |

| Example No. | Formula |
|---|---|
| 183 | 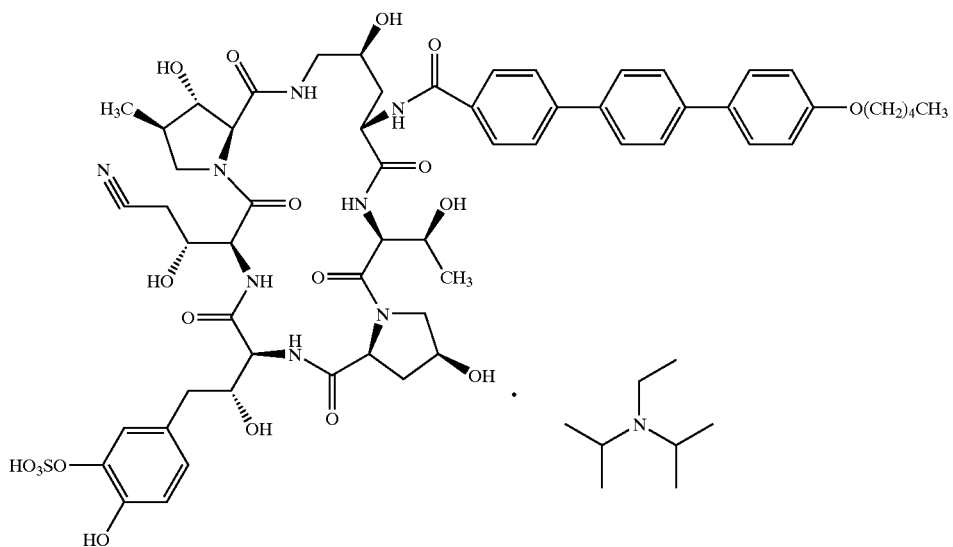 |
| | 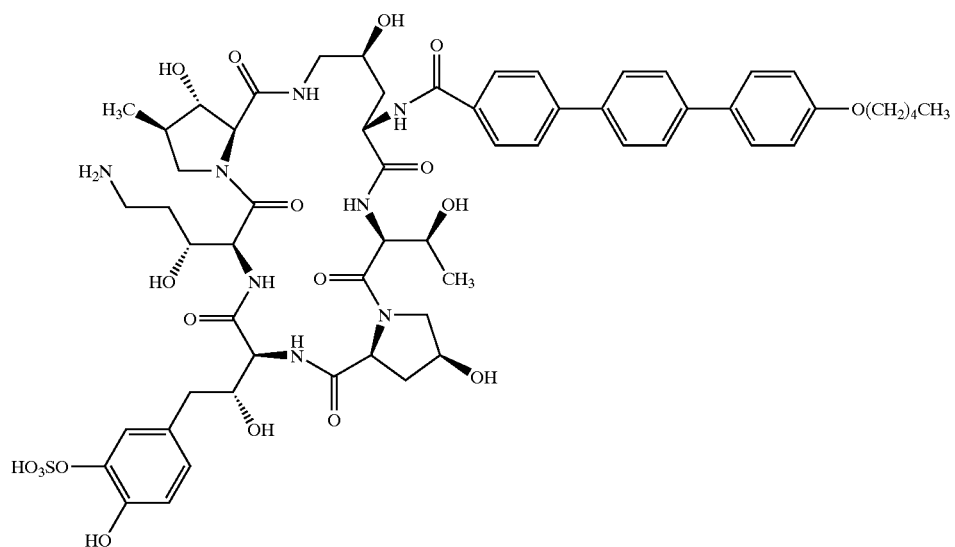 |

| Example No. | Formula |
|---|---|
| 184 | 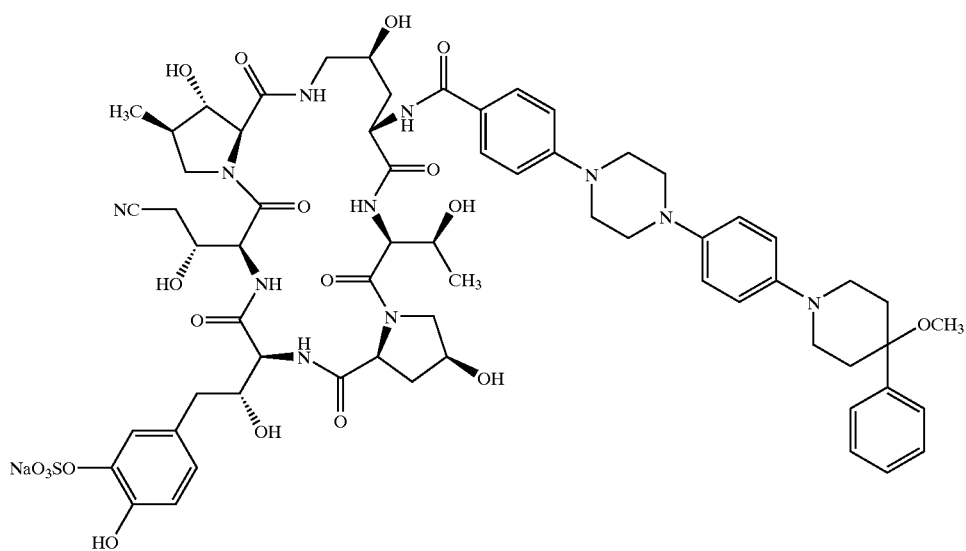 |
| | 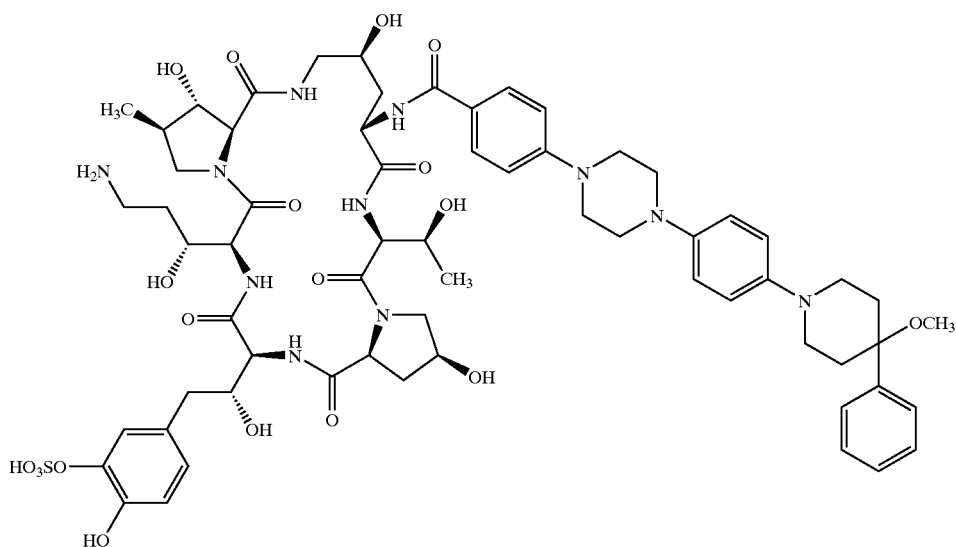 |

| Example No. | Formula |
|---|---|
| 185 | 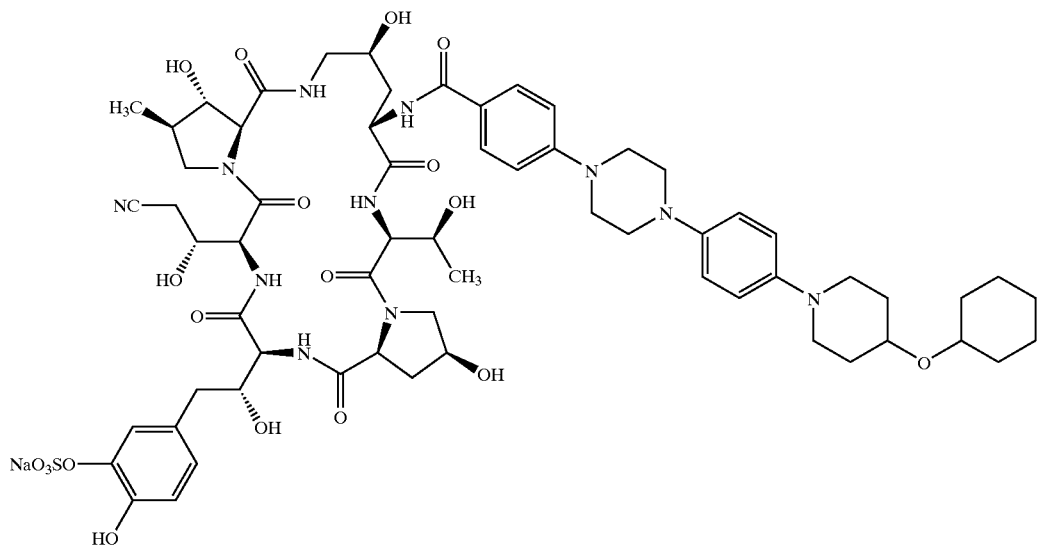 |
| | 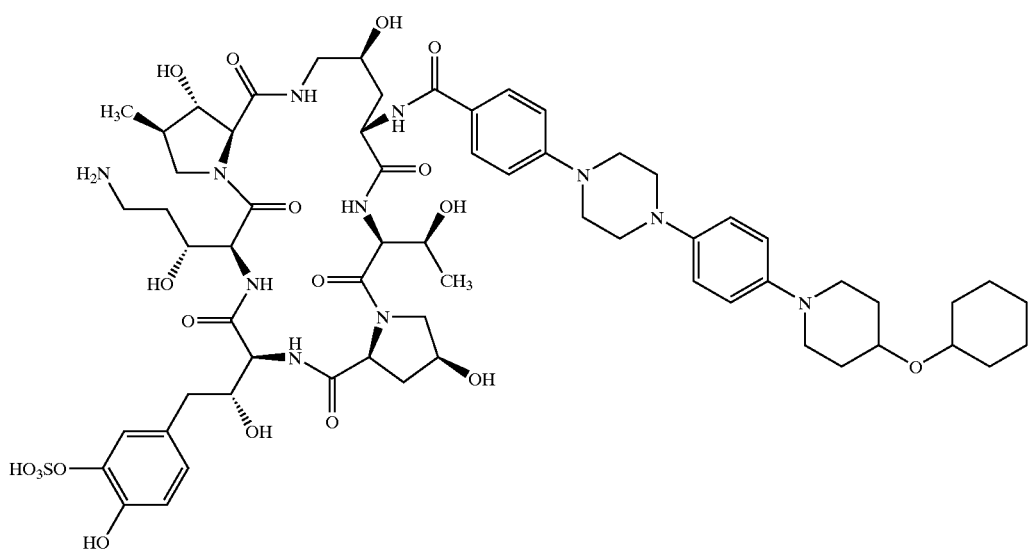 |

| Example No. | Formula |
|---|---|
| 186 | 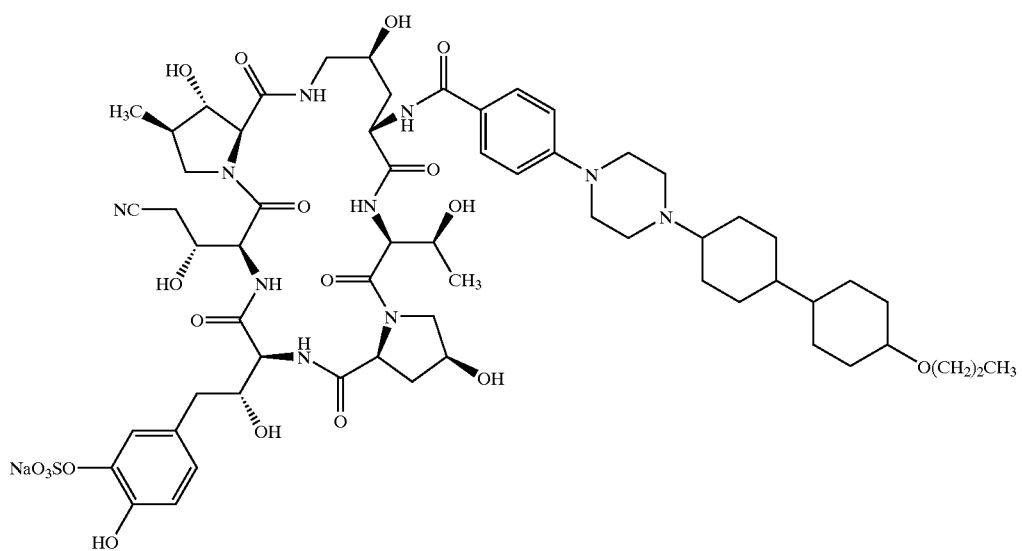 |
| | 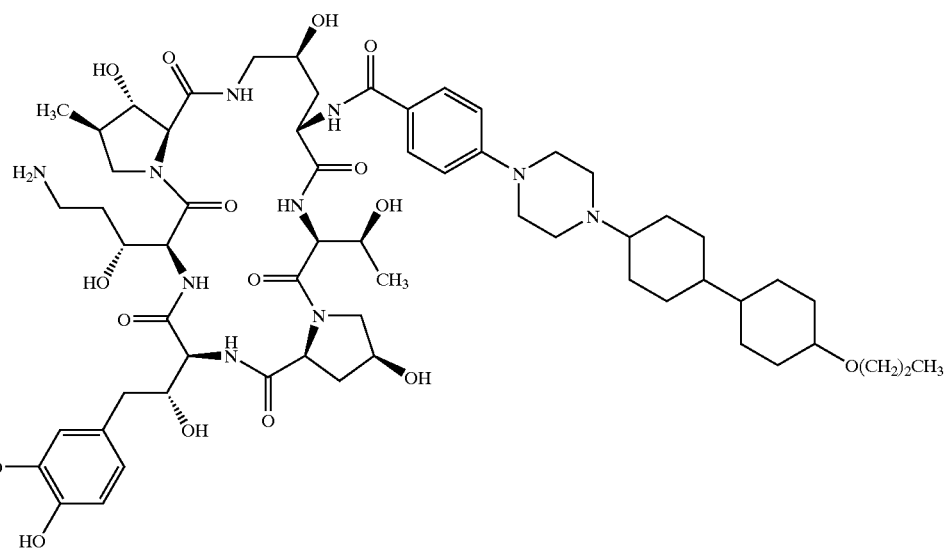 |

| Example No. | Formula |
|---|---|
| 187 | 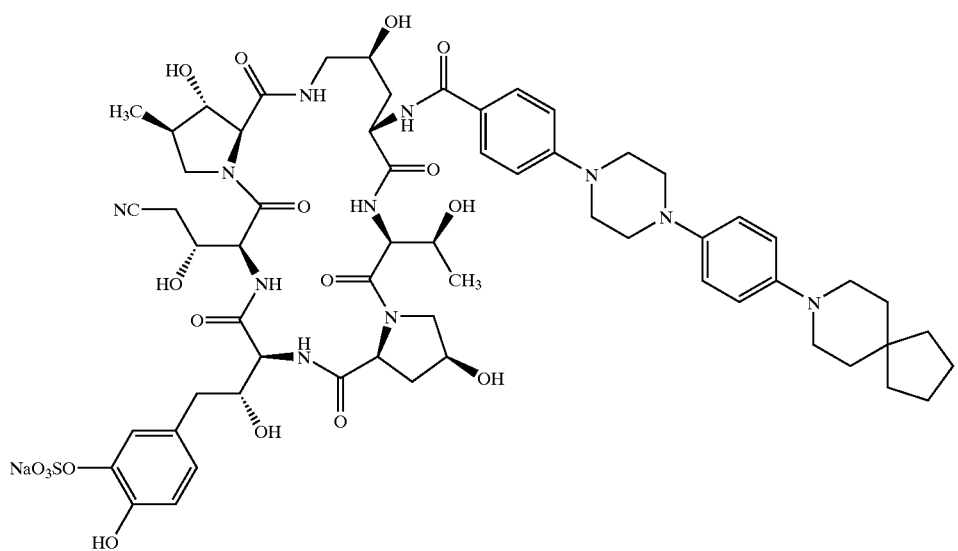 |
| | 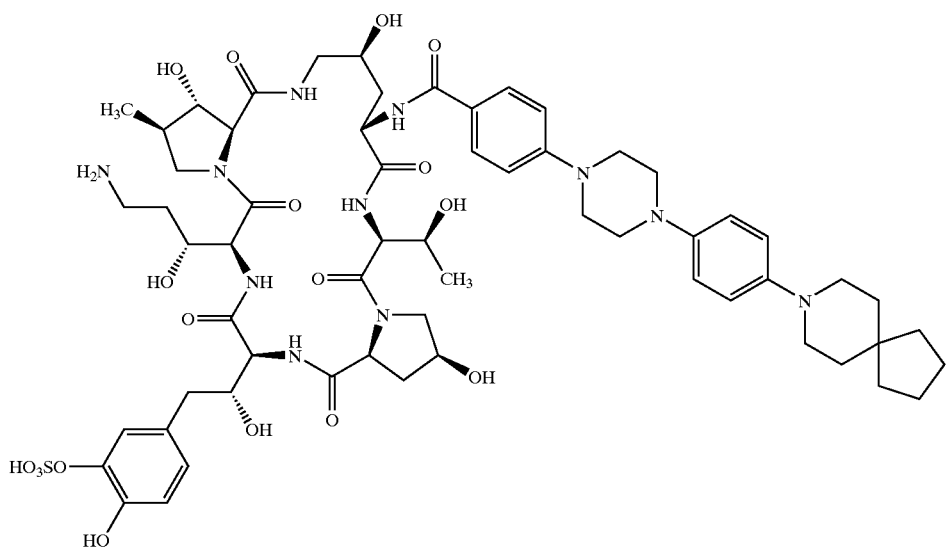 |

-continued
| Example No. | Formula |
|---|---|
| 188 | 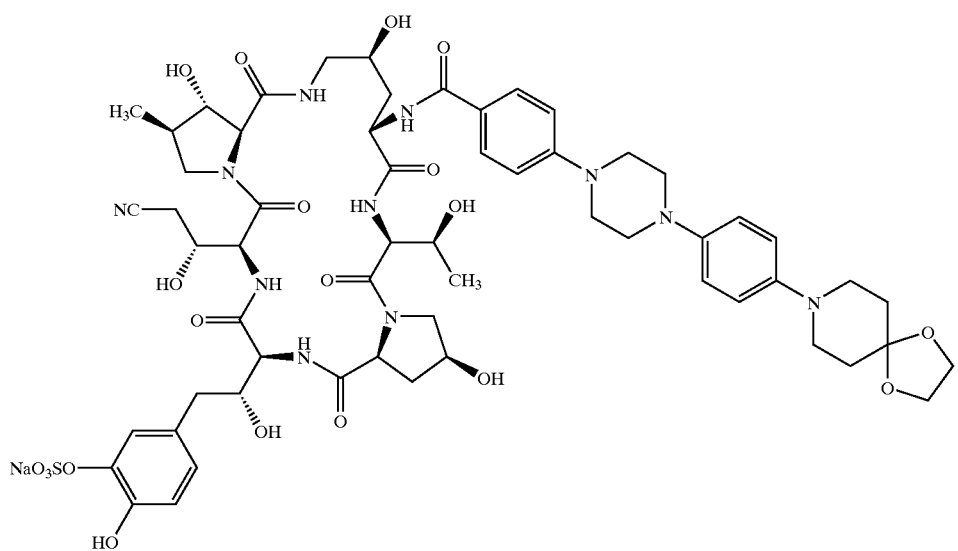 |
| | 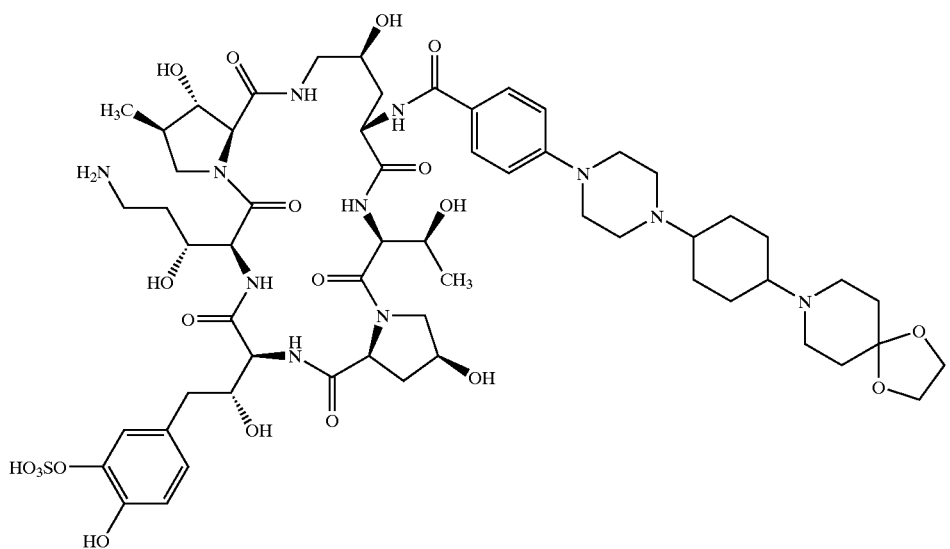 |

-continued
| Example No. | Formula |
|---|---|
| 189 | 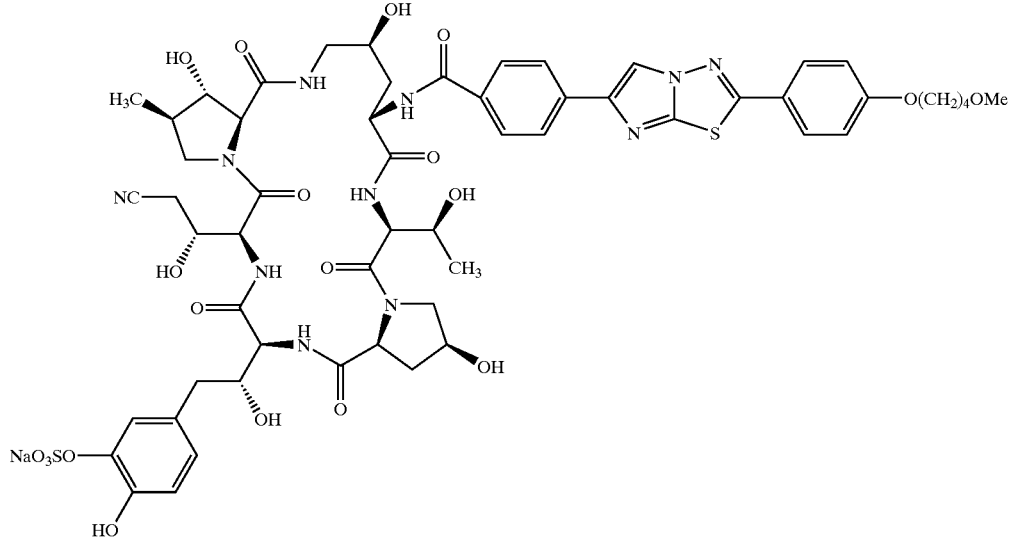<br>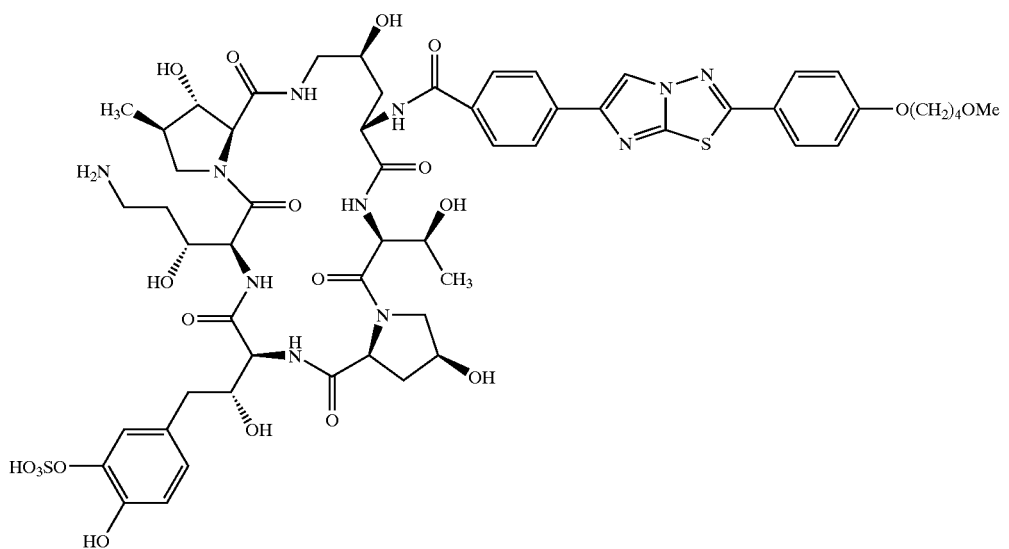 |

-continued
| Example No. | Formula |
|---|---|
| 190 | 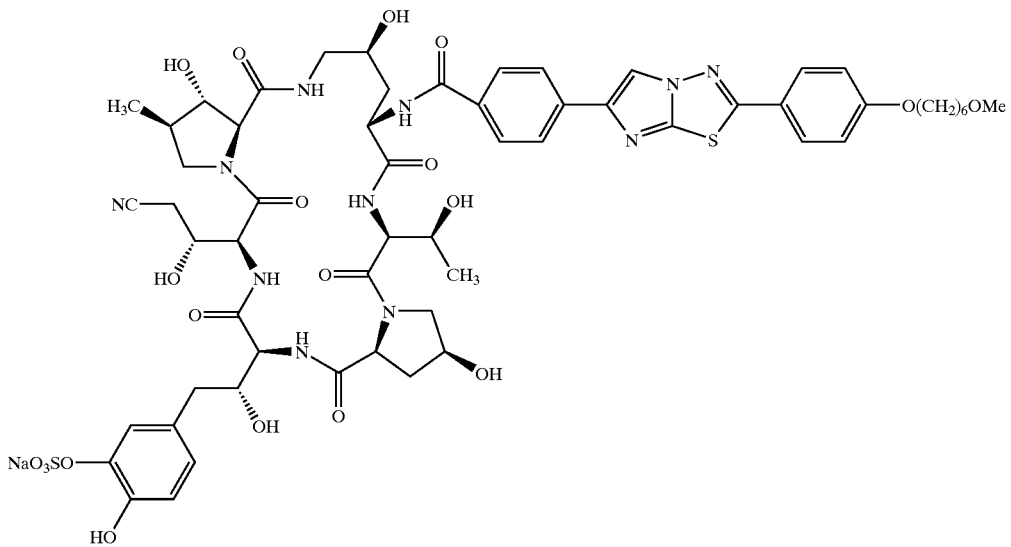 |
| | 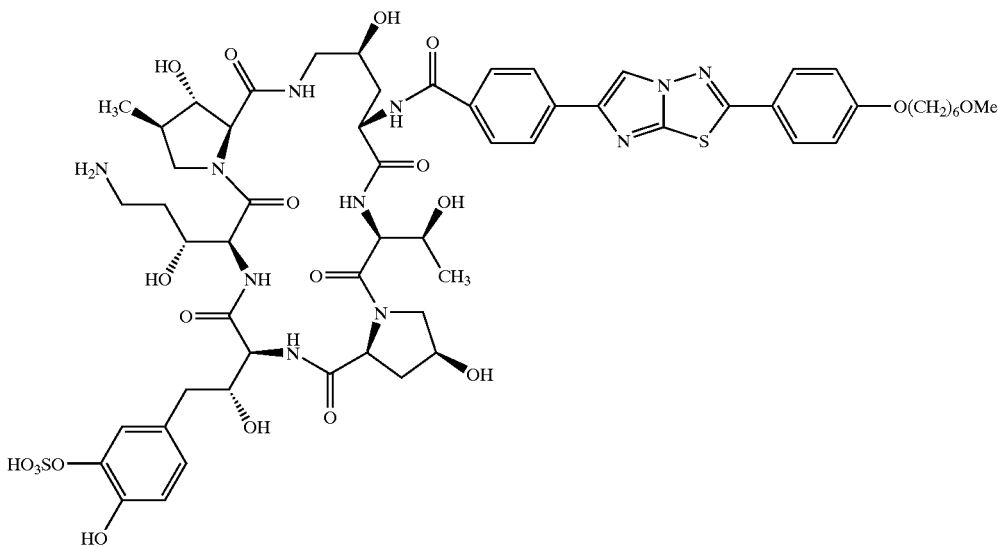 |

-continued
| Example No. | Formula |
|---|---|
| 191 | 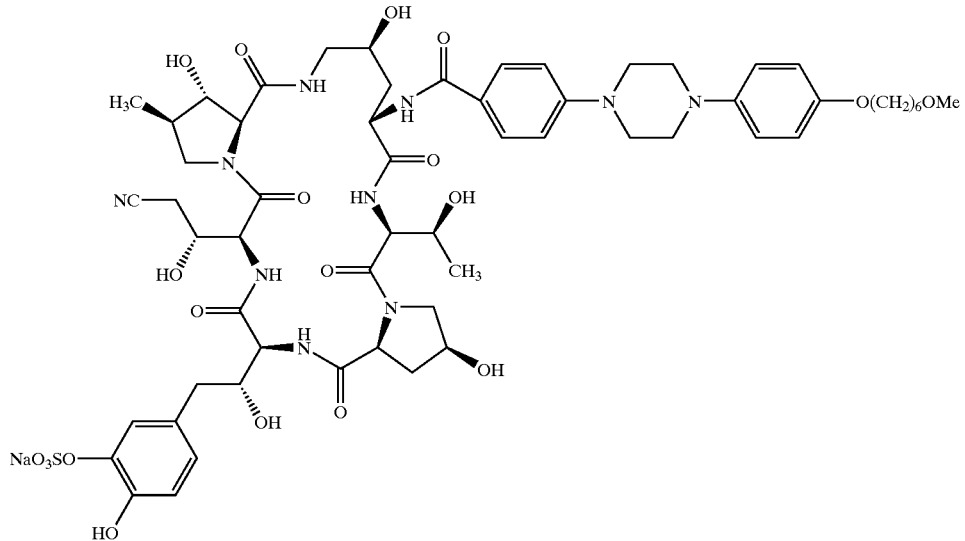 |
| | 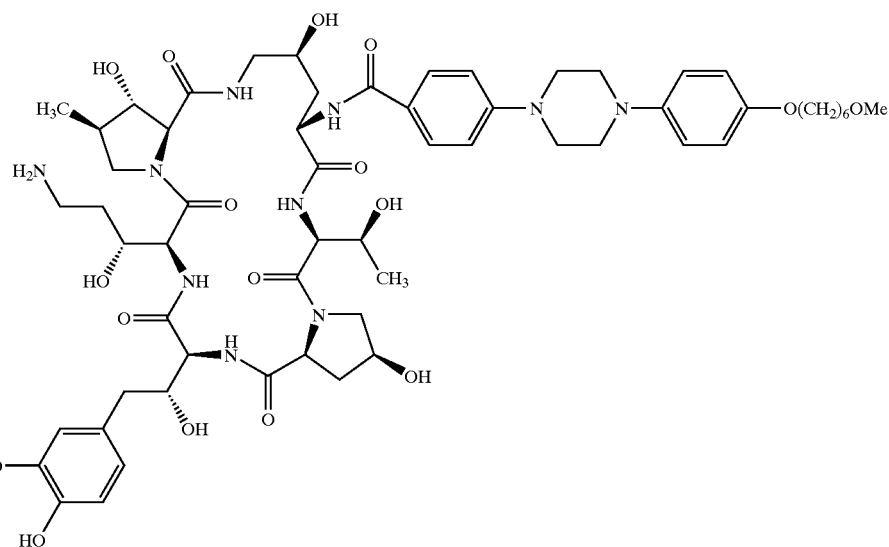 |

| Example No. | Formula |
|---|---|
| 192 | 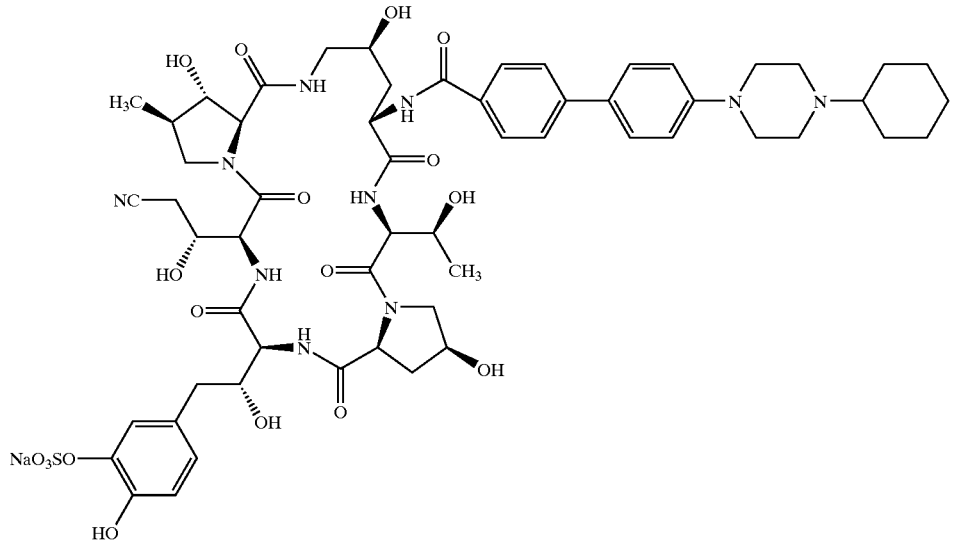 |
| | 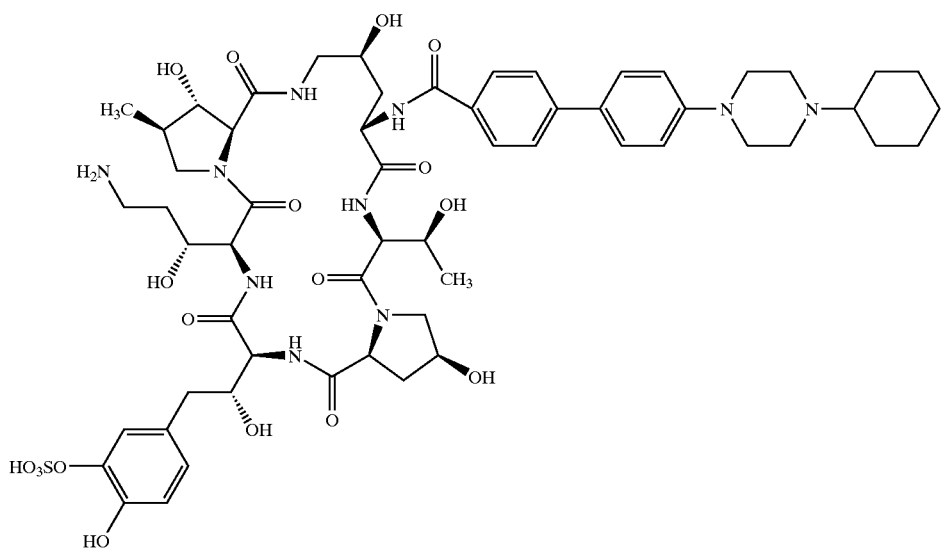 |

-continued
| Example No. | Formula |
|---|---|
| 193 | 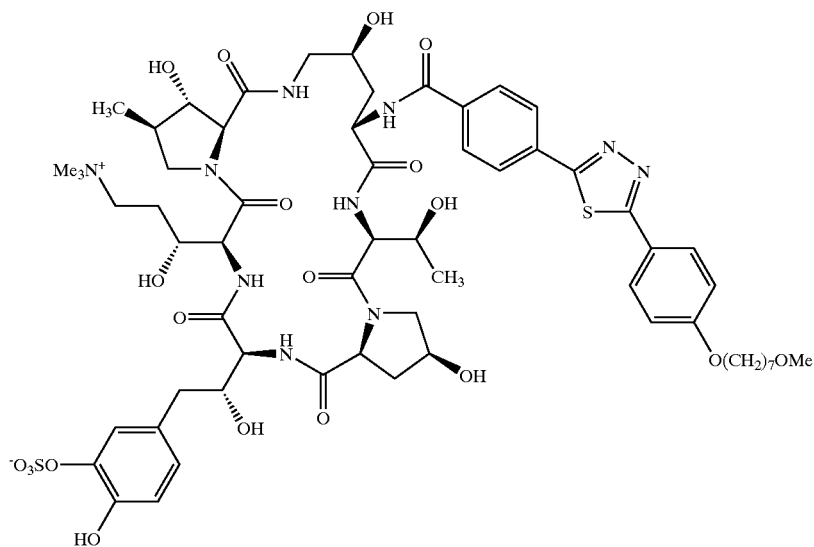 |
| | 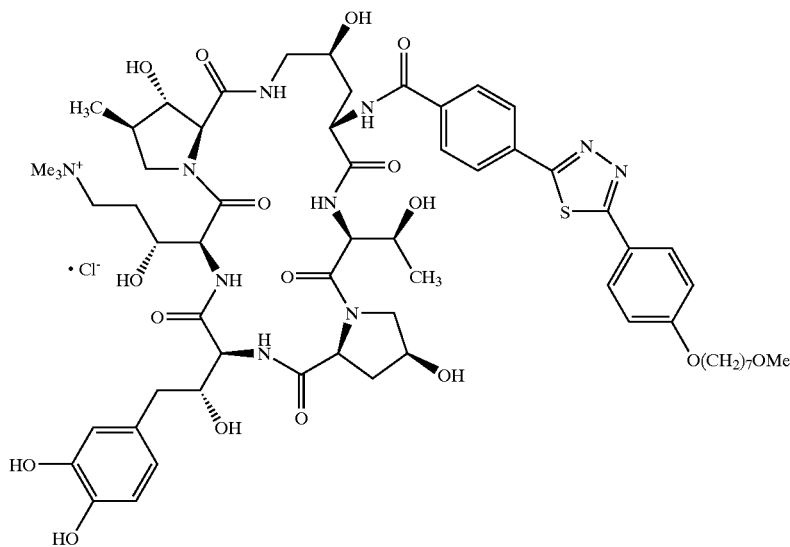 |

-continued
| Example No. | Formula |
|---|---|
| 194 | 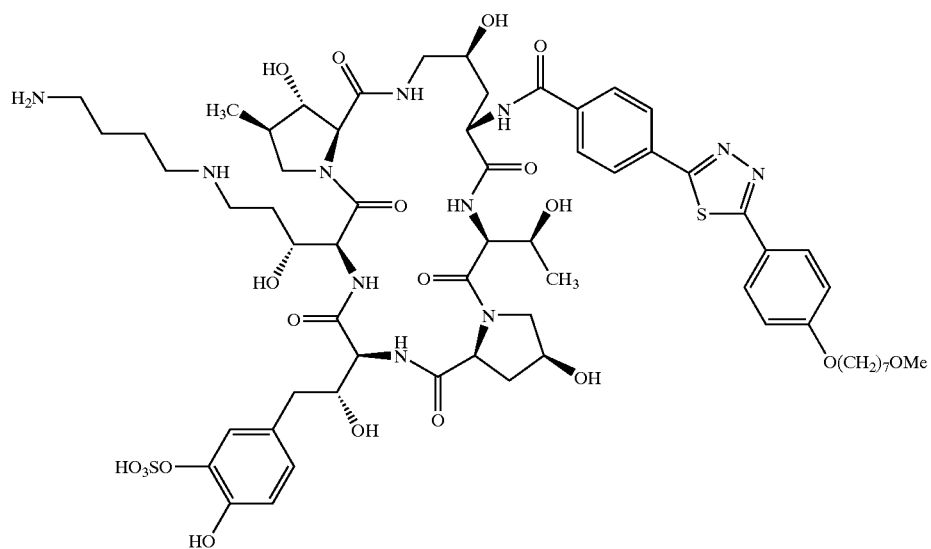<br>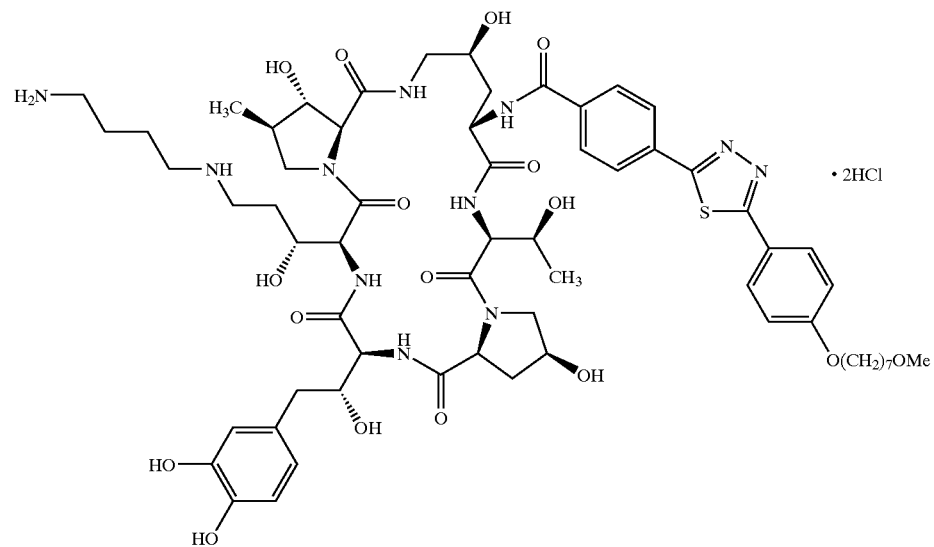 |

-continued
| Example No. | Formula |
|---|---|
| 195 | 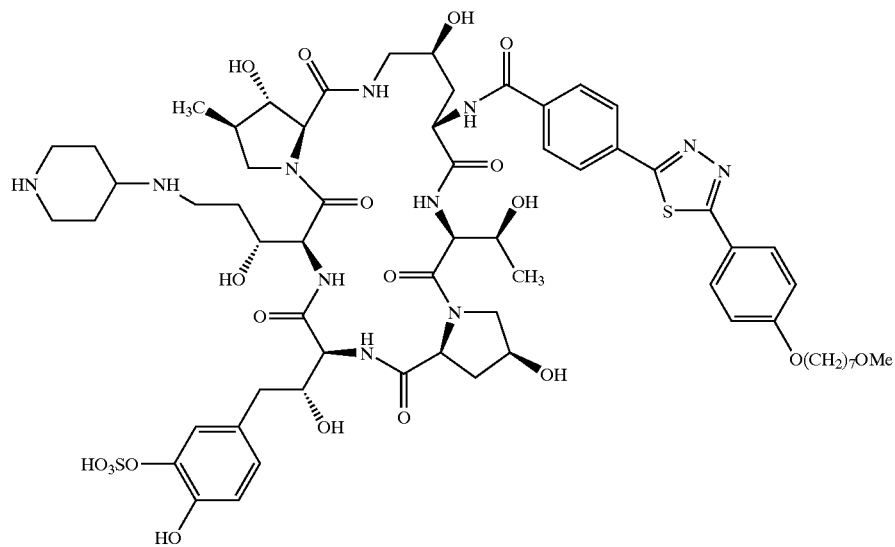 |
| | 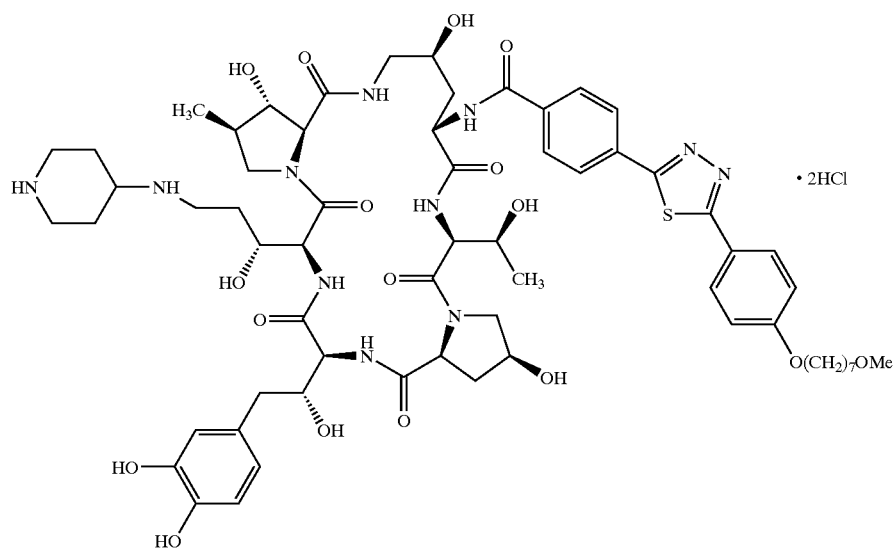 |

| Example No. | Formula |
|---|---|
| 196 | 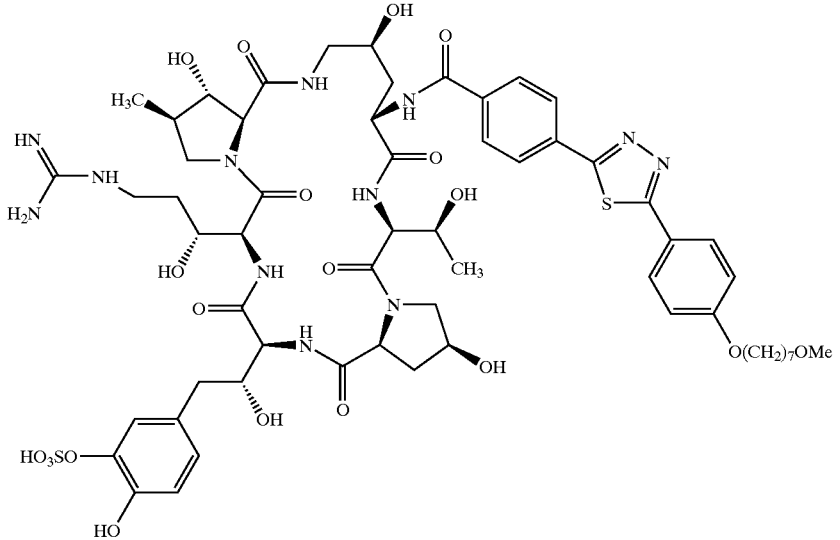 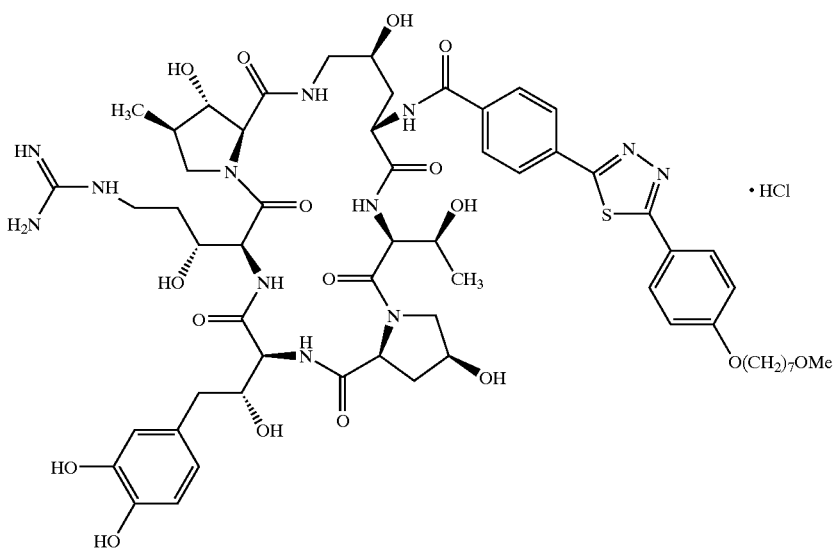 |

-continued
| Example No. | Formula |
|---|---|
| 197 | 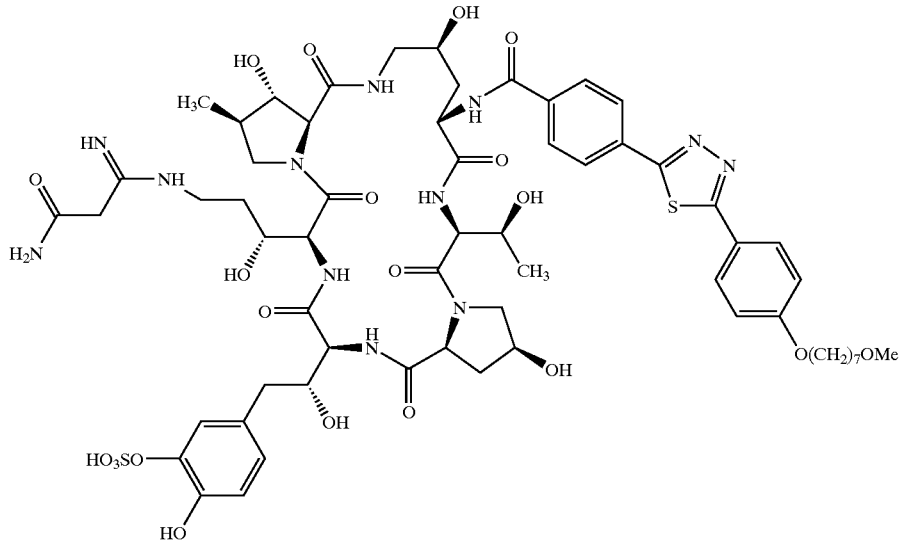<br>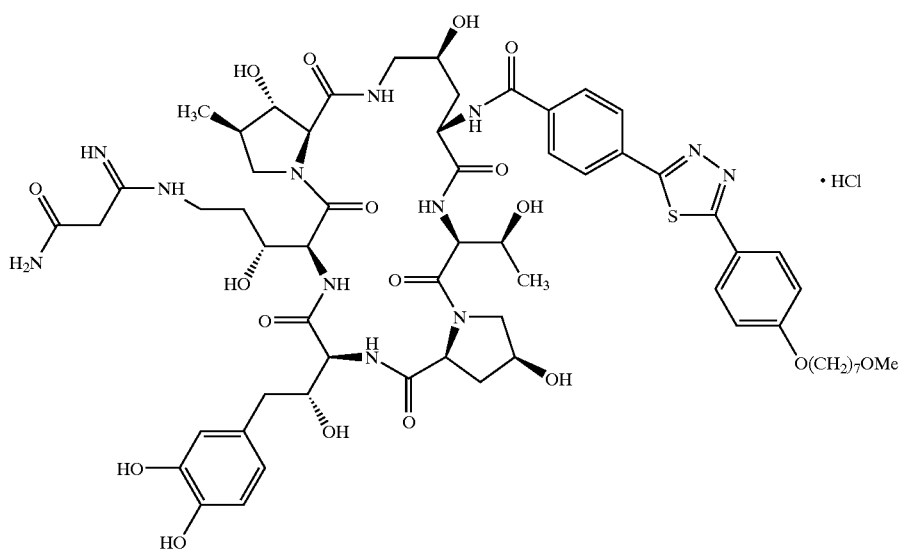 |

-continued
| Example No. | Formula |
|---|---|
| 198 | 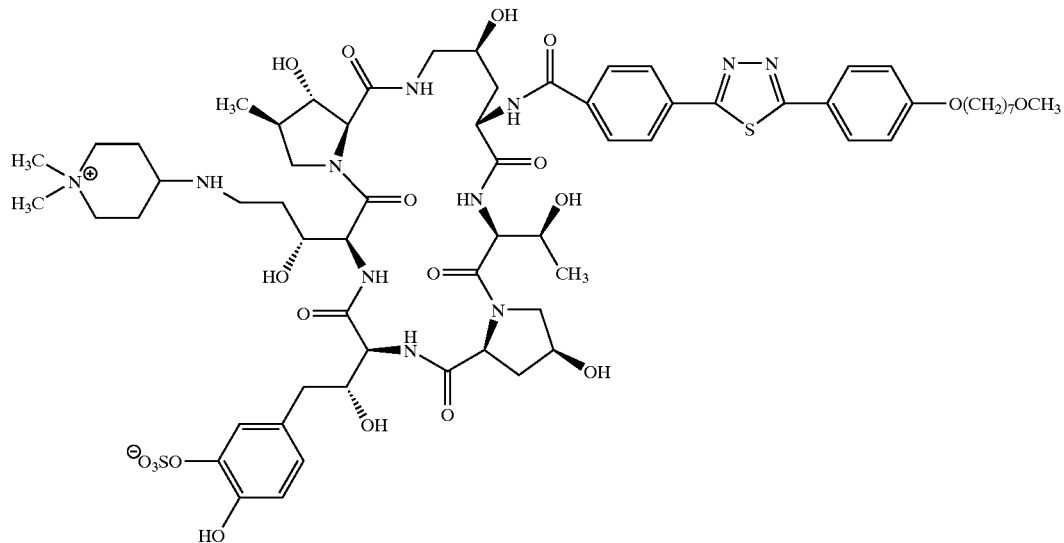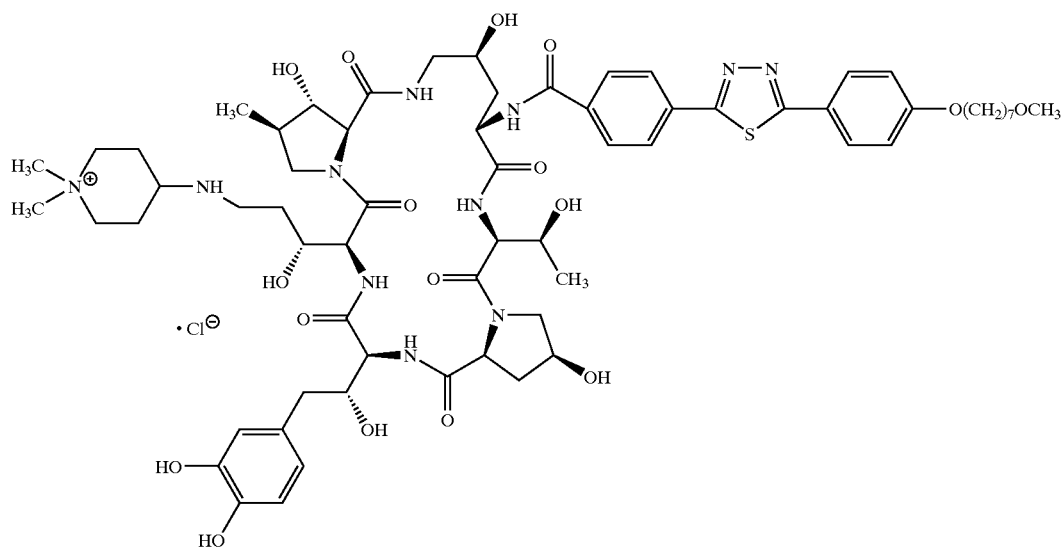 |

-continued
| Example No. | Formula |
|---|---|
| 199 | 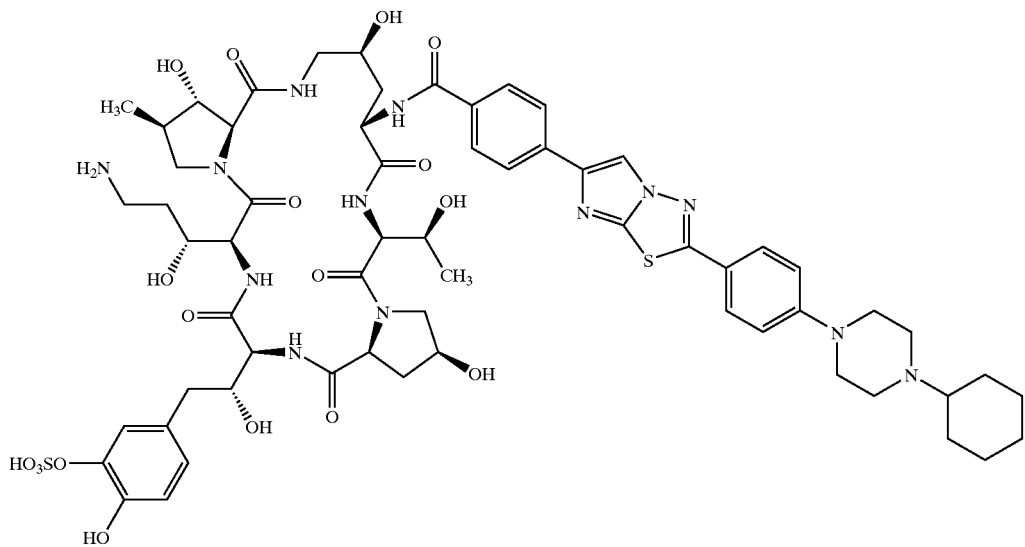<br>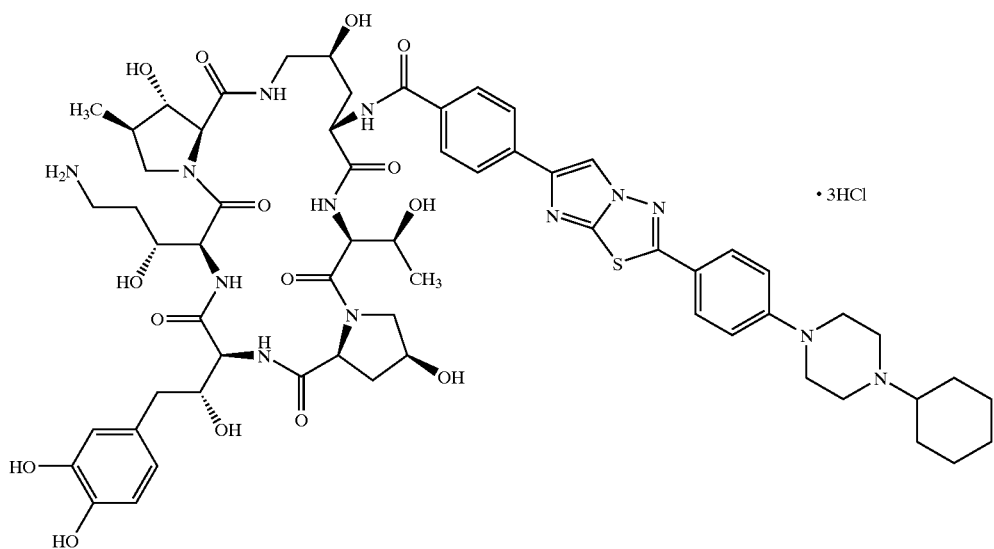 • 3HCl |

-continued
| Example No. | Formula |
|---|---|
| 200 | 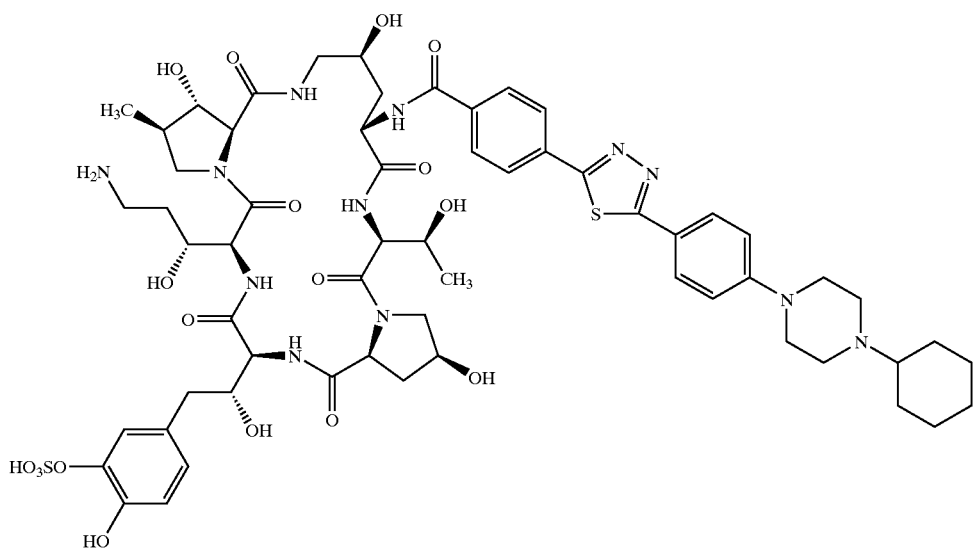 |
| | 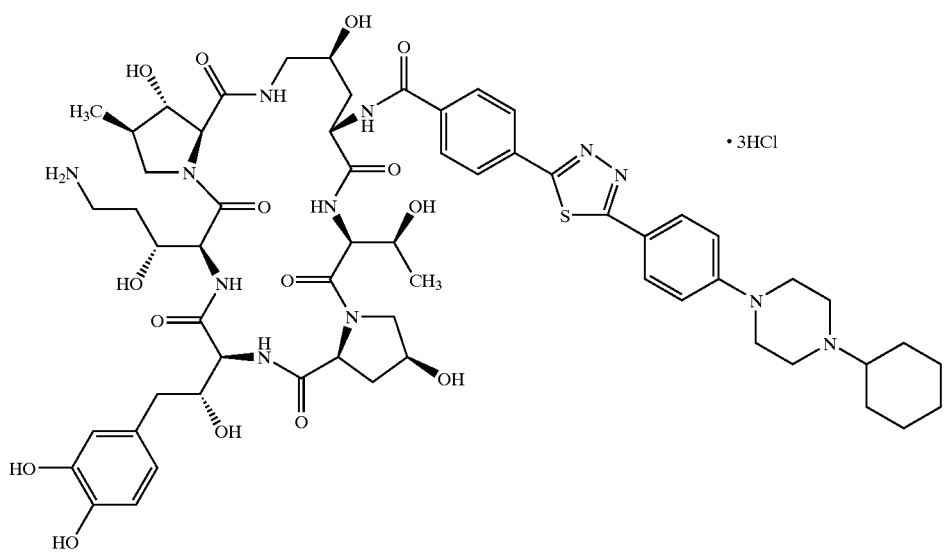 • 3HCl |

-continued
| Example No. | Formula |
|---|---|
| 201 | 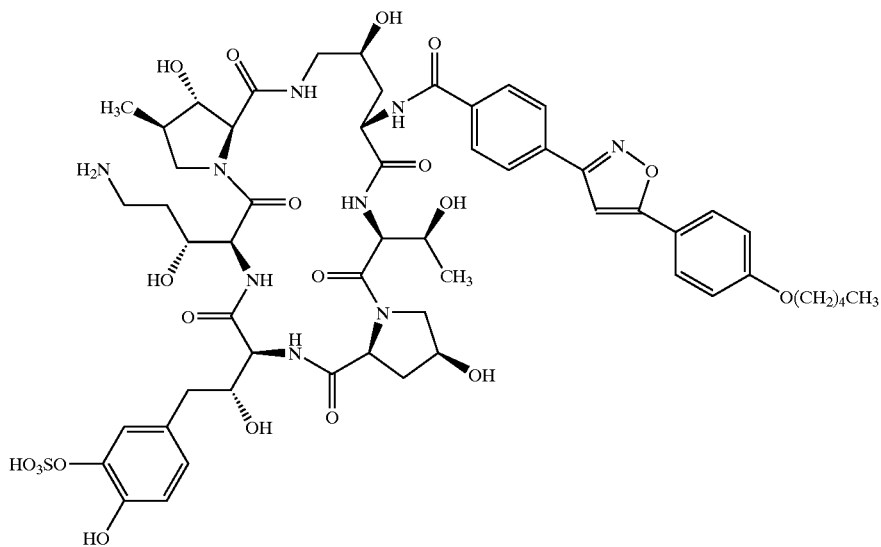 |
| | 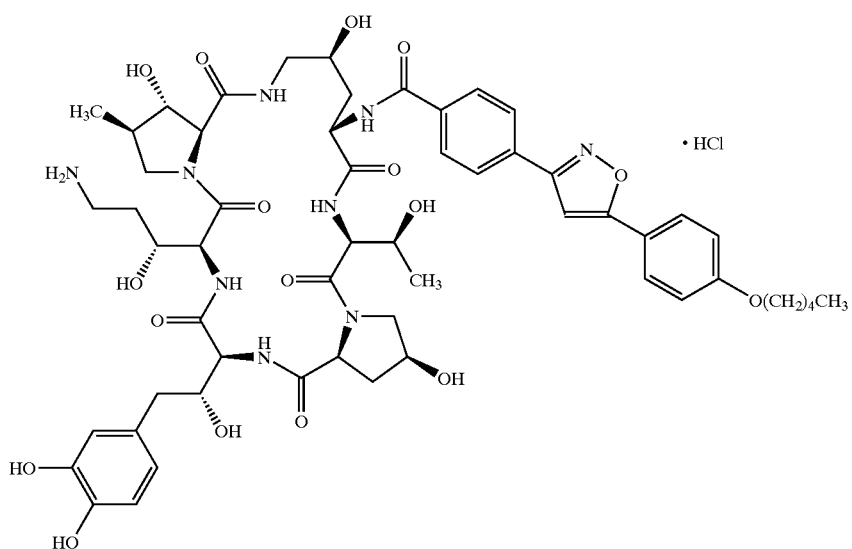 |

-continued
| Example No. | Formula |
| --- | --- |
| 202 | 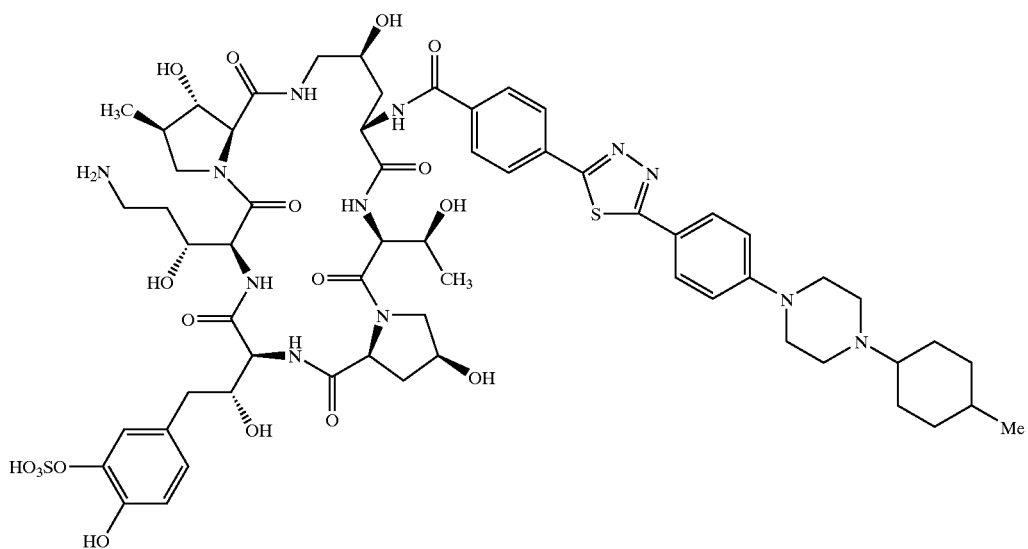<br>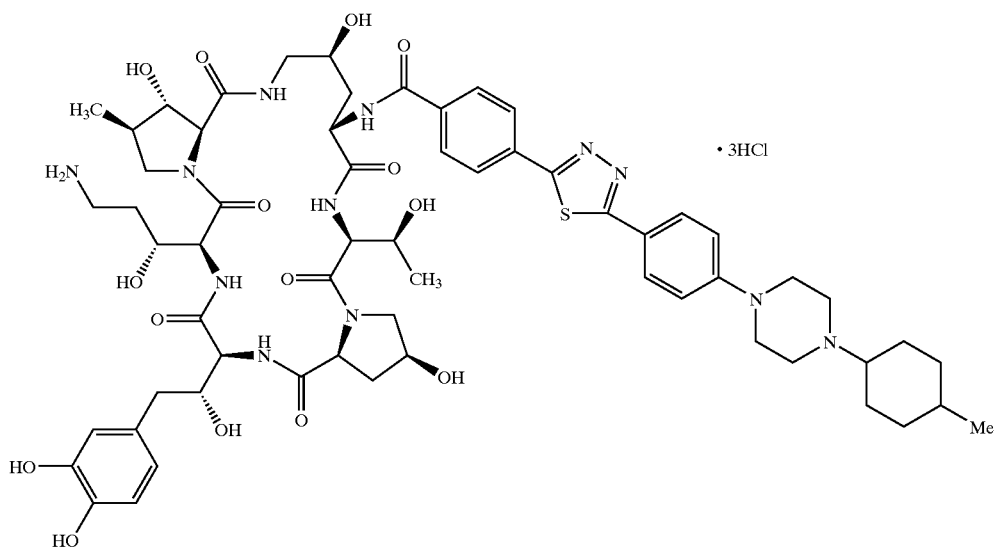 |

-continued
| Example No. | Formula |
|---|---|
| 203 | 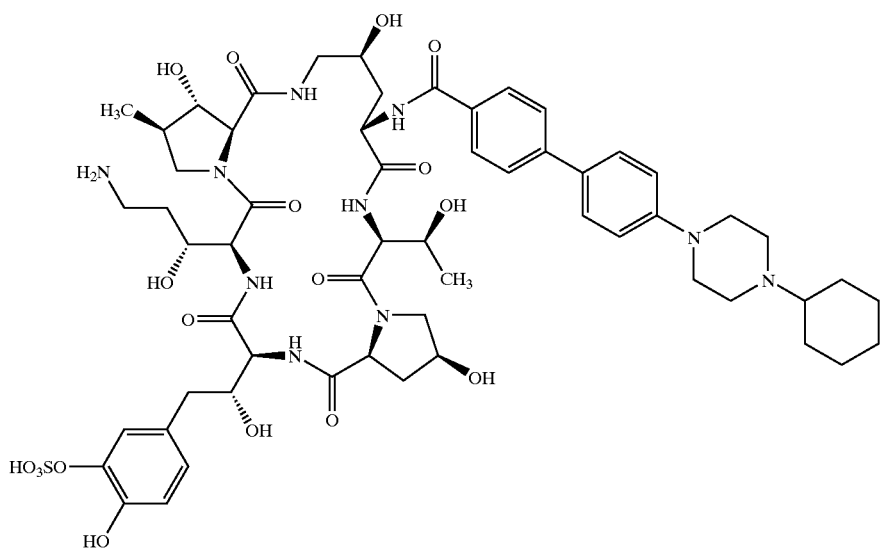 |
| | 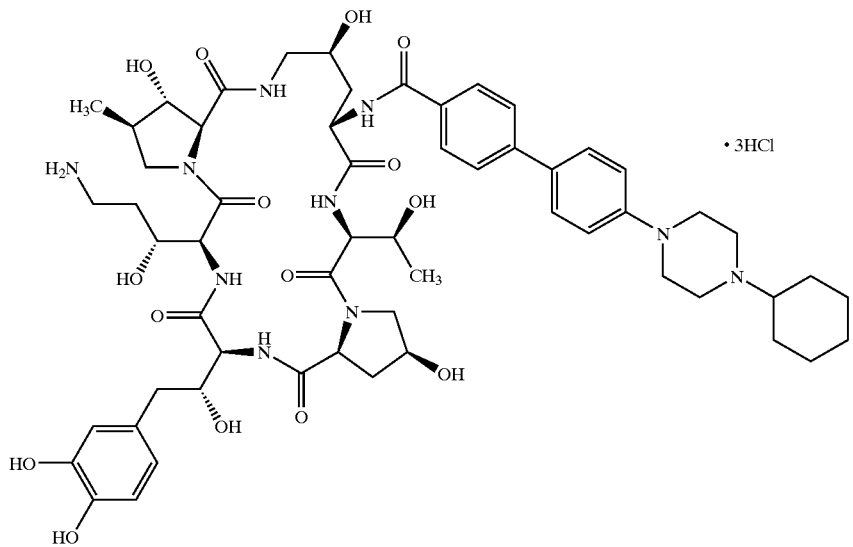 |

-continued
| Example No. | Formula |
|---|---|
| 204 | 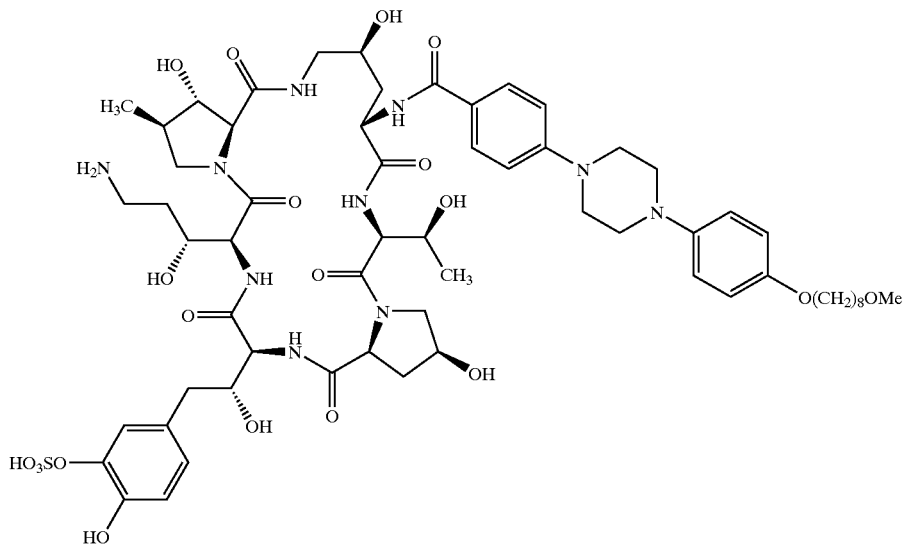 |
| | 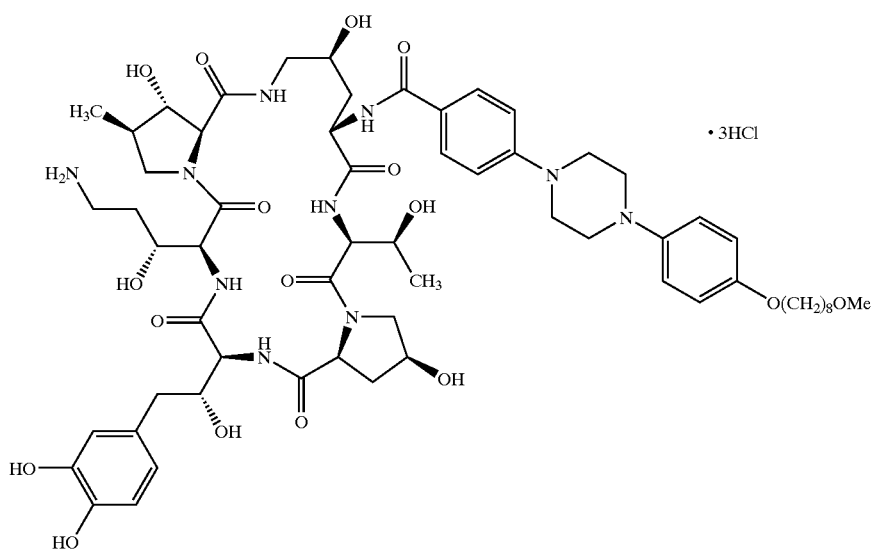 |

-continued
| Example No. | Formula |
|---|---|
| 205 | 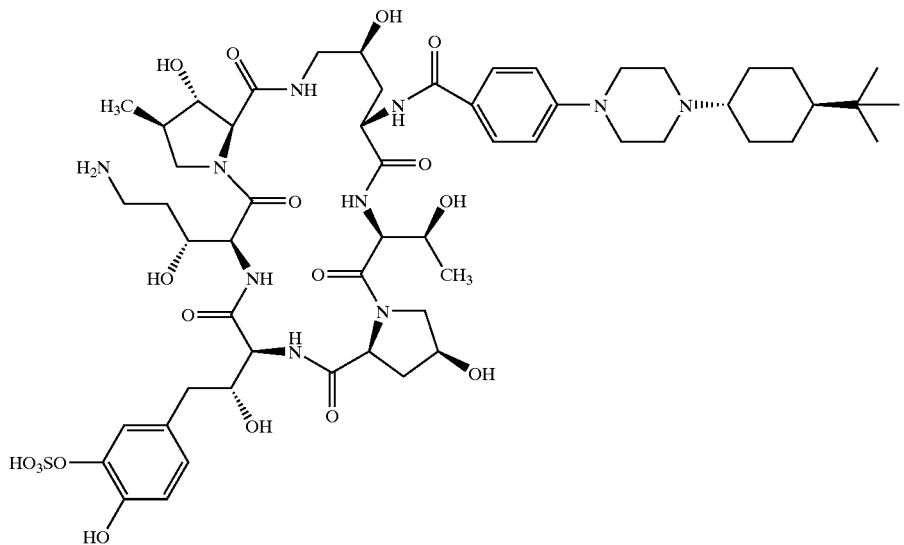<br>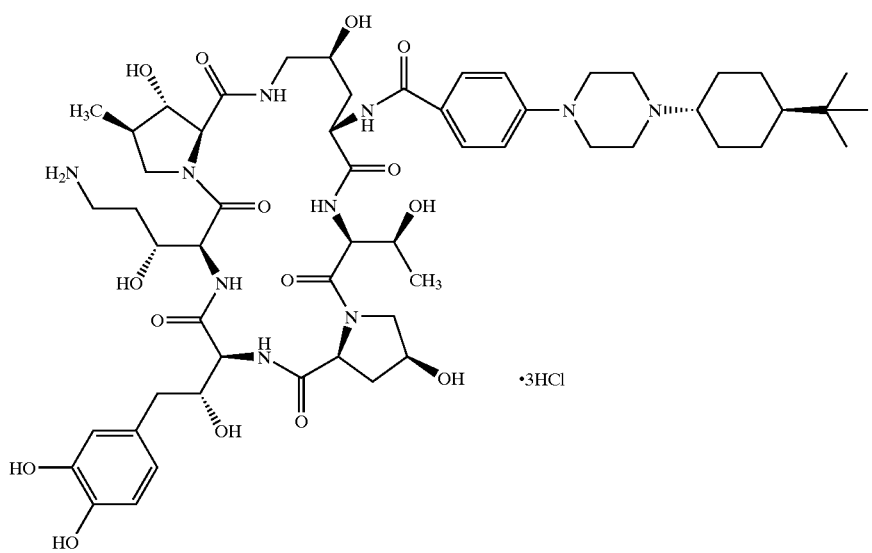 ·3HCl |

-continued

| Example No. | Formula |
|---|---|
| 206 | 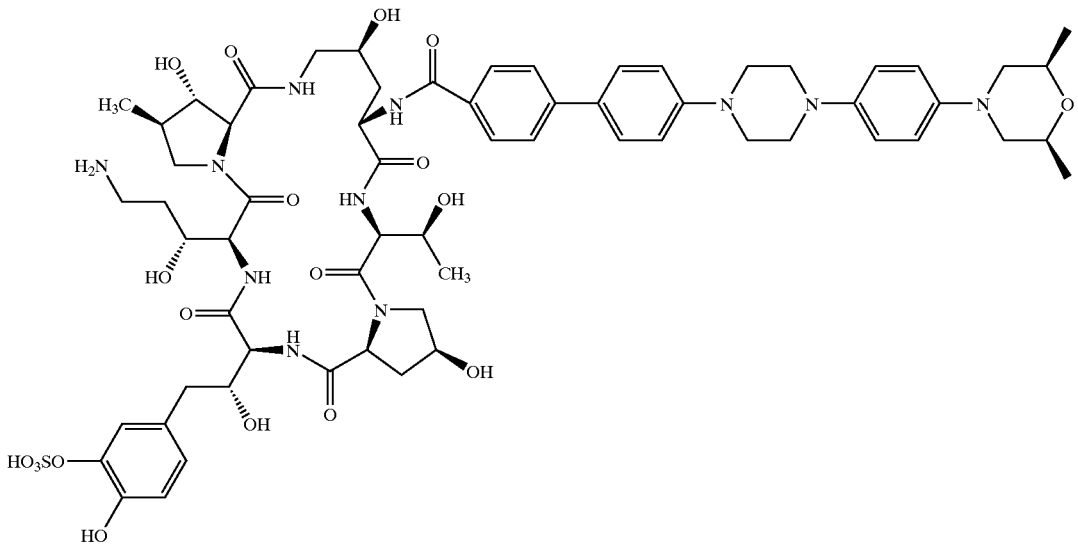<br>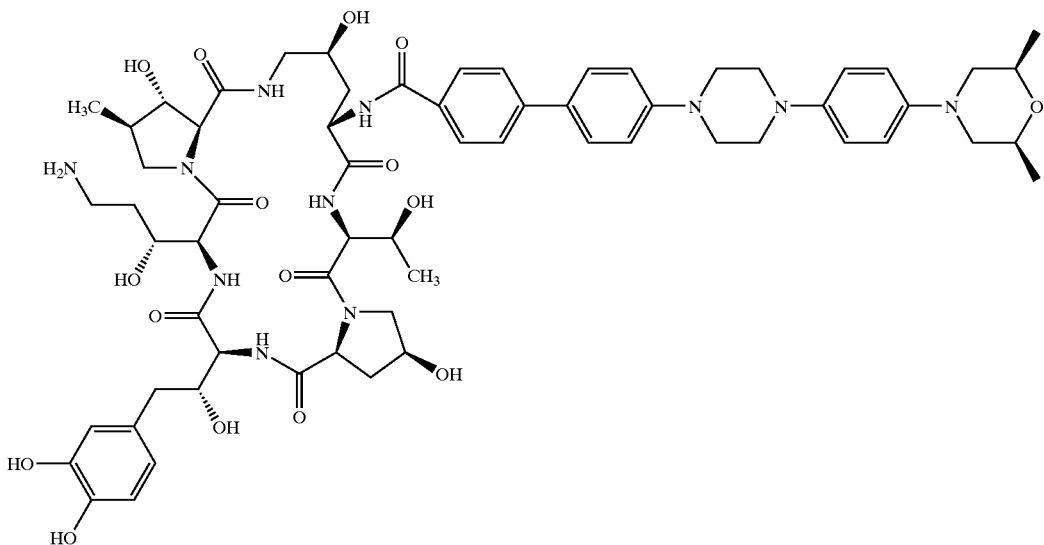 |

EXAMPLE 22

A solution of starting compound (22) (670 mg) and 10% palladium on carbon (50%, including water) (0.8 g) in a mixture of methanol (10 ml) and water (10 ml) was hydrogenated under an atmospheric pressure of hydrogen with stirring at ambient temperature for 12 hours. The catalyst was filtered off and washed with a mixture of methanol and water (1:1 v/v) (50 ml), and the filtrate and washes were combined. To the solution was added dropwise allyloxycarbonyl chloride (3.0 ml) adjusting pH to 8.5–10.0 with 1N sodium hydroxide with stirring on an ice-bath. The mixture was stirred at the same temperature for 2 hours and concentrated in vacuo. The resulting residue was dissolved in 1N sodium hydroxide (20 ml) and allowed to stand at 4° C. overnight. The solution was subjected to column chromatography on ODS (Daiso-gel, SP-120-40/60-ODS-B (Trademark: prepared by Daiso Co., Ltd.)) (100 ml) eluting with 10% acetonitrile in water. The fractions containing the object compound were collected and evaporated under reduced pressure to remove acetonitrile. The residue was lyophilized to give object compound (22) (379 mg).

NMR (DMSO-$d_6$+$D_2O$, δ): 0.96 (3H, d, J=6.73 Hz), 1.07 (3H, broad s), 1.36 (9H, s), 1.40–2.40 (8H, m), 2.70–3.45 (5H, m), 2.01 (3H, d, J=4.26 Hz), 3.21 (3H, s), 3.31 (4H, t, J=6.34 Hz), 3.70–4.50 (14H, m), 4.85–4.90 (2H, m), 3.60–4.95 (18H, m), 6.69 (1H, d, J=8.25 Hz), 6.75 (1H, d, J=9.54 Hz), 6.98 (1H, s).

ESI MASS (m/z) (Negative): 1135.3 ($M^+$+Na).

EXAMPLE 23

To a solution of starting compound (23) (1.0 g) in DMF (10 ml) were added 2-(tert-butoxycarbonyloxyimino)-2-phenylacetonitrile (0.30 g) and diisopropylethylamine (0.27 ml) with stirring at ambient temperature, and the mixture was stirred at the same temperature for 2 hours. To the reaction mixture was added pH 6.86 standard buffer solution (100 ml), and the solution was subjected to column chromatography on ODS (Daiso-gel, SP-120-40/60-ODS-B (Trademark: prepared by Daiso Co., Ltd.)) (100 ml) eluting with 20% acetonitrile in water. The fractions containing the object compound were collected and evaporated under reduced pressure to remove acetonitrile. The residue was lyophilized to give object compound (23) (302 mg).

IR (KBr): 1668, 1633, 1516, 1441, 1277, 1252 cm$^{-1}$.

NMR (DMSO-d$_6$+D$_2$O, δ): 0.97 (3H, d, J=6.64 Hz), 1.07 (3H, d, J=5.96 Hz), 1.37 (9H, s), 1.40–2.00 (4H, m), 2.10–2.50 (4H, m), 2.60–3.40 (6H, m), 3.60–4.50 (10H, m), 4.65–4.85 (2H, m), 6.71 (1H, d, J=8.14 Hz), 6.78 (1H, d, J=8.39 Hz), 6.98 (1H, s).

ESI MASS (m/z) (Negative): 989.3 (M$^+$−1).

Elemental Analysis Calcd. for C$_{40}$H$_{62}$N$_8$O$_{19}$S.5H$_2$O: C, 44.44, H, 6.71, N, 10.36. Found: C, 44.23, H, 6.42, N, 9.82.

EXAMPLE 24

A solution of starting compound (24) (211 mg), 1-methylpyrazole-4-carboxaldehyde (21.4 mg), acetic acid (29.2 mg) and sodium cyanoborohydride (13.3 mg) in 1:1 methanol-N,N-dimethylformamide (6 ml) was stirred 2 days at room temperature, then treated with ethyl acetate and the precipitate was collected, washed with ethyl acetate and dried. This crude material was dissolved in N,N-dimethylformamide (3 ml), then treated with diisopropylethylamine (42 mg) and 1,1'-carbonyldiimidazole (34.2 mg). After 2 hours at room temperature, further diisopropylethylamine (42 mg) and 1,1'-carbonyldiimidazole (34.2 mg) were added. After 4 hours, the solution was diluted with pH 6.86 standard buffer solution and the solution was subjected to ODS column chromatography eluting with acetonitrile in water mixtures. Fractions containing the object compounds were pooled, evaporated and lyophilized separately to afford major object compound (24) (60 mg) and minor object compound (24) (55 mg) as white amorphous powders.

Major Object Compound (24)

IR (KBr): 2935, 1658.5, 1635, 1444, 1259 cm$^{-1}$.

NMR (DMSO-d$_6$+D$_2$O, δ): 0.9–1.05 (6H, m), 1.23–5.00 (43H, m), 3.22 (3H, s), 3.33 (2H, t, J=6.6 Hz), 3.69 (3H, s), 6.76 (1H, d, J=7.7 Hz), 6.81–6.86 (1H, m), 7.07 (1H, br s), 7.15 (2H, d, J=9 Hz), 7.43 (1H, s), 7.68 (1H, s), 7.94–8.19 (6H, m).

MASS (m/z): 1417.4 (M$^+$−Na).

Elemental Analysis Calcd. for C$_{64}$H$_{81}$N$_{12}$O$_{21}$S$_2$Na.5H$_2$O: C, 50.19, H, 5.99, N, 10.97. Found: C, 50.16, H, 6.06, N, 10.82.

Minor Object Compound (24)

IR (KBr): 2935, 2862, 1658.5, 1635, 1529, 1516, 1444, 1412, 1257 cm$^{-1}$.

NMR (DMSO-d$_6$+D$_2$O, δ): 0.98 (3H, d, J=6.3 Hz), 1.05 (3H, d, J=5.4 Hz), 1.2–4.9 (54H, complex m), 3.21 (3H, s), 3.31 (2H, t, J=6.4 Hz), 6.7–6.75 (2H, m), 7.05 (1H, br s), 7.14 (2H, d, J=8.8 Hz), 7.4–8.14 (8H, complex m).

MASS (m/z): 1486.5 (M$^+$).

Elemental Analysis Calcd. for C$_{68}$H$_{90}$N$_{14}$O$_{20}$S$_2$.6H$_2$O: C, 51.18, H, 6.44, N, 12.29. Found: C, 51.00, H, 6.31, N, 11.81.

EXAMPLE 25

To a solution of starting compound (25) (1.5 g) and (1,3-dioxy-2-oxo-4-cyclopenten-5-yl) methoxycarbonyloxysuccinimide (0.47 g) in dimethylformamide (15 ml) was added diisopropylethylamine (0.302 ml) and stirred for 5 hours at ambient temperature. The reaction mixture was pulverized with ethyl acetate. The precipitate was collected by filtration and dried under reduced pressure. The powder was added to pH 6.86 buffer and subjected to column chromatography on ODS (YMC-gel ODS-AM-S-50) (Trademark: prepared by Yamamura Chemical Lab.) and eluted with 5–15% acetonitrile aq. The fractions containing the object compound were combined and evaporated under reduced pressure to remove acetonitrile. The residue was lyophilized to give object compound (25) (1.05 g).

IR (KBr): 3350, 1816.6, 1635.3, 1257.4 cm$^{-1}$.

NMR (DMSO-d$_6$, δ): 0.96 (3H, d, J=6.6 Hz), 1.12 (3H, d, J=5.8 Hz), 1.2–2.6 (17H, m), 2.13 (3H, s), 2.8–3.4 (7H, m), 3.21 (3H, s), 3.6–5.3 (28H, m), 6.72 (1H, d, J=8.2 Hz), 6.78 (1H, d, J=8.2 Hz), 6.88 (1H, s), 7.13 (2H, d, J=8.6 Hz), 7.25–7.8 (4H, m), 7.93 (2H, d, J=8.6 Hz), 8.09 (4H, s), 8.73 (1H, s), 8.80 (1H, d, J=6.7 Hz).

ESI MASS (m/z): 1453 (M$^+$−Na).

Elemental Analysis Calcd. for C$_{64}$H$_{81}$N$_{10}$O$_{25}$S$_2$Na.5H$_2$O: C, 49.04, H, 5.85, N, 8.94. Found: C, 48.98, H, 5.75, N, 9.05.

EXAMPLE 26

To a solution of starting compound (26) (0.2 g) and 4-acetyloxymethoxycarbonyloxynitrobenzene (58.9 mg) in dimethylformamide (1.5 ml) was added diisopropylethylamine (0.04 ml) and stirred for 5 hours at ambient temperature. The reaction mixture was pulverized with ethyl acetate. The precipitate was collected by filtration and dried under reduced pressure. The powder was added to pH 6.86 buffer and subjected to column chromatography on ODS (YHC-gel ODS-AM-S-50) (Trademark: prepared by Yamamura Chemical Lab.) and eluted with 5–15% acetonitrile aq. The fractions containing the object compound were combined and evaporated under reduced pressure to remove acetonitrile. The residue was lyophilized to give object compound (26) (26 mg).

IR (KBr): 3365.2, 1751.0, 1727.9, 1635.3, 1259.3 cm$^{-1}$.

NMR (DMSO-d$_6$, δ): 0.96 (3H, d, J=6.6 Hz), 1.12 (3H, d, J=5.8 Hz), 1.2–2.6 (17H, m), 2.04 (3H, s), 2.8–3.4 (7H, m), 3.21 (3H, s), 3.6–5.3 (26H, m), 5.61 (2H, s), 6.70 (1H, d, J=8.2 Hz), 6.77 (1H, d, J=8.2 Hz), 6.96 (1H, s), 7.13 (2H, d, J=8.6 Hz), 7.25–7.8 (4H, m), 7.93 (2H, d, J=8.6 Hz), 8.09 (4H, s), 8.73 (1H, s), 8.80 (1H, d, J=6.7 Hz).

ESI MASS (m/z): 1413 (M$^+$−Na).

EXAMPLE 27

A solution of 4-piperidone hydrochloride hydrate (28.4 mg) and succinic anhydride (18.5 mg) in DMF (2 ml) was treated with diisopropylethylamine (23.9 mg) and aged for 3 hours at room temperature. To the resulting solution was added methanol (3 ml), DMF (1 ml), and after 30 minutes, acetic acid (27.7 mg), starting compound (31) (200 mg), and finally, sodium cyanoborohydride (12.6 mg). After 3 days at room temperature, ethyl acetate was added and the precipitate was collected, washed with ethyl acetate and dried. This solid was purified by ODS column chromatography (acetonitrile-water) to give object compound (27) (164 mg) as a white amorphous powder.

NMR (DMSO-d$_6$+D$_2$O, δ): 0.96 (3H, d, J=6.6 Hz), 1.12 (3H, d, J=5.6 Hz), 1.2–4.9 (54H, complex m), 3.21 (3H, s), 3.31 (2H, t, J=6.4 Hz), 6.7–6.8 (2H, m), 6.99 (1H, br s), 7.13 (2H, d, J=8.9 Hz), 7.97 (2H, d, J=8.9 Hz), 8.08 (4H, ABq, J=8.6 Hz, separation of inner lines=6.6 Hz).

MASS (m/z): 1528.3 (M$^+$+Na).

Elemental Analysis Calcd. for C$_{67}$H$_{90}$N$_{11}$O$_{23}$S$_2$Na.8H$_2$O: C, 48.81, H, 6.48, N, 9.34. Found: C, 48.84, H, 6.46, N, 9.29.

EXAMPLE 28

To a solution of the starting compound (28) (200 mg) and molecular sieves (4A) (200 mg) in N,N-dimethylformamide (4 ml) was added methyl iodide (1 ml), and stirred for 4 days at ambient temperature. The reaction mixture was filtrated, and the filtrate was diluted in water, and subjected to column chromatography on ODS (YMC-gel-ODS-AM-S-50 (Trademark: prepared by Yamamura Chemical Lab.)) eluting with 20% acetonitrile aqueous solution. The fractions containing the object compound were combined and evaporated under reduced pressure to remove acetonitrile. The residue was lyophilized to give the object compound (28) (46 mg).

IR (KBr): 3355, 2935, 1664, 1627, 1446, 1405, 1375, 1257, 1178, 1083, 1047 cm$^{-1}$.

NMR (DMSO-d$_6$, δ): 0.96 (3H, d, J=6.8 Hz), 1.03 (3H, d, J=6.2 Hz), 1.2–1.6 (8H, m), 1.6–2.6 (15H, m), 2.6–3.8 (6H, m), 3.09 (9H, s), 3.21 (3H, s), 3.30 (4H, t, J=6.4 Hz), 3.8–4.2 (7H, m), 4.2–4.6 (4H, m), 4.6–5.0 (2H, m), 5.28 (2H, m), 5.75 (1H, m), 6.69 (1H, d, J=8.2 Hz), 6.80 (1H, d, J=8.2 Hz), 6.92 (1H, s), 7.14 (2H, d, J=8.8 Hz), 7.35 (1H, d, J=7.4 Hz), 7.5 (1H, m), 7.86 (1H, m), 7.97 (2H, d, J=8.8 Hz), 8.09 (4H, s), 8.32 (1H, s), 8.76 (1H, d, J=6.8 Hz), 8.95 (1H, s).

MASS (m/z): 1363.4 (M$^+$+Na).

EXAMPLE 29

To a solution of starting compound (29) (0.2 g) and ethyl bromoacetate (0.02 ml) in dimethylformamlide (2 ml) was bis added potassium carbonate (30.8 mg) and stirred for 24 hours at ambient temperature. The reaction mixture was pulverized with ethyl acetate. The precipitate was collected by filtration and dried under reduced pressure. The powder was added to 1N NaOH aq. (5 ml) and stirred for 1 hour at ambient temperature. The reaction mixture was adjusted to pH 7 and subjected to column chromatography on ODS (YMC-gel ODS-AM-S-50) (Trademark: prepared by Yamamura Chemical Lab.) and eluted with 30% acetonitrile aq. The fractions containing the object compound were combined and evaporated under reduced pressure to remove acetonitrile. The residue was lyophilized to give object compound (29) (76 mg).

IR (KBr): 3353.6, 1631.5, 1444.4, 1257.4 cm$^{-1}$.

ESI-MASS (m/z): 1355 (M$^+$–1).

EXAMPLE 30

To a solution of starting compound (30) (0.1 g) and ethyl bromoacetate (0.02 ml) in dimethylformamide (1 ml) was added diisopropylethylamine (0.08 ml) and stirred for 24 hours at ambient temperature. The reaction mixture was pulverized with ethyl acetate. The precipitate was collected by filtration and dried under reduced pressure. The powder was added to 1N NaOH aq. (5 ml) and stirred for 1 hour at ambient temperature. The reaction mixture was adjusted to pH 7 and subjected to column chromatography on ODS (YMC-gel ODS-AM-S-50) (Trademark: prepared by Yamamura Chemical Lab.) and eluted with 30% acetonitrile aq. The fractions containing the object compound were combined and evaporated under reduced pressure to remove acetonitrile. The residue was lyophilized to give object compound (30) (48 mg).

IR (KBr): 3357.5, 1633.4, 1444.4, 1257.4 cm$^{-1}$.

ESI-MASS (m/z): 1435 (M$^+$+Na).

EXAMPLE 31

A mixture of 4-[5-[4-[7-(cis-2,6-dimethylmorpholin-4-yl) heptyloxy]phenyl]isoxazol-3-yl]benzoic acid (100 mg), 1-hydroxybenzotriazole (41 mg) and 1-ethyl-3-(3'-dimethylaminopropyl)carbodiimide hydrochloride (46.7 mg) in N,N-dimethylformamide (2 ml) was stirred for 30 minutes at ambient temperature. To the reaction mixture was added N,N-diisopropylethylamine (53.1 μl) and stirred for 40 minutes, then starting compound (31) (246.6 mg) was added and the mixture was stirred for 4 hours. To the reaction mixture was added ethyl acetate (50 ml). The resulting precipitate was collected by filtration and washed with diisopropyl ether to give a crude light-brown powder (400.3 mg). The crude powder was purified by column chromatography on ODS (YMC-gel ODS-AM-S-50 (Trademark: prepared by YMC CO., Ltd.)) (35% acetonitrile aqueous solution). The fractions containing the object compound were combined, and evaporated under reduced pressure to remove acetonitrile. The residue was lyophilized to give object compound (31).

IR (KBr): 3372.9, 1666.2, 1648.8, 1631.5, 1538.9, 1508.9, 1452.1, 1436.7, 1257.4 cm$^{-1}$.

MASS (m/z): 1447.6 (M$^-$–1).

Elemental Analysis Calcd. for $C_{68}H_{92}N_{10}O_{23}S.7H_2O$: C, 51.83, H, 6.78, N, 8.89. Found: C, 52.10, H, 6.67, N, 8.91.

EXAMPLE 32

To a solution of starting compound (32) (0.1 g) and 1-ethoxy-1-imino-3-methoxypropane (38.7 mg) in dimethylformamide (1 ml) was added diisopropylethylamine (0.067 ml) and stirred for 20 hours at ambient temperature. The reaction mixture was pulverized with ethyl acetate. The precipitate was collected by filtration and dried under reduced pressure. The powder was added to pH 6.86 buffer and subjected to column chromatography on ODS (YMC-gel ODS-AM-S-50) (Trademark: prepared by Yamamura Chemical Lab.) and eluted with 5–50% acetonitrile aq. The fractions containing the object compound were combined and evaporated under reduced pressure to remove acetonitrile. The residue was lyophilized to give object compound (32) (42 mg).

IR (KBr): 3353.6, 1635.3, 1257.4 cm$^{-1}$.

NMR (DMSO-d$_6$, δ): 0.98 (3H, d, J=6.6 Hz), 1.13 (3H, d, J=5.8 Hz), 1.2–2.6 (19H, m), 2.8–3.4 (9H, m), 3.21 (3H, s), 3.6–5.3 (26H, m), 6.71 (1H, d, J=8.2 Hz), 6.77 (1H, d, J=8.2 Hz), 7.00 (1H, s), 7.13 (2H, d, J=8.6 Hz), 7.25–7.8 (3H, m), 7.96 (2H, d, J=8.6 Hz), 8.05 (2H, d, J=8.9 Hz), 8.11 (2H, d, J=8.9 Hz), 8.70 (1H, s), 8.85 (1H, d, J=6.7 Hz).

MASS (m/z): 1383 (M$^+$–1).

Elemental Analysis Calcd. for $C_{62}H_{85}N_{11}O_{21}S_2.8H_2O$: C, 48.71, H, 6.66, N, 10.08. Found: C, 48.50, H, 6.50, N, 9.96.

EXAMPLE 33

To a solution of starting compound (33) (0.1 g) and 2-carbamoyl-1-ethoxy-1-iminopropane (38.5 mg) in dimethylformamide (1 ml) was added diisopropylethylamine (0.067 ml) and stirred for 20 hours at ambient temperature. The reaction mixture was pulverized with ethyl acetate. The precipitate was collected by filtration and dried under reduced pressure. The powder was added to pH 6.86 buffer and subjected to column chromatography on ODS (YMC-gel ODS-AM-S-50) (Trademark: prepared by Yamamura Chemical Lab.) and eluted with 5–50% acetonitrile aq. The fractions containing the object compound were combined and evaporated under reduced pressure to remove acetonitrile. The residue was lyophilized to give object compound (33) (48 mg).

IR (KBr): 1658.5, 1635.3, 1257.4 cm$^{-1}$.

NMR (DMSO-d$_6$, δ): 0.98 (3H, d, J=6.6 Hz), 1.13 (3H, d, J=5.8 Hz), 1.2–2.6 (17H, m), 2.8–3.4 (7H, m), 3.21 (3H, s), 3.6–5.3 (28H, m), 6.71 (1H, d, J=8.2 Hz), 6.77 (1H, d, J=8.2 Hz), 7.00 (1H, s), 7.13 (2H, d, J=8.6 Hz), 7.32 (1H, s), 7.25–7.8 (4H, m), 7.96 (2H, d, J=8.6 Hz), 8.05 (2H, d, J=8.9 Hz), 8.11 (2H, d, J=8.9 Hz), 8.70 (1H, s), 8.85 (1H, d, J=6.7 Hz).

ESI-MASS (m/z): 1382 (M$^+$−1).

Elemental Analysis Calcd. for $C_{61}H_{82}N_{12}O_{21}S_2 \cdot 7H_2O$: C, 48.53, H, 6.41, N, 11.13. Found: C, 48.50, H, 6.39, N, 10.92.

EXAMPLE 34

A mixture of starting compound (34) (50 mg), N,N-diisopropylethylamine (6.70 μl) and zeolite synthetic A-4 powder (50 mg) in N,N-dimethylformamide (0.5 ml) was stirred for 30 minutes at ambient temperature. To the mixture was added acetic anhydride (3.63 μl) and stirred for 2 hours. The zeolite synthetic A-4 powder was filtered off, and to the filtrate was added ethyl acetate (100 ml). The resulting precipitate was collected by filtration and washed with diisopropyl ether to give a crude white powder (48.7 mg). The crude powder was purified by column chromatography on ODS (YMC-gel ODS-AM-S-50 (Trademark; prepared by YMC Co., Ltd.)) (25% acetonitrile aqueous solution). The fractions containing the object compound were combined, and evaporated under reduced pressure to remove acetonitrile. The residue was lyophilized to give object compound (34) (31.5 mg).

IR (KBr): 3353.6, 1658.5, 1635.3, 1546.6, 1531.2, 1517.7, 1444.4, 1259.3 cm$^{-1}$.

NMR (DMSO-d$_6$, δ): 0.97 (3H, d, J=6.7 Hz), 1.14 (3H, d, J=5.9 Hz), 1.2–5.5 (55H, m), 6.71 (1H, d, J=8.1 Hz), 6.7–6.9 (1H, m), 6.96 (1H, d, J=1.6 Hz), 7.13 (2H, d, J=8.9 Hz), 7.3–7.8 (4H, m), 7.97 (2H, d, J=8.8 Hz), 7.9–9.0 (7H, m).

MASS (m/z): 1339.3 (M$^-$−Na).

Elemental Analysis Calcd. for $C_{60}H_{79}N_{10}NaO_{21}S_3 \cdot 10H_2O$: C, 46.69, H, 6.46, N, 9.07. Found: C, 46.46, H, 6.11, N, 8.95.

EXAMPLE 35

A solution of starting compound (35) (500 mg) in water (20 ml) and 1N-sodium hydroxide (1.15 μl) was treated dropwise with a solution of allyloxycarbonyl chloride (49 μl) in tetrahydrofuran (1 ml). After 1 hour, the solution was diluted with water and purified by ODS column chromatography eluting with acetonitrile-water mixtures. Product-containing fractions were pooled, evaporated to remove organic solvent and lyophilized to give object compound (35) (350 mg) as a white amorphous powder.

IR (KBr): 2935, 1664, 1633, 1610, 1527, 1442.5, 1412, 1383, 1348, 1257, 1178, 1113, 1088, 1045 cm$^{-1}$.

NMR (DMSO-d$_6$+D$_2$O, δ): 0.97 (3H, d, J=6.7 Hz), 1.11 (3H, d, J=5.8 Hz), 1.2–5.1 (53H, complex m), 3.21 (3H, s), 3.31 (2H, t, J=6.4 Hz), 5.12–5.29 (2H, m), 5.8–6.0 (1H, m), 6.70–6.80 (2H, m), 6.99 (1H, br s), 7.14 (2H, d, J=8.8 Hz), 7.98 (2H, d, J=8.8 Hz), 8.09 (4H, s).

MASS (M/z): 1381.3 (M$^+$−Na).

Elemental Analysis Calcd. for $C_{62}H_{81}N_{10}O_{22}S_2Na \cdot 5H_2O$: C, 49.79, H, 6.13, N, 9.37. Found: C, 49.79, H, 6.07, N, 9.30.

EXAMPLE 36

To a solution of starting compound (36) (100 mg) in N,N-dimethylformamide (1 ml) was added sulfur trioxide pyridine complex (61.2 mg) and stirred for 2 days at ambient temperature. To the reaction mixture was added ethyl acetate (30 ml), and the resulting precipitate was collected by filtration and washed with diisopropyl ether to give a crude white powder. The crude powder was purified by column chromatography on ODS (YMC-gel ODS-AM-S-50 (Trademark: prepared by YMC Co., Ltd.)) (20% acetonitrile aqueous solution). The fractions containing the object compound were combined, and evaporated under reduced pressure to remove acetonitrile. The residue was lyophilized to give object compound (36) (12.7 mg).

IR (KBr): 3446.2, 1648.8, 1633.4, 1540.8, 1515.8, 1450.2, 1442.5, 1257.4 cm$^{-1}$.

NMR (DMSO-d$_6$, δ): 0.96 (3H, d, J=6.5 Hz), 1.0–5.4 (56H, m), 6.6–6.8 (2H, m), 6.9–7.1 (1H, m), 7.13 (2H, d, J=8.8 Hz), 7.97 (2H, d, J=8.8 Hz), 8.08 (4H, s), 7.3–9.0 (7H, m).

MASS (m/z): 1399.3 (M$^-$−1).

EXAMPLE 37

A mixture of starting compound (37) (100 mg), N,N-diisopropylethylamine (14.7 μl), zeolite synthetic A-4 powder (400 mg) and N,N-dimethylformamide dimethyl acetal (15.3 μl) in N,N-dimethylformamide (1 ml) was stirred for 40 minutes at ambient temperature. To the reaction mixture was added N,N-diisopropylethylamine (1.5 μl) and N,N-dimethylformamide dimethyl acetal (1.5 μl), the mixture was stirred for 1 hour at ambient temperature, and ethyl acetate (50 ml) was added, and the resulting precipitate was collected by filtration and washed with diisopropyl ether to give a crude white powder (72.2 mg). The crude powder was purified by column chromatography on ODS (YMC-gel ODS-AM-S-50 (Trademark: prepared by YMC Co., Ltd.)) (40% acetonitrile aqueous solution). The fractions containing the object compound were combined, and evaporated under reduced pressure to remove acetonitrile. The residue was lyophilized to give object compound (37) (27.9 mg).

IR (KBr): 3359.4, 1710.6, 1648.8, 1631.5, 1538.9, 1513.8, 1442.5, 1257.4 cm$^{-1}$.

NMR (DMSO-d$_6$, δ): 0.97 (3H, d, J=6.8 Hz), 1.0–5.4 (62H, m), 6.6–6.9 (2H, m), 6.99 (1H, s), 7.14 (2H, d, J=8.8 Hz), 7.3–7.9 (3H, m), 7.97 (2H, d, J=8.8 Hz), 8.0–8.2 (4H, m), 8.3–9.2 (4H, m).

MASS (m/z): 1352.5 (M$^-$−1).

Elemental Analysis Calcd. for $C_{61}H_{83}N_{11}O_{20}S_2 \cdot 6H_2O$: C, 49.02, H, 6.41, N, 10.31. Found: C, 49.20, H, 6.35, N, 10.27.

EXAMPLE 38

To a solution of the starting compound (38) (100 mg) in N,N-dimethylformamide (1 ml) was added S,S'-dimethyl N-cyanodithioiminocarbonate (113 mg) and diisopropyl ethyl amine (0.2 ml), and stirred for 2 hours at ambient temperature. The reaction mixture was pulverized with ethyl acetate and washed by diisopropyl ether. The precipitate was filtered and dried to give the object compound (38) (111 mg).

NMR (DMSO-d$_6$, δ): 0.97 (3H, d, J=6.7 Hz), 1.0–1.6 (14H, m), 1.6–3.9 (25H, m), 3.21 (3H, s), 3.9–4.3 (7H, m), 4.43 (2H, m), 4.5–4.7 (2H, m), 4.88 (2H, d, J=5.7 Hz), 5.0–5.3 (4H, m), 6.71 (1H, d, J=8.2 Hz), 6.78 (1H, d, J=8.2 Hz), 6.97 (1H, s), 7.13 (2H, d, J=8.8 Hz), 7.50 (1H, d, J=8.5 Hz), 7.63 (1H, m), 7.7 (1H, m), 7.97 (2H, d, J=8.8 Hz), 8.09 (4H, s), 8.12 (1H, m), 8.71 (1H, s), 8.78 (1H, d, J=6.4 Hz).

MASS (m/z): 1395.3 (M$^+$−1).

EXAMPLE 39

To a solution of the starting compound (39) (96 mg) in water (1 ml) was added a solution of ammonia in methanol (1 ml), and stirred for 2 days at ambient temperature. The reaction mixture was diluted in water, and subjected to column chromatography on ODS (YMC-gel ODS-AM-S-50 (Trademark: prepared by Yamamura Chemical Lab.)) eluting with 20% acetonitrile aqueous solution. The fractions containing the object compound were combined, and evaporated under reduced pressure to remove acetonitrile. The residue was lyophilized to give the object compound (39) (39 mg).

IR (KBr): 3351, 2935, 1635, 1567, 1533, 1517, 1444, 1415, 1257, 1178, 1087, 1047 cm$^{-1}$.

NMR (DMSO-d$_6$, δ): 0.98 (3H, d, J=6.7 Hz), 1.13 (3H, d, J=5.7 Hz), 1.2–1.6 (11H, m), 1.6–2.6 (10H, m), 2.90 (1H, m), 3.20 (1H, m), 3.21 (3H, s), 3.30 (4H, t, J=6.4 Hz), 3.3–4.6 (14H, m), 4.6–4.8 (2H, m), 4.87 (1H, d, J=5.7 Hz), 5.06 (1H, d, J=7.2 Hz), 5.2 (4H, m), 6.71 (1H, d, J=8.2 Hz), 6.78 (1H, d, J=8.2 Hz), 6.7 (3H, m), 6.97 (1H, s), 7.13 (2H, d, J=8.8 Hz), 7.46 (1H, d, J=8.8 Hz), 7.65 (2H, m), 7.97 (2H, d, J=8.8 Hz), 8.09 (4H, s), 8.13 (1H, m), 8.71 (1H, s), 8.84 (1H, d, J=7.7 Hz).

MASS (m/z): 1364.4 (M$^+$−Na).

Elemental Analysis Calcd. for $C_{60}H_{78}N_{13}NaO_{20}S_2 \cdot 8H_2O$: C, 47.02, H, 6.18, N, 11.88. Found: C, 47.15, H, 5.89, N, 11.82.

EXAMPLE 40

To a solution of the starting compound (40) (100 mg) in acetonitrile (1 ml) and water (1 ml) was added formaline (35% aqueous) (67 μl), and stirred for 30 minutes at ambient temperature. To a solution of the reaction mixture was added sodium cyanoborohydride (48 mg) and stirred for 5 hours. The reaction mixture was diluted in water, and subjected to column chromatography on ODS (YMC-gel ODS-AM-S-50 (Trademark: prepared by Yamamura Chemical Lab.)) eluting with 20% acetonitrile aqueous solution. The fractions containing the object compound were combined, and evaporated under reduced pressure to remove acetonitrile. The residue was lyophilized to give the object compound (40) (27 mg).

IR (KBr): 3355, 2937, 1658, 1633, 1533, 1517, 1444, 1257, 1178, 1087, 1045 cm$^{-1}$.

NMR (DMSO-d$_6$, δ): 0.95 (3H, d, J=6.7 Hz), 1.10 (3H, d, J=5.7 Hz), 1.3–2.6 (30H, m), 2.6–3.0 (4H, m), 3.21 (3H, s), 3.0–4.1 (11H, m), 4.22 (2H, m), 4.4 (4H, m), 4.80 (3H, m), 4.9 (2H, m), 5.17 (2H, m), 5.24 (1H, d, J=5.7 Hz), 6.69 (1H, d, J=8.2 Hz), 6.76 (1H, d, J=8.2 Hz), 6.99 (1H, s), 7.05 (1H, s), 7.14 (2H, d, J=8.8 Hz), 7.41 (2H, d, J=9.1 Hz), 7.85 (1H, m), 7.97 (2H, d, J=8.8 Hz), 8.10 (4H, s), 8.70 (1H, m), 8.72 (1H, s), 8.87 (1H, m).

MASS (m/z): 1365.4 (M$^+$−1).

Elemental Analysis Calcd. for $C_{63}H_{86}N_{10}O_{20}S_2 \cdot 8H_2O$: C, 50.06, H, 6.80, N, 9.27. Found: C, 49.95, H, 6.38, N, 9.21.

EXAMPLE 41

To a solution of the starting compound (41) (100 mg) and potassium carbonate (53 mg) in N,N-dimethylformamide (1 ml) was added 1,5-dibromopentane (13 μl), and stirred for 3 days at ambient temperature. The reaction mixture was filtrated, and the filtrate was diluted in water, and subjected to column chromatography on ODS (YMC-gel ODS-AM-S-50 (Trademark: prepared by Yamamura Chemical Lab.)) eluting with 20% acetonitrile aqueous solution. The fractions containing the object compound were combined, and evaporated under reduced pressure to remove acetonitrile. The residue was lyophilized to give the object compound (41) (38 mg).

IR (KBr): 3353, 2935, 1658, 1635, 1546, 1529, 1517, 1444, 1257, 1083, 1047 cm$^{-1}$.

NMR (DMSO-d$_6$, δ): 0.98 (3H, d, J=6.7 Hz), 1.09 (3H, d, J=5.7 Hz), 1.3–1.6 (8H, m), 1.6–2.4 (15H, m), 2.4–3.0 (6H, m), 3.21 (3H, s), 3.0–4.2 (1H, m), 4.23 (2H, m), 4.43 (4H, m), 4.80 (3H, m), 4.95 (2H, d, J=6.2 Hz), 5.1–5.3 (3H, m), 6.70 (1H, d, J=8.2 Hz), 6.77 (1H, d, J=8.2 Hz), 6.99 (1H, s), 7.14 (2H, d, J=8.8 Hz), 7.43 (2H, m), 7.83 (1H, d, J=7.2 Hz), 7.97 (2H, d, J=8.8 Hz), 8.10 (4H, s), 8.60 (1H, m), 8.71 (1H, s), 8.87 (1H, d, J=7.2 Hz).

MASS (m/z): 1325.4 (M$^+$−1).

Elemental Analysis Calcd. for $C_{60}H_{92}N_{10}O_{20}S_2 \cdot 8H_2O$: C, 48.97, H, 6.71, N, 9.52. Found: C, 48.97, H, 6.32, N, 9.63.

EXAMPLE 42

To a solution of the starting compound (42) (200 mg) and molecular sieves (4A) (200 mg) in N,N-dimethylformamide (4 ml) was added cyanogen bromide (80 mg), and stirred for 5 hours at ambient temperature. The reaction mixture was filtrated, and the filtrate was diluted in water, and subjected to column chromatography on ODS (YMC-gel-ODS-AM-S-50 (Trademark: prepared by Yamamura Chemical Lab.)) eluting with 20% acetonitrile aqueous solution. The fractions containing the object compound were combined, and evaporated under reduced pressure to remove acetonitrile. The residue was lyophilized to give the object compound (42) (3.8 mg).

NMR (DMSO-d$_6$, δ): 0.97 (3H, d, J=6.7 Hz), 1.13 (3H, d, J=5.7 Hz), 1.2–1.6 (8H, m), 1.6–4.5 (30H, m), 2.79 (3H, s), 3.21 (3H, s), 4.7 (2H, m), 4.85 (2H, d, J=6.0 Hz), 5.07 (2H, m), 5.2 (3H, m), 6.69 (2H, m), 6.95 (1H, s), 7.14 (2H, d, J=8.8 Hz), 7.46 (1H, m), 7.64 (2H, m), 7.97 (2H, d, J=8.8 Hz), 8.09 (4H, s), 8.07 (1H, d, J=7.8 Hz), 8.57 (1H, d, J=7.8 Hz), 8.27 (1H, m), 8.68 (1H, m), 8.72 (1H, s).

MASS (m/z): 1336.3 (M$^+$−1).

EXAMPLE 43

A solution of starting compound (43) (100 mg) in N,N-dimethylformamide (2 ml) was treated with 1,1'-carbonyldiimidazole (16.2 mg) and diisopropylethylamine (10.9 mg). After 20 hours, a further 3.7 mg of 1,1-carbonyldiimidazole was added. After a further 1 hour, the mixture was diluted with water and purified by ODS column chromatography eluting with acetonitrile-water mixtures and product-containing fractions lyophilized to afford 80.8 mg of object compound (43) as a white amorphous powder.

IR (KBr): 2935, 2864, 1658.5, 1637, 1529, 1518, 1444, 1257 cm$^{-1}$.

NMR (DMSO-d$_6$+D$_2$O, δ): 0.93–1.07 (6H, m), 1.20–4.5 (37H, m), 3.21 (3H, s), 3.31 (2H, t, J=6.4 Hz), 4.07 (2H, t, J=6.3 Hz), 4.81 (1H, m), 4.99 (1H, d, J=4 Hz), 6.71 (1H, d, J=8.2 Hz), 6.78–6.83 (1H, m), 6.98 (1H, d, J=1.7 Hz), 7.13 (2H, d, J=8.9 Hz), 7.97 (2H, d, J=8.9 Hz), 8.02–8.13 (4H, m).

MASS (m/z): 1323.2 (M$^+$−Na).

Elemental Analysis Calcd. for $C_{59}H_{75}N_{10}O_{21}S_2N_9 \cdot 6H_2O$: C, 48.39, H, 6.06, N, 9.56. Found: C, 48.37, H, 6.00, N, 9.61.

The following compound was obtained according to a similar manner to that of Example 43.

EXAMPLE 44

IR (KBr): 3352, 2935, 2864, 1635, 1547, 1516, 1444, 1255, 1174, 1045 cm$^{-1}$.

NMR (DMSO-d$_6$+D$_2$O, δ): 0.95 (3H, d, J=6.9 Hz), 1.03 (3H, d, J=5.9 Hz), 1.20–5.12 (39H, m), 3.21 (3H, s), 3.31

(2H, t, J=6.4 Hz), 4.07 (2H, t, J=6.1 Hz), 6.72 (1H, d, J=8.2 Hz), 6.82 (1H, dd, J=8.2, 1.7 Hz), 6.99 (1H, d, J=1.7 Hz), 7.13 (2H, d, J=8.9 Hz), 7.98 (2H, d, J=8.9 Hz), 8.08 (4H, m).

MASS (m/z): 1339.2 (M$^+$–Na).

Elemental Analysis Calcd. for $C_{59}H_{75}N_{10}O_{20}S_3Na.6H_2O$: C, 48.16, H, 5.96, N, 9.52. Found: C, 48.01, H, 5.74, N, 9.43.

EXAMPLE 45

A mixture of starting compound (45) (220 mg) and 1N sodium hydroxide aqueous solution (30 ml) was stirred for 1 hour at ambient temperature. The reaction mixture was adjusted to pH 9 with 1N hydrochloric acid, and purified by column chromatography on ODS (YMC-gel ODS-AM-S-50 (Trademark: prepared by YMC Co., Ltd.)) (20% acetonitrile aqueous solution). The fractions containing the object compound were combined, and evaporated under reduced pressure to remove acetonitrile. The residue was lyophilized to give object compound (45).

IR (KBr): 3382.5, 1658.5, 1635.3, 1444.4, 1257.4, 1087.7, 1045.2 cm$^{-1}$.

NMR (DMSO-d$_6$, δ): 0.97 (3H, d, J=6.9 Hz), 1.11 (3H, d, J=5.0 Hz), 1.2–5.4 (64H, m), 6.68 (1H, d, J=8.1 Hz), 6.78 (1H, d, J=8.0 Hz), 6.92 (1H, d, J=1.8 Hz), 7.13 (2H, d, J=8.9 Hz), 7.97 (2H, d, J=8.8 Hz), 8.07 (4H, s), 7.3–9.0 (6H, m).

MASS (m/z): 1411.4 (M$^-$–Na).

The following compounds were obtained according to a similar manner to that of Example 45.

EXAMPLE 46

Major Object Compound (46)

IR (KBr): 3353.6, 1658.5, 1635.3, 1546.6, 1529.3, 1517.7, 1444.4, 1257.4 cm$^{-1}$.

NMR (DMSO-d$_6$, δ): 0.97 (3H, d, J=6.7 Hz), 1.10 (3H, d, J=5.3 Hz), 1.2–5.4 (70H, m), 6.68 (1H, d, J=8.2 Hz), 6.76 (1H, d, J=9.7 Hz), 6.92 (1H, s), 7.13 (2H, d, J=8.8 Hz), 7.97 (2H, d, J=8.7 Hz), 8.04 (2H, d, J=9.3 Hz), 8.10 (2H, d, J=9.0 Hz), 7.3–9.0 (6H, m).

MASS (m/z): 1453.4 (M$^-$–Na).

Elemental Analysis calcd. for $C_{67}H_{93}N_{10}NaO_{22}S_2.9H_2O$: C, 49.08, H, 6.82, N, 8.54. Found: C, 49.20, H, 6.72, N, 8.56.

Minor Object Compound (46)

IR (KBr): 3353.6, 1658.5, 1635.3, 1567.8, 1550.5, 1533.1, 1517.7, 1444.4, 1407.8, 1257.4 cm$^{-1}$.

NMR (DMSO-d$_6$, δ): 0.96 (3H, d, J=6.6 Hz), 1.1–5.4 (88H, m), 6.70 (1H, d, J=8.2 Hz), 6.78 (1H, d, J=9.8 Hz), 6.90 (1H, s), 7.13 (2H, d, J=8.9 Hz), 7.97 (2H, d, J=8.8 Hz), 8.07 (4H, s), 7.3–9.0 (6H, m).

MASS (m/z): 1631.4 (M$^-$–Na).

Elemental Analysis Calcd. for $C_{76}H_{108}N_{10}Na_2O_{24}S_2.11H_2O$: C, 49.24, H, 7.07, N, 7.55. Found: C, 49.22, H, 6.93, N, 7.57.

EXAMPLE 47 deleted
deleted

EXAMPLE 48

A mixture of starting compound (48) (100 mg), N,N-diisopropylethylamine (13.4 µl) and zeolite synthetic A-4 powder (100 mg) in N,N-dimethylformamide (1 ml) was stirred for 30 minutes at ambient temperature. The mixture was cooled to 0° C. and treated with methanesulfonyl chloride (6 µl) and stirred for 30 minutes at ambient temperature. The mixture was then treated with further methanesulfonyl chloride (6 µl) and stirred for 30 minutes at ambient temperature. To the mixture was added N,N-diisopropylethylamine (13.4 µl) and stirred for 15 minutes at ambient temperature. The mixture was treated with methanesulfonyl chloride (6 µl) and stirred for 30 minutes at ambient temperature. To the mixture was added N,N-diisopropylethylamine (13.4 µl) and stirred for 15 minutes at ambient temperature. The zeolite synthetic A-4 powder was filtered off, and to the filtrate was added ethyl acetate (100 ml). The resulting precipitate was collected by filtration and washed with diisopropyl ether to give a crude powder. The crude powder was purified by column chromatography on ODS (YMC-gel ODS-AM-S-50 (Trademark: prepared by YMC Co., Ltd.)) (25% acetonitrile aqueous solution). The fractions containing the object compound were combined, and evaporated under reduced pressure to remove acetonitrile. The residue was lyophilized to give object compound (48) (30.0 mg).

IR (KBr): 3430.7, 1658.5, 1635.3, 1444.4, 1259.3 cm$^{-1}$.

NMR (DMSO-d$_6$, δ): 0.97 (3H, d, J=6.7 Hz), 1.14 (3H, d, J=5.9 Hz), 1.2–5.5 (55H, m), 6.6–6.9 (3H, m), 6.97 (1H, d, J=1.6 Hz), 7.13 (2H, d, J=8.9 Hz), 7.3–7.8 (3H, m), 7.97 (2H, d, J=8.8 Hz), 8.09 (4H, s), 8.0–9.0 (3H, m).

MASS (m/z): 1375.3 (M$^-$–Na).

Elemental Analysis Calcd. for $C_{59}H_{79}N_{10}NaO_{22}S_3.7H_2O$: C, 46.45, H, 6.14, N, 9.18. Found: C, 46.26, H, 6.11, N, 9.01.

The following compounds [Examples 49 to 52] were obtained according to a similar manner to that of Example 48.

EXAMPLE 49

IR (KBr): 3380.6, 1666.2, 1648.8, 1631.5, 1538.9, 1513.8, 1450.2, 1450.2, 1261.2 cm$^{-1}$.

NMR (DMSO-d$_6$, δ): 0.96 (3H, d, J=6.6 Hz), 1.16 (3H, d, J=5.9 Hz), 1.2–5.5 (60H, m), 6.4–6.6 (1H, m), 6.71 (1H, d, J=8.1 Hz), 6.78 (1H, d, J=9.8 Hz), 6.96 (1H, s), 7.13 (2H, d, J=8.8 Hz), 7.3–8.2 (4H, m), 7.93 (2H, d, J=8.6 Hz), 8.05 (2H, d, J=9.0 Hz), 8.11 (2H, d, J=8.9 Hz), 8.5–9.0 (2H, m).

MASS (m/z): 1410.4 (M$^-$–Na).

Elemental Analysis Calcd. for $C_{63}H_{84}N_{11}NaO_{22}S_2.8H_2O$: C, 47.93, H, 6.38, N, 9.76. Found: C, 48.05, H, 6.25, N, 9.56.

EXAMPLE 50

IR (KBr): 3363.2, 1666.2, 1648.8, 1631.5, 1540.8, 1513.8, 1450.2, 1442.5, 1257.4 cm$^{-1}$.

NMR (DMSO-d$_6$, δ): 0.96 (3H, d, J=6.6 Hz), 1.16 (3H, d, J=5.9 Hz), 1.2–5.5 (58H, m), 6.1–6.3 (1H, m), 6.71 (1H, d, J=18.1 Hz), 6.78 (1H, d, J=10.0 Hz), 6.96 (1H, s), 7.13 (2H, d, J=8.8 Hz), 7.4–7.9 (4H, m), 7.97 (2H, d, J=8.7 Hz), 8.06 (2H, d, J=10.4 Hz), 8.11 (2H, d, J=9.0 Hz), 8.6–8.8 (2H, m).

MASS (m/z): 1368.4 (M$^-$–Na).

Elemental Analysis Calcd. for $C_{61}H_{82}N_{11}NaO_{21}S_2.9H_2O$: C, 47.13, H, 6.48, N, 9.91. Found: C, 47.36, H, 6.24, N, 9.86.

EXAMPLE 51

IR (KBr): 3359.4, 1666.2, 1648.8, 1631.5, 1540.8, 1513.8, 1450.2, 1442.5, 1257.4 cm$^{-1}$.

NMR (DMSO-d$_6$, δ): 0.8–1.1 (9H, m), 1.17 (3H, d, J=6.0 Hz), 1.2–5.5 (56H, m), 6.0–6.2 (1H, m), 6.71 (1H, d, J=8.1 Hz), 6.7–6.9 (1H, m), 6.96 (1H, d, J=1.6 Hz), 7.13 (2H, d, J=8.9 Hz), 7.4–7.9 (4H, m), 7.97 (2H, d, J=8.8 Hz), 8.05 (2H, d, J=9.3 Hz), 8.10 (2H, d, J=9.0 Hz), 8.6–8.8 (2H, m).

MASS (m/z): 1396.5 (M$^-$–Na).

Elemental Analysis Calcd. for $C_{63}H_{86}N_{11}NaO_{21}S_2.8H_2O$: C, 48.36, H, 6.57, N, 9.85. Found: C, 48.50, H, 6.34, N, 9.82.

EXAMPLE 52

IR (KBr): 3392.2, 1631.5, 1504.8, 1515.8, 1442.5, 1257.4 cm$^{-1}$.

NMR (DMSO-d$_6$, δ): 0.96 (3H, d, J=6.6 Hz), 1.16 (3H, d, J=5.7 Hz), 1.2–5.5 (60H, m), 5.9–6.1 (1H, m), 6.71 (1H, d, J=8.1 Hz), 6.78 (1H, d, J=10.0 Hz), 6.96 (1H, s), 7.13 (2H, d, J=8.8 Hz), 7.3–7.9 (4H, m), 7.97 (2H, d, J=8.8 Hz), 8.0–8.2 (4H, m), 8.6–8.8 (2H, m).

MASS (m/z): 1394.4 (M$^-$–Na).

EXAMPLE 53

To a mixture of starting compound (53) (100 mg) and zeolite synthetic A-4 powder (100 mg) in N,N-dimethylformamide (1 ml) was added propane sulfone (9.4 mg) and stirred for 3 days 7 hours at ambient temperature. To the reaction mixture was added ethyl acetate (20 ml). The resulting precipitate was collected by filtration and washed with diisopropyl ether to give a crude white powder (104.3 mg). The crude powder was purified by column chromatography on ODS (YMC-gel ODS-AM-S-50 (Trademark: prepared by YMC Co., Ltd.)) (20% acetonitrile aqueous solution). The fractions containing the object compound were combined, and evaporated under reduced pressure to remove acetonitrile. The residue was lyophilized to give object compound (53) (34.2 mg).

IR (KBr): 3372.9, 1658.5, 1635.3, 1546.6, 1529.3, 1517.7, 1444.4, 1255.4, 1178.3, 1045.2 cm$^{-1}$.

NMR (DMSO-d$_6$, δ): 0.97 (3H, d, J=6.6 Hz), 1.13 (3H, d, J=5.8 Hz), 1.2–5.5 (60H, m), 6.71 (1H, d, J=8.2 Hz), 6.77 (1H, d, J=10.0 Hz), 6.95 (1H, s), 7.13 (2H, d, J=8.9 Hz), 7.97 (2H, d, J=8.7 Hz), 8.09 (4H, s), 7.3–9.0 (6H, m).

MASS (m/z): 1419.4 (M$^-$–Na).

Elemental Analysis Calcd. for C$_{61}$H$_{83}$N$_{10}$NaO$_{23}$S$_3$.8H$_2$O: C, 46.15, H, 6.28, N, 8.82. Found: C, 46.11, H, 6.04, N, 8.74.

The following compounds [Examples 54 to 56] were obtained according to a similar manner to that of Example 53.

EXAMPLE 54

IR (KBr): 3355.5, 2935.1, 1635.3, 1529.3, 1517.7, 1444.4, 1257.4, 1178.3, 1045.2 cm$^{-1}$.

NMR (DMSO-d$_6$, δ): 0.97 (3H, d, J=6.8 Hz), 1.12 (3H, d, J=5.3 Hz), 1.2–5.4 (62H, m), 6.71 (1H, d, J=8.1 Hz), 6.78 (1H, d, J=9.5 Hz), 6.96 (1H, s), 7.13 (2H, d, J=8.8 Hz), 7.97 (2H, d, J=8.7 Hz), 8.05 (2H, d, J=8.8 Hz), 8.12 (2H, d, J=8.5 Hz), 7.3–9.0 (6H, m).

MASS (m/z): 1455.3 (M$^-$–1).

EXAMPLE 55

IR (KBr): 3369.0, 1633.4, 1533.1, 1517.7, 1444.4, 1413.6, 1257.4 cm$^{-1}$.

NMR (DMSO-d$_6$, δ): 0.97 (3H, d, J=6.6 Hz), 1.14 (3H, d, J=5.7 Hz), 1.2–5.4 (58H, m), 6.6–6.9 (2H, m), 6.94 (1H, s), 7.13 (2H, d, J=8.9 Hz), 7.97 (2H, d, J=8.8 Hz), 8.08 (4H, s), 7.3–9.0 (6H, m).

MASS (m/z): 1391.2 (M$^-$–1).

Elemental Analysis Calcd. for C$_{61}$H$_{81}$N$_{10}$NaO$_{22}$S$_2$.8H$_2$O: C, 47.65, H, 6.36, N, 9.11. Found: C, 47.52, H, 6.10, N, 8.84.

EXAMPLE 56

IR (KBr): 3363.2, 1666.2, 1648.8, 1631.5, 1538.9, 1513.8, 1450.2, 1442.5, 1257.4 cm$^{-1}$.

NMR (DMSO-d$_6$, δ): 0.97 (3H, d, J=6.6 Hz), 1.12 (3H, d, J=35.6 Hz), 1.2–5.6 (60H, m), 6.71 (1H, d, J=8.1 Hz), 6.77 (1H, d, J=9.1 Hz), 6.97 (1H, s), 7.13 (2H, d, J=8.8 Hz), 7.97 (2H, d, J=8.7 Hz), 8.06 (2H, d, J=8.6 Hz), 8.13 (2H, d, J=8.7 Hz), 7.3–9.0 (6H, m).

MASS (m/z): 1457.4 (M$^-$–1).

Elemental Analysis Calcd. for C$_{61}$H$_{83}$N$_{10}$NaO$_{24}$S$_3$.9H$_2$O: C, 45.18, H, 6.28, N, 8.64. Found: C, 45.14, H, 6.11, N, 8.52.

The following compounds [Examples 57 to 58] were obtained according to a similar manner to that of Example 18.

EXAMPLE 57

IR (KBr): 1670, 1632, 1535, 1518, 1443 cm$^{-1}$.

NMR (DMSO-d$_6$+D$_2$O, δ): 0.94 (3H, d, J=6.70 Hz), 1.10 (3H, d, J=5.86 Hz), 1.35 (9H, s), 1.45–1.95 (6H, m), 2.10–2.40 (2H, m), 2.80–3.45 (7H, m), 3.60–4.80 (15H, m), 5.05–5.40 (2H, m), 5.70–6.05 (1H, m), 10 6.74 (1H, d, J=8.18 Hz), 6.82 (1H, d, J=10.2 Hz), 7.06 (1H, s).

ESI MASS (m/z) (Positive): 1135.2 (M$^+$+Na).

Elemental Analysis Calcd. for C$_{44}$H$_{65}$N$_8$O$_{22}$SNa.4H$_2$O: C, 44.59, H, 6.21, N, 9.45. Found: C, 44.55, H, 6.37, N, 9.39.

EXAMPLE 58

IR (KBr): 3344, 2925.5, 2854, 1664, 1635, 1529, 1518, 1446, 1277, 1252, 1171, 1086, 1045 cm$^{-1}$.

NMR (DMSO-d$_6$+D$_2$O, δ): 0.82–0.88 (3H, m), 0.97 (3H, d, J=6.6 Hz), 1.08 (3H, d, J=5.5 Hz), 1.37 (9H, s), 1.5–4.80 (57H, complex m), 6.71–6.79 (2H, m), 7.00 (1H, br s).

MASS (m/z): 1227.4 (M$^+$–Na).

Elemental Analysis Calcd. for C$_{56}$H$_{91}$N$_8$O$_{20}$SNa.5H$_2$O: C, 50.14, H, 7.59, N, 8.35. Found: C, 49.93, H, 7.51, N, 8.31.

EXAMPLE 59

A mixture of 4-[5-[4-(6-methoxyhexyloxy)phenyl] isoxazol-3-yl]benzoic acid (100 mg), 1-hydroxybenzotriazole (51.3 mg), 1-ethyl-3-(3'-dimethylaminopropyl)carbodiimide hydrochloride (58.2 mg) and N,N-diisopropylethylamine (66.1 μl) in N,N-dimethylformamide (2 ml) was stirred for 4.5 hours. To the reaction mixture was added starting compound (59) (246.6 mg) and stirred for overnight. To the reaction mixture was added ethyl acetate (100 ml). The resulting precipitate was collected by filtration and washed with diisopropyl ether to give object compound (59) as a crude white powder (406.7 mg), that was used crude in the next reaction.

The following compounds [Example 60 to 62] were obtained according to a similar manner to that of Example 59.

EXAMPLE 60

The object compound (60) was used directly in the next reaction without purification.

EXAMPLE 61

The object compound (61) was used directly in the next reaction without purification.

EXAMPLE 62

The object compound (62) was used directly in the next reaction without purification.

The following compounds [Examples 63 to 77] were obtained according to a similar manner to that of Preparation 84.

EXAMPLE 63

IR (KBr): 3369.0, 1631.5, 1538.9, 1513.8, 1442.5, 1257.4 cm$^{-1}$.

NMR (DMSO-d$_6$, δ): 0.97 (3H, d, J=6.7 Hz), 1.11 (3H, d, J=5.4 Hz), 1.2–5.6 (70H, m), 6.71 (1H, d, J=8.3 Hz), 6.77 (1H, d, J=9.6 Hz), 6.99 (1H, s), 7.14 (2H, d, J=8.9 Hz), 7.97 (2H, d, J=8.6 Hz), 8.04 (2H, d, J=8.5 Hz), 8.11 (2H, d, J=8.3 Hz), 7.3–9.0 (6H, m).

ESI MASS (m/z): 1442.6 (M$^-$−1).

Elemental Analysis Calcd. for $C_{65}H_{93}N_{11}O_{22}S_2 \cdot 7H_2O$: C, 49.70, H, 6.87, N, 9.81. Found: C, 49.43, H, 6.71, N, 9.71.

EXAMPLE 64

IR (KBr): 1633, 1606, 1527, 1518, 1466 cm$^{-1}$.

NMR (DMSO-d$_6$, δ): 0.96 (3H, d, J=6.7 Hz), 1.11 (3H, d, J=5.6 Hz), 1.2–2.5 (18H, m), 2.7–4.6 (34H, m), 4.6–5.4 (8H, m), 6.7–7.2 (5H, m), 7.3–7.6 (2H, m), 7.6–7.85 (4H, m), 7.95 (4H, s), 8.2–8.4 (1H, m), 8.6–8.75 (1H, m), 8.80 (1H, s).

MASS (m/z): 1407 (M$^+$+1).

EXAMPLE 65

IR (KBr): 3363.2, 1666.2, 1648.8, 1631.5, 1538.9, 111. 1508.1, 1452.1, 1436.7, 1257.4 cm$^{-1}$.

NMR (DMSO-d$_6$, δ): 0.98 (3H, d, J=6.8 Hz), 1.11 (3H, d, J=5.7 Hz), 1.2–5.6 (53H, m), 6.71 (1H, d, J=8.1 Hz), 6.7–6.9 (1H, m), 7.01 (1H, d, J=1.6 Hz), 7.13 (2H, d, J=8.9 Hz), 7.45 (1H, d, J=8.3 Hz), 7.55 (1H, s), 7.85 (2H, d, J=8.7 Hz), 7.6–7.9 (2H, m), 7.99 (2H, d, J=8.8 Hz), 8.05 (2H, d, J=8.9 Hz), 8.32 (1H, d, J=7.3 Hz), 8.71 (1H, s), 8.87 (1H, d, J=7.5 Hz).

MASS (m/z): 1266.4 (M$^-$−1).

Elemental Analysis Calcd. for $C_{58}H_{77}N_9O_{21}S \cdot 8H_2O$: C, 49.32, H, 6.64, N, 8.92. Found: C, 49.42, H, 6.43, N, 8.88.

EXAMPLE 66

IR (KBr): 3490, 3463, 3424, 3357, 2935, 1633, 1542, 1519 cm$^{-1}$.

NMR (DMSO-d$_6$, δ): 0.98 (3H, d, J=6.6 Hz), 1.12 (3H, d, J=5.4 Hz), 1.22–1.35 (6H, m), 1.35–2.40 (15H, m), 2.80–3.10 (3H, m), 3.18 (3H, s), 3.25 (3H, t, J=6.4 Hz), 3.45–3.60 (3H, m), 3.65–4.60 (15H, m), 4.70–5.30 (8H, m), 6.70–6.80 (2H, m), 7.00 (1H, br s), 7.40–7.75 (3H, m), 8.00–8.40 (3H, m), 8.46 (2H, d, J=8.4 Hz), 8.50–9.00 (2H, m).

MASS (m/z) (API-ES-negative): 1332 (M$^+$+1).

Elemental Analysis Calcd. for $C_{58}H_{38}N_{10}O_{22}S_2 \cdot 5H_2O$: C, 49.00, H, 6.19, N, 9.85. Found: C, 49.20, H, 6.15, N, 9.69.

EXAMPLE 67

IR (KBr): 3457, 3425, 3400, 3365, 2931, 1639, 1537, 1518 cm$^{-1}$.

NMR (DMSO-d$_6$, δ): 0.98 (3H, d, J=6.7 Hz), 1.12 (3H, d, J=5.4 Hz), 1.20–1.35 (12H, m), 1.35–1.70 (6H, m), 1.70–2.40 (7H, m), 2.80–3.10 (3H, m), 3.17 (3H, s), 3.26 (3H, t, J=6.4 Hz), 3.30–3.50 (3H, m), 3.65–4.10 (6H, m), 4.10–4.60 (7H, m), 4.65–5.40 (8H, m), 6.60–6.80 (2H, m), 7.00 (1H, br s), 7.30–7.80 (6H, m), 8.05–8.40 (7H, m), 8.47 (2H, d, J=8.4 Hz), 8.71 (1H, br s), 8.93 (1H, m).

MASS (m/z) (API-ES Negative): 1360 (M$^+$+1).

Elemental Analysis Calcd. for $C_{60}H_{82}N_{10}O_{22}S_2 \cdot 6H_2O$: C, 49.08, H, 6.41, N, 9.54. Found: C, 48.88, H, 6.41, N, 9.47.

EXAMPLE 68

IR (KBr): 3457, 3424, 3400, 3367, 2935, 1637, 1509, 1261 cm$^{-1}$.

NMR (DMSO-d$_6$, δ): 0.98 (3H, d, J=6.7 Hz), 1.12 (3H, d, J=5.4 Hz), 1.20–1.50 (9H, m), 1.60–2.45 (9H, m), 3.21 (3H, s), 3.30 (2H, t, J=6.5 Hz), 3.40–3.90 (6H, m), 3.90–4.55 (12H, m), 4.60–5.80 (6H, m), 6.72 (1H, d, J=8.1 Hz), 6.74 (1H, dd, J=1.5 and 8.4 Hz), 7.00 (1H, d, J=1.5 Hz), 7.20 (2H, d, J=8.9 Hz), 7.40–7.90 (4H, m), 8.00–8.40 (6H, m), 8.94 (1H, m).

MASS (m/z) (API-ES-Negative): 1284 (M$^+$+1).

Elemental Analysis Calcd. for $C_{58}H_{78}N_{10}O_{21}S \cdot 7H_2O$: C, 49.40, H, 6.53, N, 9.94. Found: C, 49.17, H, 6.36, N, 9.74.

EXAMPLE 69

IR (KBr): 3458, 3423, 3398, 3367, 2931, 1637, 1508, 1259 cm$^{-1}$.

NMR (DMSO-d$_6$, δ): 0.98 (3H, d, J=6.7 Hz), 1.12 (3H, d, J=5.5 Hz), 1.20–1.60 (12H, m), 1.65–2.45 (9H, m), 2.80–3.15 (3H, m), 3.20 (3H, s), 3.29 (3H, t, J=6.5 Hz), 3.80–4.50 (17H, m), 4.60–5.30 (8H, m), 6.71 (1H, d, J=8.2 Hz), 6.69–6.80 (1H, m), 7.00 (1H, br s), 7.20 (2H, d, J=8.9 Hz), 7.30–7.90 (7H, m), 8.05–8.40 (8H, m), 8.60–9.00 (2H, m).

MASS (m/z) (API-ES-Negative): 1312 (M$^+$+1).

Elemental Analysis Calcd. for $C_{60}H_{82}N_{10}O_{21}S \cdot 6H_2O$: C, 50.74, H, 6.62, N, 9.87. Found: C, 50.48, H, 6.56, N, 9.60.

EXAMPLE 70

IR (KBr): 3372.9, 1664.3, 1635.3, 1361.5, 1444.4, 1257.4 cm$^{-1}$.

NMR (DMSO-d$_6$, δ): 0.97 (3H, d, J=6.8 Hz), 1.12 (3H, d, J=5.8 Hz), 1.2–5.3 (55H, m), 6.71 (1H, d, J=8.1 Hz), 6.7–6.9 (1H, m), 7.00 (1H, d, J=1.6 Hz), 7.12 (2H, d, J=8.9 Hz), 7.45 (1H, d, J=8.6 Hz), 7.54 (1H, s), 7.6–7.8 (2H, m), 7.85 (2H, d, J=8.7 Hz), 7.99 (2H, d, J=8.7 Hz), 8.05 (2H, d, J=8.9 Hz), 8.25 (1H, d, J=6.7 Hz), 8.81 (1H, d, J=7.4 Hz).

MASS (m/z): 1280.4 (M$^-$−1).

Elemental Analysis Calcd. for $C_{59}H_{79}N_9O_{21}S \cdot 6H_2O$: C, 50.96, H, 6.60, N, 9.07. Found: C, 50.89, H, 6.43, N, 8.98.

EXAMPLE 71

IR (KBr): 3371.0, 1631.5, 1538.9, 1506.1, 1450.2, 1436.7, 1257.4 cm$^{-1}$.

NMR (DMSO-d$_6$, δ): 0.8–1.2 (12H, m), 1.2–5.5 (58H, m), 6.71 (1H, d, J=8.1 Hz), 6.7–6.9 (1H, m), 7.01 (1H, d, J=1.7 Hz), 7.12 (2H, d, J=8.9 Hz), 7.45 (1H, d, J=9.2 Hz), 7.54 (1H, s), 7.5–7.9 (2H, m), 7.85 (2H, d, J=8.8 Hz), 7.99 (2H, d, J=8.8 Hz), 8.05 (2H, d, J=8.9 Hz), 8.1–8.4 (1H, m), 8.70 (1H, m), 8.86 (1H, d, J=7.8 Hz).

MASS (m/z): 1363.5 (M$^-$−1).

Elemental Analysis Calcd. for $C_{64}H_{88}N_{10}O_{21}S \cdot 7H_2O$: C, 51.53, H, 6.89, N, 9.39. Found: C, 51.23, H, 6.80, N, 9.27.

EXAMPLE 72

IR (KBr): 3363.2, 1666.2, 1648.8, 1538.9, 1506.1, 1454.1, 1436.7, 1257.4 cm$^{-1}$.

NMR (DMSO-d$_6$, δ): 0.8–1.2 (12H, m), 1.2–5.3 (60H, m), 6.71 (1H, d, J=8.2 Hz), 6.7–6.9 (1H, m), 7.01 (1H, s), 7.12 (2H, d, J=8.9 Hz), 7.54 (1H, s), 7.3–7.8 (3H, m), 7.85 (2H, d, J=8.7 Hz), 7.9–8.2 (4H, m), 8.2–8.4 (1H, m), 8.7 (1H, s), 8.8–9.0 (1H, m).

MASS (m/z): 1377.6 (M⁻−1).

Elemental Analysis Calcd. for $C_{65}H_{90}N_{10}O_{21}S\cdot 8H_2O$: C, 51.24, H, 7.01, N, 9.19. Found: C, 51.52, H, 7.06, N, 9.16.

EXAMPLE 73

IR (KBr): 3363.2, 1631.5, 1538.9, 1510.0, 1438.6, 1243.9 cm⁻¹.

NMR (DMSO-d₆, δ): 0.98 (3H, d, J=6.7 Hz), 1.11 (3H, d, J=5.7 Hz), 1.18 (6H, d, J=6.0 Hz), 1.2–5.5 (44H, m), 6.71 (1H, d, J=8.2 Hz), 6.78 (1H, d, J=9.8 Hz), 7.00 (1H, s), 7.11 (2H, d, J=8.9 Hz), 7.46 (1H, s), 7.3–7.8 (3H, m), 7.76 (2H, d, J=8.7 Hz), 7.99 (2H, d, J=8.6 Hz), 8.05 (2H, d, J=8.7 Hz), 8.2–9.0 (3H, m).

MASS (m/z): 1249.4 (M⁻−1).

EXAMPLE 74

MASS (m/z): 1377.4 (M⁺−1).

EXAMPLE 75

MASS (m/z): 1405.4 (M⁺−1).

EXAMPLE 76

NMR (DMSO-d₆, δ): 0.86 (3H, d, J=6.3 Hz), 0.98 (3H, d, J=6.8 Hz), 1.11 (3H, d, J=5.8 Hz), 1.20–5.23 (56H, m), 6.69–8.93 (17H, m).

MASS (m/z): 1333.4 (M⁺−1).

EXAMPLE 77

MASS (m/z): 1297.3 (M⁺−1).

EXAMPLE 78

A mixture of starting compound (78) (100 mg), N-tert-butoxycarbonyl-β-alanine (13.5 mg), 1-hydroxybenzotriazole (15.5 mg), 1-ethyl-3-(3'-dimethylaminopropyl)carbodiimide hydrochloride (29.4 mg) and N,N-diisopropylethylamine (28.2 μl) in N,N-dimethylformamide (1 ml) was stirred for 3 hours at 30° C. To the reaction mixture was added ethyl acetate (30 ml). The resulting precipitate was collected by filtration and washed with diisopropyl ether to give a crude white powder (137.3 mg). The crude powder was purified by column chromatography on ODS (YMC-gel ODS-AM-S-50 (Trademark: prepared by YMC Co., Ltd.)) (30% acetonitrile aqueous solution). The fractions containing the object compound were combined, and evaporated under reduced pressure to remove acetonitrile. The residue was lyophilized to give object compound (78).

IR (KBr): 3372.9, 1658.5, 1635.3, 1546.8, 1529.3, 1517.7, 1444.4, 1255.4 cm⁻¹.

MASS (m/z): 1468.3 (M⁻−Na).

Elemental Analysis Calcd. for $C_{66}H_{90}N_{11}NaO_{23}S_2\cdot 6H_2O$: C, 49.52, H, 6.42, N, 9.63. Found: C, 49.34, H, 6.33, N, 9.73.

The following compounds [Examples 79 to 86] were obtained according to a similar manner to that of Example 78.

EXAMPLE 79

IR (KBr): 3374.8, 1658.5, 1635.3, 1529.3, 1517.7, 1444.4, 1257.4 cm⁻¹.

MASS (m/z): 1368.3 (M⁻−Na).

EXAMPLE 80

IR (KBr): 3372.9, 1656.6, 1635.3, 1531.2, 1517.7, 1444.4, 1255.4 cm⁻¹.

MASS (m/z): 1496.4 (M⁻−Na).

Elemental Analysis calcd. for $C_{68}H_{94}N_{11}NaO_{23}S_2\cdot 6H_2O$: C, 50.15, H, 6.56, N, 9.46. Found: C, 49.90, H, 6.36, N, 9.34.

EXAMPLE 81

IR (KBr): 3392.2, 1664.3, 1635.3, 1446.4, 1255.4 cm⁻¹.

MASS (m/z): 1611.5 (M⁻−Na).

Elemental Analysis Calcd. for $C_{73}H_{103}N_{12}NaO_{25}S_2\cdot 7H_2O$: C, 49.76, H, 6.69, N, 9.54. Found: C, 49.73, H, 6.59, N, 9.46.

EXAMPLE 82

IR (KBr): 3372.9, 1658.5, 1635.3, 1546.6, 1531.2, 1517.7, 1444.4, 1255.4 cm⁻¹.

MASS (m/z): 1498.5 (M⁻−Na).

Elemental Analysis Calcd. for $C_{67}H_{92}N_{11}NaO_{24}S_2\cdot 8H_2O$: C, 48.28, H, 6.53, N, 9.24. Found: C, 48.50, H, 6.35, N, 9.21.

EXAMPLE 83

IR (KBr): 3378.7, 1658.5, 1635.3, 1546.6, 1529.3, 1517.7, 1446.4, 1255.4 cm⁻¹.

MASS (m/z): 1625.5 (M⁻−Na).

Elemental Analysis Calcd. for $C_{74}H_{105}N_{12}NaO_{25}S_2\cdot 8H_2O$: C, 49.55, H, 6.80, N, 9.37. Found: C, 49.70, H, 6.68, N, 9.38.

EXAMPLE 84

IR (KBr): 3367.7, 1658.5, 1635.3, 1546.6, 1529.3, 1517.7, 1444.4, 1255.4 cm⁻¹.

MASS (m/z): 1634.6 (M⁻−Na).

Elemental Analysis Calcd. for $C_{74}H_{100}N_{13}NaO_{25}S_2\cdot 7H_2O$: C, 49.80, H, 6.44, N, 10.20. Found: C, 49.71, H, 6.34, N, 10.29.

EXAMPLE 85

IR (KBr): 3355.5, 1658.5, 1635.3, 1546.6, 1531.2, 1517.7, 1446.4, 1257.4 cm⁻¹.

MASS (m/z): 1693.5 (M⁻−Na).

Elemental Analysis Calcd. for $C_{80}H_{101}N_{12}NaO_{25}S_2\cdot 7H_2O$: C, 52.11, H, 6.29, N, 9.12. Found: C, 51.96, H, 6.28, N, 9.06.

EXAMPLE 86

IR (KBr): 3372.9, 1658.5, 1635.3, 1546.6, 1531.2, 1517.7, 1446.4, 1257.4 cm⁻¹.

MASS (m/z): 1645.4 (M⁻−Na).

Elemental Analysis Calcd. for $C_{76}H_{101}N_{12}NaO_{25}S_2\cdot 8H_2O$: C, 52.32, H, 6.50, N, 9.27. Found: C, 50.56, H, 6.37, N, 9.29.

The following compounds [Examples 87 to 95] were obtained according to a similar manner to that of Preparation 10.

EXAMPLE 87

IR (KBr): 2935, 1651, 1541, 1514, 1454, 1514, 1257 cm⁻¹.

NMR (DMSO-d₆+D₂O, δ): 0.97 (3H, d, J=6.7 Hz), 1.12 (3H, br s), 1.20–5.00 (44H, m), 3.21 43H, s), 3.31 (2H, t,

J=6.4 Hz), 4.07 (2H, t, J=6.2 Hz), 6.70–6.80 (2H, m), 7.00 (1H, s), 7.14 (2H, d, J=8.9 Hz), 7.98 (2H, d, J=8.9 Hz), 8.09 (4H, br s).

MASS (m/z): 1443.3 (M$^+$+Na).

Elemental Analysis Calcd. for $C_{62}H_{81}N_{10}O_{23}S_2Na.7H_2O$: C, 48.12, H, 6.19, N, 9.05. Found: C, 47.94, H, 6.07, N, 8.99.

EXAMPLE 88

MASS (m/z): 1492 (M$^+$).

EXAMPLE 89

IR (KBr): 3490, 3463, 3455, 3423, 3363, 2937, 1631, 1544 cm$^{-1}$.

NMR (DMSO-d$_6$, δ): 0.97 (3H, d, J=6.6 Hz), 1.21 (3H, d, J=5.4 Hz), 1.20–1.40 (9H, m), 1.40–2.40 (12H, m), 2.90–3.20 (3H, m), 3.21 (3H, s), 3.33 (3H, t, J=6.4 Hz), 3.65–4.30 (9H, m), 4.40–5.00 (6H, m), 5.11–5.30 (6H, m), 5.80–6.10 (1H, m), 6.69–6.80 (2H, m), 6.96 (1H, br s), 7.13 (1H, br s), 7.40–7.90 (3H, m), 8.00–8.30 (7H, m), 8.47 (2H, d, J=8.3 Hz), 8.72 (1H, br s), 8.75–8.90 (1H, m).

MASS (m/z) (API-ES-Negative): 1415 (M$^+$−1−Na).

Elemental Analysis Calcd. for $C_{62}H_{81}N_{10}NaO_{24}S_2.2.5H_2O$: C, 50.20, H, 5.80, N, 9.45. Found: C, 50.05, H, 5.80, N, 9.29.

EXAMPLE 90

IR (KBr): 3369, 1639, 1542, 1519, 1272 cm$^{-1}$.

NMR (DMSO-d$_6$, δ): 0.97 (3H, d, J=6.7 Hz), 1.14 (3H, d, J=5.8 Hz), 1.20–1.35 (12H, m), 1.35–1.70 (6H, m), 1.70–2.40 (6H, m), 3.17 (3H, s), 3.25 (3H, t, J=6.3 Hz), 3.30–3.50 (2H, m), 3.60–4.30 (9H, m), 4.40–4.90 (6H, m), 5.10–5.30 (6H, m), 5.80–5.90 (1H, m), 6.71 (1H, d, J=8.2 Hz), 6.60–6.80 (1H, m), 6.96 (1H, br s), 7.00–7.20 (1H, m), 7.40–7.90 (3H, m), 8.00–8.20 (6H, m), 8.48 (2H, d, J=8.4 Hz), 8.72 (1H, br s), 8.70–8.8 (1H, m).

MASS (m/z): 1441 (M$^+$−1−Na).

Elemental Analysis Calcd. for $C_{64}H_{85}N_{10}NaO_{24}S_2.6H_2O$: C, 48.82, H, 6.17, N, 8.90. Found: C, 48.83, H, 6.24, N, 8.78.

EXAMPLE 91

IR (KBr): 3363, 2935, 1637, 1626, 1540, 1261 cm$^{-1}$.

NMR (DMSO-d$_6$, δ): 0.97 (3H, d, J=6.8 Hz), 1.13 (3H, d, J=5.8 Hz), 1.30–1.60 (12H, m), 1.70–2.50 (7H, m), 2.80–3.25 (3H, m), 3.21 (3H, s), 3.30 (2H, t, J=6.5 Hz), 3.65–4.30 (12H, m), 4.40–5.00 (9H, m), 5.10–5.40 (7H, m), 5.80–6.05 (1H, m), 6.71 (1H, d, J=8.1 Hz), 6.75 (1H, dd, J=8.3 and 1.6 Hz), 6.96 (1H, d, J=1.6 Hz), 7.10 (1H, br s), 7.20 (1H, d, J=8.8 Hz), 7.40–7.80 (3H, m), 8.00–8.20 (7H, m), 8.72 (1H, br s), 8.70–8.80 (1H, m).

MASS (m/z) (API-ES-Negative): 1367 (M$^+$+1−Na).

Elemental Analysis Calcd. for $C_{62}H_{81}N_{10}NaO_{23}S.6H_2O$: C, 69.70, H, 6.21, N, 9.35. Found: C, 49.86, H, 6.22, N, 9.35.

EXAMPLE 92

IR (KBr): 3363, 2933, 2859, 1637, 1540, 1510, 1444, 1261 cm$^{-1}$.

NMR (DMSO-d$_6$, δ): 0.97 (3H, d, J=6.7 Hz), 1.13 (3H, d, J=5.8 Hz), 1.28–1.60 (15H, m), 1.69–2.45 (8H, m), 2.80–3.30 (3H, m), 3.20 (3H, s), 3.26 (2H, t, J=6.4 Hz), 3.60–4.30 (12H, m), 4.40–5.00 (9H, m), 5.10–5.30 (7H, m), 5.75–6.05 (1H, m), 6.68 (1H, d, J=8.1 Hz), 6.75 (1H, dd, J=1.7 and 8.3 Hz), 6.96 (1H, d, J=1.7 Hz), 7.10–7.20 (1H, m), 7.15 (2H, d, J=8.9 Hz), 7.40–7.90 (3H, m), 8.00–8.20 (7H, m), 8.60–8.80 (2H, m).

MASS (m/z) (APCI-ES-Negative): 1395 (M$^+$+1−Na).

Elemental Analysis Calcd. for $C_{64}H_{85}N_{10}NaO_{23}S.6H_2O$: C, 50.36, H, 6.36, N, 9.18. Found: C, 50.22, H, 6.31, N, 9.10.

EXAMPLE 93

MASS (m/z): 1461.4 (M$^+$−1).

EXAMPLE 94

MASS (m/z): 1489.5 (M$^+$−1).

EXAMPLE 95

NMR (DMSO-d$_6$, δ): 0.87 (3H, d, J=6.3 Hz), 0.97 (3H, d, J=6.7 Hz), 1.14–5.29 (81H, m), 6.69–8.72 (18H, m).

MASS (m/z): 1418.4 (free).

The following compounds [Examples 96 to 117] were obtained according to a similar manner to that of Example 19.

EXAMPLE 96

IR (KBr): 1632, 1539, 1520, 1443 cm$^{-1}$.

NMR (DMSO-d$_6$+D$_2$O, δ): 0.97 (3H, d, J=6.64 Hz), 1.07 (3H, d, J=5.68 Hz), 1.15–1.70 (3H, m), 1.70–2.50 (5H, m), 2.70–3.40 (5H, m), 4.10–4.60 (8H, m), 4.70–4.85 (2H, m), 5.00–5.35 (2H, m), 5.70–6.10 (1H, m), 6.50–6.80 (2H, m), 6.99 (1H, s).

ESI MASS (m/z) (Positive): 1019.3 (M$^+$+Na).

Elemental Analysis Calcd. for $C_{39}H_{57}N_8O_{19}SNa.8H_2O$: C, 41.05, H, 6.45, N, 9.82. Found: C, 41.02, H, 6.19, N, 9.73.

EXAMPLE 97

IR (KBr): 1647, 1635, 1539, 1518, 1439, 1269 cm$^{-1}$.

NMR (DMSO-d$_6$+D$_2$O, δ): 0.95 (3H, d, J=6.66 Hz), 1.12 (3H, d, J=5.76 Hz), 1.20–1.60 (4H, m), 1.70–2.45 (4H, m), 2.65–3.35 (6H, m), 3.70–4.55 (16H, m), 4.60–4.80 (2H, m), 5.10–5.40 (2H, m), 5.70–6.00 (1H, m), 6.75 (1H, d, J=8.15 Hz), 6.83 (1H, d, J=10.1 Hz), 7.09 (1H, s).

ESI MASS (m/z) (Negative): 989.3 (M$^+$).

Elemental Analysis Calcd. for $C_{39}H_{58}N_8O_{20}SNa.5H_2O$: C, 43.33, H, 6.34, N, 10.37. Found: C, 43.17, H, 6.25, N, 10.30.

EXAMPLE 98

IR (KBr): 1680, 1662, 1639, 1539, 1514, 1439 cm$^{-1}$.

NMR (DMSO-d$_6$+D$_2$O, δ): 0.98 (3H, d, J=6.77 Hz), 1.09 (3H, d, J=6.01 Hz), 1.15–1.40 (1H, m), 1.45–2.00 (4H, m), 2.10–2.50 (4H, m), 2.70–2.90 (3H, m), 3.15–3.40 (4H, m), 3.70–4.00 (6H, m), 4.10–4.50 (6H, m), 4.75–4.80 (2H, m), 6.70–6.80 (2H, m), 7.03 (1H, s).

ESI MASS (m/z) (Positive): 892.2 (M$^+$+1).

Elemental Analysis Calcd. for $C_{35}H_{54}N_8O_{17}S.4H_2O$: C, 43.65, H, 6.49, N, 11.64. Found: C, 43.51, H, 6.40, N, 11.48.

EXAMPLE 99

NMR (DMSO-d$_6$+D$_2$O, δ): 0.96 (3H, d, J=6.69 Hz), 1.09 (3H, d, J=5.05 Hz), 1.15–2.40 (8H, m), 2.65–3.30 (3H, m), 3.70–4.90 (18H, m), 6.65–6.85 (2H, m), 6.99 (1H, s).

ESI MASS (m/z) (Positive): 1013.4 (M$^+$+Na).

EXAMPLE 100

IR (KBr): 3377, 2935, 1658.5, 1641, 1531, 1518, 1444, 1284, 1257, 1113, 1088, 1043 cm$^{-1}$.

NMR (DMSO-d$_6$, δ): 0.96 (3H, d, J=6.7 Hz), 1.05 (3H, d, J=5.6 Hz), 3.21 (3H, s), 4.07 (2H, t, J=6.5 Hz), 1.2–5.2 (57H, complex m), 6.70 (1H, d, J=8.1 Hz), 6.78–6.83 (1H, m), 6.99 (1H, br s), 7.13 (2H, d, J=8.8 Hz), 7.4–7.6 (2H, m), 7.7–7.9 (1H, m), 7.97 (2H, d, J=8.8 Hz), 8.09 (4H, s), 8.50–8.60 (1H, m), 8.71 (1H, s), 8.68–8.80 (1H, m).

MASS (m/z): 14,07.3 (M$^+$).

Elemental Analysis Calcd. for C$_{64}$H$_{85}$N$_{11}$O$_{21}$S$_2$·7H$_2$O: C, 50.09, H, 6.50, N, 10.04. Found: C, 50.01, H, 6.41, N, 9.91.

EXAMPLE 101

NMR (DMSO-d$_6$, δ): 0.96 (3H, d, J=6.8 Hz), 1.1–5.6 (72H, m), 6.6–6.9 (2H, m), 6.99 (1H, s), 7.14 (2H, d, J=8.9 Hz), 7.97 (2H, d, J=8.7 Hz), 8.08 (4H, s), 7.4–9.0 (6H, m).

MASS (m/z): 1411.3 (M$^-$–1).

EXAMPLE 102

IR (KBr): 3384.5, 1658.5, 1635.3, 1444.4, 1257.4 cm$^{-1}$.

NMR (DMSO-d$_6$, δ): 0.96 (3H, d, J=6.7 Hz), 1.14 (3H, d, J=5.3 Hz), 1.3–5.4 (62H, m), 6.70 (1H, d, J=8.2 Hz), 6.77 (1H, d, J=9.8 Hz), 6.96 (1H, s), 7.13 (2H, d, J=8.9 Hz), 7.97 (2H, d, J=8.8 Hz), 8.05 (2H, d, J=8.83 Hz), 8.11 (2H, d, J=8.9 Hz), 7.4–9.0 (6H, m).

MASS (m/z): 1354.3 (M$^-$–1).

EXAMPLE 103

IR (KBr): 3401.8, 1664.3, 1635.3, 1627.6, 1446.4, 1257.4 cm$^{-1}$.

NMR (DMSO-d$_6$, δ): 0.96 (3H, d, J=6.8 Hz), 1.0–5.6 (69H, m), 6.68 (1H, d, J=8.1 Hz), 6.78 (1H, d, J=8.7 Hz), 6.93 (1H, d, J=8.4 Hz), 7.13 (2H, d, J=8.8 Hz), 7.97 (2H, d, J=8.8 Hz), 8.08 (4H, s), 7.4–9.0 (6H, m).

MASS (m/z): 1382.4 (M$^-$–1).

EXAMPLE 104

IR (KBr): 3403.7, 1664.3, 1635.3, 1446.4, 1257.4 cm$^{-1}$.

NMR (DMSO-d$_6$, δ): 0.96 (3H, d, J=6.6 Hz), 1.0–5.5 (71H, m), 7.13 (2H, d, J=8.9 Hz), 7.97 (2H, d, J=8.8 Hz), 6.6–8.9 (13H, m).

MASS (m/z): 1420.2 (M$^+$+Na).

EXAMPLE 105

IR (KBr): 3367.1, 1635.3, 1531.2, 1517.7, 1444.4, 1257.4 cm$^{-1}$.

NMR (DMSO-d$_6$, δ): 0.97 (3H, d, J=6.8 Hz), 1.12 (3H, d, J=5.9 Hz), 1.2–5.4 (64H, m), 6.70 (1H, d, J=8.1 Hz), 6.77 (1H, d, J=10.0 Hz), 6.99 (1H, s), 7.14 (2H, d, J=8.9 Hz), 7.44 (1H, d, J=8.6 Hz), 7.62 (1H, m), 7.78 (1H, m), 7.97 (2H, d, J=8.8 Hz), 8.05 (2H, d, J=8.8 Hz), 8.11 (2H, d, J=8.7 Hz), 8.1–8.3 (1H, m), 8.6–8.9 (2H, m).

MASS (m/z): 1368.5 (M$^-$–1).

Elemental Analysis Calcd. for C$_{62}$H$_{87}$N$_{11}$O$_{20}$S$_2$·8H$_2$O: C, 49.16, H, 6.85, N, 10.17. Found: C, 49.29, H, 6.50, N, 10.08.

EXAMPLE 106

IR (KBr): 2935.1, 2865.7, 1648.8, 1538.9, 1513.8, 1452.1, 1440.6, 1257.4 cm$^{-1}$.

NMR (DMSO-d$_6$+D$_2$O, δ): 0.97 (3H, d, J=6.3 Hz), 1.11 (3H, d, J=5.7 Hz), 1.2–4.9 (55H, complex m), 3.21 (3H, s), 3.31 (2H, t, J=6.5 Hz), 6.7–6.81 (2H, m), 7.03 (1H, br s), 7.14 (2H, d, J=8.9 Hz), 7.98 (2H, d, J=8.9 Hz), 8.0–8.15 (4H, m).

MASS (m/z): 1463.4 (M$^+$–1).

Elemental Analysis Calcd. for C$_{67}$H$_{92}$N$_{12}$O$_{21}$S$_2$·7H$_2$O: C, 50.56, H, 6.71, N, 10.56. Found: C, 50.34, H, 6.38, N, 10.46.

EXAMPLE 107

IR (KBr): 2933, 2860, 1657, 1635, 1529, 1516, 1444, 1387, 1257, 1178, 1115, 1088, 1043 cm$^{-1}$.

NMR (DMSO-d$_6$+D$_2$O, δ): 0.97 (3H, d, J=6.7 Hz), 1.12 (3H, d, J=5.9 Hz), 1.4–4.85 (50H, complex m), 3.21 (3H, s), 3.31 (2H, t, J=6.3 Hz), 6.7–6.8 (2H, m), 7.02 (1H, br s), 7.14 (2H, d, J=8.9 Hz), 7.97 (2H, d, J=8.9 Hz), 8.02–8.14 (4H, m).

MASS (m/z): 1381.4 (M$^+$–1).

Elemental Analysis Calcd. for C$_{63}$H$_{87}$N$_{11}$O$_{20}$S$_2$·6H$_2$O: C, 50.76, H, 6.69, N, 10.34. Found: C, 50.43, H, 6.70, N, 10.20.

EXAMPLE 108

IR (KBr): 2935, 2866, 1660, 1631.5, 1525, 1442.5, 1412, 1257, 1178, 1111, 1088, 1043 cm$^{-1}$.

NMR (DMSO-d$_6$, δ): 0.97 (3H, d, J=6.7 Hz), 1.10 (3H, d, J=5.5 Hz), 1.2–4.9 (55H, complex m), 3.21 (3H, s), 3.31 (2H, t, J=6.4 Hz), 6.75 (2H, br), 7.05 (1H, br), 7.14 (2H, d, J=8.8 Hz), 7.99 (2H, d, J=8.8 Hz), 8.01–8.16 (4H, m).

MASS (m/z): 1510.5 (M$^+$–1).

Elemental Analysis Calcd. for C$_{68}$H$_{94}$N$_{12}$O$_{23}$S$_2$·7H$_2$O: C, 49.87, H, 6.65, N, 10.26. Found: C, 49.64, H, 6.57, N, 10.15.

EXAMPLE 109

IR (KBr): 3372.9, 1658.5, 1635.3, 1529.3, 1517.7, 1446.4, 1255.4 cm$^{-1}$.

NMR (DMSO-d$_6$, δ): 0.97 (3H, d, J=6.7 Hz), 1.15 (3H, d, J=5.1 Hz), 1.2–5.6 (58H, m), 6.71 (1H, d, J=8.1 Hz), 6.77 (1H, d, J=10.0 Hz), 6.97 (1H, s), 7.13 (2H, d, J=8.9 Hz), 7.97 (2H, d, J=8.8 Hz), 8.09 (4H, s), 7.3–9.0 (7H, m).

MASS (m/z): 1510.5 (M$^-$–Na).

Elemental Analysis Calcd. for C$_{61}$H$_{82}$N$_{11}$NaO$_{21}$S$_2$·8H$_2$O: C, 47.68, H, 6.43, N, 10.03. Found: C, 49.75, H, 6.19, N, 10.23.

EXAMPLE 110

IR (KBr): 3374.8, 1656.5, 1635.3, 1529.3, 1517.7, 1444.4, 1257.4 cm$^{-1}$.

NMR (DMSO-d$_6$, δ): 0.98 (3H, d, J=6.8 Hz), 1.13 (3H, d, J=5.6 Hz), 1.2–5.4 (64H, m), 6.71 (1H, d, J=8.1 Hz), 6.78 (1H, d, J=10.0 Hz), 7.03 (1H, s), 7.13 (2H, d, J=8.9 Hz), 7.97 (2H, d, J=8.7 Hz), 8.0–8.2 (4H, m), 7.3–9.0 (7H, m).

MASS (m/z): 1410.54 (M$^-$–Na).

Elemental Analysis Calcd. for C$_{64}$H$_{88}$N$_{11}$NaO$_{21}$S$_2$·6H$_2$O: C, 49.83, H, 6.53, N, 9.99. Found: C, 49.72, H, 6.40, N, 9.99.

EXAMPLE 111

IR (KBr): 3374.8, 1658.5, 1635.3, 1546.6, 1531.2, 1517.7, 1444.4, 1257.4 cm$^{-1}$.

NMR (DMSO-d$_6$, δ): 0.97 (3H, d, J=6.7 Hz), 1.14 (3H, d, J=5.4 Hz), 1.2–5.6 (62H, m), 6.71 (1H, d, J=8.2 Hz), 6.78 (1H, d, J=9.8 Hz), 7.02 (1H, s), 7.13 (2H, d, J=8.9 Hz), 7.97 (2H, d, J=8.8 Hz), 8.06 (2H, d, J=9.1 Hz), 8.11 (2H, d, J=8.8 Hz), 7.3–9.0 (7H, m).

MASS (m/z): 1396.4 (M⁻−Na).

Elemental Analysis Calcd. for $C_{63}H_{86}N_{11}NaO_{21}S_2.7H_2O$: C, 48.92, H, 6.52, N, 9.96. Found: C, 48.92, H, 6.32, N, 9.85.

EXAMPLE 112

IR (KBr): 3359.4, 1658.5, 1635.3, 1546.6, 1531.2, 1517.7, 1444.4, 1257.4 cm⁻¹.

NMR (DMSO-d₆, δ): 0.97 (3H, d, J=6.6 Hz), 1.16 (3H, d, J=35.8 Hz), 1.2–5.8 (64H, m), 6.71 (1H, d, J=8.1 Hz), 6.77 (1H, d, J=9.7 Hz), 6.98 (1H, s), 7.13 (2H, d, J=8.9 Hz), 7.97 (2H, d, J=8.7 Hz), 8.08 (4H, s), 7.3–9.0 (7H, m).

MASS (m/z): 1411.4 (M⁻−Na).

Elemental Analysis Calcd. for $C_{63}H_{85}N_{12}NaO_{21}S_2.7_2O$: C, 48.45, H, 6.52, N, 10.76. Found: C, 48.44, H, 6.32, N, 10.62.

EXAMPLE 113

IR (KBr): 3374.8, 1658.5, 1635.3, 1546.6, 1531.2, 1517.7, 1444.4, 1257.4 cm⁻¹.

NMR (DMSO-d₆, δ): 0.96 (3H, d, J=6.5 Hz), 1.11 (3H, d, J=4.5 Hz), 1.2–5.8 (60H, m), 6.68 (1H, d, J=8.0 Hz), 6.80 (1H, d, J=7.9 Hz), 6.93 (1H, d, J=9.5 Hz), 7.13 (2H, d, J=8.8 Hz), 7.97 (2H, d, J=8.7 Hz), 8.08 (4H, s), 7.3–9.0 (7H, m).

MASS (m/z): 1398.4 (M⁻−Na).

EXAMPLE 114

IR (KBr): 3374.8, 1658.5, 1635.3, 1546.6, 1531.2, 1517.7, 1444.4, 1257.4 cm⁻¹.

NMR (DMSO-d₆, δ): 0.97 (3H, d, J=6.5 Hz), 1.15 (3H, d, J=5.8 Hz), 1.2–5.6 (65H, m), 6.70 (1H, d, J=8.2 Hz), 6.77 (1H, d, J=9.8 Hz), 6.97 (1H, s), 7.13 (2H, d, J=8.8 Hz), 7.97 (2H, d, J=8.7 Hz), 8.08 (4H, s), 7.3–9.0 (7H, m).

MASS (m/z): 1398.4 (M⁻−Na).

Elemental Analysis Calcd. for $C_{64}H_{89}N_{12}NaO_{21}S_2.9H_2O$: C, 47.69, H, 6.69, N, 10.43. Found: C, 47.78, H, 6.32, N, 10.17.

EXAMPLE 115

MASS (m/z): 1434.4 (M⁻−Na).

EXAMPLE 116

IR (KBr): 3348, 1658.5, 1633 cm⁻¹.

NMR (DMSO-d₆+D₂O, δ): 0.82–0.89 (3H, m), 0.95–1.03 (6H, m), 1.1–4.78 (57H, complex m), 6.7–6.8 (2H, m), 7.03 (1H, br s).

MASS (m/z): 1128.5 (M⁺−1).

Elemental Analysis Calcd. for $C_{51}H_{84}N_8O_{18}S.5H_2O$: C, 50.23, H, 7.77, N, 9.19. Found: C, 50.10, H, 7.78, N, 9.09.

EXAMPLE 117

NMR (DMSO-d₆, δ): 0.98 (3H, d, J=6.6 Hz), 1.10 (3H, d, J=5.4 Hz), 0.74–2.69 (22H, m), 2.80–3.05 (3H, m), 3.15–4.62 (18H, m), 4.68–5.35 (8H, m), 6.71 (1H, d, J=8.1 Hz), 6.78 (1H, d, J=8.1 Hz), 7.01 (1H, s), 7.12 (2H, d, J=8.6 Hz), 7.37–8.10 (3H, m), 7.73 (4H, d, J=8.5 Hz), 7.97 (2H, d, J=8.3 Hz), 8.22–8.40 (1H, m), 6.65–8.88 (2H, m).

MASS (m/z): 1224.4 (M⁺−1).

EXAMPLE 118

To a solution of a mixture of starting compound (118) (440 mg), 1-1-dimethyl-4-oxo-piperidinium Iodide (122 mg) and acetic acid (55 μl) in a mixture of methanol (6 ml) and DMF (3 ml) was added sodium cyanoborohydride (30 mg) with stirring at ambient temperature, and the mixture was stirred at the same temperature overnight. To the reaction mixture was added ethyl acetate and the resulting precipitates were collected by filtration and dried in vacuo. The precipitates were dissolved in a mixture of pH 6.86 standard buffer solution and acetonitrile, and the solution was subjected to column chromatography on ODS (Daisogel, SP-120-40/60-ODS-B (Trademark: prepared by Daiso Co., Ltd.)) eluting with 30% acetonitrile in water. The fractions containing the object compound were collected and evaporated under reduced pressure to remove acetonitrile. The residue was lyophilized to give object compound (118) (350 mg).

IR (KBr): 3353, 2942, 1673, 1633, 1517, 1463, 1438, 1268, 1232, 1201, 1135, 1085, 1045 cm⁻¹.

NMR (DMSO-d₆, δ): 0.98 (3H, d, J=6.7 Hz), 1.10 (3H, d, J=5.7 Hz), 1.3–1.6 (6H, m), 1.6–2.7 (17H, m), 2.7–4.2 (37H, m), 4.2–4.6 (7H, m), 4.80 (2H, d, J=6.7 Hz), 5.2 (1H, m), 5.4 (1H, m), 6.77 (2H, m), 7.05 (1H, s), 7.08 (2H, d, J=8.3 Hz), 7.45 (1H, d, J=8.8 Hz), 7.56 (1H, d, J=7.5 Hz), 7.75 (2H, d, J=8.8 Hz), 7.90 (1H, m), 7.96 (4H, s), 8.40 (1H, d, J=7.2 Hz), 8.6 (1H, m), 8.70 (1H, d, J=6.9 Hz), 8.79 (1H, s).

MASS (m/z): 1513.3 (M⁺+Na).

The following compounds [Examples 119 to 137] were obtained according to a similar manner to that of Example

EXAMPLE 119

IR (KBr): 3353, 2937, 1673, 1635, 1529, 1517, 1463, 1436, 1230, 1199, 1133, 1085, 1045 cm⁻¹.

NMR (DMSO-d₆, δ): 0.98 (3H, d, J=6.7 Hz), 1.10 (3H, d, J=5.7 Hz), 1.30 (4H, m), 1.50 (6H, m), 1.6–2.7 (17H, m), 2.7–4.2 (37H, m), 4.2–4.6 (7H, m), 4.80 (2H, d, J=6.7 Hz), 5.14 (1H, m), 5.35 (1H, m), 6.72 (1H, d, J=8.8 Hz), 6.80 (1H, d, J=8.8 Hz), 7.05 (1H, s), 7.08 (2H, d, J=8.8 Hz), 7.45 (1H, d, J=8.8 Hz), 7.56 (1H, d, J=7.5 Hz), 7.75 (2H, d, J=8.8 Hz), 7.91 (1H, m), 7.96 (4H, s), 8.40 (1H, d, J=7.2 Hz), 8.6 (1H, m), 8.70 (1H, d, J=6.9 Hz), 8.80 (1H, s).

MASS (m/z): 1541.6 (M⁺+Na).

Elemental Analysis Calcd. for $C_{71}H_{99}N_{13}O_{20}S_2.2TFA.9H_2O$: C, 47.19, H, 6.28, N, 9.54. Found: C, 47.13, H, 6.01, N, 9.47.

EXAMPLE 120

IR (KBr): 3355, 2937, 1673, 1635, 1529, 1519, 1444, 1276, 1253, 1201, 1135, 1085, 1045 cm⁻¹.

NMR (DMSO-d₆, δ): 0.95 (3H, d, J=6.7 Hz), 0.98 (3H, d, J=6.7 Hz), 1.10 (3H, d, J=5.7 Hz), 1.56 (5H, m), 1.6–2.7 (17H, m), 2.8–3.8 (26H, m), 3.8–4.2 (9H, m), 4.2–4.6 (7H, m), 4.8 (3H, m), 5.17 (1H, m), 5.4 (1H, m), 6.71 (1H, d, J=8.2 Hz), 6.80 (1H, d, J=8.2 Hz), 7.05 (1H, s), 7.20 (2H, d, J=8.8 Hz), 7.44 (1H, d, J=7.8 Hz), 7.62 (1H, d, J=7.8 Hz), 7.8 (1H, m), 7.93 (2H, d, J=8.8 Hz), 8.07 (2H, d, J=8.8 Hz), 8.11 (2H, d, J=8.8 Hz), 8.30 (1H, d, J=7.8 Hz), 8.67 (1H, m), 8.85 (1H, d, J=7.8 Hz).

MASS (m/z): 1465.9 (M⁺+Na).

Elemental Analysis Calcd. for $C_{68}H_{95}N_{13}O_{18}S_2.4TFA.8H_2O$: C, 44.60, H, 5.66, N, 8.90. Found: C, 44.70, H, 5.59, N, 8.95.

EXAMPLE 121

IR (KBr): 3355.5, 1635.3, 1533.1, 1515.8, 1417.4, 1257.4 cm$^{-1}$.

NMR (DMSO-d$_6$, δ): 0.97 (3H, d, J=6.6 Hz), 1.14 (3H, d, J=5.4 Hz), 1.2–5.6 (68H, m), 6.71 (1H, d, J=8.1 Hz), 6.78 (1H, d, J=9.5 Hz), 7.02 (1H, s), 7.14 (2H, d, J=8.8 Hz), 7.97 (2H, d, J=8.7 Hz), 8.05 (2H, d, J=8.6 Hz), 8.10 (2H, d, J=8.5 Hz), 7.4–9.0 (6H, m).

MASS (m/z): 1432.4 (M$^+$+Na).

Elemental Analysis Calcd. for $C_{65}H_{91}N_{11}O_{20}S_2 \cdot 7H_2O$: C, 50.80, H, 6.89, N, 10.03. Found: C, 50.59, H, 6.84, N, 10.00.

EXAMPLE 122

IR (KBr): 3374.8, 1648.8, 1631.5, 1538.9, 1513.8, 1450.2, 1442.5, 1257.4 cm$^{-1}$.

NMR (DMSO-d$_6$, δ): 0.98 (3H, d, J=6.8 Hz), 1.0–5.4 (65H, m), 6.6–6.9 (2H, m), 7.00 (1H, s), 7.14 (2H, d, J=8.4 Hz), 7.97 (2H, d, J=8.2 Hz), 8.05 (2H, d, J=8.7 Hz), 8.11 (2H, d, J=8.2 Hz), 7.3–9.0 (7H, m).

MASS (m/z): 1429.3 (M$^-$−1).

Elemental Analysis Calcd. for $C_{63}H_{86}N_{10}O_{22}S_3 \cdot 5H_2O$: C, 49.73, H, 6.36, N, 9.20. Found: C, 49.56, H, 6.74, N, 9.18.

EXAMPLE 123

IR (KBr): 2935, 2864, 1649, 1539, 1514, 1450, 1442.5, 1257 cm$^{-1}$.

NMR (DMSO-d$_6$+D$_2$O, δ): 0.98 (3H, d, J=6.7 Hz), 1.12 (3H, d, J=5.7 Hz), 1.2–4.9 (46H, complex m), 3.21 (3H, s), 3.31 (2H, t, J=6.4 Hz), 5.63 (1H, s), 6.7–6.8 (2H, m), 7.02 (1H, br s), 7.15 (2H, d, J=8.8 Hz), 7.32 (5H, s), 7.97 (2H, d, J=8.8 Hz), 8.06 (4H, s).

MASS (m/z): 1460.4 (M$^+$).

Elemental Analysis Calcd. for $C_{68}H_{88}N_{10}O_{22}S_2 \cdot 6H_2O$: C, 52.03, H, 6.42, N, 8.92. Found: C, 51.77, H, 6.39, N, 8.77.

EXAMPLE 124

IR (KBr): 2935, 1664.3, 1631.5, 1606.4, 1442.5, 1411.6 cm$^{-1}$.

NMR (DMSO-d$_6$+D$_2$O, δ): 0.97 (3H, d, J=6.8 Hz), 1.07 (3H, d, J=5.4 Hz), 1.33 (6H, d, J=6.3 Hz), 1.32–4.81 (46H, complex m), 3.21 (3H, s), 3.31 (2H, t, J=6.5 Hz), 6.7–6.8 (2H, m), 7.03 (1H, br s), 7.14 (2H, d, J=8.8 Hz), 7.98 (2H, d, J=8.8 Hz), 8.08 (4H, s).

MASS (m/z): 1411.5 (M$^+$−1). Elemental Analysis Calcd. for $C_{64}H_{88}N_{10}O_{22}S_2 \cdot 5H_2O$: C, 51.12, H, 6.57, N, 9.32. Found: C, 51.37, H, 6.49, N, 9.34.

EXAMPLE 125

IR (KBr): 3355, 2937, 1673, 1631, 1535, 1515, 1442, 1259, 1201, 1180, 1133, 1087, 1045 cm$^{-1}$.

NMR (DMSO-d$_6$, δ): 0.98 (3H, d, J=6.7 Hz), 1.10 (3H, d, J=5.7 Hz), 1.3–1.6 (9H, m), 1.6–2.7 (17H, m), 3.21 (3H, s), 2.8–3.6 (12H, m), 3.6–4.2 (14H, m), 4.2–4.6 (7H, m), 4.83 (3H, m), 5.0 (1H, m), 5.15 (2H, m), 5.30 (2H, m), 6.70 (1H, d, J=8.2 Hz), 6.78 (1H, d, J=8.2 Hz), 7.05 (1H, s), 7.14 (2H, d, J=8.8 Hz), 7.46 (1H, d, J=8.4 Hz), 7.57 (1H, d, J=8.4 Hz), 7.88 (1H, m), 7.97 (2H, d, J=8.8 Hz), 8.05 (2H, d, J=8.5 Hz), 8.12 (2H, d, J=8.5 Hz), 8.42 (1H, m), 8.7 (1H, m), 8.93 (1H, d, J=8.4 Hz).

MASS (m/z): 1408.94 (M$^+$−Na).

Elemental Analysis Calcd. for $C_{66}H_{93}N_{11}O_{21}S_2 \cdot 2TFA \cdot 5H_2O$: C, 47.80, H, 6.02, N, 8.76. Found: C, 47.80, H, 6.27, N, 8.90.

EXAMPLE 126

MASS (m/z): 1612.5 (M$^-$−1)+1.

EXAMPLE 127

IR (KBr): 3353.6, 1664.3, 1627.6, 1446.4, 1257.4 cm$^{-1}$.

MASS (m/z): 1454.4 (M$^-$−1).

Elemental Analysis Calcd. for $C_{86}H_{93}N_{11}O_{22}S_2 \cdot 7H_2O$: C, 50.09, H, 6.81, N, 9.73. Found: C, 49.80, H, 6.81, N, 9.73.

EXAMPLE 128

IR (KBr): 3353.6, 1658.5, 1635.3, 1517.7, 1444.4, 1255.4 cm$^{-1}$.

MASS (m/z): 1482.4 (M$^-$−1).

Elemental Analysis Calcd. for $C_{68}H_{97}N_{11}O_{22}S_2 \cdot 6H_2O$: C, 51.28, H, 6.90, N, 9.67. Found: C, 51.57, H, 6.80, N, 9.68.

EXAMPLE 129

IR (KBr): 3401.8, 1664.3, 1635.3, 1446.4, 1255.4 cm$^{-1}$.

MASS (m/z): 1496.5 (M$^-$−1).

EXAMPLE 130

Major Product

IR (KBr): 3351.7, 1658.5, 1635.3, 1517.7, 1444.4, 1255.4 cm$^{-1}$.

MASS (m/z): 1469.5 (M$^-$−1)+1.

Elemental Analysis Calcd. for $C_{67}H_{95}N_{11}O_{22}S_2 \cdot 8H_2O$: C, 49.84, H, 6.93, N, 9.54. Found: C, 49.95, H, 6.52, N, 9.37.

Minor Product

IR (KBr): 3351.7, 1664.3, 1635.3, 1529.3, 1517.7, 1446.4, 1255.4 cm$^{-1}$.

MASS (m/z): 1439.5 (M$^-$−1).

EXAMPLE 131

IR (KBr): 2935, 1649, 1539, 1514, 1452, 1257 cm$^{-1}$.

MASS (m/z): 1563.4 (M$^+$−1).

Elemental Analysis Calcd. for $C_{12}H_{100}N_{12}O_{23}S_2 \cdot 8H_2O$: C, 50.58, H, 6.84, N, 9.83. Found: C, 50.43, H, 6.69, N, 9.81.

EXAMPLE 132

MASS (m/z): 1480.4 (M$^+$−1).

EXAMPLE 133

The object compound (133) was used directly in the next reaction without purification.

EXAMPLE 134

The object compound (134) was used directly in the next reaction without purification.

EXAMPLE 135

The object compound (135) was used directly in the next reaction without purification.

EXAMPLE 136

IR (KBr): 1659, 1635, 1444, 1257 cm$^{-1}$.

NMR (DMSO-d$_6$, δ): 0.9–1.25 (6H, m), 1.25–2.6 (23H, m), 2.6–5.2 (34H, m), 6.65–6.8 (2H, m), 6.98 (2H, m), 7.13 (2H, d, J=9.0 Hz), 7.2–7.8 (3H, m), 7.97 (2H, d, J=8.8 Hz), 7.95–8.2 (5H, m), 8.4–8.8 (2H, m).

MASS (m/z): 1363 (M$^+$+23).

Elemental Analysis Calcd. for $C_{59}H_{80}N_{12}O_{20}S_2 \cdot 11H_2O$: C, 46.03, H, 6.68, N, 10.92. Found: C, 45.83, H, 6.26, N, 10.72.

EXAMPLE 137

IR (KBr): 1664, 1605, 1446, 1257 cm$^{-1}$.

NMR (DMSO-d$_6$, δ): 0.8–1.2 (6H, s), 1.2–2.7 (23H, m), 2.7–5.4 (38H, m), 6.6–7.0 (2H, m), 7.14 (2H, d, J=8.8 Hz), 7.29 (1H, s), 7.51 (1H, s), 7.4–7.9 (3H, m), 7.97 (2H, d, J=8.8 Hz), 8.0–8.3 (5H, m), 8.6–9.0 (2H, m).

MASS (m/z): 1391 (M$^+$−1).

The following compounds [Examples 138 to 192] were obtained according to a similar manner to that of Example 1.

EXAMPLE 138

IR (KBr): 1666, 1632, 1535, 1514, 1441, 1271 cm$^{-1}$.

NMR (DMSO-d$_6$+D$_2$O, δ): 0.98 (3H, d, J=6.72 Hz), 1.08 (3H, d, J=5.78 Hz), 1.35 (9H, s), 1.45–2.00 (6H, m), 2.10–2.40 (3H, m), 2.75–2.95 (3H, m), 3.10–3.40 (2H, m), 3.60–4.50 (14H, m), 4.70–4.80 (2H, m), 6.72 (1H, d, J=8.12 Hz), 6.77 (1H, d, J=9.72 Hz), 7.02 (1H, s).

ESI MASS (m/z) (Positive): 992 (M$^+$+1).

Elemental Analysis Calcd. for C$_{40}$H$_{74}$N$_8$O$_{25}$S.6H$_2$O: C, 43.71, H, 6.79, N, 10.19. Found: C, 43.75, H, 6.71, N, 10.11.

EXAMPLE 139

IR (KBr): 3324, 2975, 2937, 1631, 1610, 1529, 1519, 1465, 1446, 1240, 1176, 1085, 1045 cm$^{-1}$.

NMR (DMSO-d$_6$, δ): 0.96 (3H, d, J=6.7 Hz), 1.10 (3H, d, J=5.7 Hz), 1.18 (6H, d, J=6.2 Hz), 1.6–2.1 (3H, m), 2.1–2.6 (6H, m), 2.98 (2H, m), 3.20 (1H, m), 3.4 (2H, m), 3.73 (4H, m), 3.8–4.6 (14H, m), 4.6–5.6 (9H, m), 6.70 (1H, d, J=8.2 Hz), 6.81 (1H, d, J=8.2 Hz), 6.89 (1H, s), 7.04 (1H, s), 7.11 (2H, d, J=8.9 Hz), 7.2–7.7 (4H, m), 7.78 (2H, d, J=8.9 Hz), 7.95 (4H, s), 8.07 (1H, m), 8.54 (1H, m), 8.80 (1H, s), 8.95 (1H, s).

MASS (m/z): 1321.2 (M$^+$−1).

Elemental Analysis Calcd. for C$_{58}$H$_{74}$N$_{12}$O$_{20}$S$_2$.10H$_2$O: C, 46.33, H, 6.30, N, 11.18. Found: C, 46.26, H, 5.98, N, 11.04.

EXAMPLE 140

IR (KBr): 3355, 2937, 1633, 1629, 1529, 1517, 1467, 1446, 1253, 1176, 1114, 1083, 1045 cm$^{-1}$.

NMR (DMSO-d$_6$, δ): 0.96 (2H, d, J=6.7 Hz), 0.96 (3H, d, J=6.7 Hz), 1.10 (3H, d, J=5.7 Hz), 1.2–1.6 (8H, m), 1.6–2.1 (9H, m), 2.1–2.6 (2H, m), 3.0 (3H, m), 3.40 (2H, m), 3.75 (2H, m), 3.9–4.2 (6H, m), 4.2–4.6 (7H, m), 4.6–4.9 (3H, m), 5.0 (1H, m), 5.2 (2H, m), 5.30 (1H, d, J=4.4 Hz), 6.69 (1H, d, J=9.8 Hz), 6.78 (1H, d, J=9.8 Hz), 7.08 (1H, s), 7.15 (2H, d, J=9.0 Hz), 7.41 (1H, d, J=8.8 Hz), 7.5 (1H, m), 7.77 (1H, m), 7.88 (2H, d, J=8.8 Hz), 7.96 (4H, s), 8.34 (1H, d, J=6.3 Hz), 8.75 (1H, d, J=8.5 Hz), 8.85 (1H, m), 8.86 (1H, s).

MASS (m/z): 1306.3 (M$^+$−1).

Elemental Analysis Calcd. for C$_{58}$H$_{73}$N$_{11}$O$_{20}$S$_2$.9H$_2$O: C, 47.37, H, 6.24, N, 10.48. Found: C, 47.32, H, 6.05, N, 10.32.

EXAMPLE 141

IR (KBr): 3328, 2937, 1635, 1529, 1519, 1465, 1444, 1255, 1178, 1112, 1085, 1045 cm$^{-1}$.

NMR (DMSO-d$_6$, δ): 0.97 (3H, d, J=6.7 Hz), 1.10 (3H, d, J=5.7 Hz), 1.2 (2H, m), 1.4–2.1 (14H, m), 2.2–2.5 (3H, m), 2.90 (3H, m), 3.22 (3H, s), 3.75 (2H, m), 3.8–4.2 (9H, m), 4.2–4.6 (6H, m), 4.8 (3H, m), 5.2 (2H, m), 5.3 (1H, m), 6.70 (1H, d, J=8.2 Hz), 6.80 (1H, d, J=8.2 Hz), 7.08 (1H, s), 7.15 (2H, d, J=8.8 Hz), 7.42 (1H, d, J=8.0 Hz), 7.5 (2H, m), 7.77 (1H, m), 7.90 (2H, d, J=8.8 Hz), 7.96 (4H, s), 8.3 (1H, m), 8.73 (1H, d, J=6.5 Hz), 8.86 (1H, s).

MASS (m/z): 1324.3 (M$^+$−1).

Elemental Analysis Calcd. for C$_{58}$H$_{75}$N$_{11}$O$_{21}$S$_2$.9H$_2$O: C, 46.60, H, 6.30, N, 10.35. Found: C, 46.66, H, 6.13, N, 10.12.

EXAMPLE 142

IR (KBr): 1651, 1539, 1514, 1234 cm$^{-1}$.

NMR (DMSO-d$_6$, δ): 0.85–1.3 (12H, m), 1.5–2.6 (10H, m), 2.7–3.6 (18H, m), 3.6–5.4 (24H, m), 6.65–7.2 (9H, m), 7.3–8.0 (9H, m), 8.2–8.45 (1H, m), 8.6–8.95 (2H, m).

MASS (m/z): 1358 (M$^+$−1).

Elemental Analysis Calcd. for C$_{64}$H$_{85}$N$_{11}$O$_{20}$S.7H$_2$O: C, 51.73, H, 6.71, N, 10.36. Found: C, 51.50, H, 6.70, N, 11.31.

EXAMPLE 143

IR (KBr): 2931, 1659, 1633, 1531, 1506, 1444, 1385 cm$^{-1}$.

NMR (DMSO-d$_6$, δ): 0.83 (3H, t, J=6.7 Hz), 0.96 (3H, d, J=6.8 Hz), 1.07 (3H, d, J=5.4 Hz), 1.18–1.52 (10H, m), 1.60–2.08 (7H, m), 2.08–2.43 (2H, m), 2.79–3.03 (3H, m), 3.14–3.55 (2H, m), 3.65–4.54 (16H, m), 4.65–5.20 (9H, m), 6.74 (1H, d, J=8.2 Hz), 6.83 (1H, d, J=8.5 Hz), 6.97 (2H, d, J=8.8 Hz), 7.08 (1H, s), 7.40 (1H, d, J=9.2 Hz), 7.33–7.86 (2H, m), 7.85 (2H, d, J=8.8 Hz), 8.31 (1H, d, J=6.6 Hz), 8.58 (1H, d, J=7.8 Hz), 8.85 (1H, br s).

MASS (m/z): 1137.4 (M$^+$−1).

Elemental Analysis Calcd. for C$_{50}$O$_{74}$N$_8$O$_{20}$S.7H$_2$O: C, 47.46, H, 7.01, N, 8.86. Found: C, 47.31, H, 6.85, N, 8.78.

EXAMPLE 144

IR (KBr): 3344.0, 1672.0, 1658.5, 1664.3, 1635.3, 1446.4, 1257.4 cm$^{-1}$.

ESI MASS (m/z): 1219 (M$^+$+1).

EXAMPLE 145

IR (KBr): 2974, 2937, 1633, 1537, 1514, 1443, 1269 cm$^{-1}$.

NMR (DMSO-d$_6$, δ): 0.97 (3H, d, J=6.8 Hz), 1.13 (3H, d, J=5.6 Hz), 1.18 (3H, t, J=7.0 Hz), 1.35–2.56 (5H, m), 2.56–2.84 (46, m), 2.84–3.40 (5H, m), 3.52 (2H, q, J=7.0 Hz), 3.68–4.60 (13H, m), 4.53 (2H, s), 4.60–5.30 (8H, m), 6.71 (1H, d, J=8.2 Hz), 6.77 (1H, d, J=8.2 Hz), 6.96 (1H, s), 7.46 (2H, d, J=8.3 Hz), 7.77 (2H, d, J=8.2 Hz), 7.58–7.84 (2H, m), 7.92 (2H, d, J=8.5 Hz), 7.84–8.27 (8H, m), 8.70–8.85 (2H, m).

MASS (m/z): 1287.3 (M$^+$−1).

Elemental Analysis Calcd. for C$_{59}$H$_{72}$N$_{10}$O$_{19}$S$_2$.9H$_2$O: C, 48.82, H, 6.25, N, 9.65. Found: C, 48.73, H, 6.01, N, 9.45.

EXAMPLE 146

IR (KBr): 2939, 1633, 1606, 1535, 1525, 1444, 1419, 1358 cm$^{-1}$.

NMR (DMSO-d$_6$, δ): 0.96 (3H, d, J=6.7 Hz), 1.13 (3H, d, J=5.6 Hz), 1.33–2.78 (16H, m), 2.78–5.00 (26H, m), 4.56 (2H, s), 5.00–5.35 (2H, m), 6.70 (1H, d, J=8.1 Hz), 6.77 (1H, d, J=8.1 Hz), 6.96 (1H, s), 7.10 (2H, d, J=9.0 Hz), 7.20–7.80 (8H, m), 7.84 (2H, d, J=8.8 Hz), 8.06 (4H, s), 8.00–8.30 (1H, m), 8.40–8.80 (2H, m).

MASS (m/z): 1342.3 (M$^+$−1).

Elemental Analysis Calcd. for C$_{62}$H$_{77}$N$_{11}$O$_{19}$S$_2$.12H$_2$O: C, 47.72, H, 6.52, N, 9.87. Found: C, 47.98, H, 6.00, N, 9.72.

EXAMPLE 147

IR (KBr): 2937, 1633, 1533, 1512, 1443 cm$^{-1}$.

NMR (DMSO-d$_6$, δ): 0.98 (3H, d, J=6.8 Hz), 1.12 (3H, d, J=5.6 Hz), 1.60–2.64 (9H, m), 2.01 (2H, t, J=6.3 Hz), 2.83–3.03 (3H, m), 3.13–3.60 (2H, m), 3.27 (3H, s), 3.50 (2H, t, J=6.3 Hz), 3.68–4.58 (13H, m), 4.09 (2H, t, J=6.4 Hz), 4.70–5.30 (8H, m), 6.71 (1H, d, J=8.1 Hz), 6.78 (1H, dd, J=8.3 and 7 Hz), 7.01 (1H, d, J=1.6 Hz), 7.08 (2H, d, J=8.8 Hz), 7.45 (1H, d, J=8.4 Hz), 7.57–7.82 (2H, m), 7.73 (2H, d, J=8.8 Hz), 7.87 (2H, d, J=8.5 Hz), 8.02–8.20 (6H, m), 8.30 (1H, d, J=6.2 Hz), 8.71 (1H, br s), 8.93 (1H, d, J=7.4 Hz).

MASS (m/z): 1317.3 (M$^+$−1).

Elemental Analysis Calcd. for C$_{60}$H$_{74}$N$_{10}$O$_{20}$S$_2$·8H$_2$O: C, 49.24, H, 6.20, N, 9.57. Found: C, 48.95, H, 6.04, N, 9.36.

EXAMPLE 148

IR (KBr): 2929, 1633, 1608, 1518, 1444, 1419 cm$^{-1}$.

NMR (DMSO-d$_6$, δ): 0.86 (3H, d, J=6.4 Hz), 0.98 (3H, d, J=6.8 Hz), 1.14–1.40 (5H, m), 1.11 (3H, d, J=5.5 Hz), 1.60–2.74 (18H, m), 1.80–3.02 (3H, m), 3.02–3.58 (6H, m), 3.70–4.60 (13H, m), 4.70–5.40 (8H, m), 6.71 (1H, d, J=8.2 Hz), 6.78 (1H, dd, J=8.1 and 1.6 Hz), 7.01 (1H, d, J=1.7 Hz), 7.08 (2H, d, J=8.7 Hz), 7.25 (1H, d, J=8.8 Hz), 7.57–7.92 (2H, m), 7.45 (2H, d, J=8.4 Hz), 8.00–8.20 (4H, m), 8.31 (1H, d, J=6.4 Hz), 8.71 (1H, br s), 8.91 (1H, d, J=7.7 Hz).

MASS (m/z): 1333.4 (M$^+$−1).

Elemental Analysis Calcd. for C$_{61}$H$_{82}$N$_{12}$O$_{18}$S$_2$·9H$_2$O: C, 48.92, H, 6.73, N, 11.22. Found: C, 49.12, H, 6.71, N, 11.08.

EXAMPLE 149

IR (KBr): 2933, 2860, 1659, 1630, 1547, 1510, 1446, 1387, 1329 cm$^{-1}$.

NMR (DMSO-d$_6$, δ): 0.97 (3H, d, J=6.8 Hz), 1.07 (3H, d, J=5.2 Hz), 1.26–1.60 (10H, m), 1.60–2.08 (5H, m), 2.18 (6H, s), 2.12–2.67 (4H, m), 2.79–3.03 (3H, m), 3.10–3.50 (12H, m), 3.21 (3H, s), 3.64 (2H, t, J=6.2 Hz), 3.64–4.08 (6H, m), 4.12–4.52 (7H, m), 4.67–5.26 (8H, m), 6.65 (2H, s), 6.64–6.84 (2H, m), 6.94–7.10 (3H, m), 7.43 (1H, d, J=8.8 Hz), 7.34–7.97 (2H, m), 7.80 (2H, d, J=8.7 Hz), 8.22–8.40 (1H, m), 8.40–8.59 (1H, m), 8.72 (1H, br s).

MASS (m/z): 1325.6 (M$^+$−1).

Elemental Analysis Calcd. for C$_{62}$H$_{90}$N$_{10}$O$_{20}$S·6H$_2$O: C, 51.87, H, 7.16, N, 9.76. Found: C, 51.80, H, 7.15, N, 9.72.

EXAMPLE 150

NMR (DMSO-d$_6$, δ): 0.97 (3H, d, J=6.9 Hz), 1.07 (3H, d, J=5.2 Hz), 0.80–2.67 (21H, m), 2.77–3.00 (3H, m), 3.08–2.58 (10H, m), 3.52 (2H, t, J=6.3 Hz), 3.68–4.51 (16H, m), 4.70–5.28 (8H, m), 6.68–7.10 (9H, m), 7.43 (1H, d, J=8.8 Hz), 7.56–7.90 (2H, m), 7.80 (2H, d, J=8.8 Hz), 8.26–8.40 (1H, m), 8.40–8.55 (1H, m), 8.65–8.80 (1H, m).

MASS (m/z): 1309.5 (M$^+$−1).

EXAMPLE 151

NMR (DMSO-d$_6$, δ): 0.97 (3H, d, J=6.8 Hz), 1.10 (3H, d, J=6.0 Hz), 1.39 (9H, s), 1.65–2.83 (22H, m), 1.81–3.06 (3H, m), 3.20–4.54 (18H, m), 4.69–5.34 (8H, m), 6.71 (1H, d, J=8.1 Hz), 6.78 (1H, dd, J=8.3 and 1.8 Hz), 6.70–6.90 (1H, m), 6.98–7.14 (3H, m), 7.44 (1H, d, J=8.8 Hz), 7.68 (2H, d, J=8.7 Hz), 7.72 (2H, d, J=8.3 Hz), 7.38–7.86 (2H, m), 7.95 (2H, d, J=8.5 Hz), 8.33 (1H, d, J=6.8 Hz), 8.70 (1H, br s), 8.75 (1H, d, J=7.7 Hz).

MASS (m/z): 1324.5 (M$^+$−1).

EXAMPLE 152

IR (KBr): 1632, 1514, 1452, 1234 cm$^{-1}$.

NMR (DMSO-d$_6$, δ): 0.9–1.3 (12H, m), 1.5–2.6 (11H, m), 2.7–3.6 (18H, m), 3.6–5.3 (23H, m), 6.7–7.2 (9H, m), 7.4–7.55 (1H, m), 7.6–7.85 (7H, m), 7.94 (2H, d, J=8.3 Hz), 8.2–8.4 (1H, m), 8.65–8.8 (1H, m).

MASS (m/z): 1266 (M$^+$+23).

Elemental Analysis Calcd. for C$_{64}$H$_{85}$N$_{11}$O$_{19}$S·7H$_2$O: C, 52.27, H, 6.79, N, 10.48. Found: C, 52.00, H, 6.61, N, 10.42.

EXAMPLE 153

NMR (DMSO-d$_6$, δ): 0.8–1.3 (6H, m), 1.4–2.6 (13H, m), 2.6–3.6 (15H, m), 3.7–5.3 (21H, m), 6.65–6.9 (2H, m), 6.96 (1H, s), 7.15 (2H, d, J=8.3 Hz), 7.35–7.8 (7H, m), 7.86 (2H, d, J=8.7 Hz), 7.9–8.2 (5H, m), 8.6–8.9 (2H, m).

MASS (m/z): 1376 (M$^+$−23).

EXAMPLE 154

IR (KBr): 3380.6, 1645.0, 1631.5, 1608.3, 1538.9, 1515.8, 1442.5, 1419.4, 1268.9, 1240.0 cm$^{-1}$.

NMR (DMSO-d$_6$, δ): 0.98 (3H, d, J=6.8 Hz), 1.11 (3H, d, J=5.6 Hz), 1.2–5.4 (48H, m), 6.71 (1H, d, J=8.2 Hz), 6.7–6.9 (1H, m), 7.01 (1H, d, J=1.8 Hz), 7.07 (2H, d, J=9.1 Hz), 7.45 (1H, d, J=9.2 Hz), 7.5–7.9 (2H, m), 7.83 (2H, d, J=8.9 Hz), 8.07 (4H, s), 8.30 (1H, d, J=5.9 Hz), 8.5–8.8 (1H, m), 8.90 (1H, d, J=7.8 Hz).

MASS (m/z): 1236.3 (M$^-$−1).

Elemental Analysis Calcd. for C$_{55}$H$_{71}$N$_{11}$O$_{18}$S$_2$·10H$_2$O: C, 46.57, H, 6.47, N, 10.86. Found: C, 46.74, H, 6.12, N, 10.75.

EXAMPLE 155

IR (KBr): 3359.4, 1645.0, 1631.5, 1538.9, 1515.8, 1438.6, 1255.4 cm$^{-1}$.

NMR (DMSO-d$_6$, δ): 0.91 (3H, t, J=7.1 Hz), 0.97 (3H, d, J=6.8 Hz), 1.10 (3H, d, J=5.8 Hz), 1.2–5.4 (46H, m), 6.71 (1H, d, J=8.1 Hz), 6.7–6.9 (1H, m), 7.00 (1H, d, J=1.6 Hz), 7.08 (2H, d, J=8.9 Hz), 7.45 (1H, d, J=8.3 Hz), 7.5–8.1 (3H, m), 7.80 (2H, d, J=8.4 Hz), 7.91 (2H, d, J=8.8 Hz), 7.98 (2H, d, J=8.5 Hz), 8.2 (1H, m), 8.39 (1H, s), 8.79 (1H, d, J=7.9 Hz).

MASS (m/z): 1238.3 (M$^-$−1).

Elemental Analysis Calcd. for C$_{56}$H$_{73}$N$_9$O$_{19}$S$_2$·9H$_2$O: C, 47.96, H, 6.54, N, 8.99. Found: C, 48.14, H, 6.36, N, 8.90.

EXAMPLE 156

IR (KBr): 3355.5, 1635.3, 1529.3, 1517.7, 1434.8, 1255.4 cm$^{-1}$.

NMR (DMSO-d$_6$, δ): 0.87 (3H, t, J=6.5 Hz), 0.97 (3H, d, J=6.8 Hz), 1.11 (3H, d, J=5.8 Hz), 1.2–5.4 (52H, m), 6.71 (1H, d, J=8.1 Hz), 6.78 (1H, d, J=9.9 Hz), 7.00 (1H, d, J=1.6 Hz), 7.09 (2H, d, J=9.0 Hz), 7.45 (1H, d, J=8.8 Hz), 7.5–7.9 (2H, m), 7.97 (2H, d, J=8.5 Hz), 8.06 (2H, d, J=8.5 Hz), 8.29 (1H, d, J=8.9 Hz), 8.40 (2H, d, J=8.8 Hz), 8.81 (1H, d, J=7.4 Hz), 9.26 (2H, s).

MASS (m/z): 1275.4 (M$^-$−1).

Elemental Analysis Calcd. for C$_{60}$H$_{80}$N$_{10}$O$_{19}$S·8H$_2$O: C, 50.70, H, 6.81, N, 9.85. Found: C, 50.50, H, 6.69, N, 9.69.

EXAMPLE 157

IR (KBr): 3361.3, 1631.5, 1511.9, 1446.4, 1267.0, 1232.3, 1045.2 cm$^{-1}$.

NMR (DMSO-d$_6$, δ): 0.97 (3H, d, J=6.7 Hz), 1.09 (3H, d, J=5.8 Hz), 1.0–5.6 (57H, m), 6.70 (1H, d, J=8.1 Hz), 6.7–6.9 (1H, m), 6.92 (2H, d, J=8.7 Hz), 6.99 (1H, s), 7.01 (2H, d, J=9.4 Hz) 7.09 (2H, d, J=8.7 Hz), 7.3–7.9 (3H, m), 7.80 (2H, d, J=8.8 Hz), 8.1–8.5 (3H, m).

MASS (m/z): 1235.4 (M$^-$–H).

Elemental Analysis Calcd. for $C_{58}H_{80}N_{10}O_{18}S \cdot 9H_2O$: C, 49.78, H, 7.06, N, 10.01. Found: C, 49.88, H, 6.87, N, 9.89.

EXAMPLE 158

IR (KBr): 3359.4, 1633.4, 1535.1, 1511.9, 1442.5, 1251.6 cm$^{-1}$.

NMR (DMSO-d$_6$, δ): 0.8–1.1 (6H, m), 1.1–1.3 (3H, m), 1.3–5.6 (42H, m), 6.71 (1H, d, J=8.1 Hz), 6.77 (1H, d, J=9.8 Hz), 6.97 (1H, s), 7.07 (2H, d, J=8.9 Hz), 7.2–9.0 (15H, m).

MASS (m/z): 1287.4 (M$^-$–1).

EXAMPLE 159

IR (KBr): 3359.4, 1631.5, 1610.3, 1538.9, 1502.3, 1450.2, 1230.4 cm$^{-1}$.

NMR (DMSO-d$_6$, δ): 0.96 (3H, d, J=6.7 Hz), 1.0–1.3 (3H, m), 1.3–5.8 (59H, m), 6.70 (1H, d, J=8.2 Hz), 6.77 (1H, d, J=9.9 Hz), 6.8–7.3 (8H, m), 7.3–9.2 (11H, m).

MASS (m/z): 1345.5 (M$^-$–1).

EXAMPLE 160

MASS (m/z): 1222.3 (M$^-$–1).

EXAMPLE 161

IR (KBr): 3353.6, 1631.5, 1537.0, 1517.7, 1467.6, 1440.6, 1272.8, 1045.2 cm$^{-1}$.

NMR (DMSO-d$_6$, δ): 0.7–1.0 (3H, m), 0.98 (3H, d, J=6.8 Hz), 1.11 (3H, d, J=5.6 Hz), 1.2–5.5 (46H, m), 6.71 (1H, d, J=8.1 Hz), 6.7–6.9 (1H, m), 7.00 (1H, d, J=1.6 Hz), 7.45 (1H, d, J=8.1 Hz), 7.5–8.2 (13H, m), 8.30 (1H, d, J=7.6 Hz), 8.77 (1H, d, J=7.1 Hz).

MASS (m/z): 1256.4 (M$^-$–1).

Elemental Analysis Calcd. for $C_{60}H_{75}N_9O_{19}S \cdot 8H_2O$: C, 51.38, H, 6.54, N, 8.99. Found: C, 51.15, H, 6.41, N, 8.76.

EXAMPLE 162

IR (KBr): 3425.0, 3396.0, 3365.2, 1631.5, 1537.0, 1510.0, 1450.2, 1286.3, 1267.0, 1234.2 cm$^{-1}$.

NMR (DMSO-d$_6$, δ): 0.95 (3H, d, J=6.7 Hz), 1.10 (3H, d, J=5.7 Hz), 1.3–5.6 (63H, m), 6.7–7.2 (9H, m), 7.3–7.8 (3H, m), 7.80 (2H, d, J=8.8 Hz), 8.0–8.5 (2H, m).

MASS (m/z): 1313.4 (M$^-$–1).

Elemental Analysis Calcd. for $C_{60}H_{86}N_{10}O_{21}S \cdot 10H_2O$: C, 48.19, H, 7.14, N, 9.37. Found: C, 48.45, H, 6.94, N, 9.32.

EXAMPLE 163

IR (KBr): 1469, 1541, 1514 cm$^{-1}$.

NMR (DMSO-d$_6$, δ): 0.7–1.6 (11H, m), 1.6–2.7 (15H, m), 2.7–3.6 (8H, m), 3.6–5.3 (21H, m), 6.7–6.9 (2H, m), 7.00 (1H, s), 7.2–7.9 (5H, m), 7.96 (2H, d, J=8.3 Hz), 8.0–8.4 (5H, m), 8.6–9.0 (2H, m).

MASS (m/z): 1235 (M$^+$–1).

Elemental Analysis Calcd. for $C_{56}H_{72}N_{10}O_{18}S_2 \cdot 7H_2O$: C, 49.33, H, 6.36, N, 10.27. Found: C, 49.07, H, 6.40, N, 10.02.

EXAMPLE 164

IR (KBr): 1633, 1516, 1444, 1255 cm$^{-1}$.

NMR (DMSO-d$_6$, δ): 0.9–2.6 (25H, m), 2.7–3.6 (8H, m), 3.6–5.3 (22H, m), 6.65–6.85 (2H, m), 7.00 (1H, s), 7.14 (2H, d, J=9.0 Hz), 7.4–8.2 (10H, m), 8.2–8.4 (1H, m), 8.8–9.0 (1H, m).

MASS (m/z): 1251 (M$^+$–1).

Elemental Analysis Calcd. for $C_{56}H_{72}N_{10}O_{19}S_2 \cdot 8H_2O$: C, 48.13, H, 6.35, N, 10.02. Found: C, 48.26, H, 6.35, N, 9.80.

EXAMPLE 165

IR (KBr): 1633, 1518, 1444, 1250 cm$^{-1}$.

NMR (DMSO-d$_6$, δ): 0.8–1.6 (15H, m), 1.6–2.6 (11H, m), 2.7–3.6 (8H, m), 3.6–5.3 (23H, m), 6.65–6.85 (2H, m), 7.00 (1H, s), 7.10 (2H, d, J=9.0 Hz), 7.3–8.4 (12H, m), 8.8–9.0 (1H, m), 9.23 (1H, s).

MASS (m/z): 1365 (M$^+$+23).

Elemental Analysis Calcd. for $C_{59}H_{76}N_{12}O_{19}S_2 \cdot 9H_2O$: C, 47.77, H, 6.39, N, 11.33. Found: C, 47.67, H, 6.19, N, 11.20.

EXAMPLE 166

IR (KBr): 1662, 1635, 1605, 1444 cm$^{-1}$.

NMR (DMSO-d$_6$, δ): 0.8–1.4 (6H, m), 1.5–2.6 (13H, m), 2.6–3.6 (1H, m), 3.6–5.3 (23H, m), 6.65–6.85 (2H, m), 6.99 (1H, s), 7.05–8.4 (18H, m), 8.8–9.0 (1H, m).

MASS (m/z): 1312 (M$^+$–1).

Elemental Analysis Calcd. for $C_{61}H_{75}N_{11}O_{18}S_2 \cdot 9H_2O$: C, 49.62, H, 6.35, N, 10.43. Found: C, 49.73, H, 6.16, N, 10.27.

EXAMPLE 167

IR (KBr): 1659, 1628, 1605, 1444 cm$^{-1}$.

NMR (DMSO-d$_6$, δ): 0.9–2.7 (29H, m), 2.7–5.3 (35H, m), 6.65–6.85 (2H, m), 6.9–7.2 (3H, m), 7.3–7.95 (5H, m), 8.0–8.4 (6H, m), 8.8–9.0 (1H, m).

MASS (m/z): 1334 (M$^+$–1).

Elemental Analysis Calcd. for $C_{61}H_{81}N_{11}O_{19}S_2 \cdot 9H_2O$: C, 48.89, H, 6.66, N, 10.28. Found: C, 48.83, H, 6.45, N, 10.11.

EXAMPLE 168

IR (KBr): 1659, 1628, 1444 cm$^{-1}$.

NMR (DMSO-d$_6$, δ): 0.8–2.7 (34H, m), 3.8–3.6 (8H, m), 3.6–5.3 (23H, m), 6.65–6.85 (2H, m), 6.99 (1H, s), 7.3–7.85 (5H, m), 7.9–8.4 (7H, m), 8.57 (1H, s), 8.6–9.0 (1H, m).

MASS (m/z): 1283 (M$^+$–1).

Elemental Analysis Calcd. for $C_{57}H_{80}N_{12}O_{18}S_2 \cdot 8H_2O$: C, 47.89, H, 6.77, N, 11.76. Found: C, 47.65, H, 6.63, N, 11.53.

EXAMPLE 169

IR (KBr): 3324, 2937, 1658, 1629, 1529, 1517, 1465, 1446, 1255, 1178, 1112, 1085, 1045 cm$^{-1}$.

NMR (DMSO-d$_6$, δ): 0.98 (3H, d, J=6.7 Hz), 1.10 (3H, d, J=5.7 Hz), 1.3–1.6 (4H, m), 1.6–2.1 (4H, m), 2.1–2.5 (3H, m), 2.9 (3H, m), 3.23 (1H, s), 3.38 (2H, m), 3.7–4.6 (19H, m), 4.8 (4H, m), 5.2 (3H, m), 6.71 (1H, d, J=8.2 Hz), 6.78 (1H, d, J=8.2 Hz), 7.00 (18H, s), 7.15 (2H, d, J=8.8 Hz), 7.44 (1H, d, J=8.5 Hz), 7.6–7.8 (3H, m), 7.67 (1H, m), 7.90 (2H, d, J=8.8 Hz), 7.97 (4H, s), 8.34 (1H, d, J=7.1 Hz), 8.75 (1H, d, J=7.5 Hz), 8.86 (1H, s).

MASS (m/z): 1308.3 (M$^+$+1).

Elemental Analysis Calcd. for $C_{58}H_{75}N_{11}O_{20}S_2 \cdot 8H_2O$: C, 47.89, H, 6.31, N, 10.59. Found: C, 48.02, H, 6.21, N, 10.49.

EXAMPLE 170

IR (KBr): 3300, 1635.3, 1510.0, 1232.3 cm$^{-1}$.

NMR (DMSO-d$_6$, δ): 0.97 (3H, d, J=6.8 Hz), 1.07 (3H, d, J=5.3 Hz), 1.72–5.21 (58H, m), 6.69–8.67 (20H, m).

MASS (m/z): 1377.4 (M$^+$+Na).

Elemental Analysis Calcd. for C$_{64}$H$_{84}$ClN$_{11}$O$_{19}$S.6H$_2$O: C, 51.69, H, 6.51, N, 10.36. Found: C, 51.74, H, 6.54, N, 10.59.

EXAMPLE 171

IR (KBr): 3347.8, 1631.5, 1610.3, 1510.0, 1230.4 cm$^{-1}$.

NMR (DMSO-d$_6$, δ): 0.97 (3H, d, J=6.9 Hz), 1.08 (3H, d, J=4.6 Hz), 1.70–5.40 (55H, m), 6.67–8.71 (22H, m).

MASS (m/z): 1313.4.

Elemental Analysis Calcd. for C$_{63}$H$_{83}$N$_{11}$O$_{18}$S.4H$_2$O: C, 54.57, H, 6.61, N, 11.11. Found: C, 54.32, H, 6.64, N, 11.00.

EXAMPLE 172

IR (KBr): 1659, 1635, 1606, 1529, 1446, 1242 cm$^{-1}$.

NMR (DMSO-d$_6$, δ): 0.8–1.3 (12H, m), 1.4–2.6 (11H, m), 2.7–3.6 (8H, m), 3.6–5.3 (25H, m), 6.1–6.85 (2H, m), 6.99 (1H, s), 7.11 (2H, d, J=8.7 Hz), 7.4–7.85 (3H, m), 7.87 (2H, d, J=8.9 Hz), 8.0–8.4 (6H, m), 8.8 (1H, m).

MASS (m/z): 1266 (M$^+$–1).

Elemental Analysis Calcd. for C$_{56}$H$_{73}$N$_{11}$O$_{19}$S$_2$.10H$_2$O: C, 46.43, H, 6.47, N, 10.64. Found: C, 46.45, H, 5.95, N, 10.46.

EXAMPLE 173

IR (KBr): 1659, 1635, 1612, 1512, 1446, 1234 cm$^{-1}$.

NMR (DMSO-d$_6$, δ): 0.9–1.3 (12H, m), 1.5–2.4 (11H, m), 2.7–3.6 (18H, m), 3.6–5.3 (23H, m), 6.6–7.1 (9H, m), 7.3–7.9 (6H, m), 8.2–8.5 (2H, m).

MASS (m/z): 1266 (M$^+$–1).

Elemental Analysis Calcd. for C$_{58}$H$_{81}$N$_{11}$O$_{19}$S.7H$_2$O: C, 49.96, H, 6.87, N, 11.05. Found: C, 49.78, H, 6.64, N, 10.93.

EXAMPLE 174

IR (KBr): 1659, 1628, 1510, 1446, 1236 cm$^{-1}$.

NMR (DMSO-d$_6$, δ): 0.7–1.5 (22H, m), 1.5–2.6 (16H, m), 2.7–3.6 (12H, m), 3.6–5.3 (21H, m), 6.6–7.05 (5H, m), 7.3–7.9 (6H, m), 8.2–8.5 (2H, m).

MASS (m/z): 1215 (M$^+$–1).

Elemental Analysis Calcd. for C$_{56}$H$_{84}$N$_{10}$O$_{18}$S.7H$_2$O: C, 50.06, H, 7.35, N, 10.43. Found: C, 49.95, H, 7.19, N, 10.30.

EXAMPLE 175

IR (KBr): 1630, 1510, 1446, 1238 cm$^{-1}$.

NMR (DMSO-d$_6$, δ): 0.7–1.4 (20H, m), 1.6–2.75 (18H, m), 2.75–3.7 (12H, m), 3.7–4.55 (13H, m), 4.6–5.3 (8H, m), 6.6–7.1 (5H, m), 7.3–7.9 (5H, m), 8.2–8.6 (2H, m), 8.71 (1H, s).

MASS (m/z): 1215 (M$^+$–1).

Elemental Analysis Calcd. for C$_{56}$H$_{84}$N$_{10}$O$_{18}$S.8H$_2$O: C, 49.40, H, 7.40, N, 10.29. Found: C, 49.45, H, 7.28, N, 10.20.

EXAMPLE 176

IR (KBr): 1664, 1635, 1446, 1240 cm$^{-1}$.

NMR (DMSO-d$_6$, δ): 0.7–1.3 (6H, m), 1.4–2.65 (15H, m), 2.7–3.6 (12H, m), 3.65–5.3 (21H, m), 6.65–6.85 (2H, m), 6.9–7.2 (3H, m), 7.3–7.85 (5H, m), 7.9–8.4 (7H, m), 8.7–8.95 (1H, m), 9.17 (1H, s).

MASS (m/z): 1303 (M$^+$).

Elemental Analysis Calcd. for C$_{58}$H$_{73}$N$_{13}$O$_{18}$S.7H$_2$O: C, 48.70, H, 6.13, N, 12.73. Found: C, 48.48, H, 5.79, N, 12.45.

EXAMPLE 177

IR (KBr): 1649, 1632, 1539, 1512, 1454, 1238 cm$^{-1}$.

NMR (DMSO-d$_6$, δ): 0.8–2.75 (39H, m), 2.75–5.3 (36H, m), 6.65–7.05 (5H, m), 7.3–7.9 (5H, m), 8.2–8.6 (2H, m), 8.71 (1H, s).

MASS (m/z): 1271 (M$^+$–1).

Elemental Analysis Calcd. for C$_{59}$H$_{88}$N$_{10}$O$_{19}$S.7H$_2$O: C, 49.99, H, 7.39, N, 9.88. Found: C, 49.80, H, 7.21, N, 10.11.

EXAMPLE 178

IR (KBr): 1651, 1541, 1512, 1232 cm$^{-1}$.

NMR (DMSO-d$_6$, δ): 0.8–1.2 (9H, m), 1.4–2.1 (12H, m), 2.1–3.6 (26H, m), 3.6–4.5 (13H, m), 4.6–5.3 (8H, m), 6.6–7.1 (9H, m), 7.3–7.9 (5H, m), 8.2–8.8 (3H, m).

MASS (m/z): 1310 (M$^+$–1).

Elemental Analysis Calcd. for C$_{56}$H$_{84}$N$_{10}$O$_{18}$S.7H$_2$O: C, 50.09, H, 6.94, N, 10.71. Found: C, 49.86, H, 6.80, N, 10.65.

EXAMPLE 179

IR (KBr): 1649, 1632, 1539, 1512, 1454, 1238 cm$^{-1}$.

NMR (DMSO-d$_6$, δ): 0.8–2.7 (39H, m), 2.7–5.3 (36H, m), 6.65–7.1 (5H, m), 7.3–7.8 (5H, m), 8.25–8.55 (2H, m), 8.70 (1H, s).

MASS (m/z): 1273 (M$^+$+1).

Elemental Analysis Calcd. for C$_{59}$H$_{88}$N$_{10}$O$_{19}$S.7H$_2$O: C, 50.63, H, 7.35, N, 10.01. Found: C, 50.54, H, 7.24, N, 9.87.

EXAMPLE 180

IR (KBr): 1649, 1632, 1541, 1506, 1454, 1232 cm$^{-1}$.

NMR (DMSO-d$_6$, δ): 0.9–1.3 (12H, m), 1.6–2.6 (11H, m), 2.6–5.3 (41H, m), 6.7–7.2 (9H, m), 7.3–7.9 (10H, m), 8.2–8.6 (2H, m).

MASS (m/z): 1342 (M$^+$–1).

Elemental Analysis Calcd. for C$_{64}$H$_{85}$N$_{11}$O$_{19}$S.10H$_2$O: C, 50.42, H, 6.94, N, 10.11. Found: C, 50.71, H, 6.82, N, 10.03.

EXAMPLE 181

IR (KBr): 3353.6, 1633.4, 1537.0, 1508.1, 1438.6, 1257.4, 1045.2 cm$^{-1}$.

NMR (DMSO-d$_6$, δ): 0.91 (3H, t, J=7.1 Hz), 0.98 (3H, d, J=6.8 Hz), 1.11 (3H, d, J=5.8 Hz), 1.2–5.6 (45H, m), 6.71 (1H, d, J=8.1 Hz), 6.78 (1H, d, J=10.0 Hz), 7.00 (11H, s), 7.13 (2H, d, J=8.9 Hz), 7.45 (1H, d, J=8.8 Hz), 7.54 (1H, s), 7.6–8.0 (2H, m), 7.85 (2H, d, J=8.7 Hz), 7.99 (2H, d, J=8.8 Hz), 8.05 (2H, d, J=8.6 Hz), 8.31 (1H, d, J=7.1 Hz), 8.71 (1H, s), 8.87 (1H, d, J=7.1 Hz).

MASS (m/z): 1222.3 (M$^-$–1).

Elemental Analysis Calcd. for C$_{56}$H$_{73}$N$_9$O$_{20}$S.7H$_2$O: C, 49.81, H, 6.49, N, 9.33. Found: C, 49.99, H, 6.43, N, 9.30.

EXAMPLE 182

IR (KBr): 3374.6, 1658.5, 1627.6, 1529.3, 1517.7, 1486.8, 1446.4, 1276.6, 1247.7 cm$^{-1}$.

NMR (DMSO-d$_6$, δ): 0.91 (3H, t, J=7.1 Hz), 0.97 (3H, d, J=6.9 Hz), 1.12 (3H, d, J=5.8 Hz), 1.2–6.5 (46H, m), 6.71

(1H, d, J=8.1 Hz), 6.77 (1H, d, J=10.0 Hz), 6.99 (1H, d, J=1.6 Hz), 7.20 (2H, d, J=8.9 Hz), 7.46 (1H, d, J=9.5 Hz), 7.5–8.3 (3H, m), 8.08 (2H, d, J=8.6 Hz), 8.14 (2H, d, J=8.8 Hz), 8.17 (2H, d, J=8.4 Hz), 8.3–8.8 (1H, m), 8.84 (1H, d, J=7.2 Hz).

MASS (m/z): 1231.3 (M$^-$−1).

Elemental Analysis Calcd. for $C_{59}H_{72}N_9NaO_{20}S \cdot 7H_2O$: C, 49.81, H, 6.49, N, 9.33. Found: C, 49.99, H, 6.43, N, 9.30.

EXAMPLE 183

IR (KBr): 3353.6, 1633.4, 1538.9, 1502.3, 1461.8, 1444.4, 1259.3, 1045.2 cm$^{-1}$.

NMR (DMSO-d$_6$, δ): 0.91 (3H, t, J=7.1 Hz), 0.97 (3H, d, J=7.0 Hz), 1.11 (3H, d, J=5.7 Hz), 1.2–6.5 (45H, m), 6.71 (1H, d, J=8.2 Hz), 6.7–6.9 (1H, m), 6.99 (1H, d, J=1.7 Hz), 7.04 (2H, d, J=8.8 Hz), 7.45 (1H, d, J=9.0 Hz), 7.5–7.9 (10H, m), 8.00 (2H, d, J=8.4 Hz), 8.26 (1H, d, J=7.1 Hz), 8.3–8.7 (1H, m), 8.73 (1H, d, J=7.9 Hz).

MASS (m/z): 1223.3 (M$^-$−1).

Elemental Analysis Calcd. for $C_{59}H_{76}N_8O_{19}S \cdot 6H_2O$: C, 52.83, H, 6.61, N, 8.35. Found: C, 59.91, H, 6.54, N, 8.32.

EXAMPLE 184

IR (KBr): 3353.6, 1658.5, 1633.4, 1232.3 cm$^{-1}$.

NMR (DMSO-d$_6$, δ): 0.96 (3H, d, J=6.7 Hz), 1.09 (3H, d, J=5.7 Hz), 1.50–5.30 (56H, m), 6.68–8.40 (23H, m).

MASS (m/z): 1342.3 (M$^+$−1).

Elemental Analysis Calcd. for $C_{64}H_{85}N_{11}O_{19}S \cdot 7H_2O$: C, 52.27, H, 6.79, N, 10.48. Found: C, 51.98, H, 6.47, N, 10.59.

EXAMPLE 185

IR (KBr): 3347.8, 1633.4, 1511.9, 1230.4 cm$^{-1}$.

NMR (DMSO-d$_6$, δ): 0.97 (3H, d, J=6.7 Hz), 1.07 (3H, d, J=5.0 Hz), 1.20–5.22 (66H, m), 6.64–8.56 (17H, m).

MASS (m/z): 1334.5 (M$^+$+1).

Elemental Analysis Calcd. for $C_{63}H_{89}N_{11}O_{19}S \cdot 7H_2O$: C, 51.74, H, 7.10, N, 10.53. Found: C, 52.06, H, 6.95, N, 10.49.

EXAMPLE 186

IR (KBr): 3365.2, 1664.3, 1633.4, 1230.4 cm$^{-1}$.

NMR (DMSO-d$_6$, δ): 0.81–5.25 (78H, m), 6.67–8.53 (14H, m).

Elemental Analysis Calcd. for $C_{61}H_{92}N_{10}O_{19}S \cdot 12H_2O$: C, 48.28, H, 7.70, N, 9.23. Found: C, 48.02, H, 6.69, N, 9.39.

EXAMPLE 187

IR (KBr): 3350. 1631.5, 1511.9, 1232.3 cm$^{-1}$.

NMR (DMSO-d$_6$, δ): 0.96 (3H, d, J=6.6 Hz), 1.09 (3H, d, J=6.0 Hz), 1.42–5.20 (61H, m), 6.68–8.40 (18H, m).

MASS (m/z): 1292.3 (M$^+$+1).

Elemental Analysis Calcd. for $C_{61}H_{85}N_{10}O_{18}S \cdot 7H_2O$: C, 51.65, H, 7.03, N, 10.86. Found: C, 51.72, H, 6.86, N, 10.86.

EXAMPLE 188

IR (KBr): 1658.5, 1629.6, 1511.9, 1232.3 cm$^{-1}$.

NMR (DMSO-d$_6$, δ): 0.96 (3H, d, J=6.5 Hz), 1.11 (3H, d, J=5.1 Hz), 1.51–5.19 (58H, m), 6.68–8.29 (17H, m).

MASS (m/z): 1294.4 (M$^+$−1).

Elemental Analysis Calcd. for $C_{59}H_{81}N_{11}O_{20}S \cdot 7H_2O$: C, 49.82, H, 6.73, N, 10.83. Found: C, 50.33, H, 6.42, N, 11.00.

EXAMPLE 189

IR (KBr): 3328, 2940, 1664, 1629, 1529, 1519, 1467, 1446, 1257, 1178, 1112, 1085, 1047 cm$^{-1}$.

NMR (DMSO-d$_6$, δ): 0.97 (3H, d, J=6.7 Hz), 1.10 (3H, d, J=5.7 Hz), 1.5–2.1 (11H, m), 2.2–2.5 (5H, m), 2.90 (3H, m), 3.24 (3H, s), 3.38 (2H, m), 3.4 (2H, m), 3.6–4.6 (18H, m), 4.6–4.9 (3H, m), 5.20 (2H, m), 6.70 (1H, d, J=8.2 Hz), 6.80 (1H, d, J=8.2 Hz), 7.00 (1H, s), 7.15 (2H, d, J=8.8 Hz), 7.45 (1H, d, J=8.0 Hz), 7.7 (3H, m), 7.90 (2H, d, J=8.8 Hz), 7.96 (4H, s), 8.3 (1H, m), 8.70 (1H, d, J=7.8 Hz), 8.85 (1H, s).

MASS (m/z): 1294.3 (M$^+$−1).

EXAMPLE 190

IR (KBr): 3324, 2937, 1658, 1635, 1529, 1517, 1465, 1446, 1257, 1178, 1114, 1087, 1045 cm$^{-1}$.

NMR (DMSO-d$_6$, δ): 0.97 (3H, d, J=6.7 Hz), 1.10 (3H, d, J=5.7 Hz), 1.2–1.6 (6H, m), 1.6–2.1 (4H, m), 2.1–2.5 (3H, m), 2.9 (3H, m), 3.22 (3H, s), 3.38 (2H, m), 3.6–4.3 (14H, m), 4.3–4.6 (5H, m), 4.6–4.9 (4H, m), 5.2 (3H, m), 6.70 (1H, d, J=8.2 Hz), 6.78 (1H, d, J=8.2 Hz), 7.00 (1H, s), 7.14 (2H, d, J=8.8 Hz), 7.44 (1H, d, J=8.2 Hz), 7.6–7.8 (3H, m), 7.90 (2H, d, J=8.8 Hz), 7.96 (4H, s), 8.33 (1H, d, J=7.1 Hz), 8.74 (1H, d, J=7.7 Hz), 8.86 (1H, s).

MASS (m/z): 1322.4 (M$^+$−1).

EXAMPLE 191

IR (KBr): 2937, 2864, 1659, 1632, 1510, 1446, 1387, 1327 cm$^{-1}$.

NMR (DMSO-d$_6$, δ): 0.97 (3H, d, J=6.7 Hz), 1.08 (3H, d, J=5.8 Hz), 1.22–2.60 (17H, m), 2.79–3.03 (3H, m), 3.10–3.55 (12H, m), 3.21 (3H, s), 3.64–4.08 (6H, m), 3.85 (2H, t, J=6.5 Hz), 4.12–4.52 (7H, m), 4.67–4.90 (6H, m), 5.10–5.25 (2H, m), 6.65–7.08 (9H, m), 7.43 (1H, d, J=8.2 Hz), 7.53–7.88 (2H, m), 7.80 (2H, d, J=8.8 Hz), 8.27 (2H, d, J=7.8 Hz), 8.44 (1H, d, J=7.6 Hz).

MASS (m/z): 1283.4 (M$^+$−1).

Elemental Analysis Calcd. for $C_{59}H_{84}N_{10}O_{20}S \cdot 5H_2O$: C, 51.52, H, 6.89, N, 10.18. Found: C, 51.51, H, 6,96, N, 10.09.

EXAMPLE 192

IR (KBr): 2935, 2856, 1633, 1533, 1518, 1497, 1446, 1385 cm$^{-1}$.

NMR (DMSO-d$_6$, δ): 0.97 (3H, d, J=6.7 Hz), 1.10 (3H, d, J=5.4 Hz), 1.05–1.38 (6H, m), 1.50–2.14 (9H, m), 2.14–2.43 (2H, m), 2.43–2.67 (7H, m), 2.79–3.03 (3H, m), 3.10–3.50 (6H, m), 3.64–4.08 (6H, m), 4.12–4.52 (7H, m), 4.67–5.26 (8H, m), 6.67–6.84 (2H, m), 6.96–7.10 (1H, m), 7.02 (2H, d, J=8.8 Hz), 7.44 (1H, d, J=8.9 Hz), 7.61 (2H, d, J=8.8 Hz), 7.52–7.50 (2H, m), 7.70 (2H, d, J=8.2 Hz), 7.93 (2H, d, J=8.4 Hz), 8.26–8.40 (1H, m), 8.68–8.84 (2H, m).

MASS (m/z): 1235.4 (M$^+$−1).

Elemental Analysis Calcd. for $C_{58}H_{80}N_{10}O_{18}S \cdot 7H_2O$: C, 51.09, H, 6.95, N, 10.27. Found: C, 50.78, H, 6.88, N, 10.10.

EXAMPLE 193

To a solution of the starting compound (193) (21 mg) in methanol (1 ml) was added a solution of hydrogen chloride in methanol (0.5 ml), and stirred for 4 hours at ambient temperature. The reaction mixture was diluted with water, and subjected to column chromatography on ODS (YMC-gel ODS-AM-S-50 (Trademark: prepared by Yamamura Chemical Lab.)) eluting with 20% acetonitrile aqueous solution. The fractions containing the object compound were combined, and evaporated under reduced pressure to remove acetonitrile. The residue was lyophilized to give the object compound (193) (19 mg).

IR (KBr): 3355, 2935, 1658, 1635, 1529, 1446, 1255, 1180, 1083, 1006 cm$^{-1}$.

NMR (DMSO-d$_6$, δ): 0.98 (3H, d, J=6.7 Hz), 1.04 (3H, d, J=5.7 Hz), 1.2–1.6 (8H, m), 1.6–2.6 (13H, m), 2.6–3.8 (5H, m), 3.10 (9H, s), 3.21 (3H, s), 3.30 (4H, t, J=6.4 Hz), 3.8–4.7 (12H, m), 4.7–5.0 (3H, m), 5.2 (3H, m), 5.74 (1H, m), 6.38 (1H, d, J=8.2 Hz), 6.59 (1H, s), 6.60 (1H, d, J=8.2 Hz), 7.14 (2H, d, J=8.8 Hz), 7.37 (1H, d, J=9.2 Hz), 7.53 (1H, d, J=9.2 Hz), 7.84 (1H, m), 7.97 (2H, d, J=8.8 Hz), 8.06 (2H, d, J=8.8 Hz), 8.11 (2H, d, J=8.8 Hz), 8.67 (2H, d, J=4.0 Hz), 8.85 (1H, d, J=8.2 Hz), 8.91 (1H, d, J=8.2 Hz).

MASS (m/z): 1261.5 (M$^+$).

The following compounds [Examples 194 to 206] were obtained according to a similar manner to that of Example 193.

EXAMPLE 194

IR (KBr): 3353, 2937, 1664, 1627, 1606, 1529, 1446, 1255, 1178, 1112, 1087, 1066, 1006 cm$^{-1}$.

NMR (DMSO-d$_6$, δ): 0.97 (3H, d, J=6.7 Hz), 1.09 (3H, d, J=5.7 Hz), 1.2–1.6 (12H, m), 1.6–3.8 (23H, m), 3.21 (3H, s), 3.28 (4H, t, J=6.4 Hz), 3.8–4.25 (9H, m), 4.25–4.6 (4H, m), 4.8 (4H, m), 5.1 (1H, m), 5.18 (1H, d, J=3.0 Hz), 5.23 (1H, d, J=5.6 Hz), 5.40 (1H, m), 6.39 (1H, d, J=8.0 Hz), 6.57 (1H, m), 6.61 (1H, d, J=8.0 Hz), 7.14 (2H, d, J=8.8 Hz), 7.42 (1H, d, J=8.8 Hz), 7.55 (1H, m), 7.80 (1H, m), 7.97 (2H, d, J=8.8 Hz), 8.07 (2H, d, J=8.8 Hz), 8.12 (2H, d, J=8.8 Hz), 8.57 (1H, d, J=7.8 Hz), 8.68 (2H, s), 8.89 (1H, d, J=7.3 Hz).

MASS (m/z): 1290.4 (M$^+$+1).

EXAMPLE 195

IR (KBr): 3353, 2935, 1658, 1635, 1606, 1529, 1446, 1255, 1180, 1114, 1085, 1062, 1004 cm$^{-1}$.

NMR (DMSO-d$_6$, δ): 0.97 (3H, d, J=6.7 Hz), 1.08 (3H, d, J=5.7 Hz), 1.2–1.6 (10H, m), 1.6–2.6 (21H, m), 2.6–3.8 (7H, m), 3.21 (3H, s), 3.30 (4H, t, J=6.4 Hz), 3.8–4.5 (11H, m), 4.8 (3H, m), 5.05 (1H, m), 5.2–5.3 (2H, m), 5.38 (1H, m), 6.39 (1H, d, J=8.0 Hz), 6.57 (1H, m), 6.60 (1H, d, J=8.0 Hz), 7.14 (2H, d, J=8.8 Hz), 7.41 (1H, d, J=8.7 Hz), 7.45 (1H, d, J=8.7 Hz), 7.87 (1H, d, J=6.8 Hz), 7.97 (2H, d, J=8.8 Hz), 8.06 (2H, d, J=8.8 Hz), 8.12 (21H, d, J=8.8 Hz), 8.60 (1H, d, J=8.0 Hz), 8.67 (2H, s), 8.88 (11H, d, J=7.5 Hz).

MASS (m/z): 1302.4 (M$^+$+1).

EXAMPLE 196

IR (KBr): 3353, 2937, 1664, 1627, 1529, 1446, 1255, 1180, 1114, 1087, 1064, 1006 cm$^{-1}$.

NMR (DMSO-d$_6$, δ): 0.97 (3H, d, J=6.7 Hz), 1.10 (3H, d, J=5.7 Hz), 1.2–1.6 (8H, m), 1.6–2.7 (15H, m), 2.7–3.6 (5H, m), 3.21 (3H, s), 3.6–4.25 (12H, m), 4.25–4.6 (4H, m), 4.6–5.0 (3H, m), 5.11 (2H, m), 5.35 (1H, m), 6.39 (1H, d, J=8.0 Hz), 6.57 (1H, m), 6.61 (1H, d, J=8.0 Hz), 7.05 (2H, m), 7.14 (2H, d, J=8.8 Hz), 7.22 (1H, m), 7.44 (1H, d, J=8.9 Hz), 7.6–7.8 (2H, m), 7.97 (2H, d, J=8.8 Hz), 8.04 (2H, d, J=8.8 Hz), 8.11 (2H, d, J=8.8 Hz), 8.39 (1H, d, J=7.5 Hz), 8.68 (1H, m), 8.90 (1H,+d, J=6.9 Hz).

MASS (m/z): 1261.4 (M$^+$+1).

EXAMPLE 197

IR (KBr): 3349, 2935, 1658, 1635, 1529, 1446, 1255, 1180, 1114, 1087, 1062, 1006 cm$^{-1}$.

NMR (DMSO-d$_6$, δ): 0.97 (3H, d, J=6.7 Hz), 1.13 (3H, d, J=5.7 Hz), 1.3–1.6 (8H, m), 1.6–2.6 (15H, m), 2.6–3.6 (8H, m), 3.21 (3H, s), 3.6–4.3 (12H, m), 4.40 (2H, m), 4.55 (1H, m), 4.65 (1H, m), 4.8 (3H, m), 5.16 (3H, m), 6.39 (1H, d, J=8.0 Hz), 6.57 (1H, m), 6.62 (1H, d, J=8.0 Hz), 7.14 (2H, d, J=8.8 Hz), 7.34 (1H, m), 7.51 (1H, d, J=9.2 Hz), 7.68 (2H, m), 7.97 (2H, d, J=8.8 Hz), 8.04 (2H, d, J=8.8 Hz), 8.11 (2H, d, J=8.8 Hz), 8.20 (1H, d, J=6.7 Hz), 8.57 (1H, m), 8.68 (2H, m), 8.86 (1H, d, J=7.6 Hz), 9.14 (1H, s), 9.40 (1H, m).

MASS (m/z): 1303.3 (M$^+$+1).

EXAMPLE 198

IR (KBr): 3353.6, 1658.5, 1635.3, 1529.3, 1444.4, 1255.4 cm$^{-1}$.

NMR (DMSO-d$_6$, δ): 0.98 (3H, d, J=6.8 Hz), 1.08 (3H, d, J=5.6 Hz), 1.2–5.6 (68H, m), 6.40 (1H, d, J=8.0 Hz), 6.58 (1H, s), 6.60 (1H, d, J=8.1 Hz), 7.14 (2H, d, J=8.9 Hz), 7.97 (2H, d, J=8.7 Hz), 8.08 (2H, d, J=10.8 Hz), 8.13 (2H, d, J=8.9 Hz), 7.3–9.2 (7H, m).

MASS (m/z): 1330.4 (M$^+$–Cl).

EXAMPLE 199

IR (KBr): 3349, 2937, 1658, 1627, 1604, 1529, 1446, 1255, 1201, 1114, 1083, 1062, 1006 cm$^{-1}$.

NMR (DMSO-d$_6$, δ): 0.97 (3H, d, J=6.7 Hz), 1.10 (3H, d, J=5.7 Hz), 1.1–1.5 (10H, m), 1.6–2.6 (17H, m), 2.6–3.8 (12H, m), 3.8–4.3 (10H, m), 4.4 (4H, m), 4.78 (2H, m), 5.3 (1H, m), 6.39 (1H, d, J=8.0 Hz), 6.57 (1H, m), 6.60 (1H, d, J=8.0 Hz), 7.20 (2H, d, J=9.0 Hz), 7.45 (1H, m), 7.73 (3H, m), 7.86 (2H, d, J=8.8 Hz), 7.97 (4H, s), 8.42 (1H, d, J=6.7 Hz), 8.73 (1H, d, J=6.7 Hz), 8.84 (1H, s), 10.35 (1H, m).

MASS (m/z): 1280.4 (M$^+$+1).

EXAMPLE 200

IR (KBr): 3349, 2935, 1658, 1627, 1606, 1529, 1446, 1251, 1201, 1114, 1085, 1064, 1006 cm$^{-1}$.

NMR (DMSO-d$_6$, δ): 0.97 (3H, d, J=6.7 Hz), 1.09 (3H, d, J=5.7 Hz), 1.1–1.7 (7H, m), 1.7–2.7 (15H, m), 2.7–3.8 (15H, m), 3.8–4.3 (12H, m), 4.45 (4H, m), 4.75 (2H, m), 5.42 (1H, m), 6.39 (1H, d, J=8.0 Hz), 6.57 (1H, m), 6.60 (1H, d, J=8.0 Hz), 7.18 (2H, d, J=9.0 Hz), 7.45 (1H, d, J=8.6 Hz), 7.73 (3H, m), 7.92 (2H, d, J=8.8 Hz), 8.08 (4H, s), 8.41 (1H, d, J=6.7 Hz), 8.89 (1H, d, J=6.7 Hz), 10.6 (1H, m).

MASS (m/z): 1241.5 (M$^+$+1).

EXAMPLE 201

IR (KBr): 3347, 2937, 1658, 1635, 1531, 1506, 1444, 1255, 1180, 1114, 1085, 1060, 1006 cm$^{-1}$.

NMR (DMSO-d$_6$, δ): 0.8–1.0 (6H, m), 1.10 (3H, d, J=5.7 Hz), 1.2–1.6 (5H, m), 1.6–2.7 (11H, m), 2.7–3.1 (4H, m), 3.1–4.3 (12H, m), 4.3–4.6 (5H, m), 4.6–4.9 (4H, m), 4.9–5.4 (5H, m), 6.39 (1H, d, J=8.2 Hz), 6.56 (1H, s), 6.61 (1H, d, J=8.2 Hz), 7.13 (2H, d, J=8.8 Hz), 7.40 (1H, m), 7.3–7.5 (2H, m), 7.74 (1H, m), 7.85 (2H, d, J=8.8 Hz), 8.00 (2H, d, J=8.8 Hz), 8.06 (2H, d, J=8.8 Hz), 8.41 (1H, m), 8.69 (2H, m), 8.88 (1H, d, J=7.0 Hz).

MASS (m/z): 1144.3 (M$^+$+1).

EXAMPLE 202

IR (KBr): 3322, 2935, 1664, 1627, 1606, 1529, 1446, 1255, 1201, 1114, 1085, 1064, 1006 cm$^{-1}$.

NMR (DMSO-d$_6$, δ): 0.88 (3H, d, J=7.0 Hz), 0.97 (3H, d, J=6.7 Hz), 1.10 (3H, d, J=5.7 Hz), 0.8–1.2 (2H, m), 1.2–1.6 (5H, m), 1.6–2.0 (6H, m), 2.0–2.7 (9H, m), 2.7–3.1 (4H, m), 3.1–3.8 (9H, m), 3.8–4.3 (8H, m), 4.3–4.6 (4H, m), 4.6–4.9 (3H, m), 4.95 (1H, m), 5.12 (1H, d, J=7.3 Hz), 5.3–5.4 (3H, m), 6.39 (1H, d, J=8.0 Hz), 6.57 (1H, s), 6.61 (1H, d, J=8.0 Hz), 7.19 (2H, d, J=8.9 Hz), 7.44 (1H, d, J=9.8 Hz), 7.7 (1H, m), 7.93 (2H, d, J=8.8 Hz), 8.08 (4H, s), 8.41 (1H, m), 8.70 (2H, s), 8.91 (1H, d, J=6.6 Hz), 10.10 (1H, m).

MASS (m/z): 1255.4 (M⁺+1).

EXAMPLE 203

IR (KBr): 3344, 2940, 1658, 1627, 1531, 1496, 1246, 1180, 1114, 1083, 1062, 1004 cm$^{-1}$.

NMR (DMSO-$d_6$, δ): 0.97 (3H, d, J=6.7 Hz), 1.09 (3H, d, J=5.7 Hz), 1.1–1.5 (8H, m), 1.65 (2H, m), 1.7–2.0 (6H, m), 2.1–2.7 (7H, m), 2.8–3.1 (4H, m), 3.1–3.8 (9H, m), 3.97 (7H, m), 4.16 (2H, d, J=6.5), 4.23 (1H, m), 4.4 (5H, m), 4.75 (3H, m), 4.98 (1H, m), 5.27 (1H, m), 6.39 (1H, d, J=8.0 Hz), 6.57 (1H, m), 6.61 (1H, d, J=8.0 Hz), 7.12 (2H, d, J=8.8 Hz), 7.44 (1H, d, J=8.8 Hz), 7.68 (2H, d, J=8.8 Hz), 7.72 (2H, d, J=8.8 Hz), 7.6–7.9 (3H, m), 7.96 (2H, d, J=8.8 Hz), 8.42 (1H, m), 8.74 (1H, d, J=6.8 Hz), 10.06 (1H, m).

MASS (m/z): 1157.6 (M⁺+1).

EXAMPLE 204

IR (KBr): 3320, 2933, 1658, 1629, 1610, 1510, 1446, 1255, 1234, 1114, 1087, 1064, 1006 cm$^{-1}$.

NMR (DMSO-$d_6$, δ): 0.96 (3H, d, J=6.7 Hz), 1.06 (3H, d, J=5.7 Hz), 1.2–1.5 (11H, m), 1.5–1.8 (3H, m), 1.8–2.1 (5H, m), 2.1–2.7 (6H, m), 2.8–3.1 (4H, m), 3.1–3.8 (13H, m), 3.21 (3H, s), 3.8–4.1 (7H, m), 3.90 (2H, d, J=6.4 Hz), 3.95 (1H, m), 4.2–4.5 (5H, m), 4.75 (3H, m), 5.24 (1H, m), 6.39 (1H, d, J=8.0 Hz), 6.57 (1H, m), 6.60 (1H, d, J=8.0 Hz), 6.91 (2H, d, J=8.8 Hz), 7.03 (2H, d, J=8.8 Hz), 7.17 (1H, m), 7.42 (1H, d, J=8.4 Hz), 7.72 (5H, m), 7.83 (2H, d, J=8.4 Hz), 8.43 (1H, m), 8.50 (1H, d, J=6.7 Hz).

MASS (m/z): 1233.4 (M⁺+1).

EXAMPLE 205

IR (KBr): 1651, 1539, 1514, 1234 cm$^{-1}$.

NMR (DMSO-$d_6$, δ): 0.85 (9H, s), 0.8–1.3 (11H, m), 1.3–2.4 (13H, m), 2.4–5.4 (40H, m), 6.39 (1H, d, J=7.5 Hz), 6.5–6.7 (2H, m), 7.04 (2H, d, J=8.6 Hz), 7.3–8.0 (5H, m), 8.3–8.9 (3H, m), 9.9–10.1 (1H, m).

MASS (m/z): 1137 (M⁺+1).

Elemental Analysis Calcd. for $C_{56}H_{84}N_{10}O_{15}$·3HCl·8H$_2$O: C, 48.36, H, 7.46, N, 10.07. Found: C, 48.25, H, 7.20, N, 9.81.

EXAMPLE 206

IR (KBr): 1699, 1678, 1651, 1539, 1514, 1456 cm$^{-1}$.

MASS (m/z): 1264 (M⁺+1).

What is claimed is:
1. A polypeptide compound of the following general formula (I):

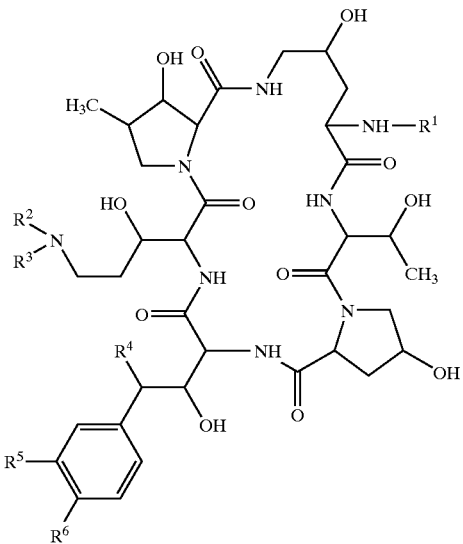

wherein
$R^1$ is hydrogen or acyl group,
$R^2$ and $R^3$ are independently hydrogen; lower alkyl which may have one or more suitable substituent(s) selected from the group consisting of amino, carboxy, sulfinic acid group, sulfonic acid group, hydroxy(lower)alkylamino which may have hydroxy(lower)alkyl, hydroxysulfonyloxy, imino, lower alkoxy, oxo, lower alkylthio, cyano(lower)alkylidene, and heterocyclic group which may have one or more lower alkyl;
lower alkoxycarbonyl which may have one or more suitable substituent(s) selected from the group consisting of lower alkanoyloxy and heterocyclic group;
lower alkenyloxycarbonyl;
ar(lower)alkoxycarbonyl;
lower alkanoyl which may have one or more suitable substituent(s) selected from the group consisting of amino, hydroxy and heterocyclic group;
heterocycliccarbonyl;
mono or di(lower)alkylcarbamoyl;
sulfonic acid group;
heterocyclic group which may have one or more suitable substituent(s) selected from the group consisting of lower alkyl, hydroxy(lower)alkyl, carboxy(lower)alkanoyl which may have amino, heterocycliccarbonyl, cyclo(lower)alkyl, and oxo;
lower alkylidene which may have mono or di lower alkylamino;
carboxy(higher)alkyl or
cyano,
$R^4$ is hydrogen or hydroxy,
$R^5$ is hydrogen, hydroxy, lower alkoxy or hydroxysulfonyloxy, and
$R^6$ is hydroxy or acyloxy,
or a salt thereof.
2. A compound of claim 1, wherein
$R^2$ and $R^3$ are independently hydrogen, methyl, aminoethyl, aminobutyl, aminopentyl, carboxymethyl, carboxyethyl, carboxypentyl, sulfonylmethyl, hydroxysulfonylpropyl, hydroxysulfonylbutyl, dihydroxyisopropylaminobutyl, hydroxysulfonyloxypropyl, 1-iminomethoxypropyl, 1-iminocarbamoylethyl, amidino, 2-cyano-1-methylthiovinyl, 2-cyano-1-aminovinyl, methylpyrazolylmethyl, tert-butoxycarbonyl, acetyloxymethoxycarbonyl, 1,3-dioxa-2-oxo-4-methylcyclopentenylmethoxycarbonyl, allyloxycarbonyl, fluorenylmethoxycarbonyl, acetyl, aminopropionyl, aminovaleryl, diaminohexanoyl, 2-hydroxy4-aminovaleryl, 2-amino-3-pyrazolylpropionyl, pyrrolidinylcarbonyl, morpholinocarbonyl, dimethylcarbamoyl, diethylcarbamoyl, hydroxysulfonyl, piperidyl, dimethylpiperidyl, hydroxyethylmethylpiperidyl, carboxypropionylpiperidyl, 4-amino-4-carboxybutyrylpiperidyl, azetidinylcarbonylpiperidyl, dimethyl-1,3-dioxacyclohexyl, cyclohexyl-1,3-dioxacyclohexyl, dioxothiopyranyl, dimethylaminomethylidene, carboxyheptyl or cyano.

3. A compound of claim 1, wherein $R^1$ is hydrogen; lower alkoxycarbonyl;

aroyl which has heterocyclic group substituted with aryl having a suitable substituent selected from the group consisting of lower alkoxy, lower alkoxy(lower)alkoxy, lower alkoxy(higher)alkoxy, aryl substituted with lower alkoxy(lower)alkoxy, cyclo(lower)alkyl, cyclo(lower)alkyloxy, aryl substituted with lower alkoxy, aryl substituted with lower alkoxy(lower)alkyl, aryl substituted with heterocyclic group, heterocyclic group substituted with cyclo(lower)alkyl, heterocyclic group, heterocyclic group substituted with aryl, heterocyclic group substituted with aryloxy, heterocyclic group substituted with ar(lower)alkoxy, heterocyclic group substituted with lower alkoxy and aryl, higher alkoxy, heterocyclic(higher)alkoxy, lower alkoxy(higher)alkylsulfonyl, aryloxy(lower)alkoxy, heterocyclic group substituted with cyclo(lower)alkyloxy, heterocyclic group substituted with aryl having lower alkoxy(lower)alkoxy, heterocyclic group substituted with lower alkylthio, heterocyclic group substituted with lower alkoxy(lower)alkylthio, and heterocyclic group substituted with lower alkoxy(lower)alkoxy;

aroyl which has aryl substituted with a suitable substituent selected from the group consisting of lower alkoxy having cyclo(lower)alkyl and amino, lower alkoxy having cyclo(lower)alkyl and protected amino, aryl having lower alkoxy, heterocyclic group having lower alkyl, heterocyclic group having cyclo(lower)alkyl, and heterocyclic group having aryl substituted with heterocyclic group;

aroyl which has heterocyclic group substituted with cyclo(lower)alkyl having one or more suitable substituent(s) selected from the group consisting of lower alkyl, lower alkoxy, cyclo(lower)alkyl, and cyclo(lower)alkyl substituted with lower alkoxy;

higher alkanoyl;

aroyl which has higher alkoxy; or heterocycliccarbonyl which has a suitable substituent(s) selected from the group consisting of heterocyclic group substituted with higher alkyl, heterocyclic group substituted with aryl having lower alkoxy, heterocyclic group substituted with aryl having heterocyclic group, and aryl substituted with lower alkoxy(higher)alkoxy.

4. A compound of claim 3, wherein $R^1$ is hydrogen; $(C_1-C_4)$alkoxycarbonyl;

benzoyl which has thiazolyl substituted with phenyl having $(C_4-C_6)$alkoxy;

benzoyl which has thiadiazolyl substituted with phenyl having a suitable substituent selected from the group consisting of $(C_1-C_4)$alkoxy$(C_4-C_6)$alkoxy, phenyl substituted with $(C_1-C_4)$alkoxy$(C_1-C_4)$alkyl, $(C_1-C_4)$alkoxy$(C_7-C_{14})$alkoxy, cyclo$(C_4-C_6)$alkyl, cyclo$(C_4-C_6)$alkyloxy, phenyl substituted with $(C_1-C_4)$alkoxy, phenyl substituted with $(C_1-C_4)$alkoxy$(C_1-C_4)$alkyl, phenyl substituted with di$(C_1-C_4)$alkylmorpholino, piperazinyl substituted with cyclo$(C_4-C_6)$alkyl, piperazinyl substituted with cyclo$(C_4-C_6)$alkyl having $(C_1-C_4)$alkyl; piperidyl, piperidyl substituted with phenyl, piperidyl substituted with phenoxy, piperidyl substituted with benzyloxy, piperidyl substituted with $(C_1-C_4)$alkoxy and chlorophenyl, and phenyl having di$(C_1-C_4)$alkylmorpholino;

benzoyl which has pyrimidinyl substituted with phenyl having $(C_7-C_{14})$alkoxy;

benzoyl which has isoxazolyl substituted with phenyl having a suitable substituent selected from the group consisting of $(C_4-C_6)$alkoxy, $(C_1-C_4)$alkoxy$(C_4-C_6)$alkoxy, $(C_1-C_4)$alkoxy$(C_7-C_{14})$alkoxy, $(C_7-C_{14})$alkoxy substituted with di$(C_1-C_4)$alkylmorpholino, and di$(C_1-C_4)$alkylmorpholino;

benzoyl which has oxadiazolyl substituted with phenyl having a suitable substituent selected from the group consisting of $(C_4-C_6)$alkoxy, $(C_1-C_4)$alkoxy$(C_7-C_{14})$alkoxy, $(C_1-C_4)$alkoxy$(C_7-C_{14})$alkoxy, and $(C_1-C_4)$alkoxy$(C_7-C_4)$alkylsulfonyl;

benzoyl which has piperazinyl substituted with phenyl having a suitable substituent selected from the group consisting of $(C_1-C_4)$alkoxy$(C_4-C_6)$alkoxy, $(C_1-C_4)$alkoxy$(C_7-C_{14})$alkoxy, phenoxy$(C_1-C_4)$alkoxy, cyclo$(C_4-C_6)$alkyl, phenyl substituted with $(C_1-C_4)$alkoxy$(C_4-C_6)$alkoxyphenyl, phenyl substituted with di$(C_1-C_4)$alkylmorpholino, piperidyl substituted with cyclo$(C_4-C_6)$alkyloxy, piperidyl substituted with phenyl, piperidyl substituted with $(C_1-C_4)$alkoxy$(C_1-C_4)$alkoxyphenyl, piperidyl substituted with $(C_1-C_4)$alkylthio, piperidyl substituted with $(C_1-C_4)$alkoxy$(C_4-C_6)$alkylthio, piperidyl substituted with cyclo$(C_4-C_6)$alkanespiro, piperidyl substituted with dioxacyclo$(C_4-C_6)$alkanespiro, piperidyl substituted with $(C_1-C_4)$alkoxy and phenyl, piperidyl substituted with $(C_1-C_4)$alkoxy and chlorophenyl, and di$(C_1-C_4)$alkylmorpholino;

benzoyl which has piperazinyl substituted with cyclo$(C_4-C_6)$alkyl having a suitable substituent selected from the group consisting of cyclo$(C_4-C_6)$alkyl, $(C_4-C_6)$alkyl, cyclo$(C_4-C_6)$alkyl and $(C_1-C_4)$alkoxy, and cyclo$(C_4-C_6)$alkyl substituted with $(C_1-C_4)$alkoxy;

benzoyl which has imidazothiadiazolyl substituted with phenyl having a suitable substituent selected from the group consisting of $(C_4-C_6)$alkoxy, $(C_1-C_4)$alkoxy$(C_4-C_6)$alkoxy, cyclo$(C_4-C_6)$alkyloxy, piperazinyl substituted with cyclo$(C_4-C_6)$alkyl, piperidyl substituted with $(C_1-C_4)$alkoxy$(C_1-C_4)$alkoxy, piperidyl substituted with $(C_1-C_4)$alkoxy$(C_4-C_6)$alkoxy, piperidyl substituted with $(C_1-C_4)$alkoxy$(C_4-C_6)$alkylthio, and di$(C_1-C_4)$alkylmorpholino;

benzoyl which has phenyl substituted with a suitable substituent selected from the group consisting of $(C_1-C_4)$alkoxy having cyclo$(C_4-C_6)$alkyl and $(C_1-C_4)$alkoxycarbonylamino, $(C_1-C_4)$alkoxy having cyclo$(C_4-C_6)$alkyl and amino, phenyl having $(C_4-C_6)$ alkoxy, thiazolyl having $(C_4-C_6)$alkyl, piperazinyl having cyclo$(C_4-C_6)$alkyl, piperazinyl having phenyl substituted with di$(C_1-C_4)$alkylmorpholino, and benzoxazolyl having $(C_4-C_6)$alkyl;

benzoyl which has $(C_7-C_{14})$alkoxy;

thiadiazolylcarbonyl which has pyrazolyl substituted with a suitable substituent selected from the group consisting of $(C_7-C_{14})$alkyl, phenyl having $(C_4-C_6)$alkoxy, and phenyl having piperidyl;

piperazinylcarbonyl which has xylyl substituted with $(C_1-C_4)$alkoxy$(C_7-C_{14})$alkoxy; or $(C_7-C_{14})$alkanoyl.

5. A compound of claim 4, wherein $R^1$ is hydrogen;

benzoyl which has thiazolyl substituted with phenyl having pentyloxy;

benzoyl which has thiadiazolyl substituted with phenyl having a suitable substituent selected from the group consisting of methoxyhexyloxy, methoxyoctyloxy, phenyl substituted with methoxyethoxy, phenyl substituted with methoxybutoxy, methoxyheptyloxy, cyclohexyl, cyclohexyloxy, phenyl substituted with propoxy, phenyl substituted with ethoxymethyl, phenyl substituted with methoxypropoxy, phenyl substituted with dimethylmorpholino, piperazinyl substituted with cyclohexyl, piperazinyl substitued with methylcyclohexyl, piperidyl, piperidyl substituted with phenyl piperidyl substituted with phenoxy, piperidyl substituted with benzyloxy, piperidyl substituted with methoxy and chlorophenyl, and dimethylmorpholino;

benzoyl which has pyrimidinyl substituted with phenyl having octyloxy;

benzoyl which has isoxazolyl substituted with phenyl having a suitable substituent selected from the group consisting of pentyloxy, methoxyhexyloxy, phenyl having methoxyheptyloxy, heptyloxy substituted with dimethylmorpholino, octyloxy substituted with dimethylmorpholino, and dimethylmorpholino;

benzoyl which has oxadiazolyl substituted with phenyl having a suitable substituent selected from the group consisting of pentyloxy, methoxyheptyloxy, methoxynonyloxy, methoxyheptylsulfonyl, and methoxynonylsulfonyl;

benzoyl which has piperazinyl substituted with phenyl having a suitable substituent selected from the group consisting of methoxyhexyloxy, methoxyheptyloxy, phenoxypropoxy, cyclohexyl, phenyl substituted with methoxypentyloxyphenyl, phenyl substituted with dimethylmorpholino, piperidyl substituted with cyclohexyloxy, piperidyl substituted with phenyl, piperidyl substituted with methoxybutoxyphenyl, piperidyl substituted with propylthio, piperidyl substituted with methoxyhexylthio, piperidyl substituted with cyclobutanespiro, piperidyl substituted with dioxacyclobutanespiro, piperidyl substituted with methoxy and phenyl, piperidyl substituted with methoxy and chlorophenyl, and dimethylmorpholino;

benzoyl which has piperazinyl substituted with cyclohexyl having a suitable substituent selected from the group consisting of tert-butyl, cyclohexyl and methoxy, and cyclohexyl substituted with propoxy;

benzoyl which has imidazothiadiazolyl substituted with phenyl having a suitable substituent selected from the group consisting of methoxybutoxy, cyclohexyloxy, piperazinyl substituted with cyclohexyl, piperidyl substitued with methoxypropoxy, piperidyl substituted with methoxybutoxy, piperidyl substituted with methoxypentyloxy, piperidyl substituted with methoxyhexyloxy, piperidyl substituted with methoxyhexylthio, and dimethylmorpholino;

benzoyl which has phenyl substituted with a suitable substituent selected from the group consisting of propoxy having cyclohexyl and tert-butoxycarbonylamino, cyclohexyl and amino, phenyl having pentyloxy, thiazolyl having pentyl, piperazinyl having cyclohexyl, piperazinyl having phenyl substituted with dimethylmorpholino, and benzoxazolyl having pentyl;

benzoyl which has octyloxy;

thiadiazolylcarbonyl which has pyrazolyl substituted with a suitable substituent selected from the group consisting of decyl, phenyl having hexyloxy, and phenyl having piperidyl;

piperazinylcarbonyl which has xylyl substituted with methoxyheptyloxy; or palmitoyl.

6. A process for preparing a polypeptide compound (I) of claim 1, or a salt thereof, which comprises, i) reducing a compound (II) of the formula:

(II)

or a salt thereof, to give a compound (Ia) of the formula:

(Ia)

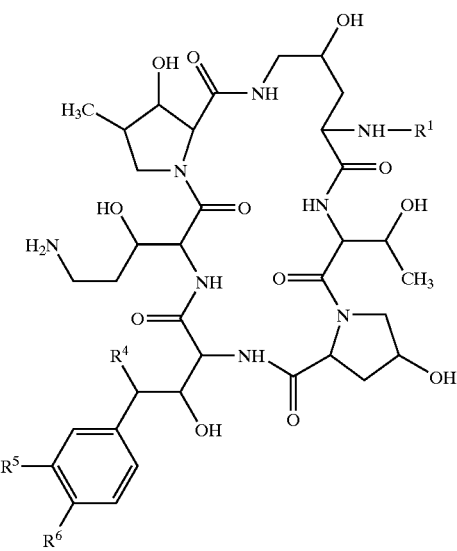

or a salt thereof, or
ii) subjecting a compound (Ia) of the formula:

(Ia)

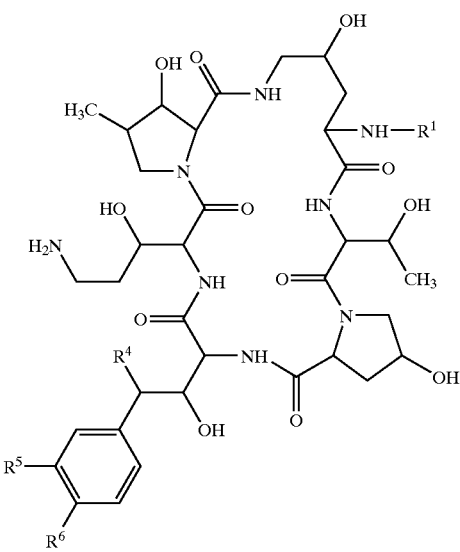

or a salt thereof, to protective reaction of amino, to give a compound (Ib) of the formula:

(Ib)

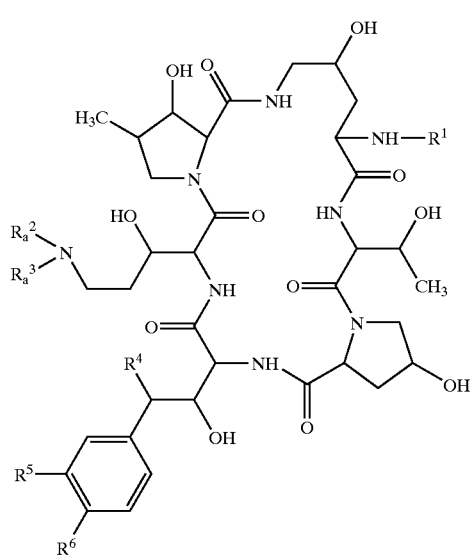

wherein $R_a^2$ is hydrogen, lower alkyl which may have one or more suitable substituent(s) selected from the group consisting of amino, carboxy, sulfinic acid group, sulfonic acid group, hydroxy(lower)alkylamino which may have hydroxy(lower)alkyl, hydroxysulfonyloxy, imino, lower alkoxy, oxo, lower alkylthio, cyano(lower)alkylidene, and heterocyclic group which may have one or more lower alkyl;

lower alkoxycarbonyl which may, have one or more suitable substituent(s) selected from the group consisting of lower alkanoyloxy and heterocyclic group;

lower alkenyloxycarbonyl;

ar(lower)alkoxycarbonyl;

lower alkanoyl which may have one or more suitable substituent(s) selected from the group consisting of amino, hydroxy and heterocyclic group;

heterocycliccarbonyl;

mono or di(lower)alkylcarbamoyl;

sulfonic acid group;

heterocyclic group which may have one or more suitable substituent(s) selected from the group consisting of lower alkyl, hydroxy(lower)alkyl, carboxy(lower)alkanoyl which may have amino, heterocycliccarbonyl, cyclo(lower)alkyl, and oxo;

lower alkylidene which may have mono or di lower alkylamino;

carboxy(higher)alkyl or cyano, and $R_a^3$ is lower alkyl which may have one or more suitable substituent(s) selected from the group consisting of amino, carboxy, sulfinic acid group, sulfonic acid group, hydroxy(lower)alkylamino which may have hydroxy(lower)alkyl, hydroxysulfonyloxy, imino, lower alkoxy oxo, lower alkylthio, cyano(lower)alkylidene, and heterocyclic group which may have one or more lower alkyl;

lower alkoxycarbonyl which may have one or more suitable substituent(s) selected from the group consisting of lower alkanoyloxy and heterocyclic group;

lower alkenyloxycarbonyl;

ar(lower)alkoxycarbonyl;

lower alkanoyl which may have one or more suitable substituent(s) selected from the group consisting of amino, hydroxy and heterocyclic group;

heterocycliccarbonyl;

mono or di(lower)alkylcarbamoyl;

sulfonic acid group;

heterocyclic group which may have one or more suitable substituent(s) selected from the group consisting of lower alkyl, hydroxy(lower)alkyl, carboxy(lower)alkanoyl which may have amino, heterocycliccarbonyl, cyclo(lower)alkyl, and oxo;

lower alkylidene which may have mono or di lower alkylamino;

carboxy(higher)alkyl or cyano, or a salt thereof, or iii) subjecting a compound (Ic) of the formula:

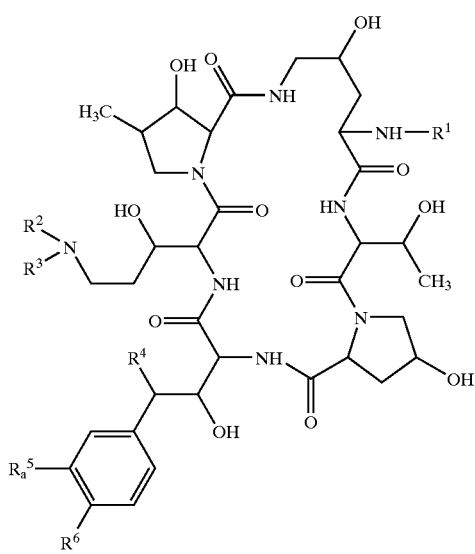

(Ic)

wherein $R_a^5$ is hydroxysulfonyloxy, or a its reactive derivative at the sulfonic acid group, or a salt thereof, to hydrolysis reaction of the sulfonic acid group, to give a compound (Id) of the formula:

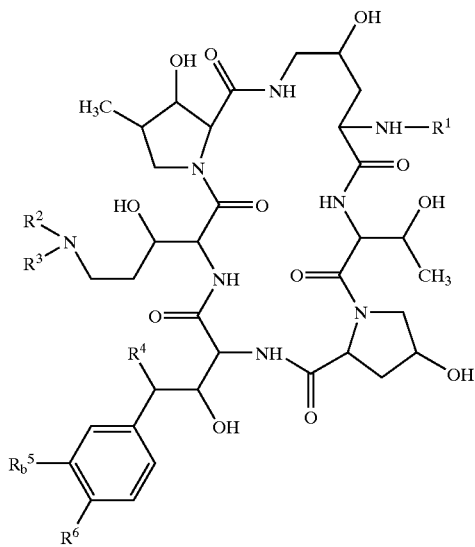

(Id)

wherein $R_b^5$ is hydroxy, or a salt thereof, or iv) subjecting a compound (Ie) of the formula:

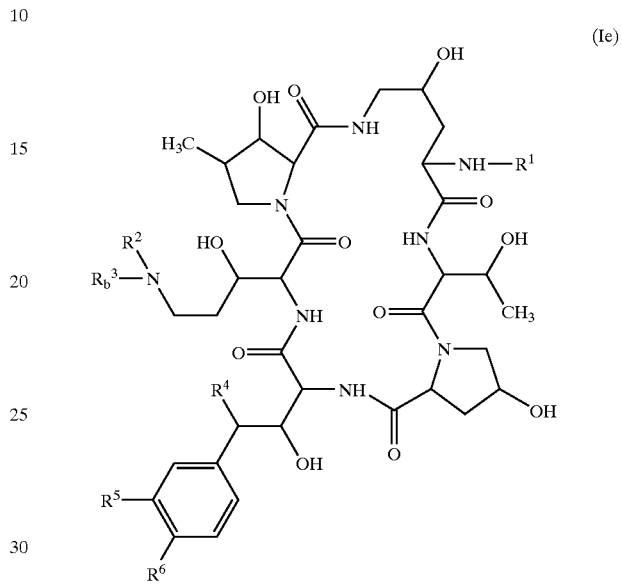

(Ie)

wherein $R_b^3$ is amino protective group, or a salt thereof, to elimination reaction of amino protective group, to give a compound (If) of the formula:

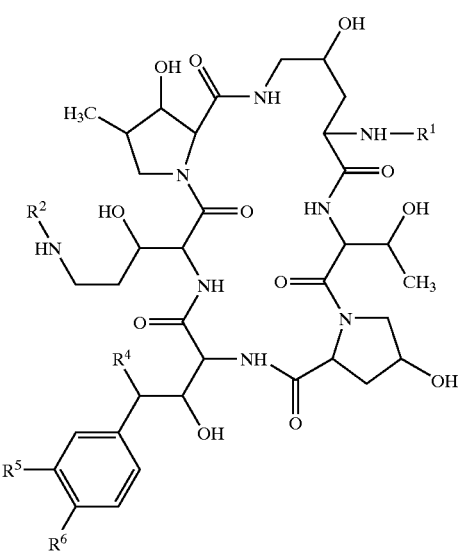

(If)

or a salt thereof, or v) reducing a compound (II) of the formula:

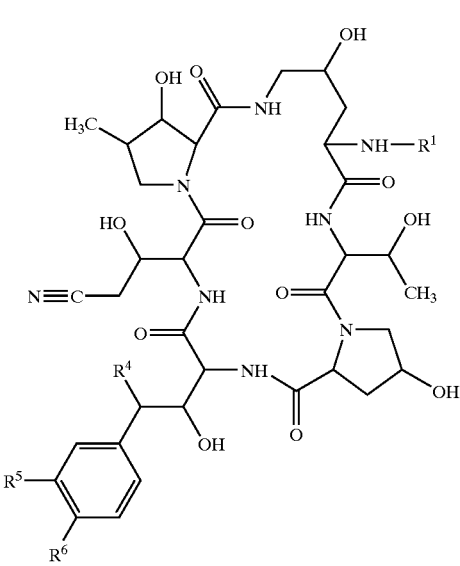

(II)

or its reactive derivative or a salt thereof, and then reacting with a compound (IV) of the formula:

$R_c^3$—OH  (IV)

wherein $R_c^3$ is lower alkoxycarbonyl which may have one or more suitable substituent(s) selected from the group consisting of lower alkanoyloxy and heterocyclic group;

lower alkenyloxycarbonyl;

ar(lower)alkoxycarbonyl;

lower alkanoyl which may have one or more suitable substituent(s) selected from the group consisting of amino, hydroxy and heterocyclic group;

heterocycliccarbonyl;

mono or di(lower)alkylcarbamoyl;

sulfonic acid group, or its reactive derivative or a salt thereof, to give a compound (Ig) of the formula:

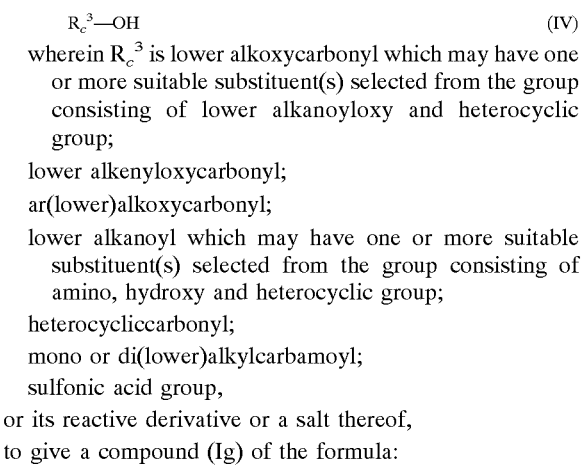

(Ig)

or a salt thereof, or vi) reacting a compound (Ih) of the formula:

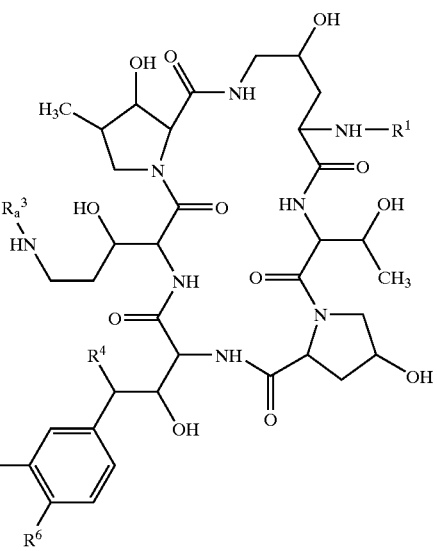

(Ih)

or its reactive derivative or a salt thereof, with a compound (V) of the formula:

$R_b^2$—OH  (V)

wherein $R_b^2$ is lower alkoxycarbonyl which may have one or more suitable substituent(s) selected from the group consisting of lower alkanoyloxy and heterocyclic group;

lower alkenyloxycarbonyl;

ar(lower)alkoxycarbonyl;

lower alkanoyl which may have one or more suitable substituent(s) selected from the group consisting of amino, hydroxy and heterocyclic group;

heterocycliccarbonyl;

mono or di(lower)alkylcarbamoyl;

sulfonic acid group, or its reactive derivative or a salt thereof, to give a compound (Ii) of the formula:

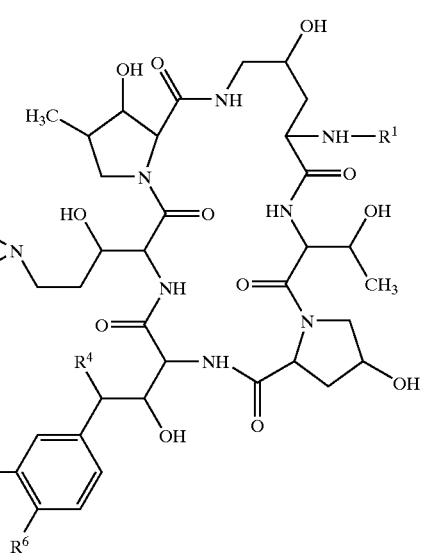

(Ii)

or a salt thereof, or vii) reacting a compound (Ij) of the formula:

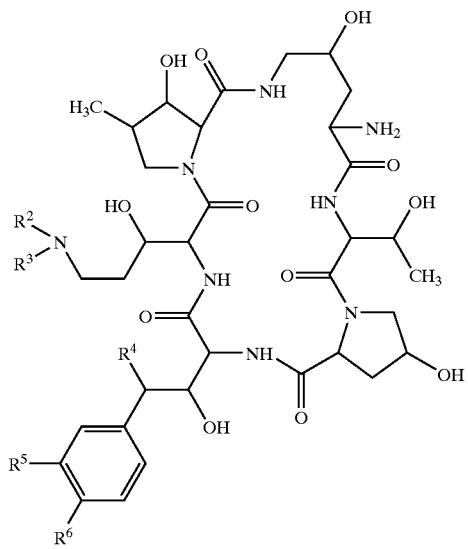

or its reactive derivative at the amino group, or a salt thereof, with a compound (III) of the formula:

$$R_a^1-OH \quad (III)$$

wherein $R_a^1$ is acyl group,
or its reactive derivative at the carboxy group, or a salt thereof, to give a compound (Ik) of the formula:

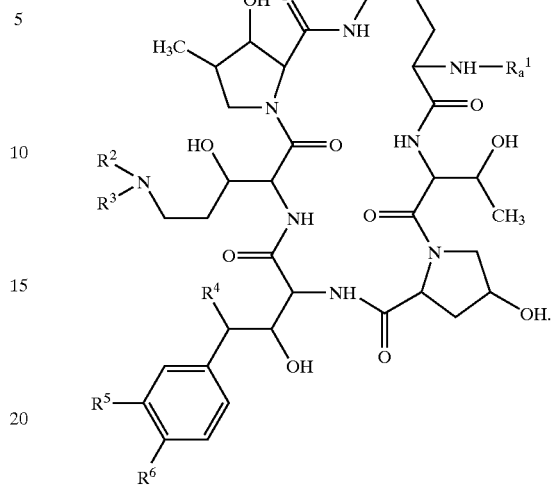

7. A composition which comprises, as an active ingredient, a compound of claim 1 or a pharmaceutically acceptable salt thereof in admixture with pharmaceutically acceptable carrier or excipients.

8. A method of treating an infectious diseases caused by a fungus comprising administering to a human being or an animal subject in need thereof a compound according to claim 1 for a time and under conditions to treat said disease.

* * * * *

UNITED STATES PATENT AND TRADEMARK OFFICE
CERTIFICATE OF CORRECTION

PATENT NO. : 6,884,868 B1
DATED : April 26, 2005
INVENTOR(S) : Takashi Tojo et al.

It is certified that error appears in the above-identified patent and that said Letters Patent is hereby corrected as shown below:

Column 669,
Line 9, "2-hydroxy4-aminovaleryl" should read -- 2-hydroxy-4-aminovaleryl --.

Column 672,
Compound II, formula

"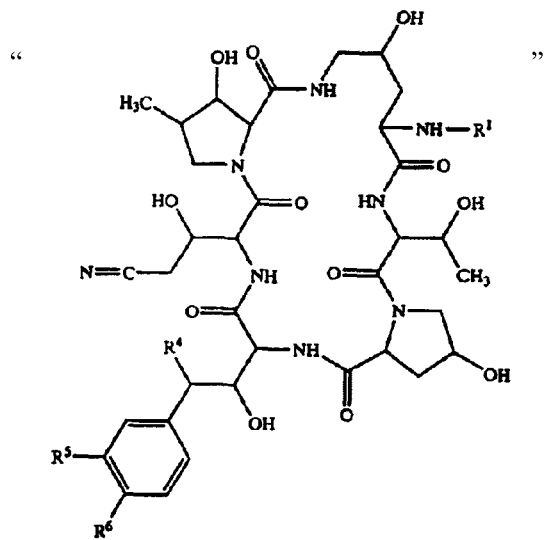"

should read

-- 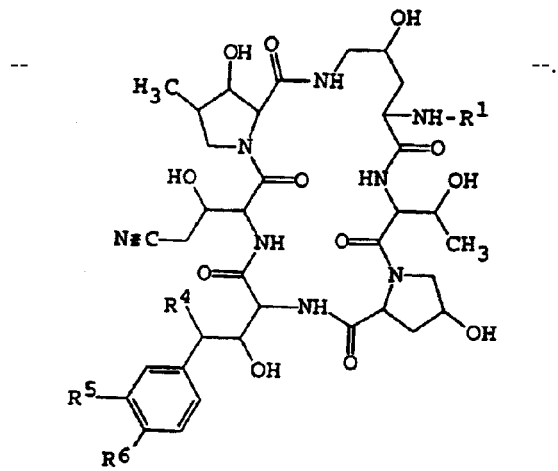 --.

UNITED STATES PATENT AND TRADEMARK OFFICE
CERTIFICATE OF CORRECTION

PATENT NO. : 6,884,868 B1
DATED :April 26, 2005
INVENTOR(S) : Takashi Tojo et al.

It is certified that error appears in the above-identified patent and that said Letters Patent is hereby corrected as shown below:

Column 674,
Line 13, "may, have" should read -- may have --;
Line 44, "alkoxy oxo" should read -- alkoxy, oxo --.

Signed and Sealed this

Twenty-seventh Day of December, 2005

JON W. DUDAS
*Director of the United States Patent and Trademark Office*